US012509684B2

(12) United States Patent
Prakash et al.

(10) Patent No.: US 12,509,684 B2
(45) **Date of Patent: *Dec. 30, 2025**

(54) COMPOSITIONS AND METHODS FOR MODULATING APOLIPOPROTEIN C-III EXPRESSION

(71) Applicant: Ionis Pharmaceuticals, Inc., Carlsbad, CA (US)

(72) Inventors: Thazha P. Prakash, Carlsbad, CA (US); Punit P. Seth, Carlsbad, CA (US); Eric E. Swayze, Encinitas, CA (US); Mark J. Graham, San Clemente, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/417,807

(22) Filed: Jan. 19, 2024

(65) Prior Publication Data

US 2024/0401038 A1 Dec. 5, 2024

Related U.S. Application Data

(63) Continuation of application No. 17/114,177, filed on Dec. 7, 2020, now abandoned, which is a continuation of application No. 15/891,118, filed on Feb. 7, 2018, now Pat. No. 10,927,372, which is a continuation of application No. 14/839,521, filed on Aug. 28, 2015, now Pat. No. 9,932,581, which is a continuation of application No. 14/586,826, filed on Dec. 30, 2014, now Pat. No. 9,163,239, which is a continuation of application No. PCT/US2014/036462, filed on May 1, 2014.

(60) Provisional application No. 61/986,867, filed on Apr. 30, 2014, provisional application No. 61/976,991, filed on Apr. 8, 2014, provisional application No. 61/880,790, filed on Sep. 20, 2013, provisional application No. 61/871,673, filed on Aug. 29, 2013, provisional application No. 61/843,887, filed on Jul. 8, 2013, provisional application No. 61/823,826, filed on May 15, 2013, provisional application No. 61/818,442, filed on May 1, 2013.

(51) Int. Cl.

| | |
|---|---|
| ***A61K 31/7088*** | (2006.01) |
| ***A61K 31/713*** | (2006.01) |
| ***A61K 47/54*** | (2017.01) |
| ***C07H 21/04*** | (2006.01) |
| ***C12N 15/11*** | (2006.01) |
| ***C12N 15/113*** | (2010.01) |

(52) U.S. Cl.

CPC ........ *C12N 15/113* (2013.01); *A61K 31/7088* (2013.01); *A61K 31/713* (2013.01); *A61K 47/549* (2017.08); *C07H 21/04* (2013.01); *C12N 15/111* (2013.01); *C12N 2310/11* (2013.01); *C12N 2310/113* (2013.01); *C12N 2310/17* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2310/351* (2013.01); *C12N 2310/3511* (2013.01); *C12N 2310/3513* (2013.01); *C12N 2310/3515* (2013.01); *C12N 2310/3525* (2013.01); *C12N 2310/353* (2013.01); *C12N 2320/32* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,751,219 | A | 6/1988 | Kempen et al. |
| 4,845,205 | A | 7/1989 | Huynh Dinh et al. |
| 4,981,957 | A | 1/1991 | Lableu et al. |

(Continued)

FOREIGN PATENT DOCUMENTS

| | | |
|---|---|---|
| CA | 2450022 | 12/2002 |
| WO | WO 1994/002499 | 2/1994 |

(Continued)

OTHER PUBLICATIONS

Akinc et al., "Targeted Delivery of RNAi Therapeutics with Endogenous and Exogenous Ligand-Based Mechanisms" Molecular Therapy (2010) 18(7): 1357-1364.

(Continued)

*Primary Examiner* — Traviss C McIntosh, III

(74) *Attorney, Agent, or Firm* — Arnold & Porter Kaye Scholer LLP

(57) ABSTRACT

Provided herein are oligomeric compounds with conjugate groups targeting apoplipoprotein C-III (ApoCIII). In certain embodiments, the ApoCIII targeting oligomeric compounds are conjugated to N-Acetylgalactosamine. Also disclosed herein are conjugated oligomeric compounds targeting ApoCIII for use in decreasing ApoCIII to treat, prevent, or ameliorate diseases, disorders or conditions related to ApoCIII. Certain diseases, disorders or conditions related to ApoCIII include inflammatory, cardiovascular and/or metabolic diseases, disorders or conditions. The conjugated oligomeric compounds disclosed herein can be used to treat such diseases, disorders or conditions in an individual in need thereof.

20 Claims, No Drawings

Specification includes a Sequence Listing.

(56) References Cited

U.S. PATENT DOCUMENTS

| | | | |
|---|---|---|---|
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,134,066 | A | 7/1992 | Rogers et al. |
| 5,166,315 | A | 11/1992 | Summerton et al. |
| 5,175,273 | A | 12/1992 | Bischofberger et al. |
| 5,177,198 | A | 1/1993 | Spielvogel et al. |
| 5,185,444 | A | 2/1993 | Summerton et al. |
| 5,223,618 | A | 6/1993 | Cook et al. |
| 5,256,775 | A | 10/1993 | Froehler |
| 5,264,562 | A | 11/1993 | Matteucci |
| 5,264,564 | A | 11/1993 | Matteucci |
| 5,319,080 | A | 6/1994 | Leumann |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,432,272 | A | 7/1995 | Benner |
| 5,434,257 | A | 7/1995 | Matteucci et al. |
| 5,446,137 | A | 8/1995 | Maag et al. |
| 5,457,187 | A | 10/1995 | Gmelner et al. |
| 5,459,255 | A | 10/1995 | Cook et al. |
| 5,466,786 | A | 11/1995 | Buhr et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,134 | A | 5/1996 | Acevedo et al. |
| 5,525,711 | A | 6/1996 | Hawkins et al. |
| 5,552,540 | A | 9/1996 | Haralambidis |
| 5,567,811 | A | 10/1996 | Mistura et al. |
| 5,576,427 | A | 11/1996 | Cook et al. |
| 5,587,469 | A | 12/1996 | Cook et al. |
| 5,591,722 | A | 1/1997 | Montgomery et al. |
| 5,594,121 | A | 1/1997 | Froehler et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,610,289 | A | 3/1997 | Cook et al. |
| 5,610,300 | A | 3/1997 | Altmann et al. |
| 5,614,617 | A | 3/1997 | Cook et al. |
| 5,625,050 | A | 4/1997 | Beaton et al. |
| 5,627,053 | A | 5/1997 | Usman et al. |
| 5,639,873 | A | 6/1997 | Barascut et al. |
| 5,645,985 | A | 7/1997 | Froehler et al. |
| 5,646,265 | A | 7/1997 | McGee |
| 5,670,633 | A | 9/1997 | Cook et al. |
| 5,681,941 | A | 10/1997 | Cook et al. |
| 5,698,685 | A | 12/1997 | Summerton et al. |
| 5,700,920 | A | 12/1997 | Altmann et al. |
| 5,750,692 | A | 5/1998 | Cook et al. |
| 5,763,588 | A | 6/1998 | Matteucci et al. |
| 5,792,847 | A | 8/1998 | Buhr et al. |
| 5,801,154 | A | 9/1998 | Baracchini et al. |
| 5,830,653 | A | 11/1998 | Froehler et al. |
| 5,994,517 | A | 11/1999 | Ts'o et al. |
| 5,998,203 | A | 12/1999 | Matulic-Adamic |
| 6,005,096 | A | 12/1999 | Matteucci et al. |
| 6,268,490 | B1 | 7/2001 | Imanishi et al. |
| 6,300,319 | B1 | 10/2001 | Manoharan |
| 6,383,812 | B1 | 5/2002 | Chen et al. |
| 6,525,031 | B2 | 2/2003 | Manoharan |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,620,916 | B1 | 9/2003 | Takahara et al. |
| 6,660,720 | B2 | 12/2003 | Manoharan et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 6,908,903 | B1 | 6/2005 | Theodore et al. |
| 7,034,133 | B2 | 4/2006 | Wengel et al. |
| 7,053,207 | B2 | 5/2006 | Wengel |
| 7,259,150 | B2 | 8/2007 | Crooke et al. |
| 7,262,177 | B2 | 8/2007 | Ts'o et al. |
| 7,267,819 | B2 | 9/2007 | Ferrara et al. |
| 7,399,845 | B2 | 7/2008 | Seth et al. |
| 7,427,672 | B2 | 9/2008 | Imanishi et al. |
| 7,439,043 | B2 | 10/2008 | DeFrees et al. |
| 7,491,805 | B2 | 2/2009 | Vargeese et al. |
| 7,569,686 | B1 | 8/2009 | Bhat et al. |
| 7,582,744 | B2 | 9/2009 | Manoharan et al. |
| 7,598,227 | B2 | 10/2009 | Crooke et al. |
| 7,723,509 | B2 | 5/2010 | Manoharan et al. |
| 7,741,457 | B2 | 6/2010 | Swayze et al. |
| 7,750,141 | B2 | 7/2010 | Crooke et al. |
| 7,851,615 | B2 | 12/2010 | Manoharan et al. |
| 7,935,796 | B2 | 5/2011 | Lee et al. |
| 8,106,022 | B2 | 1/2012 | Manoharan et al. |
| 8,137,695 | B2 | 3/2012 | Rozema et al. |
| 8,158,601 | B2 | 4/2012 | Chen et al. |
| 8,313,772 | B2 | 11/2012 | Rozema et al. |
| 8,344,125 | B2 | 1/2013 | Manoharan et al. |
| 8,349,308 | B2 | 1/2013 | Yurkovetskiy et al. |
| 8,404,862 | B2 | 3/2013 | Manoharan et al. |
| 8,435,491 | B2 | 5/2013 | Wang et al. |
| 8,450,467 | B2 | 5/2013 | Manoharan et al. |
| 8,501,805 | B2 | 8/2013 | Seth et al. |
| 8,501,930 | B2 | 8/2013 | Rozema et al. |
| 8,530,439 | B2 | 9/2013 | Crooke et al. |
| 8,530,640 | B2 | 9/2013 | Seth et al. |
| 8,541,376 | B2 | 9/2013 | Ferrara et al. |
| 8,541,548 | B2 | 9/2013 | Rozema |
| 8,546,556 | B2 | 10/2013 | Seth et al. |
| 8,552,163 | B2 | 10/2013 | Lee et al. |
| 8,653,047 | B2 | 2/2014 | Crooke et al. |
| 8,673,632 | B2 | 3/2014 | Crooke et al. |
| 8,742,075 | B2 | 6/2014 | Lee et al. |
| 9,127,276 | B2 | 9/2015 | Prakash et al. |
| 9,157,082 | B2 | 10/2015 | Mullick et al. |
| 9,163,239 | B2 * | 10/2015 | Prakash ................ A61K 47/59 |
| 9,181,550 | B2 | 11/2015 | Prakash et al. |
| 9,365,848 | B2 | 6/2016 | Crooke et al. |
| 9,550,988 | B2 | 1/2017 | Swayze et al. |
| 9,593,333 | B2 | 3/2017 | Alexander et al. |
| 9,624,496 | B2 | 4/2017 | Crooke et al. |
| 9,909,124 | B2 | 3/2018 | Crooke et al. |
| 9,932,581 | B2 | 4/2018 | Prakash et al. |
| 10,493,092 | B2 | 12/2019 | Swayze et al. |
| 10,927,372 | B2 | 2/2021 | Prakash et al. |
| 11,851,655 | B2 | 12/2023 | Prakash et al. |
| 2001/0053519 | A1 | 12/2001 | Fodor et al. |
| 2003/0017488 | A1 | 1/2003 | Koishi et al. |
| 2003/0077829 | A1 | 4/2003 | MacLachlan |
| 2003/0119724 | A1 | 6/2003 | Ts'o et al. |
| 2003/0170249 | A1 | 9/2003 | Hakomori et al. |
| 2003/0228597 | A1 | 12/2003 | Cowsert et al. |
| 2004/0171570 | A1 | 9/2004 | Allerson et al. |
| 2004/0242516 | A1 | 12/2004 | Crooke et al. |
| 2005/0009088 | A1 | 1/2005 | Crooke et al. |
| 2005/0130923 | A1 | 6/2005 | Bhat et al. |
| 2005/0164235 | A1 | 7/2005 | Manoharan et al. |
| 2005/0255487 | A1 | 11/2005 | Khvorova et al. |
| 2006/0148740 | A1 | 7/2006 | Platenburg |
| 2006/0183886 | A1 | 8/2006 | Tso et al. |
| 2006/0264395 | A1 | 11/2006 | Crooke et al. |
| 2007/0031844 | A1 | 2/2007 | Khvorova et al. |
| 2007/0054856 | A1 | 3/2007 | Gerber et al. |
| 2007/0287831 | A1 | 12/2007 | Seth et al. |
| 2008/0039618 | A1 | 2/2008 | Allerson et al. |
| 2008/0108801 | A1 | 5/2008 | Manoharan et al. |
| 2008/0113351 | A1 | 5/2008 | Nalto et al. |
| 2008/0177045 | A1 | 7/2008 | Lee et al. |
| 2008/0206869 | A1 | 8/2008 | Smith et al. |
| 2008/0255030 | A1 | 10/2008 | Yu et al. |
| 2008/0281041 | A1 | 11/2008 | Rozema et al. |
| 2008/0281044 | A1 | 11/2008 | Manoharan et al. |
| 2009/0012281 | A1 | 1/2009 | Swayze et al. |

(56) References Cited

U.S. PATENT DOCUMENTS

2009/0203132 A1 8/2009 Swayze et al.
2009/0203135 A1 8/2009 Forst et al.
2009/0286973 A1 11/2009 Manoharan et al.
2009/0306180 A1 12/2009 Bhanot et al.
2009/0318536 A1 12/2009 Freier et al.
2009/0326040 A1 12/2009 Geary et al.
2010/0240730 A1 9/2010 Beigelman et al.
2010/0331390 A1 12/2010 Crooke et al.
2011/0039910 A1 2/2011 Crooke et al.
2011/0060030 A1 3/2011 Crooke et al.
2011/0077386 A1 3/2011 Lee et al.
2011/0097264 A1 4/2011 Wang et al.
2011/0097265 A1 4/2011 Wang et al.
2011/0123520 A1 5/2011 Manoharan et al.
2011/0201798 A1 8/2011 Manoharan et al.
2011/0207799 A1 8/2011 Rozema et al.
2011/0243948 A1 10/2011 Lee et al.
2011/0269814 A1 11/2011 Manoharan et al.
2012/0035115 A1 2/2012 Manoharan et al.
2012/0095075 A1 4/2012 Manoharan et al.
2012/0101148 A1 4/2012 Aking et al.
2012/0122958 A1 5/2012 Dawson et al.
2012/0128760 A1 5/2012 Manoharan et al.
2012/0136042 A1 5/2012 Manoharan et al.
2012/0157509 A1 6/2012 Hadwiger et al.
2012/0165393 A1 6/2012 Rozema et al.
2012/0183602 A1 7/2012 Chen et al.
2012/0225927 A1 9/2012 Sah et al.
2012/0230938 A1 9/2012 Rozema et al.
2012/0270929 A1 10/2012 Crooke et al.
2013/0004427 A1 1/2013 El-Sayed et al.
2013/0017250 A1 1/2013 Ginsberg et al.
2013/0023579 A1 1/2013 Crooke et al.
2013/0035366 A1 2/2013 Swayze et al.
2013/0109817 A1 5/2013 Yurkovetskiy et al.
2013/0121954 A1 5/2013 Wakefield et al.
2013/0178512 A1 7/2013 Manoharan et al.
2013/0236968 A1 9/2013 Manoharan et al.
2013/0281511 A1 10/2013 Bettencourt et al.
2013/0317085 A1 11/2013 Crooke et al.
2014/0343123 A1 11/2014 Prakash et al.
2015/0057329 A1 2/2015 Bhanot et al.
2021/0395734 A1 12/2021 Prakash et al.

FOREIGN PATENT DOCUMENTS

WO WO 1994/017093 8/1994
WO WO 1997/020563 6/1997
WO WO 1997/046098 12/1997
WO WO 1998/013381 4/1998
WO WO 1998/039352 9/1998
WO WO 1999/014226 3/1999
WO WO 2000/014048 3/2000
WO WO 2000/063364 10/2000
WO WO 2001/005825 1/2001
WO WO 2001/049687 7/2001
WO WO 2002/043771 6/2002
WO WO 2003/004602 1/2003
WO WO 2003/044172 5/2003
WO WO 2004/035765 10/2003
WO WO 2004/024757 3/2004
WO WO 2004/044181 5/2004
WO WO 2004/063208 7/2004
WO WO 2004/093783 11/2004
WO WO 2004/101619 11/2004
WO WO 2004/106356 12/2004
WO WO 2005/000201 1/2005
WO WO 2005/021570 3/2005
WO WO 2005/028628 3/2005
WO WO 2005/097155 10/2005
WO WO 2005/121371 12/2005
WO WO 2006/014729 2/2006
WO WO 2006/031461 3/2006
WO WO 2006/047842 5/2006
WO WO 2007/035759 3/2007
WO WO 2007/090071 8/2007
WO WO 2007/134181 11/2007
WO WO 2007/146511 12/2007
WO WO 2008/073300 6/2008
WO WO 2008/098788 8/2008
WO WO 2008/101157 8/2008
WO WO 2008/150729 12/2008
WO WO 2008/154401 12/2008
WO WO 2009/003009 12/2008
WO WO 2009/006478 1/2009
WO WO 2009/073809 6/2009
WO WO 2009/082607 7/2009
WO WO 2009/126933 10/2009
WO WO 2009/134487 11/2009
WO WO 2009/143369 11/2009
WO WO 2010/036696 4/2010
WO WO 2010/036698 4/2010
WO WO 2010/048549 4/2010
WO WO 2010/048585 4/2010
WO WO 2010/054406 5/2010
WO WO 2010/077578 7/2010
WO WO 2010/083615 7/2010
WO WO 2010/088537 8/2010
WO WO 2010/101951 9/2010
WO WO 2010/103204 9/2010
WO WO 2010/129709 11/2010
WO WO 2010/144740 12/2010
WO WO 2010/148013 12/2010
WO WO 2011/005860 1/2011
WO WO 2011/005861 1/2011
WO WO 2011/038356 3/2011
WO WO 2011/085271 7/2011
WO WO 2011/100131 8/2011
WO WO 2011/115818 9/2011
WO WO 2011/120053 9/2011
WO WO 2011/123401 10/2011
WO WO 2011/133871 10/2011
WO WO 2011/139702 10/2011
WO WO 2011/139917 11/2011
WO WO 2011/163121 12/2011
WO WO 2012/037254 3/2012
WO WO 2012/068187 5/2012
WO WO 2012/083046 6/2012
WO WO 2012/083185 6/2012
WO WO 2012/089352 7/2012
WO WO 2012/089602 7/2012
WO WO 2012/135736 10/2012
WO WO 2012/142458 10/2012
WO WO 2012/145674 10/2012
WO WO 2012/145697 10/2012
WO WO 2012/149495 11/2012
WO WO 2012/177784 12/2012
WO WO 2012/177947 12/2012
WO WO 2013/033230 3/2013
WO WO 2013/075035 5/2013
WO WO 2013/119979 8/2013
WO WO 2013/142571 9/2013
WO WO 2013/165816 11/2013
WO WO 2013/166121 11/2013
WO WO 2013/173789 11/2013
WO WO 2013/177468 11/2013
WO WO 2014/076195 5/2014
WO WO 2014/076196 5/2014
WO WO 2014/118267 8/2014
WO WO 2014/118272 8/2014
WO WO 2014/127268 8/2014
WO WO 2014/179620 11/2014
WO WO 2014/179625 11/2014
WO WO 2014/179626 11/2014
WO WO 2014/179627 11/2014
WO WO 2014/179629 11/2014
WO WO 2014/207232 12/2014

OTHER PUBLICATIONS

Albaek et al., "Analogues of a Locked Nucleic Acid with Three-Carbon 2',4'-Linkages: Synthesis by Ring-Closing Metathesis and

(56) References Cited

OTHER PUBLICATIONS

Influence of Nucleic Acid Duplex Stability" J. Org. Chem. (2006) 71:7731-7740.
Andre et al., "Determination of modulation of ligand properties of synthetic complex-type biantennary N-glycans by introduction of bisecting GlcNAc in silico, in vitro and in vivo" Eur. J. Biochem. (2004) 271: 118-134.
Asseline et al., "Modification of the 5' Terminus of Oligodeoxyribonucleotides for Conjugation with Ligands" in Current Protocols in Nucleic Acid Chemistry, 2001, Supplement 5, Chapter 4: Unit 4.9 (4.9.1-4.9.28); John Wiley & Sons.
Atsma et al., "Partial characterization of low density lipoprotein preparations isolated from fresh and frozen plasma after radiolabeling by seven different methods." J Lipid Res. (1991) 32(1): 173-181.
Beaucage et al., "The functionalization of oligonucleotides via phosphoramidate derivatives" Tetrahedron (1993) 49(10): 1925-1963.
Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.
Biessen et al., "Synthesis of Cluster Galactosides with High Affinity for the Hepatic Asialoglycoprotein Receptor" J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Braasch et al., "Locked nucleic acid (LNA): fine-tuning the recognition of DNA and RNA" Chem. Biol. (2001) 8:1-7.
Braasch et al., "Novel Antisense and Peptide Nucleic Acid Strategies for Controlling Gene Expression" Biochemistry (2002) 41(14): 4503-4510.
Branda et al., "Amplification of antibody production by phosphorothioate oligodeoxynucleotides" J Lab Clin Med. (1996) 128(3): 329-338.
Coltart et al., "Principles of Mucin Architecture: Structural Studies on Synthetic Glycopeptides Bearing Clustered Mono-, Di-, Tri-, and Hexasaccharide Glycodomains" J. Am. Chem. Soc. (2002) 124: 9833-9844.
Connolly et al., "Binding and Endocytosis of Cluster Glycosides by Rabbit Hepatocytes" J Biol Chem (1982) 257: 939-945.
Crooke et al., "Pharmacokinetic Properties of Several Novel Oligonucleotide Analogs in mice" J. Pharmacol. Exp. Ther. (1996) 277(2):923-937.
Crooke et al., "Pharmacological Properties of 2'-O-Methoxyethyl Modified Oligonucleotides" in Antisense a Drug Technology, Chapter 10, pp. 273-303, Crooke, S.T., ed., 2008.
Crooke et al., "Toxicologic Properties of 2-O-Methoxyethyl Chimeric Antisense Inhibitors in Animals and Man" in Antisense a Drug Technology, Chapter 12, pp. 342-351, Crooke, S.T., ed., 2008.
Czech et al. "RNAi-based therapeutic strategies for metabolic disease" Nature Reviews Endocrinology (2011) 7: 473-484.
Davidson et al., "Apolipoprotein B: mRNA Editing, Lipoprotein Assembly, and Presecretory Degradation" Annu. Rev. Nutr. (2000) 20: 169-193.
Dellinger et al., "Solid-Phase Chemical Synthesis of Phosphonoacetate and Thiophosphonoacetate Oligodeoxynucleotides" J. Am .Chem. Soc. (2003) 125: 940-950.
Duff et al., "Intrabody Tissue-Specific Delivery of Antisense Conjugates in Animals: Ligand-Linker-Antisense Oligomer Conjugates" Methods in Enzymology (1999) 313: 297-321.
Dupouy et al., "Watson—Crick Base-Pairing Properties of Nucleic Acid Analogues with Stereocontrolled a and b Torsion Angles (a,b-D-CNAs)" Angew. Chem. Int. Ed. (2006) 45: 3623-3627.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.
Hoffman et al., "'Brain-type' N-glycosylation of asialo-transferrin from human cerebrospinal fluid" FEBS Letters (1995) 359: 164-168.
Horn et al., "Chemical synthesis and characterization of branched oligodeoxyribonucleotides (bDNA) for use as signal amplifiers in nucleic acid quantification assays." Nucleic Acids Research (1997) 25: 4842-4849.
International Search Report for Application PCT/US12/52884 dated Nov. 20, 2012.
International Search Report for Application PCT/US14/36460 dated Oct. 10, 2014.
International Search Report for Application PCT/US14/36462 dated Dec. 23, 2014.
International Search Report for Application PCT/US14/36463 dated Dec. 30, 2014.
International Search Report for Application PCT/US14/36466 dated Dec. 1, 2014.
International Search Report for Application PCT/US14/43731 dated Dec. 10, 2014.
International Search Report for Application PCT/US14/56630 dated Dec. 24, 2014.
Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Jiang et al., "The Design and Synthesis of Highly Branched and Spherically Symmetric Fluorinated Oils and Amphiles." Tetrahedron (2007) 63(19): 3982-3988.
Jin et al., "Use of α-N,N-bis[Carboxymethyl]lysine-Modified Peroxidase in Immunoassays" Analytical Biochemistry (1995) 229: 54-60.
Kanasty et al., "Delivery Materials for siRNA Therapeutics" Nature Materials (2013) 12: 967-977.
Kassim et al., "Gene therapy for dyslipidemia: a review of gene replacement and gene inhibition strategies" Clinical Lipidology (2010) 5(6): 793-809.
Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kim et al., "Synthesis of Novel Phosphoramidite Building Blocks from Pentaerythritol" Synlett (2003) 12: 1838-1840.
Koller et al., "Mechanisms of single-stranded phosphorothioate modified antisense oligonucleotide accumulation in hepatocytes." Nucleic Acids Res. (2011) 39(11): 4795-4807.
Kornilova et al., "Development of a fluorescence polarization binding assay for asialoglycoprotein receptor" Analytical Biochemistry (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.

(56) References Cited

OTHER PUBLICATIONS

Kumar et al., "The first analogues of LNA (locked nucleic acids): phosphorothioate-LNA and 2'-thio-LNA" Bioorg Med Chem Lett. (1998) 8:2219-2222.
Lazaris-Karatzas et al., "Malignant transformation by a eukaryotic initiation factor subunit that binds to mRNA 5' cap" Nature (1990) 345: 544-547.
Lee et al., "Antisense Technology: An Emerging Platform for Cardiovascular Disease Therapeutics" J of Cardiovasc Trans Res (2013) 6: 969-980.
Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.
Lee et al., "New synthetic cluster ligands for galactose/N-acetylgalactosamine-specific lectin of mammalian liver" Biochem (1984) 23: 4255-4261.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Protein microarrays to study carbohydrate-recognition events" Bioorg Med Chem Lett (2006) 16(19): 5132-5135.
Lee et al., "Synthesis of multivalent neoglyconjugates of MUC1 by the conjugation of carbohydrate-centered, triazole-linked glycoclusters to MUC1 peptides using click chemistry." J Org Chem (2012) 77: 7564-7571.
Lee et al., "Synthesis of Peptide-Based Trivalent Scaffold for Preparation of Cluster Glycosides" Methods in Enzymology (2003) 362: 38-43.
Lee et al., "Synthesis of some cluster glycosides suitable for attachment to proteins or solid matrices" Carbohydrate Research (1978) 67: 509-514.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Link, "Pharmacological regulation of hepatic glucose production" Curr Opin Investig Drugs (2003) 4: 421-429.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate—lectin interactions by an enzyme-linked lectin assay employing covalently immobilized carbohydrates" Bioorganic & Medicinal Chemistry (2007) 15: 7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "N-(2-Cyanoethoxycarbonyloxy)succinimide: A New Reagent for Protection of Amino Groups in Oligonucleotides" J. Org. Chem. (1999) 64: 6468-6472.
Manoharan et al., "Oligonucleotide Conjugates: Alteration of the Pharmacokinetic Properties of Antisense Agents" Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Marcaurelle et al., "Synthesis of Oxime-Linked Mucin Mimics Containing the Tumor-Related TN and Sialyl TN Antigens" Organic Letters (2001) 3(23): 3691-3694.
Merwin et al., "Targeted delivery of DNA using YEE(GalNAcAH)3, a synthetic glycopeptide ligand for the asialoglycoprotein receptor." Bioconjug Chem (1994) 5(6): 612-620.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Park et al., "The asialoglycoprotein receptor clears glycoconjugates terminating with sialic acid a2,6GalNAc" PNAS (2005) 102(47): 17125-17129.
Pavia et al., "Synthetic TN glycopeptide related to human glycophorin AM. High-field proton and carbon-13 nuclear magnetic resonance study." Int J Pep Protein Res (1983) 22: 539-548.
Petrova et al., "Carrier-free cellular uptake and the gene-silencing activity of the lipophilic siRNAs is strongly affected by the length of the linker between siRNA and lipophilic group" Nucleic Acids Research (2012) 40(5): 2330-2344.
Pujol et al., "A Sulfur Tripod Glycoconjugate that Releases a High-Affinity Copper Chelator in Hepatocytes" Angew. Chem. Int. Ed. (2012) 51: 7445-7448.
Rajur et al., "Covalent Protein-Oligonucleotide Conjugates for Efficient Delivery of Antisense Molecules" Bioconjugate Chem. (1997) 8: 935-940.
Raouane et al., "Synthesis, Characterization, and in Vivo Delivery of siRNA-Squalene Nanoparticles Targeting Fusion Oncogene in Papillary Thyroid Carcinoma" J. Med. Chem. (2011) 54: 4067-4076.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vasc Biol (2006) 26: 169-175.
Rossenberg et al., "Stable polyplexes based on arginine-containing oligopeptides for in vivo gene delivery" Gene Therapy (2004) 11: 457-464.
Rouchaud et al., "A New and Efficient Synthesis of Derivatives of Octahydro-4H-pyrrolo[1,2-c]pyrido[1',2'-a]imidazole" Eur. J. Org. Chem. (2011) 12: 2346-2353.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Seth et al., "Design, Synthesis And Evaluation Of Constrained Methoxyethyl (cMOE) and Constrained Ethyl (cEt) Nucleoside Analogs" Nucleic Acids Symposium Series (2008) 52(1): 553-554.
Seth et al., "Synthesis and biophysical characterization of R-6'-Me-α-L-LNA modified oligonucleotides." Bioorg. Med. Chem. (2011) 21(4): 1122-1125.

(56) References Cited

OTHER PUBLICATIONS

Seth et al., "Synthesis and Biophysical Evaluation of 2',4'-Constrained 2'O-Methoxyethyl and 2',4'-Constrained 2'O-Ethyl Nucleic Acid Analogues" J Org Chem. (2010) 75(5): 1569-1581.
Shchepinov et al., "Oligonucleotide dendrimers: stable nano-structures" Nucleic Acids Research (1999) 27(15): 3035-3041.
Shchepinov et al., "Oligonucleotide dendrimers: synthesis and use as polylabelled DNA probes." Nucleic Acids Research (1997) 25(22): 4447-4454.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Sofia et al., "Discovery of a beta-d-2'-deoxy-2'-alpha-fluoro-2'-beta-C-methyluridine Nucleotide Prodrug (PSA-7977) For the Treatment of Hepatitis C virus" J. Med. Chem. (2010) 53(19): 7202-7218.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tober et al., "Self-Metathesis of Polyol Allyl Ethers towards Carbohydrate-Based Oligohydroxy Derivatives" Eur. J. Org. Chem. (2013) 3: 566-577.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Wahlestedt et al., "Potent and nontoxic antisense oligonucleotide containing locked nucleic acids" Proc. Natl. Acad. Sci. USA (2000) 97: 5633-5638.
Weber et al., "Design and synthesis of P2-P1'-linked macrocyclic human renin inhibitors" J. Med. Chem. (1991) 34(9): 2692-2701.
Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.
Wu et al., "A New N-Acetylgalactosamine Containing Peptide as a Targeting Vehicle for Mammalian Hepatocytes Via Asialoglycoprotein Receptor Endocytosis" Current Drug Delivery (2004) 1: 119-127.
Zhao et al., "Synthesis and preliminary biochemical studies with 5'-deoxy-5'-methylidyne phosphonate linked thymidine oligonucleotides" Tetrahedron Letters (1996) 37(35): 6239-6242.
Zhou et al., "Fine Tuning of Electrostatics around the Internucleotidic Phosphate through Incorporation of Modified 2',4'-Carbocyclic-LNAs and-ENAs Leads to Significant Modulation of Antisense Properties" J. Org. Chem. (2009) 74:118-134.
Zhou et al., "Proteolytic processing in the secretory pathway." J. Biol. Chem. (1999) 274(30): 20745-20748.
Allshire, "Molecular biology. RNAi and heterochromatin—a hushed-up affair" Science (2002) 297(5588):1818-1819.
Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals " Chimia. (1996) 50(4):168-176.
Altmann et al., "Second-generation antisense oligonucleotides: structure—activity relationships and the design of improved signal-transduction inhibitors" Biochem. Soc. Trans. (1996) 24:630-637.
Ando et al., "A decreased expression of angiopoietin-like 3 is protective against atherosclerosis in apoE-deficient mice" J Lipid Res. (2003) 44(6):1216-23.
Angelakopoulou et al., "Comparative analysis of genome-wide association studies signals for lipids, diabetes, and coronary heart disease: Cardiovascular Biomarker Genetics Collaboration" Eur Heart J. (2012) 33(3):393-407.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Bligh et al., "A rapid method of total lipid extraction and purification" Can. J. Biochem. Physiol. (1959) 37(8):911-917.
Branch et al., "A good antisense molecule is hard to find," TIBS (1998) 23:45-50.
Browning et al., "Molecular mediators of hepatic steatosis and liver injury" J. Clin. Invest. (2004) 114(2):147-152.
Camenisch et al., "ANGPTL3 stimulates endothelial cell adhesion and migration via integrin alpha vbeta 3 and induces blood vessel formation in vivo." J. Biol. Chem. (2002) 277(19):17281-17290.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Conklin et al., "Identification of a mammalian angiopoietin-related protein expressed specifically in liver." Genomics (1999) 62(3):477-482.
Crooke et al., "Basic Principles of Antisense Therapeutics" Antisense Research and Application (1998) Chapter 1:1-50.
EMBL Accession No. BG400407, *Homo sapiens* cDNA clone, Mar. 17, 2001, retrieved from the Internet, Apr. 3, 2013 <http://www.ebi.ac.uk/Tools/dbfetch/emblfetch?id=BG400407&Submit=Go>.
European Search Report for application EP 11732249.5 dated Aug. 7, 2014.
Expert Panel on Detection, Evaluation, and Treatment of High Blood Cholesterol in Adults. "Executive Summary of The Third Report of The National Cholesterol Education Program (NCEP) Expert Panel on Detection, Evaluation, And Treatment of High Blood Cholesterol In Adults (Adult Treatment Panel III)" JAMA. (2001) 285(18):2486-2497.
Fujimoto et al., "Angpt13-null mice show low plasma lipid concentrations by enhanced lipoprotein lipase activity" Exp. Anim. (2006) 55(1):27-34.
Gao et al., "Angiopoietin-like protein 3 regulates the motility and permeability of podocytes by altering nephrin expression in vitro" Biochemical and Biophysical Research Communications (2010) 399: 31-36.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
Geary et al., "A nonradioisotope biomedical assay for intact oligonucleotide and its chain-shortened metabolites used for determination of exposure and elimination half-life of antisense drugs in tissue" Anal. Biochem. (1999) 274(2):241-248.
GenBank Accession No. NM_014495.1. Homo sapiens angiopoietin-like 3 (ANGPTL3) mRNA, retrieved from the Internet on Apr. 18, 2013, downloaded from http://www.ncbi.nlm.nih.gov/nuccore/NM_014495.1.
Graham et al., "Antisense oligonucleotide inhibition of apolipoprotein C-III reduces plasma triglycerides in rodents, nonhuman primates, and humans" Circ. Res. (2013) 112(11):1479-1490.
Gu et al., "Base pairing properties of D-and L-cyclohexene nucleic acids (CeNA)" Oligonucleotides (2003) 13(6):479-489.

(56) References Cited

OTHER PUBLICATIONS

Gu et al., "Enzymatic resolution and base pairing properties of D-and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Guzaev et al., "A conformationally preorganized universal solid support for efficient oligonucleotide synthesis" J. Am. Chem. Soc. (2003) 125(9):2380-2381.
Hall et al., "Establishment and maintenance of a heterochromatin domain" Science (2002) 297(5590):2232-2237.
Hanessian et al., "Synthesis of chemically and functionally diverse scaffolds from pentaerythritol" Canadian Journal of Chemistry (1996) 74(9):1731-1737.
Hatsuda et al., "Association between Plasma Angiopoietin-Like Protein 3 and Arterial Wall Thickness in Healthy Subjects" J Vasc Res (2007) 44:61-66.
Hooper et al., "Recent developments in the genetics of LDL deficiency" Curr Opin Lipidol (2013) 24(2):111-115.
Horvath et al., "Stereoselective synthesis of (−)-ara-cyclohexenyl-adenine" Tetrahedron Letters (2007) 48:3621-3623.
Ichimura et al., "Serum Angiopoietin-like Protein 3 Levels: Possible Correlation with Progressive Skin Sclerosis, Digital Ulcers and Pulmonary Vascular Involvement in Patients with Systemic Sclerosis" Acta Derma Venereol (2013) 1-6.
Inaba et al., "Angiopoietin-like protein 3 mediates hypertriglyceridemia induced by the liver X receptor." J. Biol. Chem. (2003) 278(24):21344-21351.
International Search Report for application PCT/US11/20606 dated Jun. 27, 2011.
Inukai et al., "ANGPTL3 is increased in both insulin-deficient and -resistant diabetic states." Biochem. Biophys. Res. Commun. (2004) 317(4):1075-1079.
Ishibashi et al., "Hypercholesterolemia in low density lipoprotein receptor knockout mice and its reversal by adenovirus-mediated gene delivery." J. Clin. Invest. (1993) 92(2):883-893.
Jenuwein, "Molecular biology. An RNA-guided pathway for the epigenome" Science (2002) 297(5590):2215-2218.
Jones et al., "RNA quantitation by fluorescence-based solution assay: RiboGreen reagent characterization" Anal. Biochem. (1998) 265(2):368-374.
Kaplan et al., "Regulation of the angiopoietin-like protein 3 gene by LXR" J. Lipid Res. (2003) 44(1):136-143.
Koishi et al., "Angpt13 regulates lipid metabolism in mice" Nat. Genet. (2002) 30(2):151-157.
Korstanje et al., "Locating Ath8, a locus for murine atherosclerosis susceptibility and testing several of its candidate genes in mice and humans" Atherosclerosis (2004) 177:443-450.
Koster et al., "Transgenic angiopoietin-like (angptl)4 overexpression and targeted disruption of angpt14 and angpt13: regulation of triglyceride metabolism" Endocrinology (2005) 146(11):4943-50.
Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)" Journal of Biological Chemistry (2009) 284(20): 13735-13745.
Leeds et al., "Quantitation of phosphorothioate oligonucleotides in human plasma" Anal. Biochem. (1996) 235(1):36-43.
Lichtenstein et al., "Modulation of plasma TG lipolysis by Angiopoietin-like proteins and GPIHBP1" Biochimica and Biophysica Acta (2010) 1801(4): 415-420.
Linton et al., "Transgenic mice expressing high plasma concentrations of human apolipoprotein B100 and lipoprotein(a)." J. Clin. Invest. (1993) 92: 3029-3037.
Machida et al., "Bivalent inhibitors for disrupting protein surface-substrate interactions and for dual inhibition of protein prenyltransferases" J. Am. Chem. Soc. (2011) 133(4):958-963.
Maher et al., "Comparative bybrid arrest by tandem antisense oligodeoxyribonucleotides or oligodeoxyribonucleoside methylphosphonates in a cell-free system" Nuc. Acid. Res. (1988) 16(8):3341-3358.
Makino et al., "Intravenous Injection with Antisense Oligodeoxynucleotides Against Angiotensinogen Decreases Blood Pressure in Spontaneously Hypertensive RatS" Hypertension (1998) 31: 1166-1170.
Martin, "New acces to 2'-O-alkylated ribonucleosides and properties of 2'-O-alkylated oligoribonucleotides" Helv. Chim. Acta. (1995) 78:486-504.
Martin-Campos et al., "Identification of a novel mutation in the ANGPTL3 gene in two families diagnosed of familial hypobetalipoproteinemia without APOB mutation" Clin. Chim. Acta. (2012) 413(5-6):552-555.
Minicocci et al., "Clinical characteristics and plasma lipids in subjects with familial combined hypolipidemia: a pooled analysis" J. Lipid Res. (2013) 54(12):3481-3490.
Minicocci et al., "Mutations in the ANGPTL3 gene and familial combined hypolipidemia: a clinical and biochemical characterization" J. Clin. Endocrinol. Metab. (2012) 97(7):E1266-E1275.
Musunuru et al., "Exome sequencing, ANGPTL3 mutations, and familial combined hypolipidemia" N Engl J Med (2010) 363(23):2220-7.
Naoumova et al., "A new drug target for treatment of dyslipidemia associated with type 2 diabetes and the metabolic syndrome?" Lancet (2002) 359(9325):2215-6.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.
New England Biolabs 1998/99 Catalog (cover page and pp. 121 and 284).
Noto et al., "Prevalence of ANGPTL3 and APOB gene mutations in subjects with combined hypolipidemia" Arterioscler. Thromb. Vasc. Biol. (2012) 32(3):805-809.
Pal-Bhadra et al., "Heterochromatic silencing and HP1 localization in *Drosophila* are dependent on the RNAi machinery" Science (2004) 303(5658):669-672.
Pisciotta et al., "Characterization of three kindreds with familial combined hypolipidemia caused by loss-of-function mutations of ANGPTL3" Circ. Cardiovasc. Genet. (2012) 5(1):42-50.
Reynolds et al., "Rational siRNA design for RNA interference" Nature Biotechnology (2004) 22(3):326-330.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Romeo et al., "Rare loss-of-function mutations in ANGPTL family members contribute to plasma triglyceride levels in humans" J. Clin. Invest. (2009) 119(1):70-79.
Sanan et al., "Low density lipoprotein receptor-negative mice expressing human apolipoprotein B-100 develop complex atherosclerotic lesions on a chow diet: No. accentuation by apolipoprotein(a)" PNAS (1998) 95:4544-4549.
Sanghvi et al., "Heterocyclic Base Modifications in Nucleic Acids and Their Applications in Antisense Oligonucleotides" Antisense Research and Applications (1993) pp. 273-288.
Shimamura et al., Biochem. Biophys. Res. Commun. (2003) 301:604-609.
Shimamura et al., "Angiopoietin-like protein3 regulates plasma HDL cholesterol through suppression of endothelial lipase" Arterioscler Thromb Vasc Biol. (2007) 27(2):366-72.
Shimamura et al., "Leptin and insulin down-regulate angiopoietin-like protein 3, a plasma triglyceride-increasing factor" Biochem. Biophys. Res. Commun. (2004) 322(3):1080-1085.

(56) References Cited

OTHER PUBLICATIONS

Shimizugawa et al., "ANGPTL3 decreases very low density lipoprotein triglyceride clearance by inhibition of lipoprotein lipase" J. Biol. Chem. (2002) 277:33742-33748.
Sindelka et al., "Association of obesity, diabetes, serum lipids and blood pressure regulates insulin action" Physiol. Res. (2002) 51(1):85-91.
Smith et al., "Comparison of biosequences" Adv. Appl. Math. (1981) 2(4):482-489.
Sonnenburg et al., "GPIHBP1 stabilizes lipoprotein lipase and prevents its inhibition by angiopoietin-like 3 and angiopoietin-like 4" The Journal of Lipid Research (2009) 50(12): 2421-2429.
Valdivielso et al., "Association of moderate and severe hypertriglyceridemia with obesity, diabetes mellitus and vascular disease in the Spanish working population: results of the ICARIA study" Atherosclerosis (2009) 207(2):573-578.
Verbeure et al., "RNase H mediated cleavage of RNA by cyclohexene nucleic acid (CeNA)" Nucleic Acids Res. (2001) 29(24):4941-4947.
Verdel et al., "RNAi-mediated targeting of heterochromatin by the RITS complex" Science (2004) 303(5668):672-676.
Volpe et al., "Regulation of heterochromatic silencing and histone H3 lysine-9 methylation by RNAi" Science (2002) 297(5588):1833:1837.
Wang et al., "A straightforward stereoselective synthesis of D-and L-5-hydroxy-4-hydroxymethyl-2-cyclohexenylguanine" J. Org. Chem. (2001) 66(25):8478-8482.
Wang et al., "Cyclohexene nucleic acids (CeNA) form stable duplexes with RNA and induce RNase H activity" Nucleosides Nucleotides Nucleic Acids (2001) 20(4-7):785-788.
Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.
Wang et al., "Stereocontrolled synthesis of ara-type cyclohexenyl nucleosides" J. Org. Chem. (2003) 68(11):4499-4505.
Willer et al., "Newly identified loci that influence lipid concentrations and risk of coronary artery disease" Nat. Genet. (2008) 40(2):161-169.
Woolf et al. "Specificity of antisense oligonucleotides in vivo"PNAS (1992) 89:7305-7309.
Yu et al., "Effects of ANGPTL3 antisense oligodeoxynucleotides transfection on the cell growths and invasion of human hepatocellular carcinoma cells" Hepatogastroenterology (2011) 58(110-111):1742-6.
Zhang et al., "PowerBLAST: A New Network BLAST Application for Interactive or Automated Sequence Analysis and Annotation" Genome Res. (1997) 7:649-656.
Zhang et al., "Spontaneous atherosclerosis in aged lipoprotein lipase-deficient mice with severe hypertriglyceridemia on a normal chow diet" Circ. Res. (2008) 102(2):250-256.
Rajeev, "Conjugation Strategies for In Vitro siRNA Delivery" 8th Annual Meeting of the Oligonucleotide Therapeutics Society (2012).
Extended EP Search Report for 19217148.6 dated Jul. 6, 2020.
Sehgal et al., "RNAi-Mediated Inhibition of Natural Anticoagulants for Treatment of Hemophilia" Alnylam (2012) 1 pg.
Extended European Search Report for European Application No. 24189241.3 mailed Dec. 13, 2024, 8 pages.
Borghei et al., "Familial Chylomicronemia Syndrome Presenting With Acute Necrotizing Pancreatitis in a Five Month Infant," *J. Nepal Paediatr. Soc.*, 30(2):110-112 (May-Aug. 2010, published Jul. 13, 2010).
Bury et al., "Immunonephelometric quantitation of the apolipoprotein C-III in human plasma," *Clinica Chimica Acta.*, 145(3):249-258 (Feb. 15, 1985).
Gareri et al., "Antisense Oligonucleotides and Small Interfering RNA for the Treatment of Dyslipidemias," *J Clin Med*, 11:1-16 (Jul. 4, 2022).
International Search Report for application PCT/US2014/016546 dated Aug. 18, 2014.
Viljoen et al., "Diagnosis and treatment of severe hypertriglyceridemia," *Expert Rev Cardiovasc Ther*, 10(4):505-514 (Apr. 2012).

* cited by examiner

SEQUENCE LISTING

```
Sequence total quantity: 438
SEQ ID NO: 1            moltype = RNA  length = 533
FEATURE                 Location/Qualifiers
source                  1..533
                        mol_type = mRNA
                        organism = Homo sapiens
SEQUENCE: 1
tgctcagttc atccctagag gcagctgctc caggaacaga ggtgccatgc agccccgggt  60
actccttgtt gttgccctcc tggcgctcct ggcctctgcc cgagcttcag aggccgagga  120
tgcctccctt ctcagcttca tgcagggtta catgaagcac gccaccaaga ccgccaagga  180
tgcactgagc agcgtgcagg agtcccaggt ggcccagcag gccaggggct gggtgaccga  240
tggcttcagt tccctgaaag actactggag caccgttaag gacaagttct ctgagttctg  300
ggatttggac cctgaggtca gaccaacttc agccgtggct gcctgagacc tcaatacccc  360
aagtccacct gcctatccat cctgcgagct ccttgggtcc tgcaatctcc agggctgccc  420
ctgtaggttg cttaaaaggg acagtattct cagtgctctc ctaccccacc tcatgcctgg  480
ccccctcca ggcatgctgg cctcccaata aagctggaca agaagctgct atg          533

SEQ ID NO: 2            moltype = DNA  length = 3964
FEATURE                 Location/Qualifiers
source                  1..3964
                        mol_type = genomic DNA
                        organism = Homo sapiens
SEQUENCE: 2
ctactccagg ctgtgttcag ggcttggggc tggtggaggg aggggcctga aattccagtg  60
tgaaaggctg agatgggccc gaggcccctg gcctatgtcc aagccatttc ccctctcacc  120
agcctctccc tggggagcca gtcagctagg aaggaatgag ggctccccag gcccaccccc  180
agttcctgag ctcatctggg ctgcagggct ggcgggacag cagcgtggac tcagtctcct  240
agggatttcc caactctccc gcccgcttgc tgcatctgga caccctgcct caggccctca  300
tctccactgg tcagcaggtg acctttgccc agcgccctgg gtcctcagtg cctgctgccc  360
tggagatgat ataaaacagg tcagaaccct cctgcctgtc tgctcagttc atccctagag  420
gcagctgctc caggtaatgc cctctgggga ggggaaagag gaggggagga ggatgaagag  480
gggcaagagg agctccctgc ccagcccagc cagcaagcct ggagaagcac ttgctagagc  540
taaggaagcc tcggagctgg acgggtgccc cccacccctc atcataacct gaagaacatg  600
gaggcccggg aggggtgtca cttgcccaaa gctacacagg gggtggggct ggaagtggct  660
ccaagtgcag gttcccccct cattcttcag gcttagggct ggaggaagcc ttagacagcc  720
cagtcctacc ccagacaggg aaactgaggc ctggagaggg ccagaaatca cccaaagaca  780
cacagcatgt tggctggact ggacggagat cagtccagac cgcaggtgcc ttgatgttca  840
gtctggtggg ttttctgctc catcccaccc acctcccttt gggcctcgat ccctcgcccc  900
tcaccagtcc cccttctgag agcccgtatt agcagggagc cggcccctac tccttctggc  960
agacccagct aaggttctac cttaggggcc acgccacctc cccagggagg ggtccagagg  1020
catggggacc tggggtgccc ctcacaggac acttccttgc aggaacagag gtgccatgca  1080
gccccgggta ctccttgttg ttgccctcct ggcgctcctg gcctctgccc gtaagcactt  1140
ggtgggactg ggctgggggc agggtggagg caacttgggg atcccagtcc caatgggtgg  1200
tcaagcagga gcccagggct cgtccagagg ccgatccacc ccactcagcc ctgctctttc  1260
ctcaggagct tcagaggccg aggatgcctc ccttctcagc ttcatgcagg gttacatgaa  1320
gcacgccacc aagaccgcca aggatgcact gagcagcgtg caggagtccc aggtggccca  1380
gcaggccagg tacacccgct ggcctccctc cccatccccc ctgccagctg cctccattcc  1440
cacccgcccc tgccctggtg agatcccaac aatggaatgg aggtgctcca gcctcccctg  1500
ggcctgtgcc tcttcagcct cctctttcct cacagggcct ttgtcaggct gctgcgggag  1560
agatgacaga gttgagactg cattcctccc aggtccctcc tttctccccg gagcagtcct  1620
agggcgtgcc gttttagccc tcatttccat tttcctttcc tttccctttc tttctctttc  1680
tatttctttc tttctttctt tctttctttc tttctttctt tctttctttc tttctttctt  1740
tctttctttc ctttctttct ttcctttctt tctttccttt ctttctttct ttcctttctt  1800
tctctttctt tctttctttc ctttttcttt ctttccctct cttcctttct ctctttcttt  1860
cttcttcttt ttttttaat ggagtctccc tctgtcacct aggctggagt gcagtggtgc  1920
catctcggct cactgcaacc tccgtctccc gggttcaacc cattctcctg cctcagcctc  1980
ccaagtagct gggattacag gcacgcgcca ccacacccag ctaatttttg tatttttagc  2040
agagatgggg tttcaccatg ttggccaggt tggtcttgaa ttcctgacct caggggatcc  2100
tcctgcctcg gcctcccaaa gtgctgggat tacaggcatg agccactgcg cctggcccca  2160
ttttcctttt ctgaaggtct ggctagagca gtggtcctca gcctttttgg caccagggac  2220
cagttttgtg gtggacaatt tttccatggg ccagcgggga tggttttggg atgaagctgt  2280
tccacctcag atcatcaggc attagattct cataaggagc cctccaccta gatccctggc  2340
atgtgcagtt cacaataggg ttcacactcc tatgagaatg taaggccact tgatctgaca  2400
ggaggcggag ctcaggcggt attgctcact cacccaccac tcacttcgtg ctgtgcagcc  2460
cggctcctaa cagtccatgg accagtacct atctatgact tgggggttgg ggacccctgg  2520
gctaggggtt tgccttggga ggccccacct gacccaattc aagcccgtga gtgcttctgc  2580
tttgttctaa gacctggggc cagtgtgagc agaagtgtgt ccttcctctc ccatcctgcc  2640
cctgcccatc agtactctcc tctcccctac tcccttctcc acctcaccct gactggcatt  2700
agctggcata gcagaggtgt tcataaacat tcttagtccc cagaaccggc tttggggtag  2760
gtgttatttt ctcactttgc agatgagaaa attgaggctc agagcgatta ggtgacctgc  2820
cccagatcac acaactaatc aatcctccaa tgactttcca aatgagaggc tgcctccctc  2880
tgtcctaccc tgctcagagc caccaggttg tgcaactcca ggcggtgctg tttgcacaga  2940
aaacaatgac agccttgacc tttcacatct ccccaccctg tcactttgtg cctcaggccc  3000
aggggcataa acatctgagg tgacctggag atggcagggt ttgacttgtg ctggggttcc  3060
tgcaaggata tctcttctcc cagggtggca gctgtggggg attcctgcct gaggtctcag  3120
ggctgtcgtc cagtgaagtt gagagggtgg tgtggtcctg actggtgtcg tccagtgggg  3180
acatgggtgt gggtcccatg gttgcctaca gaggagttct catgccctgc tctgttgctt  3240
cccctgactg atttaggggc tgggtgaccg atggcttcag ttccctgaaa gactactgga  3300
```

```
gcaccgttaa ggacaagttc tctgagttct gggatttgga ccctgaggtc agaccaactt  3360
cagccgtggc tgcctgagac ctcaataccc caagtccacc tgcctatcca tcctgcgagc  3420
tccttgggtc ctgcaatctc cagggctgcc cctgtaggtt gcttaaaagg gacagtattc  3480
tcagtgctct cctaccccac ctcatgcctg gcccccctcc aggcatgctg gcctcccaat  3540
aaagctggac aagaagctgc tatgagtggg ccgtcgcaag tgtgccatct gtgtctgggc  3600
atgggaaagg gccgaggctg ttctgtgggt gggcactgga cagactccag gtcaggcagg  3660
catggaggcc agcgctctat ccaccttctg gtagctgggc agtctctggg cctcagtttc  3720
ttcatctcta aggtaggaat caccctccgt accctgcctt ccttgacagc tttgtgcgga  3780
aggtcaaaca ggacaataag tttgctgata ctttgataaa ctgttaggtg ctgcacaaca  3840
tgacttgagt gtgtgcccca tgccagccac tatgcctggc acttaagttg tcatcagagt  3900
tgagactgtg tgtgtttact caaaactgtg gagctgacct cccctatcca ggccccctag  3960
ccct                                                                3964

SEQ ID NO: 3            moltype = DNA  length = 3958
FEATURE                 Location/Qualifiers
source                  1..3958
                        mol_type = genomic DNA
                        organism = Homo sapiens
SEQUENCE: 3
ctactccagg ctgtgttcag ggcttggggc tggtggaggg aggggcctga aattccagtg  60
tgaaaggctg agatgggccc gaggcccctg gcctatgtcc aagccatttc ccctctcacc  120
agcctctccc tggggagcca gtcagctagg aaggaatgag ggctccccag gcccaccccc  180
agttcctgag ctcatctggg ctgcagggct ggcgggacag cagcgtggac tcagtctcct  240
agggatttcc caactctccc gcccgcttgc tgcatctgga caccctgcct caggccctca  300
tctccactgg tcagcaggtg acctttgccc agcgccctgg gtcctcagtg cctgctgccc  360
tggagatgat ataaaacagg tcagaaccct cctgcctgtc tgctcagttc atccctagag  420
gcagctgctc caggtaatgc cctctgggga ggggaaagag gaggggagga ggatgaagag  480
gggcaagagg agctccctgc ccagcccagc cagcaagcct ggagaagcac ttgctagagc  540
taaggaagcc tcggagctgg acgggtgccc cccacccctc atcataacct gaagaacatg  600
gaggcccggg aggggtgtca cttgcccaaa gctacatagg gggtggggct ggaagtggct  660
ccaagtgcag gttccccccct cattcttcag gcttagggct ggaggaagcc ttagacagcc  720
cagtcctacc ccagacaggg aaactgaggc ctggagaggg ccagaaatca cccaaagaca  780
cacagcatgt tggctggact ggacggagat cagtccagac cgcaggtgcc ttgatgttca  840
gtctggtggg ttttctgctc catcccaccc acctcccttt gggcctcgat ccctcgcccc  900
tcaccagtcc cccttctgag agcccgtatt agcagggagc cggcccctac tccttctggc  960
agacccagct aaggttctac cttaggggcc acgccacctc cccagggagg ggtccagagg  1020
catggggacc tggggtgccc ctcacaggac acttccttgc aggaacagag gtgccatgca  1080
gccccgggta ctccttgttg ttgccctcct ggcgctcctg gcctctgccc gtaagcactt  1140
ggtgggactg ggctgggggc agggtggagg caacttgggg atcccagtcc caatgggtgg  1200
tcaagcagga gcccagggct cgtccatagg ccgatccacc ccactcagcc ctgctctttc  1260
ctcaggagct tcagaggccg aggatgcctc ccttctcagc ttcatgcagg gctacatgaa  1320
gcacgccacc aagaccgcca aggatgcact gagcagcgtg caggagtccc aggtggccca  1380
gcaggccagg tacacccgct ggcctccctc cccatccccc ctgccagctg cctccattcc  1440
cacccacccc tgccctggtg agatcccaac aatggaatgg aggtgctcca gcctcccctg  1500
ggcctgtgcc tcttcagcct cctctttcct cacagggcct ttgtcaggct gctgcgggag  1560
agatgacaga gttgagactg cattcctccc aggtccctcc tttctcccca gagcagtcct  1620
agggcgcgcc gttttagccc tcatttccat tttcctttcc tttcccttc tttccctttc  1680
tatttctttc tttctttctt tctttctttc tttctttctt tctttctttc tttctttctt  1740
tctttctttc ctttctttct ttctttttct ctttctttct ttcctttctt tctctttctt  1800
tctttctttc tttccttttt ctttctttcc ctctcttcct ttctctcttt ctttcttctt  1860
cttttttttt taatggagtc tccctctgtc acccaggctg gagtgcagtg gtgccatctc  1920
ggctcactgc aacctccgtc tcccgggttc aacccattct cctgcctcag cctcccaagt  1980
agctgggatt acaggcacgc gccaccacac ccagctaatt tttgtatttt tagcagagat  2040
ggggtttcac catgttggcc aggttggtct tgaattcctg acctcagggg atcctcctgc  2100
ctcggcctcc caaagcgctg ggattacagg catgagccac tgcgcctggc cccattttcc  2160
ttttctgaag gtctggctag agcagtggtc ctcagccttt ttggcaccag ggaccagttt  2220
tgtggtggac aatttttcca tggccagcg gggatggttt tgggatgaag ctgttccacc  2280
tcagatcatc aggcattaga ttctcataag gagccctcca cctagatccc tggcatgtgc  2340
agttcacaac agggttcaca ctcctatgag aatgtaaggc cacttgatct gacaggaggc  2400
ggagctcagg cggtattgct cactcaccca ccactcactt cgtgctgtgc agcccggctc  2460
ctaacagtcc atggaccagt acctatctat gacttggggg ttggggaccc ctgggctagg  2520
ggtttgcctt gggaggcccc acctgaccta attcaagccc gtgagtgctt ctgctttgtt  2580
ctaagacctg gggccagtgt gagcagaagt gtgtccttcc tctcccatcc tgcccctgcc  2640
catcagtact ctcctctccc ctactccctt ctccacctca ccctgactgg cattagctgg  2700
catagcagag gtgttcataa acattcttag tccccagaac cggctttggg gtaggtgtta  2760
ttttctcact ttgcagatga gaaaattgag gctcagagcg attaggtgac ctgccccaga  2820
tcacacaact aatcaatcct ccaatgactt tccaaatgag aggctgcctc cctctgtcct  2880
accctgctca gagccaccag gttgtgcaac tccaggcggt gctgtttgca cagaaaacaa  2940
tgacagcctt gacctttcac atctccccac cctgtcactt tgtgcctcag gcccaggggc  3000
ataaacatct gaggtgacct ggagatggca gggtttgact tgtgctgggg ttcctgcaag  3060
gatatctctt ctcccagggt ggcagctgtg ggggattcct gcctgaggtc tcagggctgt  3120
cgtccagtga agttgagagg gtggtgtggt cctgactggt gtcgtccagt ggggacatgg  3180
gtgtgggtcc catggttgcc tacagaggag ttctcatgcc ctgctctgtt gcttcccctg  3240
actgatttag gggctgggtg accgatggct tcagttccct gaaagactac tggagcaccg  3300
ttaaggacaa gttctctgag ttctgggatt tggaccctga ggtcagacca acttcagccg  3360
tggctgcctg agacctcaat accccaagtc cacctgccta tccatcctgc cagctccttg  3420
ggtcctgcaa tctccagggc tgcccctgta ggttgcttaa aagggacagt attctcagtg  3480
ctctcctacc ccacctcatg cctggccccc ctccaggcat gctggcctcc caataaagct  3540
ggacaagaag ctgctatgag tggccgtcg caagtgtgcc atctgtgtct gggcatggga  3600
```

-continued

```
aagggccgag gctgttctgt gggtgggcac tggacagact ccaggtcagg caggcatgga  3660
ggccagcgct ctatccacct tctggtagct gggcagtctc tgggcctcag tttcttcatc  3720
tctaaggtag gaatcaccct ccgtaccctg ccttccttga cagctttgtg cggaaggtca  3780
aacaggacaa taagtttgct gatactttga taaactgtta ggtgctgcac aacatgactt  3840
gagtgtgtgc cccatgccag ccactatgcc tggcacttaa gttgtcatca gagttgagac  3900
tgtgtgtgtt tactcaaaac tgtggagctg acctccccta tccaggccac ctagccct    3958

SEQ ID NO: 4           moltype =   length =
SEQUENCE: 4
000

SEQ ID NO: 5           moltype = DNA  length = 22
FEATURE                Location/Qualifiers
source                 1..22
                       mol_type = other DNA
                       organism = synthetic construct
SEQUENCE: 5
tcagcttcat gcagggttac at                                           22

SEQ ID NO: 6           moltype = DNA  length = 19
FEATURE                Location/Qualifiers
source                 1..19
                       mol_type = other DNA
                       organism = synthetic construct
SEQUENCE: 6
acgctgctca gtgcatcct                                               19

SEQ ID NO: 7           moltype = DNA  length = 21
FEATURE                Location/Qualifiers
source                 1..21
                       mol_type = other DNA
                       organism = synthetic construct
SEQUENCE: 7
aagcacgcca ccaagaccgc c                                            21

SEQ ID NO: 8           moltype = DNA  length = 19
FEATURE                Location/Qualifiers
source                 1..19
                       mol_type = other DNA
                       organism = synthetic construct
SEQUENCE: 8
gaaggtgaag gtcggagtc                                               19

SEQ ID NO: 9           moltype = DNA  length = 20
FEATURE                Location/Qualifiers
source                 1..20
                       mol_type = other DNA
                       organism = synthetic construct
SEQUENCE: 9
gaagatggtg atgggatttc                                              20

SEQ ID NO: 10          moltype = DNA  length = 20
FEATURE                Location/Qualifiers
source                 1..20
                       mol_type = other DNA
                       organism = synthetic construct
SEQUENCE: 10
caagcttccc gttctcagcc                                              20

SEQ ID NO: 11          moltype = RNA  length = 517
FEATURE                Location/Qualifiers
source                 1..517
                       mol_type = mRNA
                       organism = Mus musculus
SEQUENCE: 11
ctgctcagtt ttatccctag aagcagctag ctactccagg tacgtaggtg ccatgcagcc  60
ccggacgctc ctcactgtgg ccctcttggc tctcctggca tctgcccgag ctgaagaggt  120
agagggatcc ttgctgctgg gctctgtgca gggctacatg gaacaagcct ccaagacggt  180
ccaggatgcg ctaagtagcg tgcaggagtc cgatatagct gcggtggcca ggggctggat  240
ggacaatcac ttcagattcc tgaaaggcta ctggagcaag tttactgaca agttcaccgg  300
cttctgggat tctaaccctg aggaccaacc aactccagct attgagtcgt gagacttctg  360
tgttgcagat gtgcctgttc ctccatcctg ctgccccct ccaggcctgc caggtggccc   420
ctgaaggttg ctttaagggg aaagtatgtt ctcatgtctt cacccctccc tagatctcac  480
ctaaacatgc tgtccctaat aaagctggat aagaagc                           517

SEQ ID NO: 12          moltype = DNA  length = 19
FEATURE                Location/Qualifiers
source                 1..19
                       mol_type = other DNA
```

```
                        organism = synthetic construct
SEQUENCE: 12
cgagaggcgg acgggaccg                                                19

SEQ ID NO: 13           moltype = DNA  length = 21
FEATURE                 Location/Qualifiers
source                  1..21
                        mol_type = other DNA
                        organism = synthetic construct
SEQUENCE: 13
cgagaggcgg acgggaccgt t                                             21

SEQ ID NO: 14           moltype = DNA  length = 21
FEATURE                 Location/Qualifiers
source                  1..21
                        mol_type = other DNA
                        organism = synthetic construct
SEQUENCE: 14
ttgctctccg cctgccctgg c                                             21

SEQ ID NO: 15           moltype = DNA  length = 19
FEATURE                 Location/Qualifiers
source                  1..19
                        mol_type = other DNA
                        organism = synthetic construct
SEQUENCE: 15
cgagaggcgg acgggaccg                                                19

SEQ ID NO: 16           moltype = DNA  length = 19
FEATURE                 Location/Qualifiers
source                  1..19
                        mol_type = other DNA
                        organism = synthetic construct
SEQUENCE: 16
gctctccgcc tgccctggc                                                19

SEQ ID NO: 17           moltype = DNA  length = 20
FEATURE                 Location/Qualifiers
source                  1..20
                        mol_type = other DNA
                        organism = synthetic construct
SEQUENCE: 17
ctcttactgt cgtgtggaca                                               20

SEQ ID NO: 18           moltype = DNA  length = 20
FEATURE                 Location/Qualifiers
source                  1..20
                        mol_type = other DNA
                        organism = synthetic construct
SEQUENCE: 18
ggcagccctg gaggctgcag                                               20

SEQ ID NO: 19           moltype = DNA  length = 20
FEATURE                 Location/Qualifiers
source                  1..20
                        mol_type = other DNA
                        organism = synthetic construct
SEQUENCE: 19
ctggagcagc tgcctctagg                                               20

SEQ ID NO: 20           moltype = DNA  length = 20
FEATURE                 Location/Qualifiers
source                  1..20
                        mol_type = other DNA
                        organism = synthetic construct
SEQUENCE: 20
ccctgcatga agctgagaag                                               20

SEQ ID NO: 21           moltype = DNA  length = 20
FEATURE                 Location/Qualifiers
source                  1..20
                        mol_type = other DNA
                        organism = synthetic construct
SEQUENCE: 21
gtgcttcatg taaccctgca                                               20

SEQ ID NO: 22           moltype = DNA  length = 20
FEATURE                 Location/Qualifiers
source                  1..20
```

```
                        mol_type = other DNA
                        organism = synthetic construct
SEQUENCE: 22
tggcctgctg ggccacctgg                                                20

SEQ ID NO: 23           moltype = DNA  length = 20
FEATURE                 Location/Qualifiers
source                  1..20
                        mol_type = other DNA
                        organism = synthetic construct
SEQUENCE: 23
tgctccagta gtctttcagg                                                20

SEQ ID NO: 24           moltype = DNA  length = 20
FEATURE                 Location/Qualifiers
source                  1..20
                        mol_type = other DNA
                        organism = synthetic construct
SEQUENCE: 24
tgacctcagg gtccaaatcc                                                20

SEQ ID NO: 25           moltype = DNA  length = 20
FEATURE                 Location/Qualifiers
source                  1..20
                        mol_type = other DNA
                        organism = synthetic construct
SEQUENCE: 25
ctctagggat gaactgagca                                                20

SEQ ID NO: 26           moltype = DNA  length = 20
FEATURE                 Location/Qualifiers
source                  1..20
                        mol_type = other DNA
                        organism = synthetic construct
SEQUENCE: 26
cagctgcctc tagggatgaa                                                20

SEQ ID NO: 27           moltype = DNA  length = 20
FEATURE                 Location/Qualifiers
source                  1..20
                        mol_type = other DNA
                        organism = synthetic construct
SEQUENCE: 27
ttcctggagc agctgcctct                                                20

SEQ ID NO: 28           moltype = DNA  length = 20
FEATURE                 Location/Qualifiers
source                  1..20
                        mol_type = other DNA
                        organism = synthetic construct
SEQUENCE: 28
acctctgttc ctggagcagc                                                20

SEQ ID NO: 29           moltype = DNA  length = 20
FEATURE                 Location/Qualifiers
source                  1..20
                        mol_type = other DNA
                        organism = synthetic construct
SEQUENCE: 29
atggcacctc tgttcctgga                                                20

SEQ ID NO: 30           moltype = DNA  length = 20
FEATURE                 Location/Qualifiers
source                  1..20
                        mol_type = other DNA
                        organism = synthetic construct
SEQUENCE: 30
gggctgcatg gcacctctgt                                                20

SEQ ID NO: 31           moltype = DNA  length = 20
FEATURE                 Location/Qualifiers
source                  1..20
                        mol_type = other DNA
                        organism = synthetic construct
SEQUENCE: 31
ggcaacaaca aggagtaccc                                                20

SEQ ID NO: 32           moltype = DNA  length = 20
FEATURE                 Location/Qualifiers
```

```
source                  1..20
                        mol_type = other DNA
                        organism = synthetic construct
SEQUENCE: 32
ggagggcaac aacaaggagt                                              20

SEQ ID NO: 33           moltype = DNA  length = 20
FEATURE                 Location/Qualifiers
source                  1..20
                        mol_type = other DNA
                        organism = synthetic construct
SEQUENCE: 33
agctcgggca gaggccagga                                              20

SEQ ID NO: 34           moltype = DNA  length = 20
FEATURE                 Location/Qualifiers
source                  1..20
                        mol_type = other DNA
                        organism = synthetic construct
SEQUENCE: 34
tctgaagctc gggcagaggc                                              20

SEQ ID NO: 35           moltype = DNA  length = 20
FEATURE                 Location/Qualifiers
source                  1..20
                        mol_type = other DNA
                        organism = synthetic construct
SEQUENCE: 35
cggcctctga agctcgggca                                              20

SEQ ID NO: 36           moltype = DNA  length = 20
FEATURE                 Location/Qualifiers
source                  1..20
                        mol_type = other DNA
                        organism = synthetic construct
SEQUENCE: 36
catcctcggc ctctgaagct                                              20

SEQ ID NO: 37           moltype = DNA  length = 20
FEATURE                 Location/Qualifiers
source                  1..20
                        mol_type = other DNA
                        organism = synthetic construct
SEQUENCE: 37
gggaggcatc ctcggcctct                                              20

SEQ ID NO: 38           moltype = DNA  length = 20
FEATURE                 Location/Qualifiers
source                  1..20
                        mol_type = other DNA
                        organism = synthetic construct
SEQUENCE: 38
gagaagggag gcatcctcgg                                              20

SEQ ID NO: 39           moltype = DNA  length = 20
FEATURE                 Location/Qualifiers
source                  1..20
                        mol_type = other DNA
                        organism = synthetic construct
SEQUENCE: 39
gctgagaagg gaggcatcct                                              20

SEQ ID NO: 40           moltype = DNA  length = 20
FEATURE                 Location/Qualifiers
source                  1..20
                        mol_type = other DNA
                        organism = synthetic construct
SEQUENCE: 40
tgcatgaagc tgagaaggga                                              20

SEQ ID NO: 41           moltype = DNA  length = 20
FEATURE                 Location/Qualifiers
source                  1..20
                        mol_type = other DNA
                        organism = synthetic construct
SEQUENCE: 41
gcgtgcttca tgtaaccctg                                              20

SEQ ID NO: 42           moltype = DNA  length = 20
```

-continued

```
FEATURE                Location/Qualifiers
source                 1..20
                       mol_type = other DNA
                       organism = synthetic construct
SEQUENCE: 42
ttggtggcgt gcttcatgta                                              20

SEQ ID NO: 43          moltype = DNA  length = 20
FEATURE                Location/Qualifiers
source                 1..20
                       mol_type = other DNA
                       organism = synthetic construct
SEQUENCE: 43
gcatccttgg cggtcttggt                                              20

SEQ ID NO: 44          moltype = DNA  length = 20
FEATURE                Location/Qualifiers
source                 1..20
                       mol_type = other DNA
                       organism = synthetic construct
SEQUENCE: 44
ctcagtgcat ccttggcggt                                              20

SEQ ID NO: 45          moltype = DNA  length = 20
FEATURE                Location/Qualifiers
source                 1..20
                       mol_type = other DNA
                       organism = synthetic construct
SEQUENCE: 45
tgctcagtgc atccttggcg                                              20

SEQ ID NO: 46          moltype = DNA  length = 20
FEATURE                Location/Qualifiers
source                 1..20
                       mol_type = other DNA
                       organism = synthetic construct
SEQUENCE: 46
ctcctgcacg ctgctcagtg                                              20

SEQ ID NO: 47          moltype = DNA  length = 20
FEATURE                Location/Qualifiers
source                 1..20
                       mol_type = other DNA
                       organism = synthetic construct
SEQUENCE: 47
gactcctgca cgctgctcag                                              20

SEQ ID NO: 48          moltype = DNA  length = 20
FEATURE                Location/Qualifiers
source                 1..20
                       mol_type = other DNA
                       organism = synthetic construct
SEQUENCE: 48
gccacctggg actcctgcac                                              20

SEQ ID NO: 49          moltype = DNA  length = 20
FEATURE                Location/Qualifiers
source                 1..20
                       mol_type = other DNA
                       organism = synthetic construct
SEQUENCE: 49
gcccctggcc tgctgggcca                                              20

SEQ ID NO: 50          moltype = DNA  length = 20
FEATURE                Location/Qualifiers
source                 1..20
                       mol_type = other DNA
                       organism = synthetic construct
SEQUENCE: 50
agcccctggc ctgctgggcc                                              20

SEQ ID NO: 51          moltype = DNA  length = 20
FEATURE                Location/Qualifiers
source                 1..20
                       mol_type = other DNA
                       organism = synthetic construct
SEQUENCE: 51
gaagccatcg gtcacccagc                                              20
```

```
SEQ ID NO: 52          moltype = DNA  length = 20
FEATURE                Location/Qualifiers
source                 1..20
                       mol_type = other DNA
                       organism = synthetic construct
SEQUENCE: 52
ctgaagccat cggtcaccca                                              20

SEQ ID NO: 53          moltype = DNA  length = 20
FEATURE                Location/Qualifiers
source                 1..20
                       mol_type = other DNA
                       organism = synthetic construct
SEQUENCE: 53
tttcagggaa ctgaagccat                                              20

SEQ ID NO: 54          moltype = DNA  length = 20
FEATURE                Location/Qualifiers
source                 1..20
                       mol_type = other DNA
                       organism = synthetic construct
SEQUENCE: 54
cagtagtctt tcagggaact                                              20

SEQ ID NO: 55          moltype = DNA  length = 20
FEATURE                Location/Qualifiers
source                 1..20
                       mol_type = other DNA
                       organism = synthetic construct
SEQUENCE: 55
aacggtgctc cagtagtctt                                              20

SEQ ID NO: 56          moltype = DNA  length = 20
FEATURE                Location/Qualifiers
source                 1..20
                       mol_type = other DNA
                       organism = synthetic construct
SEQUENCE: 56
ccttaacggt gctccagtag                                              20

SEQ ID NO: 57          moltype = DNA  length = 20
FEATURE                Location/Qualifiers
source                 1..20
                       mol_type = other DNA
                       organism = synthetic construct
SEQUENCE: 57
gaacttgtcc ttaacggtgc                                              20

SEQ ID NO: 58          moltype = DNA  length = 20
FEATURE                Location/Qualifiers
source                 1..20
                       mol_type = other DNA
                       organism = synthetic construct
SEQUENCE: 58
ctcagagaac ttgtccttaa                                              20

SEQ ID NO: 59          moltype = DNA  length = 20
FEATURE                Location/Qualifiers
source                 1..20
                       mol_type = other DNA
                       organism = synthetic construct
SEQUENCE: 59
agaactcaga gaacttgtcc                                              20

SEQ ID NO: 60          moltype = DNA  length = 20
FEATURE                Location/Qualifiers
source                 1..20
                       mol_type = other DNA
                       organism = synthetic construct
SEQUENCE: 60
atcccagaac tcagagaact                                              20

SEQ ID NO: 61          moltype = DNA  length = 20
FEATURE                Location/Qualifiers
source                 1..20
                       mol_type = other DNA
                       organism = synthetic construct
SEQUENCE: 61
cagggtccaa atcccagaac                                              20
```

```
SEQ ID NO: 62           moltype = DNA  length = 20
FEATURE                 Location/Qualifiers
source                  1..20
                        mol_type = other DNA
                        organism = synthetic construct
SEQUENCE: 62
ttggtctgac ctcagggtcc                                              20

SEQ ID NO: 63           moltype = DNA  length = 20
FEATURE                 Location/Qualifiers
source                  1..20
                        mol_type = other DNA
                        organism = synthetic construct
SEQUENCE: 63
gttggtctga cctcagggtc                                              20

SEQ ID NO: 64           moltype = DNA  length = 20
FEATURE                 Location/Qualifiers
source                  1..20
                        mol_type = other DNA
                        organism = synthetic construct
SEQUENCE: 64
gctgaagttg gtctgacctc                                              20

SEQ ID NO: 65           moltype = DNA  length = 20
FEATURE                 Location/Qualifiers
source                  1..20
                        mol_type = other DNA
                        organism = synthetic construct
SEQUENCE: 65
cagccacggc tgaagttggt                                              20

SEQ ID NO: 66           moltype = DNA  length = 20
FEATURE                 Location/Qualifiers
source                  1..20
                        mol_type = other DNA
                        organism = synthetic construct
SEQUENCE: 66
caggcagcca cggctgaagt                                              20

SEQ ID NO: 67           moltype = DNA  length = 20
FEATURE                 Location/Qualifiers
source                  1..20
                        mol_type = other DNA
                        organism = synthetic construct
SEQUENCE: 67
attgaggtct caggcagcca                                              20

SEQ ID NO: 68           moltype = DNA  length = 20
FEATURE                 Location/Qualifiers
source                  1..20
                        mol_type = other DNA
                        organism = synthetic construct
SEQUENCE: 68
tggataggca ggtggacttg                                              20

SEQ ID NO: 69           moltype = DNA  length = 20
FEATURE                 Location/Qualifiers
source                  1..20
                        mol_type = other DNA
                        organism = synthetic construct
SEQUENCE: 69
ctcgcaggat ggataggcag                                              20

SEQ ID NO: 70           moltype = DNA  length = 20
FEATURE                 Location/Qualifiers
source                  1..20
                        mol_type = other DNA
                        organism = synthetic construct
SEQUENCE: 70
aggagctcgc aggatggata                                              20

SEQ ID NO: 71           moltype = DNA  length = 20
FEATURE                 Location/Qualifiers
source                  1..20
                        mol_type = other DNA
                        organism = synthetic construct
SEQUENCE: 71
```

```
gacccaagga gctcgcagga                                              20

SEQ ID NO: 72          moltype = DNA  length = 20
FEATURE                Location/Qualifiers
source                 1..20
                       mol_type = other DNA
                       organism = synthetic construct
SEQUENCE: 72
tgcaggaccc aaggagctcg                                              20

SEQ ID NO: 73          moltype = DNA  length = 20
FEATURE                Location/Qualifiers
source                 1..20
                       mol_type = other DNA
                       organism = synthetic construct
SEQUENCE: 73
tggagattgc aggacccaag                                              20

SEQ ID NO: 74          moltype = DNA  length = 20
FEATURE                Location/Qualifiers
source                 1..20
                       mol_type = other DNA
                       organism = synthetic construct
SEQUENCE: 74
agccctggag attgcaggac                                              20

SEQ ID NO: 75          moltype = DNA  length = 20
FEATURE                Location/Qualifiers
source                 1..20
                       mol_type = other DNA
                       organism = synthetic construct
SEQUENCE: 75
ggcagccctg gagattgcag                                              20

SEQ ID NO: 76          moltype = DNA  length = 20
FEATURE                Location/Qualifiers
source                 1..20
                       mol_type = other DNA
                       organism = synthetic construct
SEQUENCE: 76
ccttttaagc aacctacagg                                              20

SEQ ID NO: 77          moltype = DNA  length = 20
FEATURE                Location/Qualifiers
source                 1..20
                       mol_type = other DNA
                       organism = synthetic construct
SEQUENCE: 77
ctgtcccttt taagcaacct                                              20

SEQ ID NO: 78          moltype = DNA  length = 20
FEATURE                Location/Qualifiers
source                 1..20
                       mol_type = other DNA
                       organism = synthetic construct
SEQUENCE: 78
agaatactgt cccttttaag                                              20

SEQ ID NO: 79          moltype = DNA  length = 20
FEATURE                Location/Qualifiers
source                 1..20
                       mol_type = other DNA
                       organism = synthetic construct
SEQUENCE: 79
cactgagaat actgtccctt                                              20

SEQ ID NO: 80          moltype = DNA  length = 20
FEATURE                Location/Qualifiers
source                 1..20
                       mol_type = other DNA
                       organism = synthetic construct
SEQUENCE: 80
taggagagca ctgagaatac                                              20

SEQ ID NO: 81          moltype = DNA  length = 20
FEATURE                Location/Qualifiers
source                 1..20
                       mol_type = other DNA
                       organism = synthetic construct
```

```
SEQUENCE: 81
gggtaggaga gcactgagaa                                              20

SEQ ID NO: 82           moltype = DNA  length = 20
FEATURE                 Location/Qualifiers
source                  1..20
                        mol_type = other DNA
                        organism = synthetic construct
SEQUENCE: 82
aggccagcat gcctggaggg                                              20

SEQ ID NO: 83           moltype = DNA  length = 20
FEATURE                 Location/Qualifiers
source                  1..20
                        mol_type = other DNA
                        organism = synthetic construct
SEQUENCE: 83
ttgggaggcc agcatgcctg                                              20

SEQ ID NO: 84           moltype = DNA  length = 20
FEATURE                 Location/Qualifiers
source                  1..20
                        mol_type = other DNA
                        organism = synthetic construct
SEQUENCE: 84
agctttattg ggaggccagc                                              20

SEQ ID NO: 85           moltype = DNA  length = 20
FEATURE                 Location/Qualifiers
source                  1..20
                        mol_type = other DNA
                        organism = synthetic construct
SEQUENCE: 85
tgtccagctt tattgggagg                                              20

SEQ ID NO: 86           moltype = DNA  length = 20
FEATURE                 Location/Qualifiers
source                  1..20
                        mol_type = other DNA
                        organism = synthetic construct
SEQUENCE: 86
cttgtccagc tttattggga                                              20

SEQ ID NO: 87           moltype = DNA  length = 20
FEATURE                 Location/Qualifiers
source                  1..20
                        mol_type = other DNA
                        organism = synthetic construct
SEQUENCE: 87
agcttcttgt ccagctttat                                              20

SEQ ID NO: 88           moltype = DNA  length = 20
FEATURE                 Location/Qualifiers
source                  1..20
                        mol_type = other DNA
                        organism = synthetic construct
SEQUENCE: 88
catagcagct tcttgtccag                                              20

SEQ ID NO: 89           moltype = DNA  length = 20
FEATURE                 Location/Qualifiers
source                  1..20
                        mol_type = other DNA
                        organism = synthetic construct
SEQUENCE: 89
acctggagca gctgcctcta                                              20

SEQ ID NO: 90           moltype = DNA  length = 20
FEATURE                 Location/Qualifiers
source                  1..20
                        mol_type = other DNA
                        organism = synthetic construct
SEQUENCE: 90
agggcattac ctggagcagc                                              20

SEQ ID NO: 91           moltype = DNA  length = 20
FEATURE                 Location/Qualifiers
source                  1..20
                        mol_type = other DNA
```

```
                        organism = synthetic construct
SEQUENCE: 91
acctctgttc ctgcaaggaa                                                20

SEQ ID NO: 92           moltype = DNA  length = 20
FEATURE                 Location/Qualifiers
source                  1..20
                        mol_type = other DNA
                        organism = synthetic construct
SEQUENCE: 92
aagtgcttac gggcagaggc                                                20

SEQ ID NO: 93           moltype = DNA  length = 20
FEATURE                 Location/Qualifiers
source                  1..20
                        mol_type = other DNA
                        organism = synthetic construct
SEQUENCE: 93
gcgggtgtac ctggcctgct                                                20

SEQ ID NO: 94           moltype = DNA  length = 20
FEATURE                 Location/Qualifiers
source                  1..20
                        mol_type = other DNA
                        organism = synthetic construct
SEQUENCE: 94
aaccctgttg tgaactgcac                                                20

SEQ ID NO: 95           moltype = DNA  length = 20
FEATURE                 Location/Qualifiers
source                  1..20
                        mol_type = other DNA
                        organism = synthetic construct
SEQUENCE: 95
agtgagcaat accgcctgag                                                20

SEQ ID NO: 96           moltype = DNA  length = 20
FEATURE                 Location/Qualifiers
source                  1..20
                        mol_type = other DNA
                        organism = synthetic construct
SEQUENCE: 96
cgggcttgaa ttaggtcagg                                                20

SEQ ID NO: 97           moltype = DNA  length = 20
FEATURE                 Location/Qualifiers
source                  1..20
                        mol_type = other DNA
                        organism = synthetic construct
SEQUENCE: 97
tagggataaa actgagcagg                                                20

SEQ ID NO: 98           moltype = DNA  length = 20
FEATURE                 Location/Qualifiers
source                  1..20
                        mol_type = other DNA
                        organism = synthetic construct
SEQUENCE: 98
ctggagtagc tagctgcttc                                                20

SEQ ID NO: 99           moltype = DNA  length = 20
FEATURE                 Location/Qualifiers
source                  1..20
                        mol_type = other DNA
                        organism = synthetic construct
SEQUENCE: 99
gctgcatggc acctacgtac                                                20

SEQ ID NO: 100          moltype = DNA  length = 20
FEATURE                 Location/Qualifiers
source                  1..20
                        mol_type = other DNA
                        organism = synthetic construct
SEQUENCE: 100
ccacagtgag gagcgtccgg                                                20

SEQ ID NO: 101          moltype = DNA  length = 20
FEATURE                 Location/Qualifiers
source                  1..20
```

```
                         mol_type = other DNA
                         organism = synthetic construct
SEQUENCE: 101
ggcagatgcc aggagagcca                                             20

SEQ ID NO: 102           moltype = DNA  length = 20
FEATURE                  Location/Qualifiers
source                   1..20
                         mol_type = other DNA
                         organism = synthetic construct
SEQUENCE: 102
ctacctcttc agctcgggca                                             20

SEQ ID NO: 103           moltype = DNA  length = 20
FEATURE                  Location/Qualifiers
source                   1..20
                         mol_type = other DNA
                         organism = synthetic construct
SEQUENCE: 103
cagcagcaag gatccctcta                                             20

SEQ ID NO: 104           moltype = DNA  length = 20
FEATURE                  Location/Qualifiers
source                   1..20
                         mol_type = other DNA
                         organism = synthetic construct
SEQUENCE: 104
gcacagagcc cagcagcaag                                             20

SEQ ID NO: 105           moltype = DNA  length = 20
FEATURE                  Location/Qualifiers
source                   1..20
                         mol_type = other DNA
                         organism = synthetic construct
SEQUENCE: 105
ccctggccac cgcagctata                                             20

SEQ ID NO: 106           moltype = DNA  length = 20
FEATURE                  Location/Qualifiers
source                   1..20
                         mol_type = other DNA
                         organism = synthetic construct
SEQUENCE: 106
atctgaagtg attgtccatc                                             20

SEQ ID NO: 107           moltype = DNA  length = 20
FEATURE                  Location/Qualifiers
source                   1..20
                         mol_type = other DNA
                         organism = synthetic construct
SEQUENCE: 107
agtagccttt caggaatctg                                             20

SEQ ID NO: 108           moltype = DNA  length = 20
FEATURE                  Location/Qualifiers
source                   1..20
                         mol_type = other DNA
                         organism = synthetic construct
SEQUENCE: 108
cttgtcagta aacttgctcc                                             20

SEQ ID NO: 109           moltype = DNA  length = 20
FEATURE                  Location/Qualifiers
source                   1..20
                         mol_type = other DNA
                         organism = synthetic construct
SEQUENCE: 109
gaagccggtg aacttgtcag                                             20

SEQ ID NO: 110           moltype = DNA  length = 20
FEATURE                  Location/Qualifiers
source                   1..20
                         mol_type = other DNA
                         organism = synthetic construct
SEQUENCE: 110
gaatcccaga agccggtgaa                                             20

SEQ ID NO: 111           moltype = DNA  length = 20
FEATURE                  Location/Qualifiers
```

```
source                 1..20
                       mol_type = other DNA
                       organism = synthetic construct
SEQUENCE: 111
ggttagaatc ccagaagccg                                              20

SEQ ID NO: 112         moltype = DNA  length = 20
FEATURE                Location/Qualifiers
source                 1..20
                       mol_type = other DNA
                       organism = synthetic construct
SEQUENCE: 112
tggagttggt tggtcctcag                                              20

SEQ ID NO: 113         moltype = DNA  length = 20
FEATURE                Location/Qualifiers
source                 1..20
                       mol_type = other DNA
                       organism = synthetic construct
SEQUENCE: 113
tcacgactca atagctggag                                              20

SEQ ID NO: 114         moltype = DNA  length = 20
FEATURE                Location/Qualifiers
source                 1..20
                       mol_type = other DNA
                       organism = synthetic construct
SEQUENCE: 114
cccttaaagc aaccttcagg                                              20

SEQ ID NO: 115         moltype = DNA  length = 20
FEATURE                Location/Qualifiers
source                 1..20
                       mol_type = other DNA
                       organism = synthetic construct
SEQUENCE: 115
agacatgaga acatactttc                                              20

SEQ ID NO: 116         moltype = DNA  length = 20
FEATURE                Location/Qualifiers
source                 1..20
                       mol_type = other DNA
                       organism = synthetic construct
SEQUENCE: 116
catgtttagg tgagatctag                                              20

SEQ ID NO: 117         moltype = DNA  length = 20
FEATURE                Location/Qualifiers
source                 1..20
                       mol_type = other DNA
                       organism = synthetic construct
SEQUENCE: 117
tcttatccag ctttattagg                                              20

SEQ ID NO: 118         moltype = DNA  length = 20
FEATURE                Location/Qualifiers
source                 1..20
                       mol_type = other DNA
                       organism = synthetic construct
SEQUENCE: 118
cctagaggca gctgctccag                                              20

SEQ ID NO: 119         moltype = DNA  length = 20
FEATURE                Location/Qualifiers
source                 1..20
                       mol_type = other DNA
                       organism = synthetic construct
SEQUENCE: 119
cttctcagct tcatgcaggg                                              20

SEQ ID NO: 120         moltype = DNA  length = 20
FEATURE                Location/Qualifiers
source                 1..20
                       mol_type = other DNA
                       organism = synthetic construct
SEQUENCE: 120
tgcagggtta catgaagcac                                              20

SEQ ID NO: 121         moltype = DNA  length = 20
```

```
FEATURE                 Location/Qualifiers
source                  1..20
                        mol_type = other DNA
                        organism = synthetic construct
SEQUENCE: 121
ccaggtggcc cagcaggcca                                             20

SEQ ID NO: 122          moltype = DNA  length = 20
FEATURE                 Location/Qualifiers
source                  1..20
                        mol_type = other DNA
                        organism = synthetic construct
SEQUENCE: 122
cctgaaagac tactggagca                                             20

SEQ ID NO: 123          moltype = DNA  length = 20
FEATURE                 Location/Qualifiers
source                  1..20
                        mol_type = other DNA
                        organism = synthetic construct
SEQUENCE: 123
tgctcagttc atccctagag                                             20

SEQ ID NO: 124          moltype = DNA  length = 20
FEATURE                 Location/Qualifiers
source                  1..20
                        mol_type = other DNA
                        organism = synthetic construct
SEQUENCE: 124
agaggcagct gctccaggaa                                             20

SEQ ID NO: 125          moltype = DNA  length = 20
FEATURE                 Location/Qualifiers
source                  1..20
                        mol_type = other DNA
                        organism = synthetic construct
SEQUENCE: 125
gctgctccag gaacagaggt                                             20

SEQ ID NO: 126          moltype = DNA  length = 20
FEATURE                 Location/Qualifiers
source                  1..20
                        mol_type = other DNA
                        organism = synthetic construct
SEQUENCE: 126
tccaggaaca gaggtgccat                                             20

SEQ ID NO: 127          moltype = DNA  length = 20
FEATURE                 Location/Qualifiers
source                  1..20
                        mol_type = other DNA
                        organism = synthetic construct
SEQUENCE: 127
acagaggtgc catgcagccc                                             20

SEQ ID NO: 128          moltype = DNA  length = 20
FEATURE                 Location/Qualifiers
source                  1..20
                        mol_type = other DNA
                        organism = synthetic construct
SEQUENCE: 128
gggtactcct tgttgttgcc                                             20

SEQ ID NO: 129          moltype = DNA  length = 20
FEATURE                 Location/Qualifiers
source                  1..20
                        mol_type = other DNA
                        organism = synthetic construct
SEQUENCE: 129
actccttgtt gttgccctcc                                             20

SEQ ID NO: 130          moltype = DNA  length = 20
FEATURE                 Location/Qualifiers
source                  1..20
                        mol_type = other DNA
                        organism = synthetic construct
SEQUENCE: 130
tcctggcctc tgcccgagct                                             20
```

```
SEQ ID NO: 131          moltype = DNA  length = 20
FEATURE                 Location/Qualifiers
source                  1..20
                        mol_type = other DNA
                        organism = synthetic construct
SEQUENCE: 131
gcctctgccc gagcttcaga                                                20

SEQ ID NO: 132          moltype = DNA  length = 20
FEATURE                 Location/Qualifiers
source                  1..20
                        mol_type = other DNA
                        organism = synthetic construct
SEQUENCE: 132
agcttcagag gccgaggatg                                                20

SEQ ID NO: 133          moltype = DNA  length = 20
FEATURE                 Location/Qualifiers
source                  1..20
                        mol_type = other DNA
                        organism = synthetic construct
SEQUENCE: 133
agaggccgag gatgcctccc                                                20

SEQ ID NO: 134          moltype = DNA  length = 20
FEATURE                 Location/Qualifiers
source                  1..20
                        mol_type = other DNA
                        organism = synthetic construct
SEQUENCE: 134
ccgaggatgc ctcccttctc                                                20

SEQ ID NO: 135          moltype = DNA  length = 20
FEATURE                 Location/Qualifiers
source                  1..20
                        mol_type = other DNA
                        organism = synthetic construct
SEQUENCE: 135
aggatgcctc ccttctcagc                                                20

SEQ ID NO: 136          moltype = DNA  length = 20
FEATURE                 Location/Qualifiers
source                  1..20
                        mol_type = other DNA
                        organism = synthetic construct
SEQUENCE: 136
tcccttctca gcttcatgca                                                20

SEQ ID NO: 137          moltype = DNA  length = 20
FEATURE                 Location/Qualifiers
source                  1..20
                        mol_type = other DNA
                        organism = synthetic construct
SEQUENCE: 137
cagggttaca tgaagcacgc                                                20

SEQ ID NO: 138          moltype = DNA  length = 20
FEATURE                 Location/Qualifiers
source                  1..20
                        mol_type = other DNA
                        organism = synthetic construct
SEQUENCE: 138
tacatgaagc acgccaccaa                                                20

SEQ ID NO: 139          moltype = DNA  length = 20
FEATURE                 Location/Qualifiers
source                  1..20
                        mol_type = other DNA
                        organism = synthetic construct
SEQUENCE: 139
accaagaccg ccaaggatgc                                                20

SEQ ID NO: 140          moltype = DNA  length = 20
FEATURE                 Location/Qualifiers
source                  1..20
                        mol_type = other DNA
                        organism = synthetic construct
SEQUENCE: 140
accgccaagg atgcactgag                                                20
```

```
SEQ ID NO: 141          moltype = DNA  length = 20
FEATURE                 Location/Qualifiers
source                  1..20
                        mol_type = other DNA
                        organism = synthetic construct
SEQUENCE: 141
cgccaaggat gcactgagca                                              20

SEQ ID NO: 142          moltype = DNA  length = 20
FEATURE                 Location/Qualifiers
source                  1..20
                        mol_type = other DNA
                        organism = synthetic construct
SEQUENCE: 142
cactgagcag cgtgcaggag                                              20

SEQ ID NO: 143          moltype = DNA  length = 20
FEATURE                 Location/Qualifiers
source                  1..20
                        mol_type = other DNA
                        organism = synthetic construct
SEQUENCE: 143
ctgagcagcg tgcaggagtc                                              20

SEQ ID NO: 144          moltype = DNA  length = 20
FEATURE                 Location/Qualifiers
source                  1..20
                        mol_type = other DNA
                        organism = synthetic construct
SEQUENCE: 144
gtgcaggagt cccaggtggc                                              20

SEQ ID NO: 145          moltype = DNA  length = 20
FEATURE                 Location/Qualifiers
source                  1..20
                        mol_type = other DNA
                        organism = synthetic construct
SEQUENCE: 145
tggcccagca ggccaggggc                                              20

SEQ ID NO: 146          moltype = DNA  length = 20
FEATURE                 Location/Qualifiers
source                  1..20
                        mol_type = other DNA
                        organism = synthetic construct
SEQUENCE: 146
ggcccagcag gccaggggct                                              20

SEQ ID NO: 147          moltype = DNA  length = 20
FEATURE                 Location/Qualifiers
source                  1..20
                        mol_type = other DNA
                        organism = synthetic construct
SEQUENCE: 147
gctgggtgac cgatggcttc                                              20

SEQ ID NO: 148          moltype = DNA  length = 20
FEATURE                 Location/Qualifiers
source                  1..20
                        mol_type = other DNA
                        organism = synthetic construct
SEQUENCE: 148
tgggtgaccg atggcttcag                                              20

SEQ ID NO: 149          moltype = DNA  length = 20
FEATURE                 Location/Qualifiers
source                  1..20
                        mol_type = other DNA
                        organism = synthetic construct
SEQUENCE: 149
atggcttcag ttccctgaaa                                              20

SEQ ID NO: 150          moltype = DNA  length = 20
FEATURE                 Location/Qualifiers
source                  1..20
                        mol_type = other DNA
                        organism = synthetic construct
SEQUENCE: 150
```

-continued

```
aagactactg gagcaccgtt                                              20

SEQ ID NO: 151          moltype = DNA  length = 20
FEATURE                 Location/Qualifiers
source                  1..20
                        mol_type = other DNA
                        organism = synthetic construct
SEQUENCE: 151
ctactggagc accgttaagg                                              20

SEQ ID NO: 152          moltype = DNA  length = 20
FEATURE                 Location/Qualifiers
source                  1..20
                        mol_type = other DNA
                        organism = synthetic construct
SEQUENCE: 152
gcaccgttaa ggacaagttc                                              20

SEQ ID NO: 153          moltype = DNA  length = 20
FEATURE                 Location/Qualifiers
source                  1..20
                        mol_type = other DNA
                        organism = synthetic construct
SEQUENCE: 153
ttaaggacaa gttctctgag                                              20

SEQ ID NO: 154          moltype = DNA  length = 20
FEATURE                 Location/Qualifiers
source                  1..20
                        mol_type = other DNA
                        organism = synthetic construct
SEQUENCE: 154
ggacaagttc tctgagttct                                              20

SEQ ID NO: 155          moltype = DNA  length = 20
FEATURE                 Location/Qualifiers
source                  1..20
                        mol_type = other DNA
                        organism = synthetic construct
SEQUENCE: 155
gttctgggat ttggaccctg                                              20

SEQ ID NO: 156          moltype = DNA  length = 20
FEATURE                 Location/Qualifiers
source                  1..20
                        mol_type = other DNA
                        organism = synthetic construct
SEQUENCE: 156
ggaccctgag gtcagaccaa                                              20

SEQ ID NO: 157          moltype = DNA  length = 20
FEATURE                 Location/Qualifiers
source                  1..20
                        mol_type = other DNA
                        organism = synthetic construct
SEQUENCE: 157
gaccctgagg tcagaccaac                                              20

SEQ ID NO: 158          moltype = DNA  length = 20
FEATURE                 Location/Qualifiers
source                  1..20
                        mol_type = other DNA
                        organism = synthetic construct
SEQUENCE: 158
gaggtcagac caacttcagc                                              20

SEQ ID NO: 159          moltype = DNA  length = 20
FEATURE                 Location/Qualifiers
source                  1..20
                        mol_type = other DNA
                        organism = synthetic construct
SEQUENCE: 159
accaacttca gccgtggctg                                              20

SEQ ID NO: 160          moltype = DNA  length = 20
FEATURE                 Location/Qualifiers
source                  1..20
                        mol_type = other DNA
                        organism = synthetic construct
```

```
SEQUENCE: 160
acttcagccg tggctgcctg                                              20

SEQ ID NO: 161          moltype = DNA  length = 20
FEATURE                 Location/Qualifiers
source                  1..20
                        mol_type = other DNA
                        organism = synthetic construct
SEQUENCE: 161
tggctgcctg agacctcaat                                              20

SEQ ID NO: 162          moltype = DNA  length = 20
FEATURE                 Location/Qualifiers
source                  1..20
                        mol_type = other DNA
                        organism = synthetic construct
SEQUENCE: 162
caagtccacc tgcctatcca                                              20

SEQ ID NO: 163          moltype = DNA  length = 20
FEATURE                 Location/Qualifiers
source                  1..20
                        mol_type = other DNA
                        organism = synthetic construct
SEQUENCE: 163
ctgcctatcc atcctgcgag                                              20

SEQ ID NO: 164          moltype = DNA  length = 20
FEATURE                 Location/Qualifiers
source                  1..20
                        mol_type = other DNA
                        organism = synthetic construct
SEQUENCE: 164
tatccatcct gcgagctcct                                              20

SEQ ID NO: 165          moltype = DNA  length = 20
FEATURE                 Location/Qualifiers
source                  1..20
                        mol_type = other DNA
                        organism = synthetic construct
SEQUENCE: 165
tcctgcgagc tccttgggtc                                              20

SEQ ID NO: 166          moltype = DNA  length = 20
FEATURE                 Location/Qualifiers
source                  1..20
                        mol_type = other DNA
                        organism = synthetic construct
SEQUENCE: 166
cgagctcctt gggtcctgca                                              20

SEQ ID NO: 167          moltype = DNA  length = 20
FEATURE                 Location/Qualifiers
source                  1..20
                        mol_type = other DNA
                        organism = synthetic construct
SEQUENCE: 167
cttgggtcct gcaatctcca                                              20

SEQ ID NO: 168          moltype = DNA  length = 20
FEATURE                 Location/Qualifiers
source                  1..20
                        mol_type = other DNA
                        organism = synthetic construct
SEQUENCE: 168
gtcctgcaat ctccagggct                                              20

SEQ ID NO: 169          moltype = DNA  length = 20
FEATURE                 Location/Qualifiers
source                  1..20
                        mol_type = other DNA
                        organism = synthetic construct
SEQUENCE: 169
ctgcaatctc cagggctgcc                                              20

SEQ ID NO: 170          moltype = DNA  length = 20
FEATURE                 Location/Qualifiers
source                  1..20
                        mol_type = other DNA
```

```
                         organism = synthetic construct
SEQUENCE: 170
cctgtaggtt gcttaaaagg                                                 20

SEQ ID NO: 171           moltype = DNA  length = 20
FEATURE                  Location/Qualifiers
source                   1..20
                         mol_type = other DNA
                         organism = synthetic construct
SEQUENCE: 171
aggttgctta aaagggacag                                                 20

SEQ ID NO: 172           moltype = DNA  length = 20
FEATURE                  Location/Qualifiers
source                   1..20
                         mol_type = other DNA
                         organism = synthetic construct
SEQUENCE: 172
cttaaaaggg acagtattct                                                 20

SEQ ID NO: 173           moltype = DNA  length = 20
FEATURE                  Location/Qualifiers
source                   1..20
                         mol_type = other DNA
                         organism = synthetic construct
SEQUENCE: 173
aagggacagt attctcagtg                                                 20

SEQ ID NO: 174           moltype = DNA  length = 20
FEATURE                  Location/Qualifiers
source                   1..20
                         mol_type = other DNA
                         organism = synthetic construct
SEQUENCE: 174
gtattctcag tgctctccta                                                 20

SEQ ID NO: 175           moltype = DNA  length = 20
FEATURE                  Location/Qualifiers
source                   1..20
                         mol_type = other DNA
                         organism = synthetic construct
SEQUENCE: 175
ttctcagtgc tctcctaccc                                                 20

SEQ ID NO: 176           moltype = DNA  length = 20
FEATURE                  Location/Qualifiers
source                   1..20
                         mol_type = other DNA
                         organism = synthetic construct
SEQUENCE: 176
ccctccaggc atgctggcct                                                 20

SEQ ID NO: 177           moltype = DNA  length = 20
FEATURE                  Location/Qualifiers
source                   1..20
                         mol_type = other DNA
                         organism = synthetic construct
SEQUENCE: 177
caggcatgct ggcctcccaa                                                 20

SEQ ID NO: 178           moltype = DNA  length = 20
FEATURE                  Location/Qualifiers
source                   1..20
                         mol_type = other DNA
                         organism = synthetic construct
SEQUENCE: 178
gctggcctcc caataaagct                                                 20

SEQ ID NO: 179           moltype = DNA  length = 20
FEATURE                  Location/Qualifiers
source                   1..20
                         mol_type = other DNA
                         organism = synthetic construct
SEQUENCE: 179
cctcccaata aagctggaca                                                 20

SEQ ID NO: 180           moltype = DNA  length = 20
FEATURE                  Location/Qualifiers
source                   1..20
```

```
                          mol_type = other DNA
                          organism = synthetic construct
SEQUENCE: 180
tcccaataaa gctggacaag                                                  20

SEQ ID NO: 181            moltype = DNA  length = 20
FEATURE                   Location/Qualifiers
source                    1..20
                          mol_type = other DNA
                          organism = synthetic construct
SEQUENCE: 181
ataaagctgg acaagaagct                                                  20

SEQ ID NO: 182            moltype = DNA  length = 20
FEATURE                   Location/Qualifiers
source                    1..20
                          mol_type = other DNA
                          organism = synthetic construct
SEQUENCE: 182
ctggacaaga agctgctatg                                                  20

SEQ ID NO: 183            moltype = DNA  length = 20
FEATURE                   Location/Qualifiers
source                    1..20
                          mol_type = other DNA
                          organism = synthetic construct
SEQUENCE: 183
tagaggcagc tgctccaggt                                                  20

SEQ ID NO: 184            moltype = DNA  length = 20
FEATURE                   Location/Qualifiers
source                    1..20
                          mol_type = other DNA
                          organism = synthetic construct
SEQUENCE: 184
gctgctccag gtaatgccct                                                  20

SEQ ID NO: 185            moltype = DNA  length = 20
FEATURE                   Location/Qualifiers
source                    1..20
                          mol_type = other DNA
                          organism = synthetic construct
SEQUENCE: 185
ttccttgcag gaacagaggt                                                  20

SEQ ID NO: 186            moltype = DNA  length = 20
FEATURE                   Location/Qualifiers
source                    1..20
                          mol_type = other DNA
                          organism = synthetic construct
SEQUENCE: 186
gcctctgccc gtaagcactt                                                  20

SEQ ID NO: 187            moltype = DNA  length = 20
FEATURE                   Location/Qualifiers
source                    1..20
                          mol_type = other DNA
                          organism = synthetic construct
SEQUENCE: 187
agcaggccag gtacacccgc                                                  20

SEQ ID NO: 188            moltype = DNA  length = 20
FEATURE                   Location/Qualifiers
source                    1..20
                          mol_type = other DNA
                          organism = synthetic construct
SEQUENCE: 188
gtgcagttca caacagggtt                                                  20

SEQ ID NO: 189            moltype = DNA  length = 20
FEATURE                   Location/Qualifiers
source                    1..20
                          mol_type = other DNA
                          organism = synthetic construct
SEQUENCE: 189
ctcaggcggt attgctcact                                                  20

SEQ ID NO: 190            moltype = DNA  length = 20
FEATURE                   Location/Qualifiers
```

```
source                  1..20
                        mol_type = other DNA
                        organism = synthetic construct
SEQUENCE: 190
cctgacctaa ttcaagcccg                                               20

SEQ ID NO: 191          moltype = DNA  length = 20
FEATURE                 Location/Qualifiers
source                  1..20
                        mol_type = other DNA
                        organism = synthetic construct
SEQUENCE: 191
cctgctcagt tttatcccta                                               20

SEQ ID NO: 192          moltype = DNA  length = 20
FEATURE                 Location/Qualifiers
source                  1..20
                        mol_type = other DNA
                        organism = synthetic construct
SEQUENCE: 192
gtacgtaggt gccatgcagc                                               20

SEQ ID NO: 193          moltype = DNA  length = 20
FEATURE                 Location/Qualifiers
source                  1..20
                        mol_type = other DNA
                        organism = synthetic construct
SEQUENCE: 193
ccggacgctc ctcactgtgg                                               20

SEQ ID NO: 194          moltype = DNA  length = 20
FEATURE                 Location/Qualifiers
source                  1..20
                        mol_type = other DNA
                        organism = synthetic construct
SEQUENCE: 194
tggctctcct ggcatctgcc                                               20

SEQ ID NO: 195          moltype = DNA  length = 20
FEATURE                 Location/Qualifiers
source                  1..20
                        mol_type = other DNA
                        organism = synthetic construct
SEQUENCE: 195
tgcccgagct gaagaggtag                                               20

SEQ ID NO: 196          moltype = DNA  length = 20
FEATURE                 Location/Qualifiers
source                  1..20
                        mol_type = other DNA
                        organism = synthetic construct
SEQUENCE: 196
tagagggatc cttgctgctg                                               20

SEQ ID NO: 197          moltype = DNA  length = 20
FEATURE                 Location/Qualifiers
source                  1..20
                        mol_type = other DNA
                        organism = synthetic construct
SEQUENCE: 197
cttgctgctg ggctctgtgc                                               20

SEQ ID NO: 198          moltype = DNA  length = 20
FEATURE                 Location/Qualifiers
source                  1..20
                        mol_type = other DNA
                        organism = synthetic construct
SEQUENCE: 198
tatagctgcg gtggccaggg                                               20

SEQ ID NO: 199          moltype = DNA  length = 20
FEATURE                 Location/Qualifiers
source                  1..20
                        mol_type = other DNA
                        organism = synthetic construct
SEQUENCE: 199
cagattcctg aaaggctact                                               20

SEQ ID NO: 200          moltype = DNA  length = 20
```

```
FEATURE                Location/Qualifiers
source                 1..20
                       mol_type = other DNA
                       organism = synthetic construct
SEQUENCE: 200
ggagcaagtt tactgacaag                                              20

SEQ ID NO: 201         moltype = DNA  length = 20
FEATURE                Location/Qualifiers
source                 1..20
                       mol_type = other DNA
                       organism = synthetic construct
SEQUENCE: 201
ctgacaagtt caccggcttc                                              20

SEQ ID NO: 202         moltype = DNA  length = 20
FEATURE                Location/Qualifiers
source                 1..20
                       mol_type = other DNA
                       organism = synthetic construct
SEQUENCE: 202
cggcttctgg gattctaacc                                              20

SEQ ID NO: 203         moltype = DNA  length = 20
FEATURE                Location/Qualifiers
source                 1..20
                       mol_type = other DNA
                       organism = synthetic construct
SEQUENCE: 203
ctgaggacca accaactcca                                              20

SEQ ID NO: 204         moltype = DNA  length = 20
FEATURE                Location/Qualifiers
source                 1..20
                       mol_type = other DNA
                       organism = synthetic construct
SEQUENCE: 204
ctccagctat tgagtcgtga                                              20

SEQ ID NO: 205         moltype = DNA  length = 20
FEATURE                Location/Qualifiers
source                 1..20
                       mol_type = other DNA
                       organism = synthetic construct
SEQUENCE: 205
cctgaaggtt gctttaaggg                                              20

SEQ ID NO: 206         moltype = DNA  length = 20
FEATURE                Location/Qualifiers
source                 1..20
                       mol_type = other DNA
                       organism = synthetic construct
SEQUENCE: 206
gaaagtatgt tctcatgtct                                              20

SEQ ID NO: 207         moltype = DNA  length = 20
FEATURE                Location/Qualifiers
source                 1..20
                       mol_type = other DNA
                       organism = synthetic construct
SEQUENCE: 207
ctagatctca cctaaacatg                                              20

SEQ ID NO: 208         moltype = DNA  length = 20
FEATURE                Location/Qualifiers
source                 1..20
                       mol_type = other DNA
                       organism = synthetic construct
SEQUENCE: 208
cctaataaag ctggataaga                                              20

SEQ ID NO: 209         moltype = DNA  length = 20
FEATURE                Location/Qualifiers
source                 1..20
                       mol_type = other DNA
                       organism = synthetic construct
SEQUENCE: 209
gctgcatggc acctctgttc                                              20
```

SEQ ID NO: 210 moltype = DNA length = 20
FEATURE Location/Qualifiers
source 1..20
mol_type = other DNA
organism = synthetic construct
SEQUENCE: 210
ggcagaggcc aggagcgcca 20

SEQ ID NO: 211 moltype = DNA length = 20
FEATURE Location/Qualifiers
source 1..20
mol_type = other DNA
organism = synthetic construct
SEQUENCE: 211
ctgaagctcg ggcagaggcc 20

SEQ ID NO: 212 moltype = DNA length = 20
FEATURE Location/Qualifiers
source 1..20
mol_type = other DNA
organism = synthetic construct
SEQUENCE: 212
tcctcggcct ctgaagctcg 20

SEQ ID NO: 213 moltype = DNA length = 20
FEATURE Location/Qualifiers
source 1..20
mol_type = other DNA
organism = synthetic construct
SEQUENCE: 213
tcttggtggc gtgcttcatg 20

SEQ ID NO: 214 moltype = DNA length = 20
FEATURE Location/Qualifiers
source 1..20
mol_type = other DNA
organism = synthetic construct
SEQUENCE: 214
gctcagtgca tccttggcgg 20

SEQ ID NO: 215 moltype = DNA length = 20
FEATURE Location/Qualifiers
source 1..20
mol_type = other DNA
organism = synthetic construct
SEQUENCE: 215
cctgcacgct gctcagtgca 20

SEQ ID NO: 216 moltype = DNA length = 20
FEATURE Location/Qualifiers
source 1..20
mol_type = other DNA
organism = synthetic construct
SEQUENCE: 216
actgaagcca tcggtcaccc 20

SEQ ID NO: 217 moltype = DNA length = 20
FEATURE Location/Qualifiers
source 1..20
mol_type = other DNA
organism = synthetic construct
SEQUENCE: 217
cagaactcag agaacttgtc 20

SEQ ID NO: 218 moltype = DNA length = 20
FEATURE Location/Qualifiers
source 1..20
mol_type = other DNA
organism = synthetic construct
SEQUENCE: 218
gaagttggtc tgacctcagg 20

SEQ ID NO: 219 moltype = DNA length = 20
FEATURE Location/Qualifiers
source 1..20
mol_type = other DNA
organism = synthetic construct
SEQUENCE: 219
ccctggagat tgcaggaccc 20

```
SEQ ID NO: 220          moltype = DNA  length = 20
FEATURE                 Location/Qualifiers
source                  1..20
                        mol_type = other DNA
                        organism = synthetic construct
SEQUENCE: 220
gggcagccct ggagattgca                                              20

SEQ ID NO: 221          moltype = DNA  length = 20
FEATURE                 Location/Qualifiers
source                  1..20
                        mol_type = other DNA
                        organism = synthetic construct
SEQUENCE: 221
ccctttaag caacctacag                                               20

SEQ ID NO: 222          moltype = DNA  length = 16
FEATURE                 Location/Qualifiers
source                  1..16
                        mol_type = other DNA
                        organism = synthetic construct
SEQUENCE: 222
tggcaagcat cctgta                                                  16

SEQ ID NO: 223          moltype = DNA  length = 16
FEATURE                 Location/Qualifiers
source                  1..16
                        mol_type = other DNA
                        organism = synthetic construct
SEQUENCE: 223
ctcaatccat ggcagc                                                  16

SEQ ID NO: 224          moltype = DNA  length = 16
FEATURE                 Location/Qualifiers
source                  1..16
                        mol_type = other DNA
                        organism = synthetic construct
SEQUENCE: 224
accaagtttc ttcagc                                                  16

SEQ ID NO: 225          moltype = DNA  length = 13
FEATURE                 Location/Qualifiers
source                  1..13
                        mol_type = other DNA
                        organism = synthetic construct
SEQUENCE: 225
gcattggtat tca                                                     13

SEQ ID NO: 226          moltype = DNA  length = 20
FEATURE                 Location/Qualifiers
source                  1..20
                        mol_type = other DNA
                        organism = synthetic construct
SEQUENCE: 226
ttcagcattg gtattcagtg                                              20

SEQ ID NO: 227          moltype = DNA  length = 16
FEATURE                 Location/Qualifiers
source                  1..16
                        mol_type = other DNA
                        organism = synthetic construct
SEQUENCE: 227
cagcattggt attcag                                                  16

SEQ ID NO: 228          moltype = DNA  length = 15
FEATURE                 Location/Qualifiers
source                  1..15
                        mol_type = other DNA
                        organism = synthetic construct
SEQUENCE: 228
cagcattggt attca                                                   15

SEQ ID NO: 229          moltype = DNA  length = 14
FEATURE                 Location/Qualifiers
source                  1..14
                        mol_type = other DNA
                        organism = synthetic construct
SEQUENCE: 229
```

agcattggta ttca 14

SEQ ID NO: 230 moltype = DNA length = 12
FEATURE Location/Qualifiers
source 1..12
mol_type = other DNA
organism = synthetic construct
SEQUENCE: 230
gcattggtat tc 12

SEQ ID NO: 231 moltype = DNA length = 18
FEATURE Location/Qualifiers
source 1..18
mol_type = other DNA
organism = synthetic construct
SEQUENCE: 231
cggcatgtct attttgta 18

SEQ ID NO: 232 moltype = DNA length = 20
FEATURE Location/Qualifiers
source 1..20
mol_type = other DNA
organism = synthetic construct
SEQUENCE: 232
ggctaaatcg ctccaccaag 20

SEQ ID NO: 233 moltype = DNA length = 20
FEATURE Location/Qualifiers
source 1..20
mol_type = other DNA
organism = synthetic construct
SEQUENCE: 233
ctctagcgtc ttaaagccga 20

SEQ ID NO: 234 moltype = DNA length = 20
FEATURE Location/Qualifiers
source 1..20
mol_type = other DNA
organism = synthetic construct
SEQUENCE: 234
gctgcatgat ctccttggcg 20

SEQ ID NO: 235 moltype = DNA length = 20
FEATURE Location/Qualifiers
source 1..20
mol_type = other DNA
organism = synthetic construct
SEQUENCE: 235
acgttgaggg gcatcgtcgc 20

SEQ ID NO: 236 moltype = DNA length = 19
FEATURE Location/Qualifiers
source 1..19
mol_type = other DNA
organism = synthetic construct
SEQUENCE: 236
gggtctgcvg cgggvtggt 19

SEQ ID NO: 237 moltype = DNA length = 21
FEATURE Location/Qualifiers
source 1..21
mol_type = other DNA
organism = synthetic construct
SEQUENCE: 237
gttvctvctt ccvcctgcct g 21

SEQ ID NO: 238 moltype = DNA length = 25
FEATURE Location/Qualifiers
source 1..25
mol_type = other DNA
organism = synthetic construct
SEQUENCE: 238
tatccggagg gctcgccatg ctgct 25

SEQ ID NO: 239 moltype = DNA length = 20
FEATURE Location/Qualifiers
source 1..20
mol_type = other DNA
organism = synthetic construct

```
SEQUENCE: 239
tcccgcctgt gacatgcatt                                              20

SEQ ID NO: 240          moltype = DNA  length = 21
FEATURE                 Location/Qualifiers
source                  1..21
                        mol_type = other DNA
                        organism = synthetic construct
SEQUENCE: 240
cagcagcaga gtcttcatca t                                            21

SEQ ID NO: 241          moltype = DNA  length = 20
FEATURE                 Location/Qualifiers
source                  1..20
                        mol_type = other DNA
                        organism = synthetic construct
SEQUENCE: 241
gggacgcggc gctcggtcat                                              20

SEQ ID NO: 242          moltype = DNA  length = 20
FEATURE                 Location/Qualifiers
source                  1..20
                        mol_type = other DNA
                        organism = synthetic construct
SEQUENCE: 242
ccacaagctg tccagtctaa                                              20

SEQ ID NO: 243          moltype = DNA  length = 20
FEATURE                 Location/Qualifiers
source                  1..20
                        mol_type = other DNA
                        organism = synthetic construct
SEQUENCE: 243
ccgcagccat gcgctcttgg                                              20

SEQ ID NO: 244          moltype = DNA  length = 20
FEATURE                 Location/Qualifiers
source                  1..20
                        mol_type = other DNA
                        organism = synthetic construct
SEQUENCE: 244
agcttcttgt ccagctttat                                              20

SEQ ID NO: 245          moltype = DNA  length = 21
FEATURE                 Location/Qualifiers
source                  1..21
                        mol_type = other DNA
                        organism = synthetic construct
SEQUENCE: 245
agcttcttgt ccagctttat a                                            21

SEQ ID NO: 246          moltype = DNA  length = 14
FEATURE                 Location/Qualifiers
source                  1..14
                        mol_type = other DNA
                        organism = synthetic construct
SEQUENCE: 246
tcagtcatga cttc                                                    14

SEQ ID NO: 247          moltype = DNA  length = 15
FEATURE                 Location/Qualifiers
source                  1..15
                        mol_type = other DNA
                        organism = synthetic construct
SEQUENCE: 247
tcagtcatga cttca                                                   15

SEQ ID NO: 248          moltype = DNA  length = 20
FEATURE                 Location/Qualifiers
source                  1..20
                        mol_type = other DNA
                        organism = synthetic construct
SEQUENCE: 248
gctgattaga gagaggtccc                                              20

SEQ ID NO: 249          moltype = DNA  length = 20
FEATURE                 Location/Qualifiers
source                  1..20
                        mol_type = other DNA
```

```
                      organism = synthetic construct
SEQUENCE: 249
tcccatttca ggagacctgg                                                 20

SEQ ID NO: 250        moltype = DNA  length = 15
FEATURE               Location/Qualifiers
source                1..15
                      mol_type = other DNA
                      organism = synthetic construct
SEQUENCE: 250
atcagtcatg acttc                                                      15

SEQ ID NO: 251        moltype = DNA  length = 20
FEATURE               Location/Qualifiers
source                1..20
                      mol_type = other DNA
                      organism = synthetic construct
SEQUENCE: 251
cggtgcaagg cttaggaatt                                                 20

SEQ ID NO: 252        moltype = DNA  length = 20
FEATURE               Location/Qualifiers
source                1..20
                      mol_type = other DNA
                      organism = synthetic construct
SEQUENCE: 252
gcttcagtca tgacttcctt                                                 20

SEQ ID NO: 253        moltype = DNA  length = 21
FEATURE               Location/Qualifiers
source                1..21
                      mol_type = other DNA
                      organism = synthetic construct
SEQUENCE: 253
gcttcagtca tgacttcctt a                                               21

SEQ ID NO: 254        moltype = DNA  length = 21
FEATURE               Location/Qualifiers
source                1..21
                      mol_type = other DNA
                      organism = synthetic construct
SEQUENCE: 254
agcttcagtc atgacttcct t                                               21

SEQ ID NO: 255        moltype = DNA  length = 20
FEATURE               Location/Qualifiers
source                1..20
                      mol_type = other DNA
                      organism = synthetic construct
SEQUENCE: 255
tggtaatcca ctttcagagg                                                 20

SEQ ID NO: 256        moltype = DNA  length = 21
FEATURE               Location/Qualifiers
source                1..21
                      mol_type = other DNA
                      organism = synthetic construct
SEQUENCE: 256
tggtaatcca ctttcagagg a                                               21

SEQ ID NO: 257        moltype = DNA  length = 21
FEATURE               Location/Qualifiers
source                1..21
                      mol_type = other DNA
                      organism = synthetic construct
SEQUENCE: 257
tgcttcagtc atgacttcct t                                               21

SEQ ID NO: 258        moltype = DNA  length = 20
FEATURE               Location/Qualifiers
source                1..20
                      mol_type = other DNA
                      organism = synthetic construct
SEQUENCE: 258
cactgatttt tgcccaggat                                                 20

SEQ ID NO: 259        moltype = DNA  length = 21
FEATURE               Location/Qualifiers
source                1..21
```

```
                       mol_type = other DNA
                       organism = synthetic construct
SEQUENCE: 259
cactgatttt tgcccaggat a                                                21

SEQ ID NO: 260         moltype = DNA  length = 21
FEATURE                Location/Qualifiers
source                 1..21
                       mol_type = other DNA
                       organism = synthetic construct
SEQUENCE: 260
aagcttcttg tccagcttta t                                                21

SEQ ID NO: 261         moltype = DNA  length = 20
FEATURE                Location/Qualifiers
source                 1..20
                       mol_type = other DNA
                       organism = synthetic construct
SEQUENCE: 261
acccaattca gaaggaagga                                                  20

SEQ ID NO: 262         moltype = DNA  length = 21
FEATURE                Location/Qualifiers
source                 1..21
                       mol_type = other DNA
                       organism = synthetic construct
SEQUENCE: 262
acccaattca gaaggaagga a                                                21

SEQ ID NO: 263         moltype = DNA  length = 21
FEATURE                Location/Qualifiers
source                 1..21
                       mol_type = other DNA
                       organism = synthetic construct
SEQUENCE: 263
aacccaattc agaaggaagg a                                                21

SEQ ID NO: 264         moltype = DNA  length = 21
FEATURE                Location/Qualifiers
source                 1..21
                       mol_type = other DNA
                       organism = synthetic construct
SEQUENCE: 264
atggtaatcc actttcagag g                                                21

SEQ ID NO: 265         moltype = DNA  length = 20
FEATURE                Location/Qualifiers
source                 1..20
                       mol_type = other DNA
                       organism = synthetic construct
SEQUENCE: 265
tcttggttac atgaaatccc                                                  20

SEQ ID NO: 266         moltype = DNA  length = 21
FEATURE                Location/Qualifiers
source                 1..21
                       mol_type = other DNA
                       organism = synthetic construct
SEQUENCE: 266
tcttggttac atgaaatccc a                                                21

SEQ ID NO: 267         moltype = DNA  length = 20
FEATURE                Location/Qualifiers
source                 1..20
                       mol_type = other DNA
                       organism = synthetic construct
SEQUENCE: 267
attcactttc ataatgctgg                                                  20

SEQ ID NO: 268         moltype = DNA  length = 21
FEATURE                Location/Qualifiers
source                 1..21
                       mol_type = other DNA
                       organism = synthetic construct
SEQUENCE: 268
attcactttc ataatgctgg a                                                21

SEQ ID NO: 269         moltype = DNA  length = 21
FEATURE                Location/Qualifiers
```

```
source                1..21
                      mol_type = other DNA
                      organism = synthetic construct
SEQUENCE: 269
atcttggtta catgaaatcc c                                                21

SEQ ID NO: 270        moltype = DNA  length = 20
FEATURE               Location/Qualifiers
source                1..20
                      mol_type = other DNA
                      organism = synthetic construct
SEQUENCE: 270
atgcatggtg atgcttctga                                                  20

SEQ ID NO: 271        moltype = DNA  length = 20
FEATURE               Location/Qualifiers
source                1..20
                      mol_type = other DNA
                      organism = synthetic construct
SEQUENCE: 271
cagctttatt agggacagca                                                  20

SEQ ID NO: 272        moltype = DNA  length = 21
FEATURE               Location/Qualifiers
source                1..21
                      mol_type = other DNA
                      organism = synthetic construct
SEQUENCE: 272
cagctttatt agggacagca a                                                21

SEQ ID NO: 273        moltype = DNA  length = 21
FEATURE               Location/Qualifiers
source                1..21
                      mol_type = other DNA
                      organism = synthetic construct
SEQUENCE: 273
acagctttat tagggacagc a                                                21

SEQ ID NO: 274        moltype = DNA  length = 16
FEATURE               Location/Qualifiers
source                1..16
                      mol_type = other DNA
                      organism = synthetic construct
SEQUENCE: 274
ttcagtcatg acttcc                                                      16

SEQ ID NO: 275        moltype = DNA  length = 18
FEATURE               Location/Qualifiers
source                1..18
                      mol_type = other DNA
                      organism = synthetic construct
modified_base         3..4
                      mod_base = OTHER
                      note = uracil
modified_base         16
                      mod_base = OTHER
                      note = uracil
SEQUENCE: 275
gcttcagtca tgacttcc                                                    18

SEQ ID NO: 276        moltype = DNA  length = 21
FEATURE               Location/Qualifiers
source                1..21
                      mol_type = other DNA
                      organism = synthetic construct
SEQUENCE: 276
tgctccgttg gtgcttgttc a                                                21

SEQ ID NO: 277        moltype = DNA  length = 20
FEATURE               Location/Qualifiers
source                1..20
                      mol_type = other DNA
                      organism = synthetic construct
SEQUENCE: 277
tgctccgttg gtgcttgttc                                                  20

SEQ ID NO: 278        moltype = DNA  length = 20
FEATURE               Location/Qualifiers
source                1..20
```

```
                        mol_type = other DNA
                        organism = synthetic construct
modified_base
                        mod_base = OTHER
                        note = 5' triantennary N-acetylgalactosamine conjugate 7a
                         phosphodiester
modified_base           1
                        mod_base = OTHER
                        note = 2'-O-methoxyethyl adenosine 3'-phosphorothioate
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 5-methyl-2'-deoxycytidine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxythymidine 3'-phosphorothioate
modified_base           11..12
                        mod_base = OTHER
                        note = 5-methyl-2'-deoxycytidine 3'-phosphorothioate
modified_base           13
                        mod_base = OTHER
                        note = 2'-deoxyadenosine 3'-phosphorothioate
modified_base           14
                        mod_base = OTHER
                        note = 2'-deoxyguanosine 3'-phosphorothioate
modified_base           15
                        mod_base = OTHER
                        note = 5-methyl-2'-deoxycytidine 3'-phosphorothioate
modified_base           16..18
                        mod_base = OTHER
                        note = 2'-O-methoxyethyl thymidine 3'-phosphorothioate
modified_base           19
                        mod_base = OTHER
                        note = 2'-O-methoxyethyl adenosine 3'-phosphorothioate
modified_base           20
                        mod_base = OTHER
                        note = 2'-O-methoxyethyl thymidine
SEQUENCE: 278
agcttcttgt ccagctttat                                              20

SEQ ID NO: 279          moltype = DNA  length = 20
FEATURE                 Location/Qualifiers
source                  1..20
                        mol_type = other DNA
                        organism = synthetic construct
modified_base
                        mod_base = OTHER
                        note = 5' triantennary N-acetylgalactosamine conjugate 7a
                         phosphodiester
modified_base           1
                        mod_base = OTHER
                        note = 2'-O-methoxyethyl adenosine 3'-phosphorothioate
modified_base           2
                        mod_base = OTHER
                        note = 2'-O-methoxyethyl guanosine 3'-phosphodiester
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 5-methyl-2'-deoxycytidine 3'-phosphorothioate
```

```
modified_base          7..8
                       mod_base = OTHER
                       note = 2'-deoxythymidine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxythymidine 3'-phosphorothioate
modified_base          11..12
                       mod_base = OTHER
                       note = 5-methyl-2'-deoxycytidine 3'-phosphorothioate
modified_base          13
                       mod_base = OTHER
                       note = 2'-deoxyadenosine 3'-phosphorothioate
modified_base          14
                       mod_base = OTHER
                       note = 2'-deoxyguanosine 3'-phosphorothioate
modified_base          15
                       mod_base = OTHER
                       note = 5-methyl-2'-deoxycytidine 3'-phosphorothioate
modified_base          16..17
                       mod_base = OTHER
                       note = 2'-O-methoxyethyl thymidine 3'-phosphodiester
modified_base          18
                       mod_base = OTHER
                       note = 2'-O-methoxyethyl thymidine 3'-phosphorothioate
modified_base          19
                       mod_base = OTHER
                       note = 2'-O-methoxyethyl adenosine 3'-phosphorothioate
modified_base          20
                       mod_base = OTHER
                       note = 2'-O-methoxyethyl thymidine
SEQUENCE: 279
agcttcttgt ccagctttat                                              20

SEQ ID NO: 280         moltype = DNA  length = 12
FEATURE                Location/Qualifiers
source                 1..12
                       mol_type = other DNA
                       organism = synthetic construct
modified_base          1
                       mod_base = OTHER
                       note = locked nucleic acid guanosine 3'-phosphorothioate
modified_base          2
                       mod_base = OTHER
                       note = locked nucleic acid cytidine 3'-phosphorothioate
modified_base          3
                       mod_base = OTHER
                       note = 2'-deoxyadenosine 3'-phosphorothioate
modified_base          4..5
                       mod_base = OTHER
                       note = 2'-deoxythymidine 3'-phosphorothioate
modified_base          6..7
                       mod_base = OTHER
                       note = 2'-deoxyguanosine 3'-phosphorothioate
modified_base          8
                       mod_base = OTHER
                       note = 2'-deoxythymidine 3'-phosphorothioate
modified_base          9
                       mod_base = OTHER
                       note = 2'-deoxyadenosine 3'-phosphorothioate
modified_base          10
                       mod_base = OTHER
                       note = 2'-deoxythymidine 3'-phosphorothioate
modified_base          11
                       mod_base = OTHER
                       note = locked nucleic acid thymidine 3'-phosphorothioate
modified_base          12
                       mod_base = OTHER
                       note = locked nucleic acid cytidine
SEQUENCE: 280
gcattggtat tc                                                      12

SEQ ID NO: 281         moltype = DNA  length = 13
FEATURE                Location/Qualifiers
source                 1..13
                       mol_type = other DNA
                       organism = synthetic construct
```

```
modified_base         1
                      mod_base = OTHER
                      note = locked nucleic acid guanosine 3'-phosphorothioate
modified_base         2
                      mod_base = OTHER
                      note = locked nucleic acid cytidine 3'-phosphorothioate
modified_base         3
                      mod_base = OTHER
                      note = 2'-deoxyadenosine 3'-phosphorothioate
modified_base         4..5
                      mod_base = OTHER
                      note = 2'-deoxythymidine 3'-phosphorothioate
modified_base         6..7
                      mod_base = OTHER
                      note = 2'-deoxyguanosine 3'-phosphorothioate
modified_base         8
                      mod_base = OTHER
                      note = 2'-deoxythymidine 3'-phosphorothioate
modified_base         9
                      mod_base = OTHER
                      note = 2'-deoxyadenosine 3'-phosphorothioate
modified_base         10
                      mod_base = OTHER
                      note = 2'-deoxythymidine 3'-phosphorothioate
modified_base         11
                      mod_base = OTHER
                      note = locked nucleic acid thymidine 3'-phosphorothioate
modified_base         12
                      mod_base = OTHER
                      note = locked nucleic acid cytidine 3'-phosphorothioate
modified_base         13
                      mod_base = OTHER
                      note = locked nucleic acid adenosine
SEQUENCE: 281
gcattggtat tca                                                          13

SEQ ID NO: 282        moltype = DNA  length = 14
FEATURE               Location/Qualifiers
source                1..14
                      mol_type = other DNA
                      organism = synthetic construct
modified_base         1
                      mod_base = OTHER
                      note = locked nucleic acid adenosine 3'-phosphorothioate
modified_base         2
                      mod_base = OTHER
                      note = locked nucleic acid guanosine 3'-phosphorothioate
modified_base         3
                      mod_base = OTHER
                      note = locked nucleic acid cytidine 3'-phosphorothioate
modified_base         4
                      mod_base = OTHER
                      note = 2'-deoxyadenosine 3'-phosphorothioate
modified_base         5..6
                      mod_base = OTHER
                      note = 2'-deoxythymidine 3'-phosphorothioate
modified_base         7..8
                      mod_base = OTHER
                      note = 2'-deoxyguanosine 3'-phosphorothioate
modified_base         9
                      mod_base = OTHER
                      note = 2'-deoxythymidine 3'-phosphorothioate
modified_base         10
                      mod_base = OTHER
                      note = 2'-deoxyadenosine 3'-phosphorothioate
modified_base         11
                      mod_base = OTHER
                      note = 2'-deoxythymidine 3'-phosphorothioate
modified_base         12
                      mod_base = OTHER
                      note = locked nucleic acid thymidine 3'-phosphorothioate
modified_base         13
                      mod_base = OTHER
                      note = locked nucleic acid cytidine 3'-phosphorothioate
modified_base         14
                      mod_base = OTHER
                      note = locked nucleic acid adenosine
SEQUENCE: 282
agcattggta ttca                                                         14
```

```
SEQ ID NO: 283          moltype = DNA  length = 15
FEATURE                 Location/Qualifiers
source                  1..15
                        mol_type = other DNA
                        organism = synthetic construct
modified_base           1
                        mod_base = OTHER
                        note = locked nucleic acid cytidine 3'-phosphorothioate
modified_base           2
                        mod_base = OTHER
                        note = locked nucleic acid adenosine 3'-phosphorothioate
modified_base           3
                        mod_base = OTHER
                        note = locked nucleic acid guanosine 3'-phosphorothioate
modified_base           4
                        mod_base = OTHER
                        note = 2'-deoxycytidine 3'-phosphorothioate
modified_base           5
                        mod_base = OTHER
                        note = 2'-deoxyadenosine 3'-phosphorothioate
modified_base           6..7
                        mod_base = OTHER
                        note = 2'-deoxythymidine 3'-phosphorothioate
modified_base           8..9
                        mod_base = OTHER
                        note = 2'-deoxyguanosine 3'-phosphorothioate
modified_base           10
                        mod_base = OTHER
                        note = 2'-deoxythymidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = locked nucleic acid thymidine 3'-phosphorothioate
modified_base           14
                        mod_base = OTHER
                        note = locked nucleic acid cytidine 3'-phosphorothioate
modified_base           15
                        mod_base = OTHER
                        note = locked nucleic acid adenosine
SEQUENCE: 283
cagcattggt attca                                                15

SEQ ID NO: 284          moltype = DNA  length = 16
FEATURE                 Location/Qualifiers
source                  1..16
                        mol_type = other DNA
                        organism = synthetic construct
modified_base           1
                        mod_base = OTHER
                        note = locked nucleic acid thymidine 3'-phosphorothioate
modified_base           2..3
                        mod_base = OTHER
                        note = locked nucleic acid guanosine 3'-phosphorothioate
modified_base           4
                        mod_base = OTHER
                        note = 2'-deoxycytidine 3'-phosphorothioate
modified_base           5..6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxycytidine 3'-phosphorothioate
modified_base           9
                        mod_base = OTHER
                        note = 2'-deoxyadenosine 3'-phosphorothioate
modified_base           10
                        mod_base = OTHER
                        note = 2'-deoxythymidine 3'-phosphorothioate
modified_base           11..12
                        mod_base = OTHER
```

```
                        note = 2'-deoxycytidine 3'-phosphorothioate
modified_base           13
                        mod_base = OTHER
                        note = locked nucleic acid thymidine 3'-phosphorothioate
modified_base           14
                        mod_base = OTHER
                        note = locked nucleic acid guanosine 3'-phosphorothioate
modified_base           15
                        mod_base = OTHER
                        note = locked nucleic acid thymidine 3'-phosphorothioate
modified_base           16
                        mod_base = OTHER
                        note = 2'-deoxyadenosine
SEQUENCE: 284
tggcaagcat cctgta                                                 16

SEQ ID NO: 285          moltype = DNA  length = 16
FEATURE                 Location/Qualifiers
source                  1..16
                        mol_type = other DNA
                        organism = synthetic construct
SEQUENCE: 285
ctcaatccat ggcagc                                                 16

SEQ ID NO: 286          moltype = DNA  length = 16
FEATURE                 Location/Qualifiers
source                  1..16
                        mol_type = other DNA
                        organism = synthetic construct
modified_base           1
                        mod_base = OTHER
                        note = locked nucleic acid adenosine 3'-phosphorothioate
modified_base           2..3
                        mod_base = OTHER
                        note = locked nucleic acid cytidine 3'-phosphorothioate
modified_base           4..5
                        mod_base = OTHER
                        note = 2'-deoxyadenosine 3'-phosphorothioate
modified_base           6
                        mod_base = OTHER
                        note = 2'-deoxyguanosine 3'-phosphorothioate
modified_base           7..9
                        mod_base = OTHER
                        note = 2'-deoxythymidine 3'-phosphorothioate
modified_base           10
                        mod_base = OTHER
                        note = 2'-deoxycytidine 3'-phosphorothioate
modified_base           11..12
                        mod_base = OTHER
                        note = 2'-deoxythymidine 3'-phosphorothioate
modified_base           13
                        mod_base = OTHER
                        note = 2'-deoxycytidine 3'-phosphorothioate
modified_base           14
                        mod_base = OTHER
                        note = locked nucleic acid adenosine 3'-phosphorothioate
modified_base           15
                        mod_base = OTHER
                        note = locked nucleic acid guanosine 3'-phosphorothioate
modified_base           16
                        mod_base = OTHER
                        note = locked nucleic acid cytidine
SEQUENCE: 286
accaagtttc ttcagc                                                 16

SEQ ID NO: 287          moltype = DNA  length = 16
FEATURE                 Location/Qualifiers
source                  1..16
                        mol_type = other DNA
                        organism = synthetic construct
modified_base           1
                        mod_base = OTHER
                        note = locked nucleic acid cytidine 3'-phosphorothioate
modified_base           2
                        mod_base = OTHER
                        note = locked nucleic acid adenosine 3'-phosphorothioate
modified_base           3
                        mod_base = OTHER
                        note = locked nucleic acid guanosine 3'-phosphorothioate
```

```
modified_base         4
                      mod_base = OTHER
                      note = 2'-deoxycytidine 3'-phosphorothioate
modified_base         5
                      mod_base = OTHER
                      note = 2'-deoxyadenosine 3'-phosphorothioate
modified_base         6..7
                      mod_base = OTHER
                      note = 2'-deoxythymidine 3'-phosphorothioate
modified_base         8..9
                      mod_base = OTHER
                      note = 2'-deoxyguanosine 3'-phosphorothioate
modified_base         10
                      mod_base = OTHER
                      note = 2'-deoxythymidine 3'-phosphorothioate
modified_base         11
                      mod_base = OTHER
                      note = 2'-deoxyadenosine 3'-phosphorothioate
modified_base         12
                      mod_base = OTHER
                      note = 2'-deoxythymidine 3'-phosphorothioate
modified_base         13
                      mod_base = OTHER
                      note = locked nucleic acid thymidine 3'-phosphorothioate
modified_base         14
                      mod_base = OTHER
                      note = locked nucleic acid cytidine 3'-phosphorothioate
modified_base         15
                      mod_base = OTHER
                      note = locked nucleic acid adenosine 3'-phosphorothioate
modified_base         16
                      mod_base = OTHER
                      note = 2'-deoxyguanosine
SEQUENCE: 287
cagcattggt attcag                                              16

SEQ ID NO: 288        moltype = DNA  length = 19
FEATURE               Location/Qualifiers
source                1..19
                      mol_type = other DNA
                      organism = synthetic construct
modified_base         1..3
                      mod_base = OTHER
                      note = 2'-deoxyguanosine 3'-phosphorothioate
modified_base         4
                      mod_base = OTHER
                      note = 2'-deoxythymidine 3'-phosphorothioate
modified_base         5
                      mod_base = OTHER
                      note = 2'-deoxycytidine 3'-phosphorothioate
modified_base         6
                      mod_base = OTHER
                      note = 2'-deoxythymidine 3'-phosphorothioate
modified_base         7
                      mod_base = OTHER
                      note = 2'-deoxyguanosine 3'-phosphorothioate
modified_base         8
                      mod_base = OTHER
                      note = 2'-deoxycytidine 3'-phosphorothioate
modified_base         9
                      mod_base = OTHER
                      note = 2-amino-2'-deoxyadenosine phosphorothioate
modified_base         10
                      mod_base = OTHER
                      note = 2'-deoxyguanosine 3'-phosphorothioate
modified_base         11
                      mod_base = OTHER
                      note = 2'-deoxycytidine 3'-phosphorothioate
modified_base         12..14
                      mod_base = OTHER
                      note = 2'-deoxyguanosine 3'-phosphorothioate
modified_base         15
                      mod_base = OTHER
                      note = 2-amino-2'-deoxyadenosine phosphorothioate
modified_base         16
                      mod_base = OTHER
                      note = 2'-deoxythymidine 3'-phosphorothioate
modified_base         17..18
                      mod_base = OTHER
```

```
                        note = 2'-deoxyguanosine 3'-phosphorothioate
modified_base           19
                        mod_base = OTHER
                        note = 2'-deoxythymidine
SEQUENCE: 288
gggtctgcag cgggatggt                                              19

SEQ ID NO: 289          moltype = DNA  length = 20
FEATURE                 Location/Qualifiers
source                  1..20
                        mol_type = other DNA
                        organism = synthetic construct
modified_base           1..2
                        mod_base = OTHER
                        note = locked nucleic acid thymidine 3'-phosphorothioate
modified_base           3
                        mod_base = OTHER
                        note = locked nucleic acid cytidine 3'-phosphorothioate
modified_base           4
                        mod_base = OTHER
                        note = locked nucleic acid adenosine 3'-phosphorothioate
modified_base           5
                        mod_base = OTHER
                        note = locked nucleic acid guanosine 3'-phosphorothioate
modified_base           6
                        mod_base = OTHER
                        note = 2'-deoxycytidine 3'-phosphorothioate
modified_base           7
                        mod_base = OTHER
                        note = 2'-deoxyadenosine 3'-phosphorothioate
modified_base           8..9
                        mod_base = OTHER
                        note = 2'-deoxythymidine 3'-phosphorothioate
modified_base           10..11
                        mod_base = OTHER
                        note = 2'-deoxyguanosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyadenosine 3'-phosphorothioate
modified_base           14..15
                        mod_base = OTHER
                        note = 2'-deoxythymidine 3'-phosphorothioate
modified_base           16
                        mod_base = OTHER
                        note = locked nucleic acid cytidine 3'-phosphorothioate
modified_base           17
                        mod_base = OTHER
                        note = locked nucleic acid adenosine 3'-phosphorothioate
modified_base           18
                        mod_base = OTHER
                        note = locked nucleic acid guanosine 3'-phosphorothioate
modified_base           19
                        mod_base = OTHER
                        note = locked nucleic acid thymidine 3'-phosphorothioate
modified_base           20
                        mod_base = OTHER
                        note = locked nucleic acid guanosine
SEQUENCE: 289
ttcagcattg gtattcagtg                                             20

SEQ ID NO: 290          moltype = DNA  length = 20
FEATURE                 Location/Qualifiers
source                  1..20
                        mol_type = other DNA
                        organism = synthetic construct
modified_base           1
                        mod_base = OTHER
                        note = 2'-O-methoxyethyl thymidine 3'-phosphorothioate
modified_base           2..4
                        mod_base = OTHER
                        note = 2'-O-methoxyethyl cytidine 3'-phosphorothioate
modified_base           6
                        mod_base = OTHER
                        note = 2'-O-methoxyethyl cytidine 3'-phosphorothioate
modified_base           5
                        mod_base = OTHER
```

```
                        note = 2'-O-methoxyethyl guanosine 3'-phosphorothioate
modified_base           7
                        mod_base = OTHER
                        note = 2'-deoxycytidine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxythymidine 3'-phosphorothioate
modified_base           11
                        mod_base = OTHER
                        note = 2'-deoxyguanosine 3'-phosphorothioate
modified_base           12
                        mod_base = OTHER
                        note = 2'-deoxyadenosine 3'-phosphorothioate
modified_base           13
                        mod_base = OTHER
                        note = 2'-deoxycytidine 3'-phosphorothioate
modified_base           14
                        mod_base = OTHER
                        note = 2'-deoxyadenosine 3'-phosphorothioate
modified_base           15
                        mod_base = OTHER
                        note = 2'-O-methoxyethyl thymidine 3'-phosphorothioate
modified_base           16
                        mod_base = OTHER
                        note = 2'-O-methoxyethyl guanosine 3'-phosphorothioate
modified_base           17
                        mod_base = OTHER
                        note = 2'-O-methoxyethyl cytidine 3'-phosphorothioate
modified_base           18
                        mod_base = OTHER
                        note = 2'-O-methoxyethyl adenosine 3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 290
tcccgcctgt gacatgcatt                                            20

SEQ ID NO: 291          moltype = DNA  length = 20
FEATURE                 Location/Qualifiers
source                  1..20
                        mol_type = other DNA
                        organism = synthetic construct
modified_base           1..3
                        mod_base = OTHER
                        note = 2'-O-methoxyethyl guanosine 3'-phosphorothioate
modified_base           4
                        mod_base = OTHER
                        note = 2'-O-methoxyethyl adenosine 3'-phosphorothioate
modified_base           5
                        mod_base = OTHER
                        note = 2'-deoxycytidine 3'-phosphorothioate
modified_base           6
                        mod_base = OTHER
                        note = 2'-deoxyguanosine 3'-phosphorothioate
modified_base           7
                        mod_base = OTHER
                        note = 2'-deoxycytidine 3'-phosphorothioate
modified_base           8..9
                        mod_base = OTHER
                        note = 2'-deoxyguanosine 3'-phosphorothioate
modified_base           10
                        mod_base = OTHER
                        note = 2'-deoxycytidine 3'-phosphorothioate
modified_base           11
                        mod_base = OTHER
                        note = 2'-deoxyguanosine 3'-phosphorothioate
modified_base           12
                        mod_base = OTHER
                        note = 2'-deoxycytidine 3'-phosphorothioate
modified_base           13
```

```
                        mod_base = OTHER
                        note = 2'-deoxythymidine 3'-phosphorothioate
modified_base           14
                        mod_base = OTHER
                        note = 2'-deoxycytidine 3'-phosphorothioate
modified_base           15..16
                        mod_base = OTHER
                        note = 2'-deoxyguanosine 3'-phosphorothioate
modified_base           17
                        mod_base = OTHER
                        note = 2'-O-methoxyethyl thymidine 3'-phosphorothioate
modified_base           18
                        mod_base = OTHER
                        note = 2'-O-methoxyethyl cytidine 3'-phosphorothioate
modified_base           19
                        mod_base = OTHER
                        note = 2'-O-methoxyethyl adenosine 3'-phosphorothioate
modified_base           20
                        mod_base = OTHER
                        note = 2'-O-methoxyethyl thymidine
SEQUENCE: 291
gggacgcggc gctcggtcat                                              20

SEQ ID NO: 292          moltype = DNA  length = 20
FEATURE                 Location/Qualifiers
source                  1..20
                        mol_type = other DNA
                        organism = synthetic construct
modified_base           1..2
                        mod_base = OTHER
                        note = 2'-O-methoxyethyl cytidine 3'-phosphorothioate
modified_base           4
                        mod_base = OTHER
                        note = 2'-O-methoxyethyl cytidine 3'-phosphorothioate
modified_base           3
                        mod_base = OTHER
                        note = 2'-O-methoxyethyl adenosine 3'-phosphorothioate
modified_base           5
                        mod_base = OTHER
                        note = 2'-O-methoxyethyl adenosine 3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxycytidine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxythymidine 3'-phosphorothioate
modified_base           12..13
                        mod_base = OTHER
                        note = 2'-deoxycytidine 3'-phosphorothioate
modified_base           14
                        mod_base = OTHER
                        note = 2'-deoxyadenosine 3'-phosphorothioate
modified_base           15
                        mod_base = OTHER
                        note = 2'-deoxyguanosine 3'-phosphorothioate
modified_base           16
                        mod_base = OTHER
                        note = 2'-O-methoxyethyl thymidine 3'-phosphorothioate
modified_base           17
                        mod_base = OTHER
                        note = 2'-O-methoxyethyl cytidine 3'-phosphorothioate
modified_base           18
                        mod_base = OTHER
                        note = 2'-O-methoxyethyl thymidine 3'-phosphorothioate
modified_base           19
                        mod_base = OTHER
                        note = 2'-O-methoxyethyl adenosine 3'-phosphorothioate
```

```
modified_base          20
                       mod_base = OTHER
                       note = 2'-O-methoxyethyl adenosine
SEQUENCE: 292
ccacaagctg tccagtctaa                                                  20

SEQ ID NO: 293         moltype = DNA  length = 20
FEATURE                Location/Qualifiers
source                 1..20
                       mol_type = other DNA
                       organism = synthetic construct
modified_base          1..2
                       mod_base = OTHER
                       note = 2'-O-methoxyethyl cytidine 3'-phosphorothioate
modified_base          3
                       mod_base = OTHER
                       note = 2'-O-methoxyethyl guanosine 3'-phosphorothioate
modified_base          4
                       mod_base = OTHER
                       note = 2'-deoxycytidine 3'-phosphorothioate
modified_base          5
                       mod_base = OTHER
                       note = 2'-deoxyadenosine 3'-phosphorothioate
modified_base          6
                       mod_base = OTHER
                       note = 2'-deoxyguanosine 3'-phosphorothioate
modified_base          7..8
                       mod_base = OTHER
                       note = 2'-deoxycytidine 3'-phosphorothioate
modified_base          9
                       mod_base = OTHER
                       note = 2'-deoxyadenosine 3'-phosphorothioate
modified_base          10
                       mod_base = OTHER
                       note = 2'-deoxythymidine 3'-phosphorothioate
modified_base          11
                       mod_base = OTHER
                       note = 2'-deoxyguanosine 3'-phosphorothioate
modified_base          12
                       mod_base = OTHER
                       note = 2'-deoxycytidine 3'-phosphorothioate
modified_base          13
                       mod_base = OTHER
                       note = 2'-O-methoxyethyl guanosine 3'-phosphorothioate
modified_base          14
                       mod_base = OTHER
                       note = 2'-O-methoxyethyl cytidine 3'-phosphorothioate
modified_base          15
                       mod_base = OTHER
                       note = 2'-O-methoxyethyl thymidine 3'-phosphorothioate
modified_base          16
                       mod_base = OTHER
                       note = 2'-O-methoxyethyl cytidine 3'-phosphorothioate
modified_base          17..18
                       mod_base = OTHER
                       note = 2'-O-methoxyethyl thymidine 3'-phosphorothioate
modified_base          19
                       mod_base = OTHER
                       note = 2'-O-methoxyethyl guanosine 3'-phosphorothioate
modified_base          20
                       mod_base = OTHER
                       note = 2'-O-methoxyethyl guanosine
SEQUENCE: 293
ccgcagccat gcgctcttgg                                                  20

SEQ ID NO: 294         moltype = DNA  length = 21
FEATURE                Location/Qualifiers
source                 1..21
                       mol_type = other DNA
                       organism = synthetic construct
modified_base          1
                       mod_base = OTHER
                       note = 2'-deoxyguanosine 3'-phosphorothioate
modified_base          2..3
                       mod_base = OTHER
                       note = 2'-deoxythymidine 3'-phosphorothioate
modified_base          4
                       mod_base = OTHER
                       note = 2-amino-2'-deoxyadenosine phosphorothioate
```

```
modified_base          5
                       mod_base = OTHER
                       note = 2'-deoxycytidine 3'-phosphorothioate
modified_base          6
                       mod_base = OTHER
                       note = 2'-deoxythymidine 3'-phosphorothioate
modified_base          7
                       mod_base = OTHER
                       note = 2-amino-2'-deoxyadenosine phosphorothioate
modified_base          8
                       mod_base = OTHER
                       note = 2'-deoxycytidine 3'-phosphorothioate
modified_base          9..10
                       mod_base = OTHER
                       note = 2'-deoxythymidine 3'-phosphorothioate
modified_base          11..12
                       mod_base = OTHER
                       note = 2'-deoxycytidine 3'-phosphorothioate
modified_base          13
                       mod_base = OTHER
                       note = 2-amino-2'-deoxyadenosine phosphorothioate
modified_base          14..15
                       mod_base = OTHER
                       note = 2'-deoxycytidine 3'-phosphorothioate
modified_base          16
                       mod_base = OTHER
                       note = 2'-deoxythymidine 3'-phosphorothioate
modified_base          17
                       mod_base = OTHER
                       note = 2'-deoxyguanosine 3'-phosphorothioate
modified_base          18..19
                       mod_base = OTHER
                       note = 2'-deoxycytidine 3'-phosphorothioate
modified_base          20
                       mod_base = OTHER
                       note = 2'-deoxythymidine 3'-phosphorothioate
modified_base          21
                       mod_base = OTHER
                       note = 2'-deoxyguanosine
SEQUENCE: 294
gttactactt ccacctgcct g                                      21

SEQ ID NO: 295         moltype = DNA  length = 21
FEATURE                Location/Qualifiers
source                 1..21
                       mol_type = other DNA
                       organism = synthetic construct
modified_base          1
                       mod_base = OTHER
                       note = 2'-O-methoxyethyl cytidine 3'-phosphorothioate
modified_base          2
                       mod_base = OTHER
                       note = 2'-O-methoxyethyl adenosine 3'-phosphorothioate
modified_base          3
                       mod_base = OTHER
                       note = 2'-O-methoxyethyl guanosine 3'-phosphorothioate
modified_base          4
                       mod_base = OTHER
                       note = 2'-O-methoxyethyl cytidine 3'-phosphorothioate
modified_base          5
                       mod_base = OTHER
                       note = 2'-deoxyadenosine 3'-phosphorothioate
modified_base          6
                       mod_base = OTHER
                       note = 2'-deoxyguanosine 3'-phosphorothioate
modified_base          7
                       mod_base = OTHER
                       note = 2'-deoxycytidine 3'-phosphorothioate
modified_base          8
                       mod_base = OTHER
                       note = 2'-deoxyadenosine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxyadenosine 3'-phosphorothioate
modified_base          11
                       mod_base = OTHER
```

```
                        note = 2'-deoxyguanosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxycytidine 3'-phosphorothioate
modified_base           14..15
                        mod_base = OTHER
                        note = 2'-deoxythymidine 3'-phosphorothioate
modified_base           16
                        mod_base = OTHER
                        note = 2'-deoxycytidine 3'-phosphorothioate
modified_base           17
                        mod_base = OTHER
                        note = 2'-deoxyadenosine 3'-phosphorothioate
modified_base           18
                        mod_base = OTHER
                        note = 2'-O-methoxyethyl thymidine 3'-phosphorothioate
modified_base           19
                        mod_base = OTHER
                        note = 2'-O-methoxyethyl cytidine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl thymidine
SEQUENCE: 295
cagcagcaga gtcttcatca t                                              21

SEQ ID NO: 296          moltype = DNA  length = 14
FEATURE                 Location/Qualifiers
source                  1..14
                        mol_type = other DNA
                        organism = Synthetic construct
modified_base           1
                        mod_base = OTHER
                        note = 3'-fluoro hexitol nucleic acid thymidine
                         3'-phosphorothioate
modified_base           2
                        mod_base = OTHER
                        note = 3'-fluoro hexitol nucleic acid 5-methylcytidine
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           5
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           13
                        mod_base = OTHER
                        note = 3'-fluoro hexitol nucleic acid thymidine
                         3'-phosphorothioate
modified_base           14
```

```
                         mod_base = OTHER
                         note = 3'-fluoro hexitol nucleic acid 5-methylcytidine
SEQUENCE: 296
tcagtcatga cttc                                                  14

SEQ ID NO: 297           moltype = DNA  length = 14
FEATURE                  Location/Qualifiers
source                   1..14
                         mol_type = other DNA
                         organism = Synthetic construct
modified_base            1
                         mod_base = OTHER
                         note = constrained ethyl thymidine 3'-phosphorothioate
modified_base            2
                         mod_base = OTHER
                         note = constrained ethyl 5-methylcytidine
                          3'-phosphorothioate
modified_base            3
                         mod_base = OTHER
                         note = 2'-deoxyadenosine 3'-phosphorothioate
modified_base            4
                         mod_base = OTHER
                         note = 2'-deoxyguanosine 3'-phosphorothioate
modified_base            5
                         mod_base = OTHER
                         note = 2'-deoxythymidine 3'-phosphorothioate
modified_base            6
                         mod_base = OTHER
                         note = 5-methyl-2'-deoxycytidine 3'-phosphorothioate
modified_base            7
                         mod_base = OTHER
                         note = 2'-deoxyadenosine 3'-phosphorothioate
modified_base            8
                         mod_base = OTHER
                         note = 2'-deoxythymidine 3'-phosphorothioate
modified_base            9
                         mod_base = OTHER
                         note = 2'-deoxyguanosine 3'-phosphorothioate
modified_base            10
                         mod_base = OTHER
                         note = 2'-deoxyadenosine 3'-phosphorothioate
modified_base            11
                         mod_base = OTHER
                         note = 5-methyl-2'-deoxycytidine 3'-phosphorothioate
modified_base            12
                         mod_base = OTHER
                         note = 2'-deoxythymidine 3'-phosphorothioate
modified_base            13
                         mod_base = OTHER
                         note = constrained ethyl thymidine 3'-phosphorothioate
modified_base            14
                         mod_base = OTHER
                         note = constrained ethyl 5-methylcytidine
SEQUENCE: 297
tcagtcatga cttc                                                  14

SEQ ID NO: 298           moltype = DNA  length = 14
FEATURE                  Location/Qualifiers
source                   1..14
                         mol_type = other DNA
                         organism = Synthetic construct
modified_base
                         mod_base = OTHER
                         note = triantennary N-acetylgalactosamine conjugate3a
                          phosphodiester
modified_base            1
                         mod_base = OTHER
                         note = constrained ethyl thymidine 3'-phosphorothioate
modified_base            2
                         mod_base = OTHER
                         note = constrained ethyl 5-methylcytidine
                          3'-phosphorothioate
modified_base            3
                         mod_base = OTHER
                         note = 2'-deoxyadenosine 3'-phosphorothioate
modified_base            4
                         mod_base = OTHER
                         note = 2'-deoxyguanosine 3'-phosphorothioate
modified_base            5
```

```
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           13
                        mod_base = OTHER
                        note = constrained ethyl thymidine 3'-phosphorothioate
modified_base           14
                        mod_base = OTHER
                        note = constrained ethyl 5-methylcytidine
SEQUENCE: 298
tcagtcatga cttc                                                 14

SEQ ID NO: 299          moltype = DNA  length = 14
FEATURE                 Location/Qualifiers
source                  1..14
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
                        note = constrained ethyl thymidine 3'-phosphorothioate
modified_base           2
                        mod_base = OTHER
                        note = constrained ethyl 5-methylcytidine
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           5
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           13
```

```
                        mod_base = OTHER
                        note = constrained ethyl thymidine 3'-phosphorothioate
modified_base           14
                        mod_base = OTHER
                        note = constrained ethyl 5-methylcytidine
SEQUENCE: 299
tcagtcatga cttc                                                    14

SEQ ID NO: 300          moltype = DNA  length = 14
FEATURE                 Location/Qualifiers
source                  1..14
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = locked nucleic acid thymidine 3'-phosphorothioate
modified_base           2
                        mod_base = OTHER
                        note = locked nucleic acid 5-methylcytidine
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           5
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           13
                        mod_base = OTHER
                        note = locked nucleic acid thymidine 3'-phosphorothioate
modified_base           14
                        mod_base = OTHER
                        note = locked nucleic acid 5-methylcytidine
SEQUENCE: 300
tcagtcatga cttc                                                    14

SEQ ID NO: 301          moltype = DNA  length = 14
FEATURE                 Location/Qualifiers
source                  1..14
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 3'-fluoro hexitol nucleic acid thymidine
                         3'-phosphorothioate
modified_base           2
                        mod_base = OTHER
                        note = 3'-fluoro hexitol nucleic acid 5-methylcytidine
```

-continued

```
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           5
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           12
                        mod_base = OTHER
                        note = 3'-fluoro hexitol nucleic acid thymidine
                         3'-phosphorothioate
modified_base           14
                        mod_base = OTHER
                        note = 3'-fluoro hexitol nucleic acid 5-methylcytidine
SEQUENCE: 301
tcagtcatga cttc                                                  14

SEQ ID NO: 302          moltype = DNA  length = 14
FEATURE                 Location/Qualifiers
source                  1..14
                        mol_type = other DNA
                        organism = Synthetic construct
modified_base
                        mod_base = OTHER
                        note = N-acetylgalactosamine conjugate 25a phosphodiester
modified_base           1
                        mod_base = OTHER
                        note = constrained ethyl thymidine 3'-phosphorothioate
modified_base           2
                        mod_base = OTHER
                        note = constrained ethyl 5-methylcytidine
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           5
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
```

```
                       note = 2'-deoxyadenosine 3'-phosphorothioate
modified_base          11
                       mod_base = OTHER
                       note = 5-methyl-2'-deoxycytidine 3'-phosphorothioate
modified_base          12
                       mod_base = OTHER
                       note = 2'-deoxythymidine 3'-phosphorothioate
modified_base          13
                       mod_base = OTHER
                       note = constrained ethyl thymidine 3'-phosphorothioate
modified_base          14
                       mod_base = OTHER
                       note = constrained ethyl 5-methylcytidine
SEQUENCE: 302
tcagtcatga cttc                                                   14

SEQ ID NO: 303         moltype = DNA  length = 15
FEATURE                Location/Qualifiers
source                 1..15
                       mol_type = other DNA
                       organism = Synthetic construct
modified_base          1
                       mod_base = OTHER
                       note = constrained ethyl thymidine 3'-phosphorothioate
modified_base          2
                       mod_base = OTHER
                       note = constrained ethyl 5-methylcytidine
                        3'-phosphorothioate
modified_base          3
                       mod_base = OTHER
                       note = 2'-deoxyadenosine 3'-phosphorothioate
modified_base          4
                       mod_base = OTHER
                       note = 2'-deoxyguanosine 3'-phosphorothioate
modified_base          5
                       mod_base = OTHER
                       note = 2'-deoxythymidine 3'-phosphorothioate
modified_base          6
                       mod_base = OTHER
                       note = 5-methyl-2'-deoxycytidine 3'-phosphorothioate
modified_base          7
                       mod_base = OTHER
                       note = 2'-deoxyadenosine 3'-phosphorothioate
modified_base          8
                       mod_base = OTHER
                       note = 2'-deoxythymidine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxyadenosine 3'-phosphorothioate
modified_base          11
                       mod_base = OTHER
                       note = 5-methyl-2'-deoxycytidine 3'-phosphorothioate
modified_base          12
                       mod_base = OTHER
                       note = 2'-deoxythymidine 3'-phosphorothioate
modified_base          13
                       mod_base = OTHER
                       note = constrained ethyl thymidine 3'-phosphorothioate
modified_base          14
                       mod_base = OTHER
                       note = constrained ethyl 5-methylcytidine 3'-phosphodiester
modified_base          15
                       mod_base = OTHER
                       note = triantennary N-acetylgalactosamine conjugate1a
SEQUENCE: 303
tcagtcatga cttca                                                  15

SEQ ID NO: 304         moltype = DNA  length = 15
FEATURE                Location/Qualifiers
source                 1..15
                       mol_type = other DNA
                       organism = Synthetic construct
modified_base          1
                       mod_base = OTHER
                       note = locked nucleic acid thymidine 3'-phosphorothioate
modified_base          2
```

```
                        mod_base = OTHER
                        note = locked nucleic acid 5-methylcytidine
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           5
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           13
                        mod_base = OTHER
                        note = locked nucleic acid thymidine 3'-phosphorothioate
modified_base           14
                        mod_base = OTHER
                        note = locked nucleic acid 5-methylcytidine
                         3'-phosphodiester
modified_base           15
                        mod_base = OTHER
                        note = triantennary N-acetylgalactosamine conjugate1a
SEQUENCE: 304
tcagtcatga cttca                                            15

SEQ ID NO: 305          moltype = DNA  length = 15
FEATURE                 Location/Qualifiers
source                  1..15
                        mol_type = other DNA
                        organism = Synthetic construct
modified_base
                        mod_base = OTHER
                        note = triantennary N-acetylgalactosamine conjugate2a
                         phosphodiester
modified_base           2
                        mod_base = OTHER
                        note = constrained ethyl thymidine 3'-phosphorothioate
modified_base           3
                        mod_base = OTHER
                        note = constrained ethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
```

```
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = constrained ethyl 5-methylcytidine
SEQUENCE: 305
atcagtcatg acttc                                                  15

SEQ ID NO: 306          moltype = DNA  length = 15
FEATURE                 Location/Qualifiers
source                  1..15
                        mol_type = other DNA
                        organism = Synthetic construct
modified_base           1
                        mod_base = OTHER
                        note = constrained ethyl thymidine 3'-phosphorothioate
modified_base           2
                        mod_base = OTHER
                        note = constrained ethyl 5-methylcytidine
                         3'-phosphorothioate
modified_base           3
                        mod_base = OTHER
                        note = 2'-deoxyadenosine 3'-phosphorothioate
modified_base           4
                        mod_base = OTHER
                        note = 2'-deoxyguanosine 3'-phosphorothioate
modified_base           15
                        mod_base = OTHER
                        note = 2'-deoxythymidine 3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxythymidine 3'-phosphorothioate
modified_base           13
                        mod_base = OTHER
                        note = constrained ethyl thymidine 3'-phosphorothioate
modified_base           14
                        mod_base = OTHER
                        note = constrained ethyl 5-methylcytidine 3'-phosphodiester
modified_base           15
                        mod_base = OTHER
                        note = tetrantennary N-acetylgalactosamine conjugate 11a
SEQUENCE: 306
tcagtcatga cttca                                                  15

SEQ ID NO: 307          moltype = DNA  length = 15
FEATURE                 Location/Qualifiers
source                  1..15
```

```
                        mol_type = other DNA
                        organism = Synthetic construct
modified_base
                        mod_base = OTHER
                        note = biantennary N-acetylgalactosamine conjugate24a
                         phosphodiester
modified_base           2
                        mod_base = OTHER
                        note = constrained ethyl thymidine 3'-phosphorothioate
modified_base           3
                        mod_base = OTHER
                        note = constrained ethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = constrained ethyl 5-methylcytidine
SEQUENCE: 307
atcagtcatg acttc                                                15

SEQ ID NO: 308          moltype = DNA  length = 15
FEATURE                 Location/Qualifiers
source                  1..15
                        mol_type = other DNA
                        organism = Synthetic construct
modified_base
                        mod_base = OTHER
                        note = triantennary N-acetylgalactosamine conjugate13a
                         phosphodiester
modified_base           2
                        mod_base = OTHER
                        note = constrained ethyl thymidine 3'-phosphorothioate
modified_base           3
                        mod_base = OTHER
                        note = constrained ethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
```

-continued

```
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = constrained ethyl 5-methylcytidine
SEQUENCE: 308
atcagtcatg acttc                                                     15

SEQ ID NO: 309          moltype = DNA  length = 16
FEATURE                 Location/Qualifiers
source                  1..16
                        mol_type = other DNA
                        organism = Synthetic construct
modified_base           1..2
                        mod_base = OTHER
                        note = constrained ethyl thymidine 3'-phosphorothioate
modified_base           3
                        mod_base = OTHER
                        note = constrained ethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = constrained ethyl 5-methylcytidine
                         3'-phosphorothioate
modified_base           16
                        mod_base = OTHER
```

```
                        note = constrained ethyl 5-methylcytidine
SEQUENCE: 309
ttcagtcatg acttcc                                                16

SEQ ID NO: 310          moltype = DNA  length = 16
FEATURE                 Location/Qualifiers
source                  1..16
                        mol_type = other DNA
                        organism = Synthetic construct
modified_base
                        mod_base = OTHER
                        note = triantennary N-acetylgalactosamine conjugate3a
                         phosphodiester
modified_base           1..2
                        mod_base = OTHER
                        note = constrained ethyl thymidine 3'-phosphorothioate
modified_base           3
                        mod_base = OTHER
                        note = constrained ethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = constrained ethyl 5-methylcytidine
                         3'-phosphorothioate
modified_base           16
                        mod_base = OTHER
                        note = constrained ethyl 5-methylcytidine
SEQUENCE: 310
ttcagtcatg acttcc                                                16

SEQ ID NO: 311          moltype = DNA  length = 16
FEATURE                 Location/Qualifiers
source                  1..16
                        mol_type = other DNA
                        organism = Synthetic construct
modified_base
                        mod_base = OTHER
                        note = triantennary N-acetylgalactosamine conjugate7a
                         phosphodiester
modified_base           1..2
                        mod_base = OTHER
                        note = constrained ethyl thymidine 3'-phosphorothioate
modified_base           3
                        mod_base = OTHER
                        note = constrained ethyl 5-methylcytidine
                         3'-phosphorothioate
```

-continued

```
modified_base          4
                       mod_base = OTHER
                       note = 2'-deoxyadenosine 3'-phosphorothioate
modified_base          5
                       mod_base = OTHER
                       note = 2'-deoxyguanosine 3'-phosphorothioate
modified_base          6
                       mod_base = OTHER
                       note = 2'-deoxythymidine 3'-phosphorothioate
modified_base          7
                       mod_base = OTHER
                       note = 5-methyl-2'-deoxycytidine 3'-phosphorothioate
modified_base          8
                       mod_base = OTHER
                       note = 2'-deoxyadenosine 3'-phosphorothioate
modified_base          9
                       mod_base = OTHER
                       note = 2'-deoxythymidine 3'-phosphorothioate
modified_base          10
                       mod_base = OTHER
                       note = 2'-deoxyguanosine 3'-phosphorothioate
modified_base          11
                       mod_base = OTHER
                       note = 2'-deoxyadenosine 3'-phosphorothioate
modified_base          12
                       mod_base = OTHER
                       note = 5-methyl-2'-deoxycytidine 3'-phosphorothioate
modified_base          13
                       mod_base = OTHER
                       note = 2'-deoxythymidine 3'-phosphorothioate
modified_base          14
                       mod_base = OTHER
                       note = constrained ethyl thymidine 3'-phosphorothioate
modified_base          15
                       mod_base = OTHER
                       note = constrained ethyl 5-methylcytidine
                        3'-phosphorothioate
modified_base          16
                       mod_base = OTHER
                       note = constrained ethyl 5-methylcytidine
SEQUENCE: 311
ttcagtcatg acttcc                                                  16

SEQ ID NO: 312         moltype = DNA  length = 16
FEATURE                Location/Qualifiers
source                 1..16
                       mol_type = other DNA
                       organism = Synthetic construct
modified_base
                       mod_base = OTHER
                       note = triantennary N-acetylgalactosamine conjugate7a
                        phosphodiester
modified_base          1..2
                       mod_base = OTHER
                       note = constrained ethyl thymidine 3'-phosphorothioate
modified_base          3
                       mod_base = OTHER
                       note = constrained ethyl 5-methylcytidine
                        3'-phosphorothioate
modified_base          4
                       mod_base = OTHER
                       note = 2'-deoxyadenosine 3'-phosphorothioate
modified_base          5
                       mod_base = OTHER
                       note = 2'-deoxyguanosine 3'-phosphorothioate
modified_base          6
                       mod_base = OTHER
                       note = 2'-deoxythymidine 3'-phosphorothioate
modified_base          7
                       mod_base = OTHER
                       note = 5-methyl-2'-deoxycytidine 3'-phosphorothioate
modified_base          8
                       mod_base = OTHER
                       note = 2'-deoxyadenosine 3'-phosphorothioate
modified_base          9
                       mod_base = OTHER
                       note = 2'-deoxythymidine 3'-phosphorothioate
modified_base          10
                       mod_base = OTHER
```

```
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = 2'-O-methoxyethyl thymidine 3'-phosphorothioate
modified_base           15
                        mod_base = OTHER
                        note = 2'-O-methoxyethyl 5-methylcytidine
                         3'-phosphorothioate
modified_base           16
                        mod_base = OTHER
                        note = 2'-O-methoxyethyl 5-methylcytidine
SEQUENCE: 312
ttcagtcatg acttcc                                                  16

SEQ ID NO: 313          moltype = DNA  length = 16
FEATURE                 Location/Qualifiers
source                  1..16
                        mol_type = other DNA
                        organism = Synthetic construct
modified_base
                        mod_base = OTHER
                        note = triantennary N-acetylgalactosamine conjugate7a
                         phosphodiester
modified_base           1..2
                        mod_base = OTHER
                        note = 2'-O-methoxyethyl thymidine 3'-phosphorothioate
modified_base           3
                        mod_base = OTHER
                        note = 2'-O-methoxyethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = constrained ethyl 5-methylcytidine
                         3'-phosphorothioate
modified_base           16
                        mod_base = OTHER
                        note = constrained ethyl 5-methylcytidine
```

-continued

```
SEQUENCE: 313
ttcagtcatg acttcc                                                 16

SEQ ID NO: 314          moltype = DNA  length = 16
FEATURE                 Location/Qualifiers
source                  1..16
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
                        note = constrained ethyl thymidine 3'-phosphorothioate
modified_base           2
                        mod_base = OTHER
                        note = 2'-deoxythymidine 3'-phosphorothioate
modified_base           3
                        mod_base = OTHER
                        note = constrained ethyl 5-methylcytidine
                         3'-phosphorothioate
modified_base           4
                        mod_base = OTHER
                        note = 2'-deoxyadenosine 3'-phosphorothioate
modified_base           5
                        mod_base = OTHER
                        note = 2'-deoxyguanosine 3'-phosphorothioate
modified_base           6
                        mod_base = OTHER
                        note = 2'-deoxythymidine 3'-phosphorothioate
modified_base           7
                        mod_base = OTHER
                        note = 5-methyl-2'-deoxycytidine 3'-phosphorothioate
modified_base           8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13
                        mod_base = OTHER
                        note = 2'-deoxythymidine 3'-phosphorothioate
modified_base           14
                        mod_base = OTHER
                        note = constrained ethyl thymidine 3'-phosphorothioate
modified_base           15
                        mod_base = OTHER
                        note = 5-methyl-2'-deoxycytidine 3'-phosphorothioate
modified_base           16
                        mod_base = OTHER
                        note = constrained ethyl 5-methylcytidine
SEQUENCE: 314
ttcagtcatg acttcc                                                 16

SEQ ID NO: 315          moltype = DNA  length = 16
FEATURE                 Location/Qualifiers
source                  1..16
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
                        note = 2'-O-methoxyethyl thymidine 3'-phosphorothioate
modified_base           2
                        mod_base = OTHER
                        note = constrained ethyl thymidine 3'-phosphorothioate
```

```
modified_base          3
                       mod_base = OTHER
                       note = constrained ethyl 5-methylcytidine
                        3'-phosphorothioate
modified_base          4
                       mod_base = OTHER
                       note = 2'-deoxyadenosine 3'-phosphorothioate
modified_base          5
                       mod_base = OTHER
                       note = 2'-deoxyguanosine 3'-phosphorothioate
modified_base          6
                       mod_base = OTHER
                       note = 2'-deoxythymidine 3'-phosphorothioate
modified_base          7
                       mod_base = OTHER
                       note = 5-methyl-2'-deoxycytidine 3'-phosphorothioate
modified_base          8
                       mod_base = OTHER
                       note = 2'-deoxyadenosine 3'-phosphorothioate
modified_base          9
                       mod_base = OTHER
                       note = 2'-deoxythymidine 3'-phosphorothioate
modified_base          10
                       mod_base = OTHER
                       note = 2'-deoxyguanosine 3'-phosphorothioate
modified_base          11
                       mod_base = OTHER
                       note = 2'-deoxyadenosine 3'-phosphorothioate
modified_base          12
                       mod_base = OTHER
                       note = 5-methyl-2'-deoxycytidine 3'-phosphorothioate
modified_base          13
                       mod_base = OTHER
                       note = 2'-deoxythymidine 3'-phosphorothioate
modified_base          14
                       mod_base = OTHER
                       note = constrained ethyl thymidine 3'-phosphorothioate
modified_base          15
                       mod_base = OTHER
                       note = constrained ethyl 5-methylcytidine
                        3'-phosphorothioate
modified_base          16
                       mod_base = OTHER
                       note = 2'-O-methoxyethyl 5-methylcytidine
SEQUENCE: 315
ttcagtcatg acttcc                                                   16

SEQ ID NO: 316         moltype = DNA  length = 20
FEATURE                Location/Qualifiers
source                 1..20
                       mol_type = other DNA
                       organism = Synthetic construct
modified_base          1
                       mod_base = OTHER
                       note = 2'-O-methoxyethyl guanosine 3'-phosphorothioate
modified_base          2
                       mod_base = OTHER
                       note = 2'-O-methoxyethyl 5-methylcytidine
                        3'-phosphorothioate
modified_base          3
                       mod_base = OTHER
                       note = 2'-O-methoxyethyl thymidine 3'-phosphorothioate
modified_base          4
                       mod_base = OTHER
                       note = 2'-O-methoxyethyl guanosine 3'-phosphorothioate
modified_base          5
                       mod_base = OTHER
                       note = 2'-O-methoxyethyl adenosine 3'-phosphorothioate
modified_base          6..7
                       mod_base = OTHER
                       note = 2'-deoxythymidine 3'-phosphorothioate
modified_base          8
                       mod_base = OTHER
                       note = 2'-deoxyadenosine 3'-phosphorothioate
modified_base          9
                       mod_base = OTHER
                       note = 2'-deoxyguanosine 3'-phosphorothioate
modified_base          10
                       mod_base = OTHER
```

```
                        note = 2'-deoxyadenosine 3'-phosphorothioate
modified_base           11
                        mod_base = OTHER
                        note = 2'-deoxyguanosine 3'-phosphorothioate
modified_base           12
                        mod_base = OTHER
                        note = 2'-deoxyadenosine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 2'-deoxyguanosine 3'-phosphorothioate
modified_base           16
                        mod_base = OTHER
                        note = 2'-O-methoxyethyl guanosine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine
SEQUENCE: 316
gctgattaga gagaggtccc                                          20

SEQ ID NO: 317          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl adenosine 3'-phosphorothioate
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 5-methyl-2'-deoxycytidine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxythymidine 3'-phosphorothioate
modified_base           11..12
                        mod_base = OTHER
                        note = 5-methyl-2'-deoxycytidine 3'-phosphorothioate
modified_base           13
                        mod_base = OTHER
                        note = 2'-deoxyadenosine 3'-phosphorothioate
modified_base           14
                        mod_base = OTHER
                        note = 2'-deoxyguanosine 3'-phosphorothioate
modified_base           15
                        mod_base = OTHER
                        note = 5-methyl-2'-deoxycytidine 3'-phosphorothioate
modified_base           16..18
                        mod_base = OTHER
                        note = 2'-O-methoxyethyl thymidine 3'-phosphorothioate
modified_base           19
                        mod_base = OTHER
```

```
                         note = 2'-O-methoxyethyl adenosine 3'-phosphorothioate
modified_base            20
                         mod_base = OTHER
                         note = 2'-O-methoxyethyl thymidine
SEQUENCE: 317
agcttcttgt ccagctttat                                              20

SEQ ID NO: 318           moltype = DNA  length = 20
FEATURE                  Location/Qualifiers
source                   1..20
                         mol_type = other DNA
                         organism = Synthetic construct
modified_base            1
                         mod_base = OTHER
                         note = 2'-O-methoxyethyl guanosine 3'-phosphorothioate
modified_base            2
                         mod_base = OTHER
                         note = 2'-O-methoxyethyl 5-methylcytidine
                          3'-phosphorothioate
modified_base            3..4
                         mod_base = OTHER
                         note = 2'-O-methoxyethyl thymidine 3'-phosphorothioate
modified_base            5
                         mod_base = OTHER
                         note = 2'-O-methoxyethyl 5-methylcytidine
                          3'-phosphorothioate
modified_base            6
                         mod_base = OTHER
                         note = 2'-deoxyadenosine 3'-phosphorothioate
modified_base            7
                         mod_base = OTHER
                         note = 2'-deoxyguanosine 3'-phosphorothioate
modified_base            8
                         mod_base = OTHER
                         note = 2'-deoxythymidine 3'-phosphorothioate
modified_base            9
                         mod_base = OTHER
                         note = 5-methyl-2'-deoxycytidine 3'-phosphorothioate
modified_base            10
                         mod_base = OTHER
                         note = 2'-deoxyadenosine 3'-phosphorothioate
modified_base            11
                         mod_base = OTHER
                         note = 2'-deoxythymidine 3'-phosphorothioate
modified_base            12
                         mod_base = OTHER
                         note = 2'-deoxyguanosine 3'-phosphorothioate
modified_base            13
                         mod_base = OTHER
                         note = 2'-deoxyadenosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
                         note = 2'-O-methoxyethyl thymidine 3'-phosphorothioate
modified_base            17..18
                         mod_base = OTHER
                         note = 2'-O-methoxyethyl 5-methylcytidine
                          3'-phosphorothioate
modified_base            19
                         mod_base = OTHER
                         note = 2'-O-methoxyethyl thymidine 3'-phosphorothioate
modified_base            20
                         mod_base = OTHER
                         note = 2'-O-methoxyethyl thymidine
SEQUENCE: 318
gcttcagtca tgacttcctt                                              20

SEQ ID NO: 319           moltype = DNA  length = 20
FEATURE                  Location/Qualifiers
source                   1..20
                         mol_type = other DNA
                         organism = Synthetic construct
modified_base            1
                         mod_base = OTHER
```

```
                        note = 2'-O-methoxyethyl thymidine 3'-phosphorothioate
modified_base           2..3
                        mod_base = OTHER
                        note = 2'-O-methoxyethyl 5-methylcytidine
                         3'-phosphorothioate
modified_base           4
                        mod_base = OTHER
                        note = 5-methyl-2'-deoxycytidine 3'-phosphorothioate
modified_base           5
                        mod_base = OTHER
                        note = 2'-deoxyadenosine 3'-phosphorothioate
modified_base           6..8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11..12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 2'-deoxyguanosine 3'-phosphorothioate
modified_base           15
                        mod_base = OTHER
                        note = 2'-deoxyadenosine 3'-phosphorothioate
modified_base           16..17
                        mod_base = OTHER
                        note = 5-methyl-2'-deoxycytidine 3'-phosphorothioate
modified_base           18
                        mod_base = OTHER
                        note = 2'-O-methoxyethyl thymidine 3'-phosphorothioate
modified_base           19
                        mod_base = OTHER
                        note = 2'-O-methoxyethyl guanosine 3'-phosphorothioate
modified_base           20
                        mod_base = OTHER
                        note = 2'-O-methoxyethyl guanosine
SEQUENCE: 319
tcccatttca ggagacctgg                                            20

SEQ ID NO: 320          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl adenosine 3'-phosphorothioate
modified_base           2..3
                        mod_base = OTHER
                        note = 2'-O-methoxyethyl thymidine 3'-phosphorothioate
modified_base           4
                        mod_base = OTHER
                        note = 2'-O-methoxyethyl 5-methylcytidine
                         3'-phosphorothioate
modified_base           5
                        mod_base = OTHER
                        note = 2'-O-methoxyethyl adenosine 3'-phosphorothioate
modified_base           6
                        mod_base = OTHER
                        note = 2'-O-methoxyethyl 5-methylcytidine
                         3'-phosphorothioate
modified_base           7..9
                        mod_base = OTHER
                        note = 2'-O-methoxyethyl thymidine 3'-phosphorothioate
modified_base           10
                        mod_base = OTHER
                        note = 2'-O-methoxyethyl 5-methylcytidine
                         3'-phosphorothioate
modified_base           11
                        mod_base = OTHER
                        note = 2'-O-methoxyethyl adenosine 3'-phosphorothioate
```

```
modified_base           12
                        mod_base = OTHER
                        note = 2'-O-methoxyethyl thymidine 3'-phosphorothioate
modified_base           13..14
                        mod_base = OTHER
                        note = 2'-O-methoxyethyl adenosine 3'-phosphorothioate
modified_base           15
                        mod_base = OTHER
                        note = 2'-O-methoxyethyl thymidine 3'-phosphorothioate
modified_base           16
                        mod_base = OTHER
                        note = 2'-O-methoxyethyl guanosine 3'-phosphorothioate
modified_base           17
                        mod_base = OTHER
                        note = 2'-O-methoxyethyl 5-methylcytidine
                         3'-phosphorothioate
modified_base           18
                        mod_base = OTHER
                        note = 2'-O-methoxyethyl thymidine 3'-phosphorothioate
modified_base           19
                        mod_base = OTHER
                        note = 2'-O-methoxyethyl guanosine 3'-phosphorothioate
modified_base           20
                        mod_base = OTHER
                        note = 2'-O-methoxyethyl guanosine
SEQUENCE: 320
attcactttc ataatgctgg                                                20

SEQ ID NO: 321          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl thymidine 3'-phosphorothioate
modified_base           2..3
                        mod_base = OTHER
                        note = 2'-O-methoxyethyl guanosine 3'-phosphorothioate
modified_base           4
                        mod_base = OTHER
                        note = 2'-O-methoxyethyl thymidine 3'-phosphorothioate
modified_base           5
                        mod_base = OTHER
                        note = 2'-O-methoxyethyl adenosine 3'-phosphorothioate
modified_base           6
                        mod_base = OTHER
                        note = 2'-deoxyadenosine 3'-phosphorothioate
modified_base           7
                        mod_base = OTHER
                        note = 2'-deoxythymidine 3'-phosphorothioate
modified_base           8..9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12..14
                        mod_base = OTHER
                        note = 2'-deoxythymidine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-O-methoxyethyl adenosine 3'-phosphorothioate
modified_base           17
                        mod_base = OTHER
                        note = 2'-O-methoxyethyl guanosine 3'-phosphorothioate
modified_base           18
                        mod_base = OTHER
                        note = 2'-O-methoxyethyl adenosine 3'-phosphorothioate
modified_base           19
                        mod_base = OTHER
                        note = 2'-O-methoxyethyl guanosine 3'-phosphorothioate
modified_base           20
```

```
                        mod_base = OTHER
                        note = 2'-O-methoxyethyl guanosine
SEQUENCE: 321
tggtaatcca ctttcagagg                                                20

SEQ ID NO: 322          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl adenosine 3'-phosphorothioate
modified_base           2
                        mod_base = OTHER
                        note = 2'-O-methoxyethyl thymidine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5
                        mod_base = OTHER
                        note = 2'-O-methoxyethyl adenosine 3'-phosphorothioate
modified_base           6
                        mod_base = OTHER
                        note = 2'-deoxythymidine 3'-phosphorothioate
modified_base           7..8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17
                        mod_base = OTHER
                        note = 2'-O-methoxyethyl 5-methylcytidine
                         3'-phosphorothioate
modified_base           18
                        mod_base = OTHER
                        note = 2'-O-methoxyethyl thymidine 3'-phosphorothioate
modified_base           19
                        mod_base = OTHER
                        note = 2'-O-methoxyethyl guanosine 3'-phosphorothioate
modified_base           20
                        mod_base = OTHER
                        note = 2'-O-methoxyethyl adenosine
SEQUENCE: 322
atgcatggtg atgcttctga                                                20

SEQ ID NO: 323          moltype = DNA  length = 20
FEATURE                 Location/Qualifiers
source                  1..20
                        mol_type = other DNA
                        organism = Synthetic construct
modified_base           1
                        mod_base = OTHER
```

```
                        note = 2'-O-methoxyethyl thymidine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl guanosine 3'-phosphorothioate
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14..15
                        mod_base = OTHER
                        note = 2'-deoxyadenosine 3'-phosphorothioate
modified_base           16
                        mod_base = OTHER
                        note = 2'-O-methoxyethyl adenosine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine
SEQUENCE: 323
tcttggttac atgaaatccc                                          20

SEQ ID NO: 324          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl 5-methylcytidine
                         3'-phosphorothioate
modified_base           2
                        mod_base = OTHER
                        note = 2'-O-methoxyethyl adenosine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5
                        mod_base = OTHER
                        note = 2'-O-methoxyethyl thymidine 3'-phosphorothioate
modified_base           6..7
                        mod_base = OTHER
                        note = 2'-deoxythymidine 3'-phosphorothioate
modified_base           8
                        mod_base = OTHER
                        note = 2'-deoxyadenosine 3'-phosphorothioate
```

```
modified_base          9..10
                       mod_base = OTHER
                       note = 2'-deoxythymidine 3'-phosphorothioate
modified_base          11
                       mod_base = OTHER
                       note = 2'-deoxyadenosine 3'-phosphorothioate
modified_base          12..14
                       mod_base = OTHER
                       note = 2'-deoxyguanosine 3'-phosphorothioate
modified_base          16
                       mod_base = OTHER
                       note = 2'-O-methoxyethyl 5-methylcytidine
                        3'-phosphorothioate
modified_base          17
                       mod_base = OTHER
                       note = 2'-O-methoxyethyl adenosine 3'-phosphorothioate
modified_base          18
                       mod_base = OTHER
                       note = 2'-O-methoxyethyl guanosine 3'-phosphorothioate
modified_base          19
                       mod_base = OTHER
                       note = 2'-O-methoxyethyl 5-methylcytidine
                        3'-phosphorothioate
modified_base          20
                       mod_base = OTHER
                       note = 2'-O-methoxyethyl adenosine
SEQUENCE: 324
cagctttatt agggacagca                                            20

SEQ ID NO: 325         moltype = DNA  length = 20
FEATURE                Location/Qualifiers
source                 1..20
                       mol_type = other DNA
                       organism = Synthetic construct
modified_base          1
                       mod_base = OTHER
                       note = 2'-O-methoxyethyl adenosine 3'-phosphorothioate
modified_base          2..4
                       mod_base = OTHER
                       note = 2'-O-methoxyethyl 5-methylcytidine
                        3'-phosphorothioate
modified_base          5
                       mod_base = OTHER
                       note = 2'-O-methoxyethyl adenosine 3'-phosphorothioate
modified_base          6
                       mod_base = OTHER
                       note = 2'-deoxyadenosine 3'-phosphorothioate
modified_base          7..8
                       mod_base = OTHER
                       note = 2'-deoxythymidine 3'-phosphorothioate
modified_base          9
                       mod_base = OTHER
                       note = 5-methyl-2'-deoxycytidine 3'-phosphorothioate
modified_base          10
                       mod_base = OTHER
                       note = 2'-deoxyadenosine 3'-phosphorothioate
modified_base          11
                       mod_base = OTHER
                       note = 2'-deoxyguanosine 3'-phosphorothioate
modified_base          12..13
                       mod_base = OTHER
                       note = 2'-deoxyadenosine 3'-phosphorothioate
modified_base          14..15
                       mod_base = OTHER
                       note = 2'-deoxyguanosine 3'-phosphorothioate
modified_base          16..17
                       mod_base = OTHER
                       note = 2'-O-methoxyethyl adenosine 3'-phosphorothioate
modified_base          18..19
                       mod_base = OTHER
                       note = 2'-O-methoxyethyl guanosine 3'-phosphorothioate
modified_base          20
                       mod_base = OTHER
                       note = 2'-O-methoxyethyl adenosine
SEQUENCE: 325
acccaattca gaaggaagga                                            20

SEQ ID NO: 326         moltype = DNA  length = 20
FEATURE                Location/Qualifiers
```

-continued

```
source                  1..20
                        mol_type = other DNA
                        organism = Synthetic construct
modified_base           1
                        mod_base = OTHER
                        note = 2'-O-methoxyethyl thymidine 3'-phosphorothioate
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10..11
                        mod_base = OTHER
                        note = 2'-deoxyguanosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17
                        mod_base = OTHER
                        note = 2'-O-methoxyethyl guanosine 3'-phosphorothioate
modified_base           18..19
                        mod_base = OTHER
                        note = 2'-O-methoxyethyl thymidine 3'-phosphorothioate
modified_base           20
                        mod_base = OTHER
                        note = 2'-O-methoxyethyl 5-methylcytidine
SEQUENCE: 326
tgctccgttg gtgcttgttc                                             20

SEQ ID NO: 327          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl adenosine 3'-phosphorothioate
modified_base           2
                        mod_base = OTHER
                        note = 2'-O-methoxyethyl guanosine 3'-phosphodiester
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 5-methyl-2'-deoxycytidine 3'-phosphorothioate
```

```
modified_base          7..8
                       mod_base = OTHER
                       note = 2'-deoxythymidine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxythymidine 3'-phosphorothioate
modified_base          11..12
                       mod_base = OTHER
                       note = 5-methyl-2'-deoxycytidine 3'-phosphorothioate
modified_base          13
                       mod_base = OTHER
                       note = 2'-deoxyadenosine 3'-phosphorothioate
modified_base          14
                       mod_base = OTHER
                       note = 2'-deoxyguanosine 3'-phosphorothioate
modified_base          15
                       mod_base = OTHER
                       note = 5-methyl-2'-deoxycytidine 3'-phosphorothioate
modified_base          16..17
                       mod_base = OTHER
                       note = 2'-O-methoxyethyl thymidine 3'-phosphodiester
modified_base          18
                       mod_base = OTHER
                       note = 2'-O-methoxyethyl thymidine 3'-phosphorothioate
modified_base          19
                       mod_base = OTHER
                       note = 2'-O-methoxyethyl adenosine 3'-phosphorothioate
modified_base          20
                       mod_base = OTHER
                       note = 2'-O-methoxyethyl thymidine
SEQUENCE: 327
agcttcttgt ccagctttat                                              20

SEQ ID NO: 328         moltype = DNA  length = 20
FEATURE                Location/Qualifiers
source                 1..20
                       mol_type = other DNA
                       organism = Synthetic construct
modified_base
                       mod_base = OTHER
                       note = triantennary N-acetylgalactosamine conjugate3a
                        phosphodiester
modified_base          1
                       mod_base = OTHER
                       note = 2'-O-methoxyethyl 5-methylcytidine
                        3'-phosphorothioate
modified_base          2..3
                       mod_base = OTHER
                       note = 2'-O-methoxyethyl guanosine 3'-phosphorothioate
modified_base          4
                       mod_base = OTHER
                       note = 2'-O-methoxyethyl thymidine 3'-phosphorothioate
modified_base          5
                       mod_base = OTHER
                       note = 2'-O-methoxyethyl guanosine 3'-phosphorothioate
modified_base          6
                       mod_base = OTHER
                       note = 5-methyl-2'-deoxycytidine 3'-phosphorothioate
modified_base          7..8
                       mod_base = OTHER
                       note = 2'-deoxyadenosine 3'-phosphorothioate
modified_base          9..10
                       mod_base = OTHER
                       note = 2'-deoxyguanosine 3'-phosphorothioate
modified_base          11
                       mod_base = OTHER
                       note = 5-methyl-2'-deoxycytidine 3'-phosphorothioate
modified_base          12..13
                       mod_base = OTHER
                       note = 2'-deoxythymidine 3'-phosphorothioate
modified_base          14
                       mod_base = OTHER
                       note = 2'-deoxyadenosine 3'-phosphorothioate
modified_base          15
                       mod_base = OTHER
                       note = 2'-deoxyguanosine 3'-phosphorothioate
```

```
modified_base          16
                       mod_base = OTHER
                       note = 2'-O-methoxyethyl guanosine 3'-phosphorothioate
modified_base          17..18
                       mod_base = OTHER
                       note = 2'-O-methoxyethyl adenosine 3'-phosphorothioate
modified_base          19
                       mod_base = OTHER
                       note = 2'-O-methoxyethyl thymidine 3'-phosphorothioate
modified_base          20
                       mod_base = OTHER
                       note = 2'-O-methoxyethyl thymidine
SEQUENCE: 328
cggtgcaagg cttaggaatt                                              20

SEQ ID NO: 329         moltype = DNA  length = 20
FEATURE                Location/Qualifiers
source                 1..20
                       mol_type = other DNA
                       organism = Synthetic construct
modified_base          1
                       mod_base = OTHER
                       note = 2'-O-methoxyethyl guanosine 3'-phosphorothioate
modified_base          2
                       mod_base = OTHER
                       note = 2'-O-methoxyethyl 5-methylcytidine 3'-phosphodiester
modified_base          3..4
                       mod_base = OTHER
                       note = 2'-O-methoxyethyl thymidine 3'-phosphodiester
modified_base          5
                       mod_base = OTHER
                       note = 2'-O-methoxyethyl 5-methylcytidine
                        3'-phosphorothioate
modified_base          6
                       mod_base = OTHER
                       note = 2'-deoxyadenosine 3'-phosphorothioate
modified_base          7
                       mod_base = OTHER
                       note = 2'-deoxyguanosine 3'-phosphorothioate
modified_base          8
                       mod_base = OTHER
                       note = 2'-deoxythymidine 3'-phosphorothioate
modified_base          9
                       mod_base = OTHER
                       note = 5-methyl-2'-deoxycytidine 3'-phosphorothioate
modified_base          10
                       mod_base = OTHER
                       note = 2'-deoxyadenosine 3'-phosphorothioate
modified_base          11
                       mod_base = OTHER
                       note = 2'-deoxythymidine 3'-phosphorothioate
modified_base          12
                       mod_base = OTHER
                       note = 2'-deoxyguanosine 3'-phosphorothioate
modified_base          13
                       mod_base = OTHER
                       note = 2'-deoxyadenosine 3'-phosphorothioate
modified_base          14
                       mod_base = OTHER
                       note = 5-methyl-2'-deoxycytidine 3'-phosphorothioate
modified_base          15
                       mod_base = OTHER
                       note = 2'-deoxythymidine 3'-phosphorothioate
modified_base          16
                       mod_base = OTHER
                       note = 2'-O-methoxyethyl thymidine 3'-phosphodiester
modified_base          17
                       mod_base = OTHER
                       note = 2'-O-methoxyethyl 5-methylcytidine 3'-phosphodiester
modified_base          18
                       mod_base = OTHER
                       note = 2'-O-methoxyethyl 5-methylcytidine
                        3'-phosphorothioate
modified_base          19
                       mod_base = OTHER
                       note = 2'-O-methoxyethyl thymidine 3'-phosphorothioate
modified_base          20
                       mod_base = OTHER
                       note = 2'-O-methoxyethyl thymidine
```

```
SEQUENCE: 329
gcttcagtca tgacttcctt                                              20

SEQ ID NO: 330          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 330
gcttcagtca tgacttcctt                                              20

SEQ ID NO: 331          moltype = DNA  length = 20
FEATURE                 Location/Qualifiers
source                  1..20
                        mol_type = other DNA
                        organism = Synthetic construct
modified_base
                        mod_base = OTHER
```

```
                         note = triantennary N-acetylgalactosamine conjugate3a
                          phosphodiester
modified_base            1
                         mod_base = OTHER
                         note = 2'-O-methoxyethyl 5-methylcytidine
                          3'-phosphorothioate
modified_base            2
                         mod_base = OTHER
                         note = 2'-O-methoxyethyl adenosine 3'-phosphorothioate
modified_base            3
                         mod_base = OTHER
                         note = 2'-O-methoxyethyl guanosine 3'-phosphorothioate
modified_base            4
                         mod_base = OTHER
                         note = 2'-O-methoxyethyl 5-methylcytidine
                          3'-phosphorothioate
modified_base            5
                         mod_base = OTHER
                         note = 2'-O-methoxyethyl thymidine 3'-phosphorothioate
modified_base            6..7
                         mod_base = OTHER
                         note = 2'-deoxythymidine 3'-phosphorothioate
modified_base            8
                         mod_base = OTHER
                         note = 2'-deoxyadenosine 3'-phosphorothioate
modified_base            9..10
                         mod_base = OTHER
                         note = 2'-deoxythymidine 3'-phosphorothioate
modified_base            11
                         mod_base = OTHER
                         note = 2'-deoxyadenosine 3'-phosphorothioate
modified_base            12..14
                         mod_base = OTHER
                         note = 2'-deoxyguanosine 3'-phosphorothioate
modified_base            15
                         mod_base = OTHER
                         note = 2'-deoxyadenosine 3'-phosphorothioate
modified_base            16
                         mod_base = OTHER
                         note = 2'-O-methoxyethyl 5-methylcytidine
                          3'-phosphorothioate
modified_base            17
                         mod_base = OTHER
                         note = 2'-O-methoxyethyl adenosine 3'-phosphorothioate
modified_base            18
                         mod_base = OTHER
                         note = 2'-O-methoxyethyl guanosine 3'-phosphorothioate
modified_base            19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl adenosine
SEQUENCE: 331
cagctttatt agggacagca                                              20

SEQ ID NO: 332           moltype = DNA  length = 20
FEATURE                  Location/Qualifiers
source                   1..20
                         mol_type = other DNA
                         organism = Synthetic construct
modified_base
                         mod_base = OTHER
                         note = triantennary N-acetylgalactosamine conjugate7a
                          phosphodiester
modified_base            1
                         mod_base = OTHER
                         note = 2'-O-methoxyethyl 5-methylcytidine
                          3'-phosphorothioate
modified_base            2
                         mod_base = OTHER
                         note = 2'-O-methoxyethyl adenosine 3'-phosphorothioate
modified_base            3
                         mod_base = OTHER
                         note = 2'-O-methoxyethyl guanosine 3'-phosphorothioate
modified_base            4
                         mod_base = OTHER
                         note = 2'-O-methoxyethyl 5-methylcytidine
```

```
                        3'-phosphorothioate
modified_base           5
                        mod_base = OTHER
                        note = 2'-O-methoxyethyl thymidine 3'-phosphorothioate
modified_base           6..7
                        mod_base = OTHER
                        note = 2'-deoxythymidine 3'-phosphorothioate
modified_base           8
                        mod_base = OTHER
                        note = 2'-deoxyadenosine 3'-phosphorothioate
modified_base           9..10
                        mod_base = OTHER
                        note = 2'-deoxythymidine 3'-phosphorothioate
modified_base           11
                        mod_base = OTHER
                        note = 2'-deoxyadenosine 3'-phosphorothioate
modified_base           12..14
                        mod_base = OTHER
                        note = 2'-deoxyguanosine 3'-phosphorothioate
modified_base           15
                        mod_base = OTHER
                        note = 2'-deoxyadenosine 3'-phosphorothioate
modified_base           16
                        mod_base = OTHER
                        note = 2'-O-methoxyethyl 5-methylcytidine
                         3'-phosphorothioate
modified_base           17
                        mod_base = OTHER
                        note = 2'-O-methoxyethyl adenosine 3'-phosphorothioate
modified_base           18
                        mod_base = OTHER
                        note = 2'-O-methoxyethyl guanosine 3'-phosphorothioate
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl adenosine
SEQUENCE: 332
cagctttatt agggacagca                                              20

SEQ ID NO: 333          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate10a
                         phosphodiester
modified_base           1
                        mod_base = OTHER
                        note = 2'-O-methoxyethyl 5-methylcytidine
                         3'-phosphorothioate
modified_base           2
                        mod_base = OTHER
                        note = 2'-O-methoxyethyl adenosine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5
                        mod_base = OTHER
                        note = 2'-O-methoxyethyl thymidine 3'-phosphorothioate
modified_base           6..7
                        mod_base = OTHER
                        note = 2'-deoxythymidine 3'-phosphorothioate
modified_base           8
                        mod_base = OTHER
                        note = 2'-deoxyadenosine 3'-phosphorothioate
modified_base           9..10
                        mod_base = OTHER
                        note = 2'-deoxythymidine 3'-phosphorothioate
modified_base           11
                        mod_base = OTHER
```

```
                        note = 2'-deoxyadenosine 3'-phosphorothioate
modified_base           12..14
                        mod_base = OTHER
                        note = 2'-deoxyguanosine 3'-phosphorothioate
modified_base           15
                        mod_base = OTHER
                        note = 2'-deoxyadenosine 3'-phosphorothioate
modified_base           16
                        mod_base = OTHER
                        note = 2'-O-methoxyethyl 5-methylcytidine
                         3'-phosphorothioate
modified_base           17
                        mod_base = OTHER
                        note = 2'-O-methoxyethyl adenosine 3'-phosphorothioate
modified_base           18
                        mod_base = OTHER
                        note = 2'-O-methoxyethyl guanosine 3'-phosphorothioate
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl adenosine
SEQUENCE: 333
cagctttatt agggacagca                                              20

SEQ ID NO: 334          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate13a
                         phosphodiester
modified_base           1
                        mod_base = OTHER
                        note = 2'-O-methoxyethyl 5-methylcytidine
                         3'-phosphorothioate
modified_base           2
                        mod_base = OTHER
                        note = 2'-O-methoxyethyl adenosine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5
                        mod_base = OTHER
                        note = 2'-O-methoxyethyl thymidine 3'-phosphorothioate
modified_base           6..7
                        mod_base = OTHER
                        note = 2'-deoxythymidine 3'-phosphorothioate
modified_base           8
                        mod_base = OTHER
                        note = 2'-deoxyadenosine 3'-phosphorothioate
modified_base           9..10
                        mod_base = OTHER
                        note = 2'-deoxythymidine 3'-phosphorothioate
modified_base           11
                        mod_base = OTHER
                        note = 2'-deoxyadenosine 3'-phosphorothioate
modified_base           12..14
                        mod_base = OTHER
                        note = 2'-deoxyguanosine 3'-phosphorothioate
modified_base           15
                        mod_base = OTHER
                        note = 2'-deoxyadenosine 3'-phosphorothioate
modified_base           16
                        mod_base = OTHER
                        note = 2'-O-methoxyethyl 5-methylcytidine
                         3'-phosphorothioate
modified_base           17
                        mod_base = OTHER
                        note = 2'-O-methoxyethyl adenosine 3'-phosphorothioate
modified_base           18
```

```
                        mod_base = OTHER
                        note = 2'-O-methoxyethyl guanosine 3'-phosphorothioate
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl adenosine
SEQUENCE: 334
cagctttatt agggacagca                                              20

SEQ ID NO: 335          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 5-methyl-2'-deoxycytidine 3'-phosphorothioate
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10..11
                        mod_base = OTHER
                        note = 2'-deoxyguanosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17
                        mod_base = OTHER
                        note = 2'-O-methoxyethyl guanosine 3'-phosphorothioate
modified_base           18..19
                        mod_base = OTHER
                        note = 2'-O-methoxyethyl thymidine 3'-phosphorothioate
modified_base           20
                        mod_base = OTHER
                        note = 2'-O-methoxyethyl 5-methylcytidine
SEQUENCE: 335
tgctccgttg gtgcttgttc                                              20

SEQ ID NO: 336          moltype = DNA  length = 20
FEATURE                 Location/Qualifiers
```

```
source                  1..20
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl guanosine 3'-phosphodiester
modified_base           3
                        mod_base = OTHER
                        note = 2'-O-methoxyethyl 5-methylcytidine 3'-phosphodiester
modified_base           4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 5-methyl-2'-deoxycytidine 3'-phosphorothioate
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10..11
                        mod_base = OTHER
                        note = 2'-deoxyguanosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphodiester
modified_base           17
                        mod_base = OTHER
                        note = 2'-O-methoxyethyl guanosine 3'-phosphodiester
modified_base           18..19
                        mod_base = OTHER
                        note = 2'-O-methoxyethyl thymidine 3'-phosphorothioate
modified_base           20
                        mod_base = OTHER
                        note = 2'-O-methoxyethyl 5-methylcytidine
SEQUENCE: 336
tgctccgttg gtgcttgttc                                              20

SEQ ID NO: 337          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate10a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl guanosine 3'-phosphodiester
modified_base           3
                        mod_base = OTHER
                        note = 2'-O-methoxyethyl 5-methylcytidine 3'-phosphodiester
```

```
modified_base          4
                       mod_base = OTHER
                       note = 2'-O-methoxyethyl thymidine 3'-phosphodiester
modified_base          5
                       mod_base = OTHER
                       note = 2'-O-methoxyethyl 5-methylcytidine 3'-phosphodiester
modified_base          6
                       mod_base = OTHER
                       note = 5-methyl-2'-deoxycytidine 3'-phosphorothioate
modified_base          7
                       mod_base = OTHER
                       note = 2'-deoxyguanosine 3'-phosphorothioate
modified_base          8..9
                       mod_base = OTHER
                       note = 2'-deoxythymidine 3'-phosphorothioate
modified_base          10..11
                       mod_base = OTHER
                       note = 2'-deoxyguanosine 3'-phosphorothioate
modified_base          12
                       mod_base = OTHER
                       note = 2'-deoxythymidine 3'-phosphorothioate
modified_base          13
                       mod_base = OTHER
                       note = 2'-deoxyguanosine 3'-phosphorothioate
modified_base          14
                       mod_base = OTHER
                       note = 5-methyl-2'-deoxycytidine 3'-phosphorothioate
modified_base          15
                       mod_base = OTHER
                       note = 2'-deoxythymidine 3'-phosphorothioate
modified_base          16
                       mod_base = OTHER
                       note = 2'-O-methoxyethyl thymidine 3'-phosphodiester
modified_base          17
                       mod_base = OTHER
                       note = 2'-O-methoxyethyl guanosine 3'-phosphodiester
modified_base          18..19
                       mod_base = OTHER
                       note = 2'-O-methoxyethyl thymidine 3'-phosphorothioate
modified_base          20
                       mod_base = OTHER
                       note = 2'-O-methoxyethyl 5-methylcytidine
SEQUENCE: 337
tgctccgttg gtgcttgttc                                              20

SEQ ID NO: 338         moltype = DNA  length = 20
FEATURE                Location/Qualifiers
source                 1..20
                       mol_type = other DNA
                       organism = Synthetic construct
modified_base
                       mod_base = OTHER
                       note = triantennary N-acetylgalactosamine conjugate7a
                        phosphodiester
modified_base          1
                       mod_base = OTHER
                       note = 2'-O-methoxyethyl thymidine 3'-phosphorothioate
modified_base          2
                       mod_base = OTHER
                       note = 2'-O-methoxyethyl guanosine 3'-phosphodiester
modified_base          3
                       mod_base = OTHER
                       note = 2'-O-methoxyethyl 5-methylcytidine 3'-phosphodiester
modified_base          4
                       mod_base = OTHER
                       note = 2'-O-methoxyethyl thymidine 3'-phosphodiester
modified_base          5
                       mod_base = OTHER
                       note = 2'-O-methoxyethyl 5-methylcytidine 3'-phosphodiester
modified_base          6
                       mod_base = OTHER
                       note = 5-methyl-2'-deoxycytidine 3'-phosphorothioate
modified_base          7
                       mod_base = OTHER
                       note = 2'-deoxyguanosine 3'-phosphorothioate
modified_base          8..9
                       mod_base = OTHER
                       note = 2'-deoxythymidine 3'-phosphorothioate
modified_base          10..11
```

```
                         mod_base = OTHER
                         note = 2'-deoxyguanosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
                         note = 2'-O-methoxyethyl thymidine 3'-phosphodiester
modified_base            17
                         mod_base = OTHER
                         note = 2'-O-methoxyethyl guanosine 3'-phosphodiester
modified_base            18..19
                         mod_base = OTHER
                         note = 2'-O-methoxyethyl thymidine 3'-phosphorothioate
modified_base            20
                         mod_base = OTHER
                         note = 2'-O-methoxyethyl 5-methylcytidine
SEQUENCE: 338
tgctccgttg gtgcttgttc                                                  20

SEQ ID NO: 339           moltype = DNA  length = 20
FEATURE                  Location/Qualifiers
source                   1..20
                         mol_type = other DNA
                         organism = Synthetic construct
modified_base
                         mod_base = OTHER
                         note = triantennary N-acetylgalactosamine conjugate13a
                          phosphodiester
modified_base            1
                         mod_base = OTHER
                         note = 2'-O-methoxyethyl thymidine 3'-phosphorothioate
modified_base            2
                         mod_base = OTHER
                         note = 2'-O-methoxyethyl guanosine 3'-phosphodiester
modified_base            3
                         mod_base = OTHER
                         note = 2'-O-methoxyethyl 5-methylcytidine 3'-phosphodiester
modified_base            4
                         mod_base = OTHER
                         note = 2'-O-methoxyethyl thymidine 3'-phosphodiester
modified_base            5
                         mod_base = OTHER
                         note = 2'-O-methoxyethyl 5-methylcytidine 3'-phosphodiester
modified_base            6
                         mod_base = OTHER
                         note = 5-methyl-2'-deoxycytidine 3'-phosphorothioate
modified_base            17
                         mod_base = OTHER
                         note = 2'-deoxyguanosine 3'-phosphorothioate
modified_base            8..9
                         mod_base = OTHER
                         note = 2'-deoxythymidine 3'-phosphorothioate
modified_base            10..11
                         mod_base = OTHER
                         note = 2'-deoxyguanosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
```

```
                        note = 2'-O-methoxyethyl thymidine 3'-phosphodiester
modified_base           17
                        mod_base = OTHER
                        note = 2'-O-methoxyethyl guanosine 3'-phosphodiester
modified_base           18..19
                        mod_base = OTHER
                        note = 2'-O-methoxyethyl thymidine 3'-phosphorothioate
modified_base           20
                        mod_base = OTHER
                        note = 2'-O-methoxyethyl 5-methylcytidine
SEQUENCE: 339
tgctccgttg gtgcttgttc                                             20

SEQ ID NO: 340          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 2'-O-methoxyethyl 5-methylcytidine
                         3'-phosphorothioate
modified_base           2
                        mod_base = OTHER
                        note = 2'-O-methoxyethyl adenosine 3'-phosphodiester
modified_base           3
                        mod_base = OTHER
                        note = 2'-O-methoxyethyl guanosine 3'-phosphodiester
modified_base           4
                        mod_base = OTHER
                        note = 2'-O-methoxyethyl 5-methylcytidine 3'-phosphodiester
modified_base           5
                        mod_base = OTHER
                        note = 2'-O-methoxyethyl thymidine 3'-phosphodiester
modified_base           6..7
                        mod_base = OTHER
                        note = 2'-deoxythymidine 3'-phosphorothioate
modified_base           8
                        mod_base = OTHER
                        note = 2'-deoxyadenosine 3'-phosphorothioate
modified_base           9..10
                        mod_base = OTHER
                        note = 2'-deoxythymidine 3'-phosphorothioate
modified_base           11
                        mod_base = OTHER
                        note = 2'-deoxyadenosine 3'-phosphorothioate
modified_base           12..14
                        mod_base = OTHER
                        note = 2'-deoxyguanosine 3'-phosphorothioate
modified_base           15
                        mod_base = OTHER
                        note = 2'-deoxyadenosine 3'-phosphorothioate
modified_base           16
                        mod_base = OTHER
                        note = 2'-O-methoxyethyl 5-methylcytidine 3'-phosphodiester
modified_base           17
                        mod_base = OTHER
                        note = 2'-O-methoxyethyl adenosine 3'-phosphodiester
modified_base           18
                        mod_base = OTHER
                        note = 2'-O-methoxyethyl guanosine 3'-phosphorothioate
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl adenosine
SEQUENCE: 340
cagctttatt agggacagca                                             20

SEQ ID NO: 341          moltype = DNA  length = 20
FEATURE                 Location/Qualifiers
source                  1..20
                        mol_type = other DNA
```

```
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl guanosine 3'-phosphorothioate
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14..15
                        mod_base = OTHER
                        note = 2'-deoxyadenosine 3'-phosphorothioate
modified_base           16
                        mod_base = OTHER
                        note = 2'-O-methoxyethyl adenosine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine
SEQUENCE: 341
tcttggttac atgaaatccc                                              20

SEQ ID NO: 342          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
```

```
                        note = 2'-O-methoxyethyl guanosine 3'-phosphorothioate
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14..15
                        mod_base = OTHER
                        note = 2'-deoxyadenosine 3'-phosphorothioate
modified_base           16
                        mod_base = OTHER
                        note = 2'-O-methoxyethyl adenosine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine
SEQUENCE: 342
tcttggttac atgaaatccc                                          20

SEQ ID NO: 343          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate10a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl guanosine 3'-phosphorothioate
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
```

```
                          mod_base = OTHER
                          note = 2'-deoxythymidine 3'-phosphorothioate
modified_base             13
                          mod_base = OTHER
                          note = 2'-deoxyguanosine 3'-phosphorothioate
modified_base             14..15
                          mod_base = OTHER
                          note = 2'-deoxyadenosine 3'-phosphorothioate
modified_base             16
                          mod_base = OTHER
                          note = 2'-O-methoxyethyl adenosine 3'-phosphorothioate
modified_base             17
                          mod_base = OTHER
                          note = 2'-O-methoxyethyl thymidine 3'-phosphorothioate
modified_base             18..19
                          mod_base = OTHER
                          note = 2'-O-methoxyethyl 5-methylcytidine
                           3'-phosphorothioate
modified_base             20
                          mod_base = OTHER
                          note = 2'-O-methoxyethyl 5-methylcytidine
SEQUENCE: 343
tcttggttac atgaaatccc                                              20

SEQ ID NO: 344            moltype = DNA  length = 20
FEATURE                   Location/Qualifiers
source                    1..20
                          mol_type = other DNA
                          organism = Synthetic construct
modified_base
                          mod_base = OTHER
                          note = triantennary N-acetylgalactosamine conjugate13a
                           phosphodiester
modified_base             1
                          mod_base = OTHER
                          note = 2'-O-methoxyethyl thymidine 3'-phosphorothioate
modified_base             2
                          mod_base = OTHER
                          note = 2'-O-methoxyethyl 5-methylcytidine
                           3'-phosphorothioate
modified_base             3..4
                          mod_base = OTHER
                          note = 2'-O-methoxyethyl thymidine 3'-phosphorothioate
modified_base             5
                          mod_base = OTHER
                          note = 2'-O-methoxyethyl guanosine 3'-phosphorothioate
modified_base             6
                          mod_base = OTHER
                          note = 2'-deoxyguanosine 3'-phosphorothioate
modified_base             7..8
                          mod_base = OTHER
                          note = 2'-deoxythymidine 3'-phosphorothioate
modified_base             9
                          mod_base = OTHER
                          note = 2'-deoxyadenosine 3'-phosphorothioate
modified_base             10
                          mod_base = OTHER
                          note = 5-methyl-2'-deoxycytidine 3'-phosphorothioate
modified_base             11
                          mod_base = OTHER
                          note = 2'-deoxyadenosine 3'-phosphorothioate
modified_base             12
                          mod_base = OTHER
                          note = 2'-deoxythymidine 3'-phosphorothioate
modified_base             13
                          mod_base = OTHER
                          note = 2'-deoxyguanosine 3'-phosphorothioate
modified_base             14..15
                          mod_base = OTHER
                          note = 2'-deoxyadenosine 3'-phosphorothioate
modified_base             16
                          mod_base = OTHER
                          note = 2'-O-methoxyethyl adenosine 3'-phosphorothioate
modified_base             17
                          mod_base = OTHER
                          note = 2'-O-methoxyethyl thymidine 3'-phosphorothioate
modified_base             18..19
                          mod_base = OTHER
                          note = 2'-O-methoxyethyl 5-methylcytidine
```

```
                        3'-phosphorothioate
modified_base           20
                        mod_base = OTHER
                        note = 2'-O-methoxyethyl 5-methylcytidine
SEQUENCE: 344
tcttggttac atgaaatccc                                              20

SEQ ID NO: 345          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl guanosine 3'-phosphodiester
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14..15
                        mod_base = OTHER
                        note = 2'-deoxyadenosine 3'-phosphorothioate
modified_base           16
                        mod_base = OTHER
                        note = 2'-O-methoxyethyl adenosine 3'-phosphodiester
modified_base           17
                        mod_base = OTHER
                        note = 2'-O-methoxyethyl thymidine 3'-phosphodiester
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine
SEQUENCE: 345
tcttggttac atgaaatccc                                              20

SEQ ID NO: 346          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
```

```
                        note = 2'-O-methoxyethyl thymidine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl guanosine 3'-phosphodiester
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14..15
                        mod_base = OTHER
                        note = 2'-deoxyadenosine 3'-phosphorothioate
modified_base           16
                        mod_base = OTHER
                        note = 2'-O-methoxyethyl adenosine 3'-phosphodiester
modified_base           17
                        mod_base = OTHER
                        note = 2'-O-methoxyethyl thymidine 3'-phosphodiester
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine
SEQUENCE: 346
tcttggttac atgaaatccc                                        20

SEQ ID NO: 347          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate10a
                         phosphodiester
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl guanosine 3'-phosphodiester
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
```

```
                         note = 2'-deoxyadenosine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14..15
                         mod_base = OTHER
                         note = 2'-deoxyadenosine 3'-phosphorothioate
modified_base            16
                         mod_base = OTHER
                         note = 2'-O-methoxyethyl adenosine 3'-phosphodiester
modified_base            17
                         mod_base = OTHER
                         note = 2'-O-methoxyethyl thymidine 3'-phosphodiester
modified_base            18..19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl 5-methylcytidine
SEQUENCE: 347
tcttggttac atgaaatccc                                              20

SEQ ID NO: 348           moltype = DNA  length = 20
FEATURE                  Location/Qualifiers
source                   1..20
                         mol_type = other DNA
                         organism = Synthetic construct
modified_base
                         mod_base = OTHER
                         note = triantennary N-acetylgalactosamine conjugate13a
                          phosphodiester
modified_base            1
                         mod_base = OTHER
                         note = 2'-O-methoxyethyl thymidine 3'-phosphorothioate
modified_base            2
                         mod_base = OTHER
                         note = 2'-O-methoxyethyl 5-methylcytidine 3'-phosphodiester
modified_base            3..4
                         mod_base = OTHER
                         note = 2'-O-methoxyethyl thymidine 3'-phosphodiester
modified_base            5
                         mod_base = OTHER
                         note = 2'-O-methoxyethyl guanosine 3'-phosphodiester
modified_base            6
                         mod_base = OTHER
                         note = 2'-deoxyguanosine 3'-phosphorothioate
modified_base            7..8
                         mod_base = OTHER
                         note = 2'-deoxythymidine 3'-phosphorothioate
modified_base            9
                         mod_base = OTHER
                         note = 2'-deoxyadenosine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14..15
                         mod_base = OTHER
                         note = 2'-deoxyadenosine 3'-phosphorothioate
modified_base            16
                         mod_base = OTHER
```

```
                         note = 2'-O-methoxyethyl adenosine 3'-phosphodiester
modified_base            17
                         mod_base = OTHER
                         note = 2'-O-methoxyethyl thymidine 3'-phosphodiester
modified_base            18..19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl 5-methylcytidine
SEQUENCE: 348
tcttggttac atgaaatccc                                                  20

SEQ ID NO: 349           moltype = DNA  length = 20
FEATURE                  Location/Qualifiers
source                   1..20
                         mol_type = other DNA
                         organism = Synthetic construct
modified_base
                         mod_base = OTHER
                         note = triantennary N-acetylgalactosamine conjugate10a
                          phosphodiester
modified_base            1
                         mod_base = OTHER
                         note = 2'-O-methoxyethyl adenosine 3'-phosphorothioate
modified_base            2
                         mod_base = OTHER
                         note = 2'-O-methoxyethyl thymidine 3'-phosphorothioate
modified_base            3
                         mod_base = OTHER
                         note = 2'-O-methoxyethyl guanosine 3'-phosphorothioate
modified_base            4
                         mod_base = OTHER
                         note = 2'-O-methoxyethyl 5-methylcytidine
                          3'-phosphorothioate
modified_base            5
                         mod_base = OTHER
                         note = 2'-O-methoxyethyl adenosine 3'-phosphorothioate
modified_base            6
                         mod_base = OTHER
                         note = 2'-deoxythymidine 3'-phosphorothioate
modified_base            7..8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 2'-deoxyguanosine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
                         note = 2'-O-methoxyethyl thymidine 3'-phosphorothioate
modified_base            17
                         mod_base = OTHER
                         note = 2'-O-methoxyethyl 5-methylcytidine
                          3'-phosphorothioate
modified_base            18
                         mod_base = OTHER
                         note = 2'-O-methoxyethyl thymidine 3'-phosphorothioate
modified_base            19
                         mod_base = OTHER
                         note = 2'-O-methoxyethyl guanosine 3'-phosphorothioate
```

```
modified_base           20
                        mod_base = OTHER
                        note = 2'-O-methoxyethyl adenosine
SEQUENCE: 349
atgcatggtg atgcttctga                                              20

SEQ ID NO: 350          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl thymidine 3'-phosphorothioate
modified_base           2
                        mod_base = OTHER
                        note = 2'-O-methoxyethyl guanosine 3'-phosphodiester
modified_base           3
                        mod_base = OTHER
                        note = 2'-O-methoxyethyl 5-methylcytidine 3'-phosphodiester
modified_base           4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 5-methyl-2'-deoxycytidine 3'-phosphorothioate
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10..11
                        mod_base = OTHER
                        note = 2'-deoxyguanosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphodiester
modified_base           17
                        mod_base = OTHER
                        note = 2'-O-methoxyethyl guanosine 3'-phosphodiester
modified_base           18..19
                        mod_base = OTHER
                        note = 2'-O-methoxyethyl thymidine 3'-phosphorothioate
modified_base           20
                        mod_base = OTHER
                        note = 2'-O-methoxyethyl 5-methylcytidine
SEQUENCE: 350
tgctccgttg gtgcttgttc                                              20

SEQ ID NO: 351          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate7a
                         phosphorothioate
modified_base           1
                        mod_base = OTHER
                        note = 2'-O-methoxyethyl 5-methylcytidine
                         3'-phosphorothioate
modified_base           2
```

```
                          mod_base = OTHER
                          note = 2'-O-methoxyethyl adenosine 3'-phosphorothioate
modified_base             3
                          mod_base = OTHER
                          note = 2'-O-methoxyethyl guanosine 3'-phosphorothioate
modified_base             4
                          mod_base = OTHER
                          note = 2'-O-methoxyethyl 5-methylcytidine
                           3'-phosphorothioate
modified_base             5
                          mod_base = OTHER
                          note = 2'-O-methoxyethyl thymidine 3'-phosphorothioate
modified_base             6..7
                          mod_base = OTHER
                          note = 2'-deoxythymidine 3'-phosphorothioate
modified_base             8
                          mod_base = OTHER
                          note = 2'-deoxyadenosine 3'-phosphorothioate
modified_base             9..10
                          mod_base = OTHER
                          note = 2'-deoxythymidine 3'-phosphorothioate
modified_base             11
                          mod_base = OTHER
                          note = 2'-deoxyadenosine 3'-phosphorothioate
modified_base             12..14
                          mod_base = OTHER
                          note = 2'-deoxyguanosine 3'-phosphorothioate
modified_base             15
                          mod_base = OTHER
                          note = 2'-deoxyadenosine 3'-phosphorothioate
modified_base             16
                          mod_base = OTHER
                          note = 2'-O-methoxyethyl 5-methylcytidine
                           3'-phosphorothioate
modified_base             17
                          mod_base = OTHER
                          note = 2'-O-methoxyethyl adenosine 3'-phosphorothioate
modified_base             18
                          mod_base = OTHER
                          note = 2'-O-methoxyethyl guanosine 3'-phosphorothioate
modified_base             19
                          mod_base = OTHER
                          note = 2'-O-methoxyethyl 5-methylcytidine
                           3'-phosphorothioate
modified_base             20
                          mod_base = OTHER
                          note = 2'-O-methoxyethyl adenosine
SEQUENCE: 351
cagctttatt agggacagca                                             20

SEQ ID NO: 352            moltype = DNA  length = 20
FEATURE                   Location/Qualifiers
source                    1..20
                          mol_type = other DNA
                          organism = Synthetic construct
modified_base
                          mod_base = OTHER
                          note = triantennary N-acetylgalactosamine conjugate7a
                           phosphodiester
modified_base             1
                          mod_base = OTHER
                          note = 2'-O-methoxyethyl adenosine 3'-phosphorothioate
modified_base             2..3
                          mod_base = OTHER
                          note = 2'-O-methoxyethyl thymidine 3'-phosphorothioate
modified_base             4
                          mod_base = OTHER
                          note = 2'-O-methoxyethyl 5-methylcytidine
                           3'-phosphorothioate
modified_base             5
                          mod_base = OTHER
                          note = 2'-O-methoxyethyl adenosine 3'-phosphorothioate
modified_base             6
                          mod_base = OTHER
                          note = 2'-O-methoxyethyl 5-methylcytidine
                           3'-phosphorothioate
modified_base             7..9
                          mod_base = OTHER
                          note = 2'-O-methoxyethyl thymidine 3'-phosphorothioate
```

```
modified_base          10
                       mod_base = OTHER
                       note = 2'-O-methoxyethyl 5-methylcytidine
                        3'-phosphorothioate
modified_base          11
                       mod_base = OTHER
                       note = 2'-O-methoxyethyl adenosine 3'-phosphorothioate
modified_base          12
                       mod_base = OTHER
                       note = 2'-O-methoxyethyl thymidine 3'-phosphorothioate
modified_base          13..14
                       mod_base = OTHER
                       note = 2'-O-methoxyethyl adenosine 3'-phosphorothioate
modified_base          15
                       mod_base = OTHER
                       note = 2'-O-methoxyethyl thymidine 3'-phosphorothioate
modified_base          16
                       mod_base = OTHER
                       note = 2'-O-methoxyethyl guanosine 3'-phosphorothioate
modified_base          17
                       mod_base = OTHER
                       note = 2'-O-methoxyethyl 5-methylcytidine
                        3'-phosphorothioate
modified_base          18
                       mod_base = OTHER
                       note = 2'-O-methoxyethyl thymidine 3'-phosphorothioate
modified_base          19
                       mod_base = OTHER
                       note = 2'-O-methoxyethyl guanosine 3'-phosphorothioate
modified_base          20
                       mod_base = OTHER
                       note = 2'-O-methoxyethyl guanosine
SEQUENCE: 352
attcactttc ataatgctgg                                              20

SEQ ID NO: 353         moltype = DNA  length = 20
FEATURE                Location/Qualifiers
source                 1..20
                       mol_type = other DNA
                       organism = Synthetic construct
modified_base
                       mod_base = OTHER
                       note = triantennary N-acetylgalactosamine conjugate7a
                        phosphodiester
modified_base          1
                       mod_base = OTHER
                       note = 2'-O-methoxyethyl adenosine 3'-phosphorothioate
modified_base          2..3
                       mod_base = OTHER
                       note = 2'-O-methoxyethyl thymidine 3'-phosphodiester
modified_base          4
                       mod_base = OTHER
                       note = 2'-O-methoxyethyl 5-methylcytidine 3'-phosphodiester
modified_base          5
                       mod_base = OTHER
                       note = 2'-O-methoxyethyl adenosine 3'-phosphodiester
modified_base          6
                       mod_base = OTHER
                       note = 2'-O-methoxyethyl 5-methylcytidine 3'-phosphodiester
modified_base          7..9
                       mod_base = OTHER
                       note = 2'-O-methoxyethyl thymidine 3'-phosphodiester
modified_base          10
                       mod_base = OTHER
                       note = 2'-O-methoxyethyl 5-methylcytidine 3'-phosphodiester
modified_base          11
                       mod_base = OTHER
                       note = 2'-O-methoxyethyl adenosine 3'-phosphodiester
modified_base          12
                       mod_base = OTHER
                       note = 2'-O-methoxyethyl thymidine 3'-phosphodiester
modified_base          13..14
                       mod_base = OTHER
                       note = 2'-O-methoxyethyl adenosine 3'-phosphodiester
modified_base          15
                       mod_base = OTHER
                       note = 2'-O-methoxyethyl thymidine 3'-phosphodiester
modified_base          16
                       mod_base = OTHER
```

-continued

```
                         note = 2'-O-methoxyethyl guanosine 3'-phosphodiester
modified_base            17
                         mod_base = OTHER
                         note = 2'-O-methoxyethyl 5-methylcytidine 3'-phosphodiester
modified_base            18
                         mod_base = OTHER
                         note = 2'-O-methoxyethyl thymidine 3'-phosphorothioate
modified_base            19
                         mod_base = OTHER
                         note = 2'-O-methoxyethyl guanosine 3'-phosphorothioate
modified_base            20
                         mod_base = OTHER
                         note = 2'-O-methoxyethyl guanosine
SEQUENCE: 353
attcactttc ataatgctgg                                                  20

SEQ ID NO: 354           moltype = DNA  length = 20
FEATURE                  Location/Qualifiers
source                   1..20
                         mol_type = other DNA
                         organism = Synthetic construct
modified_base            1
                         mod_base = OTHER
                         note = 2'-O-methyl guanosine 3'-phosphorothioate
modified_base            2
                         mod_base = OTHER
                         note = 2'-O-methyl cytidine 3'-phosphorothioate
modified_base            3..4
                         mod_base = OTHER
                         note = 2'-O-methyl uridine 3'-phosphorothioate
modified_base            5
                         mod_base = OTHER
                         note = 2'-O-methyl cytidine 3'-phosphorothioate
modified_base            6
                         mod_base = OTHER
                         note = 2'-deoxyadenosine 3'-phosphorothioate
modified_base            7
                         mod_base = OTHER
                         note = 2'-deoxyguanosine 3'-phosphorothioate
modified_base            8
                         mod_base = OTHER
                         note = 2'-deoxythymidine 3'-phosphorothioate
modified_base            9
                         mod_base = OTHER
                         note = 5-methyl-2'-deoxycytidine 3'-phosphorothioate
modified_base            10
                         mod_base = OTHER
                         note = 2'-deoxyadenosine 3'-phosphorothioate
modified_base            11
                         mod_base = OTHER
                         note = 2'-deoxythymidine 3'-phosphorothioate
modified_base            12
                         mod_base = OTHER
                         note = 2'-deoxyguanosine 3'-phosphorothioate
modified_base            13
                         mod_base = OTHER
                         note = 2'-deoxyadenosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
                         note = 2'-O-methyl uridine 3'-phosphorothioate
modified_base            17..18
                         mod_base = OTHER
                         note = 2'-O-methyl cytidine 3'-phosphorothioate
modified_base            19
                         mod_base = OTHER
                         note = 2'-O-methyl uridine 3'-phosphorothioate
modified_base            20
                         mod_base = OTHER
                         note = 2'-O-methyl uridine
modified_base            1..5
                         mod_base = OTHER
                         note = uracil
modified_base            16..20
```

```
                        mod_base = OTHER
                        note = uracil
SEQUENCE: 354
gcttcagtca tgacttcctt                                           20

SEQ ID NO: 355          moltype = DNA  length = 20
FEATURE                 Location/Qualifiers
source                  1..20
                        mol_type = other DNA
                        organism = Synthetic construct
modified_base
                        mod_base = OTHER
                        note = triantennary N-acetylgalactosamine conjugate7a
                         phosphodiester
modified_base           1
                        mod_base = OTHER
                        note = 2'-O-methyl guanosine 3'-phosphorothioate
modified_base           2
                        mod_base = OTHER
                        note = 2'-O-methyl cytidine 3'-phosphorothioate
modified_base           3..4
                        mod_base = OTHER
                        note = 2'-O-methyl uridine 3'-phosphorothioate
modified_base           5
                        mod_base = OTHER
                        note = 2'-O-methyl cytidine 3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methyl uridine 3'-phosphorothioate
modified_base           17..18
                        mod_base = OTHER
                        note = 2'-O-methyl cytidine 3'-phosphorothioate
modified_base           19
                        mod_base = OTHER
                        note = 2'-O-methyl uridine 3'-phosphorothioate
modified_base           20
                        mod_base = OTHER
                        note = 2'-O-methyl uridine
modified_base           1..5
                        mod_base = OTHER
                        note = uracil
modified_base           16..20
                        mod_base = OTHER
                        note = uracil
SEQUENCE: 355
gcttcagtca tgacttcctt                                           20

SEQ ID NO: 356          moltype = DNA  length = 20
FEATURE                 Location/Qualifiers
```

-continued

```
source                  1..20
                        mol_type = other DNA
                        organism = Synthetic construct
modified_base
                        mod_base = OTHER
                        note = N-acetylgalactosamine conjugate 25a phosphodiester
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 356
gcttcagtca tgacttcctt                                              20

SEQ ID NO: 357          moltype = DNA  length = 20
FEATURE                 Location/Qualifiers
source                  1..20
                        mol_type = other DNA
                        organism = Synthetic construct
modified_base
                        mod_base = OTHER
                        note = N-acetylgalactosamine conjugate 25a phosphodiester
modified_base           1
                        mod_base = OTHER
                        note = 2'-O-methoxyethyl guanosine 3'-phosphorothioate
modified_base           2
                        mod_base = OTHER
```

```
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphodiester
modified_base           17
                        mod_base = OTHER
                        note = 2'-O-methoxyethyl 5-methylcytidine 3'-phosphodiester
modified_base           18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 357
gcttcagtca tgacttcctt                                              20

SEQ ID NO: 358          moltype = DNA  length = 20
FEATURE                 Location/Qualifiers
source                  1..20
                        mol_type = other DNA
                        organism = Synthetic construct
modified_base
                        mod_base = OTHER
                        note = N-acetylgalactosamine conjugate 26a phosphodiester
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
```

-continued

```
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 358
gcttcagtca tgacttcctt                                                 20

SEQ ID NO: 359          moltype = DNA  length = 20
FEATURE                 Location/Qualifiers
source                  1..20
                        mol_type = other DNA
                        organism = Synthetic construct
modified_base
                        mod_base = OTHER
                        note = N-acetylgalactosamine conjugate 26a phosphodiester
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
```

```
                         note = 2'-deoxyadenosine 3'-phosphorothioate
modified_base            11
                         mod_base = OTHER
                         note = 2'-deoxythymidine 3'-phosphorothioate
modified_base            12
                         mod_base = OTHER
                         note = 2'-deoxyguanosine 3'-phosphorothioate
modified_base            13
                         mod_base = OTHER
                         note = 2'-deoxyadenosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
                         note = 2'-O-methoxyethyl thymidine 3'-phosphodiester
modified_base            17
                         mod_base = OTHER
                         note = 2'-O-methoxyethyl 5-methylcytidine 3'-phosphodiester
modified_base            18
                         mod_base = OTHER
                         note = 2'-O-methoxyethyl 5-methylcytidine
                          3'-phosphorothioate
modified_base            19
                         mod_base = OTHER
                         note = 2'-O-methoxyethyl thymidine 3'-phosphorothioate
modified_base            20
                         mod_base = OTHER
                         note = 2'-O-methoxyethyl thymidine
SEQUENCE: 359
gcttcagtca tgacttcctt                                            20

SEQ ID NO: 360           moltype = DNA  length = 20
FEATURE                  Location/Qualifiers
source                   1..20
                         mol_type = other DNA
                         organism = Synthetic construct
modified_base
                         mod_base = OTHER
                         note = N-acetylgalactosamine conjugate 28a phosphodiester
modified_base            1
                         mod_base = OTHER
                         note = 2'-O-methoxyethyl guanosine 3'-phosphorothioate
modified_base            2
                         mod_base = OTHER
                         note = 2'-O-methoxyethyl 5-methylcytidine
                          3'-phosphorothioate
modified_base            3..4
                         mod_base = OTHER
                         note = 2'-O-methoxyethyl thymidine 3'-phosphorothioate
modified_base            5
                         mod_base = OTHER
                         note = 2'-O-methoxyethyl 5-methylcytidine
                          3'-phosphorothioate
modified_base            6
                         mod_base = OTHER
                         note = 2'-deoxyadenosine 3'-phosphorothioate
modified_base            7
                         mod_base = OTHER
                         note = 2'-deoxyguanosine 3'-phosphorothioate
modified_base            8
                         mod_base = OTHER
                         note = 2'-deoxythymidine 3'-phosphorothioate
modified_base            9
                         mod_base = OTHER
                         note = 5-methyl-2'-deoxycytidine 3'-phosphorothioate
modified_base            10
                         mod_base = OTHER
                         note = 2'-deoxyadenosine 3'-phosphorothioate
modified_base            11
                         mod_base = OTHER
                         note = 2'-deoxythymidine 3'-phosphorothioate
modified_base            12
                         mod_base = OTHER
                         note = 2'-deoxyguanosine 3'-phosphorothioate
modified_base            13
```

```
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 360
gcttcagtca tgacttcctt                                              20

SEQ ID NO: 361          moltype = DNA  length = 20
FEATURE                 Location/Qualifiers
source                  1..20
                        mol_type = other DNA
                        organism = Synthetic construct
modified_base
                        mod_base = OTHER
                        note = N-acetylgalactosamine conjugate 28a phosphodiester
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphodiester
modified_base           17
                        mod_base = OTHER
```

```
                        note = 2'-O-methoxyethyl 5-methylcytidine 3'-phosphodiester
modified_base           18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine
SEQUENCE: 361
gcttcagtca tgacttcctt                                                   20

SEQ ID NO: 362          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine phosphodiester
modified_base           20
                        mod_base = OTHER
                        note = N-acetylgalactosamine conjugate 27a
```

```
SEQUENCE: 362
gcttcagtca tgacttcctt                                              20

SEQ ID NO: 363          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphodiester
modified_base           17
                        mod_base = OTHER
                        note = 2'-O-methoxyethyl 5-methylcytidine 3'-phosphodiester
modified_base           18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine phosphodiester
modified_base           20
                        mod_base = OTHER
                        note = N-acetylgalactosamine conjugate 27a
SEQUENCE: 363
gcttcagtca tgacttcctt                                              20

SEQ ID NO: 364          moltype = DNA  length = 20
FEATURE                 Location/Qualifiers
source                  1..20
                        mol_type = other DNA
                        organism = Synthetic construct
modified_base           1
                        mod_base = OTHER
```

```
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine phosphodiester
modified_base           20
                        mod_base = OTHER
                        note = N-acetylgalactosamine conjugate 29a
SEQUENCE: 364
gcttcagtca tgacttcctt                                                20

SEQ ID NO: 365          moltype = DNA  length = 20
FEATURE                 Location/Qualifiers
source                  1..20
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
```

```
                         mod_base = OTHER
                         note = 2'-deoxyadenosine 3'-phosphorothioate
modified_base            7
                         mod_base = OTHER
                         note = 2'-deoxyguanosine 3'-phosphorothioate
modified_base            8
                         mod_base = OTHER
                         note = 2'-deoxythymidine 3'-phosphorothioate
modified_base            9
                         mod_base = OTHER
                         note = 5-methyl-2'-deoxycytidine 3'-phosphorothioate
modified_base            10
                         mod_base = OTHER
                         note = 2'-deoxyadenosine 3'-phosphorothioate
modified_base            11
                         mod_base = OTHER
                         note = 2'-deoxythymidine 3'-phosphorothioate
modified_base            12
                         mod_base = OTHER
                         note = 2'-deoxyguanosine 3'-phosphorothioate
modified_base            13
                         mod_base = OTHER
                         note = 2'-deoxyadenosine 3'-phosphorothioate
modified_base            14
                         mod_base = OTHER
                         note = 5-methyl-2'-deoxycytidine 3'-phosphorothioate
modified_base            15
                         mod_base = OTHER
                         note = 2'-deoxythymidine 3'-phosphorothioate
modified_base            16
                         mod_base = OTHER
                         note = 2'-O-methoxyethyl thymidine 3'-phosphodiester
modified_base            17
                         mod_base = OTHER
                         note = 2'-O-methoxyethyl 5-methylcytidine 3'-phosphodiester
modified_base            18
                         mod_base = OTHER
                         note = 2'-O-methoxyethyl 5-methylcytidine
                          3'-phosphorothioate
modified_base            19
                         mod_base = OTHER
                         note = 2'-O-methoxyethyl thymidine 3'-phosphorothioate
modified_base            20
                         mod_base = OTHER
                         note = 2'-O-methoxyethyl thymidine phosphodiester
modified_base            20
                         mod_base = OTHER
                         note = N-acetylgalactosamine conjugate 29a
SEQUENCE: 365
gcttcagtca tgacttcctt                                                20

SEQ ID NO: 366           moltype = DNA  length = 20
FEATURE                  Location/Qualifiers
source                   1..20
                         mol_type = other DNA
                         organism = Synthetic construct
modified_base            1
                         mod_base = OTHER
                         note = 2'-O-methoxyethyl 5-methylcytidine
                          3'-phosphorothioate
modified_base            2
                         mod_base = OTHER
                         note = 2'-O-methoxyethyl adenosine 3'-phosphorothioate
modified_base            3
                         mod_base = OTHER
                         note = 2'-O-methoxyethyl 5-methylcytidine
                          3'-phosphorothioate
modified_base            4
                         mod_base = OTHER
                         note = 2'-O-methoxyethyl thymidine 3'-phosphorothioate
modified_base            5
                         mod_base = OTHER
                         note = 2'-O-methoxyethyl guanosine 3'-phosphorothioate
modified_base            6
                         mod_base = OTHER
                         note = 2'-deoxyadenosine 3'-phosphorothioate
modified_base            7..11
                         mod_base = OTHER
                         note = 2'-deoxythymidine 3'-phosphorothioate
```

```
modified_base          12
                       mod_base = OTHER
                       note = 2'-deoxyguanosine 3'-phosphorothioate
modified_base          13..15
                       mod_base = OTHER
                       note = 5-methyl-2'-deoxycytidine 3'-phosphorothioate
modified_base          16
                       mod_base = OTHER
                       note = 2'-O-methoxyethyl adenosine 3'-phosphorothioate
modified_base          17..18
                       mod_base = OTHER
                       note = 2'-O-methoxyethyl guanosine 3'-phosphorothioate
modified_base          19
                       mod_base = OTHER
                       note = 2'-O-methoxyethyl adenosine 3'-phosphorothioate
modified_base          20
                       mod_base = OTHER
                       note = 2'-O-methoxyethyl thymidine
SEQUENCE: 366
cactgatttt tgcccaggat                                              20

SEQ ID NO: 367         moltype = DNA  length = 21
FEATURE                Location/Qualifiers
source                 1..21
                       mol_type = other DNA
                       organism = Synthetic construct
modified_base          1
                       mod_base = OTHER
                       note = 2'-O-methoxyethyl adenosine 3'-phosphorothioate
modified_base          2
                       mod_base = OTHER
                       note = 2'-O-methoxyethyl guanosine 3'-phosphorothioate
modified_base          3
                       mod_base = OTHER
                       note = 2'-O-methoxyethyl 5-methylcytidine
                        3'-phosphorothioate
modified_base          4..5
                       mod_base = OTHER
                       note = 2'-O-methoxyethyl thymidine 3'-phosphorothioate
modified_base          6
                       mod_base = OTHER
                       note = 5-methyl-2'-deoxycytidine 3'-phosphorothioate
modified_base          7..8
                       mod_base = OTHER
                       note = 2'-deoxythymidine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxythymidine 3'-phosphorothioate
modified_base          11..12
                       mod_base = OTHER
                       note = 5-methyl-2'-deoxycytidine 3'-phosphorothioate
modified_base          13
                       mod_base = OTHER
                       note = 2'-deoxyadenosine 3'-phosphorothioate
modified_base          14
                       mod_base = OTHER
                       note = 2'-deoxyguanosine 3'-phosphorothioate
modified_base          15
                       mod_base = OTHER
                       note = 5-methyl-2'-deoxycytidine 3'-phosphorothioate
modified_base          16..18
                       mod_base = OTHER
                       note = 2'-O-methoxyethyl thymidine 3'-phosphorothioate
modified_base          19
                       mod_base = OTHER
                       note = 2'-O-methoxyethyl adenosine 3'-phosphorothioate
modified_base          20
                       mod_base = OTHER
                       note = 2'-O-methoxyethyl thymidine 3'-phosphodiester
modified_base          21
                       mod_base = OTHER
                       note = triantennary N-acetylgalactosamine conjugate1a
SEQUENCE: 367
agcttcttgt ccagctttat a                                            21

SEQ ID NO: 368         moltype = DNA  length = 21
```

```
FEATURE                Location/Qualifiers
source                 1..21
                       mol_type = other DNA
                       organism = Synthetic construct
modified_base          1
                       mod_base = OTHER
                       note = 2'-O-methoxyethyl adenosine 3'-phosphorothioate
modified_base          2
                       mod_base = OTHER
                       note = 2'-O-methoxyethyl guanosine 3'-phosphodiester
modified_base          3
                       mod_base = OTHER
                       note = 2'-O-methoxyethyl 5-methylcytidine 3'-phosphodiester
modified_base          4..5
                       mod_base = OTHER
                       note = 2'-O-methoxyethyl thymidine 3'-phosphodiester
modified_base          6
                       mod_base = OTHER
                       note = 5-methyl-2'-deoxycytidine 3'-phosphorothioate
modified_base          7..8
                       mod_base = OTHER
                       note = 2'-deoxythymidine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxythymidine 3'-phosphorothioate
modified_base          11..12
                       mod_base = OTHER
                       note = 5-methyl-2'-deoxycytidine 3'-phosphorothioate
modified_base          13
                       mod_base = OTHER
                       note = 2'-deoxyadenosine 3'-phosphorothioate
modified_base          14
                       mod_base = OTHER
                       note = 2'-deoxyguanosine 3'-phosphorothioate
modified_base          15
                       mod_base = OTHER
                       note = 5-methyl-2'-deoxycytidine 3'-phosphorothioate
modified_base          16..17
                       mod_base = OTHER
                       note = 2'-O-methoxyethyl thymidine 3'-phosphodiester
modified_base          18
                       mod_base = OTHER
                       note = 2'-O-methoxyethyl thymidine 3'-phosphorothioate
modified_base          19
                       mod_base = OTHER
                       note = 2'-O-methoxyethyl adenosine 3'-phosphorothioate
modified_base          20
                       mod_base = OTHER
                       note = 2'-O-methoxyethyl thymidine 3'-phosphodiester
modified_base          21
                       mod_base = OTHER
                       note = triantennary N-acetylgalactosamine conjugate1a
SEQUENCE: 368
agcttcttgt ccagctttat a                                            21

SEQ ID NO: 369         moltype = DNA  length = 21
FEATURE                Location/Qualifiers
source                 1..21
                       mol_type = other DNA
                       organism = Synthetic construct
modified_base          1
                       mod_base = OTHER
                       note = 2'-O-methoxyethyl guanosine 3'-phosphorothioate
modified_base          2
                       mod_base = OTHER
                       note = 2'-O-methoxyethyl 5-methylcytidine
                        3'-phosphorothioate
modified_base          3..4
                       mod_base = OTHER
                       note = 2'-O-methoxyethyl thymidine 3'-phosphorothioate
modified_base          5
                       mod_base = OTHER
                       note = 2'-O-methoxyethyl 5-methylcytidine
                        3'-phosphorothioate
modified_base          6
                       mod_base = OTHER
```

```
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine 3'-phosphodiester
modified_base           21
                        mod_base = OTHER
                        note = triantennary N-acetylgalactosamine conjugate1a
SEQUENCE: 369
gcttcagtca tgacttcctt a                                             21

SEQ ID NO: 370          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
```

```
modified_base         11
                      mod_base = OTHER
                      note = 2'-deoxythymidine 3'-phosphorothioate
modified_base         12
                      mod_base = OTHER
                      note = 2'-deoxyguanosine 3'-phosphorothioate
modified_base         13
                      mod_base = OTHER
                      note = 2'-deoxyadenosine 3'-phosphorothioate
modified_base         14
                      mod_base = OTHER
                      note = 5-methyl-2'-deoxycytidine 3'-phosphorothioate
modified_base         15
                      mod_base = OTHER
                      note = 2'-deoxythymidine 3'-phosphorothioate
modified_base         16
                      mod_base = OTHER
                      note = 2'-O-methoxyethyl thymidine 3'-phosphodiester
modified_base         17
                      mod_base = OTHER
                      note = 2'-O-methoxyethyl 5-methylcytidine 3'-phosphodiester
modified_base         18
                      mod_base = OTHER
                      note = 2'-O-methoxyethyl 5-methylcytidine
                       3'-phosphorothioate
modified_base         19
                      mod_base = OTHER
                      note = 2'-O-methoxyethyl thymidine 3'-phosphorothioate
modified_base         20
                      mod_base = OTHER
                      note = 2'-O-methoxyethyl thymidine 3'-phosphodiester
modified_base         21
                      mod_base = OTHER
                      note = triantennary N-acetylgalactosamine conjugate1a
SEQUENCE: 370
gcttcagtca tgacttcctt a                                                21

SEQ ID NO: 371        moltype = DNA  length = 21
FEATURE               Location/Qualifiers
source                1..21
                      mol_type = other DNA
                      organism = Synthetic construct
modified_base         1
                      mod_base = OTHER
                      note = 2'-O-methoxyethyl thymidine 3'-phosphorothioate
modified_base         2..3
                      mod_base = OTHER
                      note = 2'-O-methoxyethyl guanosine 3'-phosphorothioate
modified_base         4
                      mod_base = OTHER
                      note = 2'-O-methoxyethyl thymidine 3'-phosphorothioate
modified_base         5
                      mod_base = OTHER
                      note = 2'-O-methoxyethyl adenosine 3'-phosphorothioate
modified_base         6
                      mod_base = OTHER
                      note = 2'-deoxyadenosine 3'-phosphorothioate
modified_base         7
                      mod_base = OTHER
                      note = 2'-deoxythymidine 3'-phosphorothioate
modified_base         8..9
                      mod_base = OTHER
                      note = 5-methyl-2'-deoxycytidine 3'-phosphorothioate
modified_base         10
                      mod_base = OTHER
                      note = 2'-deoxyadenosine 3'-phosphorothioate
modified_base         11
                      mod_base = OTHER
                      note = 5-methyl-2'-deoxycytidine 3'-phosphorothioate
modified_base         12..14
                      mod_base = OTHER
                      note = 2'-deoxythymidine 3'-phosphorothioate
modified_base         15
                      mod_base = OTHER
                      note = 5-methyl-2'-deoxycytidine 3'-phosphorothioate
modified_base         16
                      mod_base = OTHER
                      note = 2'-O-methoxyethyl adenosine 3'-phosphorothioate
modified_base         17
```

```
                        mod_base = OTHER
                        note = 2'-O-methoxyethyl guanosine 3'-phosphorothioate
modified_base           18
                        mod_base = OTHER
                        note = 2'-O-methoxyethyl adenosine 3'-phosphorothioate
modified_base           19
                        mod_base = OTHER
                        note = 2'-O-methoxyethyl guanosine 3'-phosphorothioate
modified_base           20
                        mod_base = OTHER
                        note = 2'-O-methoxyethyl guanosine 3'-phosphodiester
SEQUENCE: 371
tggtaatcca ctttcagagg a                                              21

SEQ ID NO: 372          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl thymidine 3'-phosphorothioate
modified_base           2..3
                        mod_base = OTHER
                        note = 2'-O-methoxyethyl guanosine 3'-phosphodiester
modified_base           4
                        mod_base = OTHER
                        note = 2'-O-methoxyethyl thymidine 3'-phosphodiester
modified_base           5
                        mod_base = OTHER
                        note = 2'-O-methoxyethyl adenosine 3'-phosphodiester
modified_base           6
                        mod_base = OTHER
                        note = 2'-deoxyadenosine 3'-phosphorothioate
modified_base           7
                        mod_base = OTHER
                        note = 2'-deoxythymidine 3'-phosphorothioate
modified_base           8..9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12..14
                        mod_base = OTHER
                        note = 2'-deoxythymidine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-O-methoxyethyl adenosine 3'-phosphodiester
modified_base           17
                        mod_base = OTHER
                        note = 2'-O-methoxyethyl guanosine 3'-phosphodiester
modified_base           18
                        mod_base = OTHER
                        note = 2'-O-methoxyethyl adenosine 3'-phosphorothioate
modified_base           19
                        mod_base = OTHER
                        note = 2'-O-methoxyethyl guanosine 3'-phosphorothioate
modified_base           20
                        mod_base = OTHER
                        note = 2'-O-methoxyethyl guanosine 3'-phosphodiester
modified_base           21
                        mod_base = OTHER
                        note = triantennary N-acetylgalactosamine conjugate1a
SEQUENCE: 372
tggtaatcca ctttcagagg a                                              21

SEQ ID NO: 373          moltype = DNA  length = 21
FEATURE                 Location/Qualifiers
source                  1..21
                        mol_type = other DNA
                        organism = Synthetic construct
modified_base           1
```

```
                         mod_base = OTHER
                         note = 2'-O-methoxyethyl adenosine 3'-phosphorothioate
modified_base            2..4
                         mod_base = OTHER
                         note = 2'-O-methoxyethyl 5-methylcytidine
                          3'-phosphorothioate
modified_base            5
                         mod_base = OTHER
                         note = 2'-O-methoxyethyl adenosine 3'-phosphorothioate
modified_base            6
                         mod_base = OTHER
                         note = 2'-deoxyadenosine 3'-phosphorothioate
modified_base            7..8
                         mod_base = OTHER
                         note = 2'-deoxythymidine 3'-phosphorothioate
modified_base            9
                         mod_base = OTHER
                         note = 5-methyl-2'-deoxycytidine 3'-phosphorothioate
modified_base            10
                         mod_base = OTHER
                         note = 2'-deoxyadenosine 3'-phosphorothioate
modified_base            11
                         mod_base = OTHER
                         note = 2'-deoxyguanosine 3'-phosphorothioate
modified_base            12..13
                         mod_base = OTHER
                         note = 2'-deoxyadenosine 3'-phosphorothioate
modified_base            14..15
                         mod_base = OTHER
                         note = 2'-deoxyguanosine 3'-phosphorothioate
modified_base            16..17
                         mod_base = OTHER
                         note = 2'-O-methoxyethyl adenosine 3'-phosphorothioate
modified_base            18..19
                         mod_base = OTHER
                         note = 2'-O-methoxyethyl guanosine 3'-phosphorothioate
modified_base            20
                         mod_base = OTHER
                         note = 2'-O-methoxyethyl adenosine 3'-phosphodiester
modified_base            21
                         mod_base = OTHER
                         note = triantennary N-acetylgalactosamine conjugate1a
SEQUENCE: 373
acccaattca gaaggaagga a                                          21

SEQ ID NO: 374           moltype = DNA  length = 21
FEATURE                  Location/Qualifiers
source                   1..21
                         mol_type = other DNA
                         organism = Synthetic construct
modified_base
                         mod_base = OTHER
                         note = hexylamine phosphodiester
modified_base            2
                         mod_base = OTHER
                         note = 2'-O-methoxyethyl guanosine 3'-phosphorothioate
modified_base            3
                         mod_base = OTHER
                         note = 2'-O-methoxyethyl 5-methylcytidine
                          3'-phosphorothioate
modified_base            4..5
                         mod_base = OTHER
                         note = 2'-O-methoxyethyl thymidine 3'-phosphorothioate
modified_base            6
                         mod_base = OTHER
                         note = 2'-O-methoxyethyl 5-methylcytidine
                          3'-phosphorothioate
modified_base            7
                         mod_base = OTHER
                         note = 2'-deoxyadenosine 3'-phosphorothioate
modified_base            8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
```

```
modified_base         11
                      mod_base = OTHER
                      note = 2'-deoxyadenosine 3'-phosphorothioate
modified_base         12
                      mod_base = OTHER
                      note = 2'-deoxythymidine 3'-phosphorothioate
modified_base         13
                      mod_base = OTHER
                      note = 2'-deoxyguanosine 3'-phosphorothioate
modified_base         14
                      mod_base = OTHER
                      note = 2'-deoxyadenosine 3'-phosphorothioate
modified_base         15
                      mod_base = OTHER
                      note = 5-methyl-2'-deoxycytidine 3'-phosphorothioate
modified_base         16
                      mod_base = OTHER
                      note = 2'-deoxythymidine 3'-phosphorothioate
modified_base         17
                      mod_base = OTHER
                      note = 2'-O-methoxyethyl thymidine 3'-phosphorothioate
modified_base         18..19
                      mod_base = OTHER
                      note = 2'-O-methoxyethyl 5-methylcytidine
                       3'-phosphorothioate
modified_base         20
                      mod_base = OTHER
                      note = 2'-O-methoxyethyl thymidine 3'-phosphorothioate
modified_base         21
                      mod_base = OTHER
                      note = 2'-O-methoxyethyl thymidine
SEQUENCE: 374
agcttcagtc atgacttcct t                                           21

SEQ ID NO: 375        moltype = DNA  length = 21
FEATURE               Location/Qualifiers
source                1..21
                      mol_type = other DNA
                      organism = Synthetic construct
modified_base         1
                      mod_base = OTHER
                      note = 2'-O-methoxyethyl thymidine 3'-phosphorothioate
modified_base         2
                      mod_base = OTHER
                      note = 2'-O-methoxyethyl 5-methylcytidine
                       3'-phosphorothioate
modified_base         3..4
                      mod_base = OTHER
                      note = 2'-O-methoxyethyl thymidine 3'-phosphorothioate
modified_base         5
                      mod_base = OTHER
                      note = 2'-O-methoxyethyl guanosine 3'-phosphorothioate
modified_base         6
                      mod_base = OTHER
                      note = 2'-deoxyguanosine 3'-phosphorothioate
modified_base         7..8
                      mod_base = OTHER
                      note = 2'-deoxythymidine 3'-phosphorothioate
modified_base         9
                      mod_base = OTHER
                      note = 2'-deoxyadenosine 3'-phosphorothioate
modified_base         10
                      mod_base = OTHER
                      note = 5-methyl-2'-deoxycytidine 3'-phosphorothioate
modified_base         11
                      mod_base = OTHER
                      note = 2'-deoxyadenosine 3'-phosphorothioate
modified_base         12
                      mod_base = OTHER
                      note = 2'-deoxythymidine 3'-phosphorothioate
modified_base         13
                      mod_base = OTHER
                      note = 2'-deoxyguanosine 3'-phosphorothioate
modified_base         14..15
                      mod_base = OTHER
                      note = 2'-deoxyadenosine 3'-phosphorothioate
modified_base         16
                      mod_base = OTHER
                      note = 2'-O-methoxyethyl adenosine 3'-phosphorothioate
```

```
modified_base          17
                       mod_base = OTHER
                       note = 2'-O-methoxyethyl thymidine 3'-phosphorothioate
modified_base          18..19
                       mod_base = OTHER
                       note = 2'-O-methoxyethyl 5-methylcytidine
                        3'-phosphorothioate
modified_base          20
                       mod_base = OTHER
                       note = 2'-O-methoxyethyl 5-methylcytidine 3'-phosphodiester
modified_base          21
                       mod_base = OTHER
                       note = triantennary N-acetylgalactosamine conjugate1a
SEQUENCE: 375
tcttggttac atgaaatccc a                                            21

SEQ ID NO: 376         moltype = DNA  length = 21
FEATURE                Location/Qualifiers
source                 1..21
                       mol_type = other DNA
                       organism = Synthetic construct
modified_base
                       mod_base = OTHER
                       note = triantennary N-acetylgalactosamine conjugate3a
                        phosphodiester
modified_base          2
                       mod_base = OTHER
                       note = 2'-O-methoxyethyl guanosine 3'-phosphorothioate
modified_base          3
                       mod_base = OTHER
                       note = 2'-O-methoxyethyl 5-methylcytidine
                        3'-phosphorothioate
modified_base          4..5
                       mod_base = OTHER
                       note = 2'-O-methoxyethyl thymidine 3'-phosphorothioate
modified_base          6
                       mod_base = OTHER
                       note = 2'-O-methoxyethyl 5-methylcytidine
                        3'-phosphorothioate
modified_base          7
                       mod_base = OTHER
                       note = 2'-deoxyadenosine 3'-phosphorothioate
modified_base          8
                       mod_base = OTHER
                       note = 2'-deoxyguanosine 3'-phosphorothioate
modified_base          9
                       mod_base = OTHER
                       note = 2'-deoxythymidine 3'-phosphorothioate
modified_base          10
                       mod_base = OTHER
                       note = 5-methyl-2'-deoxycytidine 3'-phosphorothioate
modified_base          11
                       mod_base = OTHER
                       note = 2'-deoxyadenosine 3'-phosphorothioate
modified_base          12
                       mod_base = OTHER
                       note = 2'-deoxythymidine 3'-phosphorothioate
modified_base          13
                       mod_base = OTHER
                       note = 2'-deoxyguanosine 3'-phosphorothioate
modified_base          14
                       mod_base = OTHER
                       note = 2'-deoxyadenosine 3'-phosphorothioate
modified_base          15
                       mod_base = OTHER
                       note = 5-methyl-2'-deoxycytidine 3'-phosphorothioate
modified_base          16
                       mod_base = OTHER
                       note = 2'-deoxythymidine 3'-phosphorothioate
modified_base          17
                       mod_base = OTHER
                       note = 2'-O-methoxyethyl thymidine 3'-phosphorothioate
modified_base          18..19
                       mod_base = OTHER
                       note = 2'-O-methoxyethyl 5-methylcytidine
                        3'-phosphorothioate
modified_base          20
                       mod_base = OTHER
                       note = 2'-O-methoxyethyl thymidine 3'-phosphorothioate
```

```
modified_base         21
                      mod_base = OTHER
                      note = 2'-O-methoxyethyl thymidine
SEQUENCE: 376
agcttcagtc atgacttcct t                                              21

SEQ ID NO: 377        moltype = DNA  length = 21
FEATURE               Location/Qualifiers
source                1..21
                      mol_type = other DNA
                      organism = Synthetic construct
modified_base
                      mod_base = OTHER
                      note = triantennary N-acetylgalactosamine conjugate3a
                       phosphodiester
modified_base         2
                      mod_base = OTHER
                      note = 2'-O-methoxyethyl guanosine 3'-phosphorothioate
modified_base         3
                      mod_base = OTHER
                      note = 2'-O-methoxyethyl 5-methylcytidine 3'-phosphodiester
modified_base         4..5
                      mod_base = OTHER
                      note = 2'-O-methoxyethyl thymidine 3'-phosphodiester
modified_base         6
                      mod_base = OTHER
                      note = 2'-O-methoxyethyl 5-methylcytidine 3'-phosphodiester
modified_base         7
                      mod_base = OTHER
                      note = 2'-deoxyadenosine 3'-phosphorothioate
modified_base         8
                      mod_base = OTHER
                      note = 2'-deoxyguanosine 3'-phosphorothioate
modified_base         9
                      mod_base = OTHER
                      note = 2'-deoxythymidine 3'-phosphorothioate
modified_base         10
                      mod_base = OTHER
                      note = 5-methyl-2'-deoxycytidine 3'-phosphorothioate
modified_base         11
                      mod_base = OTHER
                      note = 2'-deoxyadenosine 3'-phosphorothioate
modified_base         12
                      mod_base = OTHER
                      note = 2'-deoxythymidine 3'-phosphorothioate
modified_base         13
                      mod_base = OTHER
                      note = 2'-deoxyguanosine 3'-phosphorothioate
modified_base         14
                      mod_base = OTHER
                      note = 2'-deoxyadenosine 3'-phosphorothioate
modified_base         15
                      mod_base = OTHER
                      note = 5-methyl-2'-deoxycytidine 3'-phosphorothioate
modified_base         16
                      mod_base = OTHER
                      note = 2'-deoxythymidine 3'-phosphorothioate
modified_base         17
                      mod_base = OTHER
                      note = 2'-O-methoxyethyl thymidine 3'-phosphodiester
modified_base         18
                      mod_base = OTHER
                      note = 2'-O-methoxyethyl 5-methylcytidine 3'-phosphodiester
modified_base         19
                      mod_base = OTHER
                      note = 2'-O-methoxyethyl 5-methylcytidine
                       3'-phosphorothioate
modified_base         20
                      mod_base = OTHER
                      note = 2'-O-methoxyethyl thymidine 3'-phosphorothioate
modified_base         21
                      mod_base = OTHER
                      note = 2'-O-methoxyethyl thymidine
SEQUENCE: 377
agcttcagtc atgacttcct t                                              21

SEQ ID NO: 378        moltype = DNA  length = 21
FEATURE               Location/Qualifiers
source                1..21
```

```
                         mol_type = other DNA
                         organism = Synthetic construct
modified_base            1
                         mod_base = OTHER
                         note = 2'-O-methoxyethyl 5-methylcytidine
                          3'-phosphorothioate
modified_base            2
                         mod_base = OTHER
                         note = 2'-O-methoxyethyl adenosine 3'-phosphorothioate
modified_base            3
                         mod_base = OTHER
                         note = 2'-O-methoxyethyl guanosine 3'-phosphorothioate
modified_base            4
                         mod_base = OTHER
                         note = 2'-O-methoxyethyl 5-methylcytidine
                          3'-phosphorothioate
modified_base            5
                         mod_base = OTHER
                         note = 2'-O-methoxyethyl thymidine 3'-phosphorothioate
modified_base            6..7
                         mod_base = OTHER
                         note = 2'-deoxythymidine 3'-phosphorothioate
modified_base            8
                         mod_base = OTHER
                         note = 2'-deoxyadenosine 3'-phosphorothioate
modified_base            9..10
                         mod_base = OTHER
                         note = 2'-deoxythymidine 3'-phosphorothioate
modified_base            11
                         mod_base = OTHER
                         note = 2'-deoxyadenosine 3'-phosphorothioate
modified_base            12..14
                         mod_base = OTHER
                         note = 2'-deoxyguanosine 3'-phosphorothioate
modified_base            15
                         mod_base = OTHER
                         note = 2'-deoxyadenosine 3'-phosphorothioate
modified_base            16
                         mod_base = OTHER
                         note = 2'-O-methoxyethyl 5-methylcytidine
                          3'-phosphorothioate
modified_base            17
                         mod_base = OTHER
                         note = 2'-O-methoxyethyl adenosine 3'-phosphorothioate
modified_base            18
                         mod_base = OTHER
                         note = 2'-O-methoxyethyl guanosine 3'-phosphorothioate
modified_base            19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl adenosine 3'-phosphodiester
modified_base            21
                         mod_base = OTHER
                         note = triantennary N-acetylgalactosamine conjugate1a
SEQUENCE: 378
cagctttatt agggacagca a                                                21

SEQ ID NO: 379           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate3a
                          phosphodiester
modified_base            2
                         mod_base = OTHER
                         note = 2'-O-methoxyethyl adenosine 3'-phosphorothioate
modified_base            3
                         mod_base = OTHER
                         note = 2'-O-methoxyethyl guanosine 3'-phosphorothioate
modified_base            4
                         mod_base = OTHER
                         note = 2'-O-methoxyethyl 5-methylcytidine
                          3'-phosphorothioate
```

```
modified_base          5..6
                       mod_base = OTHER
                       note = 2'-O-methoxyethyl thymidine 3'-phosphorothioate
modified_base          7
                       mod_base = OTHER
                       note = 5-methyl-2'-deoxycytidine 3'-phosphorothioate
modified_base          8..9
                       mod_base = OTHER
                       note = 2'-deoxythymidine 3'-phosphorothioate
modified_base          10
                       mod_base = OTHER
                       note = 2'-deoxyguanosine 3'-phosphorothioate
modified_base          11
                       mod_base = OTHER
                       note = 2'-deoxythymidine 3'-phosphorothioate
modified_base          12..13
                       mod_base = OTHER
                       note = 5-methyl-2'-deoxycytidine 3'-phosphorothioate
modified_base          14
                       mod_base = OTHER
                       note = 2'-deoxyadenosine 3'-phosphorothioate
modified_base          15
                       mod_base = OTHER
                       note = 2'-deoxyguanosine 3'-phosphorothioate
modified_base          16
                       mod_base = OTHER
                       note = 5-methyl-2'-deoxycytidine 3'-phosphorothioate
modified_base          17..19
                       mod_base = OTHER
                       note = 2'-O-methoxyethyl thymidine 3'-phosphorothioate
modified_base          20
                       mod_base = OTHER
                       note = 2'-O-methoxyethyl adenosine 3'-phosphorothioate
modified_base          21
                       mod_base = OTHER
                       note = 2'-O-methoxyethyl thymidine
SEQUENCE: 379
aagcttcttg tccagcttta t                                             21

SEQ ID NO: 380         moltype = DNA  length = 21
FEATURE                Location/Qualifiers
source                 1..21
                       mol_type = other DNA
                       organism = Synthetic construct
modified_base
                       mod_base = OTHER
                       note = triantennary N-acetylgalactosamine conjugate3a
                        phosphodiester
modified_base          2
                       mod_base = OTHER
                       note = 2'-O-methoxyethyl adenosine 3'-phosphorothioate
modified_base          3
                       mod_base = OTHER
                       note = 2'-O-methoxyethyl guanosine 3'-phosphodiester
modified_base          4
                       mod_base = OTHER
                       note = 2'-O-methoxyethyl 5-methylcytidine 3'-phosphodiester
modified_base          5..6
                       mod_base = OTHER
                       note = 2'-O-methoxyethyl thymidine 3'-phosphodiester
modified_base          7
                       mod_base = OTHER
                       note = 5-methyl-2'-deoxycytidine 3'-phosphorothioate
modified_base          8..9
                       mod_base = OTHER
                       note = 2'-deoxythymidine 3'-phosphorothioate
modified_base          10
                       mod_base = OTHER
                       note = 2'-deoxyguanosine 3'-phosphorothioate
modified_base          11
                       mod_base = OTHER
                       note = 2'-deoxythymidine 3'-phosphorothioate
modified_base          12..13
                       mod_base = OTHER
                       note = 5-methyl-2'-deoxycytidine 3'-phosphorothioate
modified_base          14
                       mod_base = OTHER
                       note = 2'-deoxyadenosine 3'-phosphorothioate
modified_base          15
```

```
                         mod_base = OTHER
                         note = 2'-deoxyguanosine 3'-phosphorothioate
modified_base            16
                         mod_base = OTHER
                         note = 5-methyl-2'-deoxycytidine 3'-phosphorothioate
modified_base            17..18
                         mod_base = OTHER
                         note = 2'-O-methoxyethyl thymidine 3'-phosphodiester
modified_base            19
                         mod_base = OTHER
                         note = 2'-O-methoxyethyl thymidine 3'-phosphorothioate
modified_base            20
                         mod_base = OTHER
                         note = 2'-O-methoxyethyl adenosine 3'-phosphorothioate
modified_base            21
                         mod_base = OTHER
                         note = 2'-O-methoxyethyl thymidine
SEQUENCE: 380
aagcttcttg tccagcttta t                                                21

SEQ ID NO: 381           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate3a
                          phosphodiester
modified_base            2
                         mod_base = OTHER
                         note = 2'-O-methoxyethyl thymidine 3'-phosphorothioate
modified_base            3..4
                         mod_base = OTHER
                         note = 2'-O-methoxyethyl guanosine 3'-phosphodiester
modified_base            5
                         mod_base = OTHER
                         note = 2'-O-methoxyethyl thymidine 3'-phosphodiester
modified_base            6
                         mod_base = OTHER
                         note = 2'-O-methoxyethyl adenosine 3'-phosphodiester
modified_base            7
                         mod_base = OTHER
                         note = 2'-deoxyadenosine 3'-phosphorothioate
modified_base            8
                         mod_base = OTHER
                         note = 2'-deoxythymidine 3'-phosphorothioate
modified_base            9..10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 5-methyl-2'-deoxycytidine 3'-phosphorothioate
modified_base            13..15
                         mod_base = OTHER
                         note = 2'-deoxythymidine 3'-phosphorothioate
modified_base            16
                         mod_base = OTHER
                         note = 5-methyl-2'-deoxycytidine 3'-phosphorothioate
modified_base            17
                         mod_base = OTHER
                         note = 2'-O-methoxyethyl adenosine 3'-phosphodiester
modified_base            18
                         mod_base = OTHER
                         note = 2'-O-methoxyethyl guanosine 3'-phosphodiester
modified_base            19
                         mod_base = OTHER
                         note = 2'-O-methoxyethyl adenosine 3'-phosphorothioate
modified_base            20
                         mod_base = OTHER
                         note = 2'-O-methoxyethyl guanosine 3'-phosphorothioate
modified_base            21
                         mod_base = OTHER
                         note = 2'-O-methoxyethyl guanosine
SEQUENCE: 381
atggtaatcc actttcagag g                                                21
```

```
SEQ ID NO: 382          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine 3'-phosphodiester
modified_base           21
                        mod_base = OTHER
                        note = triantennary N-acetylgalactosamine conjugate9a
SEQUENCE: 382
gcttcagtca tgacttcctt a                                           21

SEQ ID NO: 383          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate2a
                         phosphodiester
modified_base           2
```

```
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 383
agcttcagtc atgacttcct t                                      21

SEQ ID NO: 384          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate8a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
```

```
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 384
agcttcagtc atgacttcct t                                            21

SEQ ID NO: 385          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate5a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
```

```
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 385
agcttcagtc atgacttcct t                                               21

SEQ ID NO: 386          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate10a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
```

```
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 386
agcttcagtc atgacttcct t                                              21

SEQ ID NO: 387          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate3a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
```

```
modified_base         16
                      mod_base = OTHER
                      note = 2'-deoxythymidine 3'-phosphorothioate
modified_base         17
                      mod_base = OTHER
                      note = 2'-O-methoxyethyl thymidine 3'-phosphorothioate
modified_base         18..19
                      mod_base = OTHER
                      note = 2'-O-methoxyethyl 5-methylcytidine
                       3'-phosphorothioate
modified_base         20
                      mod_base = OTHER
                      note = 2'-O-methoxyethyl thymidine 3'-phosphorothioate
modified_base         21
                      mod_base = OTHER
                      note = 2'-O-methoxyethyl thymidine
SEQUENCE: 387
tgcttcagtc atgacttcct t                                            21

SEQ ID NO: 388        moltype = DNA  length = 21
FEATURE               Location/Qualifiers
source                1..21
                      mol_type = other DNA
                      organism = Synthetic construct
modified_base
                      mod_base = OTHER
                      note = triantennary N-acetylgalactosamine conjugate3a
                       phosphodiester
modified_base         2
                      mod_base = OTHER
                      note = 2'-O-methoxyethyl thymidine 3'-phosphorothioate
modified_base         3
                      mod_base = OTHER
                      note = 2'-O-methoxyethyl 5-methylcytidine
                       3'-phosphorothioate
modified_base         4..5
                      mod_base = OTHER
                      note = 2'-O-methoxyethyl thymidine 3'-phosphorothioate
modified_base         6
                      mod_base = OTHER
                      note = 2'-O-methoxyethyl guanosine 3'-phosphorothioate
modified_base         7
                      mod_base = OTHER
                      note = 2'-deoxyguanosine 3'-phosphorothioate
modified_base         8..9
                      mod_base = OTHER
                      note = 2'-deoxythymidine 3'-phosphorothioate
modified_base         10
                      mod_base = OTHER
                      note = 2'-deoxyadenosine 3'-phosphorothioate
modified_base         11
                      mod_base = OTHER
                      note = 5-methyl-2'-deoxycytidine 3'-phosphorothioate
modified_base         12
                      mod_base = OTHER
                      note = 2'-deoxyadenosine 3'-phosphorothioate
modified_base         13
                      mod_base = OTHER
                      note = 2'-deoxythymidine 3'-phosphorothioate
modified_base         14
                      mod_base = OTHER
                      note = 2'-deoxyguanosine 3'-phosphorothioate
modified_base         15..16
                      mod_base = OTHER
                      note = 2'-deoxyadenosine 3'-phosphorothioate
modified_base         17
                      mod_base = OTHER
                      note = 2'-O-methoxyethyl adenosine 3'-phosphorothioate
modified_base         18
                      mod_base = OTHER
                      note = 2'-O-methoxyethyl thymidine 3'-phosphorothioate
modified_base         19..20
                      mod_base = OTHER
                      note = 2'-O-methoxyethyl 5-methylcytidine
                       3'-phosphorothioate
modified_base         21
                      mod_base = OTHER
                      note = 2'-O-methoxyethyl 5-methylcytidine
SEQUENCE: 388
```

-continued atcttggtta catgaaatcc c 21

SEQ ID NO: 389 moltype = DNA length = 21
FEATURE Location/Qualifiers
source 1..21
mol_type = other DNA
organism = Synthetic construct
modified_base 1
mod_base = OTHER
note = 2'-O-methoxyethyl thymidine 3'-phosphorothioate
modified_base 2
mod_base = OTHER
note = 2'-O-methoxyethyl 5-methylcytidine 3'-phosphodiester
modified_base 3..4
mod_base = OTHER
note = 2'-O-methoxyethyl thymidine 3'-phosphodiester
modified_base 5
mod_base = OTHER
note = 2'-O-methoxyethyl guanosine 3'-phosphodiester
modified_base 6
mod_base = OTHER
note = 2'-deoxyguanosine 3'-phosphorothioate
modified_base 7..8
mod_base = OTHER
note = 2'-deoxythymidine 3'-phosphorothioate
modified_base 9
mod_base = OTHER
note = 2'-deoxyadenosine 3'-phosphorothioate
modified_base 10
mod_base = OTHER
note = 5-methyl-2'-deoxycytidine 3'-phosphorothioate
modified_base 11
mod_base = OTHER
note = 2'-deoxyadenosine 3'-phosphorothioate
modified_base 12
mod_base = OTHER
note = 2'-deoxythymidine 3'-phosphorothioate
modified_base 13
mod_base = OTHER
note = 2'-deoxyguanosine 3'-phosphorothioate
modified_base 14..15
mod_base = OTHER
note = 2'-deoxyadenosine 3'-phosphorothioate
modified_base 16
mod_base = OTHER
note = 2'-O-methoxyethyl adenosine 3'-phosphodiester
modified_base 17
mod_base = OTHER
note = 2'-O-methoxyethyl thymidine 3'-phosphodiester
modified_base 18..19
mod_base = OTHER
note = 2'-O-methoxyethyl 5-methylcytidine
3'-phosphorothioate
modified_base 20
mod_base = OTHER
note = 2'-O-methoxyethyl 5-methylcytidine 3'-phosphodiester
modified_base 21
mod_base = OTHER
note = triantennary N-acetylgalactosamine conjugate3a
SEQUENCE: 389
tcttggttac atgaaatccc a 21

SEQ ID NO: 390 moltype = DNA length = 21
FEATURE Location/Qualifiers
source 1..21
mol_type = other DNA
organism = Synthetic construct
modified_base
mod_base = OTHER
note = triantennary N-acetylgalactosamine conjugate3a
phosphodiester
modified_base 2
mod_base = OTHER
note = 2'-O-methoxyethyl thymidine 3'-phosphorothioate
modified_base 3
mod_base = OTHER
note = 2'-O-methoxyethyl 5-methylcytidine 3'-phosphodiester
modified_base 4..5
mod_base = OTHER

```
                        note = 2'-O-methoxyethyl thymidine 3'-phosphodiester
modified_base           6
                        mod_base = OTHER
                        note = 2'-O-methoxyethyl guanosine 3'-phosphodiester
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxyadenosine 3'-phosphorothioate
modified_base           13
                        mod_base = OTHER
                        note = 2'-deoxythymidine 3'-phosphorothioate
modified_base           14
                        mod_base = OTHER
                        note = 2'-deoxyguanosine 3'-phosphorothioate
modified_base           15..16
                        mod_base = OTHER
                        note = 2'-deoxyadenosine 3'-phosphorothioate
modified_base           17
                        mod_base = OTHER
                        note = 2'-O-methoxyethyl adenosine 3'-phosphodiester
modified_base           18
                        mod_base = OTHER
                        note = 2'-O-methoxyethyl thymidine 3'-phosphodiester
modified_base           19..20
                        mod_base = OTHER
                        note = 2'-O-methoxyethyl 5-methylcytidine
                         3'-phosphorothioate
modified_base           21
                        mod_base = OTHER
                        note = 2'-O-methoxyethyl 5-methylcytidine
SEQUENCE: 390
atcttggtta catgaaatcc c                                              21

SEQ ID NO: 391          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate6a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
```

```
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 391
agcttcagtc atgacttcct t                                              21

SEQ ID NO: 392          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate7a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
```

```
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphorothioate
modified_base            18..19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl thymidine 3'-phosphorothioate
modified_base            21
                         mod_base = OTHER
                         note = 2'-O-methoxyethyl thymidine
SEQUENCE: 392
agcttcagtc atgacttcct t                                                21

SEQ ID NO: 393           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate13a
                          phosphodiester
modified_base            2
                         mod_base = OTHER
                         note = 2'-O-methoxyethyl guanosine 3'-phosphorothioate
modified_base            3
                         mod_base = OTHER
                         note = 2'-O-methoxyethyl 5-methylcytidine
                          3'-phosphorothioate
modified_base            4..5
                         mod_base = OTHER
                         note = 2'-O-methoxyethyl thymidine 3'-phosphorothioate
modified_base            6
                         mod_base = OTHER
                         note = 2'-O-methoxyethyl 5-methylcytidine
                          3'-phosphorothioate
modified_base            7
                         mod_base = OTHER
                         note = 2'-deoxyadenosine 3'-phosphorothioate
modified_base            8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
```

```
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 393
agcttcagtc atgacttcct t                                              21

SEQ ID NO: 394          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate3a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 2'-O-methoxyethyl 5-methylcytidine 3'-phosphodiester
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphodiester
modified_base           18
                        mod_base = OTHER
                        note = 2'-O-methoxyethyl 5-methylcytidine 3'-phosphodiester
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
```

```
                        mod_base = OTHER
                        note = 2'-O-methoxyethyl thymidine
SEQUENCE: 394
tgcttcagtc atgacttcct t                                             21

SEQ ID NO: 395          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate3a
                         phosphodiester
modified_base           1
                        mod_base = OTHER
                        note = 2'-O-methoxyethyl adenosine 3'-phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 2'-O-methoxyethyl 5-methylcytidine 3'-phosphodiester
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphodiester
modified_base           18
                        mod_base = OTHER
                        note = 2'-O-methoxyethyl 5-methylcytidine 3'-phosphodiester
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 395
agcttcagtc atgacttcct t                                             21

SEQ ID NO: 396          moltype = DNA  length = 21
```

-continued

```
FEATURE                Location/Qualifiers
source                 1..21
                       mol_type = other DNA
                       organism = Synthetic construct
modified_base
                       mod_base = OTHER
                       note = triantennary N-acetylgalactosamine conjugate3a
                        phosphodiester
modified_base          1
                       mod_base = OTHER
                       note = 2'-O-methoxyethyl thymidine 3'-phosphodiester
modified_base          2
                       mod_base = OTHER
                       note = 2'-O-methoxyethyl guanosine 3'-phosphorothioate
modified_base          3
                       mod_base = OTHER
                       note = 2'-O-methoxyethyl 5-methylcytidine 3'-phosphodiester
modified_base          4..5
                       mod_base = OTHER
                       note = 2'-O-methoxyethyl thymidine 3'-phosphodiester
modified_base          6
                       mod_base = OTHER
                       note = 2'-O-methoxyethyl 5-methylcytidine 3'-phosphodiester
modified_base          7
                       mod_base = OTHER
                       note = 2'-deoxyadenosine 3'-phosphorothioate
modified_base          8
                       mod_base = OTHER
                       note = 2'-deoxyguanosine 3'-phosphorothioate
modified_base          9
                       mod_base = OTHER
                       note = 2'-deoxythymidine 3'-phosphorothioate
modified_base          10
                       mod_base = OTHER
                       note = 5-methyl-2'-deoxycytidine 3'-phosphorothioate
modified_base          11
                       mod_base = OTHER
                       note = 2'-deoxyadenosine 3'-phosphorothioate
modified_base          12
                       mod_base = OTHER
                       note = 2'-deoxythymidine 3'-phosphorothioate
modified_base          13
                       mod_base = OTHER
                       note = 2'-deoxyguanosine 3'-phosphorothioate
modified_base          14
                       mod_base = OTHER
                       note = 2'-deoxyadenosine 3'-phosphorothioate
modified_base          15
                       mod_base = OTHER
                       note = 5-methyl-2'-deoxycytidine 3'-phosphorothioate
modified_base          16
                       mod_base = OTHER
                       note = 2'-deoxythymidine 3'-phosphorothioate
modified_base          17
                       mod_base = OTHER
                       note = 2'-O-methoxyethyl thymidine 3'-phosphodiester
modified_base          18
                       mod_base = OTHER
                       note = 2'-O-methoxyethyl 5-methylcytidine 3'-phosphodiester
modified_base          19
                       mod_base = OTHER
                       note = 2'-O-methoxyethyl 5-methylcytidine
                        3'-phosphorothioate
modified_base          20
                       mod_base = OTHER
                       note = 2'-O-methoxyethyl thymidine 3'-phosphorothioate
modified_base          21
                       mod_base = OTHER
                       note = 2'-O-methoxyethyl thymidine
SEQUENCE: 396
tgcttcagtc atgacttcct t                                                21

SEQ ID NO: 397         moltype = DNA  length = 21
FEATURE                Location/Qualifiers
source                 1..21
                       mol_type = other DNA
                       organism = Synthetic construct
modified_base
                       mod_base = OTHER
```

```
                        note = triantennary N-acetylgalactosamine conjugate12a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 397
agcttcagtc atgacttcct t                                                  21

SEQ ID NO: 398          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate13a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine 3'-phosphodiester
modified_base           4..5
                        mod_base = OTHER
```

-continued

```
                        note = 2'-O-methoxyethyl thymidine 3'-phosphodiester
modified_base           6
                        mod_base = OTHER
                        note = 2'-O-methoxyethyl 5-methylcytidine 3'-phosphodiester
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphodiester
modified_base           18
                        mod_base = OTHER
                        note = 2'-O-methoxyethyl 5-methylcytidine 3'-phosphodiester
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 398
agcttcagtc atgacttcct t                                              21

SEQ ID NO: 399          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate14a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
```

```
modified_base          8
                       mod_base = OTHER
                       note = 2'-deoxyguanosine 3'-phosphorothioate
modified_base          9
                       mod_base = OTHER
                       note = 2'-deoxythymidine 3'-phosphorothioate
modified_base          10
                       mod_base = OTHER
                       note = 5-methyl-2'-deoxycytidine 3'-phosphorothioate
modified_base          11
                       mod_base = OTHER
                       note = 2'-deoxyadenosine 3'-phosphorothioate
modified_base          12
                       mod_base = OTHER
                       note = 2'-deoxythymidine 3'-phosphorothioate
modified_base          13
                       mod_base = OTHER
                       note = 2'-deoxyguanosine 3'-phosphorothioate
modified_base          14
                       mod_base = OTHER
                       note = 2'-deoxyadenosine 3'-phosphorothioate
modified_base          15
                       mod_base = OTHER
                       note = 5-methyl-2'-deoxycytidine 3'-phosphorothioate
modified_base          16
                       mod_base = OTHER
                       note = 2'-deoxythymidine 3'-phosphorothioate
modified_base          17
                       mod_base = OTHER
                       note = 2'-O-methoxyethyl thymidine 3'-phosphorothioate
modified_base          18..19
                       mod_base = OTHER
                       note = 2'-O-methoxyethyl 5-methylcytidine
                        3'-phosphorothioate
modified_base          20
                       mod_base = OTHER
                       note = 2'-O-methoxyethyl thymidine 3'-phosphorothioate
modified_base          21
                       mod_base = OTHER
                       note = 2'-O-methoxyethyl thymidine
SEQUENCE: 399
agcttcagtc atgacttcct t                                                21

SEQ ID NO: 400         moltype = DNA  length = 21
FEATURE                Location/Qualifiers
source                 1..21
                       mol_type = other DNA
                       organism = Synthetic construct
modified_base
                       mod_base = OTHER
                       note = triantennary N-acetylgalactosamine conjugate15a
                        phosphodiester
modified_base          2
                       mod_base = OTHER
                       note = 2'-O-methoxyethyl guanosine 3'-phosphorothioate
modified_base          3
                       mod_base = OTHER
                       note = 2'-O-methoxyethyl 5-methylcytidine
                        3'-phosphorothioate
modified_base          4..5
                       mod_base = OTHER
                       note = 2'-O-methoxyethyl thymidine 3'-phosphorothioate
modified_base          6
                       mod_base = OTHER
                       note = 2'-O-methoxyethyl 5-methylcytidine
                        3'-phosphorothioate
modified_base          7
                       mod_base = OTHER
                       note = 2'-deoxyadenosine 3'-phosphorothioate
modified_base          8
                       mod_base = OTHER
                       note = 2'-deoxyguanosine 3'-phosphorothioate
modified_base          9
                       mod_base = OTHER
                       note = 2'-deoxythymidine 3'-phosphorothioate
modified_base          10
                       mod_base = OTHER
                       note = 5-methyl-2'-deoxycytidine 3'-phosphorothioate
modified_base          11
```

```
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 400
agcttcagtc atgacttcct t                                              21

SEQ ID NO: 401          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate7a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 2'-O-methoxyethyl 5-methylcytidine 3'-phosphodiester
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
```

```
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphodiester
modified_base            18
                         mod_base = OTHER
                         note = 2'-O-methoxyethyl 5-methylcytidine 3'-phosphodiester
modified_base            19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl thymidine 3'-phosphorothioate
modified_base            21
                         mod_base = OTHER
                         note = 2'-O-methoxyethyl thymidine
SEQUENCE: 401
agcttcagtc atgacttcct t                                                21

SEQ ID NO: 402           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate10a
                          phosphodiester
modified_base            2
                         mod_base = OTHER
                         note = 2'-O-methoxyethyl guanosine 3'-phosphorothioate
modified_base            3
                         mod_base = OTHER
                         note = 2'-O-methoxyethyl 5-methylcytidine 3'-phosphodiester
modified_base            4..5
                         mod_base = OTHER
                         note = 2'-O-methoxyethyl thymidine 3'-phosphodiester
modified_base            6
                         mod_base = OTHER
                         note = 2'-O-methoxyethyl 5-methylcytidine 3'-phosphodiester
modified_base            7
                         mod_base = OTHER
                         note = 2'-deoxyadenosine 3'-phosphorothioate
modified_base            8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphodiester
modified_base            18
```

```
                        mod_base = OTHER
                        note = 2'-O-methoxyethyl 5-methylcytidine 3'-phosphodiester
modified_base           19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 402
agcttcagtc atgacttcct t                                              21

SEQ ID NO: 403          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate7a
                         phosphodiester
modified_base           2
                        mod_base = OTHER
                        note = 2'-O-methoxyethyl adenosine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5..6
                        mod_base = OTHER
                        note = 2'-O-methoxyethyl thymidine 3'-phosphorothioate
modified_base           7
                        mod_base = OTHER
                        note = 5-methyl-2'-deoxycytidine 3'-phosphorothioate
modified_base           8..9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxythymidine 3'-phosphorothioate
modified_base           12..13
                        mod_base = OTHER
                        note = 5-methyl-2'-deoxycytidine 3'-phosphorothioate
modified_base           14
                        mod_base = OTHER
                        note = 2'-deoxyadenosine 3'-phosphorothioate
modified_base           15
                        mod_base = OTHER
                        note = 2'-deoxyguanosine 3'-phosphorothioate
modified_base           16
                        mod_base = OTHER
                        note = 5-methyl-2'-deoxycytidine 3'-phosphorothioate
modified_base           17..19
                        mod_base = OTHER
                        note = 2'-O-methoxyethyl thymidine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl thymidine
SEQUENCE: 403
aagcttcttg tccagcttta t                                              21

SEQ ID NO: 404          moltype = DNA  length = 21
FEATURE                 Location/Qualifiers
source                  1..21
                        mol_type = other DNA
                        organism = Synthetic construct
modified_base
```

```
                        mod_base = OTHER
                        note = triantennary N-acetylgalactosamine conjugate10a
                         phosphodiester
modified_base           2
                        mod_base = OTHER
                        note = 2'-O-methoxyethyl adenosine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5..6
                        mod_base = OTHER
                        note = 2'-O-methoxyethyl thymidine 3'-phosphorothioate
modified_base           7
                        mod_base = OTHER
                        note = 5-methyl-2'-deoxycytidine 3'-phosphorothioate
modified_base           8..9
                        mod_base = OTHER
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxythymidine 3'-phosphorothioate
modified_base           12..13
                        mod_base = OTHER
                        note = 5-methyl-2'-deoxycytidine 3'-phosphorothioate
modified_base           14
                        mod_base = OTHER
                        note = 2'-deoxyadenosine 3'-phosphorothioate
modified_base           15
                        mod_base = OTHER
                        note = 2'-deoxyguanosine 3'-phosphorothioate
modified_base           16
                        mod_base = OTHER
                        note = 5-methyl-2'-deoxycytidine 3'-phosphorothioate
modified_base           17..19
                        mod_base = OTHER
                        note = 2'-O-methoxyethyl thymidine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl thymidine
SEQUENCE: 404
aagcttcttg tccagcttta t                                            21

SEQ ID NO: 405          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate13a
                         phosphodiester
modified_base           2
                        mod_base = OTHER
                        note = 2'-O-methoxyethyl adenosine 3'-phosphorothioate
modified_base           3
                        mod_base = OTHER
                        note = 2'-O-methoxyethyl guanosine 3'-phosphorothioate
modified_base           4
                        mod_base = OTHER
                        note = 2'-O-methoxyethyl 5-methylcytidine
                         3'-phosphorothioate
modified_base           5..6
                        mod_base = OTHER
                        note = 2'-O-methoxyethyl thymidine 3'-phosphorothioate
modified_base           7
                        mod_base = OTHER
                        note = 5-methyl-2'-deoxycytidine 3'-phosphorothioate
modified_base           8..9
                        mod_base = OTHER
```

```
                        note = 2'-deoxythymidine 3'-phosphorothioate
modified_base           10
                        mod_base = OTHER
                        note = 2'-deoxyguanosine 3'-phosphorothioate
modified_base           11
                        mod_base = OTHER
                        note = 2'-deoxythymidine 3'-phosphorothioate
modified_base           12..13
                        mod_base = OTHER
                        note = 5-methyl-2'-deoxycytidine 3'-phosphorothioate
modified_base           14
                        mod_base = OTHER
                        note = 2'-deoxyadenosine 3'-phosphorothioate
modified_base           15
                        mod_base = OTHER
                        note = 2'-deoxyguanosine 3'-phosphorothioate
modified_base           16
                        mod_base = OTHER
                        note = 5-methyl-2'-deoxycytidine 3'-phosphorothioate
modified_base           17..19
                        mod_base = OTHER
                        note = 2'-O-methoxyethyl thymidine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl thymidine
SEQUENCE: 405
aagcttcttg tccagcttta t                                                21

SEQ ID NO: 406          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate17a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
```

```
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphorothioate
modified_base            18..19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl thymidine 3'-phosphorothioate
modified_base            21
                         mod_base = OTHER
                         note = 2'-O-methoxyethyl thymidine
SEQUENCE: 406
agcttcagtc atgacttcct t                                              21

SEQ ID NO: 407           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate18a
                          phosphodiester
modified_base            2
                         mod_base = OTHER
                         note = 2'-O-methoxyethyl guanosine 3'-phosphorothioate
modified_base            3
                         mod_base = OTHER
                         note = 2'-O-methoxyethyl 5-methylcytidine
                          3'-phosphorothioate
modified_base            4..5
                         mod_base = OTHER
                         note = 2'-O-methoxyethyl thymidine 3'-phosphorothioate
modified_base            6
                         mod_base = OTHER
                         note = 2'-O-methoxyethyl 5-methylcytidine
                          3'-phosphorothioate
modified_base            7
                         mod_base = OTHER
                         note = 2'-deoxyadenosine 3'-phosphorothioate
modified_base            8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphorothioate
modified_base            18..19
                         mod_base = OTHER
```

```
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 407
agcttcagtc atgacttcct t                                              21

SEQ ID NO: 408          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine 3'-phosphodiester
modified_base           21
                        mod_base = OTHER
                        note = triantennary N-acetylgalactosamine conjugate19a
SEQUENCE: 408
gcttcagtca tgacttcctt a                                              21
```

-continued

```
SEQ ID NO: 409          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = 2'-O-methoxyethyl thymidine 3'-phosphorothioate
modified_base           5
                        mod_base = OTHER
                        note = 2'-O-methoxyethyl 5-methylcytidine
                         3'-phosphorothioate
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphorothioate
modified_base           17..18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine 3'-phosphodiester
modified_base           21
                        mod_base = OTHER
                        note = triantennary N-acetylgalactosamine conjugate20a
SEQUENCE: 409
gcttcagtca tgacttcctt a                                            21

SEQ ID NO: 410          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate23a
                         phosphodiester
modified_base           2
                        mod_base = OTHER
```

```
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 410
agcttcagtc atgacttcct t                                              21

SEQ ID NO: 411          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate9a
                         phosphodiester
modified_base           2
                        mod_base = OTHER
                        note = 2'-O-methoxyethyl guanosine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
```

```
                        note = 2'-O-methoxyethyl 5-methylcytidine
                         3'-phosphorothioate
modified_base           7
                        mod_base = OTHER
                        note = 2'-deoxyadenosine 3'-phosphorothioate
modified_base           8
                        mod_base = OTHER
                        note = 2'-deoxyguanosine 3'-phosphorothioate
modified_base           9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 5-methyl-2'-deoxycytidine 3'-phosphorothioate
modified_base           16
                        mod_base = OTHER
                        note = 2'-deoxythymidine 3'-phosphorothioate
modified_base           17
                        mod_base = OTHER
                        note = 2'-O-methoxyethyl thymidine 3'-phosphorothioate
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl thymidine 3'-phosphorothioate
modified_base           21
                        mod_base = OTHER
                        note = 2'-O-methoxyethyl thymidine
SEQUENCE: 411
agcttcagtc atgacttcct t                                             21

SEQ ID NO: 412          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate7a
                         phosphodiester
modified_base           2
                        mod_base = OTHER
                        note = 2'-O-methoxyethyl thymidine 3'-phosphorothioate
modified_base           3..4
                        mod_base = OTHER
                        note = 2'-O-methoxyethyl guanosine 3'-phosphodiester
modified_base           5
                        mod_base = OTHER
                        note = 2'-O-methoxyethyl thymidine 3'-phosphodiester
modified_base           6
                        mod_base = OTHER
                        note = 2'-O-methoxyethyl adenosine 3'-phosphodiester
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9..10
                        mod_base = OTHER
                        note = 5-methyl-2'-deoxycytidine 3'-phosphorothioate
modified_base           11
```

```
                         mod_base = OTHER
                         note = 2'-deoxyadenosine 3'-phosphorothioate
modified_base            12
                         mod_base = OTHER
                         note = 5-methyl-2'-deoxycytidine 3'-phosphorothioate
modified_base            13..15
                         mod_base = OTHER
                         note = 2'-deoxythymidine 3'-phosphorothioate
modified_base            16
                         mod_base = OTHER
                         note = 5-methyl-2'-deoxycytidine 3'-phosphorothioate
modified_base            17
                         mod_base = OTHER
                         note = 2'-O-methoxyethyl adenosine 3'-phosphodiester
modified_base            18
                         mod_base = OTHER
                         note = 2'-O-methoxyethyl guanosine 3'-phosphodiester
modified_base            19
                         mod_base = OTHER
                         note = 2'-O-methoxyethyl adenosine 3'-phosphorothioate
modified_base            20
                         mod_base = OTHER
                         note = 2'-O-methoxyethyl guanosine 3'-phosphorothioate
modified_base            21
                         mod_base = OTHER
                         note = 2'-O-methoxyethyl guanosine
SEQUENCE: 412
atggtaatcc actttcagag g                                            21

SEQ ID NO: 413           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate10a
                          phosphodiester
modified_base            2
                         mod_base = OTHER
                         note = 2'-O-methoxyethyl thymidine 3'-phosphorothioate
modified_base            3..4
                         mod_base = OTHER
                         note = 2'-O-methoxyethyl guanosine 3'-phosphodiester
modified_base            5
                         mod_base = OTHER
                         note = 2'-O-methoxyethyl thymidine 3'-phosphodiester
modified_base            6
                         mod_base = OTHER
                         note = 2'-O-methoxyethyl adenosine 3'-phosphodiester
modified_base            7
                         mod_base = OTHER
                         note = 2'-deoxyadenosine 3'-phosphorothioate
modified_base            8
                         mod_base = OTHER
                         note = 2'-deoxythymidine 3'-phosphorothioate
modified_base            9..10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 5-methyl-2'-deoxycytidine 3'-phosphorothioate
modified_base            13..15
                         mod_base = OTHER
                         note = 2'-deoxythymidine 3'-phosphorothioate
modified_base            16
                         mod_base = OTHER
                         note = 5-methyl-2'-deoxycytidine 3'-phosphorothioate
modified_base            17
                         mod_base = OTHER
                         note = 2'-O-methoxyethyl adenosine 3'-phosphodiester
modified_base            18
                         mod_base = OTHER
                         note = 2'-O-methoxyethyl guanosine 3'-phosphodiester
modified_base            19
                         mod_base = OTHER
```

```
                        note = 2'-O-methoxyethyl adenosine 3'-phosphorothioate
modified_base           20
                        mod_base = OTHER
                        note = 2'-O-methoxyethyl guanosine 3'-phosphorothioate
modified_base           21
                        mod_base = OTHER
                        note = 2'-O-methoxyethyl guanosine
SEQUENCE: 413
atggtaatcc actttcagag g                                            21

SEQ ID NO: 414          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate13a
                         phosphodiester
modified_base           2
                        mod_base = OTHER
                        note = 2'-O-methoxyethyl thymidine 3'-phosphorothioate
modified_base           3..4
                        mod_base = OTHER
                        note = 2'-O-methoxyethyl guanosine 3'-phosphodiester
modified_base           5
                        mod_base = OTHER
                        note = 2'-O-methoxyethyl thymidine 3'-phosphodiester
modified_base           6
                        mod_base = OTHER
                        note = 2'-O-methoxyethyl adenosine 3'-phosphodiester
modified_base           7
                        mod_base = OTHER
                        note = 2'-deoxyadenosine 3'-phosphorothioate
modified_base           8
                        mod_base = OTHER
                        note = 2'-deoxythymidine 3'-phosphorothioate
modified_base           9..10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 5-methyl-2'-deoxycytidine 3'-phosphorothioate
modified_base           13..15
                        mod_base = OTHER
                        note = 2'-deoxythymidine 3'-phosphorothioate
modified_base           16
                        mod_base = OTHER
                        note = 5-methyl-2'-deoxycytidine 3'-phosphorothioate
modified_base           17
                        mod_base = OTHER
                        note = 2'-O-methoxyethyl adenosine 3'-phosphodiester
modified_base           18
                        mod_base = OTHER
                        note = 2'-O-methoxyethyl guanosine 3'-phosphodiester
modified_base           19
                        mod_base = OTHER
                        note = 2'-O-methoxyethyl adenosine 3'-phosphorothioate
modified_base           20
                        mod_base = OTHER
                        note = 2'-O-methoxyethyl guanosine 3'-phosphorothioate
modified_base           21
                        mod_base = OTHER
                        note = 2'-O-methoxyethyl guanosine
SEQUENCE: 414
atggtaatcc actttcagag g                                            21

SEQ ID NO: 415          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate3a
                         phosphodiester
```

```
modified_base          2
                       mod_base = OTHER
                       note = 2'-O-methoxyethyl adenosine 3'-phosphorothioate
modified_base          3..5
                       mod_base = OTHER
                       note = 2'-O-methoxyethyl 5-methylcytidine
                        3'-phosphorothioate
modified_base          6
                       mod_base = OTHER
                       note = 2'-O-methoxyethyl adenosine 3'-phosphorothioate
modified_base          7
                       mod_base = OTHER
                       note = 2'-deoxyadenosine 3'-phosphorothioate
modified_base          8..9
                       mod_base = OTHER
                       note = 2'-deoxythymidine 3'-phosphorothioate
modified_base          10
                       mod_base = OTHER
                       note = 5-methyl-2'-deoxycytidine 3'-phosphorothioate
modified_base          11
                       mod_base = OTHER
                       note = 2'-deoxyadenosine 3'-phosphorothioate
modified_base          12
                       mod_base = OTHER
                       note = 2'-deoxyguanosine 3'-phosphorothioate
modified_base          13..14
                       mod_base = OTHER
                       note = 2'-deoxyadenosine 3'-phosphorothioate
modified_base          15..16
                       mod_base = OTHER
                       note = 2'-deoxyguanosine 3'-phosphorothioate
modified_base          17..18
                       mod_base = OTHER
                       note = 2'-O-methoxyethyl adenosine 3'-phosphorothioate
modified_base          19..20
                       mod_base = OTHER
                       note = 2'-O-methoxyethyl guanosine 3'-phosphorothioate
modified_base          21
                       mod_base = OTHER
                       note = 2'-O-methoxyethyl adenosine
SEQUENCE: 415
aacccaattc agaaggaagg a                                                  21

SEQ ID NO: 416         moltype = DNA  length = 21
FEATURE                Location/Qualifiers
source                 1..21
                       mol_type = other DNA
                       organism = Synthetic construct
modified_base
                       mod_base = OTHER
                       note = triantennary N-acetylgalactosamine conjugate7a
                        phosphodiester
modified_base          2
                       mod_base = OTHER
                       note = 2'-O-methoxyethyl adenosine 3'-phosphorothioate
modified_base          3..5
                       mod_base = OTHER
                       note = 2'-O-methoxyethyl 5-methylcytidine
                        3'-phosphorothioate
modified_base          6
                       mod_base = OTHER
                       note = 2'-O-methoxyethyl adenosine 3'-phosphorothioate
modified_base          7
                       mod_base = OTHER
                       note = 2'-deoxyadenosine 3'-phosphorothioate
modified_base          8..9
                       mod_base = OTHER
                       note = 2'-deoxythymidine 3'-phosphorothioate
modified_base          10
                       mod_base = OTHER
                       note = 5-methyl-2'-deoxycytidine 3'-phosphorothioate
modified_base          11
                       mod_base = OTHER
                       note = 2'-deoxyadenosine 3'-phosphorothioate
modified_base          12
                       mod_base = OTHER
                       note = 2'-deoxyguanosine 3'-phosphorothioate
modified_base          13..14
                       mod_base = OTHER
```

```
                        note = 2'-deoxyadenosine 3'-phosphorothioate
modified_base           15..16
                        mod_base = OTHER
                        note = 2'-deoxyguanosine 3'-phosphorothioate
modified_base           17..18
                        mod_base = OTHER
                        note = 2'-O-methoxyethyl adenosine 3'-phosphorothioate
modified_base           19..20
                        mod_base = OTHER
                        note = 2'-O-methoxyethyl guanosine 3'-phosphorothioate
modified_base           21
                        mod_base = OTHER
                        note = 2'-O-methoxyethyl adenosine
SEQUENCE: 416
aacccaattc agaaggaagg a                                            21

SEQ ID NO: 417          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate10a
                         phosphodiester
modified_base           2
                        mod_base = OTHER
                        note = 2'-O-methoxyethyl adenosine 3'-phosphorothioate
modified_base           3..5
                        mod_base = OTHER
                        note = 2'-O-methoxyethyl 5-methylcytidine
                         3'-phosphorothioate
modified_base           6
                        mod_base = OTHER
                        note = 2'-O-methoxyethyl adenosine 3'-phosphorothioate
modified_base           7
                        mod_base = OTHER
                        note = 2'-deoxyadenosine 3'-phosphorothioate
modified_base           8..9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxyguanosine 3'-phosphorothioate
modified_base           13..14
                        mod_base = OTHER
                        note = 2'-deoxyadenosine 3'-phosphorothioate
modified_base           15..16
                        mod_base = OTHER
                        note = 2'-deoxyguanosine 3'-phosphorothioate
modified_base           17..18
                        mod_base = OTHER
                        note = 2'-O-methoxyethyl adenosine 3'-phosphorothioate
modified_base           19..20
                        mod_base = OTHER
                        note = 2'-O-methoxyethyl guanosine 3'-phosphorothioate
modified_base           21
                        mod_base = OTHER
                        note = 2'-O-methoxyethyl adenosine
SEQUENCE: 417
aacccaattc agaaggaagg a                                            21

SEQ ID NO: 418          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate13a
                         phosphodiester
modified_base           2
                        mod_base = OTHER
```

```
                        note = 2'-O-methoxyethyl adenosine 3'-phosphorothioate
modified_base           3..5
                        mod_base = OTHER
                        note = 2'-O-methoxyethyl 5-methylcytidine
                         3'-phosphorothioate
modified_base           6
                        mod_base = OTHER
                        note = 2'-O-methoxyethyl adenosine 3'-phosphorothioate
modified_base           7
                        mod_base = OTHER
                        note = 2'-deoxyadenosine 3'-phosphorothioate
modified_base           8..9
                        mod_base = OTHER
                        note = 2'-deoxythymidine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxyguanosine 3'-phosphorothioate
modified_base           13..14
                        mod_base = OTHER
                        note = 2'-deoxyadenosine 3'-phosphorothioate
modified_base           15..16
                        mod_base = OTHER
                        note = 2'-deoxyguanosine 3'-phosphorothioate
modified_base           17..18
                        mod_base = OTHER
                        note = 2'-O-methoxyethyl adenosine 3'-phosphorothioate
modified_base           19..20
                        mod_base = OTHER
                        note = 2'-O-methoxyethyl guanosine 3'-phosphorothioate
modified_base           21
                        mod_base = OTHER
                        note = 2'-O-methoxyethyl adenosine
SEQUENCE: 418
aacccaattc agaaggaagg a                                       21

SEQ ID NO: 419          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl adenosine 3'-phosphorothioate
modified_base           2
                        mod_base = OTHER
                        note = 2'-O-methoxyethyl guanosine 3'-phosphodiester
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 5-methyl-2'-deoxycytidine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxythymidine 3'-phosphorothioate
modified_base           11..12
                        mod_base = OTHER
                        note = 5-methyl-2'-deoxycytidine 3'-phosphorothioate
modified_base           13
                        mod_base = OTHER
                        note = 2'-deoxyadenosine 3'-phosphorothioate
modified_base           14
                        mod_base = OTHER
                        note = 2'-deoxyguanosine 3'-phosphorothioate
```

```
modified_base          15
                       mod_base = OTHER
                       note = 5-methyl-2'-deoxycytidine 3'-phosphorothioate
modified_base          16..17
                       mod_base = OTHER
                       note = 2'-O-methoxyethyl thymidine 3'-phosphodiester
modified_base          18
                       mod_base = OTHER
                       note = 2'-O-methoxyethyl thymidine 3'-phosphorothioate
modified_base          19
                       mod_base = OTHER
                       note = 2'-O-methoxyethyl adenosine 3'-phosphorothioate
modified_base          20
                       mod_base = OTHER
                       note = 2'-O-methoxyethyl thymidine 3'-phosphodiester
modified_base          21
                       mod_base = OTHER
                       note = triantennary N-acetylgalactosamine conjugate19a
SEQUENCE: 419
agcttcttgt ccagctttat a                                              21

SEQ ID NO: 420         moltype = DNA  length = 21
FEATURE                Location/Qualifiers
source                 1..21
                       mol_type = other DNA
                       organism = Synthetic construct
modified_base          1
                       mod_base = OTHER
                       note = 2'-O-methoxyethyl thymidine 3'-phosphorothioate
modified_base          2
                       mod_base = OTHER
                       note = 2'-O-methoxyethyl guanosine 3'-phosphodiester
modified_base          3
                       mod_base = OTHER
                       note = 2'-O-methoxyethyl 5-methylcytidine 3'-phosphodiester
modified_base          4
                       mod_base = OTHER
                       note = 2'-O-methoxyethyl thymidine 3'-phosphodiester
modified_base          5
                       mod_base = OTHER
                       note = 2'-O-methoxyethyl 5-methylcytidine 3'-phosphodiester
modified_base          6
                       mod_base = OTHER
                       note = 5-methyl-2'-deoxycytidine 3'-phosphorothioate
modified_base          7
                       mod_base = OTHER
                       note = 2'-deoxyguanosine 3'-phosphorothioate
modified_base          8..9
                       mod_base = OTHER
                       note = 2'-deoxythymidine 3'-phosphorothioate
modified_base          10..11
                       mod_base = OTHER
                       note = 2'-deoxyguanosine 3'-phosphorothioate
modified_base          12
                       mod_base = OTHER
                       note = 2'-deoxythymidine 3'-phosphorothioate
modified_base          13
                       mod_base = OTHER
                       note = 2'-deoxyguanosine 3'-phosphorothioate
modified_base          14
                       mod_base = OTHER
                       note = 5-methyl-2'-deoxycytidine 3'-phosphorothioate
modified_base          15
                       mod_base = OTHER
                       note = 2'-deoxythymidine 3'-phosphorothioate
modified_base          16
                       mod_base = OTHER
                       note = 2'-O-methoxyethyl thymidine 3'-phosphodiester
modified_base          17
                       mod_base = OTHER
                       note = 2'-O-methoxyethyl guanosine 3'-phosphodiester
modified_base          18..19
                       mod_base = OTHER
                       note = 2'-O-methoxyethyl thymidine 3'-phosphorothioate
modified_base          20
                       mod_base = OTHER
                       note = 2'-O-methoxyethyl 5-methylcytidine 3'-phosphodiester
modified_base          21
                       mod_base = OTHER
```

```
                         note = triantennary N-acetylgalactosamine conjugate19a
SEQUENCE: 420
tgctccgttg gtgcttgttc a                                            21

SEQ ID NO: 421           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate3a
                          phosphodiester
modified_base            2
                         mod_base = OTHER
                         note = 2'-O-methoxyethyl 5-methylcytidine
                          3'-phosphorothioate
modified_base            3
                         mod_base = OTHER
                         note = 2'-O-methoxyethyl adenosine 3'-phosphorothioate
modified_base            4
                         mod_base = OTHER
                         note = 2'-O-methoxyethyl guanosine 3'-phosphorothioate
modified_base            5
                         mod_base = OTHER
                         note = 2'-O-methoxyethyl 5-methylcytidine
                          3'-phosphorothioate
modified_base            6
                         mod_base = OTHER
                         note = 2'-O-methoxyethyl thymidine 3'-phosphorothioate
modified_base            7..8
                         mod_base = OTHER
                         note = 2'-deoxythymidine 3'-phosphorothioate
modified_base            9
                         mod_base = OTHER
                         note = 2'-deoxyadenosine 3'-phosphorothioate
modified_base            10..11
                         mod_base = OTHER
                         note = 2'-deoxythymidine 3'-phosphorothioate
modified_base            12
                         mod_base = OTHER
                         note = 2'-deoxyadenosine 3'-phosphorothioate
modified_base            13..15
                         mod_base = OTHER
                         note = 2'-deoxyguanosine 3'-phosphorothioate
modified_base            16
                         mod_base = OTHER
                         note = 2'-deoxyadenosine 3'-phosphorothioate
modified_base            17
                         mod_base = OTHER
                         note = 2'-O-methoxyethyl 5-methylcytidine
                          3'-phosphorothioate
modified_base            18
                         mod_base = OTHER
                         note = 2'-O-methoxyethyl adenosine 3'-phosphorothioate
modified_base            19
                         mod_base = OTHER
                         note = 2'-O-methoxyethyl guanosine 3'-phosphorothioate
modified_base            20
                         mod_base = OTHER
                         note = 2'-O-methoxyethyl 5-methylcytidine
                          3'-phosphorothioate
modified_base            21
                         mod_base = OTHER
                         note = 2'-O-methoxyethyl adenosine
SEQUENCE: 421
acagctttat tagggacagc a                                            21

SEQ ID NO: 422           moltype = DNA  length = 21
FEATURE                  Location/Qualifiers
source                   1..21
                         mol_type = other DNA
                         organism = Synthetic construct
modified_base
                         mod_base = OTHER
                         note = triantennary N-acetylgalactosamine conjugate7a
                          phosphodiester
modified_base            2
                         mod_base = OTHER
```

```
                        note = 2'-O-methoxyethyl thymidine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl guanosine 3'-phosphorothioate
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxyadenosine 3'-phosphorothioate
modified_base           13
                        mod_base = OTHER
                        note = 2'-deoxythymidine 3'-phosphorothioate
modified_base           14
                        mod_base = OTHER
                        note = 2'-deoxyguanosine 3'-phosphorothioate
modified_base           15..16
                        mod_base = OTHER
                        note = 2'-deoxyadenosine 3'-phosphorothioate
modified_base           17
                        mod_base = OTHER
                        note = 2'-O-methoxyethyl adenosine 3'-phosphorothioate
modified_base           18
                        mod_base = OTHER
                        note = 2'-O-methoxyethyl thymidine 3'-phosphorothioate
modified_base           19..20
                        mod_base = OTHER
                        note = 2'-O-methoxyethyl 5-methylcytidine
                         3'-phosphorothioate
modified_base           21
                        mod_base = OTHER
                        note = 2'-O-methoxyethyl 5-methylcytidine
SEQUENCE: 422
atcttggtta catgaaatcc c                                                21

SEQ ID NO: 423          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate10a
                         phosphodiester
modified_base           2
                        mod_base = OTHER
                        note = 2'-O-methoxyethyl thymidine 3'-phosphorothioate
modified_base           3
                        mod_base = OTHER
                        note = 2'-O-methoxyethyl 5-methylcytidine
                         3'-phosphorothioate
modified_base           4..5
                        mod_base = OTHER
                        note = 2'-O-methoxyethyl thymidine 3'-phosphorothioate
modified_base           6
                        mod_base = OTHER
                        note = 2'-O-methoxyethyl guanosine 3'-phosphorothioate
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
```

```
modified_base          10
                       mod_base = OTHER
                       note = 2'-deoxyadenosine 3'-phosphorothioate
modified_base          11
                       mod_base = OTHER
                       note = 5-methyl-2'-deoxycytidine 3'-phosphorothioate
modified_base          12
                       mod_base = OTHER
                       note = 2'-deoxyadenosine 3'-phosphorothioate
modified_base          13
                       mod_base = OTHER
                       note = 2'-deoxythymidine 3'-phosphorothioate
modified_base          14
                       mod_base = OTHER
                       note = 2'-deoxyguanosine 3'-phosphorothioate
modified_base          15..16
                       mod_base = OTHER
                       note = 2'-deoxyadenosine 3'-phosphorothioate
modified_base          17
                       mod_base = OTHER
                       note = 2'-O-methoxyethyl adenosine 3'-phosphorothioate
modified_base          18
                       mod_base = OTHER
                       note = 2'-O-methoxyethyl thymidine 3'-phosphorothioate
modified_base          19..20
                       mod_base = OTHER
                       note = 2'-O-methoxyethyl 5-methylcytidine
                        3'-phosphorothioate
modified_base          21
                       mod_base = OTHER
                       note = 2'-O-methoxyethyl 5-methylcytidine
SEQUENCE: 423
atcttggtta catgaaatcc c                                            21

SEQ ID NO: 424         moltype = DNA  length = 21
FEATURE                Location/Qualifiers
source                 1..21
                       mol_type = other DNA
                       organism = Synthetic construct
modified_base
                       mod_base = OTHER
                       note = triantennary N-acetylgalactosamine conjugate13a
                        phosphodiester
modified_base          2
                       mod_base = OTHER
                       note = 2'-O-methoxyethyl thymidine 3'-phosphorothioate
modified_base          3
                       mod_base = OTHER
                       note = 2'-O-methoxyethyl 5-methylcytidine
                        3'-phosphorothioate
modified_base          4..5
                       mod_base = OTHER
                       note = 2'-O-methoxyethyl thymidine 3'-phosphorothioate
modified_base          6
                       mod_base = OTHER
                       note = 2'-O-methoxyethyl guanosine 3'-phosphorothioate
modified_base          7
                       mod_base = OTHER
                       note = 2'-deoxyguanosine 3'-phosphorothioate
modified_base          8..9
                       mod_base = OTHER
                       note = 2'-deoxythymidine 3'-phosphorothioate
modified_base          10
                       mod_base = OTHER
                       note = 2'-deoxyadenosine 3'-phosphorothioate
modified_base          11
                       mod_base = OTHER
                       note = 5-methyl-2'-deoxycytidine 3'-phosphorothioate
modified_base          12
                       mod_base = OTHER
                       note = 2'-deoxyadenosine 3'-phosphorothioate
modified_base          13
                       mod_base = OTHER
                       note = 2'-deoxythymidine 3'-phosphorothioate
modified_base          14
                       mod_base = OTHER
                       note = 2'-deoxyguanosine 3'-phosphorothioate
modified_base          15..16
                       mod_base = OTHER
```

```
                        note = 2'-deoxyadenosine 3'-phosphorothioate
modified_base           17
                        mod_base = OTHER
                        note = 2'-O-methoxyethyl adenosine 3'-phosphorothioate
modified_base           18
                        mod_base = OTHER
                        note = 2'-O-methoxyethyl thymidine 3'-phosphorothioate
modified_base           19..20
                        mod_base = OTHER
                        note = 2'-O-methoxyethyl 5-methylcytidine
                         3'-phosphorothioate
modified_base           21
                        mod_base = OTHER
                        note = 2'-O-methoxyethyl 5-methylcytidine
SEQUENCE: 424
atcttggtta catgaaatcc c                                              21

SEQ ID NO: 425          moltype = DNA  length = 21
FEATURE                 Location/Qualifiers
source                  1..21
                        mol_type = other DNA
                        organism = Synthetic construct
modified_base
                        mod_base = OTHER
                        note = triantennary N-acetylgalactosamine conjugate7a
                         phosphodiester
modified_base           2
                        mod_base = OTHER
                        note = 2'-O-methoxyethyl thymidine 3'-phosphorothioate
modified_base           3
                        mod_base = OTHER
                        note = 2'-O-methoxyethyl 5-methylcytidine 3'-phosphodiester
modified_base           4..5
                        mod_base = OTHER
                        note = 2'-O-methoxyethyl thymidine 3'-phosphodiester
modified_base           6
                        mod_base = OTHER
                        note = 2'-O-methoxyethyl guanosine 3'-phosphodiester
modified_base           7
                        mod_base = OTHER
                        note = 2'-deoxyguanosine 3'-phosphorothioate
modified_base           8..9
                        mod_base = OTHER
                        note = 2'-deoxythymidine 3'-phosphorothioate
modified_base           10
                        mod_base = OTHER
                        note = 2'-deoxyadenosine 3'-phosphorothioate
modified_base           11
                        mod_base = OTHER
                        note = 5-methyl-2'-deoxycytidine 3'-phosphorothioate
modified_base           12
                        mod_base = OTHER
                        note = 2'-deoxyadenosine 3'-phosphorothioate
modified_base           13
                        mod_base = OTHER
                        note = 2'-deoxythymidine 3'-phosphorothioate
modified_base           14
                        mod_base = OTHER
                        note = 2'-deoxyguanosine 3'-phosphorothioate
modified_base           15..16
                        mod_base = OTHER
                        note = 2'-deoxyadenosine 3'-phosphorothioate
modified_base           17
                        mod_base = OTHER
                        note = 2'-O-methoxyethyl adenosine 3'-phosphodiester
modified_base           18
                        mod_base = OTHER
                        note = 2'-O-methoxyethyl thymidine 3'-phosphodiester
modified_base           19..20
                        mod_base = OTHER
                        note = 2'-O-methoxyethyl 5-methylcytidine
                         3'-phosphorothioate
modified_base           21
                        mod_base = OTHER
                        note = 2'-O-methoxyethyl 5-methylcytidine
SEQUENCE: 425
atcttggtta catgaaatcc c                                              21

SEQ ID NO: 426          moltype = DNA  length = 21
```

-continued

| | |
|---|---|
| FEATURE | Location/Qualifiers |
| source | 1..21 |
| | mol_type = other DNA |
| | organism = Synthetic construct |
| modified_base | |
| | mod_base = OTHER |
| | note = triantennary N-acetylgalactosamine conjugate10a phosphodiester |
| modified_base | 2 |
| | mod_base = OTHER |
| | note = 2′-O-methoxyethyl thymidine 3′-phosphorothioate |
| modified_base | 3 |
| | mod_base = OTHER |
| | note = 2′-O-methoxyethyl 5-methylcytidine 3′-phosphodiester |
| modified_base | 4..5 |
| | mod_base = OTHER |
| | note = 2′-O-methoxyethyl thymidine 3′-phosphodiester |
| modified_base | 6 |
| | mod_base = OTHER |
| | note = 2′-O-methoxyethyl guanosine 3′-phosphodiester |
| modified_base | 7 |
| | mod_base = OTHER |
| | note = 2′-deoxyguanosine 3′-phosphorothioate |
| modified_base | 8..9 |
| | mod_base = OTHER |
| | note = 2′-deoxythymidine 3′-phosphorothioate |
| modified_base | 10 |
| | mod_base = OTHER |
| | note = 2′-deoxyadenosine 3′-phosphorothioate |
| modified_base | 11 |
| | mod_base = OTHER |
| | note = 5-methyl-2′-deoxycytidine 3′-phosphorothioate |
| modified_base | 12 |
| | mod_base = OTHER |
| | note = 2′-deoxyadenosine 3′-phosphorothioate |
| modified_base | 13 |
| | mod_base = OTHER |
| | note = 2′-deoxythymidine 3′-phosphorothioate |
| modified_base | 14 |
| | mod_base = OTHER |
| | note = 2′-deoxyguanosine 3′-phosphorothioate |
| modified_base | 14..15 |
| | mod_base = OTHER |
| | note = 2′-deoxyadenosine 3′-phosphorothioate |
| modified_base | 17 |
| | mod_base = OTHER |
| | note = 2′-O-methoxyethyl adenosine 3′-phosphodiester |
| modified_base | 18 |
| | mod_base = OTHER |
| | note = 2′-O-methoxyethyl thymidine 3′-phosphodiester |
| modified_base | 19..20 |
| | mod_base = OTHER |
| | note = 2′-O-methoxyethyl 5-methylcytidine 3′-phosphorothioate |
| modified_base | 21 |
| | mod_base = OTHER |
| | note = 2′-O-methoxyethyl 5-methylcytidine |

SEQUENCE: 426
atcttggtta catgaaatcc c 21

| | |
|---|---|
| SEQ ID NO: 427 | moltype = DNA length = 21 |
| FEATURE | Location/Qualifiers |
| source | 1..21 |
| | mol_type = other DNA |
| | organism = Synthetic construct |
| modified_base | |
| | mod_base = OTHER |
| | note = triantennary N-acetylgalactosamine conjugate13a phosphodiester |
| modified_base | 2 |
| | mod_base = OTHER |
| | note = 2′-O-methoxyethyl thymidine 3′-phosphorothioate |
| modified_base | 3 |
| | mod_base = OTHER |
| | note = 2′-O-methoxyethyl 5-methylcytidine 3′-phosphodiester |
| modified_base | 4..5 |
| | mod_base = OTHER |
| | note = 2′-O-methoxyethyl thymidine 3′-phosphodiester |
| modified_base | 6 |

```
                         mod_base = OTHER
                         note = 2'-O-methoxyethyl guanosine 3'-phosphodiester
modified_base            7
                         mod_base = OTHER
                         note = 2'-deoxyguanosine 3'-phosphorothioate
modified_base            8..9
                         mod_base = OTHER
                         note = 2'-deoxythymidine 3'-phosphorothioate
modified_base            10
                         mod_base = OTHER
                         note = 2'-deoxyadenosine 3'-phosphorothioate
modified_base            11
                         mod_base = OTHER
                         note = 5-methyl-2'-deoxycytidine 3'-phosphorothioate
modified_base            12
                         mod_base = OTHER
                         note = 2'-deoxyadenosine 3'-phosphorothioate
modified_base            13
                         mod_base = OTHER
                         note = 2'-deoxythymidine 3'-phosphorothioate
modified_base            14
                         mod_base = OTHER
                         note = 2'-deoxyguanosine 3'-phosphorothioate
modified_base            15..16
                         mod_base = OTHER
                         note = 2'-deoxyadenosine 3'-phosphorothioate
modified_base            17
                         mod_base = OTHER
                         note = 2'-O-methoxyethyl adenosine 3'-phosphodiester
modified_base            18
                         mod_base = OTHER
                         note = 2'-O-methoxyethyl thymidine 3'-phosphodiester
modified_base            19..20
                         mod_base = OTHER
                         note = 2'-O-methoxyethyl 5-methylcytidine
                          3'-phosphorothioate
modified_base            21
                         mod_base = OTHER
                         note = 2'-O-methoxyethyl 5-methylcytidine
SEQUENCE: 427
atcttggtta catgaaatcc c                                21

SEQ ID NO: 428           moltype = DNA  length = 21
FEATURE                  Location/Qualifiers
source                   1..21
                         mol_type = other DNA
                         organism = Synthetic construct
modified_base            1
                         mod_base = OTHER
                         note = 2'-O-methoxyethyl 5-methylcytidine
                          3'-phosphorothioate
modified_base            2
                         mod_base = OTHER
                         note = 2'-O-methoxyethyl adenosine 3'-phosphorothioate
modified_base            3
                         mod_base = OTHER
                         note = 2'-O-methoxyethyl guanosine 3'-phosphorothioate
modified_base            4
                         mod_base = OTHER
                         note = 2'-O-methoxyethyl 5-methylcytidine
                          3'-phosphorothioate
modified_base            5
                         mod_base = OTHER
                         note = 2'-O-methoxyethyl thymidine 3'-phosphorothioate
modified_base            6..7
                         mod_base = OTHER
                         note = 2'-deoxythymidine 3'-phosphorothioate
modified_base            8
                         mod_base = OTHER
                         note = 2'-deoxyadenosine 3'-phosphorothioate
modified_base            9..10
                         mod_base = OTHER
                         note = 2'-deoxythymidine 3'-phosphorothioate
modified_base            11
                         mod_base = OTHER
                         note = 2'-deoxyadenosine 3'-phosphorothioate
modified_base            12..14
                         mod_base = OTHER
                         note = 2'-deoxyguanosine 3'-phosphorothioate
```

```
modified_base         15
                      mod_base = OTHER
                      note = 2'-deoxyadenosine 3'-phosphorothioate
modified_base         16
                      mod_base = OTHER
                      note = 2'-O-methoxyethyl 5-methylcytidine
                       3'-phosphorothioate
modified_base         17
                      mod_base = OTHER
                      note = 2'-O-methoxyethyl adenosine 3'-phosphorothioate
modified_base         18
                      mod_base = OTHER
                      note = 2'-O-methoxyethyl guanosine 3'-phosphorothioate
modified_base         19
                      mod_base = OTHER
                      note = 2'-O-methoxyethyl 5-methylcytidine
                       3'-phosphorothioate
modified_base         20
                      mod_base = OTHER
                      note = 2'-O-methoxyethyl adenosine 3'-phosphodiester
modified_base         21
                      mod_base = OTHER
                      note = triantennary N-acetylgalactosamine conjugate19a
SEQUENCE: 428
cagctttatt agggacagca a                                              21

SEQ ID NO: 429        moltype = DNA  length = 21
FEATURE               Location/Qualifiers
source                1..21
                      mol_type = other DNA
                      organism = Synthetic construct
modified_base         1
                      mod_base = OTHER
                      note = 2'-O-methoxyethyl thymidine 3'-phosphorothioate
modified_base         2
                      mod_base = OTHER
                      note = 2'-O-methoxyethyl 5-methylcytidine
                       3'-phosphorothioate
modified_base         3..4
                      mod_base = OTHER
                      note = 2'-O-methoxyethyl thymidine 3'-phosphorothioate
modified_base         5
                      mod_base = OTHER
                      note = 2'-O-methoxyethyl guanosine 3'-phosphorothioate
modified_base         6
                      mod_base = OTHER
                      note = 2'-deoxyguanosine 3'-phosphorothioate
modified_base         7..8
                      mod_base = OTHER
                      note = 2'-deoxythymidine 3'-phosphorothioate
modified_base         9
                      mod_base = OTHER
                      note = 2'-deoxyadenosine 3'-phosphorothioate
modified_base         10
                      mod_base = OTHER
                      note = 5-methyl-2'-deoxycytidine 3'-phosphorothioate
modified_base         11
                      mod_base = OTHER
                      note = 2'-deoxyadenosine 3'-phosphorothioate
modified_base         12
                      mod_base = OTHER
                      note = 2'-deoxythymidine 3'-phosphorothioate
modified_base         13
                      mod_base = OTHER
                      note = 2'-deoxyguanosine 3'-phosphorothioate
modified_base         14..15
                      mod_base = OTHER
                      note = 2'-deoxyadenosine 3'-phosphorothioate
modified_base         16
                      mod_base = OTHER
                      note = 2'-O-methoxyethyl adenosine 3'-phosphorothioate
modified_base         17
                      mod_base = OTHER
                      note = 2'-O-methoxyethyl thymidine 3'-phosphorothioate
modified_base         18..19
                      mod_base = OTHER
                      note = 2'-O-methoxyethyl 5-methylcytidine
                       3'-phosphorothioate
modified_base         20
```

```
                        mod_base = OTHER
                        note = 2'-O-methoxyethyl 5-methylcytidine 3'-phosphodiester
modified_base           21
                        mod_base = OTHER
                        note = triantennary N-acetylgalactosamine conjugate19a
SEQUENCE: 429
tcttggttac atgaaatccc a                                               21

SEQ ID NO: 430          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl guanosine 3'-phosphodiester
modified_base           6
                        mod_base = OTHER
                        note = 2'-deoxyguanosine 3'-phosphorothioate
modified_base           7..8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14..15
                        mod_base = OTHER
                        note = 2'-deoxyadenosine 3'-phosphorothioate
modified_base           16
                        mod_base = OTHER
                        note = 2'-O-methoxyethyl adenosine 3'-phosphodiester
modified_base           17
                        mod_base = OTHER
                        note = 2'-O-methoxyethyl thymidine 3'-phosphodiester
modified_base           18..19
                        mod_base = OTHER
                        note = 2'-O-methoxyethyl 5-methylcytidine
                         3'-phosphorothioate
modified_base           20
                        mod_base = OTHER
                        note = 2'-O-methoxyethyl 5-methylcytidine 3'-phosphodiester
modified_base           21
                        mod_base = OTHER
                        note = triantennary N-acetylgalactosamine conjugate19a
SEQUENCE: 430
tcttggttac atgaaatccc a                                               21

SEQ ID NO: 431          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl adenosine 3'-phosphorothioate
modified_base           2..3
                        mod_base = OTHER
                        note = 2'-O-methoxyethyl thymidine 3'-phosphorothioate
```

```
modified_base          4
                       mod_base = OTHER
                       note = 2'-O-methoxyethyl 5-methylcytidine
                        3'-phosphorothioate
modified_base          5
                       mod_base = OTHER
                       note = 2'-O-methoxyethyl adenosine 3'-phosphorothioate
modified_base          6
                       mod_base = OTHER
                       note = 2'-O-methoxyethyl 5-methylcytidine
                        3'-phosphorothioate
modified_base          7..9
                       mod_base = OTHER
                       note = 2'-O-methoxyethyl thymidine 3'-phosphorothioate
modified_base          10
                       mod_base = OTHER
                       note = 2'-O-methoxyethyl 5-methylcytidine
                        3'-phosphorothioate
modified_base          11
                       mod_base = OTHER
                       note = 2'-O-methoxyethyl adenosine 3'-phosphorothioate
modified_base          12
                       mod_base = OTHER
                       note = 2'-O-methoxyethyl thymidine 3'-phosphorothioate
modified_base          13..14
                       mod_base = OTHER
                       note = 2'-O-methoxyethyl adenosine 3'-phosphorothioate
modified_base          15
                       mod_base = OTHER
                       note = 2'-O-methoxyethyl thymidine 3'-phosphorothioate
modified_base          16
                       mod_base = OTHER
                       note = 2'-O-methoxyethyl guanosine 3'-phosphorothioate
modified_base          17
                       mod_base = OTHER
                       note = 2'-O-methoxyethyl 5-methylcytidine
                        3'-phosphorothioate
modified_base          18
                       mod_base = OTHER
                       note = 2'-O-methoxyethyl thymidine 3'-phosphorothioate
modified_base          19
                       mod_base = OTHER
                       note = 2'-O-methoxyethyl guanosine 3'-phosphorothioate
modified_base          20
                       mod_base = OTHER
                       note = 2'-O-methoxyethyl guanosine 3'-phosphodiester
modified_base          21
                       mod_base = OTHER
                       note = triantennary N-acetylgalactosamine conjugate1a
SEQUENCE: 431
attcactttc ataatgctgg a                                            21

SEQ ID NO: 432         moltype = DNA  length = 21
FEATURE                Location/Qualifiers
source                 1..21
                       mol_type = other DNA
                       organism = Synthetic construct
modified_base
                       mod_base = OTHER
                       note = N-acetylgalactosamine conjugate 25a phosphodiester
modified_base          2
                       mod_base = OTHER
                       note = 2'-O-methoxyethyl guanosine 3'-phosphorothioate
modified_base          3
                       mod_base = OTHER
                       note = 2'-O-methoxyethyl 5-methylcytidine
                        3'-phosphorothioate
modified_base          4..5
                       mod_base = OTHER
                       note = 2'-O-methoxyethyl thymidine 3'-phosphorothioate
modified_base          6
                       mod_base = OTHER
                       note = 2'-O-methoxyethyl 5-methylcytidine
                        3'-phosphorothioate
modified_base          7
                       mod_base = OTHER
                       note = 2'-deoxyadenosine 3'-phosphorothioate
modified_base          8
                       mod_base = OTHER
```

```
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphorothioate
modified_base            18..19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl thymidine 3'-phosphorothioate
modified_base            21
                         mod_base = OTHER
                         note = 2'-O-methoxyethyl thymidine
SEQUENCE: 432
agcttcagtc atgacttcct t                                          21

SEQ ID NO: 433           moltype = DNA  length = 21
FEATURE                  Location/Qualifiers
source                   1..21
                         mol_type = other DNA
                         organism = Synthetic construct
modified_base
                         mod_base = OTHER
                         note = N-acetylgalactosamine conjugate 26a phosphodiester
modified_base            2
                         mod_base = OTHER
                         note = 2'-O-methoxyethyl guanosine 3'-phosphorothioate
modified_base            2
                         mod_base = OTHER
                         note = 2'-O-methoxyethyl 5-methylcytidine
                          3'-phosphorothioate
modified_base            4..5
                         mod_base = OTHER
                         note = 2'-O-methoxyethyl thymidine 3'-phosphorothioate
modified_base            6
                         mod_base = OTHER
                         note = 2'-O-methoxyethyl 5-methylcytidine
                          3'-phosphorothioate
modified_base            7
                         mod_base = OTHER
                         note = 2'-deoxyadenosine 3'-phosphorothioate
modified_base            8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
```

```
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
modified_base            16
                         mod_base = OTHER
                         note = 2'-deoxythymidine 3'-phosphorothioate
modified_base            17
                         mod_base = OTHER
                         note = 2'-O-methoxyethyl thymidine 3'-phosphorothioate
modified_base            18..19
                         mod_base = OTHER
                         note = 2'-O-methoxyethyl 5-methylcytidine
                          3'-phosphorothioate
modified_base            20
                         mod_base = OTHER
                         note = 2'-O-methoxyethyl thymidine 3'-phosphorothioate
modified_base            21
                         mod_base = OTHER
                         note = 2'-O-methoxyethyl thymidine
SEQUENCE: 433
agcttcagtc atgacttcct t                                              21

SEQ ID NO: 434           moltype = DNA  length = 21
FEATURE                  Location/Qualifiers
source                   1..21
                         mol_type = other DNA
                         organism = Synthetic construct
modified_base
                         mod_base = OTHER
                         note = N-acetylgalactosamine conjugate 28a phosphodiester
modified_base            2
                         mod_base = OTHER
                         note = 2'-O-methoxyethyl guanosine 3'-phosphorothioate
modified_base            3
                         mod_base = OTHER
                         note = 2'-O-methoxyethyl 5-methylcytidine
                          3'-phosphorothioate
modified_base            4..5
                         mod_base = OTHER
                         note = 2'-O-methoxyethyl thymidine 3'-phosphorothioate
modified_base            6
                         mod_base = OTHER
                         note = 2'-O-methoxyethyl 5-methylcytidine
                          3'-phosphorothioate
modified_base            7
                         mod_base = OTHER
                         note = 2'-deoxyadenosine 3'-phosphorothioate
modified_base            8
                         mod_base = OTHER
                         note = 2'-deoxyguanosine 3'-phosphorothioate
modified_base            9
                         mod_base = OTHER
                         note = 2'-deoxythymidine 3'-phosphorothioate
modified_base            10
                         mod_base = OTHER
                         note = 5-methyl-2'-deoxycytidine 3'-phosphorothioate
modified_base            11
                         mod_base = OTHER
                         note = 2'-deoxyadenosine 3'-phosphorothioate
modified_base            12
                         mod_base = OTHER
                         note = 2'-deoxythymidine 3'-phosphorothioate
modified_base            13
                         mod_base = OTHER
                         note = 2'-deoxyguanosine 3'-phosphorothioate
modified_base            14
                         mod_base = OTHER
                         note = 2'-deoxyadenosine 3'-phosphorothioate
modified_base            15
                         mod_base = OTHER
                         note = 5-methyl-2'-deoxycytidine 3'-phosphorothioate
```

```
modified_base          16
                       mod_base = OTHER
                       note = 2'-deoxythymidine 3'-phosphorothioate
modified_base          17
                       mod_base = OTHER
                       note = 2'-O-methoxyethyl thymidine 3'-phosphorothioate
modified_base          18..19
                       mod_base = OTHER
                       note = 2'-O-methoxyethyl 5-methylcytidine
                        3'-phosphorothioate
modified_base          20
                       mod_base = OTHER
                       note = 2'-O-methoxyethyl thymidine 3'-phosphorothioate
modified_base          21
                       mod_base = OTHER
                       note = 2'-O-methoxyethyl thymidine
SEQUENCE: 434
agcttcagtc atgacttcct t                                            21

SEQ ID NO: 435         moltype = DNA  length = 21
FEATURE                Location/Qualifiers
source                 1..21
                       mol_type = other DNA
                       organism = Synthetic construct
modified_base          1
                       mod_base = OTHER
                       note = 2'-O-methoxyethyl guanosine 3'-phosphorothioate
modified_base          2
                       mod_base = OTHER
                       note = 2'-O-methoxyethyl 5-methylcytidine 3'-phosphodiester
modified_base          3..4
                       mod_base = OTHER
                       note = 2'-O-methoxyethyl thymidine 3'-phosphodiester
modified_base          5
                       mod_base = OTHER
                       note = 2'-O-methoxyethyl 5-methylcytidine 3'-phosphodiester
modified_base          6
                       mod_base = OTHER
                       note = 2'-deoxyadenosine 3'-phosphorothioate
modified_base          7
                       mod_base = OTHER
                       note = 2'-deoxyguanosine 3'-phosphorothioate
modified_base          8
                       mod_base = OTHER
                       note = 2'-deoxythymidine 3'-phosphorothioate
modified_base          9
                       mod_base = OTHER
                       note = 5-methyl-2'-deoxycytidine 3'-phosphorothioate
modified_base          10
                       mod_base = OTHER
                       note = 2'-deoxyadenosine 3'-phosphorothioate
modified_base          11
                       mod_base = OTHER
                       note = 2'-deoxythymidine 3'-phosphorothioate
modified_base          12
                       mod_base = OTHER
                       note = 2'-deoxyguanosine 3'-phosphorothioate
modified_base          13
                       mod_base = OTHER
                       note = 2'-deoxyadenosine 3'-phosphorothioate
modified_base          14
                       mod_base = OTHER
                       note = 5-methyl-2'-deoxycytidine 3'-phosphorothioate
modified_base          15
                       mod_base = OTHER
                       note = 2'-deoxythymidine 3'-phosphorothioate
modified_base          16
                       mod_base = OTHER
                       note = 2'-O-methoxyethyl thymidine 3'-phosphodiester
modified_base          17
                       mod_base = OTHER
                       note = 2'-O-methoxyethyl 5-methylcytidine 3'-phosphodiester
modified_base          18
                       mod_base = OTHER
                       note = 2'-O-methoxyethyl 5-methylcytidine
                        3'-phosphorothioate
modified_base          19
                       mod_base = OTHER
                       note = 2'-O-methoxyethyl thymidine 3'-phosphorothioate
```

```
modified_base          20
                       mod_base = OTHER
                       note = 2'-O-methoxyethyl thymidine 3'-phosphodiester
modified_base          21
                       mod_base = OTHER
                       note = N-acetylgalactosamine conjugate 27a
SEQUENCE: 435
gcttcagtca tgacttcctt a                                            21

SEQ ID NO: 436         moltype = DNA  length = 21
FEATURE                Location/Qualifiers
source                 1..21
                       mol_type = other DNA
                       organism = Synthetic construct
modified_base          1
                       mod_base = OTHER
                       note = 2'-O-methoxyethyl guanosine 3'-phosphorothioate
modified_base          2
                       mod_base = OTHER
                       note = 2'-O-methoxyethyl 5-methylcytidine
                        3'-phosphorothioate
modified_base          3..4
                       mod_base = OTHER
                       note = 2'-O-methoxyethyl thymidine 3'-phosphorothioate
modified_base          5
                       mod_base = OTHER
                       note = 2'-O-methoxyethyl 5-methylcytidine
                        3'-phosphorothioate
modified_base          6
                       mod_base = OTHER
                       note = 2'-deoxyadenosine 3'-phosphorothioate
modified_base          7
                       mod_base = OTHER
                       note = 2'-deoxyguanosine 3'-phosphorothioate
modified_base          8
                       mod_base = OTHER
                       note = 2'-deoxythymidine 3'-phosphorothioate
modified_base          9
                       mod_base = OTHER
                       note = 5-methyl-2'-deoxycytidine 3'-phosphorothioate
modified_base          10
                       mod_base = OTHER
                       note = 2'-deoxyadenosine 3'-phosphorothioate
modified_base          11
                       mod_base = OTHER
                       note = 2'-deoxythymidine 3'-phosphorothioate
modified_base          12
                       mod_base = OTHER
                       note = 2'-deoxyguanosine 3'-phosphorothioate
modified_base          13
                       mod_base = OTHER
                       note = 2'-deoxyadenosine 3'-phosphorothioate
modified_base          14
                       mod_base = OTHER
                       note = 5-methyl-2'-deoxycytidine 3'-phosphorothioate
modified_base          15
                       mod_base = OTHER
                       note = 2'-deoxythymidine 3'-phosphorothioate
modified_base          16
                       mod_base = OTHER
                       note = 2'-O-methoxyethyl thymidine 3'-phosphorothioate
modified_base          17..18
                       mod_base = OTHER
                       note = 2'-O-methoxyethyl 5-methylcytidine
                        3'-phosphorothioate
modified_base          19
                       mod_base = OTHER
                       note = 2'-O-methoxyethyl thymidine 3'-phosphorothioate
modified_base          20
                       mod_base = OTHER
                       note = 2'-O-methoxyethyl thymidine 3'-phosphodiester
modified_base          21
                       mod_base = OTHER
                       note = N-acetylgalactosamine conjugate 29a
SEQUENCE: 436
gcttcagtca tgacttcctt a                                            21

SEQ ID NO: 437         moltype = DNA  length = 21
FEATURE                Location/Qualifiers
```

```
source                  1..21
                        mol_type = other DNA
                        organism = Synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl thymidine 3'-phosphodiester
modified_base           5
                        mod_base = OTHER
                        note = 2'-O-methoxyethyl 5-methylcytidine 3'-phosphodiester
modified_base           6
                        mod_base = OTHER
                        note = 2'-deoxyadenosine 3'-phosphorothioate
modified_base           7
                        mod_base = OTHER
                        note = 2'-deoxyguanosine 3'-phosphorothioate
modified_base           8
                        mod_base = OTHER
                        note = 2'-deoxythymidine 3'-phosphorothioate
modified_base           9
                        mod_base = OTHER
                        note = 5-methyl-2'-deoxycytidine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxythymidine 3'-phosphorothioate
modified_base           12
                        mod_base = OTHER
                        note = 2'-deoxyguanosine 3'-phosphorothioate
modified_base           13
                        mod_base = OTHER
                        note = 2'-deoxyadenosine 3'-phosphorothioate
modified_base           14
                        mod_base = OTHER
                        note = 5-methyl-2'-deoxycytidine 3'-phosphorothioate
modified_base           15
                        mod_base = OTHER
                        note = 2'-deoxythymidine 3'-phosphorothioate
modified_base           16
                        mod_base = OTHER
                        note = 2'-O-methoxyethyl thymidine 3'-phosphodiester
modified_base           17
                        mod_base = OTHER
                        note = 2'-O-methoxyethyl 5-methylcytidine 3'-phosphodiester
modified_base           18
                        mod_base = OTHER
                        note = 2'-O-methoxyethyl 5-methylcytidine
                         3'-phosphorothioate
modified_base           19
                        mod_base = OTHER
                        note = 2'-O-methoxyethyl thymidine 3'-phosphorothioate
modified_base           20
                        mod_base = OTHER
                        note = 2'-O-methoxyethyl thymidine 3'-phosphodiester
modified_base           21
                        mod_base = OTHER
                        note = N-acetylgalactosamine conjugate 29a
SEQUENCE: 437
gcttcagtca tgacttcctt a                                             21

SEQ ID NO: 438          moltype = DNA  length = 21
FEATURE                 Location/Qualifiers
source                  1..21
                        mol_type = other DNA
                        organism = Synthetic construct
modified_base           1
                        mod_base = OTHER
                        note = 2'-O-methoxyethyl 5-methylcytidine
                         3'-phosphorothioate
modified_base           2
                        mod_base = OTHER
                        note = 2'-O-methoxyethyl adenosine 3'-phosphorothioate
```

-continued modified_base 3
mod_base = OTHER
note = 2'-O-methoxyethyl 5-methylcytidine
3'-phosphorothioate
modified_base 4
mod_base = OTHER
note = 2'-O-methoxyethyl thymidine 3'-phosphorothioate
modified_base 5
mod_base = OTHER
note = 2'-O-methoxyethyl guanosine 3'-phosphorothioate
modified_base 6
mod_base = OTHER
note = 2'-deoxyadenosine 3'-phosphorothioate
modified_base 7..11
mod_base = OTHER
note = 2'-deoxythymidine 3'-phosphorothioate
modified_base 12
mod_base = OTHER
note = 2'-deoxyguanosine 3'-phosphorothioate
modified_base 13..15
mod_base = OTHER
note = 5-methyl-2'-deoxycytidine 3'-phosphorothioate
modified_base 16
mod_base = OTHER
note = 2'-O-methoxyethyl adenosine 3'-phosphorothioate
modified_base 17..18
mod_base = OTHER
note = 2'-O-methoxyethyl guanosine 3'-phosphorothioate
modified_base 19
mod_base = OTHER
note = 2'-O-methoxyethyl adenosine 3'-phosphorothioate
modified_base 20
mod_base = OTHER
note = 2'-O-methoxyethyl thymidine 3'-phosphodiester
modified_base 21
mod_base = OTHER
note = triantennary N-acetylgalactosamine conjugate1a
SEQUENCE: 438
cactgatttt tgcccaggat a 21

COMPOSITIONS AND METHODS FOR MODULATING APOLIPOPROTEIN C-III EXPRESSION

RELATED APPLICATIONS

This application is a continuation of U.S. patent application Ser. No. 17/114,177, filed Dec. 7, 2020, which is a continuation of U.S. patent application Ser. No. 15/891,118, filed Feb. 7, 2018, now U.S. Pat. No. 10,927,372, which is a continuation of U.S. patent application Ser. No. 14/839,521, filed Aug. 28, 2015, now U.S. Pat. No. 9,932,581, which is a continuation of U.S. patent application Ser. No. 14/586,826, filed Dec. 30, 2014, now U.S. Pat. No. 9,163,239, which is a continuation of International Application No. PCT/US2014/036462, filed May 1, 2014, which claims priority to U.S. Patent Application No. 61/986,867, filed Apr. 30, 2014, U.S. Patent Application No. 61/976,991, filed Apr. 8, 2014, U.S. Patent Application No. 61/880,790, filed Sep. 20, 2013, U.S. Patent Application No. 61/871,673, filed Aug. 29, 2013, U.S. Patent Application No. 61/843,887, filed Jul. 8, 2013, U.S. Patent Application No. 61/823,826, filed May 15, 2013, U.S. Patent Application No. 61/818,442, filed May 1, 2013, the entire contents of each of which are incorporated herein by reference.

SEQUENCE LISTING

The present application is being filed along with a Sequence Listing in electronic format. The Sequence Listing is provided as an XML file entitled BIOL0249SEQ.xml, created on Jul. 2, 2024, which is 1,981,408 bytes in size. The information in the electronic format of the sequence listing is incorporated herein by reference in its entirety.

BACKGROUND OF THE INVENTION

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, CA) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Apolipoprotein C-III (also called APOC3, APOC-III, ApoCIII, and APO C-III) is a constituent of HDL and of triglyceride (TG)-rich lipoproteins. Elevated ApoCIII levels are associated with elevated TG levels and diseases such as cardiovascular disease, metabolic syndrome, obesity and diabetes (Chan et al., *Int J Clin Pract,* 2008, 62:799-809; Onat et at., *Atherosclerosis,* 2003, 168:81-89; Mendivil et al., *Circulation,* 2011, 124:2065-2072; Mauger et al., *J. Lipid Res,* 2006. 47: 1212-1218; Chan et al., *Clin. Chem,* 2002. 278-283; Ooi et al., *Clin. Sci,* 2008. 114: 611-624; Davidsson et al., *J. Lipid Res.* 2005. 46: 1999-2006; Sacks et al., *Circulation,* 2000. 102: 1886-1892; Lee et al., *Arterioscler Thromb Vasc Biol,* 2003. 23: 853-858). ApoCIII slows clearance of TG-rich lipoproteins by inhibiting lipolysis through inhibition of lipoprotein lipase (LPL) and through interfering with lipoprotein binding to cell-surface glycosaminoglycan matrix (Shachter, *Curr. Opin. Lipidol,* 2001, 12, 297-304).

Antisense technology is emerging as an effective means for reducing the expression of certain gene products and may prove to be uniquely useful in a number of therapeutic, diagnostic, and research applications for the modulation of ApoCIII. Antisense compounds targeting ApoCIII and associated methods for inhibiting ApoCIII have been previously disclosed (see e.g., U.S. Pat. Nos. 7,598,227, 7,750,141, PCT publication WO 2004/093783, PCT publication WO 2012/149495 and PCT/US14/016546, all incorporated-by-reference herein). An antisense compound targeting ApoCIII, ISIS-APOCIII$_{Rx}$, has been tested in a Phase I and II clinical trials. However, no antisense compounds targeting ApoCIII have been approved for commercial use, accordingly, there is still a need to provide patients with additional and more potent treatment options.

SUMMARY OF THE INVENTION

In certain embodiments, the present disclosure provides conjugated antisense compounds. In certain embodiments, the present disclosure provides conjugated antisense compounds comprising an antisense oligonucleotide complementary to a nucleic acid transcript. In certain embodiments, the present disclosure provides methods comprising contacting a cell with a conjugated antisense compound comprising an antisense oligonucleotide complementary to a nucleic acid transcript. In certain embodiments, the present disclosure provides methods comprising contacting a cell with a conjugated antisense compound comprising an antisense oligonucleotide and reducing the amount or activity of a nucleic acid transcript in a cell.

The asialoglycoprotein receptor (ASGP-R) has been described previously. See e.g., Park et al., PNAS vol. 102, No. 47, pp 17125-17129 (2005). Such receptors are expressed on liver cells, particularly hepatocytes. Further, it has been shown that compounds comprising clusters of three N-acetylgalactosamine (GalNAc) ligands are capable of binding to the ASGP-R, resulting in uptake of the compound into the cell. See e.g., Khorev et al., Bioorganic and Medicinal Chemistry, 16, 9, pp 5216-5231 (May 2008). Accordingly, conjugates comprising such GalNAc clusters have been used to facilitate uptake of certain compounds into liver cells, specifically hepatocytes. For example it has been shown that certain GalNAc-containing conjugates increase activity of duplex siRNA compounds in liver cells in vivo. In such instances, the GalNAc-containing conjugate is typically attached to the sense strand of the siRNA duplex. Since the sense strand is discarded before the antisense strand ultimately hybridizes with the target nucleic acid, there is little concern that the conjugate will interfere with activity. Typically, the conjugate is attached to the 3' end of the sense strand of the siRNA. See e.g., U.S. Pat. No. 8,106,022. Certain conjugate groups described herein are more active and/or easier to synthesize than conjugate groups previously described.

In certain embodiments of the present invention, conjugates are attached to single-stranded antisense compounds, including, but not limited to RNase H based antisense compounds and antisense compounds that alter splicing of a pre-mRNA target nucleic acid. In such embodiments, the conjugate should remain attached to the antisense compound long enough to provide benefit (improved uptake into cells) but then should either be cleaved, or otherwise not interfere with the subsequent steps necessary for activity, such as hybridization to a target nucleic acid and interaction with RNase H or enzymes associated with splicing or splice modulation. This balance of properties is more important in the setting of single-stranded antisense compounds than in siRNA compounds, where the conjugate may simply be attached to the sense strand. Disclosed herein are conjugated single-stranded antisense compounds having improved potency in liver cells in vivo compared with the same antisense compound lacking the conjugate. Given the required balance of properties for these compounds such improved potency is surprising.

In certain embodiments, conjugate groups herein comprise a cleavable moiety. As noted, without wishing to be bound by mechanism, it is logical that the conjugate should remain on the compound long enough to provide enhancement in uptake, but after that, it is desirable for some portion or, ideally, all of the conjugate to be cleaved, releasing the parent compound (e.g., antisense compound) in its most active form. In certain embodiments, the cleavable moiety is a cleavable nucleoside. Such embodiments take advantage of endogenous nucleases in the cell by attaching the rest of the conjugate (the cluster) to the antisense oligonucleotide through a nucleoside via one or more cleavable bonds, such as those of a phosphodiester linkage. In certain embodiments, the cluster is bound to the cleavable nucleoside through a phosphodiester linkage. In certain embodiments, the cleavable nucleoside is attached to the antisense oligonucleotide (antisense compound) by a phosphodiester linkage. In certain embodiments, the conjugate group may comprise two or three cleavable nucleosides. In such embodiments, such cleavable nucleosides are linked to one another, to the antisense compound and/or to the cluster via cleavable bonds (such as those of a phosphodiester linkage). Certain conjugates herein do not comprise a cleavable nucleoside and instead comprise a cleavable bond. It is shown that that sufficient cleavage of the conjugate from the oligonucleotide is provided by at least one bond that is vulnerable to cleavage in the cell (a cleavable bond).

In certain embodiments, conjugated antisense compounds are prodrugs. Such prodrugs are administered to an animal and are ultimately metabolized to a more active form. For example, conjugated antisense compounds are cleaved to remove all or part of the conjugate resulting in the active (or more active) form of the antisense compound lacking all or some of the conjugate.

In certain embodiments, conjugates are attached at the 5' end of an oligonucleotide. Certain such 5'-conjugates are cleaved more efficiently than counterparts having a similar conjugate group attached at the 3' end. In certain embodiments, improved activity may correlate with improved cleavage. In certain embodiments, oligonucleotides comprising a conjugate at the 5' end have greater efficacy than oligonucleotides comprising a conjugate at the 3' end (see, for example, Examples 56, 81, 83, and 84). Further, 5'-attachment allows simpler oligonucleotide synthesis. Typically, oligonucleotides are synthesized on a solid support in the 3' to 5' direction. To make a 3'-conjugated oligonucleotide, typically one attaches a pre-conjugated 3' nucleoside to the solid support and then builds the oligonucleotide as usual. However, attaching that conjugated nucleoside to the solid support adds complication to the synthesis. Further, using that approach, the conjugate is then present throughout the synthesis of the oligonucleotide and can become degraded during subsequent steps or may limit the sorts of reactions and reagents that can be used. Using the structures and techniques described herein for 5'-conjugated oligonucleotides, one can synthesize the oligonucleotide using standard automated techniques and introduce the conjugate with the final (5'-most) nucleoside or after the oligonucleotide has been cleaved from the solid support.

In view of the art and the present disclosure, one of ordinary skill can easily make any of the conjugates and conjugated oligonucleotides herein. Moreover, synthesis of certain such conjugates and conjugated oligonucleotides disclosed herein is easier and/or requires few steps, and is therefore less expensive than that of conjugates previously disclosed, providing advantages in manufacturing. For example, the synthesis of certain conjugate groups consists of fewer synthetic steps, resulting in increased yield, relative to conjugate groups previously described. Conjugate groups such as GalNAc3-10 in Example 46 and GalNAc3-7 in Example 48 are much simpler than previously described conjugates such as those described in U.S. Pat. No. 8,106,022 or U.S. Pat. No. 7,262,177 that require assembly of more chemical intermediates. Accordingly, these and other conjugates described herein have advantages over previously described compounds for use with any oligonucleotide, including single-stranded oligonucleotides and either strand of double-stranded oligonucleotides (e.g., siRNA).

Similarly, disclosed herein are conjugate groups having only one or two GalNAc ligands. As shown, such conjugates groups improve activity of antisense compounds. Such compounds are much easier to prepare than conjugates comprising three GalNAc ligands. Conjugate groups comprising one or two GalNAc ligands may be attached to any antisense compounds, including single-stranded oligonucleotides and either strand of double-stranded oligonucleotides (e.g., siRNA).

In certain embodiments, the conjugates herein do not substantially alter certain measures of tolerability. For example, it is shown herein that conjugated antisense compounds are not more immunogenic than unconjugated parent compounds. Since potency is improved, embodiments in which tolerability remains the same (or indeed even if tolerability worsens only slightly compared to the gains in potency) have improved properties for therapy.

In certain embodiments, conjugation allows one to alter antisense compounds in ways that have less attractive consequences in the absence of conjugation. For example, in certain embodiments, replacing one or more phosphorothioate linkages of a fully phosphorothioate antisense compound with phosphodiester linkages results in improvement in some measures of tolerability. For example, in certain instances, such antisense compounds having one or more phosphodiester are less immunogenic than the same compound in which each linkage is a phosphorothioate. However, in certain instances, as shown in Example 26, that same replacement of one or more phosphorothioate linkages with phosphodiester linkages also results in reduced cellular uptake and/or loss in potency. In certain embodiments, conjugated antisense compounds described herein tolerate such change in linkages with little or no loss in uptake and potency when compared to the conjugated full-phosphorothioate counterpart. In fact, in certain embodiments, for example, in Examples 44, 57, 59, and 86, oligonucleotides comprising a conjugate and at least one phosphodiester internucleoside linkage actually exhibit increased potency in vivo even relative to a full phosphorothioate counterpart also comprising the same conjugate. Moreover, since conjugation results in substantial increases in uptake/potency a small loss in that substantial gain may be acceptable to achieve improved tolerability. Accordingly, in certain embodiments, conjugated antisense compounds comprise at least one phosphodiester linkage.

In certain embodiments, conjugation of antisense compounds herein results in increased delivery, uptake and activity in hepatocytes. Thus, more compound is delivered to liver tissue. However, in certain embodiments, that increased delivery alone does not explain the entire increase in activity. In certain such embodiments, more compound enters hepatocytes. In certain embodiments, even that increased hepatocyte uptake does not explain the entire increase in activity. In such embodiments, productive uptake of the conjugated compound is increased. For example, as shown in Example 102, certain embodiments of GalNAc-containing conjugates increase enrichment of antisense oligonucleotides in hepatocytes versus non-parenchymal cells. This enrichment is beneficial for oligonucleotides that target genes that are expressed in hepatocytes.

In certain embodiments, conjugated antisense compounds herein result in reduced kidney exposure. For example, as shown in Example 20, the concentrations of antisense oligonucleotides comprising certain embodiments of GalNAc-containing conjugates are lower in the kidney than that of antisense oligonucleotides lacking a GalNAc-containing conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly for non-kidney targets, kidney accumulation is undesired.

In certain embodiments, the present disclosure provides conjugated antisense compounds represented by the formula:

$$A-B-C-D-(E-F)_q$$

wherein

A is the antisense oligonucleotide;

B is the cleavable moiety

C is the conjugate linker

D is the branching group each E is a tether;

each F is a ligand; and q is an integer between 1 and 5.

In the above diagram and in similar diagrams herein, the branching group "D" branches as many times as is necessary to accommodate the number of (E-F) groups as indicated by "q". Thus, where q=1, the formula is:

A-B—C-D-E-F where q=2, the formula is:

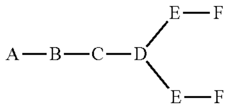

where q=3, the formula is:

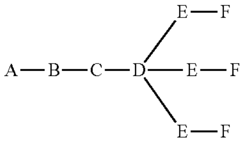

where q=4, the formula is:

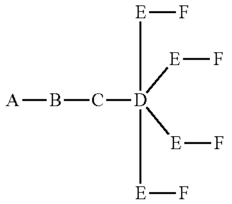

where q=5, the formula is:

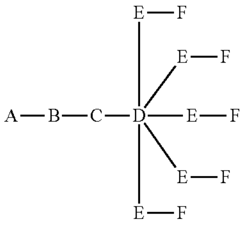

In certain embodiments, conjugated antisense compounds are provided having the structure:
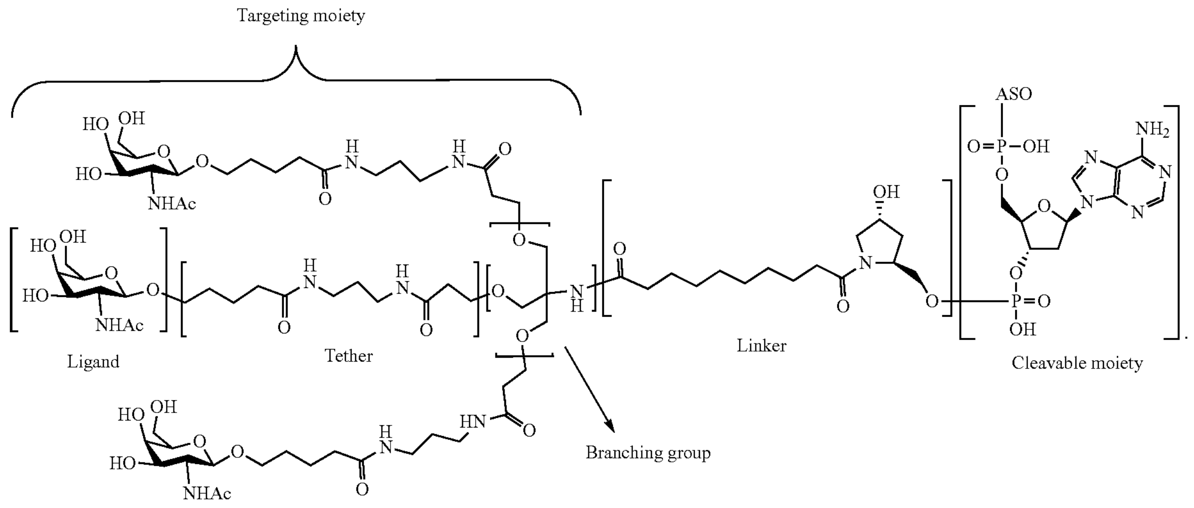
In certain embodiments, conjugated antisense compounds are provided having the structure:
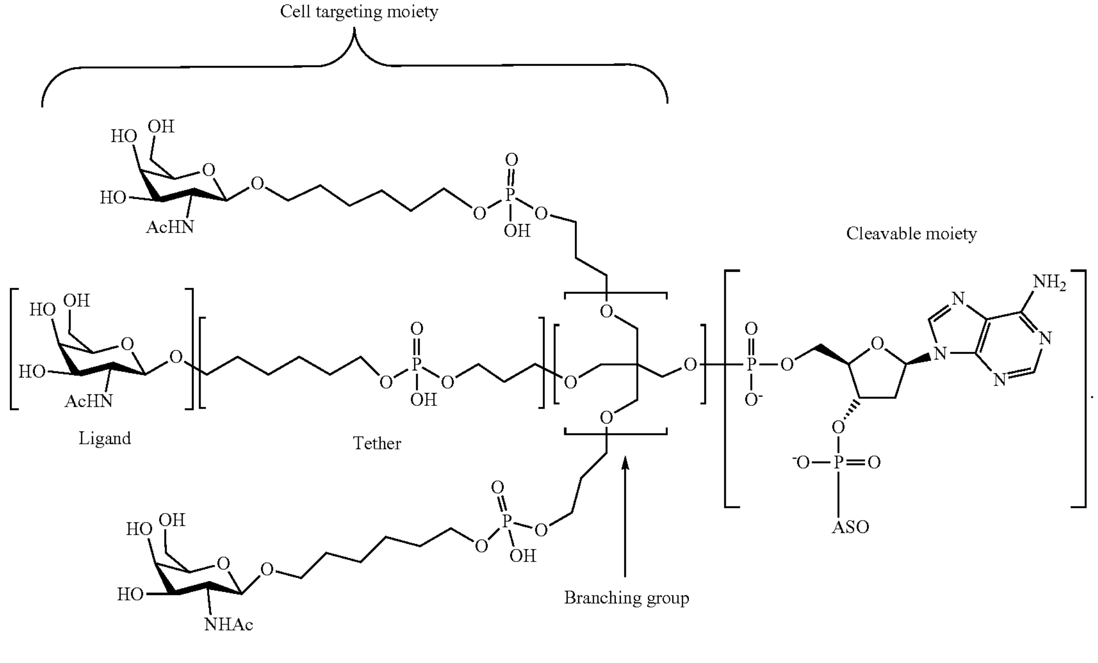

In certain embodiments, conjugated antisense compounds are provided having the structure:
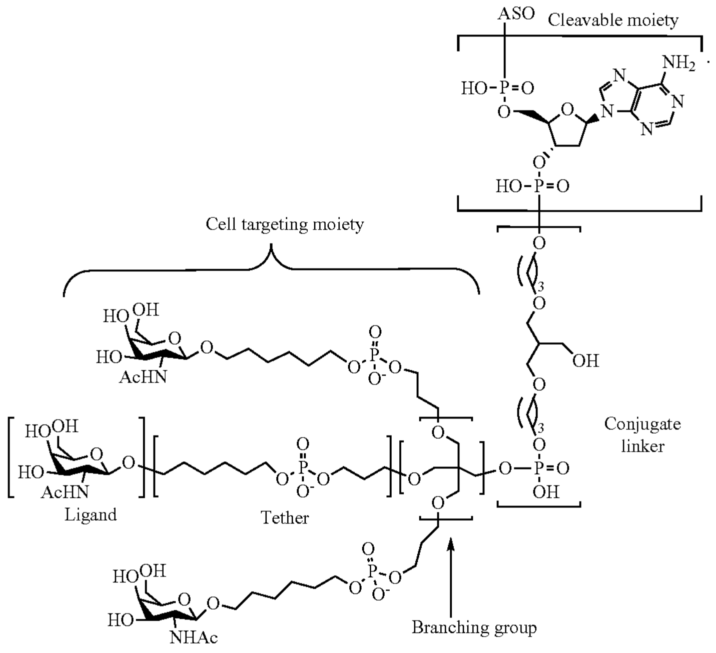
In certain embodiments, conjugated antisense compounds are provided having the structure:
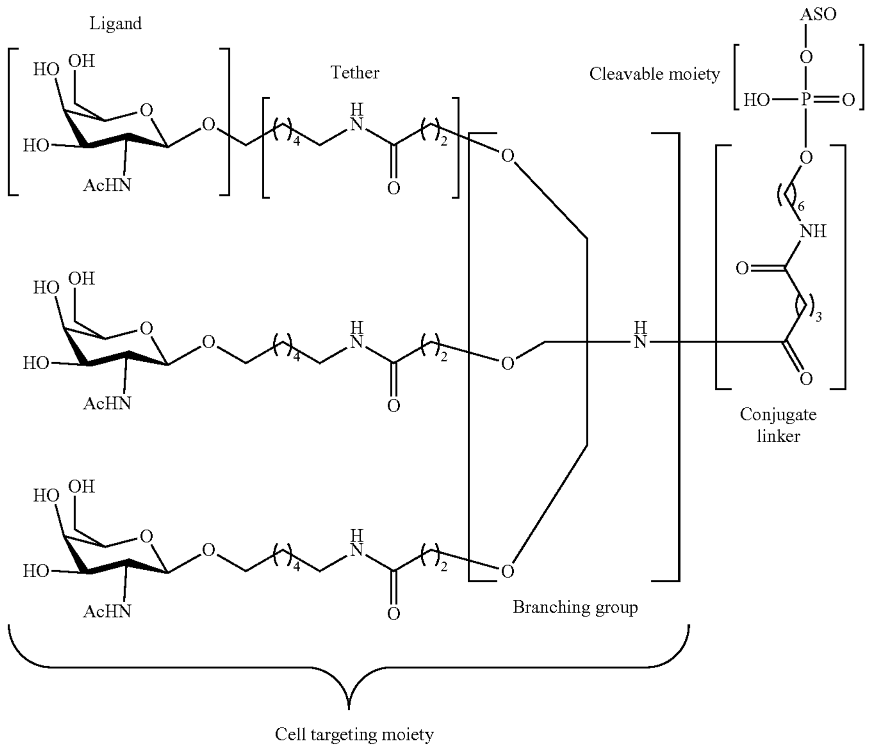

The present disclosure provides the following non-limiting embodiments:

In embodiments having more than one of a particular variable (e.g., more than one "m" or "n"), unless otherwise indicated, each such particular variable is selected independently. Thus, for a structure having more than one n, each n is selected independently, so they may or may not be the same as one another.

Certain embodiments provide a compound comprising a modified oligonucleotide targeting ApoCIII and a conjugate group, wherein the modified oligonucleotide consists of 12 to 30 linked nucleosides. In certain embodiments, the modified oligonucleotide with the conjugate group consists of 20 linked nucleosides.

Certain embodiments provide a compound comprising a modified oligonucleotide targeting ApoCIII and a conjugate group, wherein the modified oligonucleotide consists of 12 to 30 linked nucleosides and comprises a nucleobase sequence complementary to an equal length portion of nucleobases 3533 to 3552 of SEQ ID NO: 3, wherein the nucleobase sequence of the modified oligonucleotide is at least 80% complementary to SEQ ID NO: 3.

Certain embodiments provide a compound comprising a modified oligonucleotide targeting ApoCIII and a conjugate group, wherein the modified oligonucleotide consists of 12 to 30 linked nucleosides and comprises a nucleobase sequence complementary to an equal length portion of nucleobases 3514 to 3558 of SEQ ID NO: 3, wherein the nucleobase sequence of the modified oligonucleotide is at least 80% complementary to SEQ ID NO: 3.

Certain embodiments provide a compound comprising a modified oligonucleotide targeting ApoCIII and a conjugate group, wherein the modified oligonucleotide consists of 12 to 30 linked nucleosides and has a nucleobase sequence of any of the nucleobase sequences of SEQ ID NOs: 19-96, 209-221. In certain embodiments, the conjugated modified oligonucleotide has a nucleobase sequence comprising at least 8 contiguous nucleobases of any one of the nucleobase sequences of SEQ ID NOs: 19-96, 209-221. In certain embodiments, the compound consists of any one of SEQ ID NOs: 19-96, 209-221 and a conjugate group.

Certain embodiments provide a compound comprising a modified oligonucleotide targeting ApoCIII and a conjugate group, wherein the modified oligonucleotide consists of 12 to 30 linked nucleosides and has a nucleobase sequence of SEQ ID NO: 87. In certain embodiments, the modified oligonucleotide with the conjugate group has a nucleobase sequence comprising at least 8 contiguous nucleobases of the nucleobase sequence of SEQ ID NO: 87. In certain embodiments, the compound consists of SEQ ID NO: 87 and a conjugate group.

In certain embodiments, the present disclosure provides conjugated antisense compounds represented by the following structure. In certain embodiments, the antisense compound comprises the modified oligonucleotide ISIS 304801 with a 5'-X, wherein X is a conjugate group comprising GalNAc. In certain embodiments, the antisense compound consists of the modified oligonucleotide ISIS 304801 with a 5'-X, wherein X is a conjugate group comprising GalNAc.

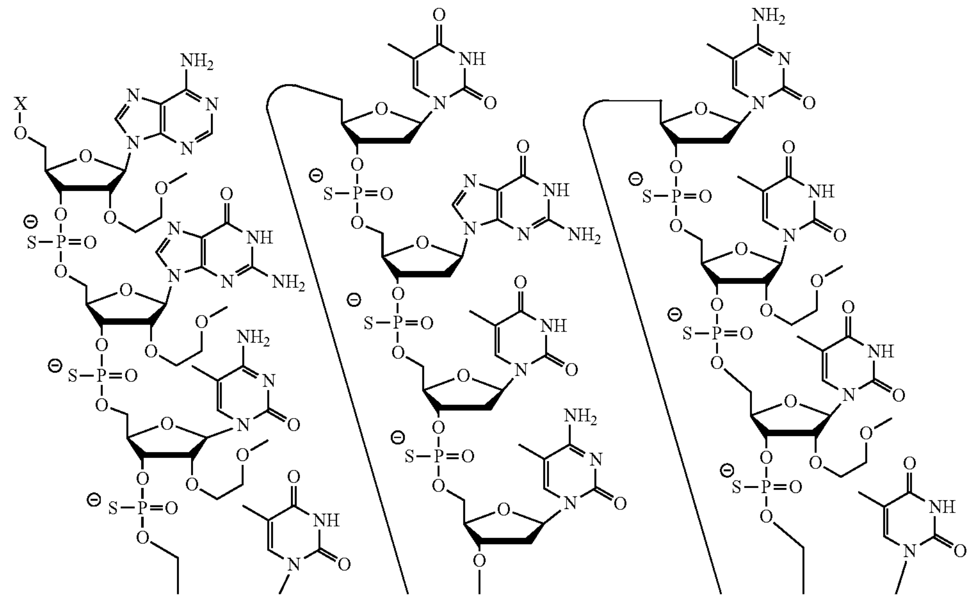

-continued
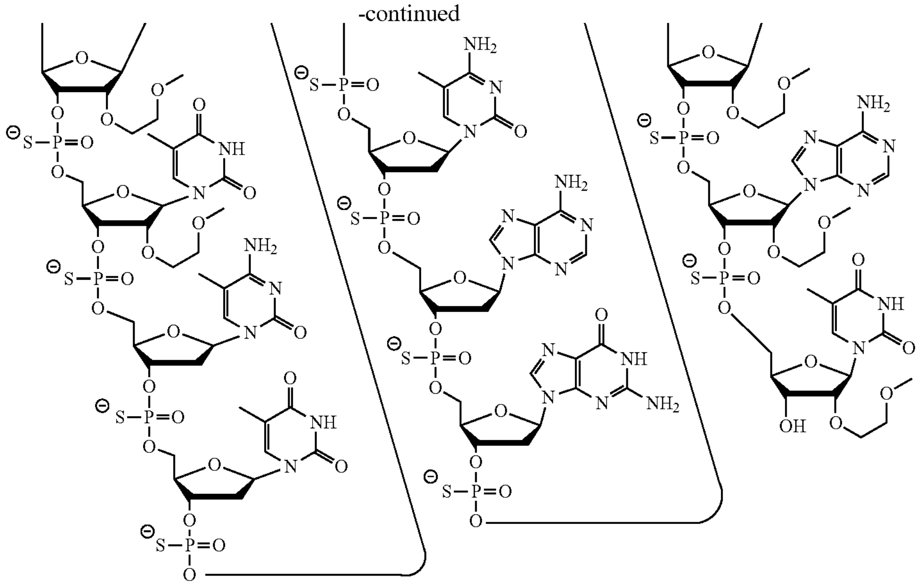
In certain embodiments, the present disclosure provides conjugated antisense compounds represented by the following structure. In certain embodiments, the antisense compound comprises the conjugated modified oligonucleotide ISIS 678354. In certain embodiments, the antisense compound consists of the conjugated modified oligonucleotide ISIS 678354.
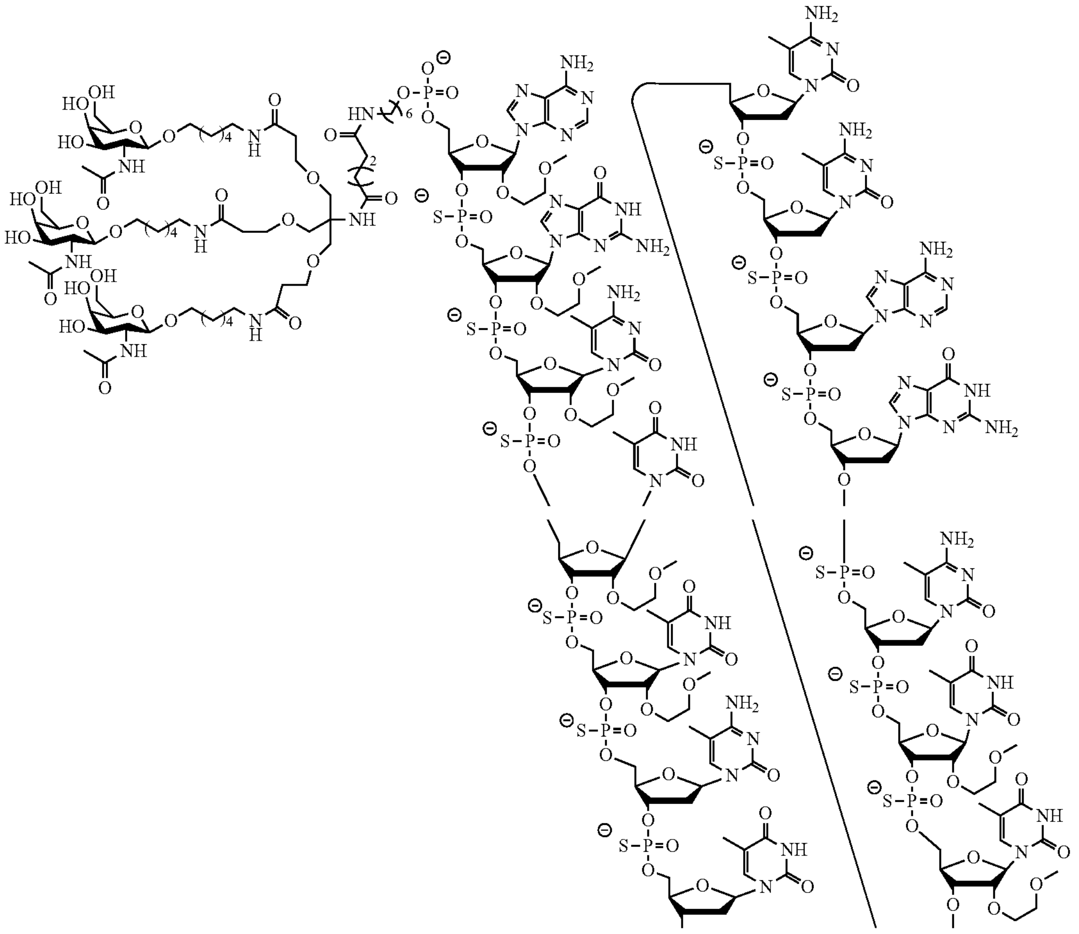

-continued
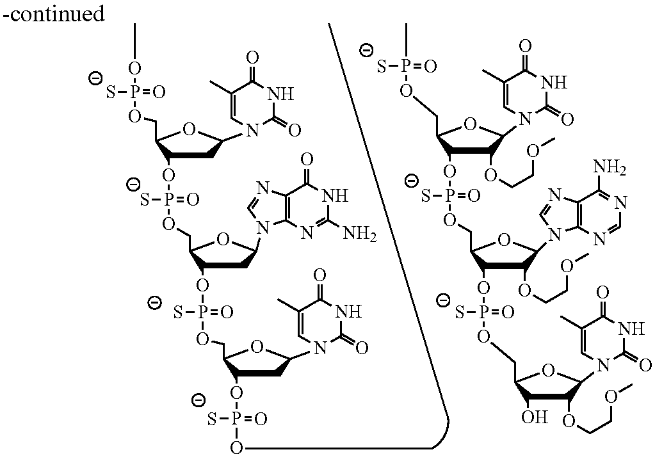
In certain embodiments, the present disclosure provides conjugated antisense compounds represented by the following structure. In certain embodiments, the antisense compound comprises the conjugated modified oligonucleotide ISIS 678357. In certain embodiments, the antisense compound consists of the conjugated modified oligonucleotide ISIS 678357.
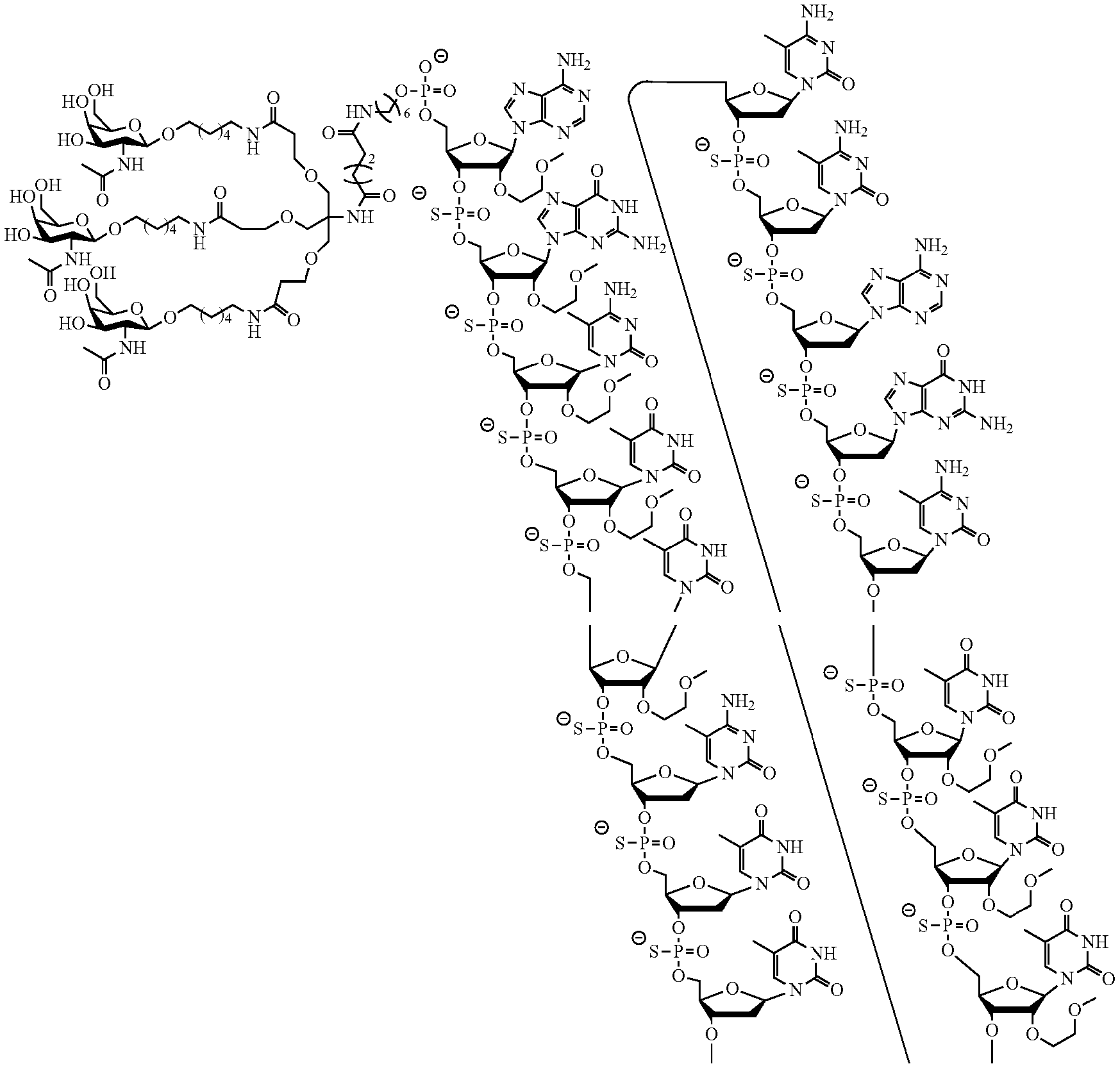

-continued

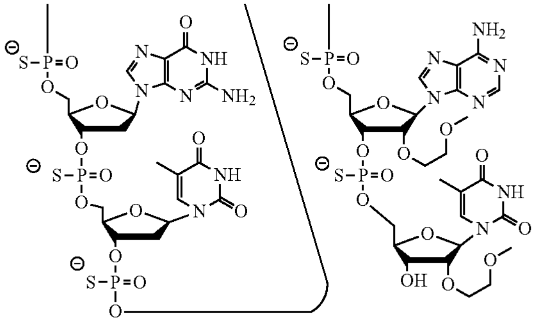

In certain embodiments, the present disclosure provides conjugated antisense compounds represented by the following structure. In certain embodiments, the antisense compound comprises a modified oligonucleotide with the nucleobase sequence of SEQ ID NO: 87 with a 5'-GalNAc with variability in the sugar mods of the wings. In certain embodiments, the antisense compound consists of a modified oligonucleotide with the nucleobase sequence of SEQ ID NO: 87 with a 5'-GalNAc with variability in the sugar mods of the wings.

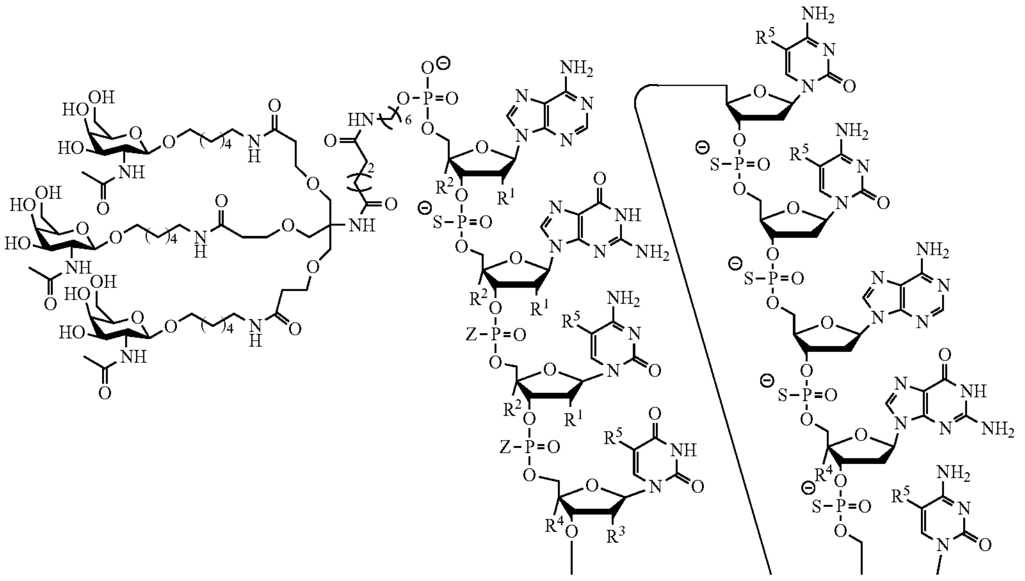

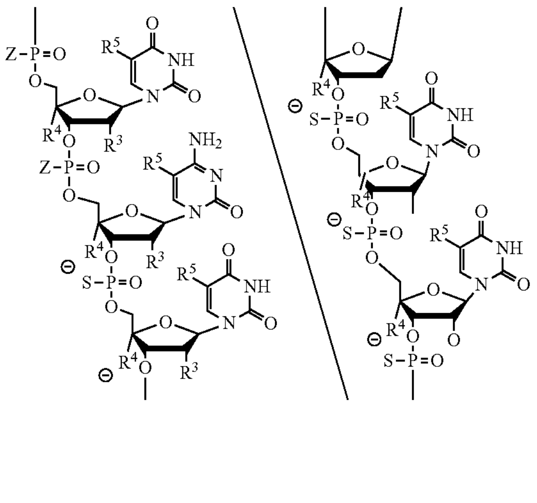

-continued

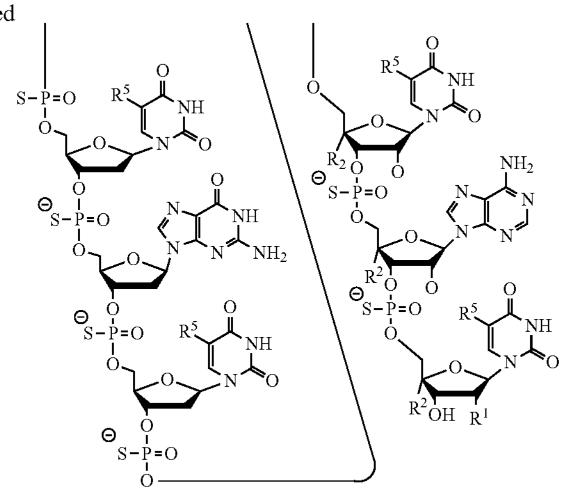

Wherein either $R^1$ is —$OCH_2CH_2OCH_3$ (MOE) and $R^2$ is H; or $R^1$ and $R^2$ together form a bridge, wherein $R^1$ is —O— and $R^2$ is —$CH_2$—, —$CH(CH_3)$—, or —$CH_2CH_2$—, and $R^1$ and $R^2$ are directly connected such that the resulting bridge is selected from: —O—$CH_2$—, —O—$CH(CH_3)$—, and —O—$CH_2CH_2$—;

And for each pair of $R^3$ and $R^4$ on the same ring, independently for each ring: either $R^3$ is selected from H and —$OCH_2CH_2OCH_3$ and $R^4$ is H; or $R^3$ and $R^4$ together form a bridge, wherein $R^3$ is —O—, and $R^4$ is —$CH_2$—, —$CH(CH_3)$—, or —$CH_2CH_2$— and $R^3$ and $R^4$ are directly connected such that the resulting bridge is selected from: —O—$CH_2$—, —O—$CH(CH_3)$—, and —O—$CH_2CH_2$—;

And $R^5$ is selected from H and —$CH_3$;

And Z is selected from $S^-$ and $O^-$.

The present disclosure provides the following non-limiting numbered embodiments:

DETAILED DESCRIPTION

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21st edition, 2005; and "Antisense Drug Technology, Principles, Strategies, and Applications" Edited by Stanley T. Crooke, CRC Press, Boca Raton, Florida; and Sambrook et al., "Molecular Cloning, A laboratory Manual," 2nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety.

Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means $—OCH_2CH_2OCH_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid.

Nucleobases may be naturally occurring or may be modified. As used herein, "nucleobase sequence" means the order of contiguous nucleobases independent of any sugar, linkage, or nucleobase modification.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a $4'-CH(CH_3)—O-2'$bridge.

As used herein, "locked nucleic acid nucleoside" or "LNA" means a nucleoside comprising a bicyclic sugar moiety comprising a $4'-CH_2—O-2'$bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom.

Phosphorus linking groups include without limitation groups having the formula:

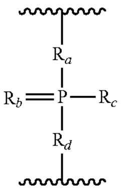

wherein:

$R_a$ and $R_d$ are each, independently, O, S, $CH_2$, NH, or $NJ_1$ wherein $J_1$ is $C_1$-$C_6$ alkyl or substituted $C_1$-$C_6$ alkyl;

$R_b$ is O or S;

$R_c$ is OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $J_1$ is $R_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI ($—CH_2—N(CH_3)—O—$), amide-3 ($—CH_2—C(=O)—N(H)—$), amide-4 ($—CH_2—N(H)—C(=O)—$), formacetal ($—O—CH_2—O—$), and thioformacetal ($—S—CH_2—O—$). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and $CH_2$ component parts.

As used herein, "internucleoside neutral linking group" means a neutral linking group that directly links two nucleosides.

As used herein, "non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites. In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "$GalNAc_3$". In certain embodiments, the carbohydrate cluster portion comprises 4 GalNAc groups and is designated "$GalNAc_4$". Specific carbohydrate cluster portions (having specific tether, branching and conjugate linker groups) are described herein and designated by Roman numeral followed by subscript "a". Accordingly "GalNac3-$1_a$" refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

As used herein, "cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

As used herein, "cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

As used herein, "carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry,* 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

As used herein "protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

As used herein, "single-stranded" means an oligomeric compound that is not hybridized to its complement and which lacks sufficient self-complementarity to form a stable self-duplex.

As used herein, "double stranded" means a pair of oligomeric compounds that are hybridized to one another or a single self-complementary oligomeric compound that forms a hairpin structure. In certain embodiments, a double-stranded oligomeric compound comprises a first and a second oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity includes modulation of the amount or activity of a target nucleic acid transcript (e.g. mRNA). In certain embodiments, antisense activity includes modulation of the splicing of pre-mRNA.

As used herein, "RNase H based antisense compound" means an antisense compound wherein at least some of the antisense activity of the antisense compound is attributable to hybridization of the antisense compound to a target nucleic acid and subsequent cleavage of the target nucleic acid by RNase H.

As used herein, "RISC based antisense compound" means an antisense compound wherein at least some of the antisense activity of the antisense compound is attributable to the RNA Induced Silencing Complex (RISC).

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize to result in a desired antisense activity. Antisense oligonucleotides have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein the term "metabolic disorder" means a disease or condition principally characterized by dysregulation of metabolism—the complex set of chemical reactions associated with breakdown of food to produce energy.

As used herein, the term "cardiovascular disorder" means a disease or condition principally characterized by impaired function of the heart or blood vessels.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein, "prodrug" means an inactive or less active form of a compound which, when administered to a subject, is metabolized to form the active, or more active, compound (e.g., drug).

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($—C(O)R_{aa}$), carboxyl ($—C(O)O—R_{aa}$), aliphatic groups, alicyclic groups, alkoxy, substituted oxy ($—O—R_{aa}$), aryl, aralkyl, heterocyclic radical, heteroaryl, heteroarylalkyl, amino ($—N(R_{bb})(R_{cc})$), imino($=NR_{bb}$), amido ($—C(O)N—(R_{bb})(R_{cc})$ or $—N(R_{bb})C(O)R_{aa}$), azido ($—N_3$), nitro ($—NO_2$), cyano ($—CN$), carbamido ($—OC(O)N(R_{bb})(R_{cc})$ or $—N(R_{bb})C(O)OR_{aa}$), ureido ($—N(R_{bb})C(O)N(R_{bb})(R_{cc})$), thioureido ($—N(R_{bb})C(S)N(R_{bb})(R_{cc})$), guanidinyl ($—N(R_{bb})C(=NR_{bb})N(R_{bb})(R_{cc})$), amidinyl ($—C(=NR_{bb})N(R_{bb})(R_{cc})$ or $—N(R_{bb})C(=NR_{bb})(R_{aa})$), thiol ($—SR_{bb}$), sulfinyl ($—S(O)R_{bb}$), sulfonyl ($—S(O)_2R_{bb}$) and sulfonamidyl ($—S(O)_2N(R_{bb})(R_{cc})$ or $—N(R_{bb})S(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "conjugate compound" means any atoms, group of atoms, or group of linked atoms suitable for use as a conjugate group. In certain embodiments, conjugate compounds may possess or impart one or more properties, including, but not limited to pharmacodynamic, pharmacokinetic, binding, absorption, cellular distribution, cellular uptake, charge and/or clearance properties.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

As used herein, "5' target site" refers to the nucleotide of a target nucleic acid which is complementary to the 5'-most nucleotide of a particular antisense compound.

As used herein, "about" means within ±10% of a value. For example, if it is stated, "a marker may be increased by about 50%", it is implied that the marker may be increased between 45%-55%.

As used herein, "administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

As used herein, "agent" means an active substance that can provide a therapeutic benefit when administered to an animal. "First agent" means a therapeutic compound of the invention. For example, a first agent can be an antisense oligonucleotide targeting apoCIII. "Second agent" means a second therapeutic compound of the invention (e.g. a second antisense oligonucleotide targeting apoCIII) and/or a non-apoCIII therapeutic compound.

As used herein, "amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

As used herein, "animal" refers to a human or non-human animal, including, but not limited to, mice, rats, rabbits, dogs, cats, pigs, and non-human primates, including, but not limited to, monkeys and chimpanzees.

As used herein, "ApoCIII", "Apolipoprotein C-III" or "ApoC3" means any nucleic acid or protein sequence encoding ApoCIII. For example, in certain embodiments, an ApoCIII includes a DNA sequence encoding ApoCIII, a RNA sequence transcribed from DNA encoding ApoCIII (including genomic DNA comprising introns and exons), a mRNA sequence encoding ApoCIII, or a peptide sequence encoding ApoCIII.

As used herein, "ApoCIII nucleic acid" means any nucleic acid encoding ApoCIII. For example, in certain embodiments, an ApoCIII nucleic acid includes a DNA sequence encoding ApoCIII, a RNA sequence transcribed from DNA encoding ApoCIII (including genomic DNA comprising introns and exons), and a mRNA sequence encoding ApoCIII.

As used herein, "ApoCIII specific inhibitor" refers to any agent capable of specifically inhibiting the expression of ApoCIII mRNA and/or the expression or activity of ApoCIII protein at the molecular level. For example, ApoCIII specific inhibitors include nucleic acids (including antisense compounds), peptides, antibodies, small molecules, and other agents capable of inhibiting the expression of ApoCIII mRNA and/or ApoCIII protein. In certain embodiments, the nucleic acid is an antisense compound. In certain embodiments, the antisense compound is a an oligonucleotide targeting ApoCIII. In certain embodiments, the oligonucleotide targeting ApoCIII is a modified oligonucleotide targeting ApoCIII. In certain embodiments, the oligonucleotide targeting ApoCIII is a modified oligonucleotide targeting ApoCIII with a conjugate group. In certain embodiments, the oligonucleotide targeting ApoCIII has a sequence as shown in SEQ ID NOs:19-96, 209-221 or another sequence (for example, such as those disclosed in PCT Publication WO 2004/093783 or PCT Publication WO 2012/149495, all incorporated-by-reference herein). In certain embodiments, by specifically modulating ApoCIII mRNA level and/or ApoCIII protein expression, ApoCIII specific inhibitors may affect components of the lipogenic or glucogenic pathway. Similarly, in certain embodiments, ApoCIII specific inhibitors may affect other molecular processes in an animal.

As used herein, "ApoCIII mRNA" means a mRNA encoding an ApoCIII protein.

As used herein, "ApoCIII protein" means any protein sequence encoding ApoCIII.

As used herein, "atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

As used herein, "coronary heart disease (CHD)" means a narrowing of the small blood vessels that supply blood and oxygen to the heart, which is often a result of atherosclerosis.

As used herein, "diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

As used herein, "diabetic dyslipidemia" or "type 2 diabetes with dyslipidemia" means a condition characterized by Type 2 diabetes, reduced HDL-C, elevated triglycerides (TG), and elevated small, dense LDL particles.

As used herein, "diluent" means an ingredient in a composition that lacks pharmacological activity, but is pharmaceutically necessary or desirable. For example, the diluent in an injected composition can be a liquid, e.g. saline solution.

As used herein, "dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

As used herein, "dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

As used herein, "dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

As used herein, "effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, "Fredrickson Type I" is also known as "Lipoprotein lipase deficiency", "LPLD", "Familial Chylomicronemia Syndrome" or "FCS" and exists in several forms: Type 1a (also known as Buerger-Gruestz syndrome) is a lipoprotein lipase deficiency commonly due to a deficiency of LPL or altered ApoC-II; Type Ib (also known as familial apoprotein CII deficiency) is a condition caused by lack of lipoprotein lipase activator apoprotein C-II; and Type Ic is a chylomicronemia due to circulating inhibitor of lipoprotein lipase. Type I is a rare disorder that usually presents in childhood. It is characterized by severe elevations in chylomicrons and extremely elevated TG levels (always reaching well above 1000 mg/dL and not infrequently rising as high as 10,000 mg/dL or more) with episodes of abdominal pain, recurrent acute pancreatitis, eruptive cutaneous xanthomata, and hepatosplenomegaly. Patients rarely develop atherosclerosis, perhaps because their plasma lipoprotein particles are too large to enter into the arterial intima (Nordestgaard et al., J Lipid Res, 1988, 29:1491-1500; Nordestgaard et al., Arteriosclerosis, 1988, 8:421-428). Type I is usually caused by mutations of either the LPL gene, or of the gene's cofactor ApoC-II, resulting in the inability of affected individuals to produce sufficient functionally active LPL. Patients are either homozygous for such mutations or compound heterozygous. Fredrickson Type I can also be due to mutations in the GPIHBP1, APOA5, LMF1 or other genes leading to dysfunctional LPL. Brunzell, In: Pagon R A, Adam M P, Bird T D, Dolan C R, Fong C T, Stephens K, editors. GeneReviews™ [Internet]. Seattle (WA): University of Washington, Seattle; 1993-2013.1999 Oct. 12 [updated 2011 Dec. 15]. Further, Fredrickson Type I, in some instances, can be due to the presence of LPL inhibitors (e.g., anti-LPL antibodies) in an individual causing dysfunctional LPL. The prevalence of Fredrickson Type I is approximately 1 in 1,000,000 in the general population and much higher in South Africa and Eastern Quebec as a result of a founder effect. Patients respond minimally, or not at all, to TG-lowering drugs (Tremblay et al., J Clin Lipidol, 2011, 5:37-44; Brisson et al., Pharmacogenet Genom, 2010, 20:742-747) and hence restriction of dietary fat to 20 grams/day or less is used to manage the symptoms of this rare disorder.

As used herein, "fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

As used herein, "glucose" is a monosaccharide used by cells as a source of energy and inflammatory intermediate. "Plasma glucose" refers to glucose present in the plasma.

As used herein, "high density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

As used herein, "HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

As used herein, "hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

As used herein, "hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

As used herein, "hypertriglyceridemia" means a condition characterized by elevated triglyceride levels. Hypertriglyceridemia is the consequence of increased production and/or reduced or delayed catabolism of triglyceride (TG)-rich lipoproteins: VLDL and, to a lesser extent, chylomicrons (CM). Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ,* 2007, 176:1113-1120). Hypertriglyceridemia is a common clinical trait associated with an increased risk of cardiometabolic disease (Hegele et al. 2009, Hum Mol Genet, 18: 4189-4194; Hegele and Pollex 2009, Mol Cell Biochem, 326: 35-43) as well as of occurrence of acute pancreatitis in the most severe forms (Toskes 1990, Gastroenterol Clin North Am, 19: 783-791; Gaudet et al. 2010, Atherosclerosis Supplements, 11: 55-60; Catapano et al. 2011, Atherosclerosis, 217S: S1-S44; Tremblay et al. 2011, J Clin Lipidol, 5: 37-44). Examples of cardiometabolic disease include, but are not limited to, diabetes, metabolic syndrome/insulin resistance, and genetic disorders such as familial chylomicronemia syndrome (FCS), familial combined hyperlipidemia and familial hypertriglyceridemia. Borderline high TG levels (150-199 mg/dL) are commonly found in the general population and are a common component of the metabolic syndrome/insulin resistance states. The same is true for high TG levels (200-499 mg/dL) except that as plasma TG levels increase, underlying genetic factors play an increasingly important etiologic role. Very high TG levels (≥500 mg/dL) are most often associated with elevated CM levels as well, and are accompanied by increasing risk for acute pancreatitis. The risk of pancreatitis is considered clinically significant if TG levels exceed 880 mg/dL (>10 mmol) and the European Atherosclerosis Society/European Society of Cardiology (EAS/ESC) 2011 guidelines state that actions to prevent acute pancreatitis are mandatory (Catapano et al. 2011, Atherosclerosis, 217S: S1-S44). According to the EAS/ESC 2011 guidelines, hypertriglyceridemia is the cause of approximately 10% of all cases of pancreatitis, and development of pancreatitis can occur at TG levels between 440-880 mg/dL. Based on evidence from clinical studies demonstrating that elevated TG levels are an independent risk factor for atherosclerotic CVD, the guidelines from both the National Cholesterol Education Program Adult Treatment Panel III (NCEP 2002, Circulation, 106: 3143-421) and the American Diabetes Association (ADA 2008, Diabetes Care, 31: S12-S54.) recommend a target TG level of less than 150 mg/dL to reduce cardiovascular risk.

As used herein, "identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

As used herein, "improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

As used herein, "immediately adjacent" means there are no intervening elements between the immediately adjacent elements, for example, between regions, segments, nucleotides and/or nucleosides.

As used herein, "increasing HDL" or "raising HDL" means increasing the level of HDL in an animal after administration of at least one compound of the invention, compared to the HDL level in an animal not administered any compound.

As used herein, "individual" or "subject" or "animal" means a human or non-human animal selected for treatment or therapy.

As used herein, "individual in need thereof" refers to a human or non-human animal selected for treatment or therapy that is in need of such treatment or therapy.

As used herein, "induce", "inhibit", "potentiate", "elevate", "increase", "decrease", "reduce" or the like denote quantitative differences between two states. For example, "an amount effective to inhibit the activity or expression of apoCIII" means that the level of activity or expression of apoCIII in a treated sample will differ from the level of apoCIII activity or expression in an untreated sample. Such terms are applied to, for example, levels of expression, and levels of activity.

As used herein, "inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

As used herein, "inhibiting the expression or activity" refers to a reduction or blockade of the expression or activity of a RNA or protein and does not necessarily indicate a total elimination of expression or activity.

As used herein, "insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

As used herein, "insulin sensitivity" is a measure of how effectively an individual processes glucose.

An individual having high insulin sensitivity effectively processes glucose whereas an individual with low insulin sensitivity does not effectively process glucose.

As used herein, "lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

As used herein, "lipid-lowering therapy" or "lipid lowering agent" means a therapeutic regimen provided to a subject to reduce one or more lipids in a subject. In certain embodiments, a lipid-lowering therapy is provided to reduce one or more of apo(a), apoCIII, CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

As used herein, "lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

As used herein, "Lipoprotein Lipase" or "LPL" refers to an enzyme that hydrolyzes TGs found in lipoproteins, such as CM or VLDL, into free fatty acids and monoacylglycerols. LPL requires apo C-II as a cofactor to function in hydrolyzing TGs. LPL is mainly produced in skeletal muscle, fat tissue, and heart muscle. Hydrolysis and removal of TG from CM and VLDL normally protects against excessive postprandial rise in CM mass and TG.

As used herein, "Lipoprotein lipase deficient", "lipoprotein lipase deficiency", "LPL deficiency" or "LPLD" is also known as "Fredrickson's Type I dyslipidemia", "chylomicronemia", "Familial Chylomicronemia Syndrome" or "FCS". Although subjects with LPLD generally lack LPL or LPL activity necessary for effective breakdown of fatty acids such as TGs, these subjects may still have a minimal LPL activity or express a minimal level of LPL. In some instances, a LPLD subject may express LPL or have LPL activity up to about, or no more than, 20%, 19%, 18%, 17%, 16%, 15%, 14%, 13%, 12%, 11%, 10%, 9%, 8%, 7%, 6%, 5%, 4%, 3%, 2% or 1% activity. In other instances, the LPLD subject has no measurable LPL or LPL activity. One embodiment of LPLD encompasses subjects with "hyperlipoproteinemia type Ia" (also known as "Fredrickson's Type Ia") and refers to the inability of the subjects to produce sufficient functional lipoprotein lipase enzymes necessary for effective breakdown of fatty acids such as TGs. The inability to breakdown TGs leads to hypertriglyceridemia in the subject and, often more than 12 hours after meals, hyperTG and chylomicronemia are still present and visible as lipemia. Type Ia is commonly caused by one or more mutations in the LPL gene. As disclosed herein, LPLD also encompasses subjects that have dysfunctional lipoprotein lipase such as those subjects with "hyperlipoproteinemia type Ib" (also known as "Fredrickson's Type Ib") and "hyperlipoproteinemia type Ic" (also known as "Fredrickson's Type Ic"). Type Ib is caused by lack of lipoprotein lipase activator apoprotein C-II. Type Ic is due to a circulating inhibitor of lipoprotein lipase. As with Type 1a, Type 1b/1c subjects suffer from an inability to breakdown TGs leading to hypertriglyceridemia and hyperTG and chylomicronemia are still present and visible as lipemia often more than 12 hours after meals. In certain embodiments, LPLD is associated with at least one mutation in the LPL gene such as P207L, G188L or D9N or other mutations that affect LPL (Brunzell, In: Pagon R A, Adam M P, Bird T D, Dolan C R, Fong C T, Stephens K, editors. GeneReviews™ [Internet]. Seattle (WA): University of Washington, Seattle; 1993-2013.1999 Oct. 12 [updated 2011 Dec. 15]).

As used herein, "low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

As used herein, "major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

As used herein, "metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

As used herein, "metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

As used herein, "peptide" means a molecule formed by linking at least two amino acids by amide bonds. Peptide refers to polypeptides and proteins.

As used herein, "pharmaceutical agent" means a substance that provides a therapeutic benefit when administered to an individual. For example, in certain embodiments, an antisense oligonucleotide targeted to apoCIII is a pharmaceutical agent.

As used herein, "pharmaceutical composition" or "composition" means a mixture of substances suitable for administering to an individual. For example, a pharmaceutical composition can comprise one or more active agents and a pharmaceutical carrier e.g., a sterile aqueous solution.

As used herein, "pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

As used herein, "pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

As used herein, "portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

As used herein, "prevent" or "preventing" refers to delaying or forestalling the onset or development of a disease, disorder, or condition for a period of time from minutes to indefinitely. Prevent also means reducing risk of developing a disease, disorder, or condition.

As used herein, "raise" means to increase in amount. For example, to raise plasma HDL levels means to increase the amount of HDL in the plasma.

As used herein, "reduce" means to bring down to a smaller extent, size, amount, or number. For example, to reduce plasma triglyceride levels means to bring down the amount of triglyceride in the plasma.

As used herein, "region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

As used herein, "second agent" or "second therapeutic agent" means an agent that can be used in combination with a "first agent". A second therapeutic agent can include, but is not limited to, antisense oligonucleotides targeting apoCIII. A second agent can also include anti-apoCIII antibodies, apoCIII peptide inhibitors, cholesterol lowering agents, lipid lowering agents, glucose lowering agents and anti-inflammatory agents.

As used herein, "segments" are defined as smaller, subportions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

As used herein, "statin" means an agent that inhibits the activity of HMG-CoA reductase.

As used herein, "subcutaneous administration" means administration just below the skin.

As used herein, "subject" means a human or non-human animal selected for treatment or therapy.

As used herein, "symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

As used herein, "targeting" or "targeted" means the process of design and selection of an antisense compound that will specifically hybridize to a target nucleic acid and induce a desired effect.

As used herein, "therapeutically effective amount" means an amount of a pharmaceutical agent that provides a therapeutic benefit to an individual.

As used herein, "therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

As used herein, "treat" or "treating" refers to administering a compound described herein to effect an alteration or improvement of a disease, disorder, or condition.

As used herein, "triglyceride" or "TG" means a lipid or neutral fat consisting of glycerol combined with three fatty acid molecules.

As used herein, "type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

CERTAIN EMBODIMENTS

Certain embodiments provide a compounds and methods for decreasing ApoCIII mRNA and protein expression. In certain embodiments, the compound is an ApoCIII specific inhibitor for treating, preventing, or ameliorating an ApoCIII associated disease. In certain embodiments, the compound is an antisense oligonucleotide targeting ApoCIII. In certain embodiments, the compound is an modified oligonucleotide targeting ApoCIII and a conjugate group.

In certain embodiments, a compound comprises a siRNA or antisense oligonucleotide targeted to Apolipoprotein C-III (ApoC-III) known in the art and a conjugate group described herein. Examples of antisense oligonucleotides targeted to ApoC-III suitable for conjugation include but are not limited to those disclosed in US Patent Application Publication No. US 2013/0317085, which is incorporated by reference in its entirety herein. In certain embodiments, a compound comprises an antisense oligonucleotide having a nucleobase sequence of any of SEQ ID NOs 19-96 and 209-221 disclosed in US 2013/0317085 and a conjugate group described herein. The nucleobase sequences of all of the aforementioned referenced SEQ ID NOs are incorporated by reference herein.

In certain embodiments, the modified oligonucleotide with the conjugate group has a nucleobase sequence comprising at least 8 contiguous nucleobases of a sequence selected from any sequence disclosed in U.S. Pat. Nos. 7,598,227, 7,750,141, PCT Publication WO 2004/093783 or PCT Publication WO 2012/149495, all incorporated-by-reference herein. In certain embodiments, the modified oligonucleotide has a sequence selected from any sequence disclosed in U.S. Pat. Nos. 7,598,227, 7,750,141, PCT Publication WO 2004/093783 or PCT Publication WO 2012/149495, all incorporated-by-reference herein.

Certain embodiments provide a compound comprising a modified oligonucleotide targeting ApoCIII and a conjugate group, wherein the modified oligonucleotide consists of 12 to 30 linked nucleosides. In certain embodiments, the modified oligonucleotide with the conjugate group consists of 15 to 30, 18 to 24, 19 to 22, 13 to 25, 14 to 25, 15 to 25 linked nucleosides. In certain embodiments, the modified oligonucleotide with the conjugate group comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide with the conjugate group consists of 20 linked nucleosides.

Certain embodiments provide a compound comprising a modified oligonucleotide with a conjugate group targeting ApoCIII and has a sequence complementary to any of the sequences set forth in GENBANK Accession No. NM_000040.1 (incorporated herein as SEQ ID NO: 1), GENBANK Accession No. NT_033899.8 truncated from nucleotides 20262640 to 20266603 (incorporated herein as SEQ ID NO: 2), and/or GenBank Accession No. NT_035088.1 truncated from nucleotides 6238608 to U.S. Pat. No. 6,242,565 (incorporated herein as SEQ ID NO: 3). In certain embodiments, the modified oligonucleotide is at least 70%, at least 75%, at least 80%, at least 85%, at least 90%, at least 95%, at least 98% or at least 100% complementary to any of SEQ ID NOs: 1-3. In certain embodiments, the compound comprises a modified oligonucleotide targeting ApoCIII and a conjugate group, wherein the modified oligonucleotide comprises at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-3. In certain embodiments, the compound comprises a modified oligonucleotide targeting an ApoCIII segment and a conjugate group, wherein the modified oligonucleotide comprises at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in Tables 121 and 124. In the tables, the “Start Site” refers to the 5'-most nucleotide of a target segment and “Stop Site” refers to the 3'-most nucleotide of a target segment. A target segment can range from the start site to the stop site of each sequence listed in the tables. Alternatively, the target segment can range from the start site of one sequence and end at the stop site of another sequence. For example, as shown in the tables, a target segment can range from 3533 to 3552, the start site to the stop site of SEQ ID NO: 87. In another example, as shown in the tables, a target segment can range from 3514 to 3558, the start site of SEQ ID NO: 83 to the stop site of SEQ ID NO: 88. In certain embodiments, the antisense compound comprises at least 8 nucleobases of the sequence of SEQ ID NO: 87. In certain embodiments, the antisense compound comprises the sequence of SEQ ID NO: 87. In certain embodiments, the antisense compound consists of the sequence of SEQ ID NO: 87. In certain embodiments, the antisense compound is ISIS 304801.

Certain embodiments provide a compound comprising a modified oligonucleotide targeting ApoCIII and a conjugate group, wherein the nucleobase sequence of the modified oligonucleotide is at least 80%, at least 85%, at least 90%, at least 95%, or 100% complementary to any of SEQ ID NOs: 1-3. Certain embodiments provide a compound comprising a modified oligonucleotide targeting ApoCIII and a conjugate group, wherein the nucleobase sequence of the modified oligonucleotide is at least 80%, at least 85%, at least 90%, at least 95%, or 100% complementary to any of the target segments disclosed herein.

Certain embodiments provide a compound comprising a modified oligonucleotide targeting ApoCIII and a conjugate group, wherein the modified oligonucleotide consists of 12 to 30 linked nucleosides and comprises a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3533 to 3552 of SEQ ID NO: 3, wherein the nucleobase sequence of the modified oligonucleotide is at least 80% complementary to SEQ ID NO: 3.

Certain embodiments provide a compound comprising a modified oligonucleotide targeting ApoCIII and a conjugate group, wherein the modified oligonucleotide consists of 12 to 30 linked nucleosides and comprises a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3514 to 3558 of SEQ ID NO: 3, wherein the nucleobase sequence of the modified oligonucleotide is at least 80% complementary to SEQ ID NO: 3.

Certain embodiments provide a compound comprising a modified oligonucleotide targeting ApoCIII and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NOs: 19-96, 209-221. In certain embodiments, the conjugated modified oligonucleotide has a nucleobase sequence comprising at least 8 contiguous nucleobases of any one of the nucleobase sequences of SEQ ID NOs: 19-96, 209-221. In certain embodiments, the compound consists of any one of SEQ ID NOs: 19-96, 209-221 and a conjugate group.

Certain embodiments provide a compound comprising a modified oligonucleotide targeting ApoCIII and a conjugate group, wherein the modified oligonucleotide consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, or 20 contiguous nucleobases of the nucleobase sequence of SEQ ID NO: 87. In certain embodiments, the modified oligonucleotide with the conjugate group has a nucleobase sequence comprising at least 8 contiguous nucleobases of the nucleobase sequence of SEQ ID NO: 87. In certain embodiments, the compound consists of SEQ ID NO: 87 and a conjugate group.

In certain embodiments, the present disclosure provides conjugated antisense compounds represented by the following structure. In certain embodiments, the antisense compound comprises a modified oligonucleotide with ISIS 304801 with a 5'-X, wherein X is a conjugate group comprising GalNAc. In certain embodiments, the antisense compound consists of a modified oligonucleotide with ISIS 304801 with a 5'-X, wherein X is a conjugate group comprising GalNAc.

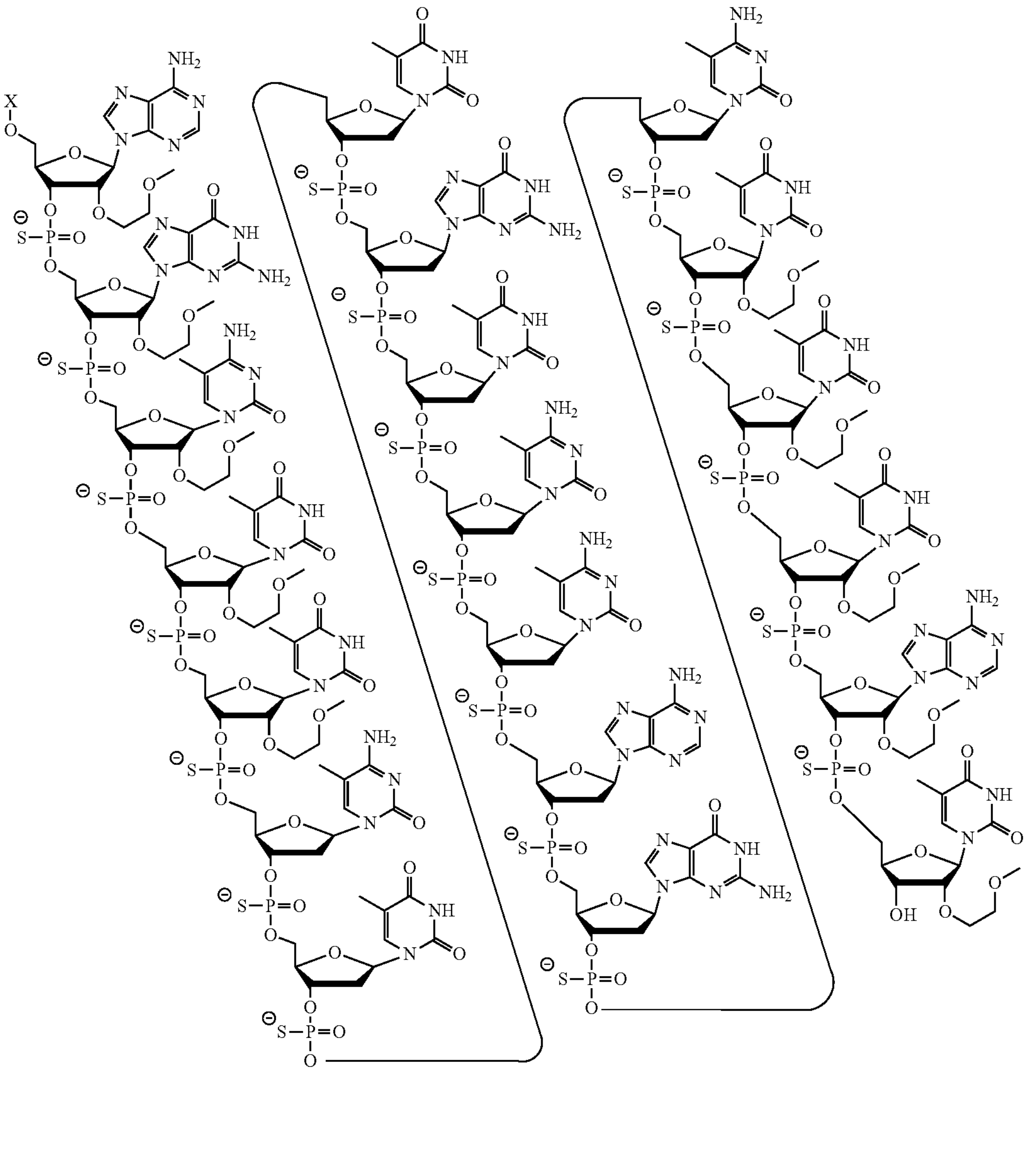

In certain embodiments, the present disclosure provides conjugated antisense compounds represented by the following structure. In certain embodiments, the antisense compound comprises the conjugated modified oligonucleotide ISIS 678354. In certain embodiments, the antisense compound consists of the conjugated modified oligonucleotide ISIS 678354.

In certain embodiments, the present disclosure provides conjugated antisense compounds represented by the following structure. In certain embodiments, the antisense compound comprises the conjugated modified oligonucleotide ISIS 678357. In certain embodiments, the antisense compound consists of the conjugated modified oligonucleotide ISIS 678357.

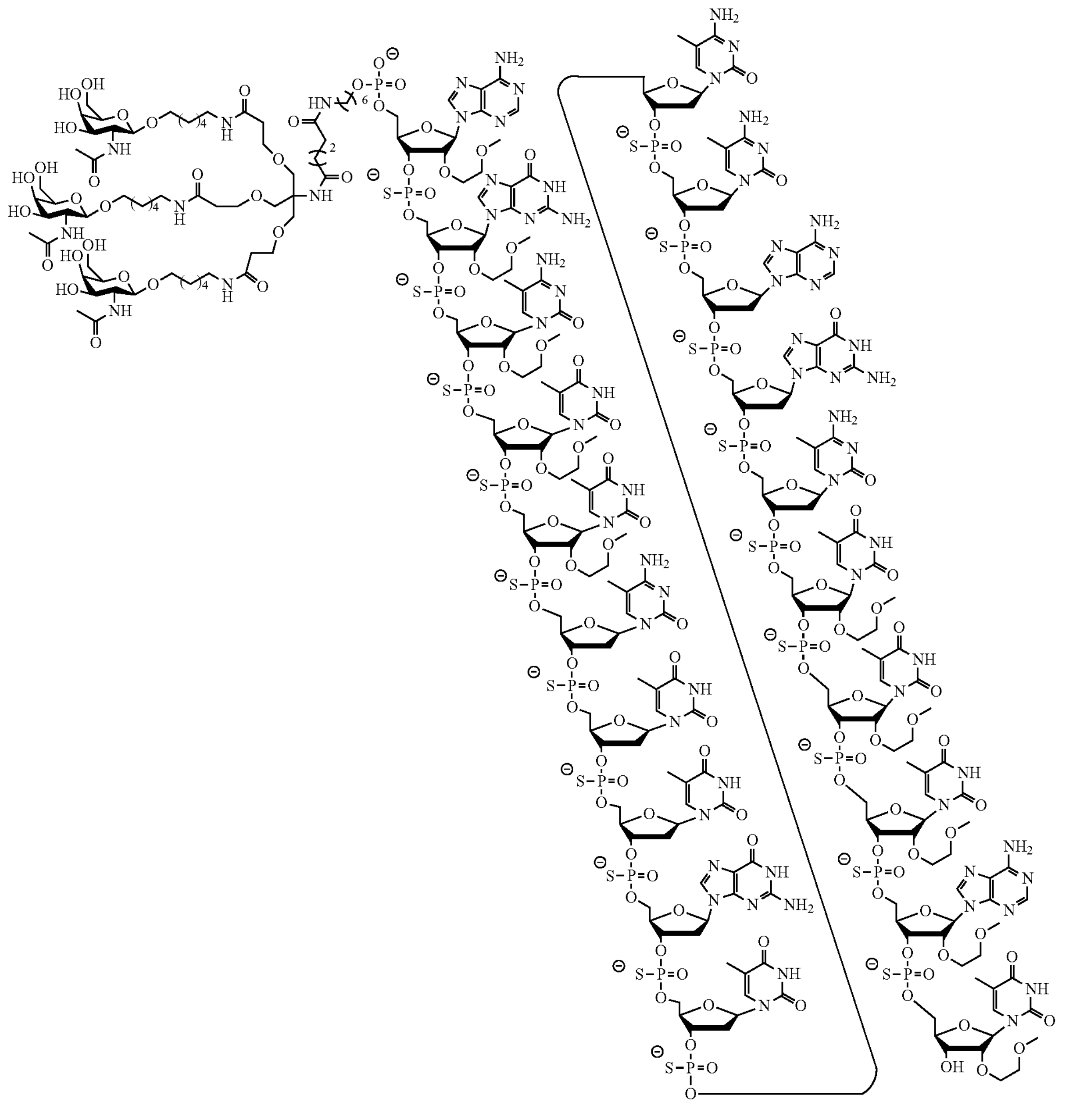

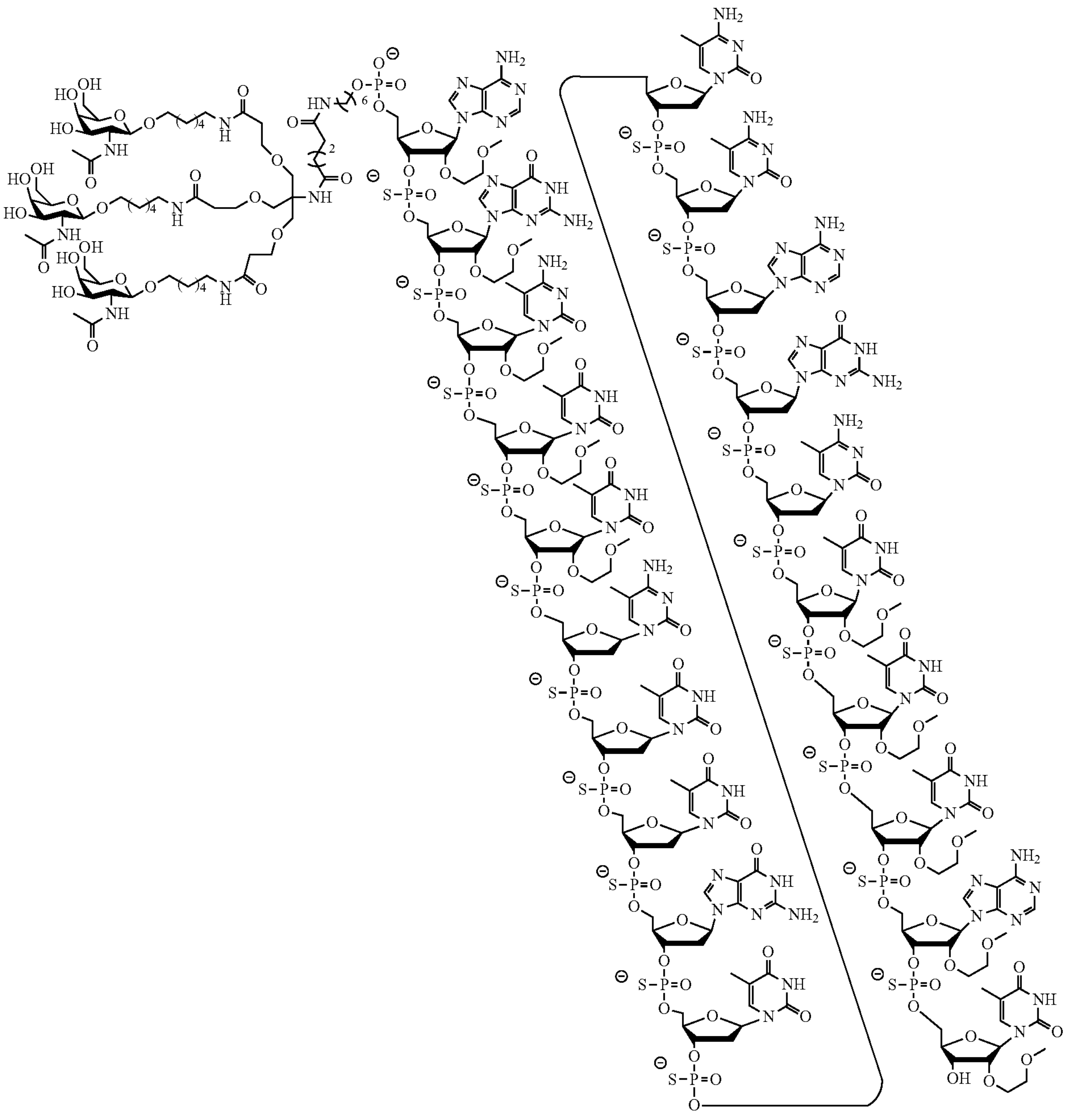

In certain embodiments, the present disclosure provides conjugated antisense compounds represented by the following structure. In certain embodiments, the antisense compound comprises a modified oligonucleotide with the nucleobase sequence of SEQ ID NO: 87 with a 5'-GalNAc with variability in the sugar mods of the wings. In certain embodiments, the antisense compound consists of a modified oligonucleotide with the nucleobase sequence of SEQ ID NO: 87 with a 5'-GalNAc with variability in the sugar mods of the wings.

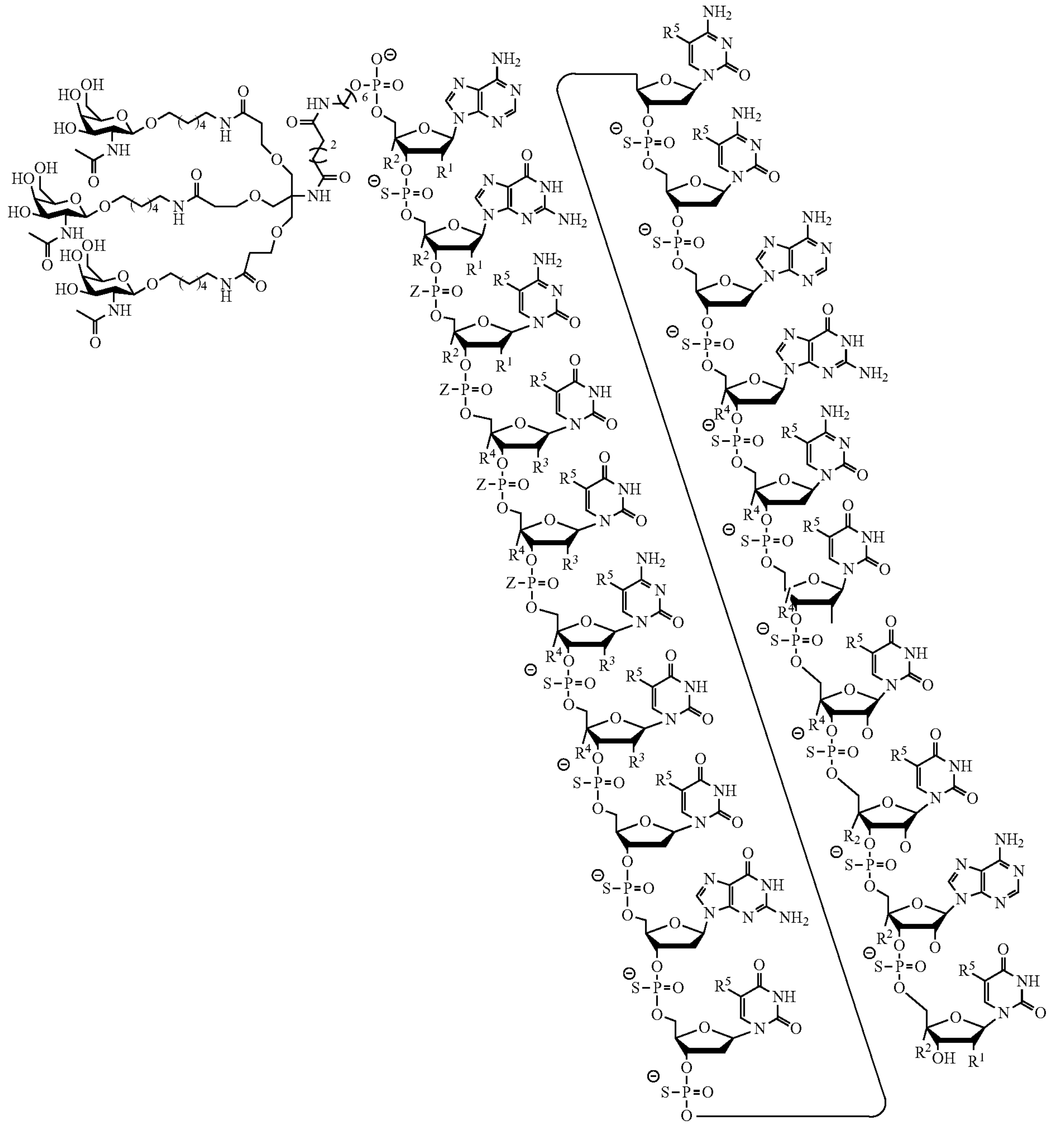

Wherein either $R^1$ is —$OCH_2CH_2OCH_3$ (MOE) and $R^2$ is H; or $R^1$ and $R^2$ together form a bridge, wherein $R^1$ is —O— and $R^2$ is —$CH_2$—, —$CH(CH_3)$—, or —$CH_2CH_2$—, and R and $R^2$ are directly connected such that the resulting bridge is selected from: —O—$CH_2$—, —O—$CH(CH_3)$—, and —O—$CH_2CH_2$—;

And for each pair of $R^3$ and $R^4$ on the same ring, independently for each ring: either $R^3$ is selected from H and —$OCH_2CH_2OCH_3$ and $R^4$ is H; or $R^3$ and $R^4$ together form a bridge, wherein $R^3$ is —O—, and $R^4$ is —$CH_2$—, —$CH(CH_3)$—, or —$CH_2CH_2$— and $R^3$ and $R^4$ are directly connected such that the resulting bridge is selected from: —O—$CH_2$—, —O—$CH(CH_3)$—, and —O—$CH_2CH_2$—;

And $R^5$ is selected from H and —$CH_3$;

And Z is selected from $S^-$ and $O^-$.

Certain embodiments provide a compound comprising a modified oligonucleotide targeting ApoCIII and a conjugate group, wherein the modified oligonucleotide is single-stranded.

Certain embodiments provide a compound comprising a modified oligonucleotide targeting ApoCIII and a conjugate group, wherein at least one internucleoside linkage is a modified internucleoside linkage. In certain embodiments, the modified internucleoside linkage is a phosphorothioate internucleoside linkage. In certain embodiments, at least 1, at least 2, at least 3, at least 4, at least 5, at least 6, at least 7, at least 8, at least 9 or at least 10 internucleoside linkages of said modified oligonucleotide are phosphorothioate internucleoside linkages. In certain embodiments, each internucleoside linkage is a phosphorothioate internucleoside linkage. In certain embodiments, the modified oligonucleotide comprises at least 1, at least 2, at least 3, at least 4, at least 5, at least 6, at least 7, at least 8, at least 9 or at least 10 phosphodiester internucleoside linkages. In certain embodiments, each internucleoside linkage of the modified oligonucleotide is selected from a phosphodiester internucleoside linkage and a phosphorothioate internucleoside linkage.

Certain embodiments provide a compound comprising a modified oligonucleotide targeting ApoCIII and a conjugate group, wherein at least one nucleoside comprises a modified nucleobase. In certain embodiments, the modified nucleobase is a 5-methylcytosine.

Certain embodiments provide a compound comprising a modified oligonucleotide targeting ApoCIII and a conjugate group, wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-$(CH_2)_n$—O-2' bridge, wherein n is 1 or 2.

Certain embodiments provide a compound comprising a modified oligonucleotide targeting ApoCIII and a conjugate group, wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting ApoCIII and a conjugate group, wherein the modified oligonucleotide consists of 20 linked nucleosides and comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting ApoCIII and a conjugate group, wherein the modified oligonucleotide consists of 20 linked nucleosides and has a nucleobase sequence comprising at least 8 contiguous nucleobases of any of SEQ ID NOs: 19-96, 209-221, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting ApoCIII and a conjugate group, wherein the modified oligonucleotide consists of 20 linked nucleosides and has a nucleobase sequence comprising at least 8 contiguous nucleobases of SEQ ID NO: 87, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a modified oligonucleotide targeting ApoCIII and a conjugate group, wherein the modified oligonucleotide consists of 20 linked nucleosides with the nucleobase sequence of SEQ ID NO: 87, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide.

In certain embodiments, the conjugate group comprises exactly one ligand. In certain embodiments, the conjugate group comprises one or more ligands. In certain embodiments, the conjugate group comprises exactly two ligands. In certain embodiments, the conjugate group comprises two or more ligands. In certain embodiments, the conjugate group comprises three or more ligands. In certain embodiments, the conjugate group comprises exactly three ligands. In certain embodiments, each ligand is selected from among: a polysaccharide, modified polysaccharide, mannose, galactose, a mannose derivative, a galactose derivative, D-mannopyranose, L-Mannopyranose, D-Arabinose, L-Galactose, D-xylofuranose, L-xylofuranose, D-glucose, L-glucose, D-Galactose, L-Galactose, α-D-Mannofuranose, β-D-Mannofuranose, α-D-Mannopyranose, β-D-Mannopyranose, α-D-Glucopyranose, β-D-Glucopyranose, α-D-Glucofuranose, β-D-Glucofuranose, α-D-fructofuranose, α-D-fructopyranose, α-D-Galactopyranose, β-D-Galactopyranose, α-D-Galactofuranose, β-D-Galactofuranose, glucosamine, sialic acid, α-D-galactosamine, N-Acetylgalactosamine, 2-Amino-3-O—[(R)-1-carboxyethyl]-2-deoxy-β-D-glucopyranose, 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose, N-Glycoloyl-α-neuraminic acid, 5-thio-β-D-glucopyranose, methyl 2,3,4-tri-O-acetyl-1-thio-6-O-trityl-α-D-glucopyranoside, 4-Thio-β-D-galactopyranose, ethyl 3,4,6,7-tetra-O-acetyl-2-deoxy-1,5-dithio-α-D-gluco-heptopyranoside, 2,5-Anhydro-D-allononitrile, ribose, D-ribose, D-4-thioribose, L-ribose, L-4-thioribose. In certain embodiments, each ligand is N-acetyl galactosamine.

In certain embodiments, the conjugate group comprises:
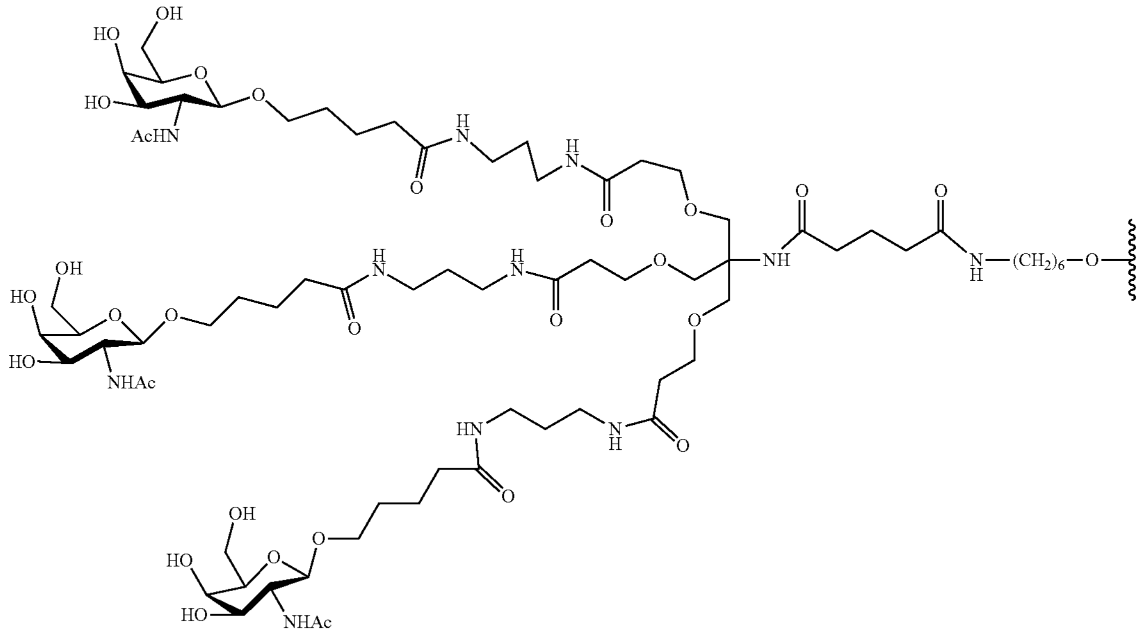
In certain embodiments, the conjugate group comprises:
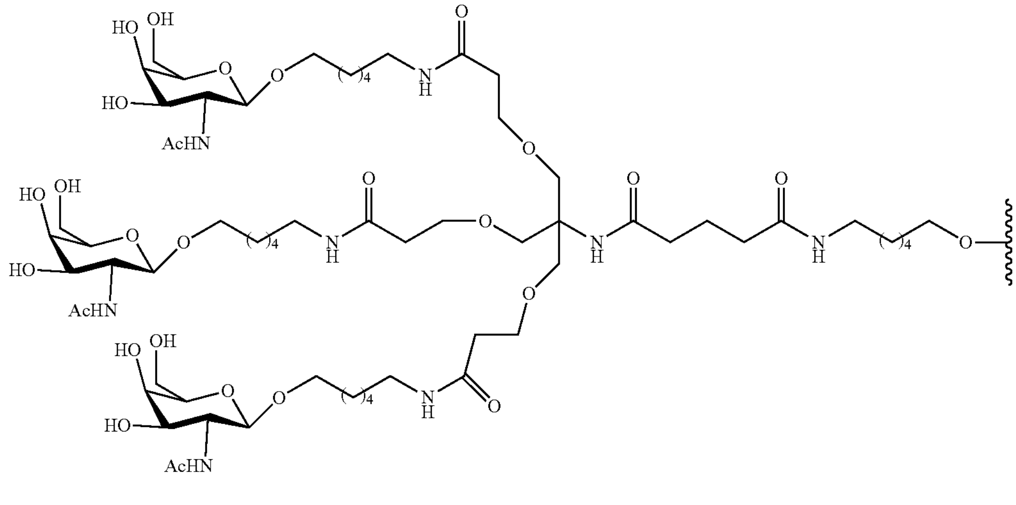

In certain embodiments, the conjugate group comprises:
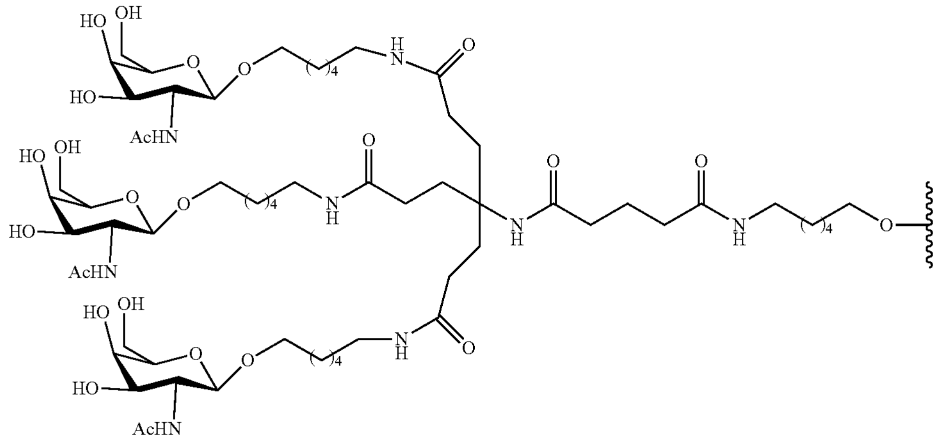
In certain embodiments, the conjugate group comprises:
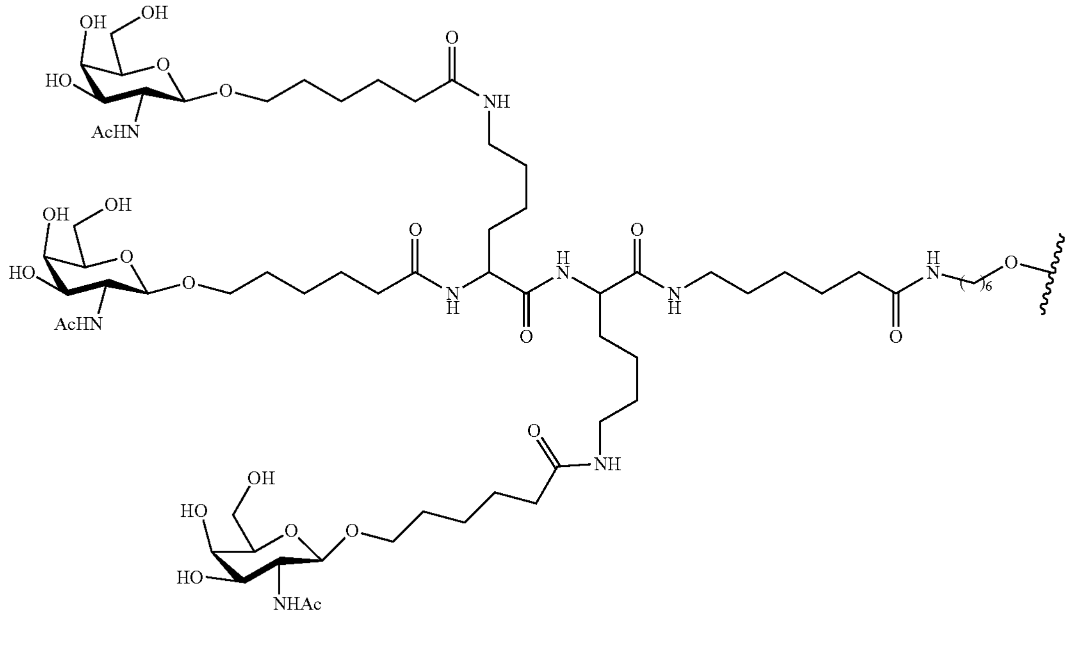

In certain embodiments, the conjugate group comprises:

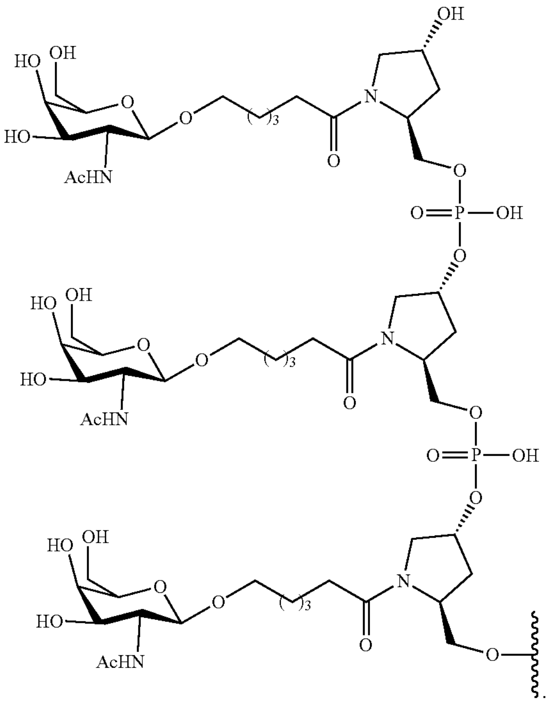

In certain embodiments, the conjugate group comprises at least one phosphorus linking group or neutral linking group.

In certain embodiments, the conjugate group comprises a structure selected from among:

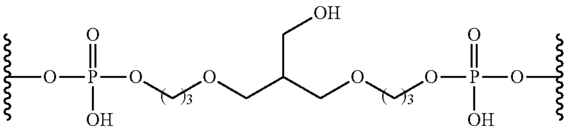

,

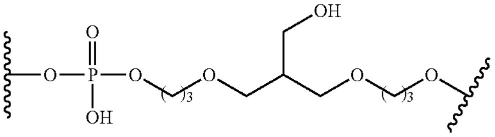

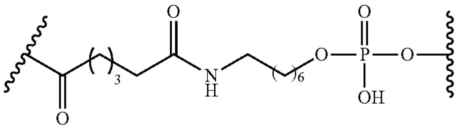

and

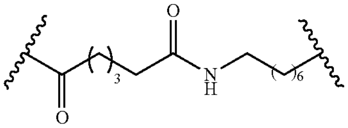

.

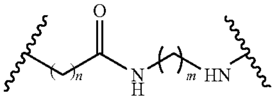

;

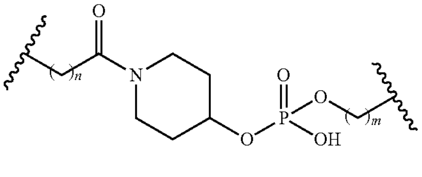

;

-continued

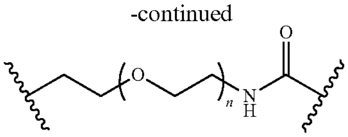

;

wherein n is from 1 to 12; and wherein m is from to 12.

In certain embodiments, the conjugate group has a tether having a structure selected from among:

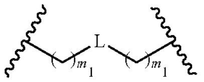

and

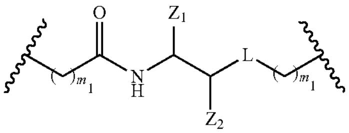

wherein L is either a phosphorus linking group or a neutral linking group;

$Z_1$ is C(=O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, the conjugate group has a tether having a structure selected from among:

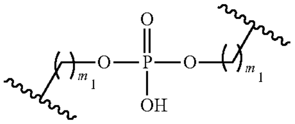

or

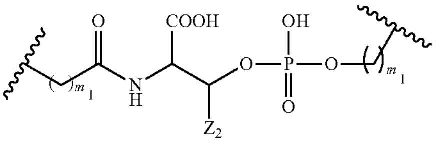

wherein $Z_2$ is H or $CH_3$; and each $m_1$ is, independently, from 0 to 20 wherein at least one $m_1$ is greater than 0 for each tether.

In certain embodiments, the conjugate group has tether having a structure selected from among:

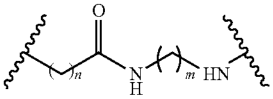

;

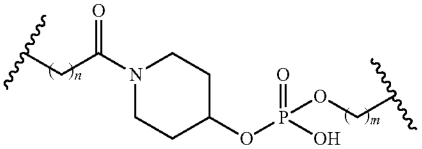

;

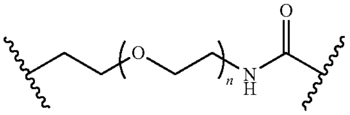

;

wherein n is from 1 to 12; and wherein m is from 1 to 12.

In certain embodiments, the conjugate group is covalently attached to the modified oligonucleotide.

In certain embodiments, the compound has a structure represented by the formula:

$$A—B—C—D\!\left(E—F\right)_q$$

wherein

A is the modified oligonucleotide;

B is the cleavable moiety

C is the conjugate linker

D is the branching group each E is a tether;

each F is a ligand; and q is an integer between 1 and 5.

In certain embodiments, the compound has a structure represented by the formula:

$$A\!\left(B\right)_{n_2}\!\left(C\right)_{n_1}\!\left(D\right)_{n_3}\!\left(E—F\right)_q$$

wherein:

A is the modified oligonucleotide;

B is the cleavable moiety

C is the conjugate linker

D is the branching group each E is a tether;

each F is a ligand;

each n is independently 0 or 1; and q is an integer between 1 and 5.

In certain embodiments, the compound has a structure represented by the formula:

$$A—B—C\!\left(E—F\right)_q$$

wherein

A is the modified oligonucleotide;

B is the cleavable moiety;

C is the conjugate linker;

each E is a tether;

each F is a ligand; and q is an integer between 1 and 5.

In certain embodiments, the compound has a structure represented by the formula:

$$A—C—D\!\left(E—F\right)_q$$

wherein

A is the modified oligonucleotide;

C is the conjugate linker;

D is the branching group;

each E is a tether;

each F is a ligand; and q is an integer between 1 and 5.

In certain embodiments, the compound has a structure represented by the formula:

$$A—C\!\left(E—F\right)_q$$

wherein

A is the modified oligonucleotide;

C is the conjugate linker;

each E is a tether;

each F is a ligand; and q is an integer between 1 and 5.

In certain embodiments, the compound has a structure represented by the formula:

$$A—B—D\!\left(E—F\right)_q$$

wherein

A is the modified oligonucleotide;

B is the cleavable moiety;

D is the branching group;

each E is a tether;

each F is a ligand; and q is an integer between 1 and 5.

In certain embodiments, the compound has a structure represented by the formula:

$$A—B\!\left(E—F\right)_q$$

wherein

A is the modified oligonucleotide;

B is the cleavable moiety;

each E is a tether;

each F is a ligand; and q is an integer between 1 and 5.

In certain embodiments, the compound has a structure represented by the formula:

$$A—D\!\left(E—F\right)_q$$

wherein

A is the modified oligonucleotide;

D is the branching group;

each E is a tether;

each F is a ligand; and q is an integer between 1 and 5.

In certain embodiments, the conjugate linker has a structure selected from among:

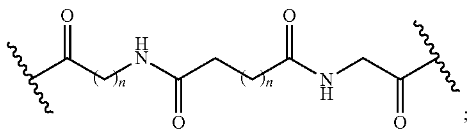

;

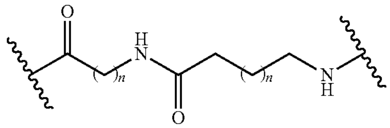

;

-continued
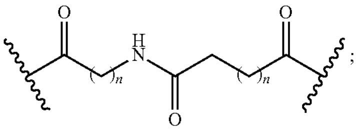
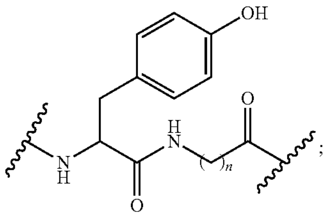
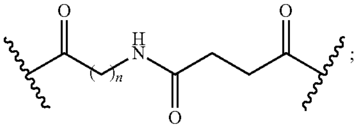
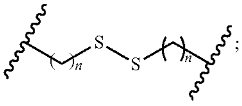
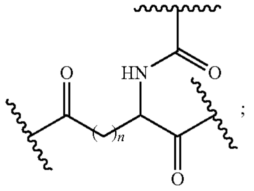
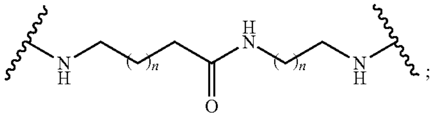
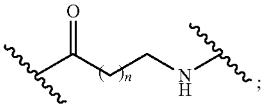
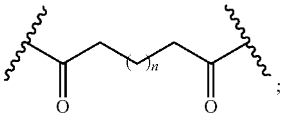
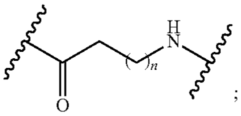
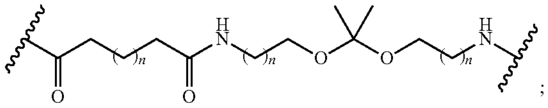
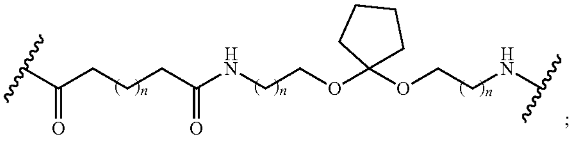
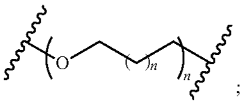
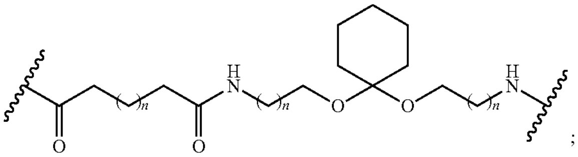
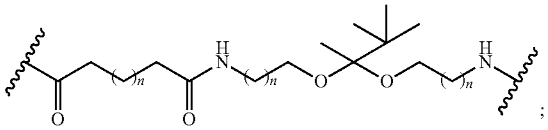
-continued
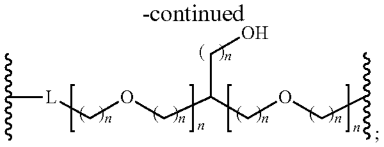
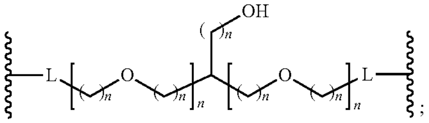
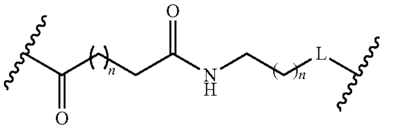
and
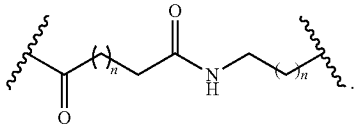
wherein each L is, independently, a phosphorus linking group or a neutral linking group; and
each n is, independently, from 1 to 20.
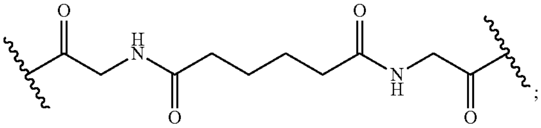
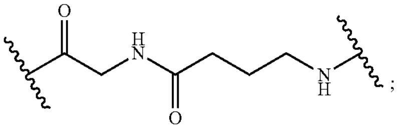
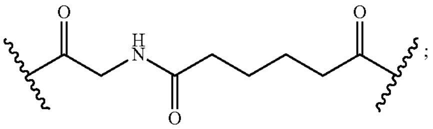
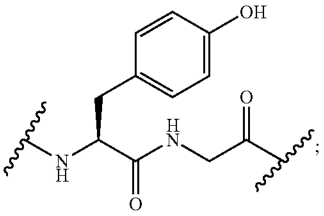
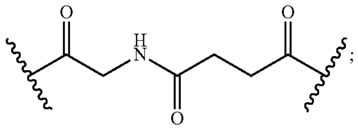
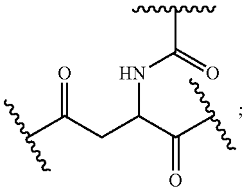
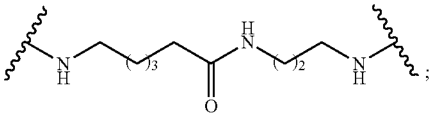

-continued
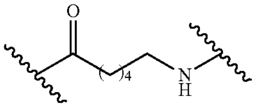;
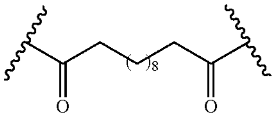;
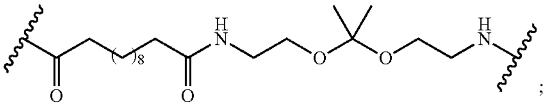;
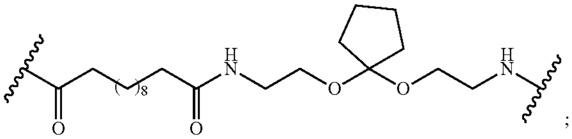;
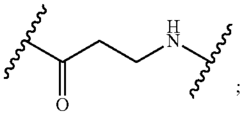;
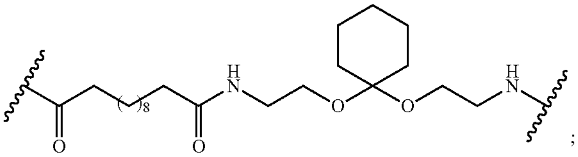;
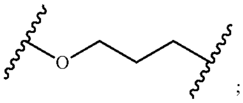;
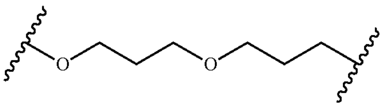;
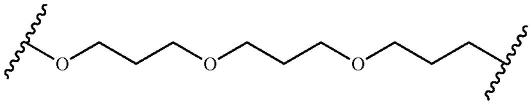;
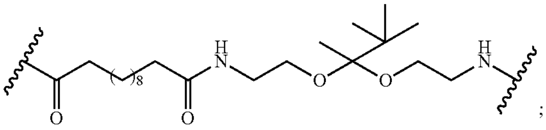;
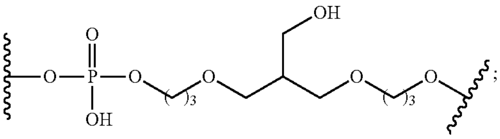;
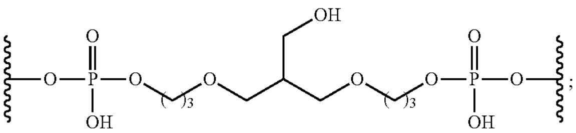;
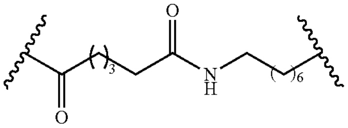
and
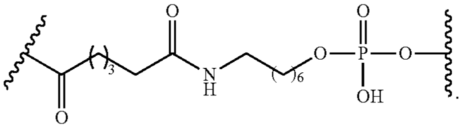.
In certain embodiments, the conjugate linker has the following structure:
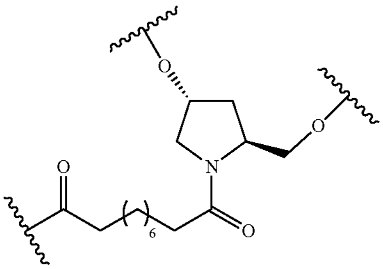.
In certain embodiments, the conjugate linker has a structure selected from among:
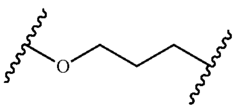;
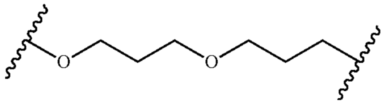; and
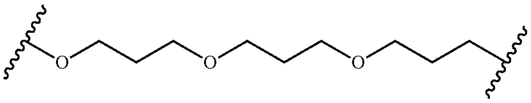.
In certain embodiments, the conjugate linker has a structure selected from among:
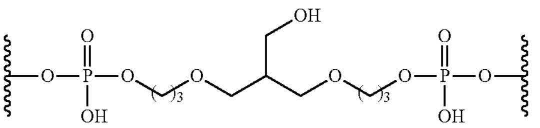
and
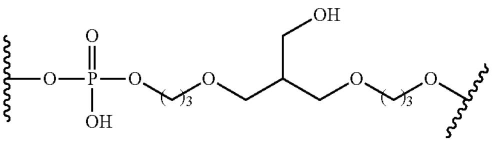.
In certain embodiments, the conjugate linker has a structure selected from among:
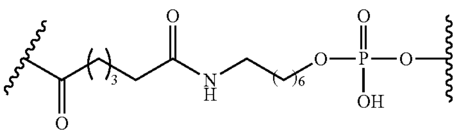;
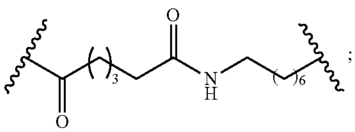; and -continued

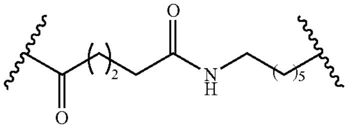

In certain embodiments, the conjugate linker comprises a pyrrolidine. In certain embodiments, the conjugate linker does not comprise a pyrrolidine.

In certain embodiments, the conjugate linker comprises PEG.

In certain embodiments, the conjugate linker comprises an amide. In certain embodiments, the conjugate linker comprises at least two amides. In certain embodiments, the conjugate linker does not comprise an amide. In certain embodiments, the conjugate linker comprises a polyamide.

In certain embodiments, the conjugate linker comprises an amine.

In certain embodiments, the conjugate linker comprises one or more disulfide bonds.

In certain embodiments, the conjugate linker comprises a protein binding moiety. In certain embodiments, the protein binding moiety comprises a lipid. In certain embodiments, the protein binding moiety is selected from among: cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is selected from among: a C16 to C22 long chain saturated or unsaturated fatty acid, cholesterol, cholic acid, vitamin E, adamantane or 1-pentafluoropropyl.

In certain embodiments, the conjugate linker has a structure selected from among:

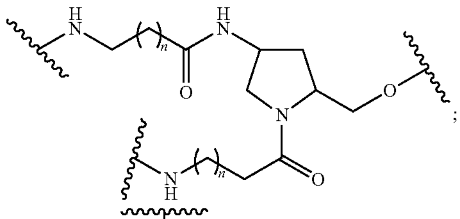

;

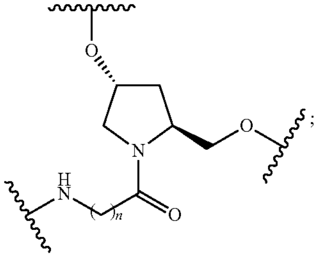

;

-continued

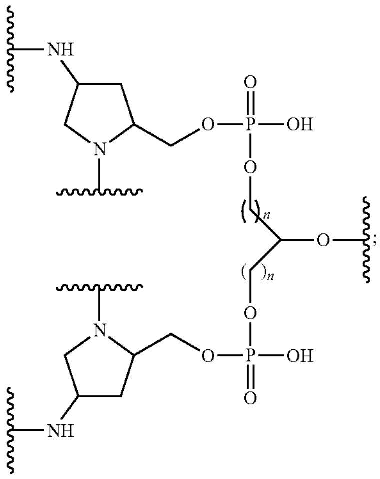

;

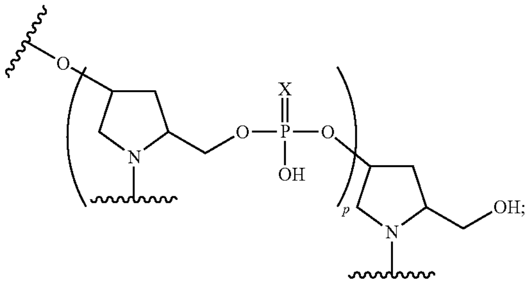

;

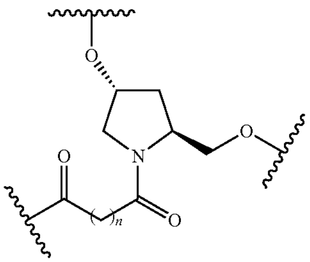

;

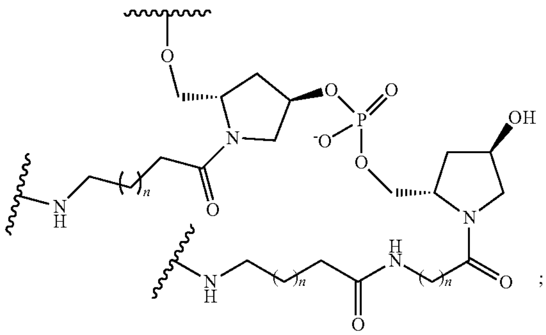

;

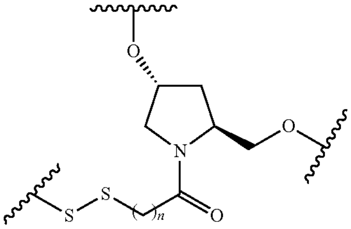

;

-continued
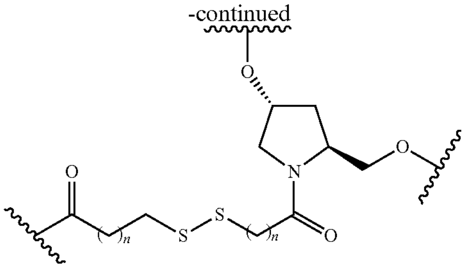
;
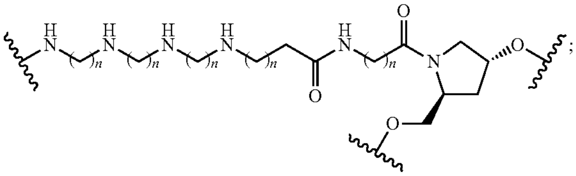
;
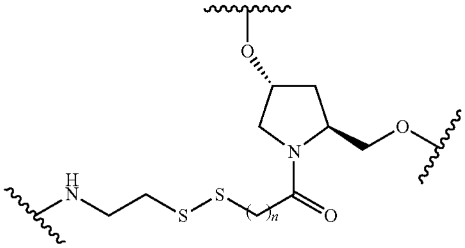
;
-continued
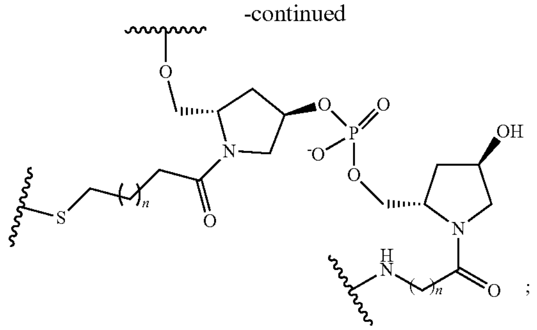
; and
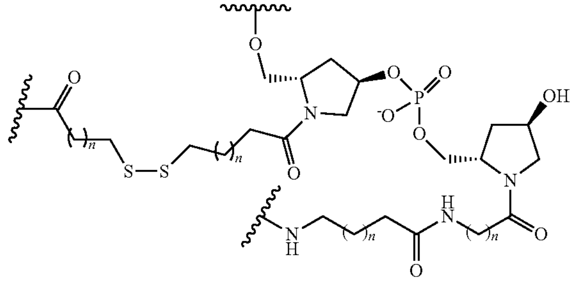
wherein each n is, independently, is from 1 to 20; and p is from 1 to 6.
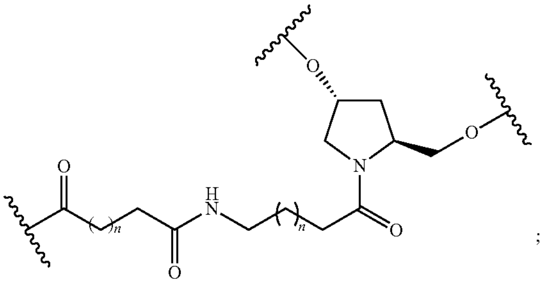
;
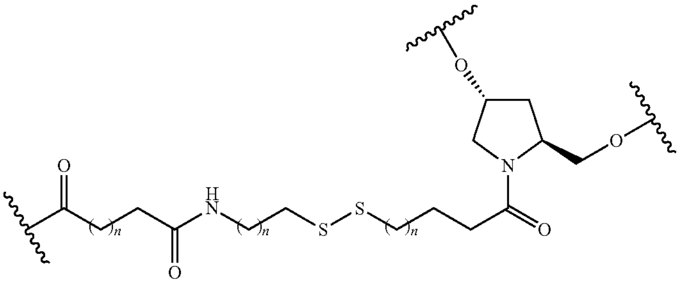
;
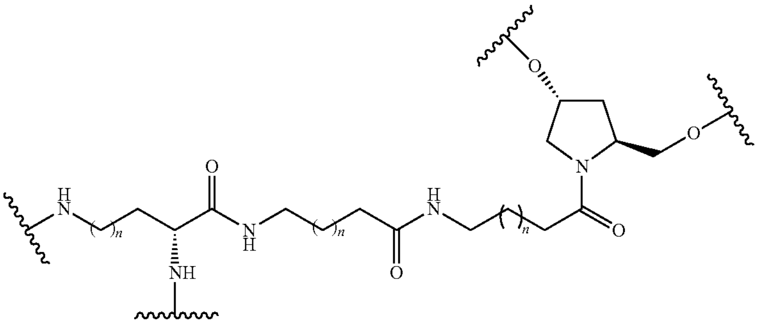
;

-continued
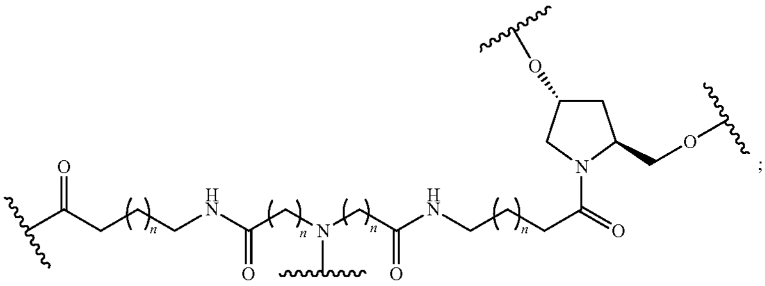
;
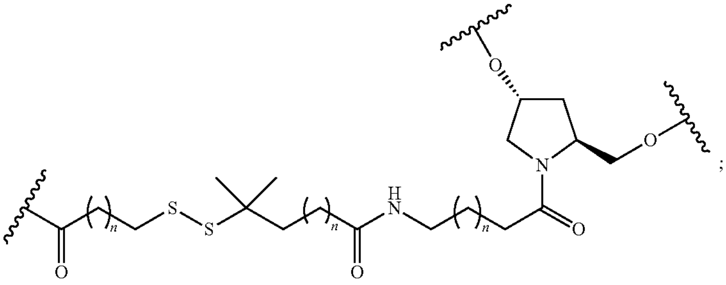
;
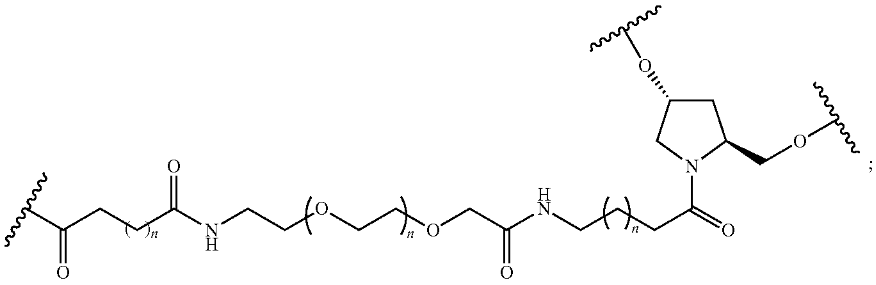
;
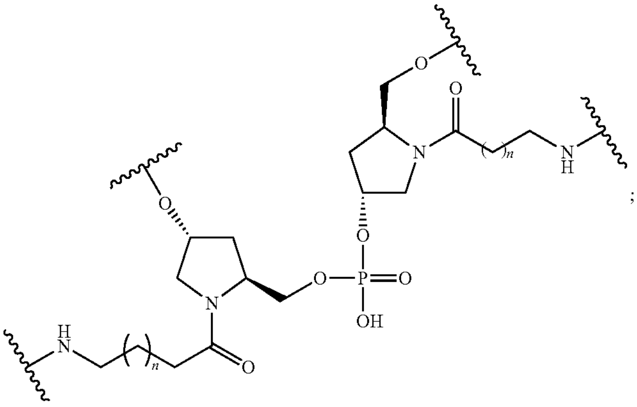
;
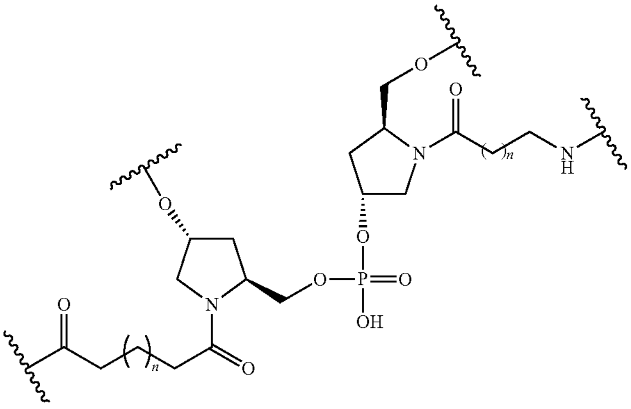
; and -continued
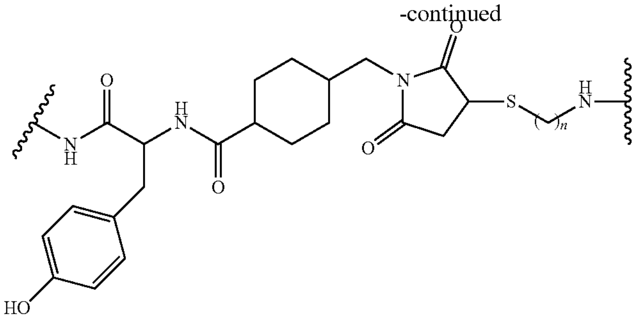
wherein each n is, independently, from 1 to 20.
In certain embodiments, the conjugate linker has a structure selected from among:
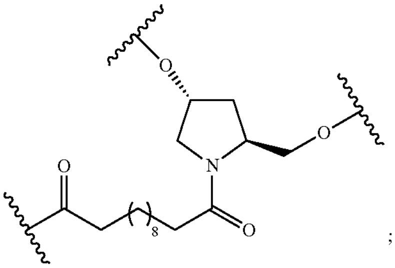
;
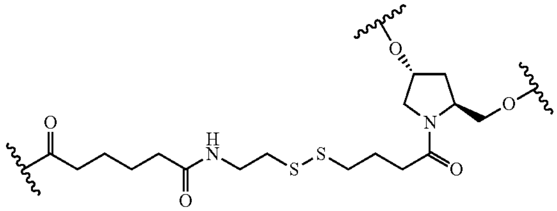
;
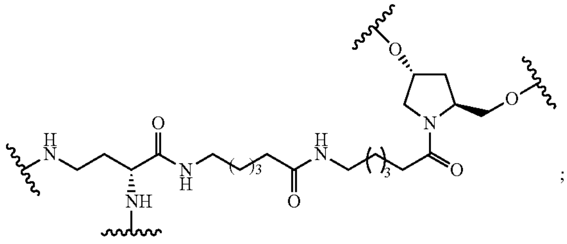
;
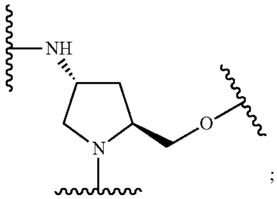
;
-continued
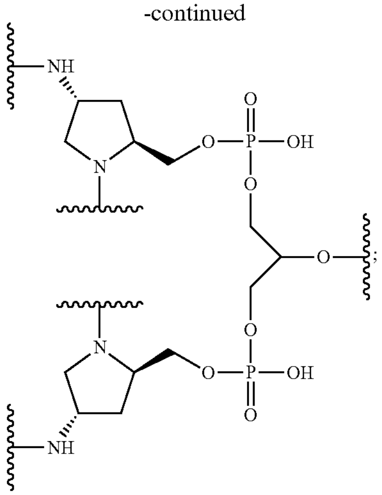
;
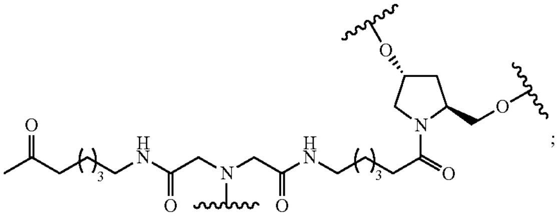
;
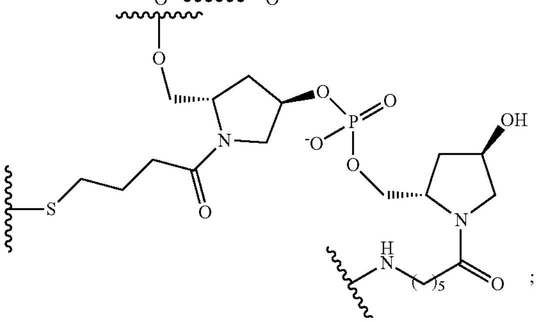
;
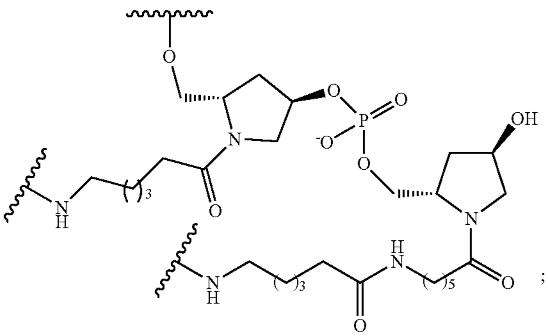
;

-continued
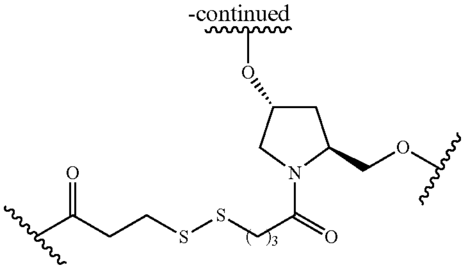
;
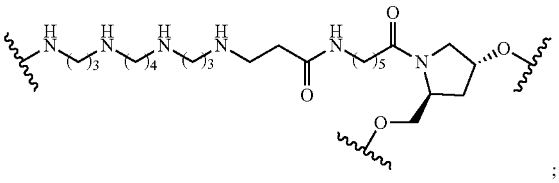
;
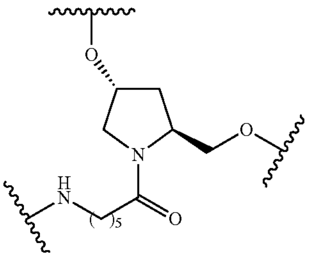
;
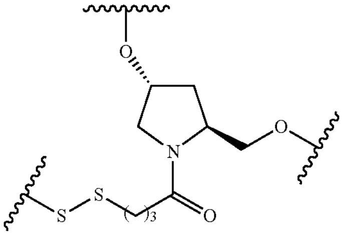
;
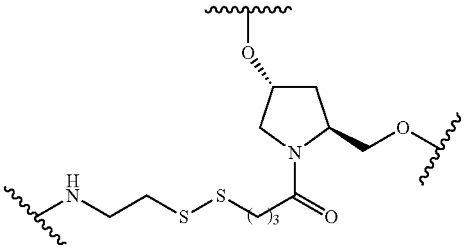
;
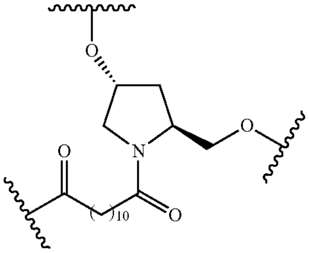
; and
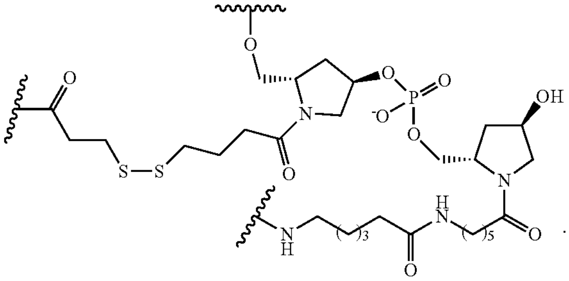
.
In certain embodiments, the conjugate linker has a structure selected from among:
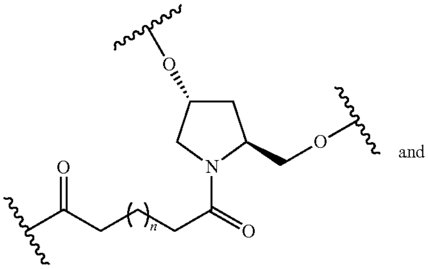
and
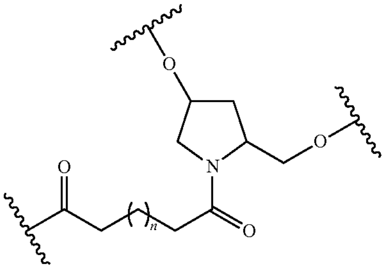
wherein n is from 1 to 20.
In certain embodiments, the conjugate linker has a structure selected from among:
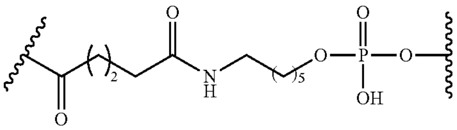
and
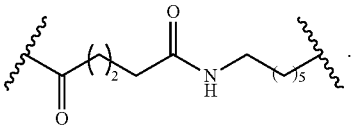
.
In certain embodiments, the conjugate linker has a structure selected from among:
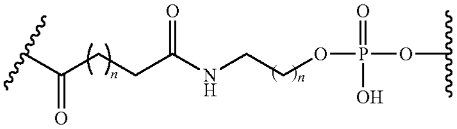
and
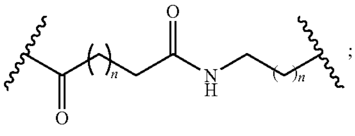
;
wherein each n is independently, 0, 1, 2, 3, 4, 5, 6, or 7.

In certain embodiments, the conjugate linker has the following structure:

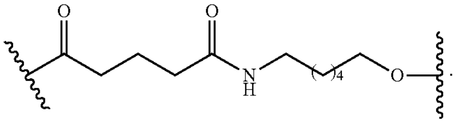

In certain embodiments, the branching group has one of the following structures:

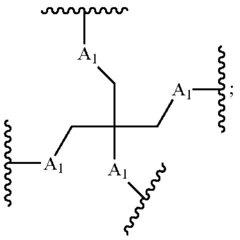

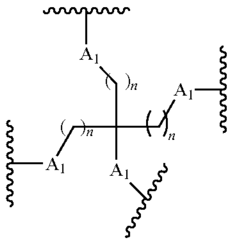

and

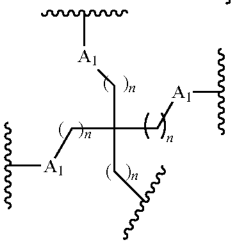

wherein each $A_1$ is independently, O, S, C═O or NH; and each n is, independently, from 1 to 20.

In certain embodiments, the branching group has one of the following structures:

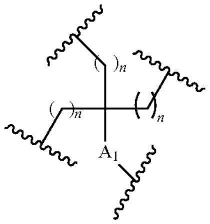

and

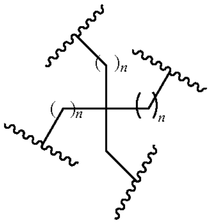

wherein each $A_1$ is independently, O, S, C═O or NH; and each n is, independently, from 1 to 20.

In certain embodiments, the branching group has the following structure:

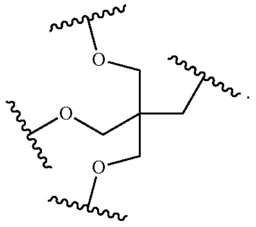 [SMILES: *CC(CO*)(CO*)CO*]

In certain embodiments, the branching group has the following structure:

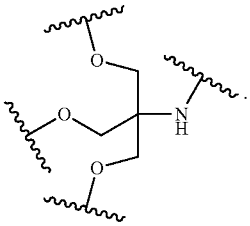 [SMILES: *NC(CO*)(CO*)CO*]

In certain embodiments, the branching group has the following structure:

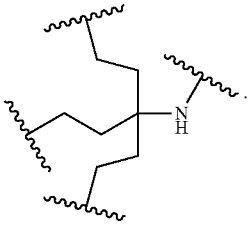 [SMILES: *CCC(CC*)(CC*)N*]

In certain embodiments, the branching group has the following structure:

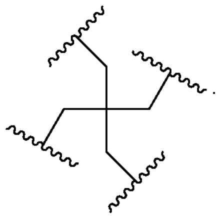 [SMILES: *CC(C*)(C*)C*]

In certain embodiments, the branching group comprises an ether.

In certain embodiments, the branching group has the following structure:

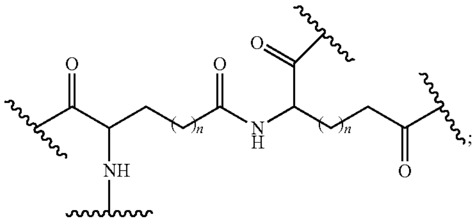

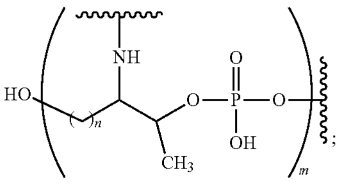

-continued
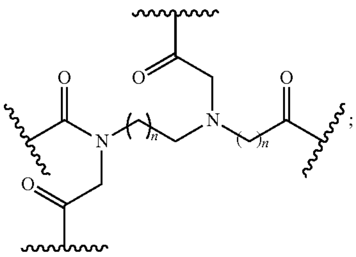;
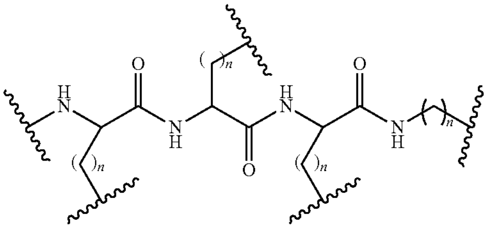;
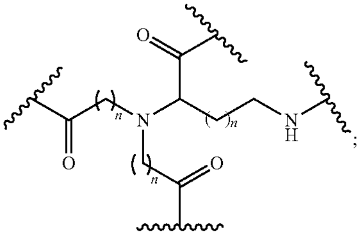;
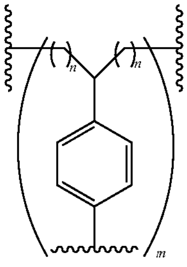;
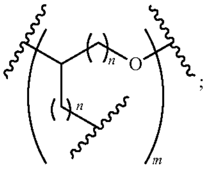;
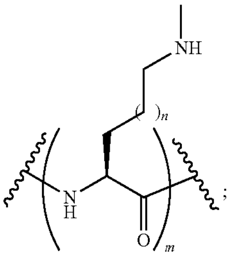;
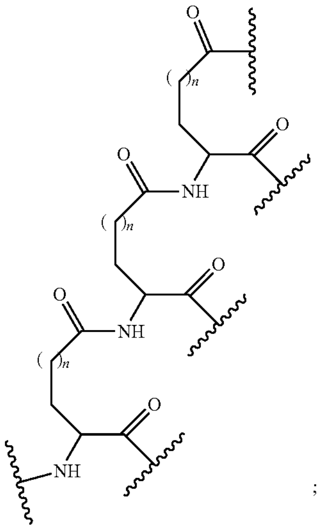;
-continued
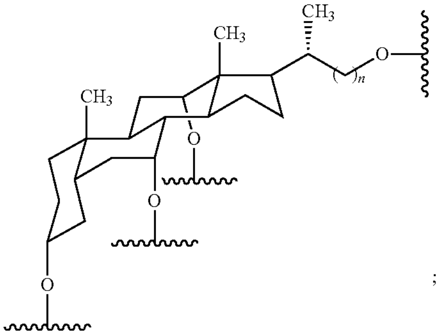; and
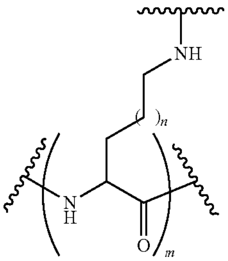
each n is, independently, from 1 to 20; and
m is from 2 to 6.
In certain embodiments, the branching group has the following structure:
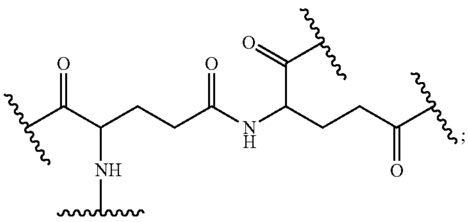;
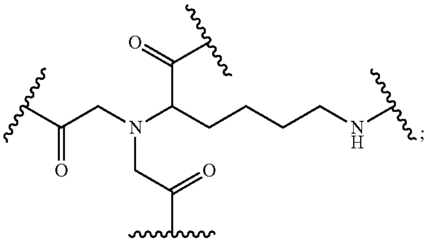;
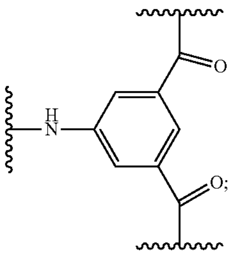

-continued
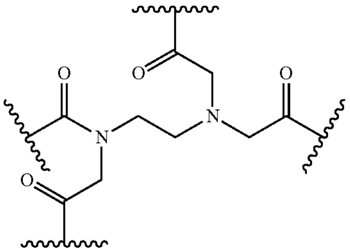
;
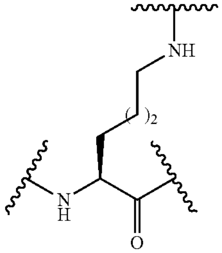
; and
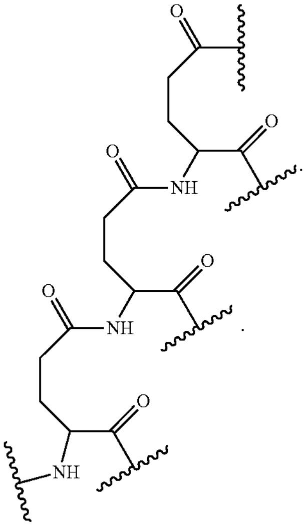
In certain embodiments, the branching group has the following structure:
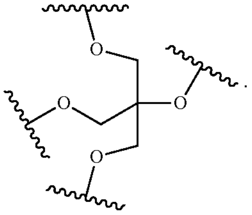 [SMILES: *OCC(CO*)(CO*)O*]
In certain embodiments, the branching group comprises:
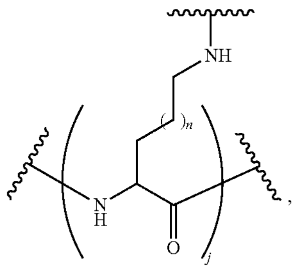
,
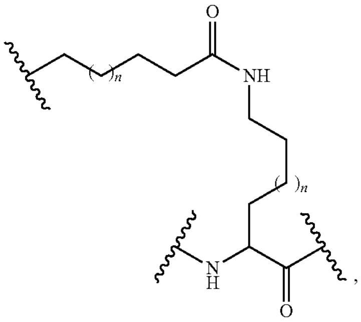
,
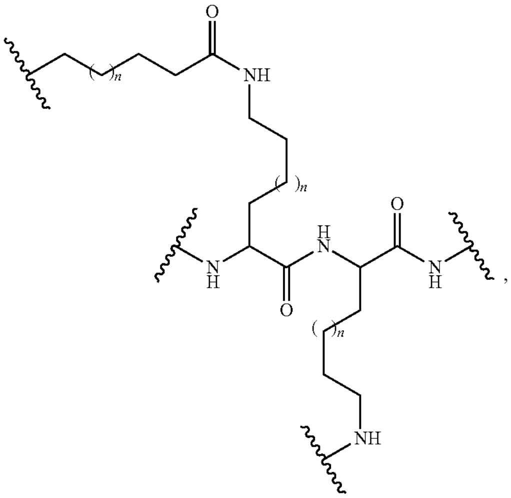
,
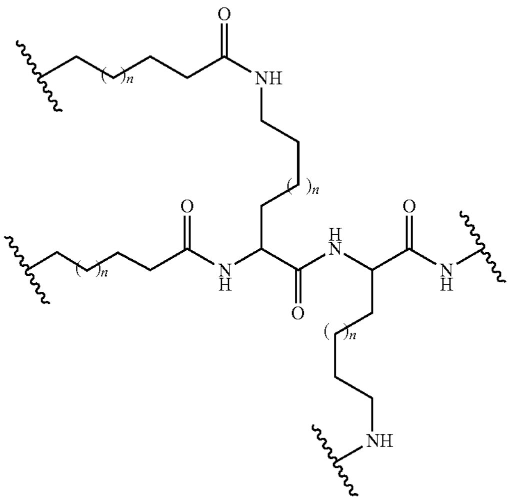
, or -continued
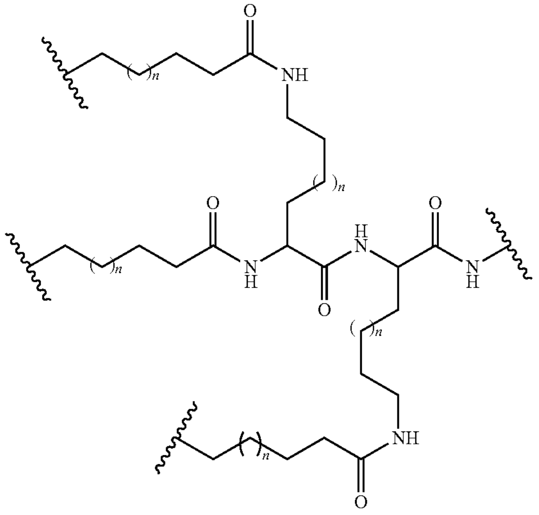
;
wherein each j is an integer from 1 to 3; and
wherein each n is an integer from 1 to 20.
In certain embodiments, the branching group comprises:
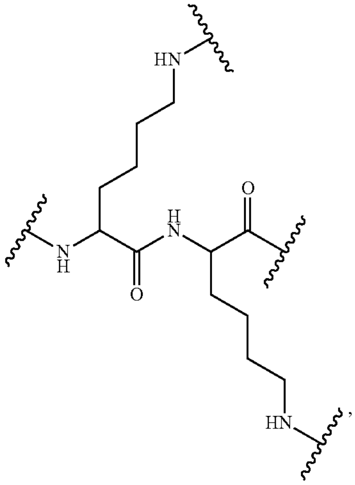
,
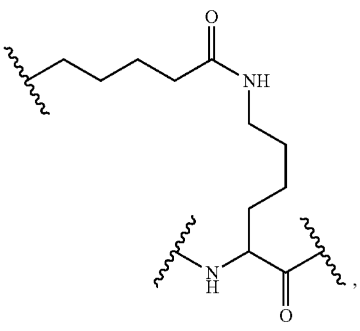
,
-continued
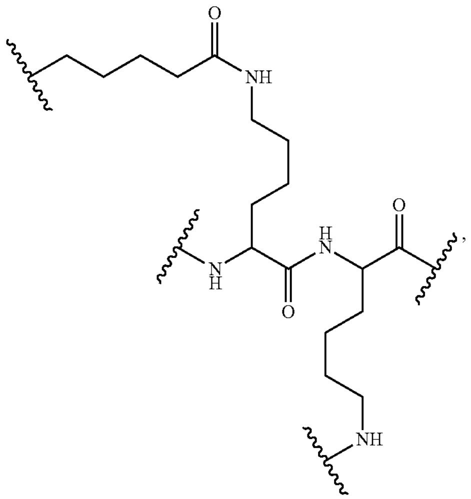
,
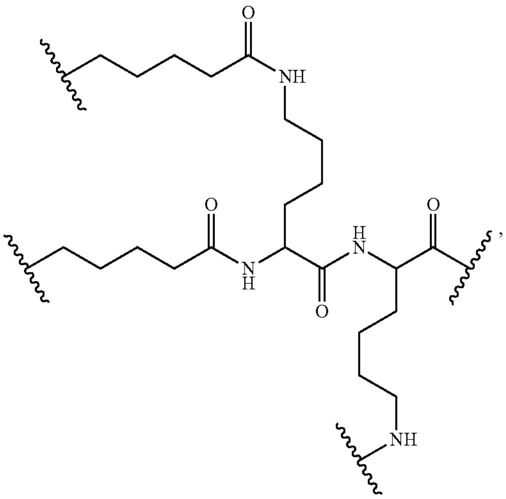
, or
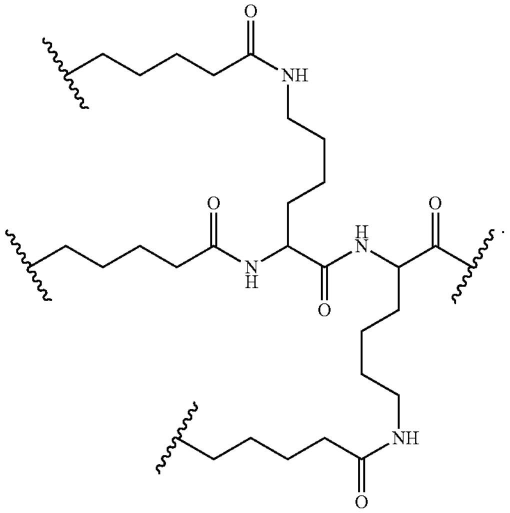
.

In certain embodiments, each tether is selected from among:

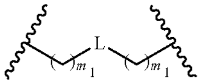

and

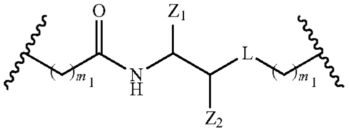

wherein L is selected from a phosphorus linking group and a neutral linking group;

$Z_1$ is C(═O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, each tether is selected from among:

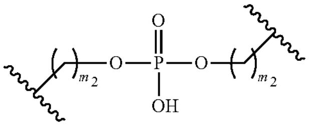

and

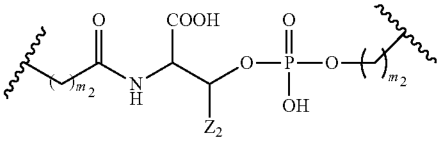

wherein $Z_2$ is H or $CH_3$; and each $m_2$ is, independently, from 0 to 20 wherein at least one $m_2$ is greater than 0 for each tether.

In certain embodiments, each tether is selected from among:

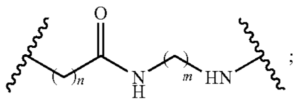

;

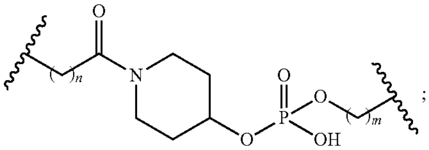

;

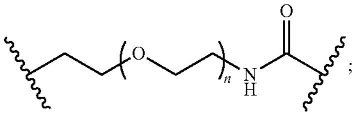

;

wherein n is from 1 to 12; and wherein m is from 1 to 12.

In certain embodiments, at least one tether comprises ethylene glycol.

In certain embodiments, at least one tether comprises an amide. In certain embodiments, at least one tether comprises a polyamide.

In certain embodiments, at least one tether comprises an amine.

In certain embodiments, at least two tethers are different from one another. In certain embodiments, all of the tethers are the same as one another.

In certain embodiments, each tether is selected from among:

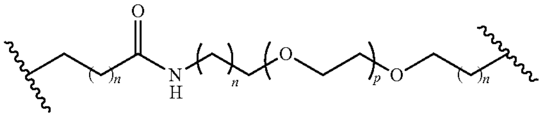

;

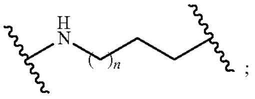

;

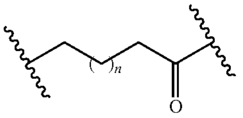

;

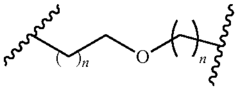

;

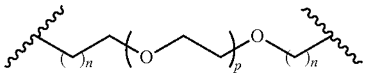

;

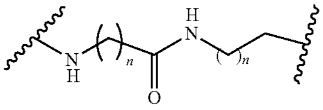

;

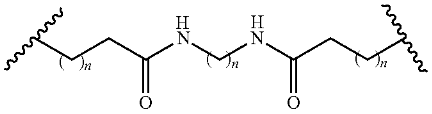

;

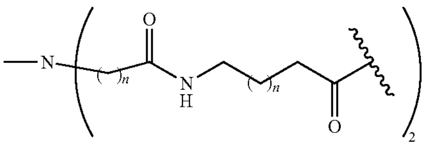

;

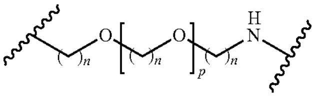

;

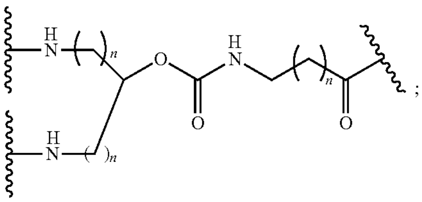

;

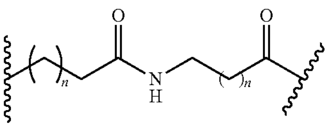

;

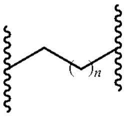

; and

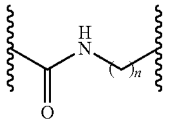

wherein each n is, independently, from 1 to 20; and each p is from 1 to about 6.

In certain embodiments, each tether is selected from among:

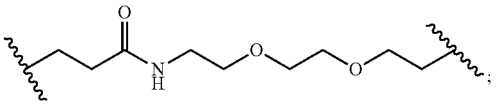

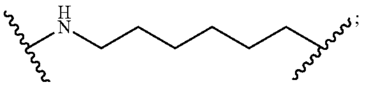

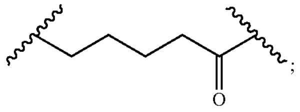

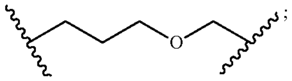

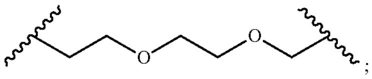

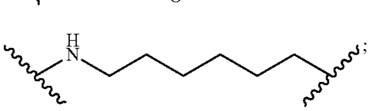

and

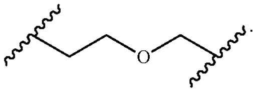

In certain embodiments, each tether has the following structure:

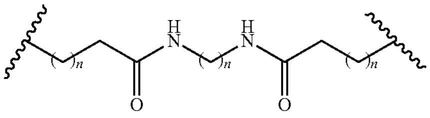

wherein each n is, independently, from 1 to 20.

In certain embodiments, each tether has the following structure:

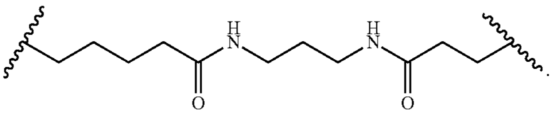 [SMILES: *CCCCC(=O)NCCCNC(=O)CC*]

In certain embodiments, the tether has a structure selected from among:

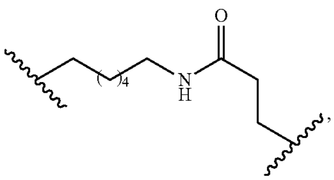

or

-continued

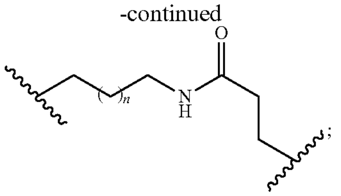

wherein each n is independently, 0, 1, 2, 3, 4, 5, 6, or 7.

In certain embodiments, the tether has a structure selected from among:

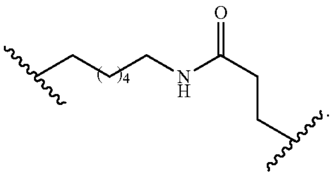

In certain embodiments, the ligand is galactose.

In certain embodiments, the ligand is mannose-6-phosphate.

In certain embodiments, each ligand is selected from among:

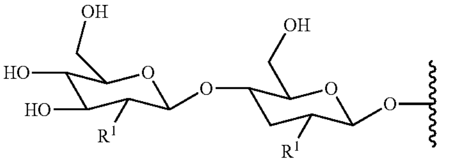

and

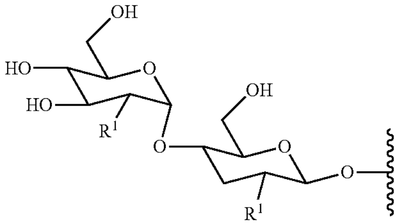

wherein each $R_1$ is selected from OH and NHCOOH.

In certain embodiments, each ligand is selected from among:

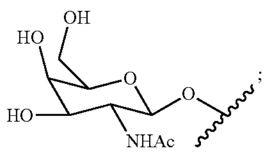

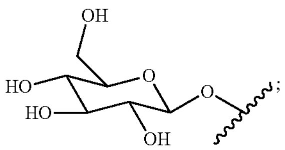

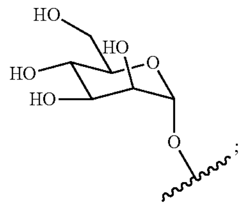

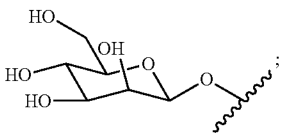

-continued

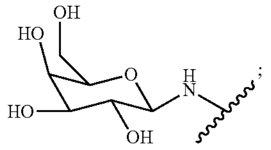

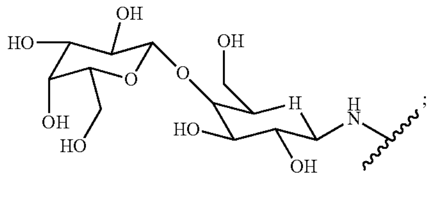

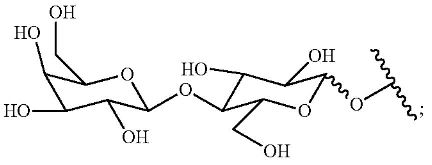

and

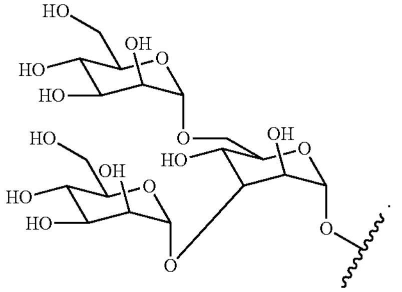

In certain embodiments, each ligand has the following structure:

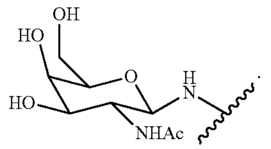 [SMILES: *NC1OC(CO)C(O)C(O)C1NC(C)=O]

In certain embodiments, each ligand has the following structure:

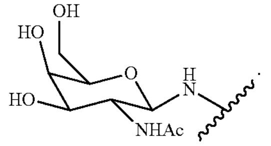 [SMILES: *NC1OC(CO)C(O)C(O)C1NC(C)=O]

In certain embodiments, the conjugate group comprises a cell-targeting moiety.

In certain embodiments, the conjugate group comprises a cell-targeting moiety having the following structure:

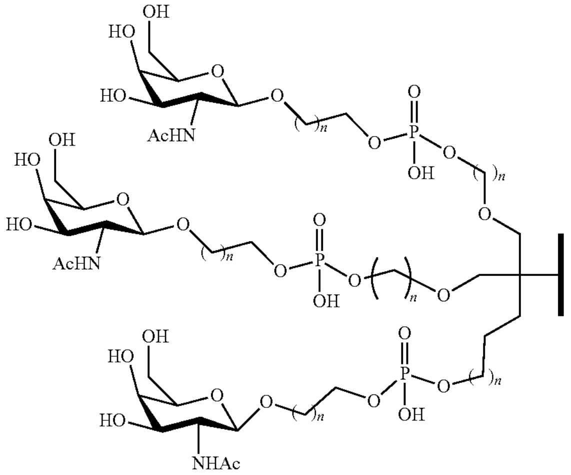

wherein each n is, independently, from 1 to 20.

In certain embodiments, the cell-targeting moiety has the following structure:

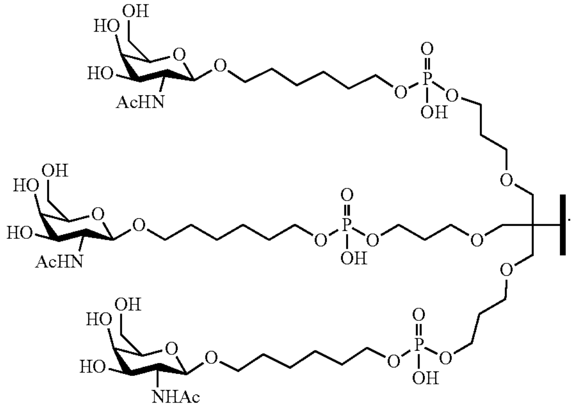

In certain embodiments, the cell-targeting moiety has the following structure:

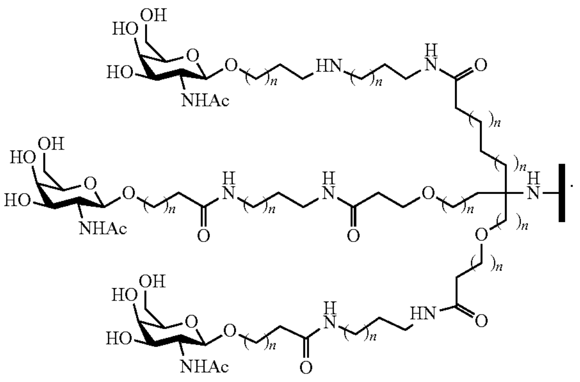

wherein each n is, independently, from 1 to 20.

In certain embodiments, the cell-targeting moiety has the following structure:

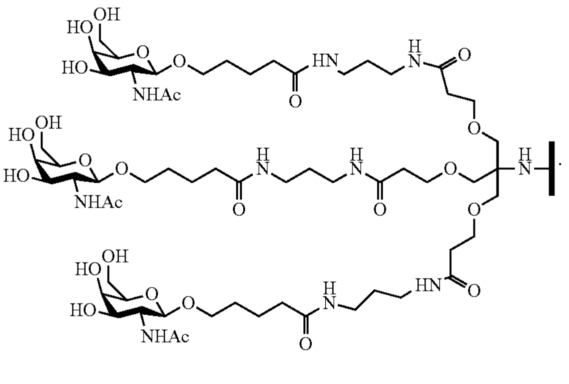

In certain embodiments, the cell-targeting moiety comprises:

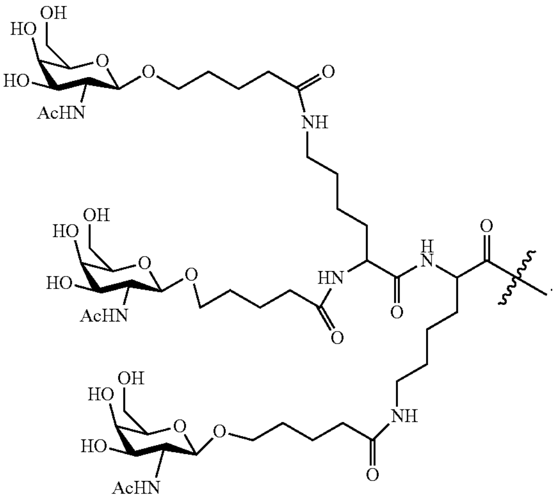

In certain embodiments, the cell-targeting moiety comprises:

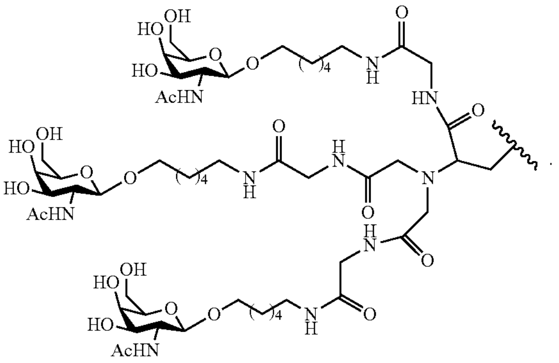

In certain embodiments, the cell-targeting moiety has the following structure:

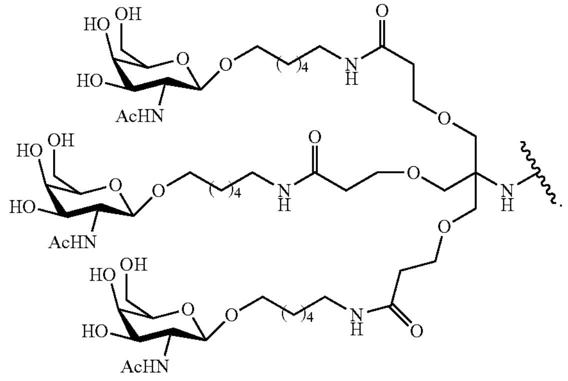

In certain embodiments, the cell-targeting moiety has the following structure:

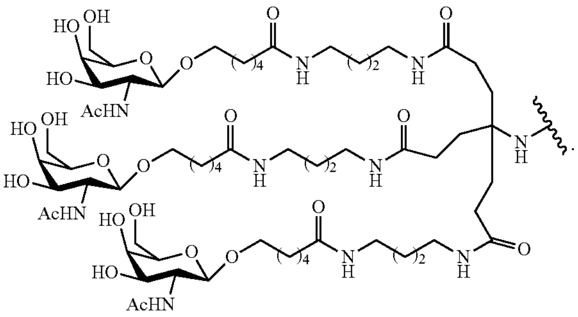

In certain embodiments, the cell-targeting moiety comprises:

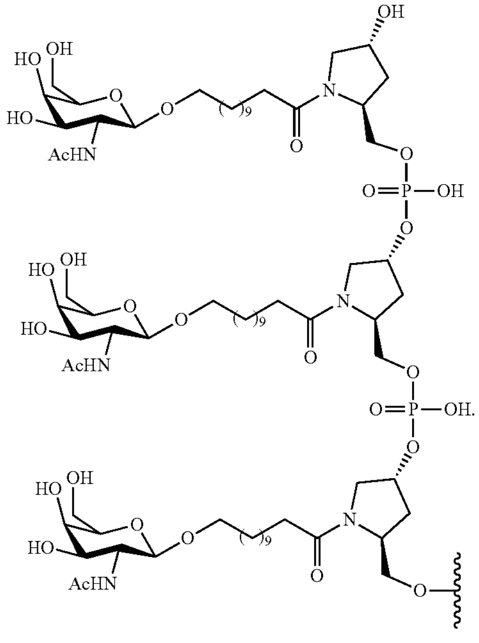

In certain embodiments, the cell-targeting moiety has the following structure:
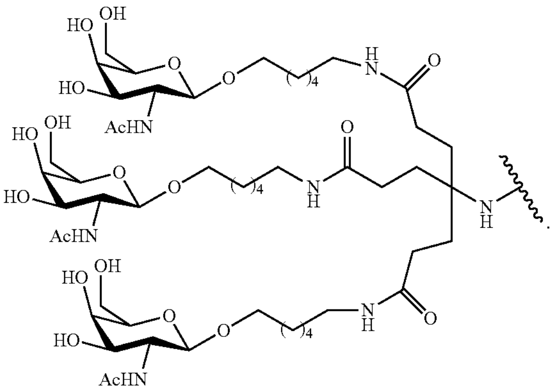
In certain embodiments, the cell-targeting moiety comprises:
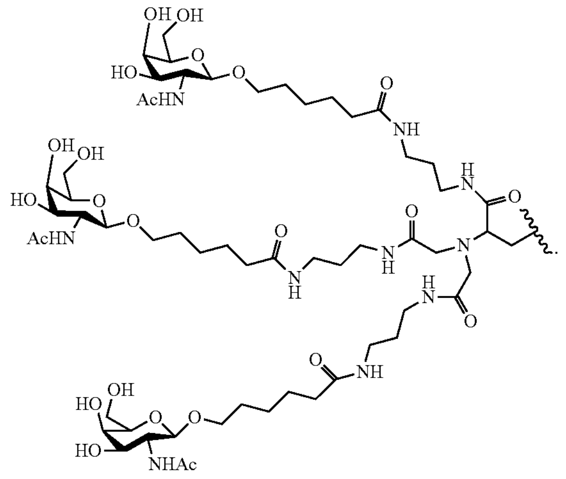
In certain embodiments, the cell-targeting moiety comprises:
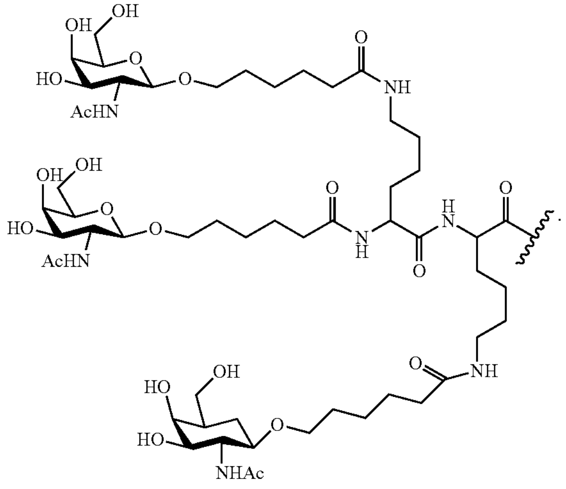
In certain embodiments, the cell-targeting moiety comprises:
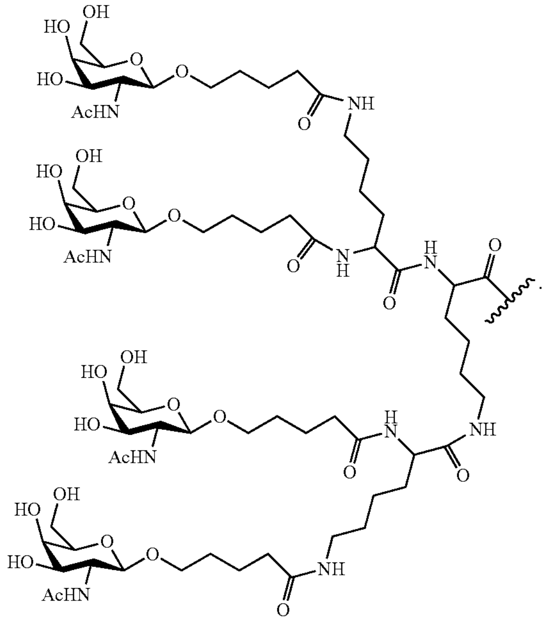
In certain embodiments, the cell-targeting moiety has the following structure:
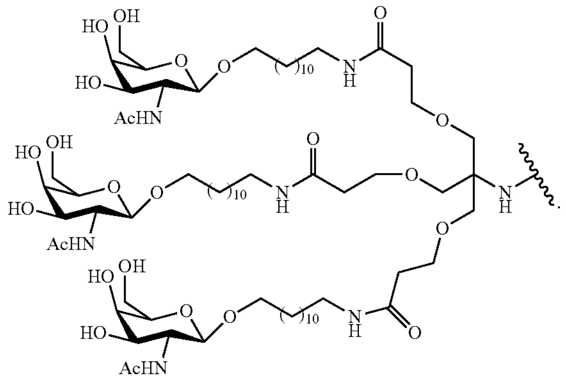

In certain embodiments, the cell-targeting moiety has the following structure:

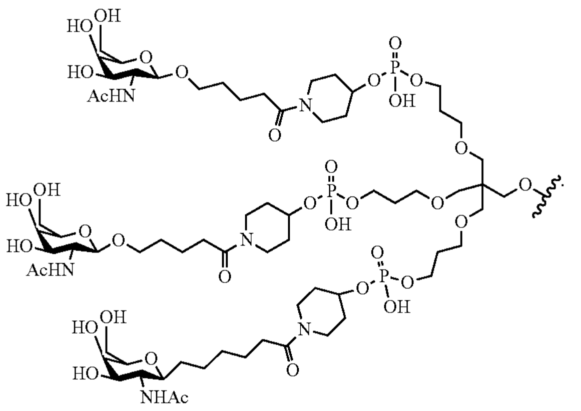

In certain embodiments, the cell-targeting moiety has the following structure:

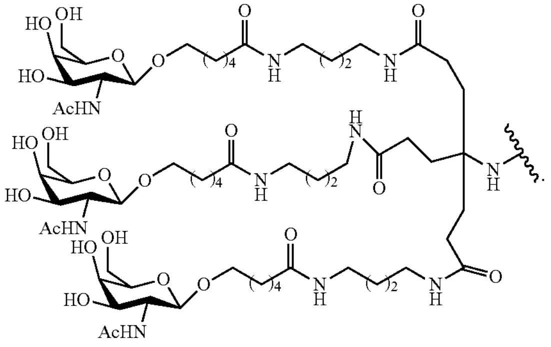

In certain embodiments, the cell-targeting moiety has the following structure:

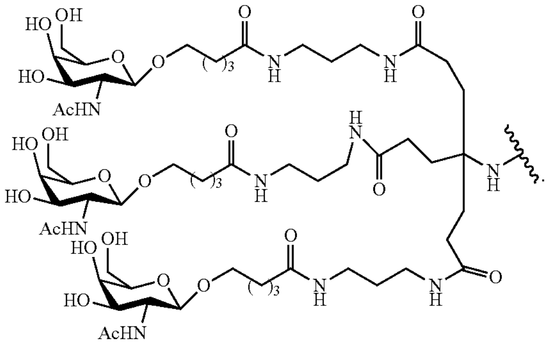

In certain embodiments, the cell-targeting moiety has the following structure:

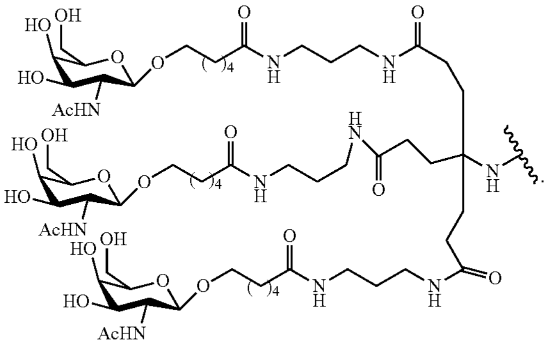

In certain embodiments, the cell-targeting moiety comprises:

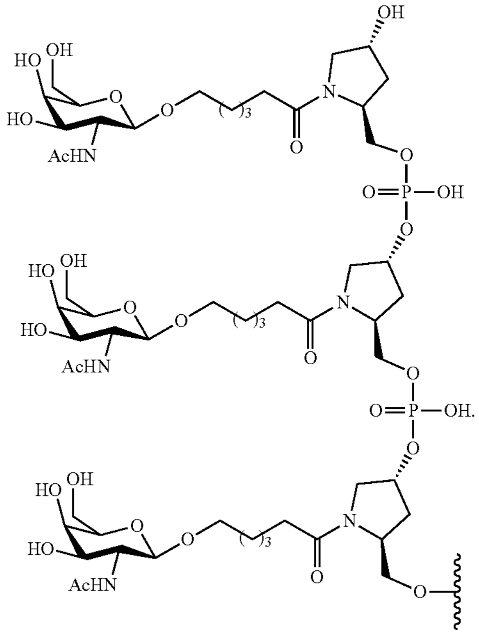

In certain embodiments, the cell-targeting moiety comprises:

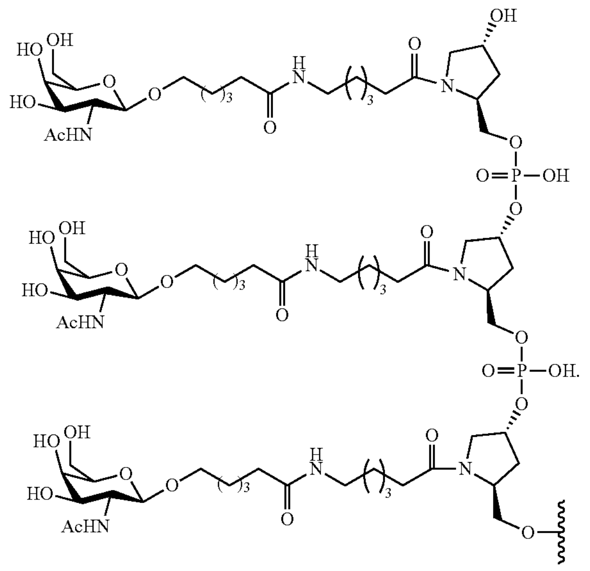

In certain embodiments, the cell-targeting moiety comprises:

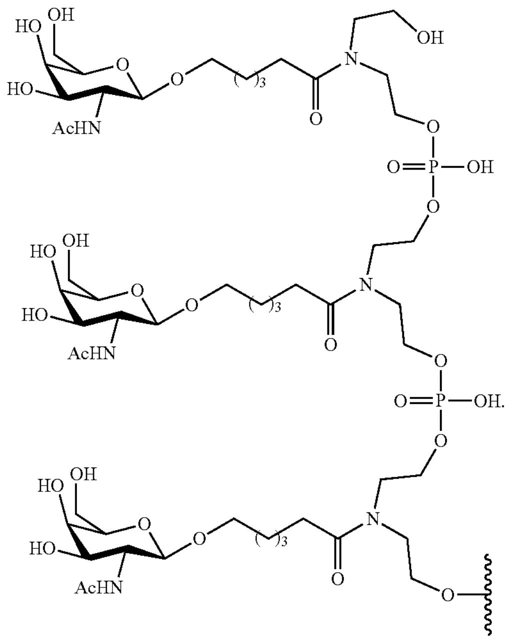

In certain embodiments, the cell-targeting moiety comprises:

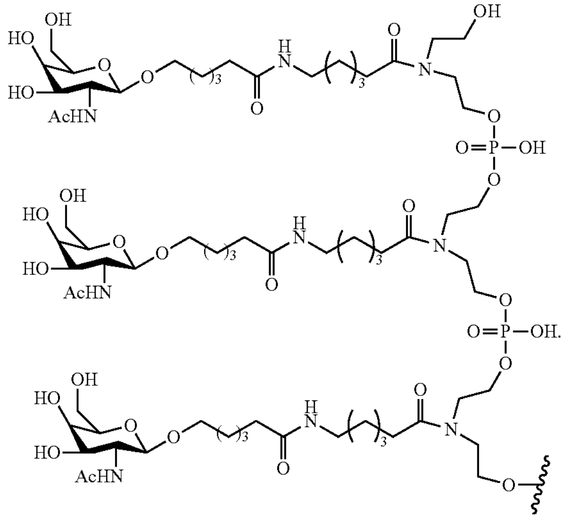

In certain embodiments, the cell-targeting moiety has the following structure:

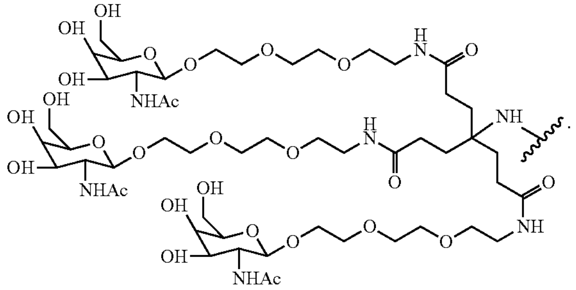 [SMILES: *NC(CCC(=O)NCCOCCOCCOC1OC(CO)C(O)C(O)C1NC(C)=O)(CCC(=O)NCCOCCOCCOC1OC(CO)C(O)C(O)C1NC(C)=O)CCC(=O)NCCOCCOCCOC1OC(CO)C(O)C(O)C1NC(C)=O]

In certain embodiments, the cell-targeting moiety comprises:

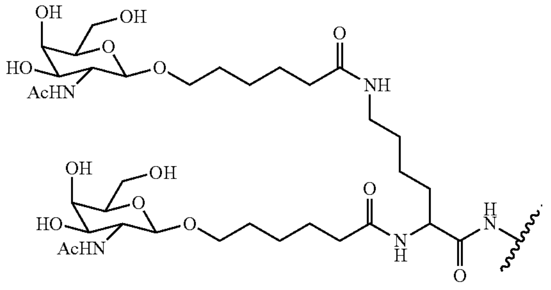 [SMILES: *NC(=O)C(CCCCNC(=O)CCCCCOC1OC(CO)C(O)C(O)C1NC(C)=O)NC(=O)CCCCCOC1OC(CO)C(O)C(O)C1NC(C)=O]

In certain embodiments, the cell-targeting moiety has the following structure:

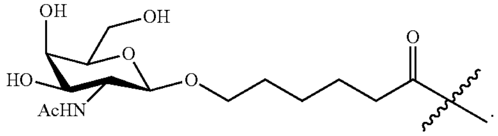

In certain embodiments, the cell-targeting moiety comprises:

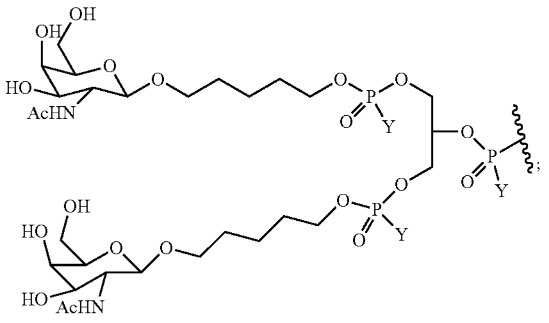

wherein each Y is selected from O, S, a substituted or unsubstituted $C_1$-$C_{10}$ alkyl, amino, substituted amino, azido, alkenyl or alkynyl.

In certain embodiments, the conjugate group comprises:

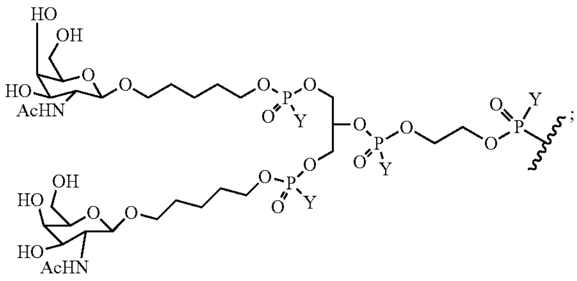

wherein each Y is selected from O, S, a substituted or unsubstituted $C_1$-$C_{10}$ alkyl, amino, substituted amino, azido, alkenyl or alkynyl.

In certain embodiments, the cell-targeting moiety has the following structure:

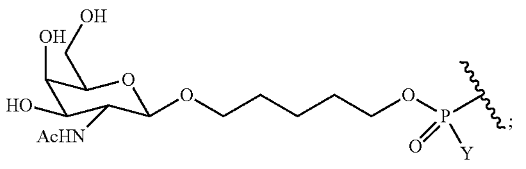

wherein each Y is selected from O, S, a substituted or unsubstituted $C_1$-$C_{10}$ alkyl, amino, substituted amino, azido, alkenyl or alkynyl.

In certain embodiments, the conjugate group comprises:

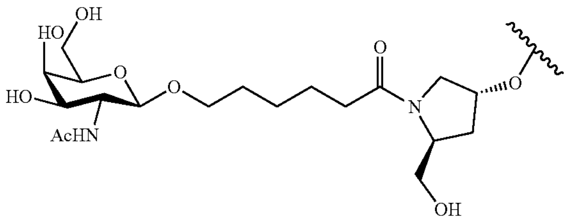

In certain embodiments, the conjugate group comprises:

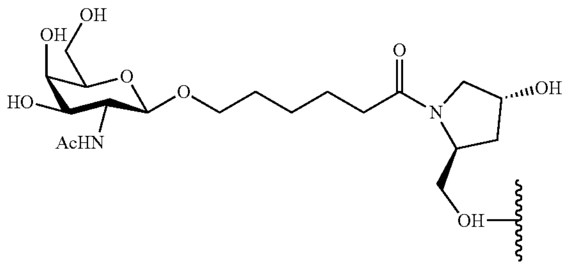

In certain embodiments, the conjugate group comprises:

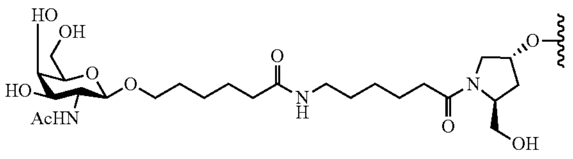

In certain embodiments, the conjugate group comprises:

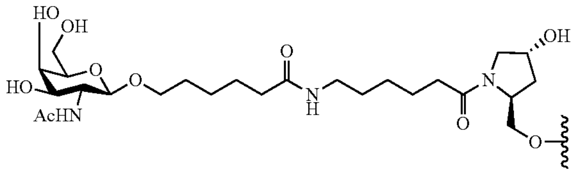

In certain embodiments, the conjugate group comprises a cleavable moiety selected from among: a phosphodiester, an amide, or an ester.

In certain embodiments, the conjugate group comprises a phosphodiester cleavable moiety.

In certain embodiments, the conjugate group does not comprise a cleavable moiety, and wherein the conjugate group comprises a phosphorothioate linkage between the conjugate group and the oligonucleotide.

In certain embodiments, the conjugate group comprises an amide cleavable moiety.

In certain embodiments, the conjugate group comprises an ester cleavable moiety.

In certain embodiments, the compound has the following structure:

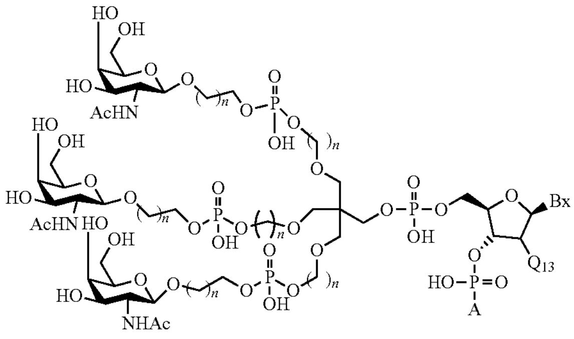

wherein each n is, independently, from 1 to 20;

$Q_{13}$ is H or $O(CH_2)_2$—$OCH_3$;

A is the modified oligonucleotide; and

Bx is a heterocyclic base moiety.

In certain embodiments, the compound has the following structure:

wherein each n is, independently, from 1 to 20;

$Q_{13}$ is H or $O(CH_2)_2$—$OCH_3$;

A is the modified oligonucleotide;

Z is H or a linked solid support; and

Bx is a heterocyclic base moiety.

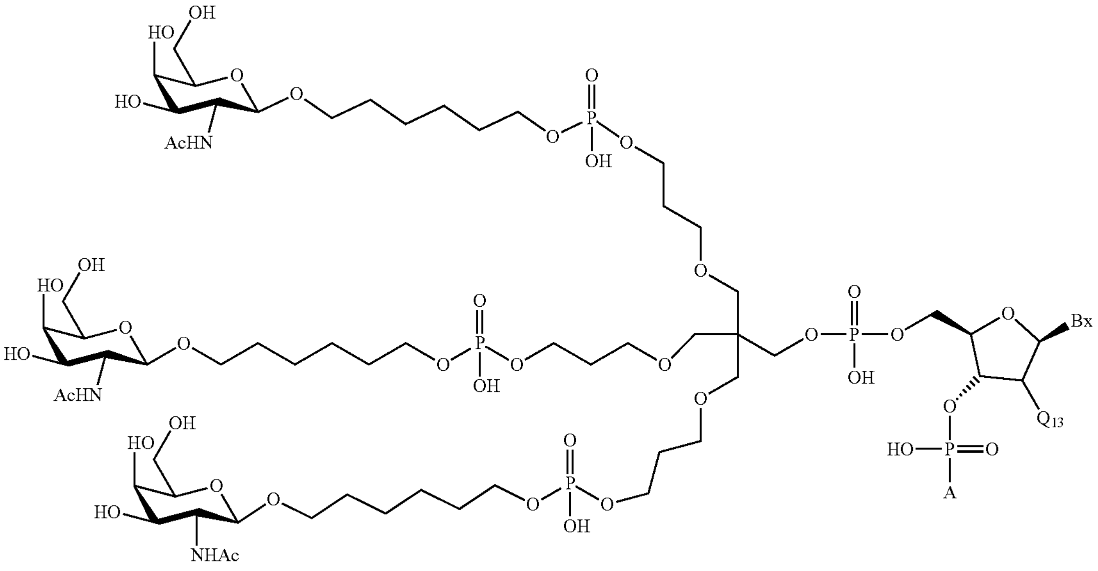

wherein each n is, independently, from 1 to 20;

$Q_{13}$ is H or $O(CH_2)_2$—$OCH_3$;

A is the modified oligonucleotide; and

Bx is a heterocyclic base moiety.

In certain embodiments, the compound has the following structure:

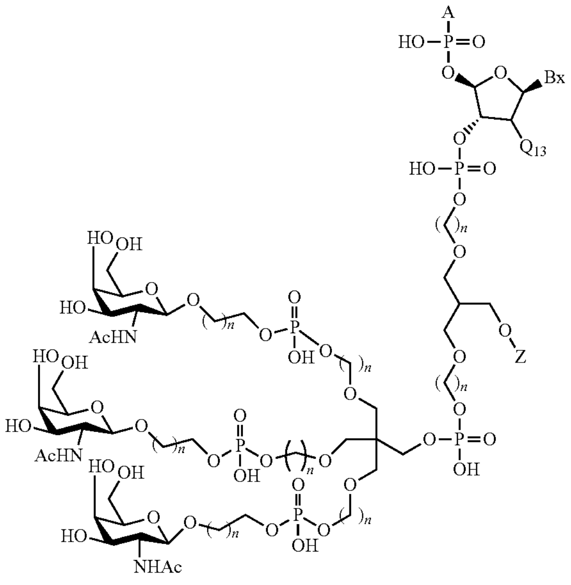

In certain embodiments, the compound has the following structure:

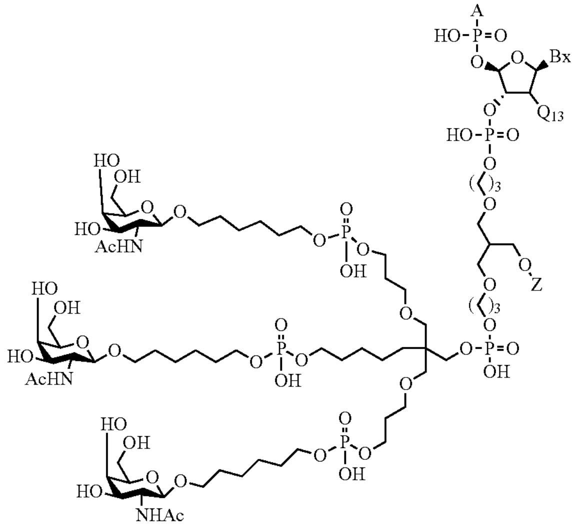

wherein each n is, independently, from 1 to 20;

$Q_{13}$ is H or $O(CH_2)_2$—$OCH_3$;

A is the modified oligonucleotide;

Z is H or a linked solid support; and

Bx is a heterocyclic base moiety.

In certain embodiments, the compound has the following structure:
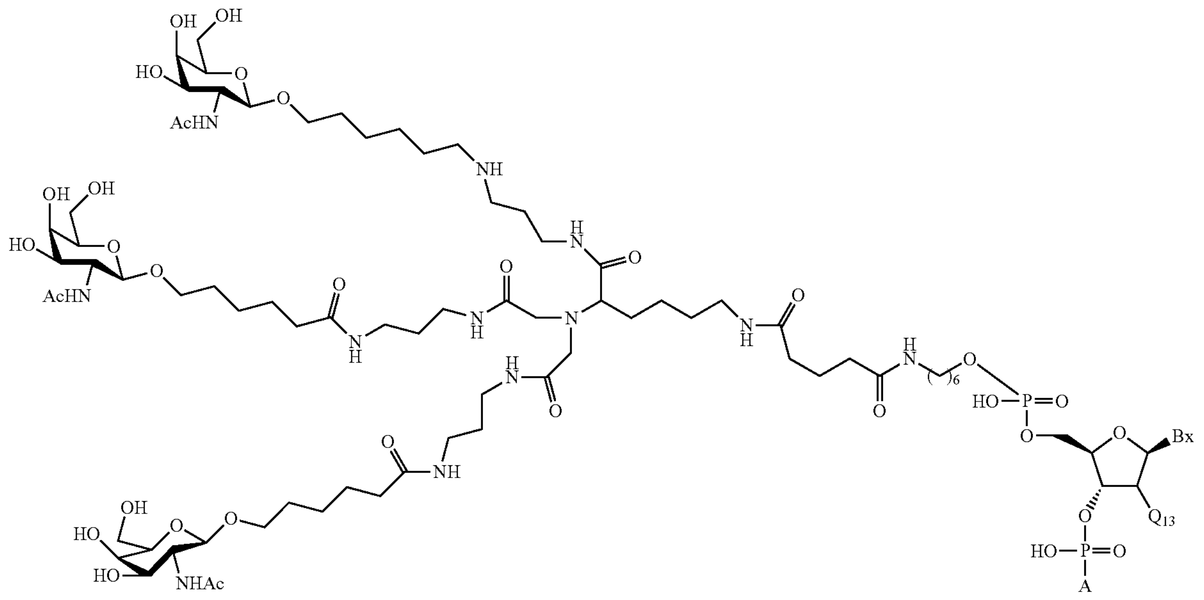
wherein $Q_{13}$ is H or $O(CH_2)_2$—$OCH_3$;
A is the modified oligonucleotide; and
Bx is a heterocyclic base moiety.
In certain embodiments, the compound has the following structure:
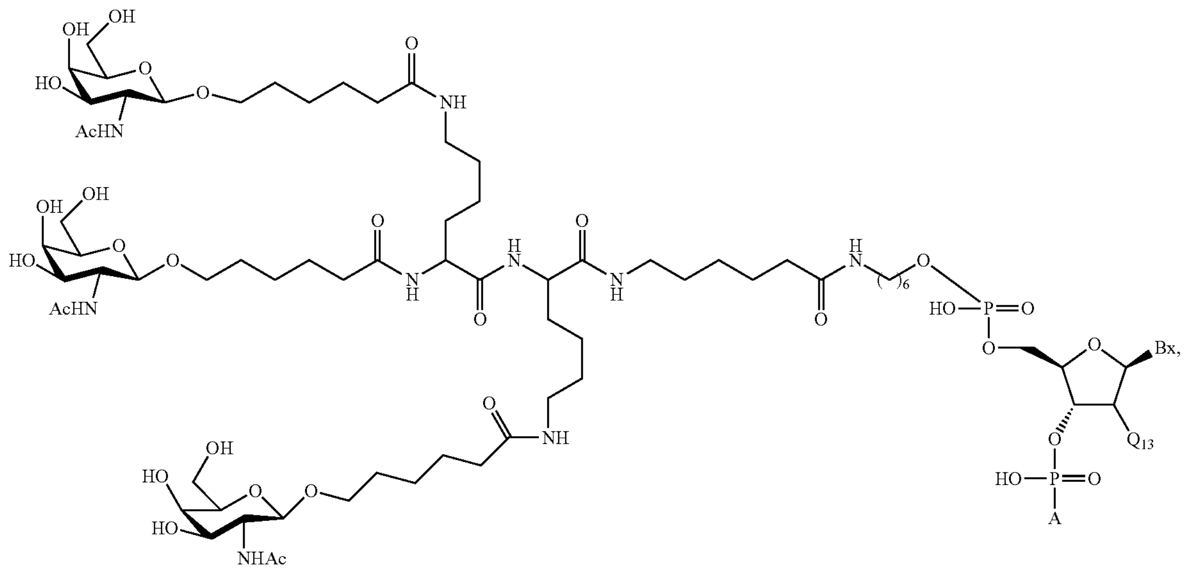

wherein $Q_{13}$ is H or $O(CH_2)_2—OCH_3$;
A is the modified oligonucleotide; and
Bx is a heterocyclic base moiety.
In certain embodiments, the compound has the following structure:
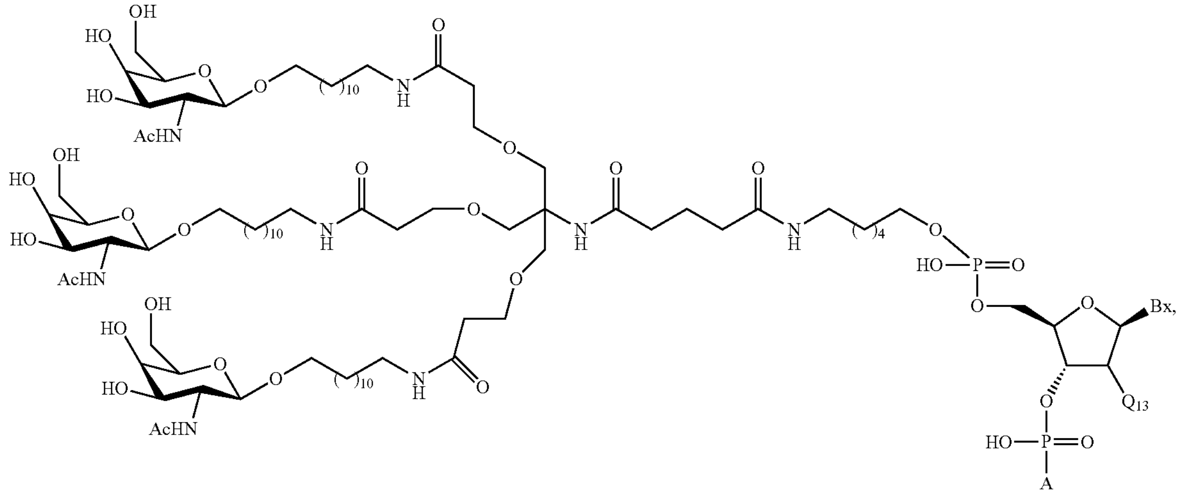
wherein $Q_{13}$ is H or $O(CH_2)_2—OCH_3$;
A is the modified oligonucleotide; and
Bx is a heterocyclic base moiety.
In certain embodiments, the compound has the following structure:
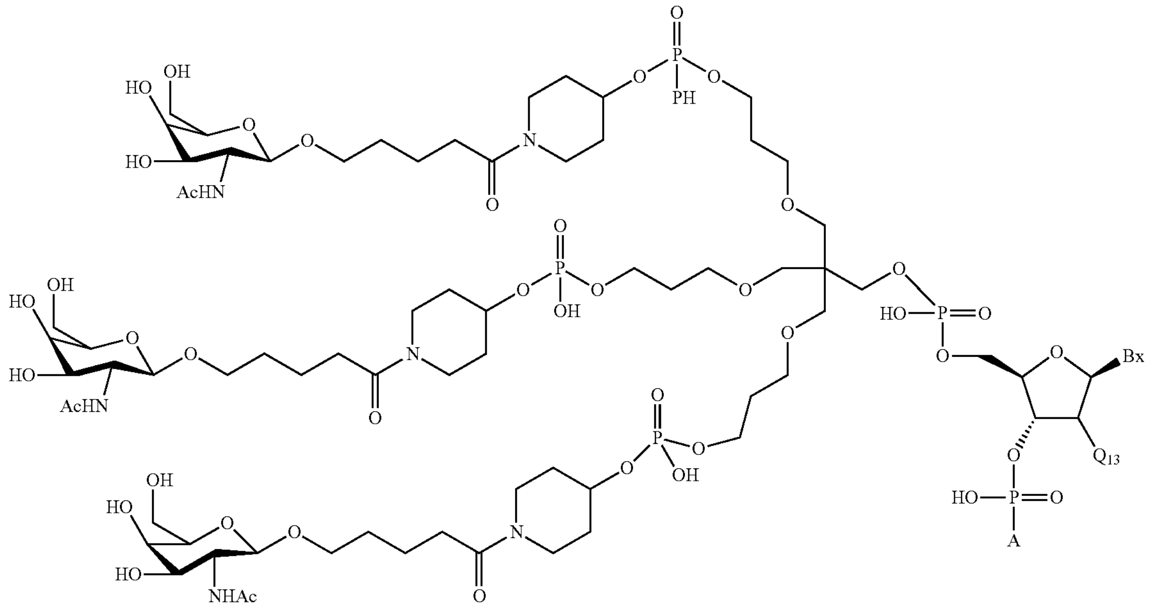

wherein $Q_{13}$ is H or $O(CH_2)_2$—$OCH_3$;
A is the modified oligonucleotide; and
Bx is a heterocyclic base moiety.
In certain embodiments, the compound has the following structure:
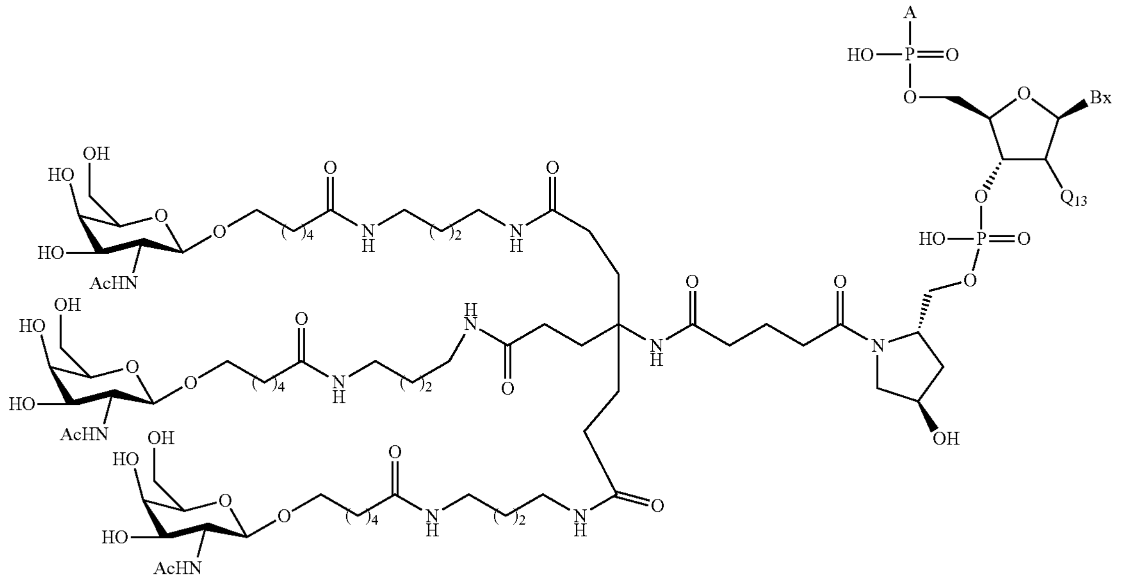
wherein $Q_{13}$ is H or $O(CH_2)_2$—$OCH_3$;
A is the modified oligonucleotide; and
Bx is a heterocyclic base moiety.
In certain embodiments, the compound has the following structure:
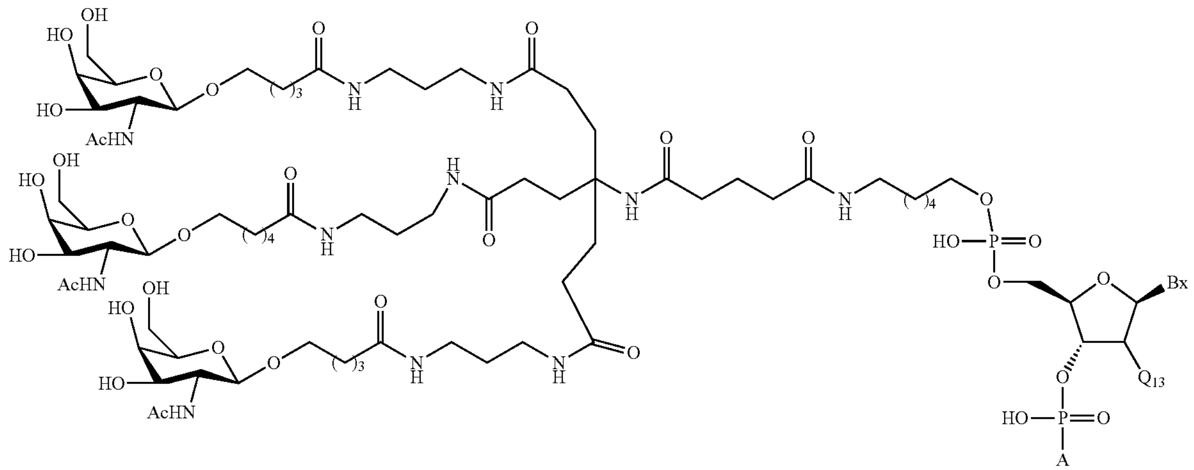

wherein $Q_{13}$ is H or $O(CH_2)_2$—$OCH_3$;
A is the modified oligonucleotide; and
Bx is a heterocyclic base moiety.
In certain embodiments, the compound has the following structure:
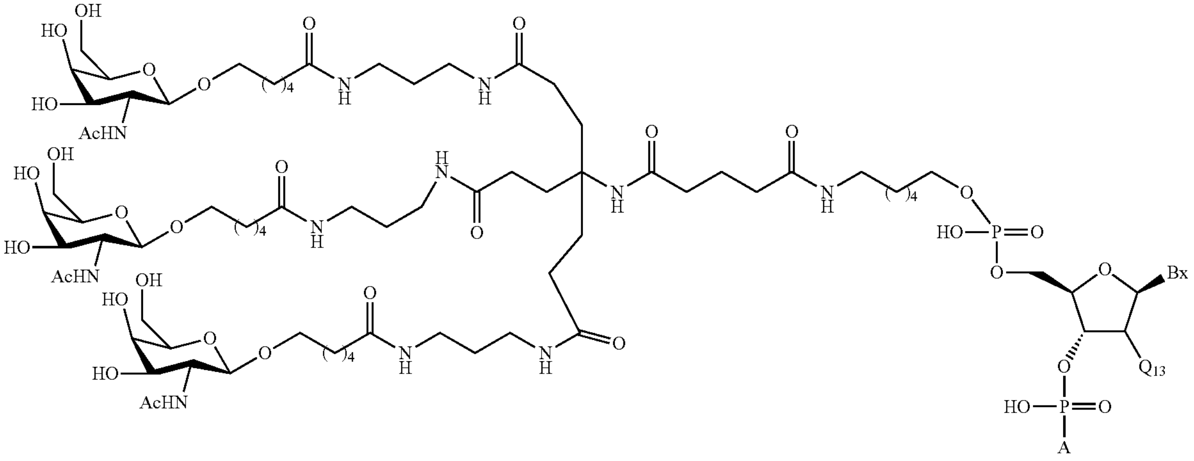
wherein $Q_{13}$ is H or $O(CH_2)_2$—$OCH_3$;
A is the modified oligonucleotide; and
Bx is a heterocyclic base moiety.
In certain embodiments, the compound has the following structure:
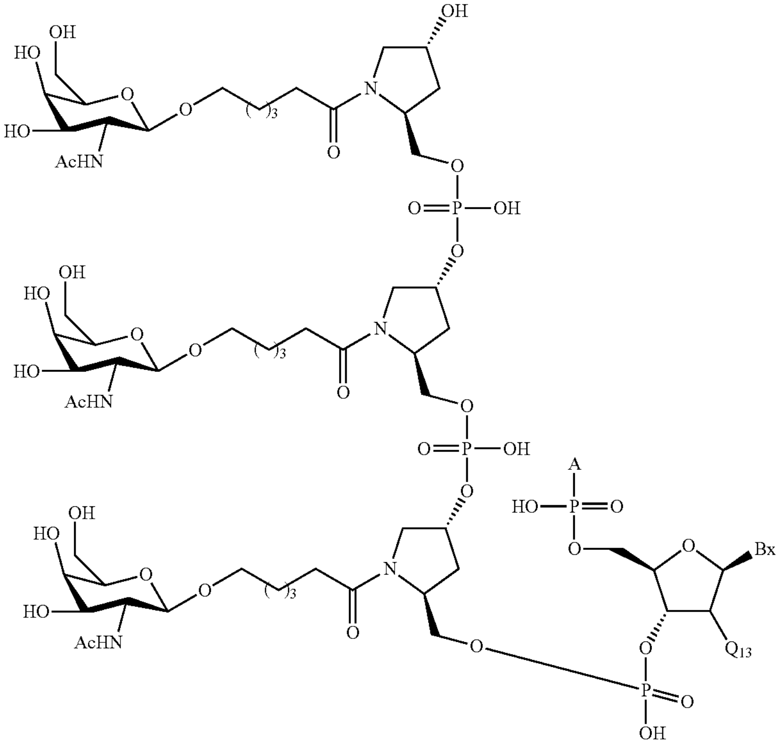

wherein $Q_{13}$ is H or $O(CH_2)_2$—$OCH_3$;

A is the modified oligonucleotide; and

Bx is a heterocyclic base moiety.

In certain embodiments, the compound has the following structure:

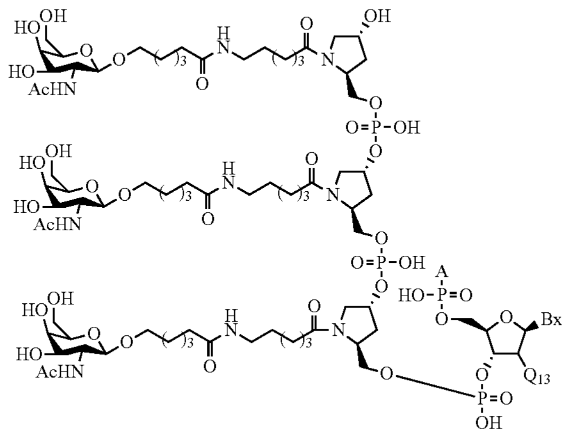

wherein $Q_{13}$ is H or $O(CH_2)_2$—$OCH_3$;

A is the modified oligonucleotide; and

Bx is a heterocyclic base moiety.

In certain embodiments, the compound has the following structure:

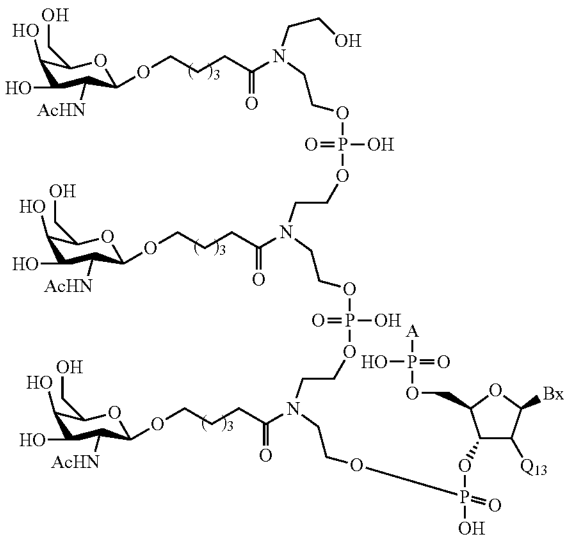

wherein $Q_{13}$ is H or $O(CH_2)_2$—$OCH_3$;

A is the modified oligonucleotide; and

Bx is a heterocyclic base moiety.

In certain embodiments, the compound has the following structure:

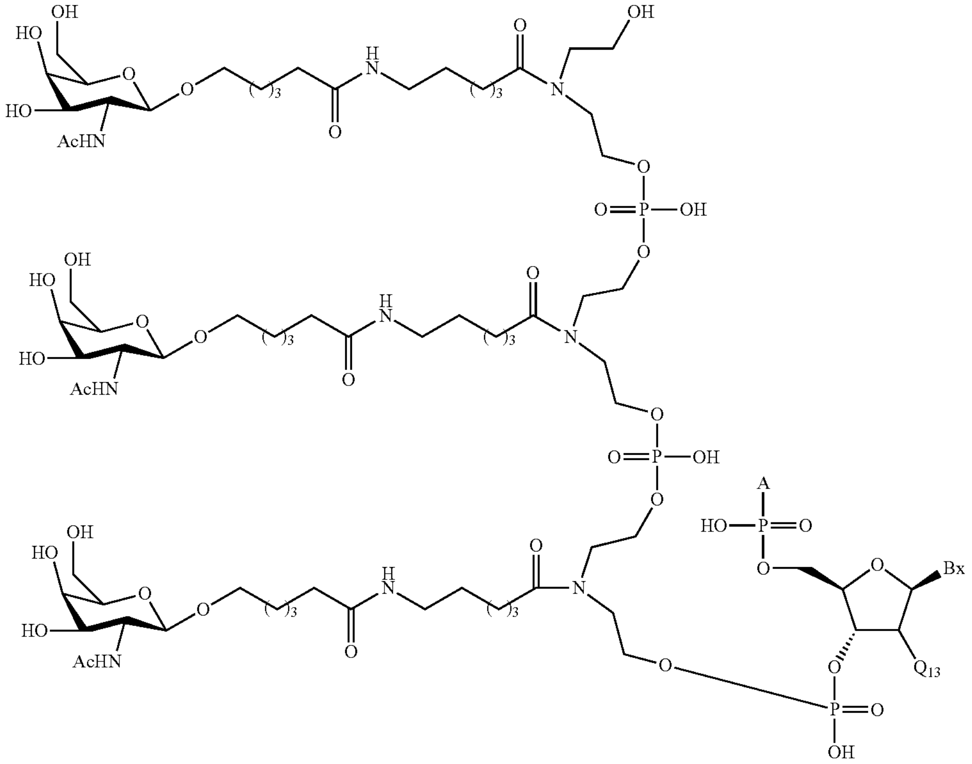

wherein $Q_{13}$ is H or $O(CH_2)_2—OCH_3$;
A is the modified oligonucleotide; and
Bx is a heterocyclic base moiety.
In certain embodiments, the conjugate group comprises:
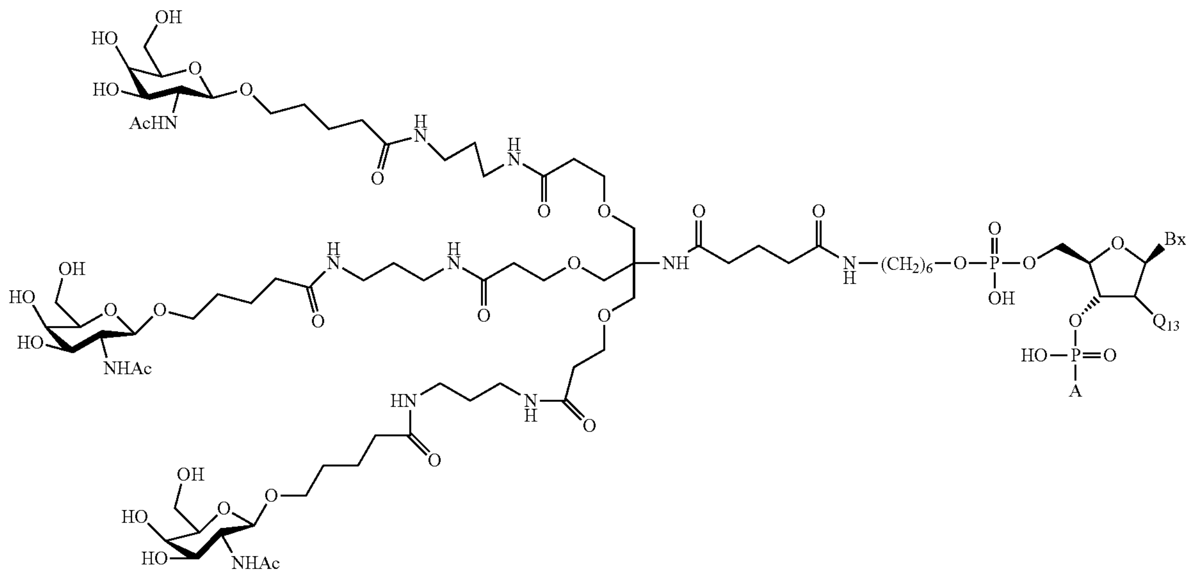
wherein $Q_{13}$ is H or $O(CH_2)_2—OCH_3$;
A is the modified oligonucleotide; and
Bx is a heterocyclic base moiety.
In certain embodiments, the conjugate group comprises:
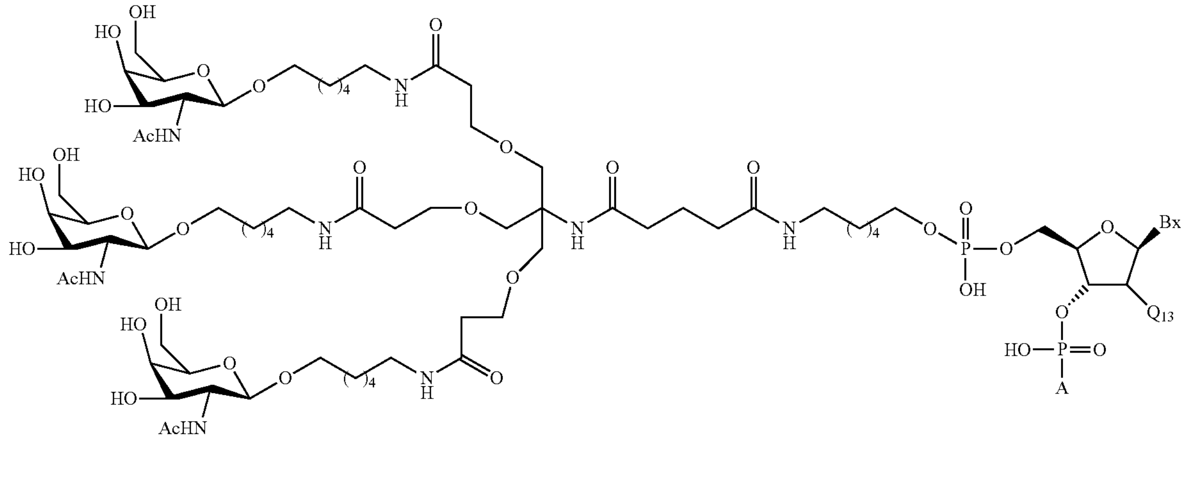

wherein $Q_{13}$ is H or $O(CH_2)_2$—$OCH_3$;

A is the modified oligonucleotide; and

Bx is a heterocyclic base moiety.

In certain embodiments, the conjugate group comprises:

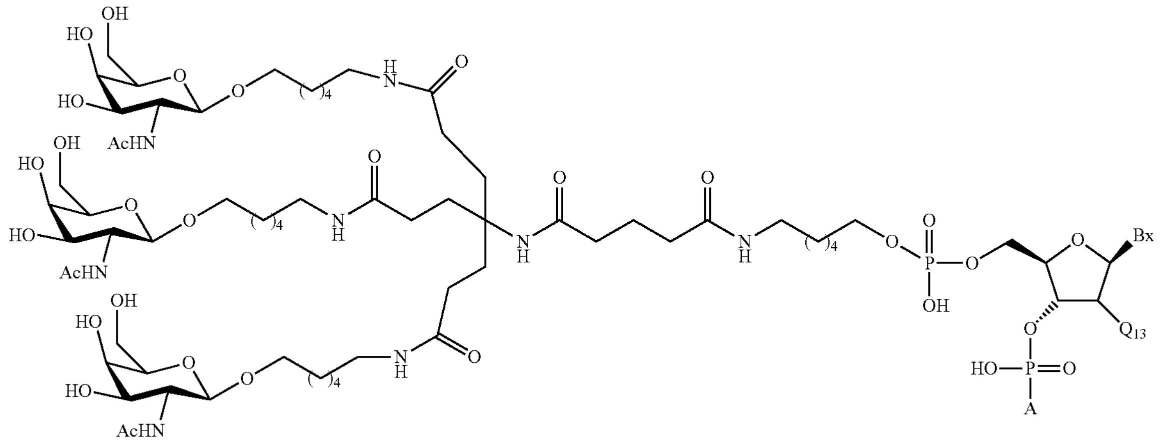

wherein $Q_{13}$ is H or $O(CH_2)_2$—$OCH_3$;

A is the modified oligonucleotide; and

Bx is a heterocyclic base moiety.

In certain embodiments, $B_x$ is selected from among from adenine, guanine, thymine, uracil, or cytosine, or 5-methyl cytosine. In certain embodiments, $B_x$ is adenine. In certain embodiments, $B_x$ is thymine. In certain embodiments, $Q_{13}$ is $O(CH_2)_2$—$OCH_3$. In certain embodiments, $Q_{13}$ is H.

Certain embodiments of the invention provide a prodrug comprising the compositions or compounds disclosed herein.

In certain embodiments, the compound is in a salt form. In further embodiments, the compound further comprises of a pharmaceutically acceptable carrier or diluent. In certain embodiments, the compound comprises a modified oligonucleotide targeting ApoCIII and a conjugate group, or a salt thereof, and a pharmaceutically acceptable carrier or diluent.

Certain embodiments provide compositions and methods comprising administering to an animal a conjugated antisense compound or composition disclosed herein. In certain embodiments, administering the conjugated antisense compound prevents, treats, ameliorates, or slows progression of a cardiovascular, metabolic and/or inflammatory disease.

Certain embodiments provide compositions and methods for use in therapy to treat an ApoCIII related disease, disorder or condition. In certain embodiments, the ApoCIII levels are elevated in an animal. In certain embodiments, the composition is a compound comprising an ApoCIII specific inhibitor. In certain embodiments, the ApoCIII specific inhibitor is a nucleic acid. In certain embodiments, the nucleic acid is an antisense compound. In certain embodiments, the antisense compound is a modified oligonucleotide targeting ApoCIII. In certain embodiments, the antisense compound is a modified oligonucleotide targeting ApoCIII and a conjugate group. In certain embodiments, the modified oligonucleotide targeting ApoCIII with the conjugate group, is used in treating, preventing, slowing progression, ameliorating an inflammatory, cardiovascular and/or metabolic disease, disorder or condition. In certain embodiments, the compositions and methods for therapy include administering an ApoCIII specific inhibitor to an individual in need thereof.

Certain embodiments provide conjugated antisense compounds and compositions and methods for reducing ApoCIII levels. In certain embodiments, ApoCIII levels are reduced in the liver, adipose tissue, heart, skeletal muscle or small intestine.

In certain embodiments, reducing ApoCIII levels in a tissue, organ or subject increases HDL levels. In certain embodiments, the HDL levels are increased by at least 90%, by at least 80%, by at least 70%, by at least 60%, by at least 50%, by at least 45%, at least 40%, by at least 35%, by at least 30%, by at least 25%, by at least 20%, by at least 15%, by at least 10% or by at least 5% from the baseline HDL level.

In certain embodiments, reducing ApoCIII levels in a tissue, organ or subject reduces TG levels. In certain embodiments, the subject has a triglyceride level ≥100 mg/dL, ≥200 mg/dL, ≥300 mg/dL, ≥400 mg/dL, ≥440 mg/dL, ≥500 mg/dL, ≥600 mg/dL, ≥700 mg/dL, ≥800 mg/dL, ≥880 mg/dL, ≥900 mg/dL, ≥1000 mg/dL, ≥1100 mg/dL, ≥1200 mg/dL, ≥1300 mg/dL, ≥1400 mg/dL, ≥1500 mg/dL, ≥1600 mg/dL, ≥1700 mg/dL, ≥1800 mg/dL, ≥1900 mg/dL, ≥2000 mg/dL.

In certain embodiments, the TG levels (postprandial or fasting) are decreased by at least 90%, by at least 80%, by at least 70%, by at least 60%, by at least 50%, by at least 45%, at least 40%, by at least 35%, by at least 30%, by at least 25%, by at least 20%, by at least 15%, by at least 10%, by at least 5% or by at least 1% from the baseline TG level. In certain embodiments, the TG (postprandial or fasting) level is decreased to ≤1900 mg/dL, ≤1800 mg/dL, ≤1700 mg/dL, ≤1600 mg/dL, ≤1500 mg/dL, ≤1400 mg/dL, ≤1300 mg/dL, ≤1200 mg/dL, ≤1100 mg/dL, ≤1000 mg/dL, ≤900 mg/dL, ≤800 mg/dL, ≤750 mg/dL, ≤700 mg/dL, ≤650 mg/dL, ≤600 mg/dL, ≤550 mg/dL, ≤500 mg/dL, ≤450 mg/dL, ≤400 mg/dL, ≤350 mg/dL, ≤300 mg/dL, ≤250 mg/dL, ≤200 mg/dL, ≤150 mg/dL or ≤100 mg/dL.

In certain embodiments, reducing ApoCIII levels in a tissue, organ or subject improves the ratio of LDL to HDL or the ratio of TG to HDL.

In certain embodiments, reducing ApoCIII levels in a tissue, organ or subject improves insulin sensitivity.

In certain embodiments, reducing ApoCIII levels in a tissue, organ or subject increases chylomicron clearance.

Certain embodiments provide compositions and methods to reduce ApoCIII mRNA or protein expression in an animal comprising administering to the animal a conjugated antisense compound or composition disclosed herein to reduce ApoCIII mRNA or protein expression in the animal.

Certain embodiments provide conjugated antisense compounds and compositions and methods for preventing, treating, delaying, slowing the progression and/or ameliorating ApoCIII related diseases, disorders, and conditions in a subject in need thereof. In certain embodiments, such diseases, disorders, and conditions include inflammatory, cardiovascular and/or metabolic diseases, disorders, and conditions. Certain such cardiovascular diseases, disorders or conditions include, but are not limited to, chylomicronemia, hypertriglyceridemia, aortic stenosis, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, myocardial infarction, peripheral vascular disease (e.g., peripheral artery disease, peripheral artery occlusive disease), Fredrickson Type I dyslipidemia, FCS, LPL deficiency, retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, pancreatitis, aortic stenosis, coronary artey disease (CAD), Alzheimer's Disease and thromboembolic diseases, disorder or conditions. Certain thromboembolic diseases, disorders or conditions include, but are not limited to, stroke, thrombosis (e.g., venous thromboembolism), myocardial infarction and peripheral vascular disease. Certain embodiments provide conjugated antisense compounds and compositions and methods for preventing, treating, delaying, slowing the progression and/or ameliorating hypertriglyceridemia. Certain embodiments provide conjugated antisense compounds and compositions and methods for preventing, treating, delaying, slowing the progression and/or ameliorating chylomicronemia. Certain embodiments provide conjugated antisense compounds and compositions and methods for preventing, treating, delaying, slowing the progression and/or ameliorating pancreatitis.

Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever. In certain embodiments, symptoms of a metabolic disease, disorder or condition include, but are not limited to, frequent urination, unusual thirst, extreme hunger, unusual weight loss, extreme fatigue, ilrritability, frequent infections, blurred vision, cuts/bruises that are slow to heal, tingling/numbness in the hands/feet and recurring skin, gum, or bladder infections. Certain embodiments provide a method of reducing at least one symptom of hypertriglyceridemia. Certain embodiments provide a method of reducing at least one symptom of chylomicronemia. Certain embodiments provide a method of reducing at least one symptom of pancreatitis.

In certain embodiments, the modulation of ApoCIII expression occurs in a cell, tissue or organ. In certain embodiments, the modulations occur in a cell, tissue or organ in an animal. In certain embodiments, the modulation is a reduction in ApoCIII mRNA level. In certain embodiments, the modulation is a reduction in ApoCIII protein level. In certain embodiments, both ApoCIII mRNA and protein levels are reduced. Such reduction may occur in a time-dependent or in a dose-dependent manner.

In certain embodiments, the subject or animal is human.

In certain embodiments, the compound is parenterally administered. In further embodiments, the parenteral administration is subcutaneous.

In certain embodiments, the conjugated antisense compound or composition is co-administered with a second agent or therapy. In certain embodiments, the conjugated antisense compound or composition and the second agent are administered concomitantly.

In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). Agents or therapies can be co-administered or administered concomitantly. Agents or therapies can be sequentially or subsequently administered.

Certain embodiments provide use of the compositions and conjugated antisense compounds described herein targeted to ApoCIII for decreasing ApoCIII levels in an animal. Certain embodiments provide use of a compound targeted to ApoCIII for decreasing ApoCIII levels in an animal. Certain embodiments provide use of a compound targeted to ApoCIII for increasing HDL levels in an animal. Certain embodiments provide use of a compound targeted to ApoCIII for increasing HDL chylomicron clearance in an animal. Certain embodiments provide use of a compounds targeted to ApoCIII for the treatment, prevention, or amelioration of a disease, disorder, or condition associated with ApoCIII. Certain embodiments provide use of a compound targeted to ApoCIII for the treatment, prevention, or amelioration of a hypertriglyceridemia. Certain embodiments provide use of a compound targeted to ApoCIII for the treatment, prevention, or amelioration of a chylomicronemia (e.g., FCS and/or LPLD). Certain embodiments provide use of a compound targeted to ApoCIII for the treatment, prevention, or amelioration of a pancreatitis.

Certain embodiments provide use of the compositions and conjugated antisense compounds described herein targeted to ApoCIII in the preparation of a medicament for decreasing ApoCIII levels in an animal. Certain embodiments provide use of the compositions and compounds for the preparation of a medicament for the treatment, prevention, or amelioration of a disease, disorder, or condition associated with ApoCIII.

Certain embodiments provide the use of the compositions and conjugated antisense compounds as described herein in the manufacture of a medicament for treating, ameliorating, delaying or preventing one or more of a disease related to ApoCIII.

Certain embodiments provide a kit for treating, preventing, or ameliorating a disease, disorder or condition as described herein wherein the kit comprises: (i) an ApoCIII specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

B. Certain Compounds

In certain embodiments, the invention provides conjugated antisense compounds comprising antisense oligonucleotides and a conjugate.

a. Certain Antisense Oligonucleotides

In certain embodiments, the invention provides antisense oligonucleotides. Such antisense oligonucleotides comprise linked nucleosides, each nucleoside comprising a sugar moiety and a nucleobase. The structure of such antisense oligonucleotides may be considered in terms of chemical features (e.g., modifications and patterns of modifications) and nucleobase sequence (e.g., sequence of antisense oligonucleotide, identity and sequence of target nucleic acid).

i. Certain Chemistry Features

In certain embodiments, antisense oligonucleotide comprise one or more modification. In certain such embodiments, antisense oligonucleotides comprise one or more modified nucleosides and/or modified internucleoside linkages. In certain embodiments, modified nucleosides comprise a modified sugar moiety and/or modified nucleobase.

1. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, 0-allyl, O—$C_1$-$C_{10}$ alkyl, O—$C_1$-$C_{10}$ substituted alkyl; $OCF_3$, $O(CH_2)_2SCH_3$, $O(CH_2)_2$—O—N(Rm)(Rn), and O—$CH_2$—C(═O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or N($R_m$)-alkyl; O, S, or N($R_m$)-alkenyl; O, S or N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)_2SCH_3$, O—$(CH_2)_2$—O—N($R_m$)($R_n$), $O(CH_2)_2O(CH_2)_2N(CH_3)_2$, and N-substituted acetamide (O—$CH_2$—C(═O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, O—$(CH_2)_2$—O—$N(CH_3)_2$, —$O(CH_2)_2O(CH_2)_2N(CH_3)_2$, and O—$CH_2$—C(═O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_aR_b$)—N(R)—O— or, —C($R_aR_b$)—O—N(R)—; 4'-$CH_2$-2', 4'-$(CH_2)_2$-2', 4'-$(CH_2)_3$-2', 4'-($CH_2$)—O-2' (LNA); 4'-($CH_2$)—S-2'; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*, 2009, 74, 118-134); and 4'-$CH_2$—C(═$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)═C($R_b$)—, —C($R_a$)═N—, —C(═N$R_a$)—, —C(═O)—, —C(═S)—, —O—, —Si$(R_a)_2$—, —S(═O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-$CH(CH_3)$—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

(A)

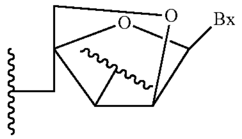

(B)

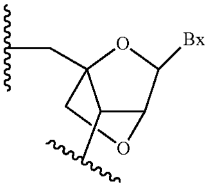

(C)

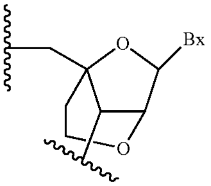

(D)

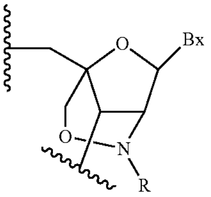

(E)

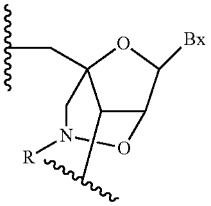

-continued (F)

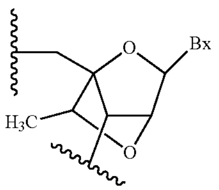

(G)

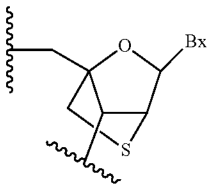

(H)

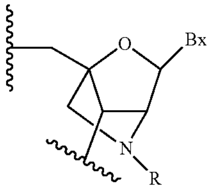

(I)

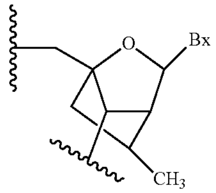

(J)

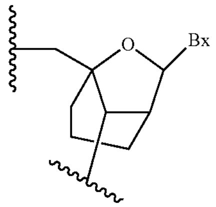

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a morphlino. Morpholino compounds and their use in oligomeric compounds has been reported in numerous patents and published articles (see for example: Braasch et al., *Biochemistry,* 2002, 41, 4503-4510; and U.S. Pat. Nos. 5,698,685; 5,166,315; 5,185,444; and 5,034,506). As used here, the term "morpholino" means a sugar surrogate having the following structure:

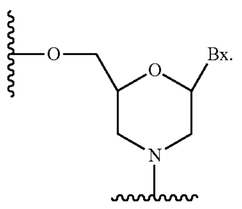

In certain embodiments, morpholinos may be modified, for example by adding or altering various substituent groups from the above morpholino structure. Such sugar surrogates are referred to herein as "modified morpholinos."

For another example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VI:

VI

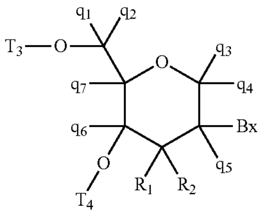

wherein independently for each of said at least one tetrahydropyran nucleoside analog of Formula VI:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3C$(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VI are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present disclosure provides oligonucleotides comprising modified nucleosides.

Those modified nucleotides may include modified sugars, modified nucleobases, and/or modified linkages.

The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

2. Certain Nucleobase Modifications

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C≡C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cyto-sines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie, International Edition,* 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

3. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (PO), phosphotriesters, methylphosphonates, phosphoramidate, and phosphorothioates (PS). Representative non-phosphorus containing internucleoside linking groups include, but are not limited to, methylenemethylimino ($—CH_2—N(CH_3)—O—CH_2—$), thiodiester (—O—C(O)—S—), thionocarbamate (—O—C(O)(NH)—S—); siloxane ($—O—Si(H)_2—O—$); and N,N'-dimethylhydrazine ($—CH_2—N(CH_3)—N(CH_3)—$). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI ($3'-CH_2—N(CH_3)—O-5'$), amide-3 ($3'-CH_2—C(=O)—N(H)-5'$), amide-4 ($3'-CH_2—N(H)—C(=O)-5'$), formacetal ($3'-O—CH_2—O-5'$), and thioformacetal ($3'-S—CH_2—O-5'$). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

4. Certain Motifs

In certain embodiments, antisense oligonucleotides comprise one or more modified nucleoside (e.g., nucleoside comprising a modified sugar and/or modified nucleobase) and/or one or more modified internucleoside linkage. The pattern of such modifications on an oligonucleotide is referred to herein as a motif. In certain embodiments, sugar, nucleobase, and linkage motifs are independent of one another.

a. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain 5'-Wings

In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

ii. Certain 3'-Wings

In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

iii. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides.

In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

b. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 7 phosphorothioate internucleoside linkages. In certain embodiments, the oligonucleotide comprises at least 8 phosphorothioate internucleoside linkages. In certain embodiments, the oligonucleotide comprises at least 9 phosphorothioate internucleoside linkages. In certain embodiments, the oligonucleotide comprises at least 10 phosphorothioate internucleoside linkages. In certain embodiments, the oligonucleotide comprises at least 11 phosphorothioate internucleoside linkages. In certain embodiments, the oligonucleotide comprises at least 12 phosphorothioate internucleoside linkages. In certain embodiments, the oligonucleotide comprises at least 13 phosphorothioate internucleoside linkages. In certain embodiments, the oligonucleotide comprises at least 14 phosphorothioate internucleoside linkages.

In certain embodiments, the oligonucleotide comprises at least one block of at least 6 consecutive phosphorothioate internucleoside linkages. In certain embodiments, the oligonucleotide comprises at least one block of at least 7 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 9 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide. In certain embodiments, the oligonucleotide comprises less than 15 phosphorothioate internucleoside linkages. In certain embodiments, the oligonucleotide comprises less than 14 phosphorothioate internucleoside linkages. In certain embodiments, the oligonucleotide comprises less than 13 phosphorothioate internucleoside linkages. In certain embodiments, the oligonucleotide comprises less than 12 phosphorothioate internucleoside linkages. In certain embodiments, the oligonucleotide comprises less than 11 phosphorothioate internucleoside linkages. In certain embodiments, the oligonucleotide comprises less than 10 phosphorothioate internucleoside linkages. In certain embodiments, the oligonucleotide comprises less than 9 phosphorothioate internucleoside linkages. In certain embodiments, the oligonucleotide comprises less than 8 phosphorothioate internucleoside linkages. In certain embodiments, the oligonucleotide comprises less than 7 phosphorothioate internucleoside linkages. In certain embodiments, the oligonucleotide comprises less than 6 phosphorothioate internucleoside linkages. In certain embodiments, the oligonucleotide comprises less than 5 phosphorothioate internucleoside linkages.

c. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

In certain embodiments, chemical modifications to nucleobases comprise attachment of certain conjugate groups to nucleobases. In certain embodiments, each purine or each pyrimidine in an oligonucleotide may be optionally modified to comprise a conjugate group.

d. Certain Overall Lengths

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

5. Certain Antisense Oligonucleotide Chemistry Motifs

In certain embodiments, the chemical structural features of antisense oligonucleotides are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides.

In certain embodiments, the selection of internucleoside linkage and nucleoside modification are not independent of one another.

i. Certain Sequences and Targets

In certain embodiments, the invention provides antisense oligonucleotides having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessibility of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

In certain embodiments, a conjugate group comprises a cleavable moiety. In certain embodiments, a conjugate group comprises one or more cleavable bond. In certain embodiments, a conjugate group comprises a linker. In certain embodiments, a linker comprises a protein binding moiety. In certain embodiments, a conjugate group comprises a cell-targeting moiety (also referred to as a cell-targeting group). In certain embodiments a cell-targeting moiety comprises a branching group. In certain embodiments, a cell-targeting moiety comprises one or more tethers. In certain embodiments, a cell-targeting moiety comprises a carbohydrate or carbohydrate cluster.

ii. Certain Cleavable Moieties

In certain embodiments, a cleavable moiety is a cleavable bond. In certain embodiments, a cleavable moiety comprises a cleavable bond. In certain embodiments, the conjugate group comprises a cleavable moiety. In certain such embodiments, the cleavable moiety attaches to the antisense oligonucleotide. In certain such embodiments, the cleavable moiety attaches directly to the cell-targeting moiety. In certain such embodiments, the cleavable moiety attaches to the conjugate linker. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, the cleavable moiety is cleaved after the complex has been administered to an animal only after being internalized by a targeted cell. Inside the cell the cleavable moiety is cleaved thereby releasing the active antisense oligonucleotide. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

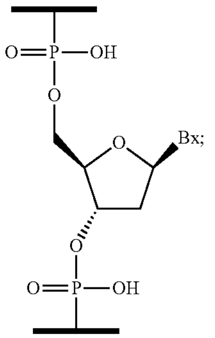

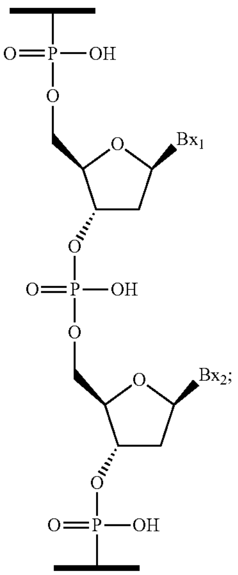

and

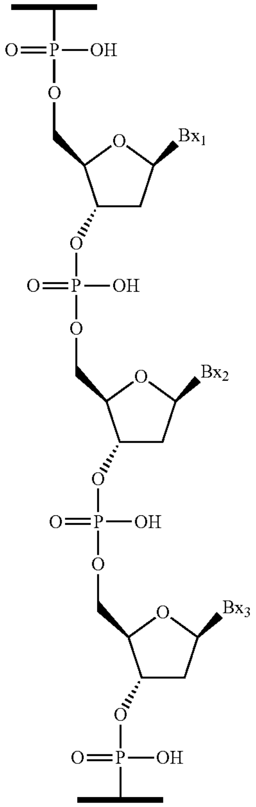

wherein each of Bx, $Bx_1$, $Bx_2$, and $Bx_3$ is independently a heterocyclic base moiety. In certain embodiments, the cleavable moiety has a structure selected from among the following:

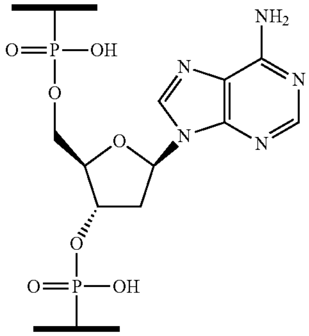

iii. Certain Linkers

In certain embodiments, the conjugate groups comprise a linker. In certain such embodiments, the linker is covalently bound to the cleavable moiety. In certain such embodiments, the linker is covalently bound to the antisense oligonucleotide. In certain embodiments, the linker is covalently bound to a cell-targeting moiety. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker includes multiple positions for attachment of tethered ligands and is not attached to a branching group. In certain embodiments, the linker further comprises one or more cleavable bond. In certain embodiments, the conjugate group does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.

In certain embodiments, a linker has a structure selected from among:

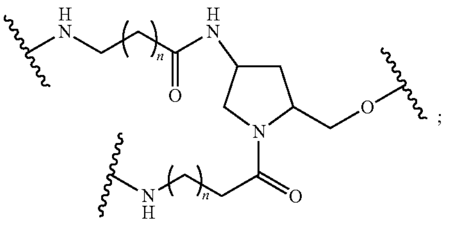

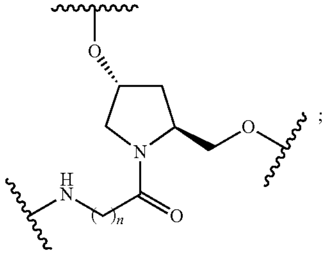

-continued

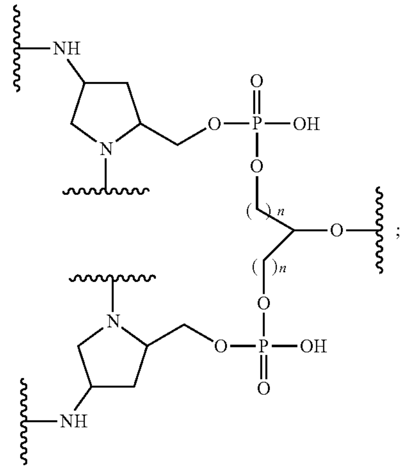

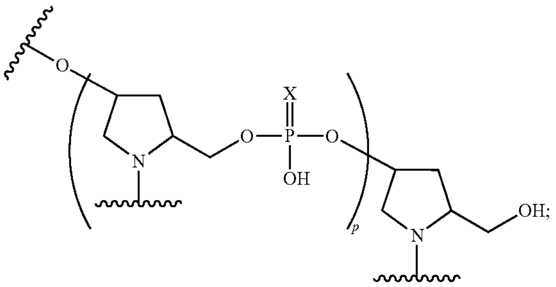

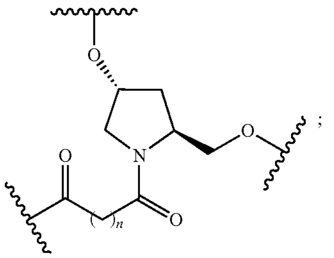

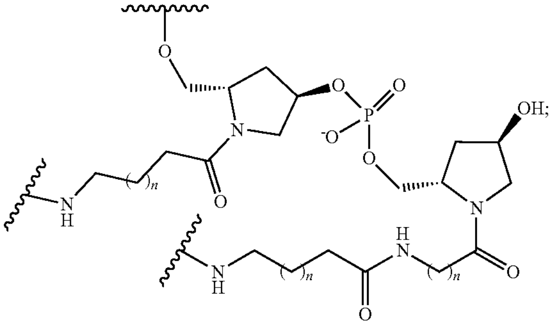

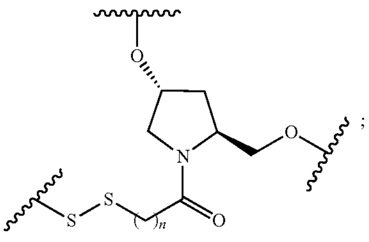

-continued
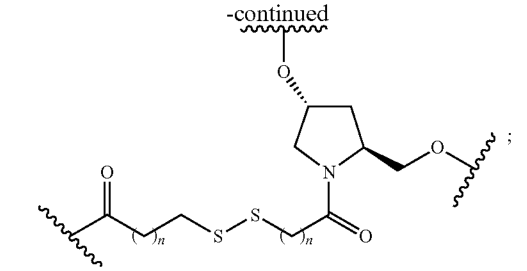
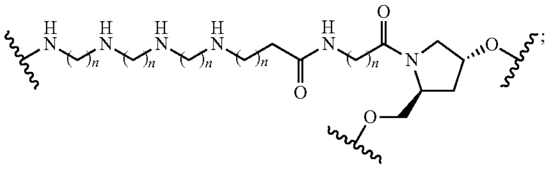
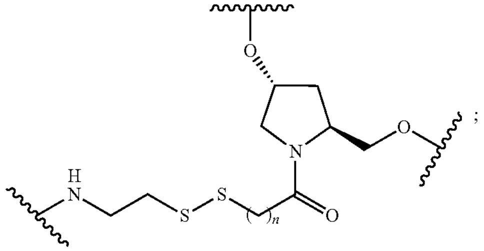
-continued
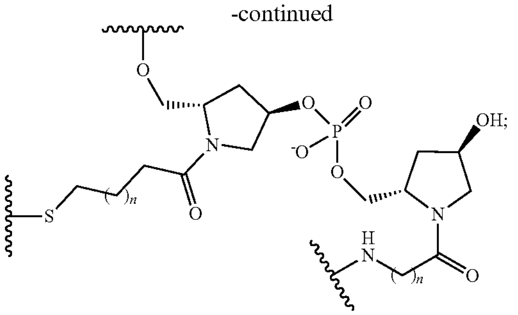
and
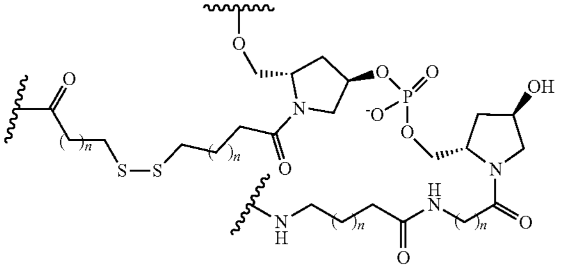
wherein each n is, independently, from 1 to 20; and p is from 1 to 6.
In certain embodiments, a linker has a structure selected from among:
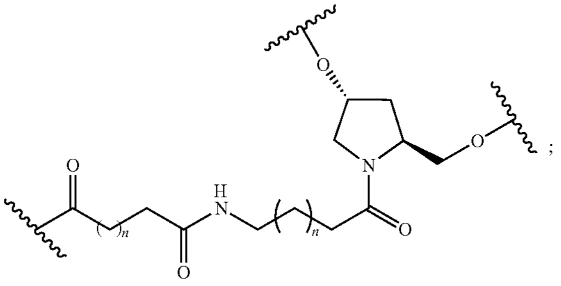
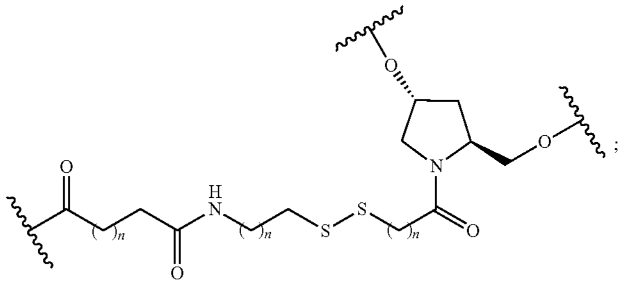
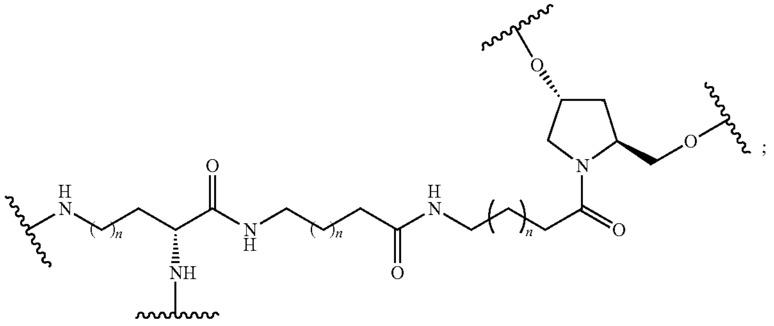
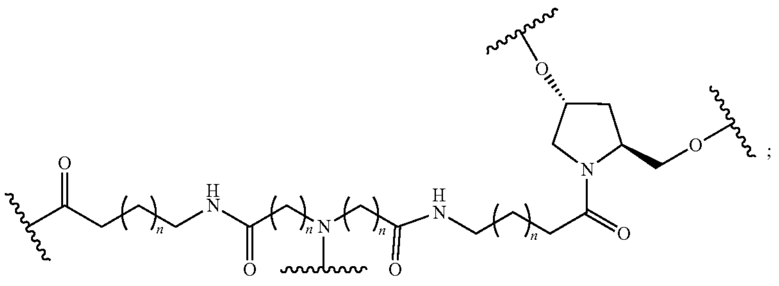

-continued
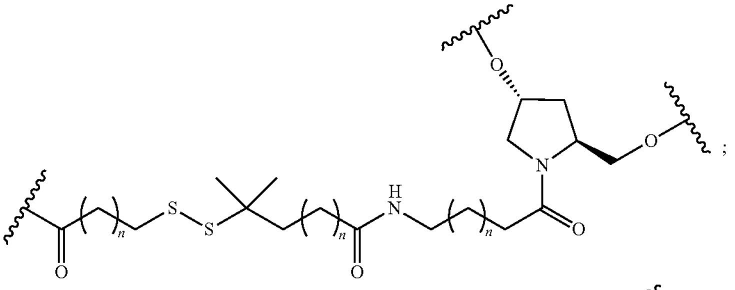
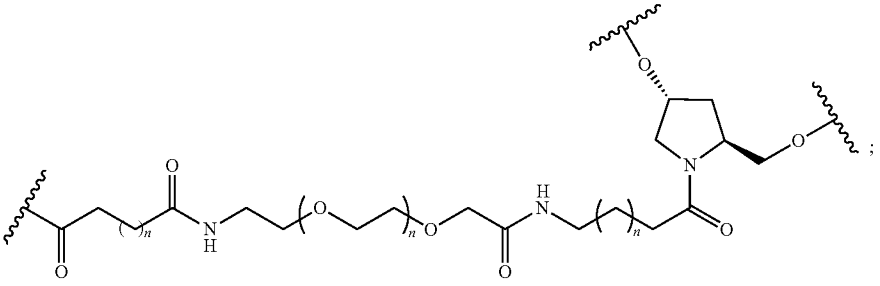
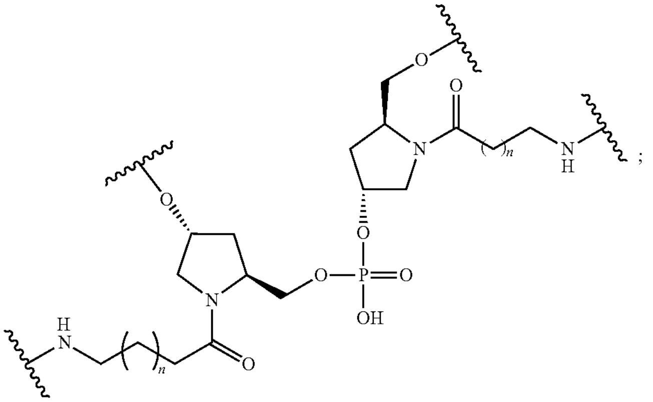
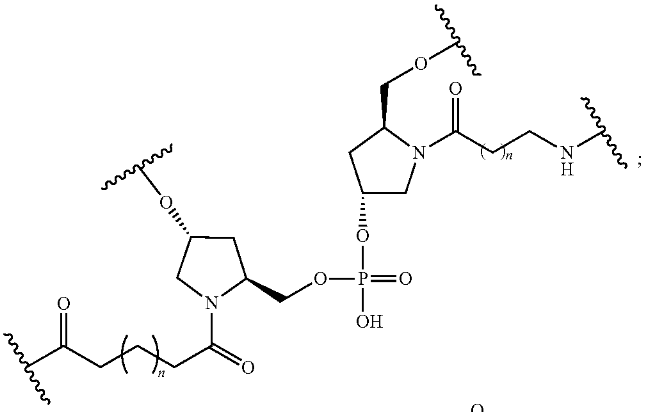
and
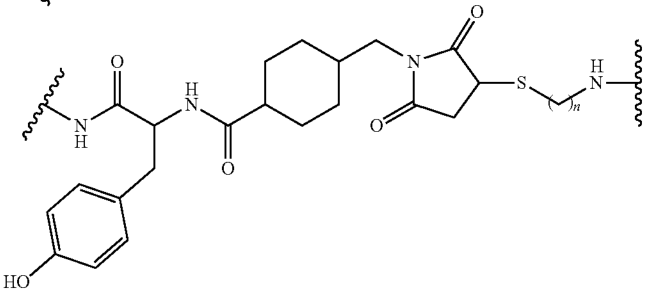
wherein each n is, independently, from 1 to 20.

In certain embodiments, a linker has a structure selected from among:
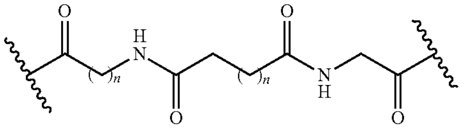
;
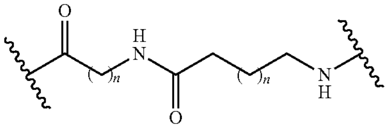
;
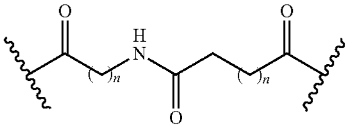
;
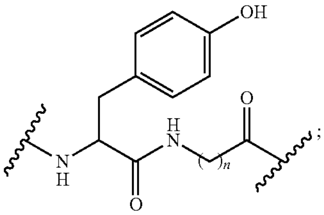
;
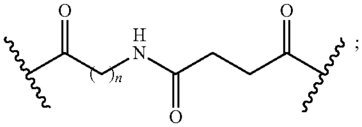
;
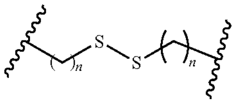
;
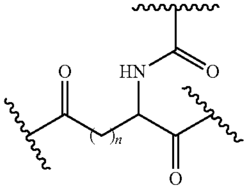
;
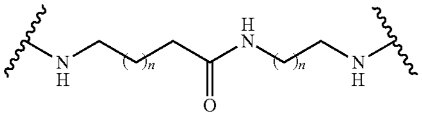
;
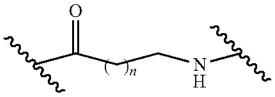
;
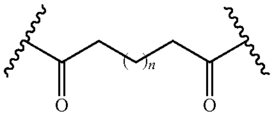
;
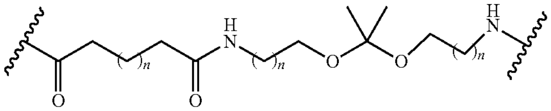
;
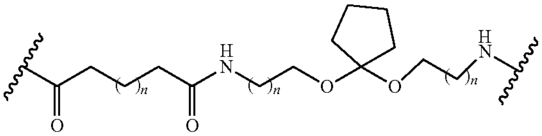
;
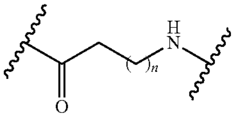
;
-continued
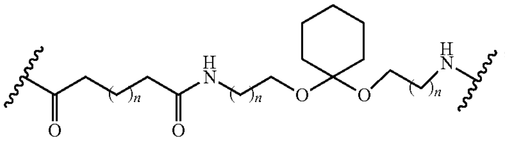
; and
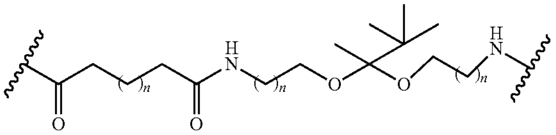
wherein n is from 1 to 20.
In certain embodiments, a linker has a structure selected from among:
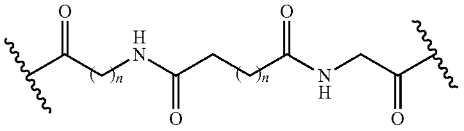
;
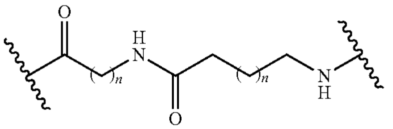
;
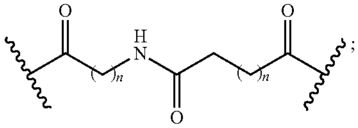
;
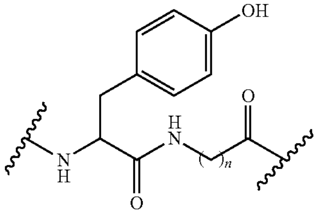
;
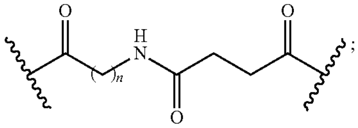
;
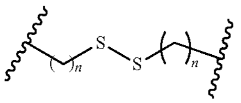
;
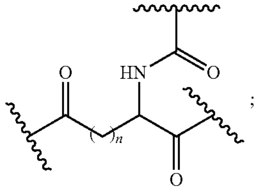
;
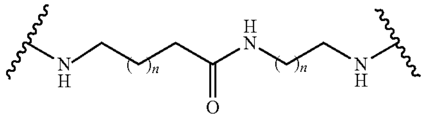
;
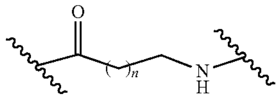
;
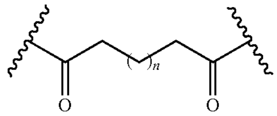
;
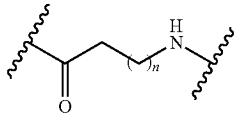
;

-continued
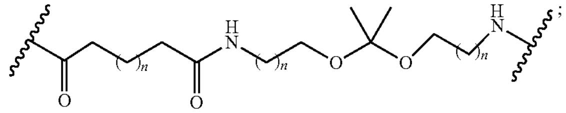
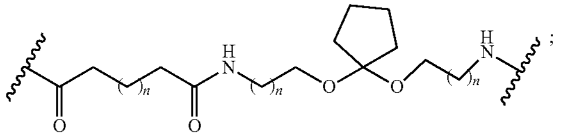
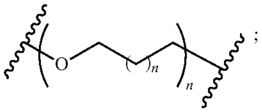
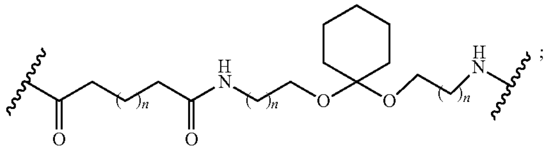
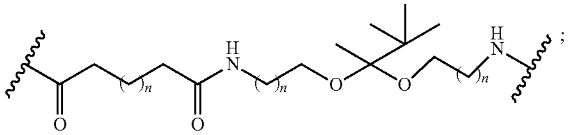
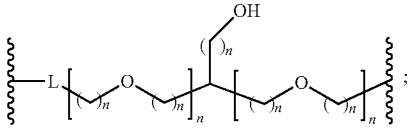
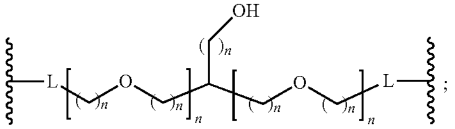
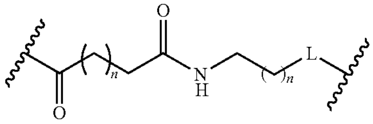
and
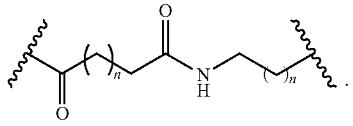
wherein each L is, independently, a phosphorus linking group or a neutral linking group; and
each n is, independently, from 1 to 20.
In certain embodiments, a linker has a structure selected from among:
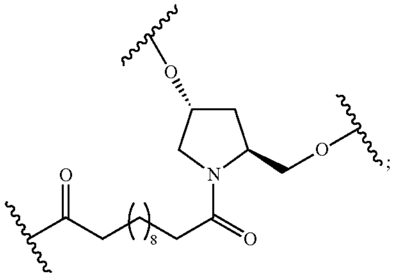
-continued
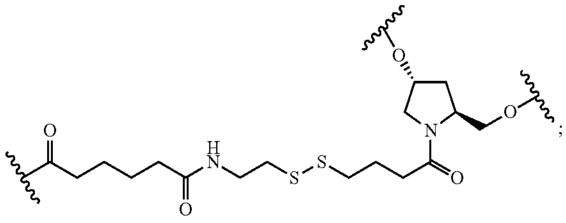
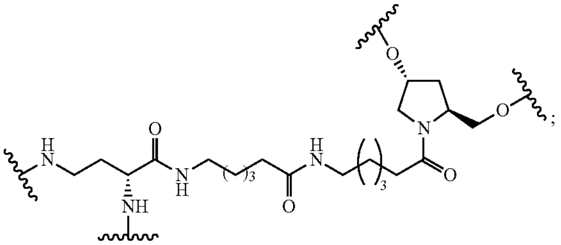
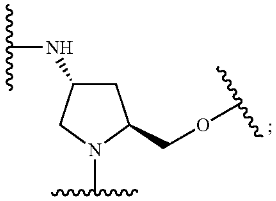
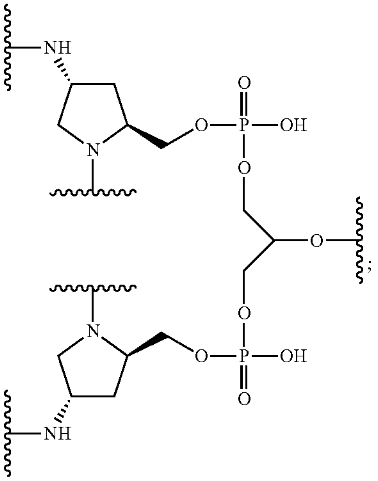
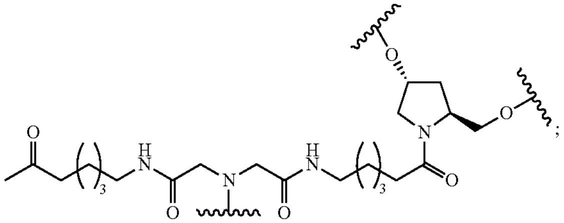
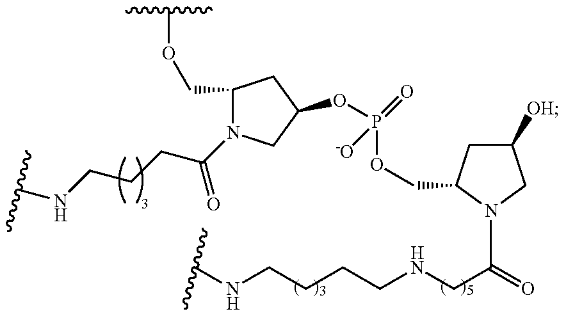

-continued
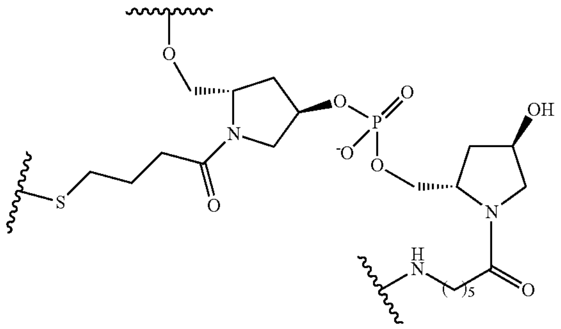
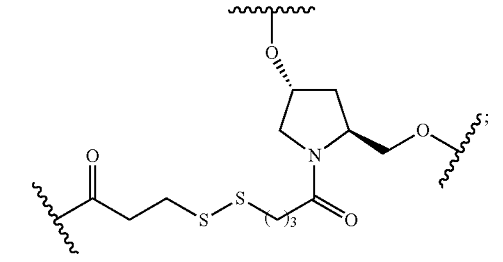
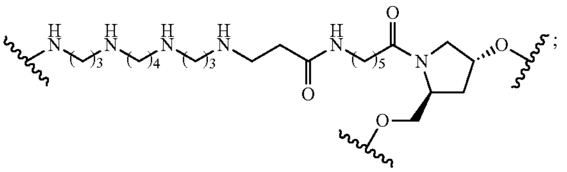
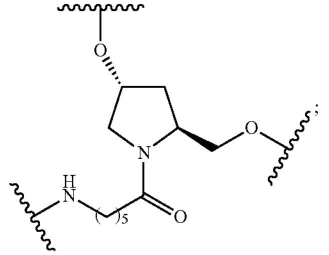
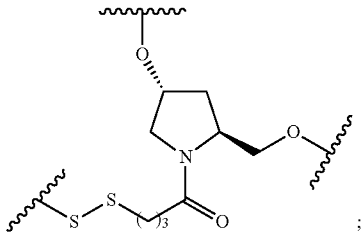
;
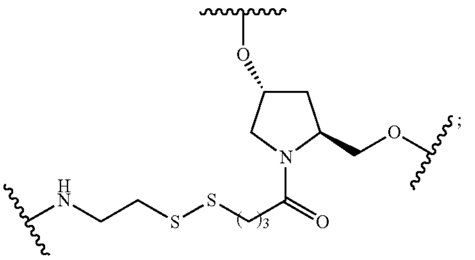
-continued
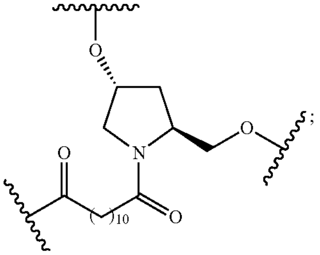
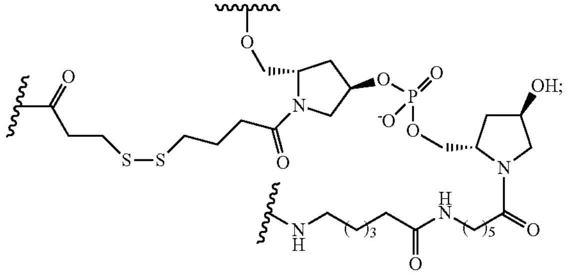
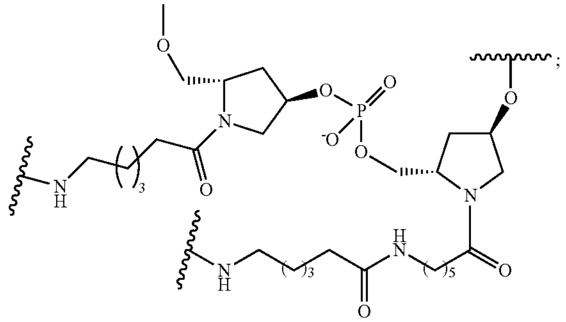
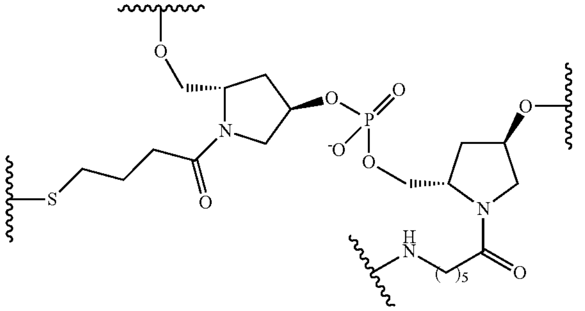
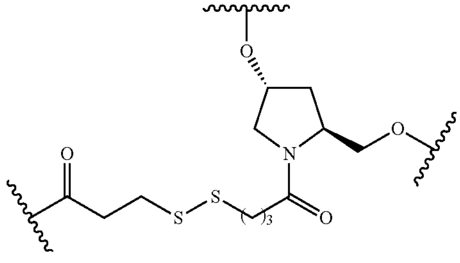
; and
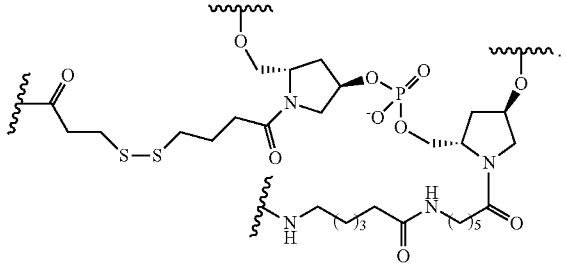

In certain embodiments, a linker has a structure selected from among:
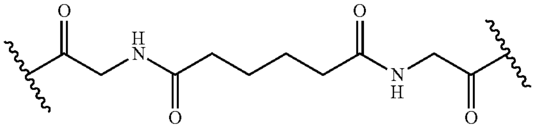
;
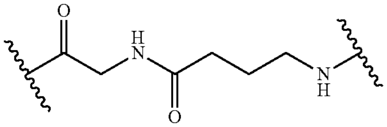
;
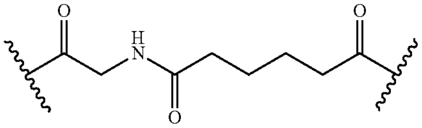
;
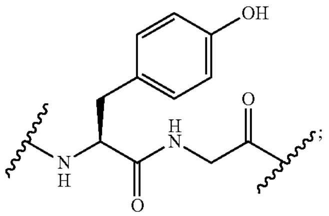
;
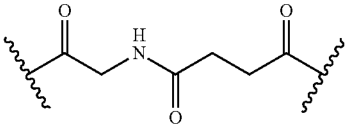
;
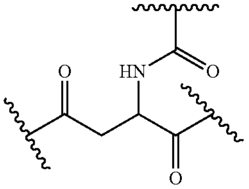
;
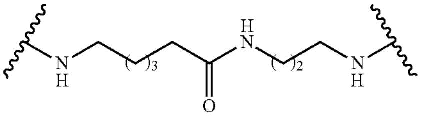
;
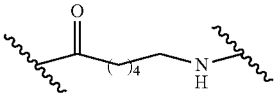
;
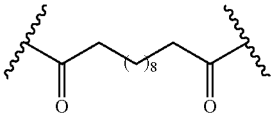
;
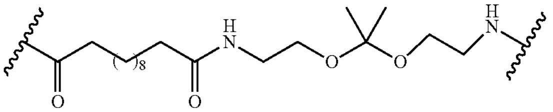
;
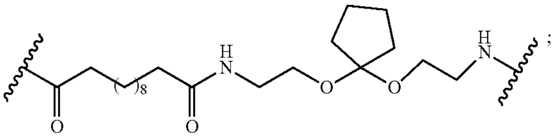
;
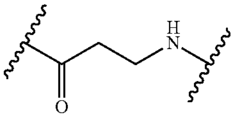
;
-continued
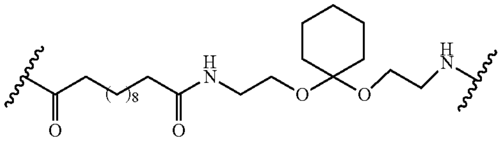
; and
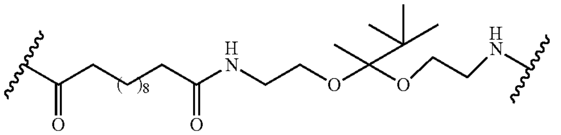
.
In certain embodiments, a linker has a structure selected from among:
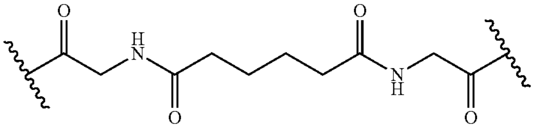
;
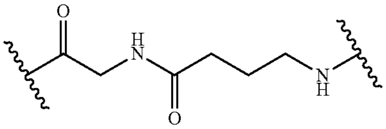
;
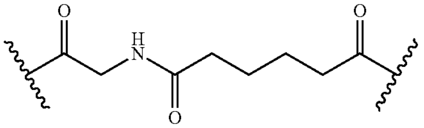
;
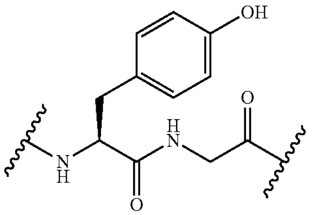
;
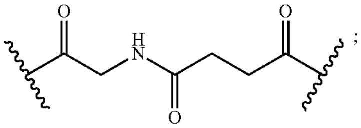
;
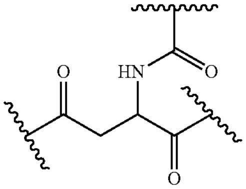
;
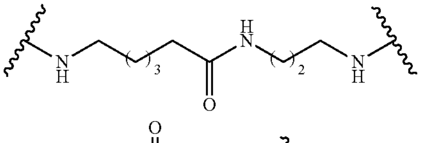
;
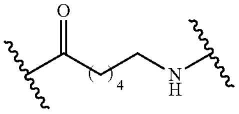
;
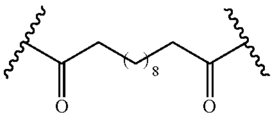
;

-continued
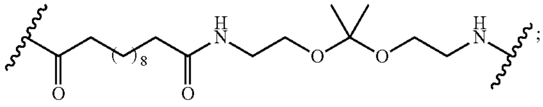;
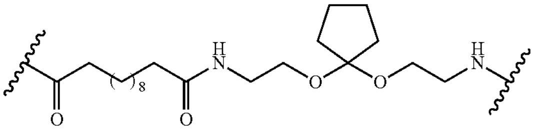;
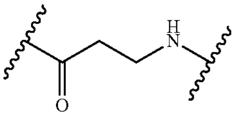;
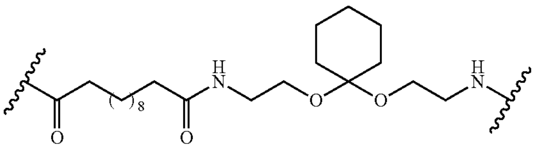;
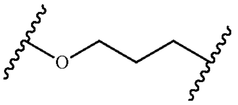;
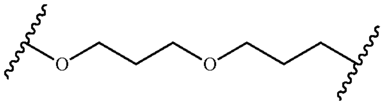;
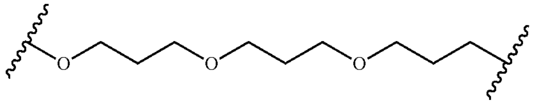;
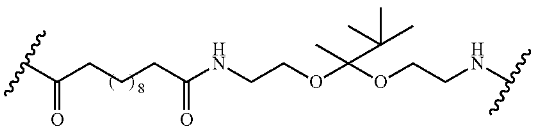;
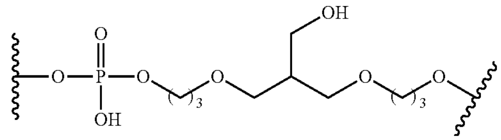;
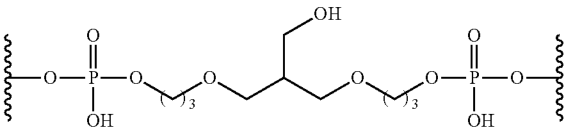;
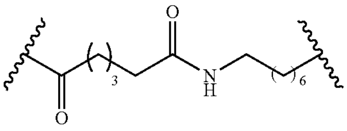 and
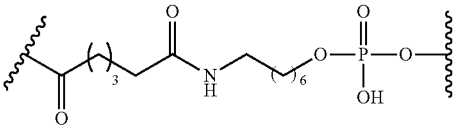.
In certain embodiments, a linker has a structure selected from among:
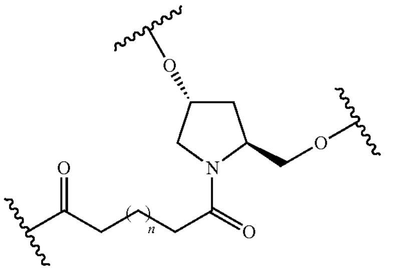 and
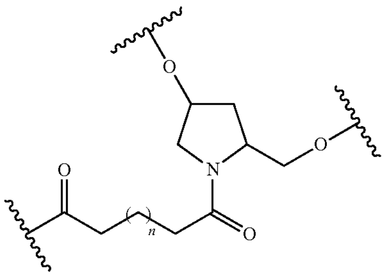
wherein n is from 1 to 20.
In certain embodiments, a linker has a structure selected from among:
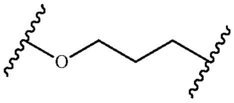;
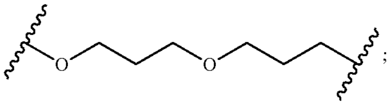; and
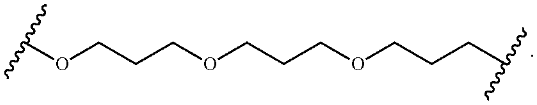.
In certain embodiments, a linker has a structure selected from among:
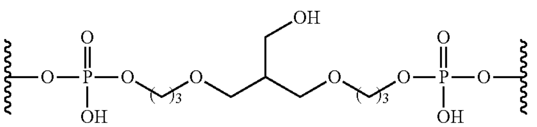 and
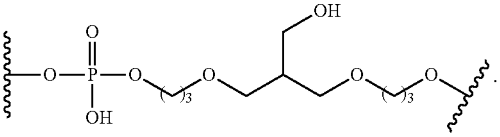.

In certain embodiments, a linker has a structure selected from among:

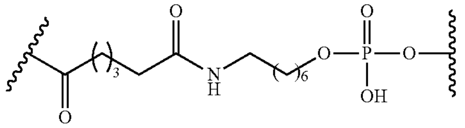

and

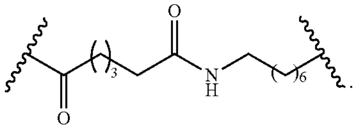

In certain embodiments, the conjugate linker has the structure:

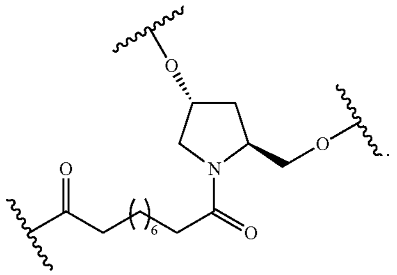

In certain embodiments, the conjugate linker has the structure:

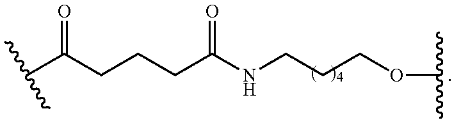

In certain embodiments, a linker has a structure selected from among:

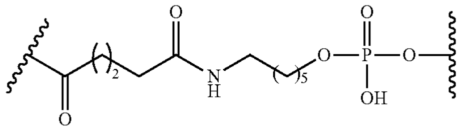

and

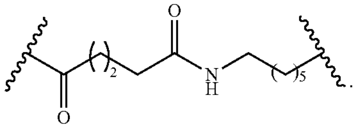

In certain embodiments, a linker has a structure selected from among:

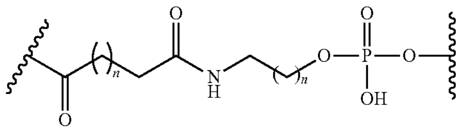

and

-continued

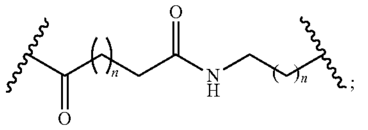

wherein each n is independently, 0, 1, 2, 3, 4, 5, 6, or 7.

iv. Certain Cell-Targeting Moieties

In certain embodiments, conjugate groups comprise cell-targeting moieties. Certain such cell-targeting moieties increase cellular uptake of antisense compounds. In certain embodiments, cell-targeting moieties comprise a branching group, one or more tether, and one or more ligand. In certain embodiments, cell-targeting moieties comprise a branching group, one or more tether, one or more ligand and one or more cleavable bond.

1. Certain Branching Groups

In certain embodiments, the conjugate groups comprise a targeting moiety comprising a branching group and at least two tethered ligands. In certain embodiments, the branching group attaches the conjugate linker. In certain embodiments, the branching group attaches the cleavable moiety. In certain embodiments, the branching group attaches the antisense oligonucleotide. In certain embodiments, the branching group is covalently attached to the linker and each of the tethered ligands. In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the conjugate group does not include a branching group.

In certain embodiments, a branching group has a structure selected from among:

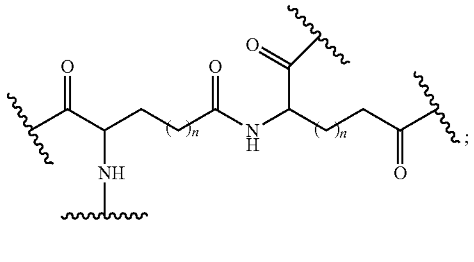

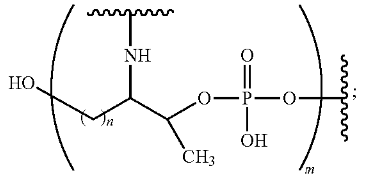

-continued
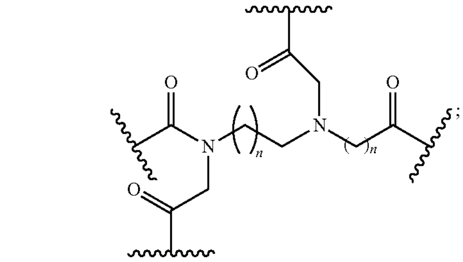
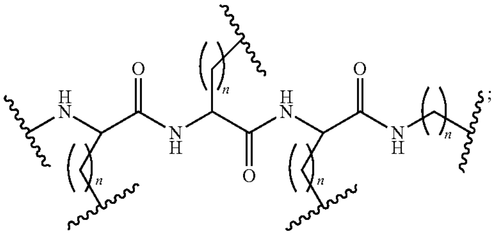
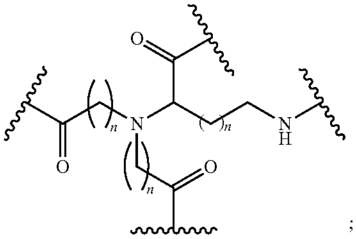
;
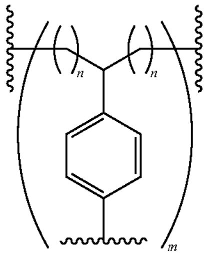
;
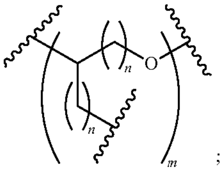
;
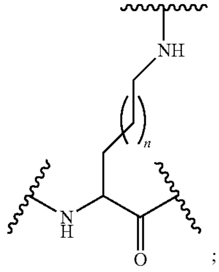
;
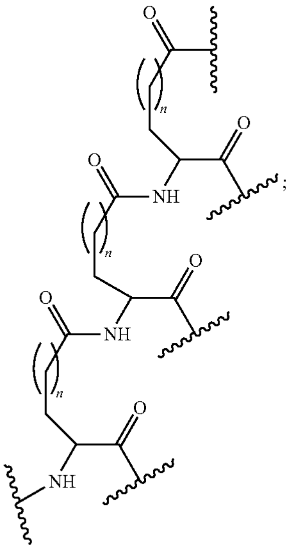
-continued
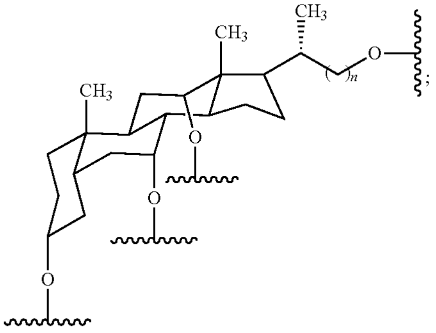
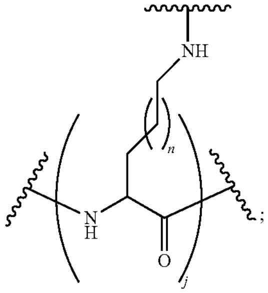
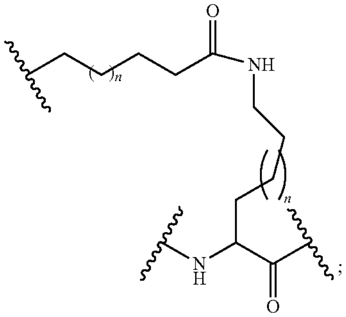
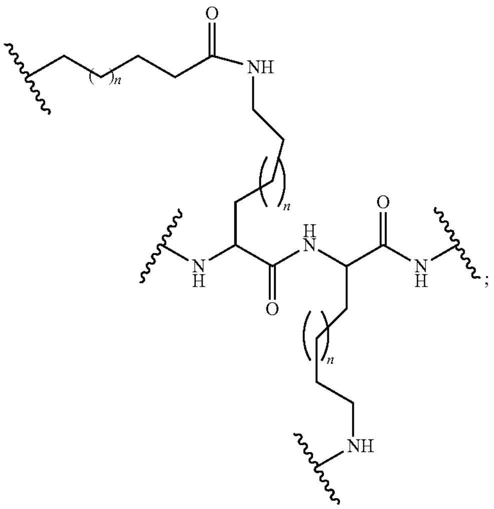

-continued
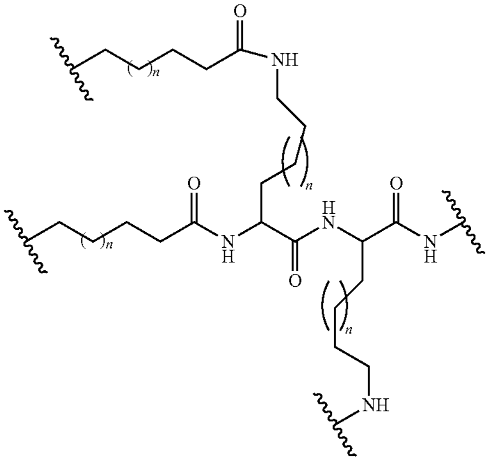
; and
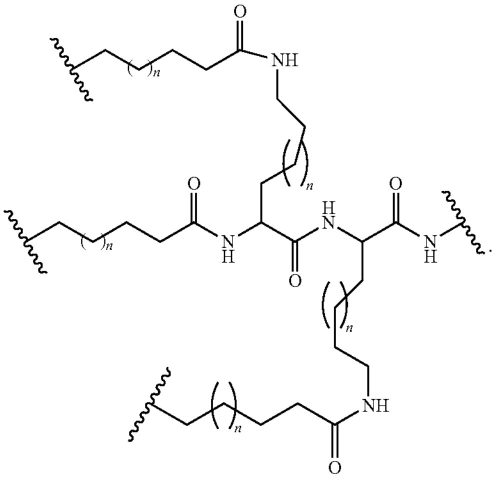
wherein each n is, independently, from 1 to 20;
j is from 1 to 3; and
m is from 2 to 6.
In certain embodiments, a branching group has a structure selected from among:
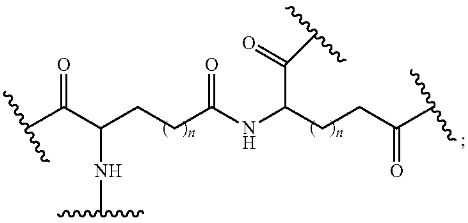
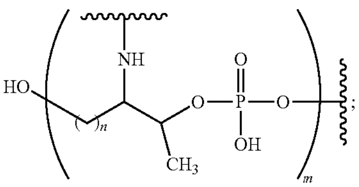
-continued
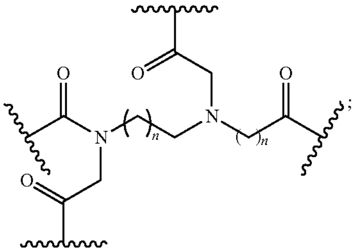
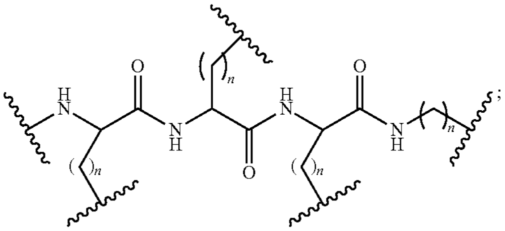
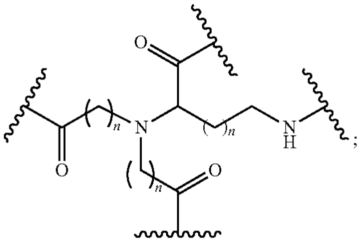
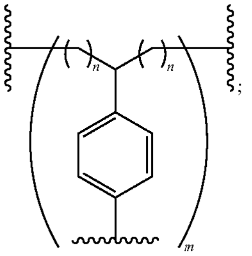
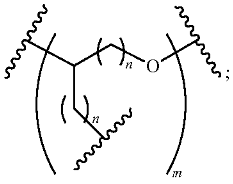
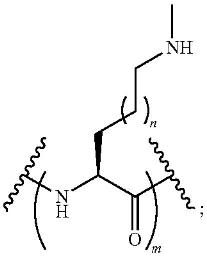

-continued
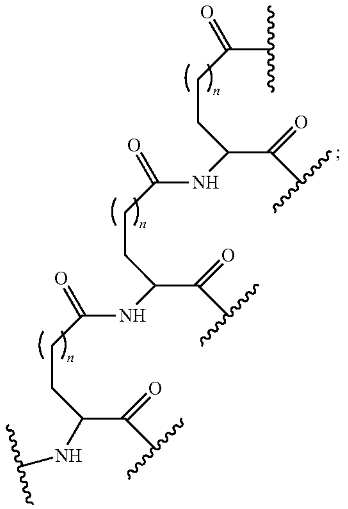
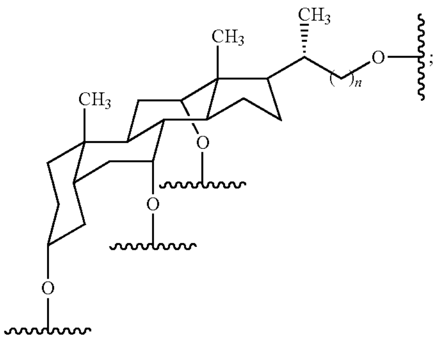
; and
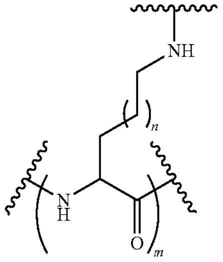
wherein each n is, independently, from 1 to 20; and m is from 2 to 6.
In certain embodiments, a branching group has a structure selected from among:
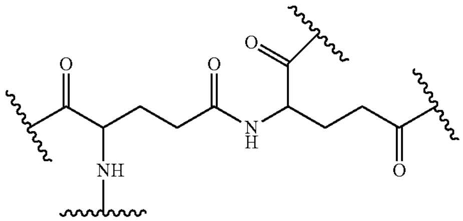
;
-continued
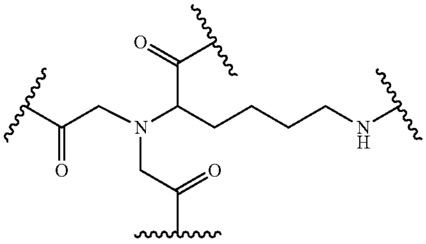
;
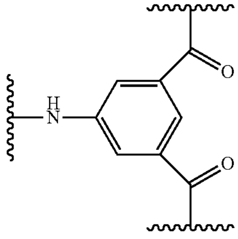
;
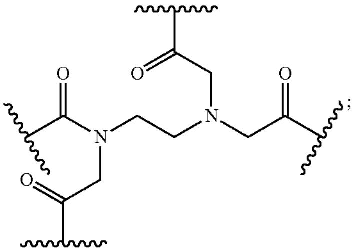
;
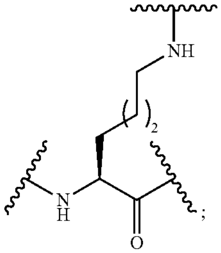
;
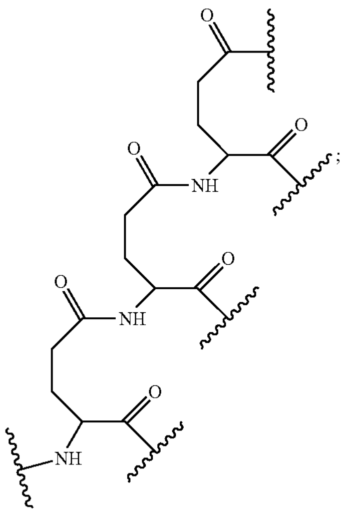
;

-continued
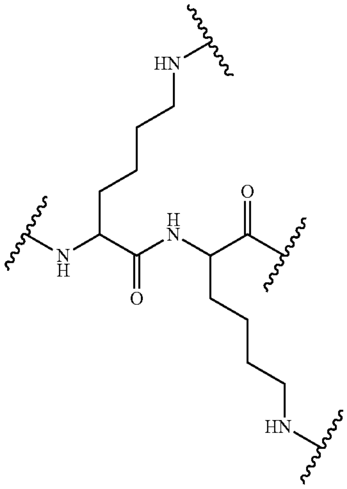
;
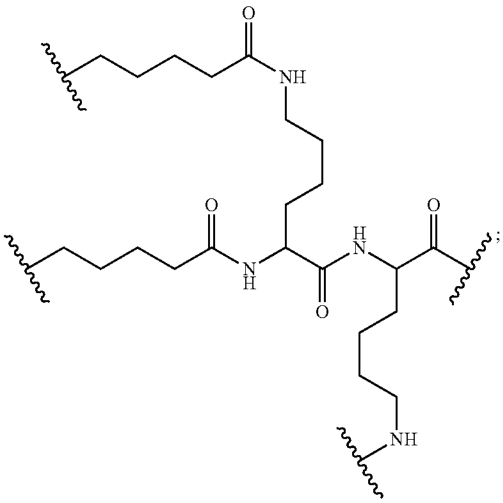
; and
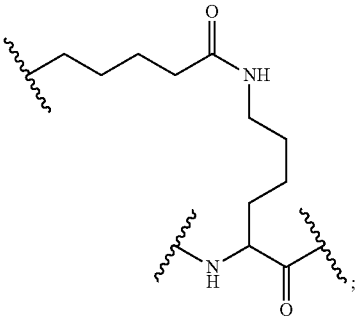
;
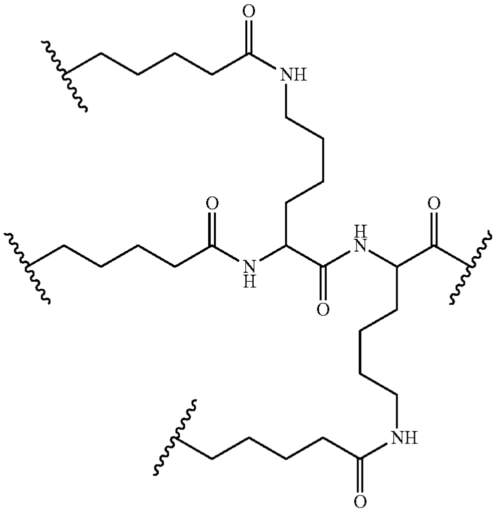
;
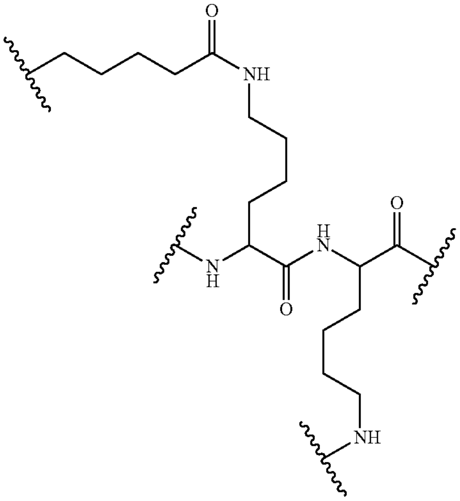
.
In certain embodiments, a branching group has a structure selected from among:
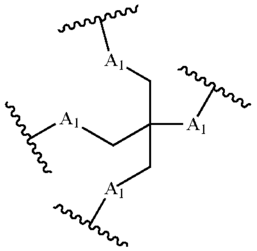
and
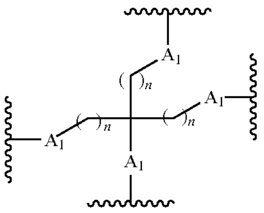
wherein each $A_1$ is independently, O, S, C═O or NH; and each n is, independently, from 1 to 20.

In certain embodiments, a branching group has a structure selected from among:

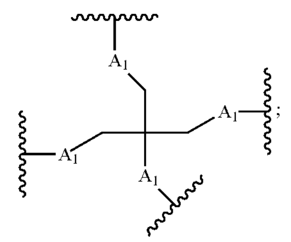

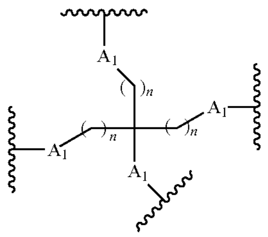

and

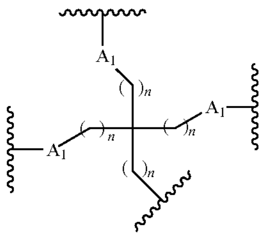

wherein each $A_1$ is independently, O, S, C═O or NH; and each n is, independently, from 1 to 20.

In certain embodiments, a branching group has a structure selected from among:

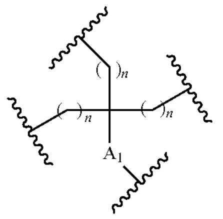

and

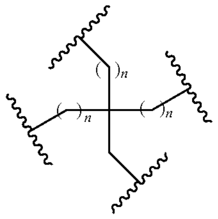

wherein $A_1$ is O, S, C═O or NH; and each n is, independently, from 1 to 20.

In certain embodiments, a branching group has a structure selected from among:

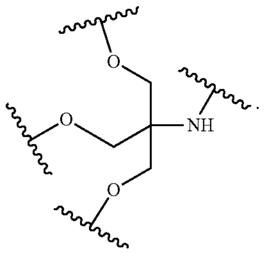 [SMILES: *NC(CO*)(CO*)CO*]

In certain embodiments, a branching group has a structure selected from among:

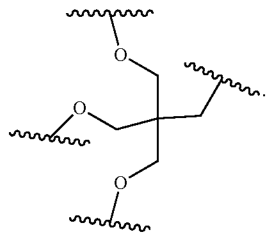 [SMILES: *CC(CO*)(CO*)CO*]

In certain embodiments, a branching group has a structure selected from among:

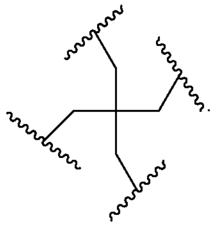 [SMILES: *CC(C*)(C*)C*]

2. Certain Tethers

In certain embodiments, conjugate groups comprise one or more tethers covalently attached to the branching group. In certain embodiments, conjugate groups comprise one or more tethers covalently attached to the linking group. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

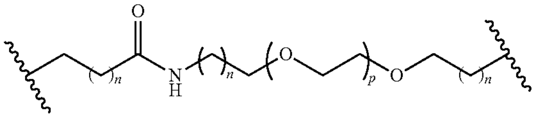
;
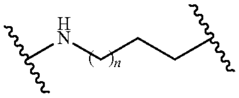
;
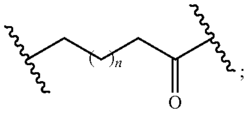
;
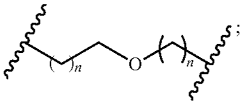
;
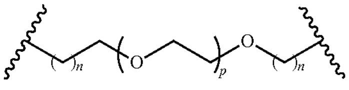
;
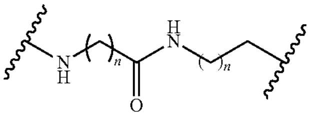
;
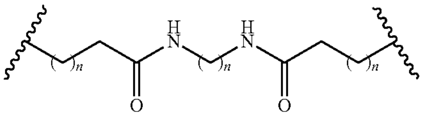
;
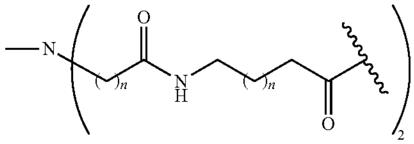
;
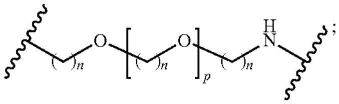
;
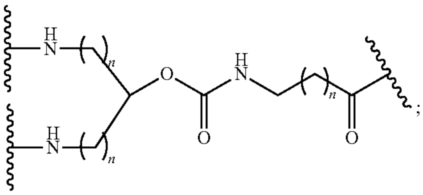
;
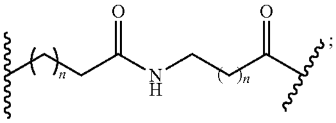
;
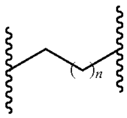
; and
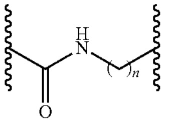

wherein each n is, independently, from 1 to 20; and each p is from 1 to about 6.

In certain embodiments, a tether has a structure selected from among:

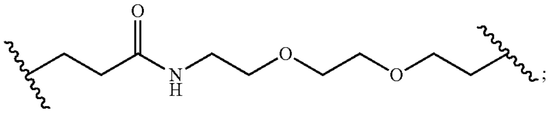
;
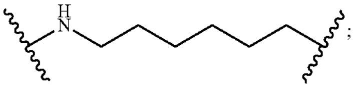
;
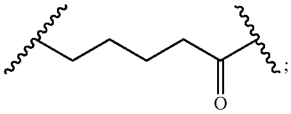
;
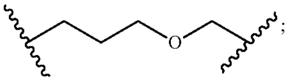
;
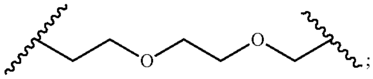
;
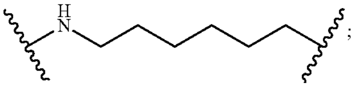
; and
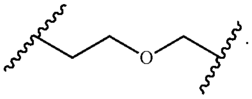
.

In certain embodiments, a tether has a structure selected from among:

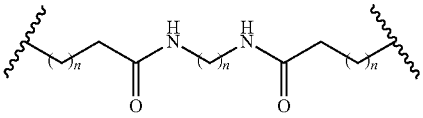

wherein each n is, independently, from 1 to 20.

In certain embodiments, a tether has a structure selected from among:

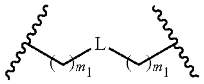
and
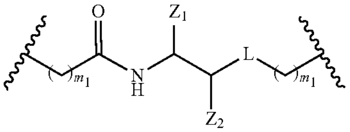

wherein L is either a phosphorus linking group or a neutral linking group;

$Z_1$ is C(═O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, a tether has a structure selected from among:

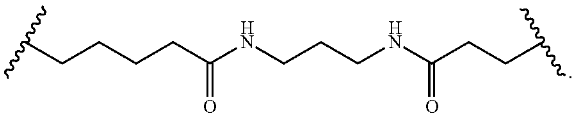 [SMILES: *CCCCC(=O)NCCCNC(=O)CC*]

In certain embodiments, a tether has a structure selected from among:

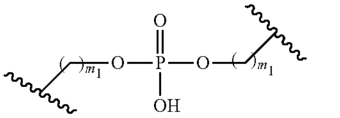

and

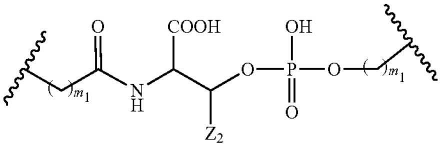

wherein $Z_2$ is H or $CH_3$; and each $m_1$ is, independently, from 0 to 20 wherein at least one $m_1$ is greater than 0 for each tether.

In certain embodiments, a tether has a structure selected from among:

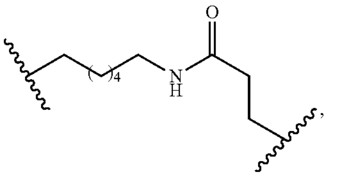

or

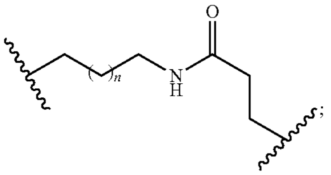

wherein each n is independently, 0, 1, 2, 3, 4, 5, 6, or 7.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Ligands

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, "GalNac" or "Gal-NAc" refers to 2-(Acetylamino)-2-deoxy-D-galactopyranose, commonly referred to in the literature as N-acetyl galactosamine. In certain embodiments, "N-acetyl galactosamine" refers to 2-(Acetylamino)-2-deoxy-D-galactopyranose. In certain embodiments, "GalNac" or "Gal-NAc" refers to 2-(Acetylamino)-2-deoxy-D-galactopyranose. In certain embodiments, "GalNac" or "Gal-NAc" refers to 2-(Acetylamino)-2-deoxy-D-galactopyranose, which includes both the β-form: 2-(Acetylamino)-2-deoxy-β-D-galactopyranose and α-form: 2-(Acetylamino)-2-deoxy-D-galactopyranose. In certain embodiments, both the β-form: 2-(Acetylamino)-2-deoxy-β-D-galactopyranose and α-form: 2-(Acetylamino)-2-deoxy-D-galactopyranose may be used interchangeably. Accordingly, in structures in which one form is depicted, these structures are intended to include the other form as well. For example, where the structure for an α-form: 2-(Acetylamino)-2-deoxy-D-galactopyranose is shown, this structure is intended to include the other form as well. In certain embodiments, In certain preferred embodiments, the β-form 2-(Acetylamino)-2-deoxy-D-galactopyranose is the preferred embodiment.

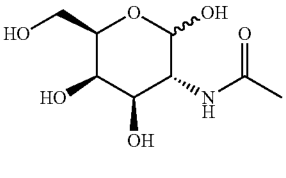

2-(Acetylamino)-2-deoxy-D-galactopyranose

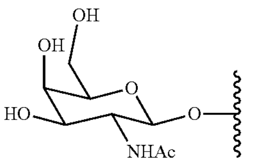 [SMILES: *OC1OC(CO)C(O)C(O)C1NC(C)=O]

2-(Acetylamino)-2-deoxy-β-D-galactopyranose

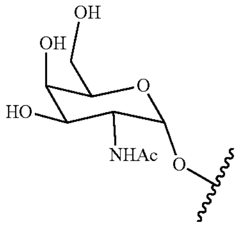 [SMILES: *OC1OC(CO)C(O)C(O)C1NC(C)=O]

2-(Acetylamino)-2-deoxy-α-D-galactopyranose

In certain embodiments one or more ligand has a structure selected from among:

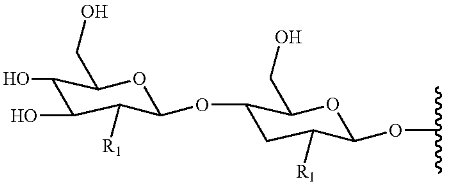

and

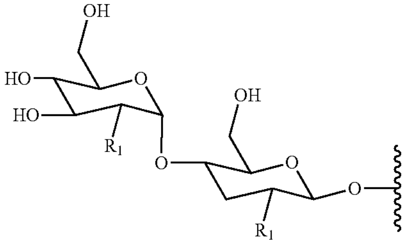

wherein each $R_1$ is selected from OH and NHCOOH.

In certain embodiments one or more ligand has a structure selected from among:

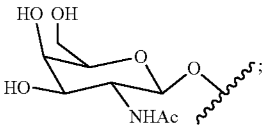

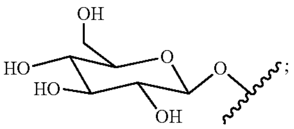

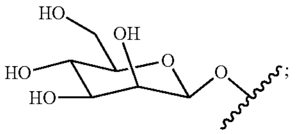

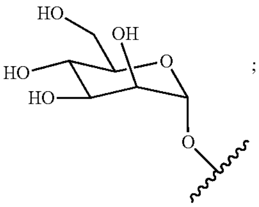

;

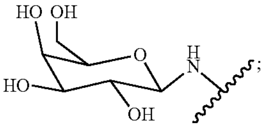

-continued

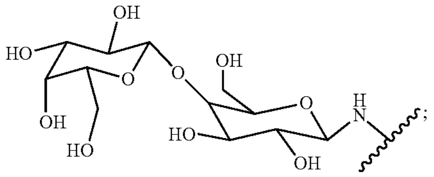

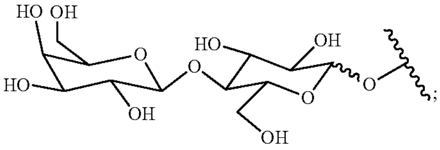

and

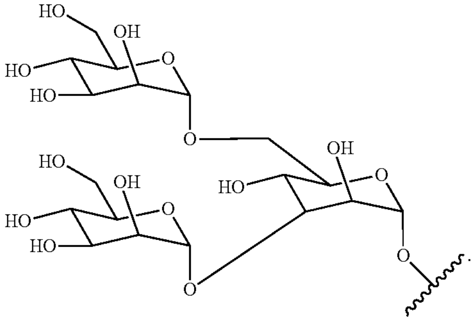

In certain embodiments one or more ligand has a structure selected from among:

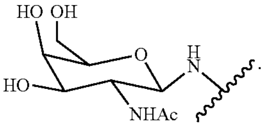 [SMILES: *NC1OC(CO)C(O)C(O)C1NC(C)=O]

In certain embodiments one or more ligand has a structure selected from among:

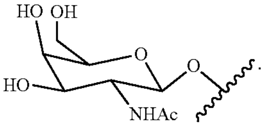 [SMILES: *OC1OC(CO)C(O)C(O)C1NC(C)=O]

i. Certain Conjugates
In certain embodiments, conjugate groups comprise the structural features above. In certain such embodiments, conjugate groups have the following structure:
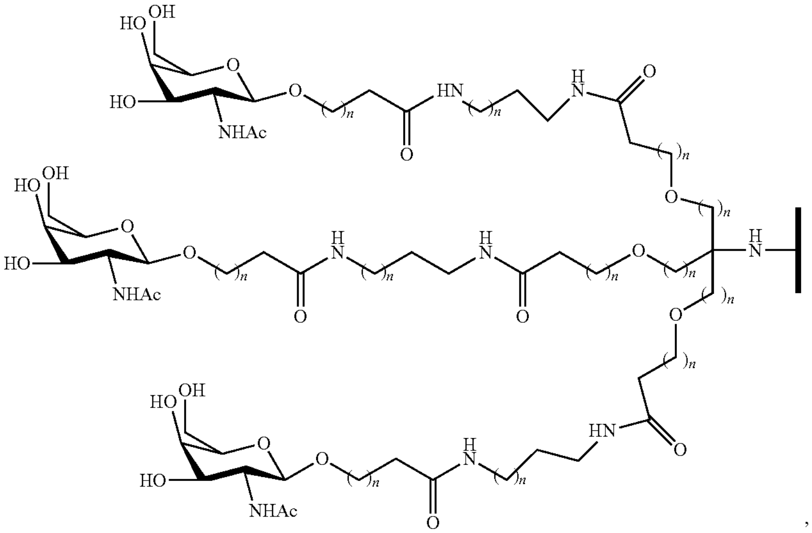
,
wherein each n is, independently, from 1 to 20.
In certain such embodiments, conjugate groups have the following structure:
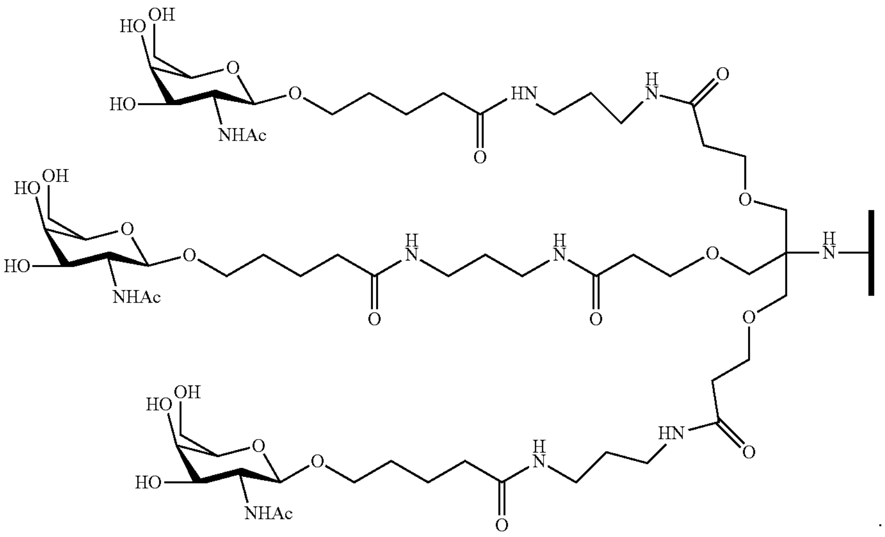
.

In certain such embodiments, conjugate groups have the following structure:
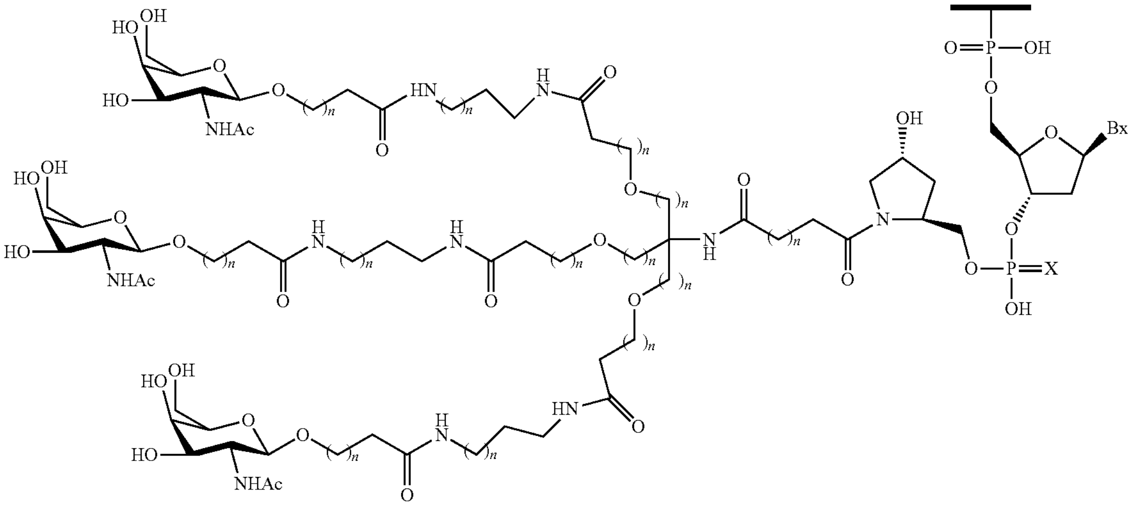
wherein each n is, independently, is from 1 to 20;
Z is H or a linked solid support; and
W is an antisense compound;
X is O or S; and
Bx is a heterocyclic base moiety.
In certain such embodiments, conjugate groups have the following structure:
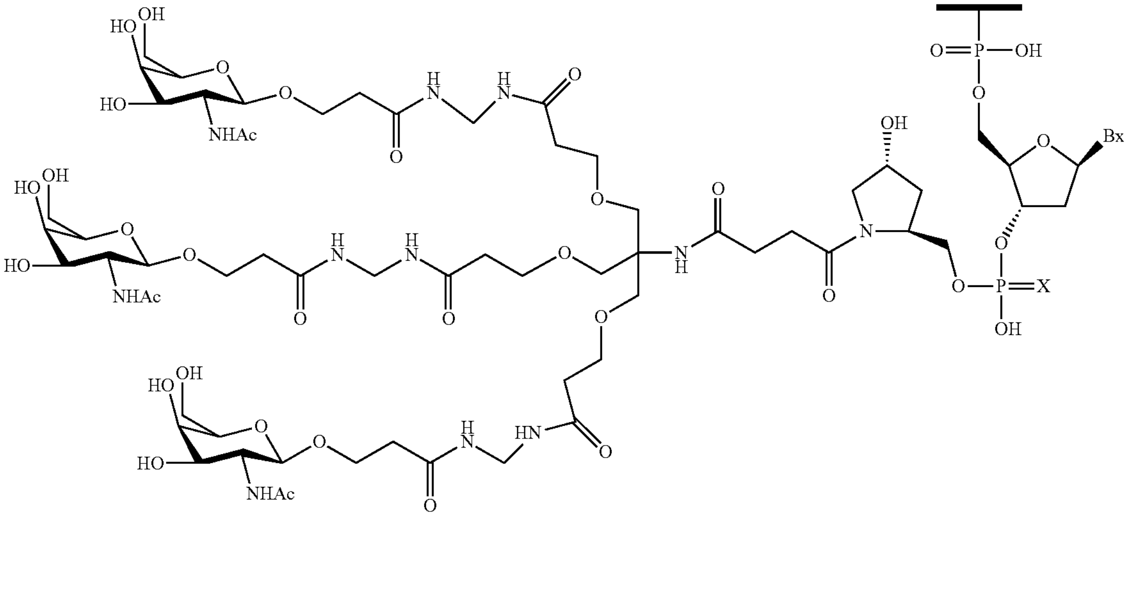

In certain such embodiments, conjugate groups have the following structure:
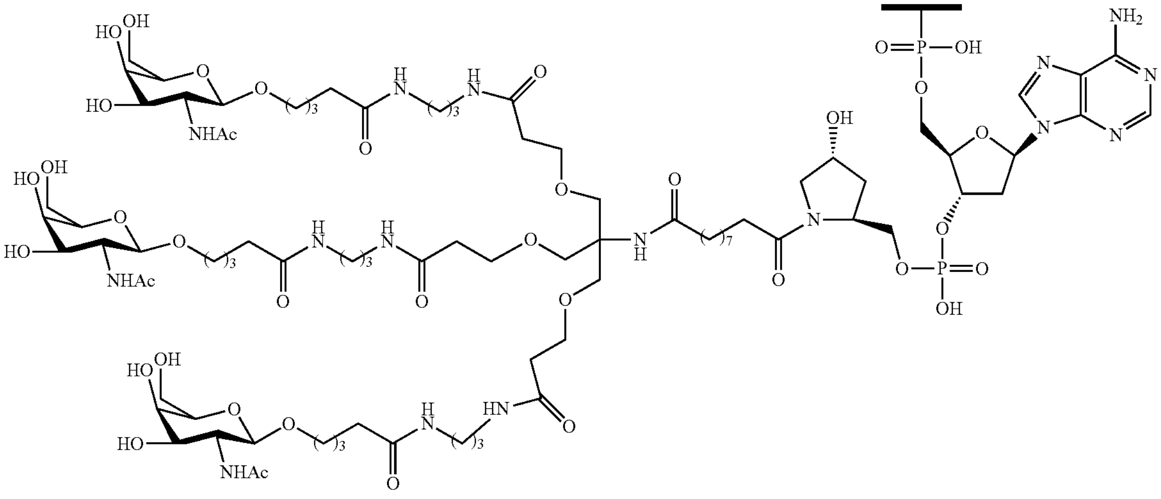
In certain such embodiments, conjugate groups have the following structure:
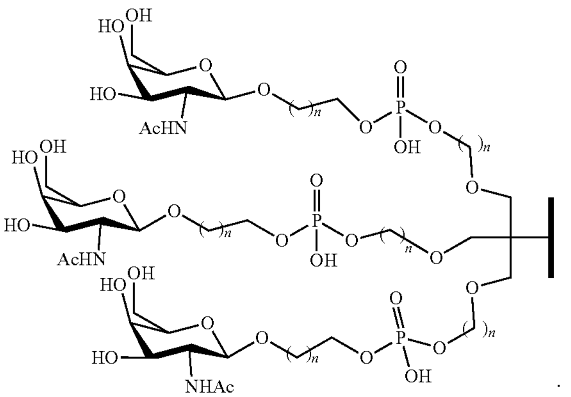
In certain such embodiments, conjugate groups have the following structure:
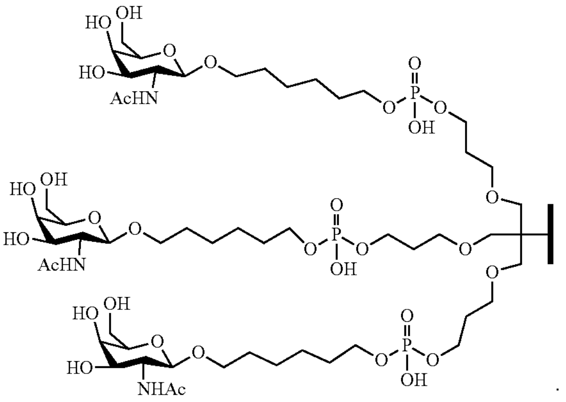
In certain such embodiments, conjugate groups have the following structure:
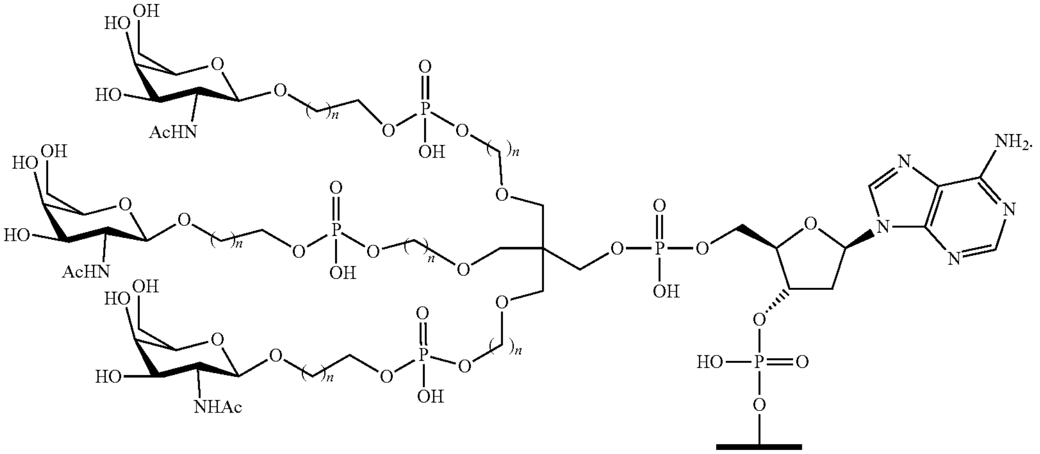

In certain such embodiments, conjugate groups have the following structure:
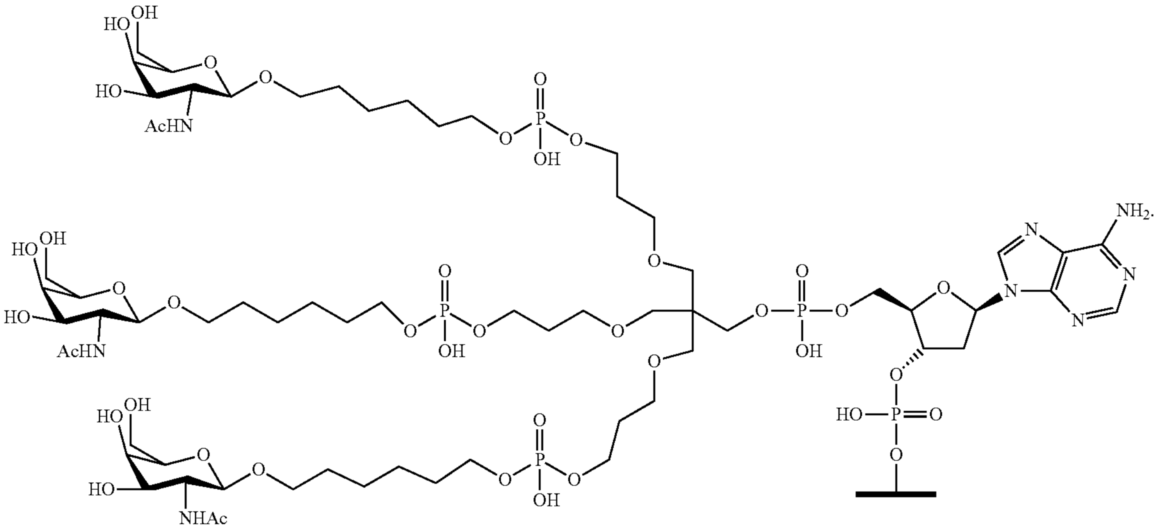
In certain such embodiments, conjugate groups have the following structure:
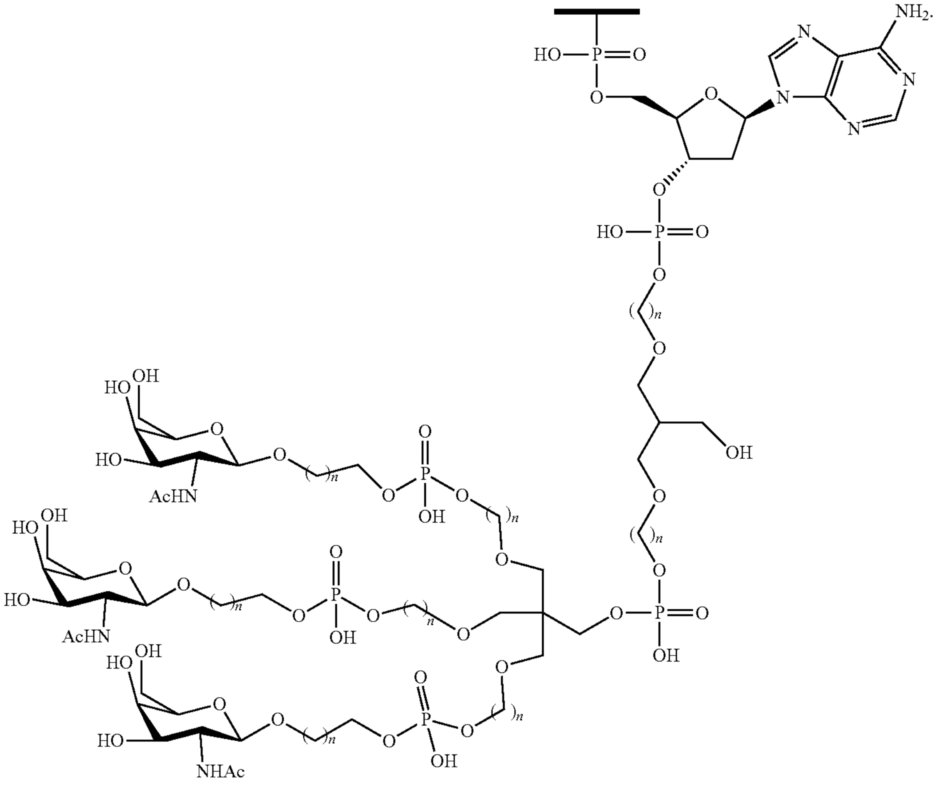

In certain such embodiments, conjugate groups have the following structure:
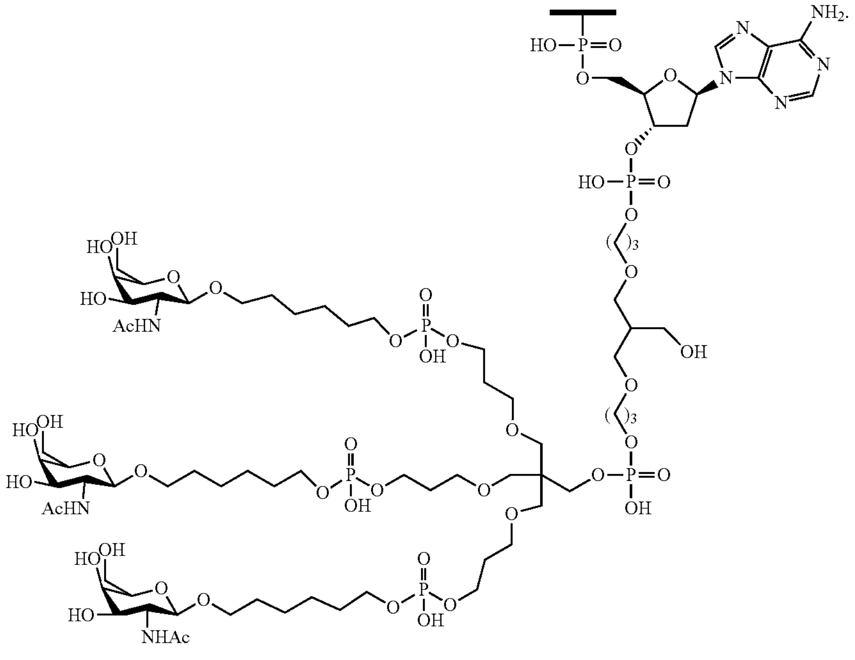
In certain embodiments, conjugates do not comprise a pyrrolidine.
In certain such embodiments, conjugate groups have the following structure:
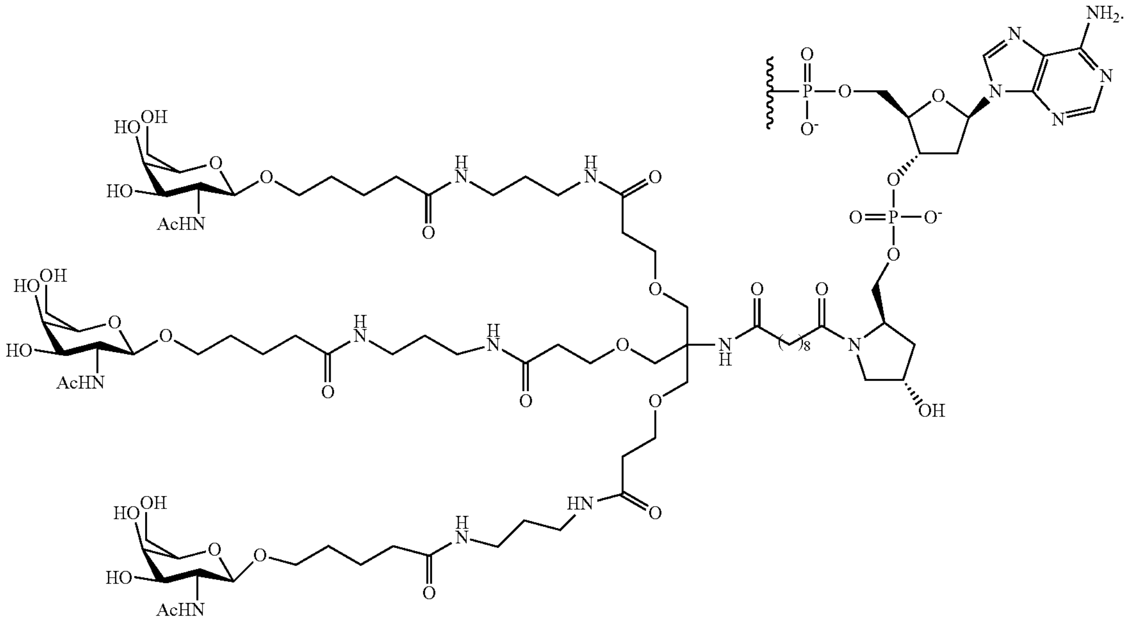

In certain such embodiments, conjugate groups have the following structure:
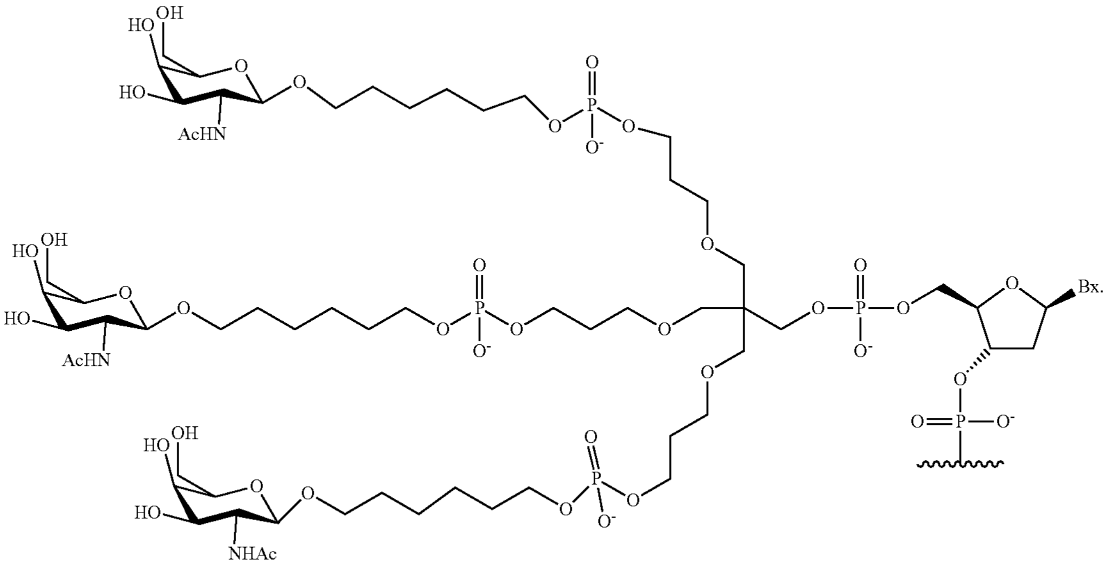
In certain such embodiments, conjugate groups have the following structure:
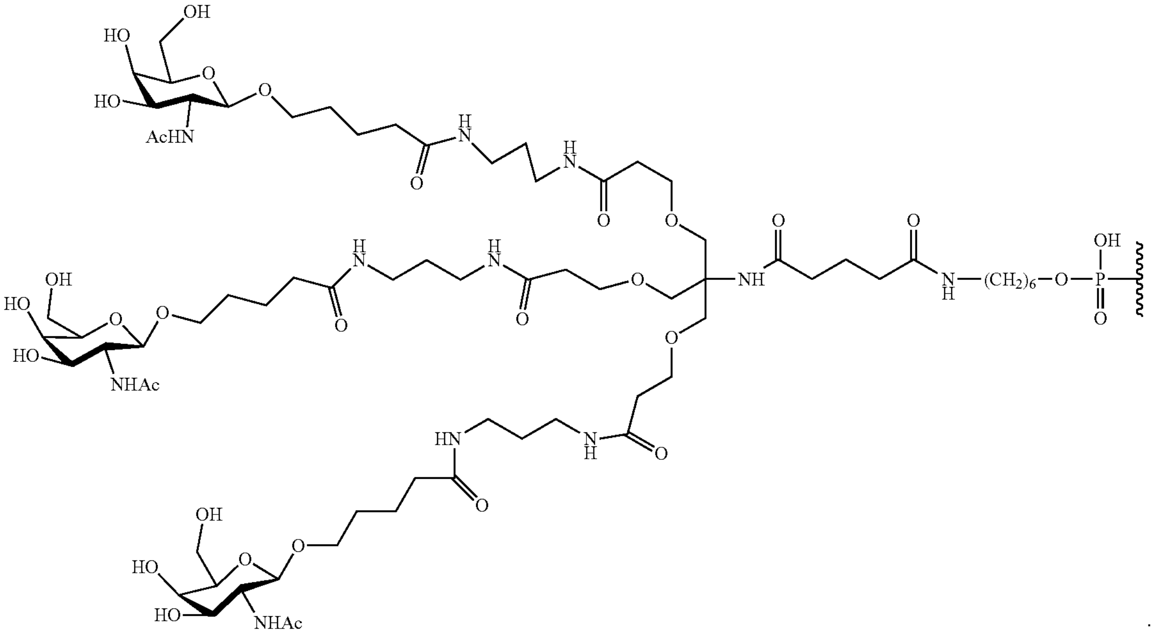

In certain such embodiments, conjugate groups have the following structure:
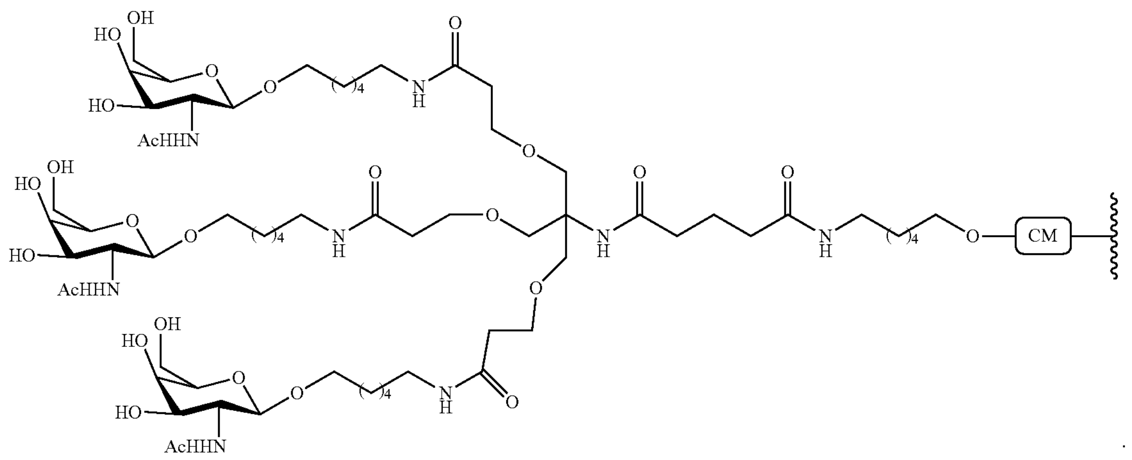
In certain such embodiments, conjugate groups have the following structure:
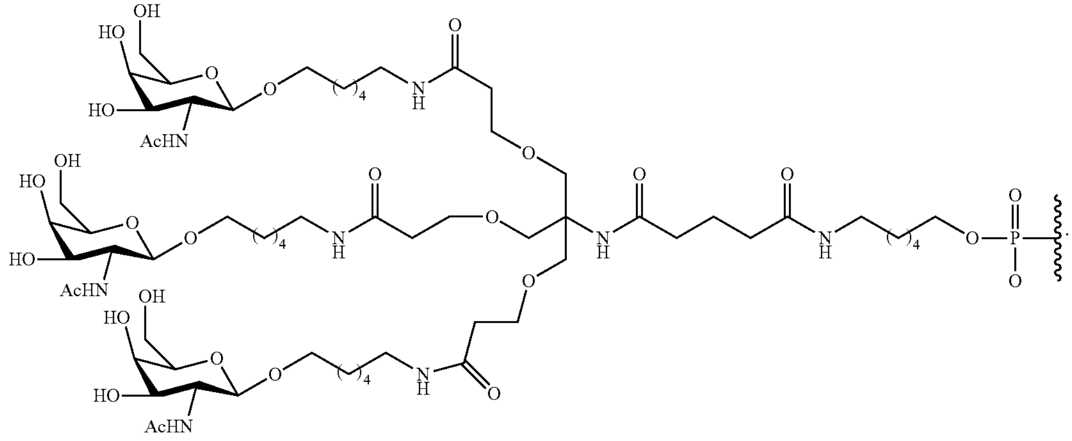

In certain such embodiments, conjugate groups have the following structure:
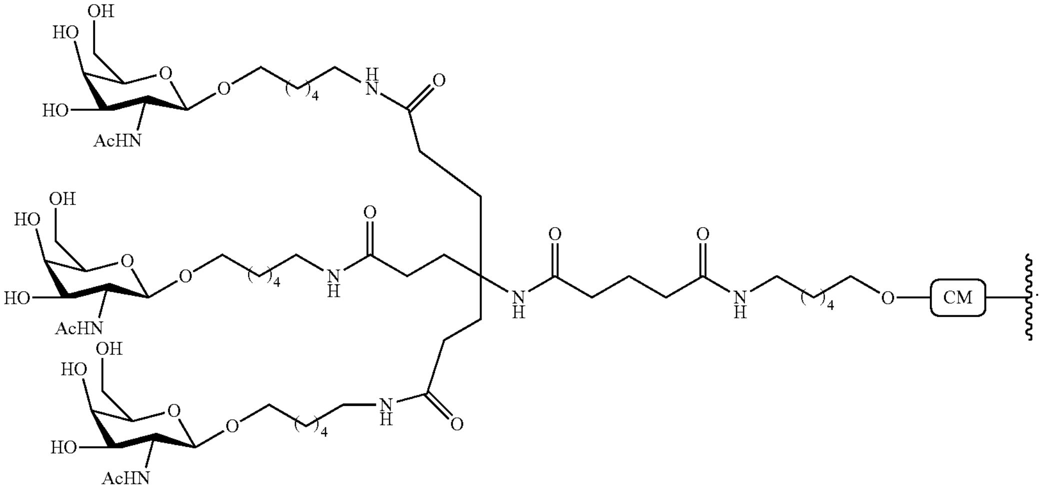
In certain such embodiments, conjugate groups have the following structure:
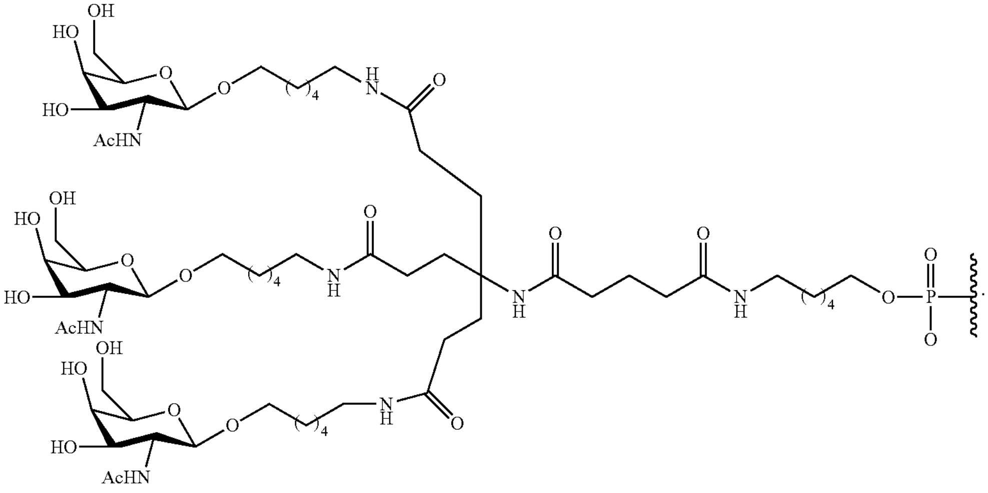

In certain such embodiments, conjugate groups have the following structure:
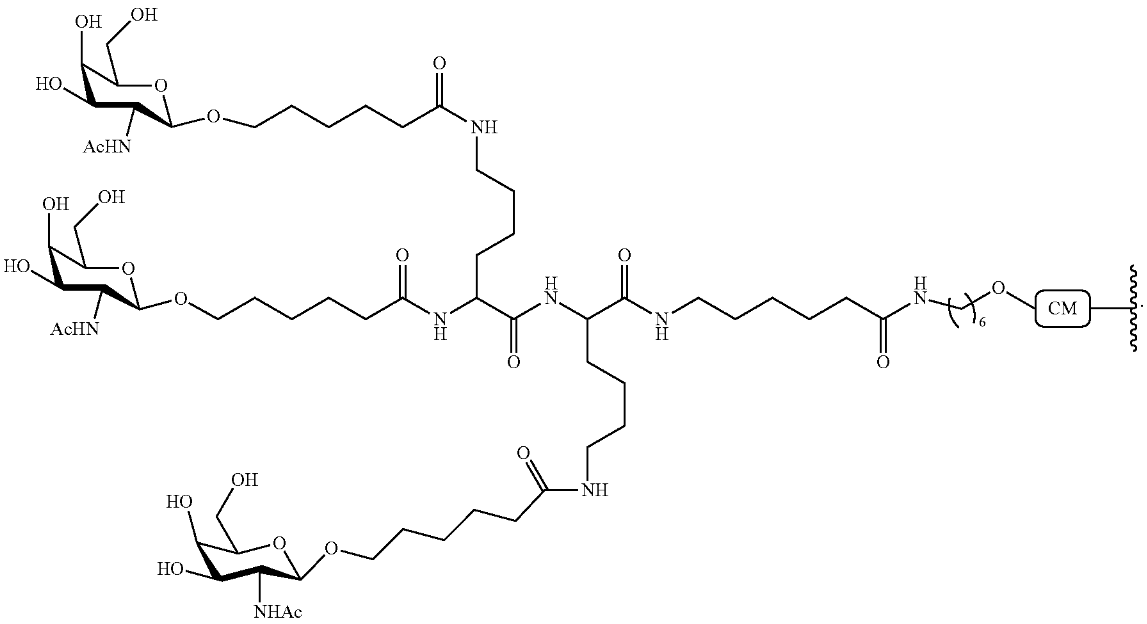
In certain such embodiments, conjugate groups have the following structure:
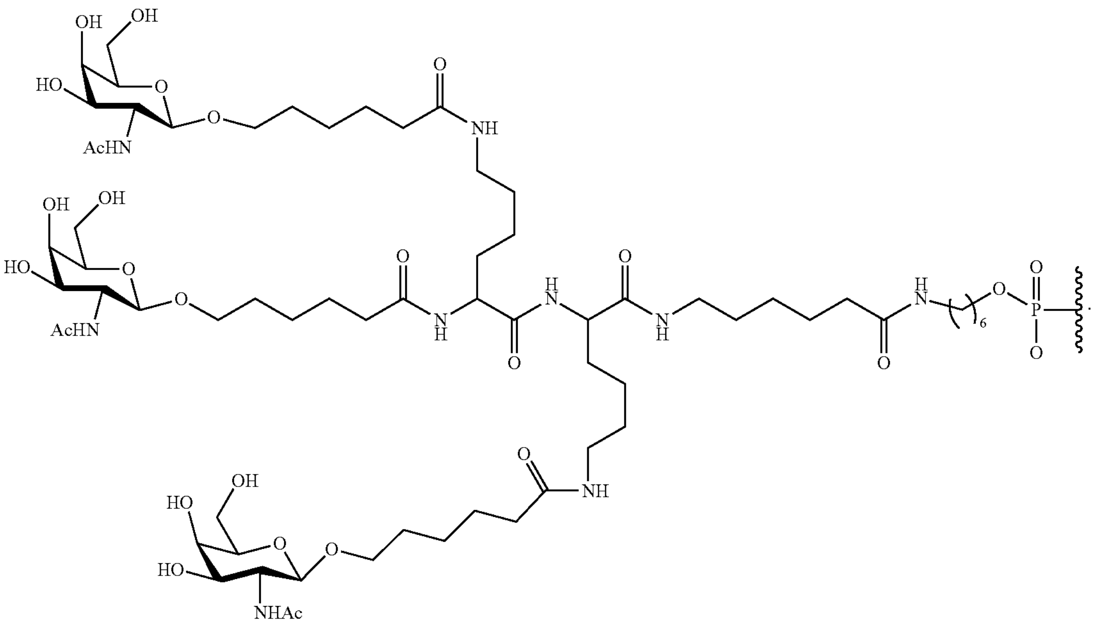

In certain such embodiments, conjugate groups have the following structure:

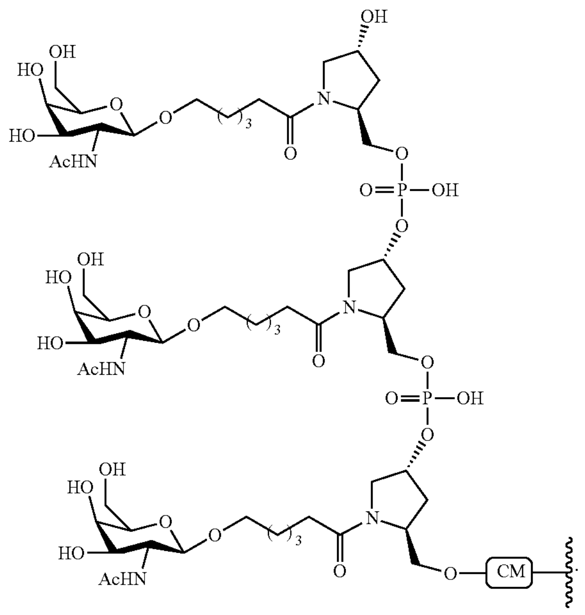

In certain such embodiments, conjugate groups have the following structure:

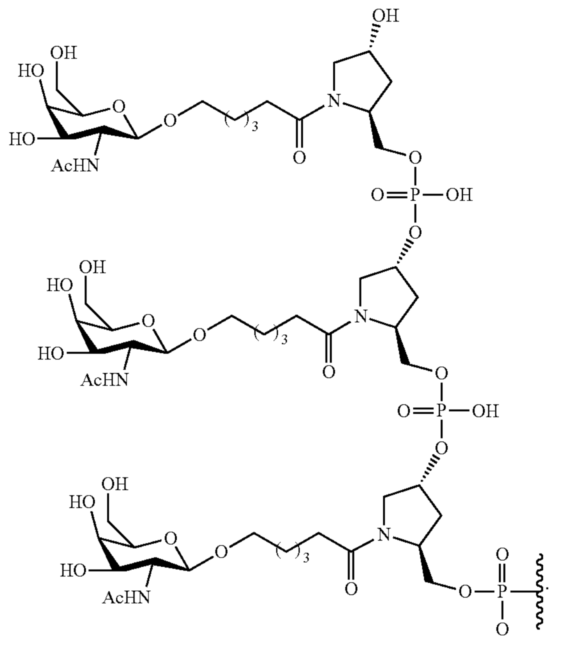

In certain embodiments, the cell-targeting moiety of the conjugate group has the following structure:

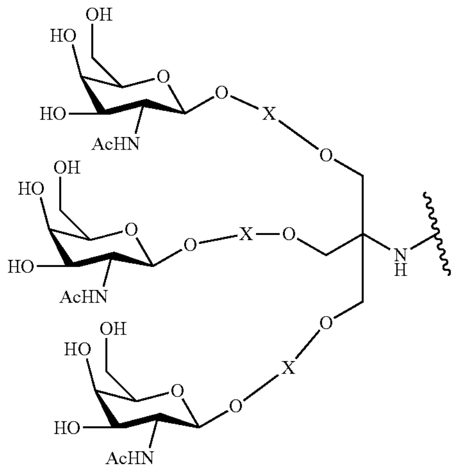

wherein X is a substituted or unsubstituted tether of six to eleven consecutively bonded atoms.

In certain embodiments, the cell-targeting moiety of the conjugate group has the following structure:

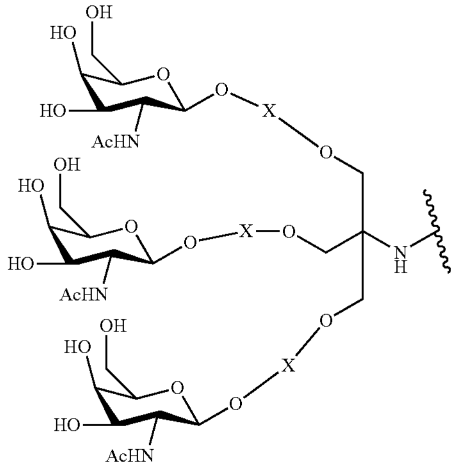

wherein X is a substituted or unsubstituted tether of ten consecutively bonded atoms.

In certain embodiments, the cell-targeting moiety of the conjugate group has the following structure:

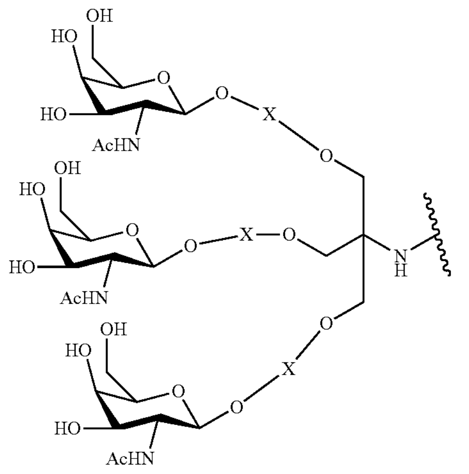

wherein X is a substituted or unsubstituted tether of four to eleven consecutively bonded atoms and wherein the tether comprises exactly one amide bond.

In certain embodiments, the cell-targeting moiety of the conjugate group has the following structure:

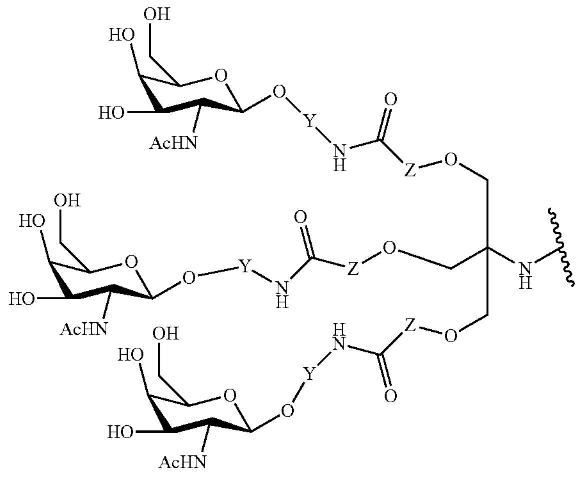

wherein Y and Z are independently selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

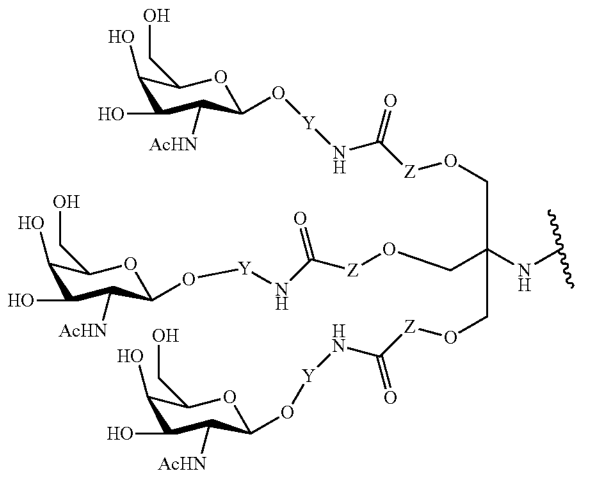

wherein Y and Z are independently selected from a $C_1$-$C_{12}$ substituted or unsubstituted alkyl group, or a group comprising exactly one ether or exactly two ethers, an amide, an amine, a piperidine, a phosphate, a phosphodiester, or a phosphorothioate.

In certain such embodiments, the cell-targeting moiety of the conjugate group has the following structure:

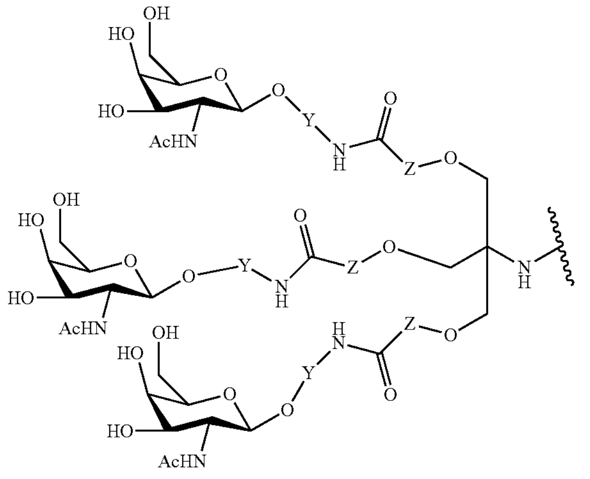

wherein Y and Z are independently selected from a $C_1$-$C_{12}$ substituted or unsubstituted alkyl group.

In certain such embodiments, the cell-targeting moiety of the conjugate group has the following structure:

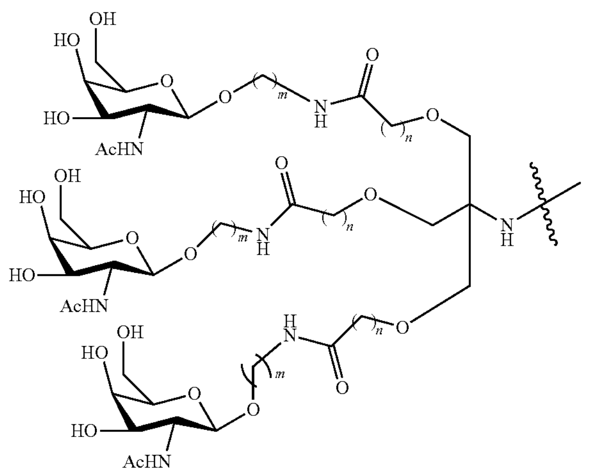

wherein m and n are independently selected from 1, 2, 3, 4, 5, 6, 7, 8, 9, 10, 11, and 12.

In certain such embodiments, the cell-targeting moiety of the conjugate group has the following structure:

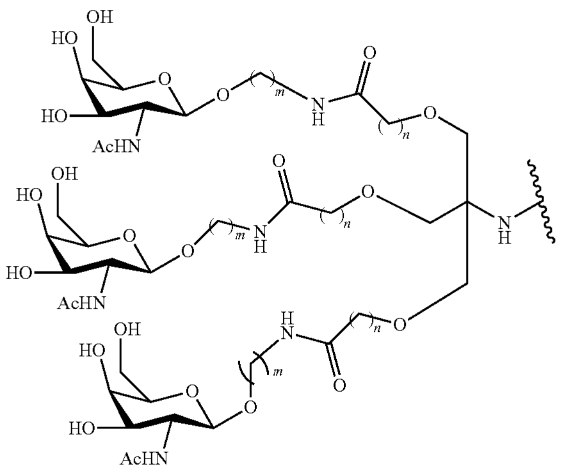

wherein m is 4, 5, 6, 7, or 8, and n is 1, 2, 3, or 4.

In certain embodiments, the cell-targeting moiety of the conjugate group has the following structure:

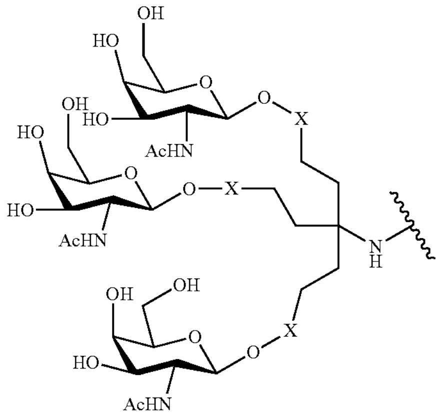

wherein X is a substituted or unsubstituted tether of four to thirteen consecutively bonded atoms, and wherein X does not comprise an ether group.

In certain embodiments, the cell-targeting moiety of the conjugate group has the following structure:

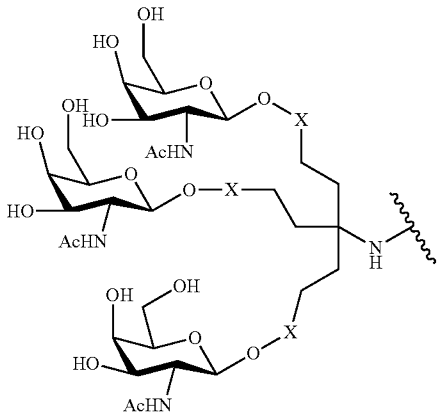

wherein X is a substituted or unsubstituted tether of eight consecutively bonded atoms, and wherein X does not comprise an ether group.

In certain embodiments, the cell-targeting moiety of the conjugate group has the following structure:

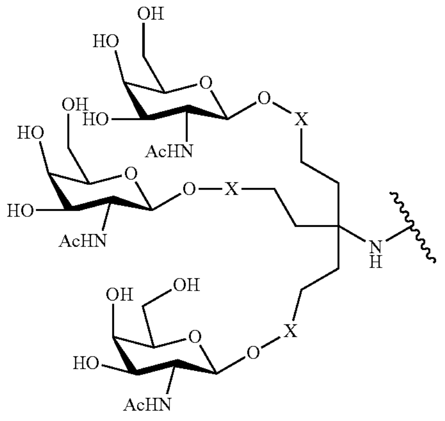

wherein X is a substituted or unsubstituted tether of four to thirteen consecutively bonded atoms, and wherein the tether comprises exactly one amide bond, and wherein X does not comprise an ether group.

In certain embodiments, the cell-targeting moiety of the conjugate group has the following structure:

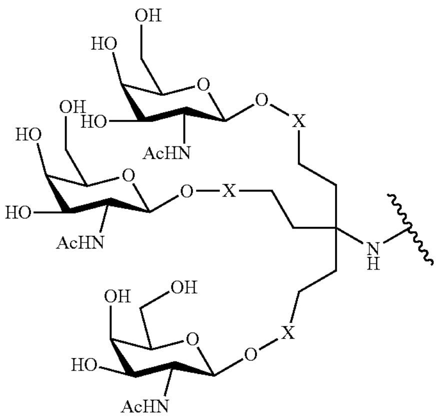

wherein X is a substituted or unsubstituted tether of four to thirteen consecutively bonded atoms and wherein the tether consists of an amide bond and a substituted or unsubstituted $C_2$-$C_{11}$ alkyl group.

In certain embodiments, the cell-targeting moiety of the conjugate group has the following structure:

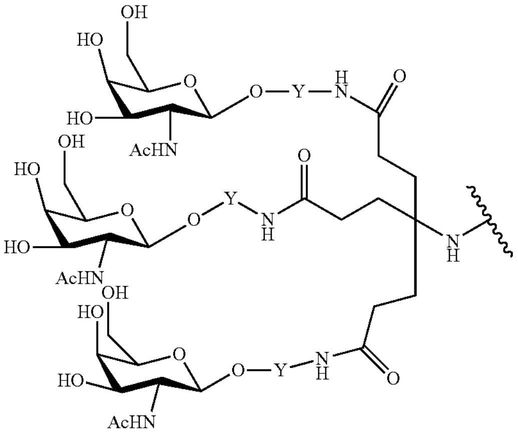

wherein Y is selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

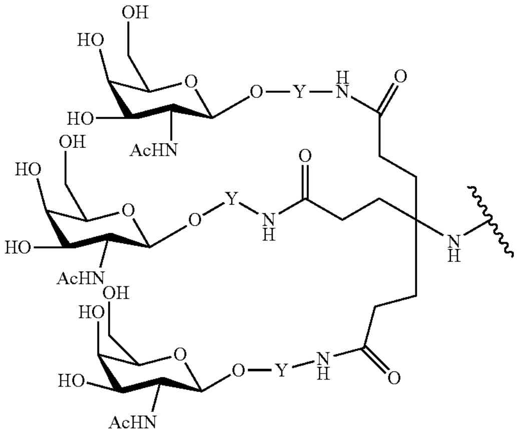

wherein Y is selected from a $C_1$-$C_{12}$ substituted or unsubstituted alkyl group, or a group comprising an ether, an amine, a piperidine, a phosphate, a phosphodiester, or a phosphorothioate.

In certain such embodiments, the cell-targeting moiety of the conjugate group has the following structure:

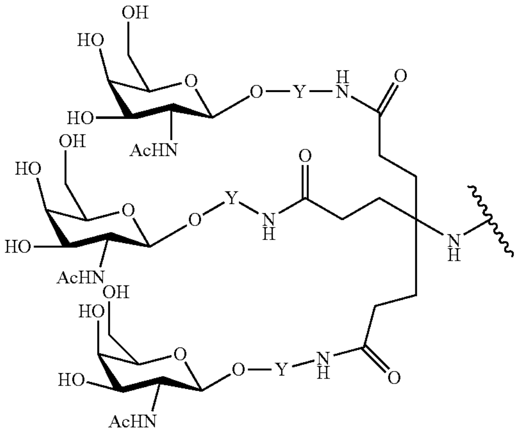

wherein Y is selected from a $C_1$-$C_{12}$ substituted or unsubstituted alkyl group.

In certain such embodiments, the cell-targeting moiety of the conjugate group has the following structure:

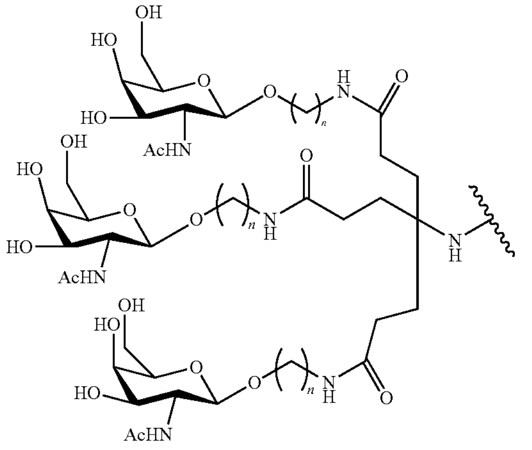

Wherein n is 1, 2, 3, 4, 5, 6, 7, 8, 9, 10, 11, or 12.

In certain such embodiments, the cell-targeting moiety of the conjugate group has the following structure:

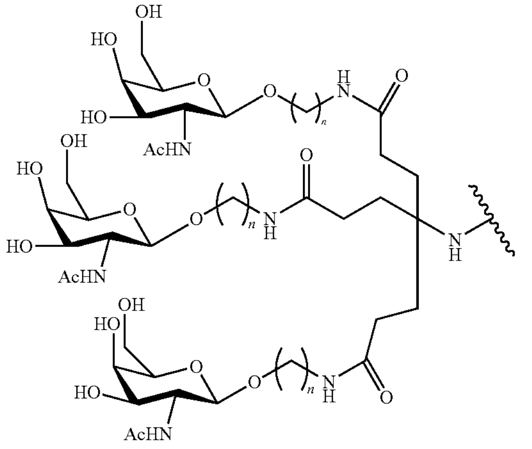

wherein n is 4, 5, 6, 7, or 8.

b. Certain Conjugated Antisense Compounds

In certain embodiments, the conjugates are bound to a nucleoside of the antisense oligonucleotide at the 2', 3', of 5' position of the nucleoside. In certain embodiments, a conjugated antisense compound has the following structure:

$$A—B—C—D\!\left(E—F\right)_q$$

wherein

A is the antisense oligonucleotide;

B is the cleavable moiety

C is the conjugate linker

D is the branching group each E is a tether;

each F is a ligand; and q is an integer between 1 and 5.

In certain embodiments, a conjugated antisense compound has the following structure:

$$A—C—D\!\left(E—F\right)_q$$

wherein

A is the antisense oligonucleotide;

C is the conjugate linker

D is the branching group each E is a tether;

each F is a ligand; and q is an integer between 1 and 5.

In certain such embodiments, the conjugate linker comprises at least one cleavable bond.

In certain such embodiments, the branching group comprises at least one cleavable bond.

In certain embodiments each tether comprises at least one cleavable bond.

In certain embodiments, the conjugates are bound to a nucleoside of the antisense oligonucleotide at the 2', 3', of 5' position of the nucleoside.

In certain embodiments, a conjugated antisense compound has the following structure:

$$A—B—C\!\left(E—F\right)_q$$

wherein

A is the antisense oligonucleotide;

B is the cleavable moiety

C is the conjugate linker each E is a tether;

each F is a ligand; and q is an integer between 1 and 5.

In certain embodiments, the conjugates are bound to a nucleoside of the antisense oligonucleotide at the 2', 3', of 5' position of the nucleoside. In certain embodiments, a conjugated antisense compound has the following structure:

$$A—C\!\left(E—F\right)_q$$

wherein

A is the antisense oligonucleotide;

C is the conjugate linker each E is a tether;

each F is a ligand; and q is an integer between 1 and 5.

In certain embodiments, a conjugated antisense compound has the following structure:

$$A—B—D\!\left(E—F\right)_q$$

wherein

A is the antisense oligonucleotide;

B is the cleavable moiety

D is the branching group each E is a tether;

each F is a ligand; and q is an integer between 1 and 5.

In certain embodiments, a conjugated antisense compound has the following structure:

$$A-D\left(E-F\right)_q$$

wherein

A is the antisense oligonucleotide;

D is the branching group each E is a tether;

each F is a ligand; and q is an integer between 1 and 5.

In certain such embodiments, the conjugate linker comprises at least one cleavable bond.

In certain embodiments each tether comprises at least one cleavable bond.

In certain embodiments, a conjugated antisense compound has a structure selected from among the following:

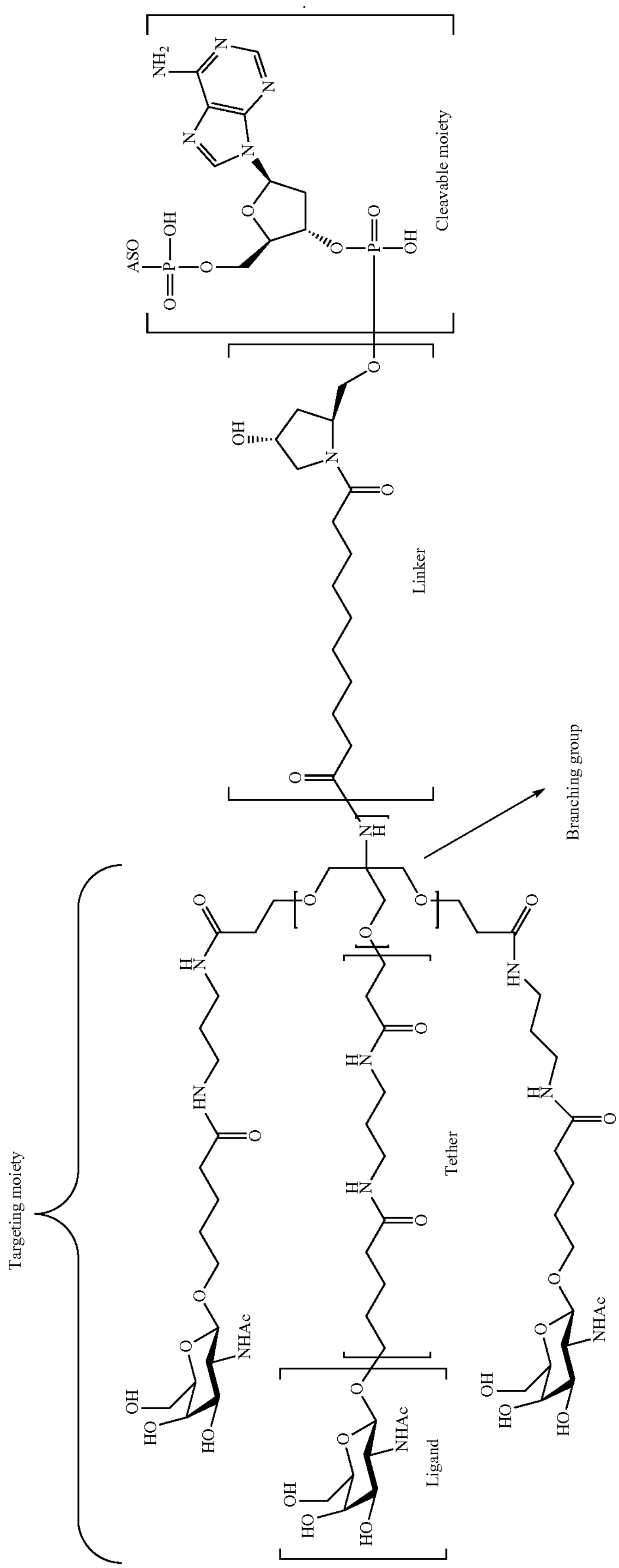
Cleavable moiety
Linker
Branching group
Tether
Ligand
Targeting moiety In certain embodiments, a conjugated antisense compound has a structure selected from among the following:
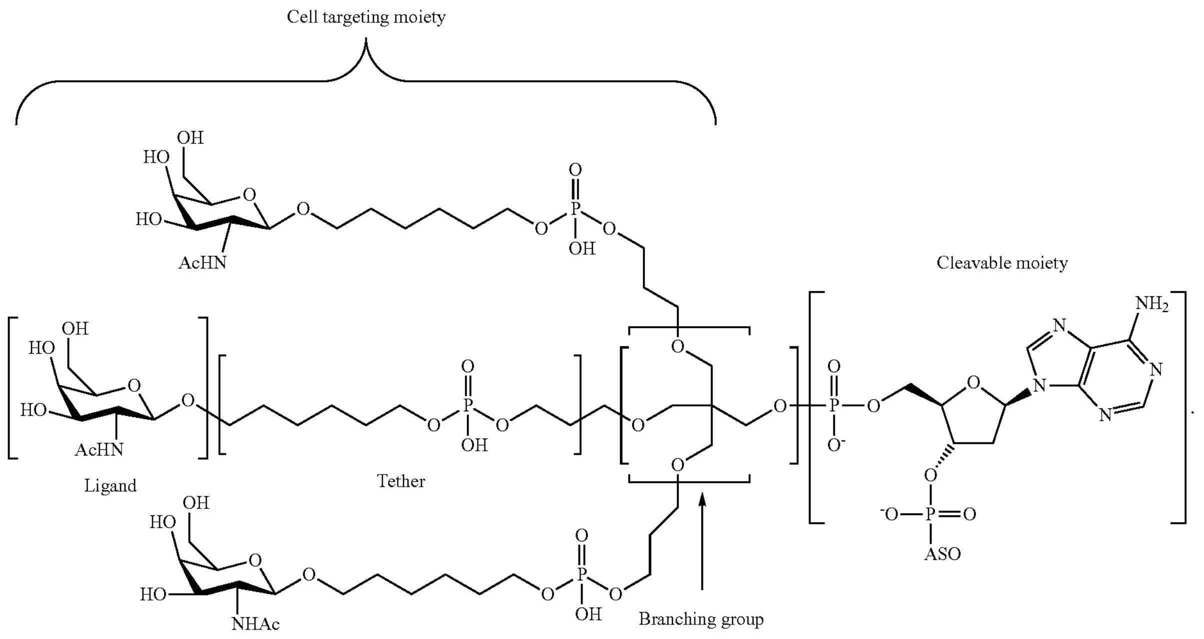
In certain embodiments, a conjugated antisense compound has a structure selected from among the following:
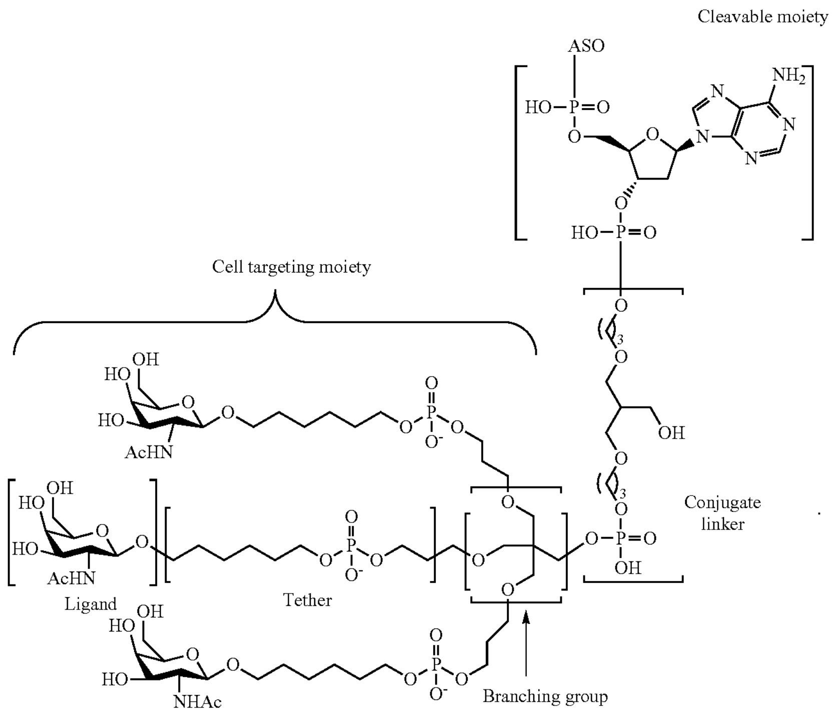

In certain embodiments, the conjugated antisense compound has the following structure:

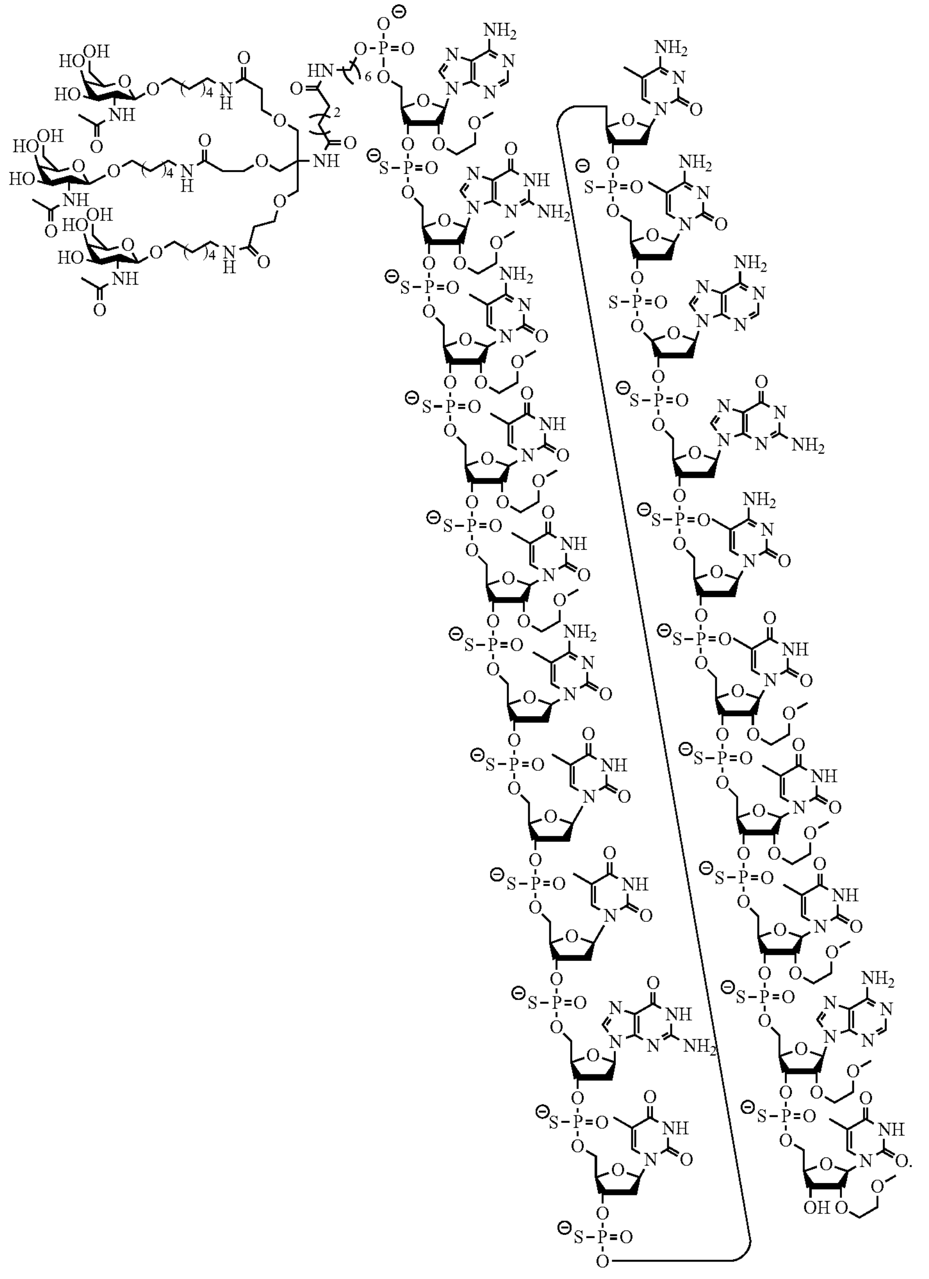

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol.

Chem. (2001) 276(40):37577-37584, RENSEN et al., “Design and Synthesis of Novel N-Acetylgalactosamine-Terminated Glycolipids for Targeting of Lipoproteins to the Hepatic Asialoglycoprotein Receptor” J. Med. Chem. (2004) 47:5798-5808, SLIEDREGT et al., “Design and Synthesis of Novel Amphiphilic Dendritic Galactosides for Selective Targeting of Liposomes to the Hepatic Asialoglycoprotein Receptor” J. Med. Chem. (1999) 42:609-618, and Valentijn et al., “Solid-phase synthesis of lysine-based cluster galactosides with high affinity for the Asialoglycoprotein Receptor” Tetrahedron, 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, *Carbohydr Res,* 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., *Analyt Biochem,* 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., *Arterioscler Thromb Vasc Biol,* 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, Antisense *Nucleic Acid Drug Dev,* 2002, 12, 103-128; Merwin et al., *Bioconjug Chem,* 1994, 5, 612-620; Tomiya et al., *Bioorg Med Chem,* 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

C. Certain Uses and Features

In certain embodiments, conjugated antisense compounds exhibit potent target RNA reduction in vivo. In certain embodiments, unconjugated antisense compounds accumulate in the kidney. In certain embodiments, conjugated antisense compounds accumulate in the liver. In certain embodiments, conjugated antisense compounds are well tolerated. Such properties render conjugated antisense compounds particularly useful for inhibition of many target RNAs, including, but not limited to those involved in metabolic, cardiovascular and other diseases, disorders or conditions. Thus, provided herein are methods of treating such diseases, disorders or conditions by contacting liver tissues with the conjugated antisense compounds targeted to RNAs associated with such diseases, disorders or conditions. Thus, also provided are methods for ameliorating any of a variety of metabolic, cardiovascular and other diseases, disorders or conditions with the conjugated antisense compounds of the present invention.

In certain embodiments, conjugated antisense compounds are more potent than unconjugated counterpart at a particular tissue concentration. Without wishing to be bound by any theory or mechanism, in certain embodiments, the conjugate may allow the conjugated antisense compound to enter the cell more efficiently or to enter the cell more productively. For example, in certain embodiments conjugated antisense compounds may exhibit greater target reduction as compared to its unconjugated counterpart wherein both the conjugated antisense compound and its unconjugated counterpart are present in the tissue at the same concentrations. For example, in certain embodiments conjugated antisense compounds may exhibit greater target reduction as compared to its unconjugated counterpart wherein both the conjugated antisense compound and its unconjugated counterpart are present in the liver at the same concentrations.

Productive and non-productive uptake of oligonucleotides has been discussed previously (See e.g. Geary, R. S., E. Wancewicz, et al. (2009). “Effect of Dose and Plasma Concentration on Liver Uptake and Pharmacologic Activity of a 2'-Methoxyethyl Modified Chimeric Antisense Oligonucleotide Targeting PTEN.” Biochem. Pharmacol. 78(3): 284-91; & Koller, E., T. M. Vincent, et al. (2011). “Mechanisms of single-stranded phosphorothioate modified antisense oligonucleotide accumulation in hepatocytes.” Nucleic Acids Res. 39(11): 4795-807). Conjugate groups described herein may improve productive uptake.

In certain embodiments, the conjugate groups described herein may further improve potency by increasing the affinity of the conjugated antisense compound for a particular type of cell or tissue. In certain embodiments, the conjugate groups described herein may further improve potency by increasing recognition of the conjugated antisense compound by one or more cell-surface receptors. In certain embodiments, the conjugate groups described herein may further improve potency by facilitating endocytosis of the conjugated antisense compound.

In certain embodiments, the cleavable moiety may further improve potency by allowing the conjugate to be cleaved from the antisense oligonucleotide after the conjugated antisense compound has entered the cell. Accordingly, in certain embodiments, conjugated antisense compounds can be administered at doses lower than would be necessary for unconjugated antisense oligonucleotides.

Phosphorothioate linkages have been incorporated into antisense oligonucleotides previously. Such phosphorothioate linkages are resistant to nucleases and so improve stability of the oligonucleotide. Further, phosphorothioate linkages also bind certain proteins, which results in accumulation of antisense oligonucleotide in the liver. Oligonucleotides with fewer phosphorothioate linkages accumulate less in the liver and more in the kidney (see, for example, Geary, R., "Pharmacokinetic Properties of 2'-O-(2-Methoxyethyl)-Modified Oligonucleotide Analogs in Rats," *Journal of Pharmacology and Experimental Therapeutics*, Vol. 296, No. 3, 890-897; & *Pharmacological Properties of* 2'-*O-Methoxyethyl Modified Oligonucleotides* in Antisense a Drug Technology, Chapter 10, Crooke, S. T., ed., 2008) In certain embodiments, oligonucleotides with fewer phosphorothioate internucleoside linkages and more phosphodiester internucleoside linkages accumulate less in the liver and more in the kidney. When treating diseases in the liver, this is undesirable for several reasons (1) less drug is getting to the site of desired action (liver); (2) drug is escaping into the urine; and (3) the kidney is exposed to relatively high concentration of drug which can result in toxicities in the kidney. Thus, for liver diseases, phosphorothioate linkages provide important benefits.

In certain embodiments, however, administration of oligonucleotides uniformly linked by phosphoro-thioate internucleoside linkages induces one or more proinflammatory reactions. (see for example: *J Lab Clin Med.* 1996 September; 128(3):329-38. "Amplification of antibody production by phosphorothioate oligodeoxynucleotides". Branda et al.; and see also for example: *Toxicologic Properties* in Antisense a Drug Technology, Chapter 12, pages 342-351, Crooke, S. T., ed., 2008). In certain embodiments, administration of oligonucleotides wherein most of the internucleoside linkages comprise phosphorothioate internucleoside linkages induces one or more proinflammatory reactions.

In certain embodiments, the degree of proinflammatory effect may depend on several variables (e.g. backbone modification, off-target effects, nucleobase modifications, and/or nucleoside modifications) see for example: *Toxicologic Properties* in Antisense a Drug Technology, Chapter 12, pages 342-351, Crooke, S. T., ed., 2008). In certain embodiments, the degree of proinflammatory effect may be mitigated by adjusting one or more variables. For example the degree of proinflammatory effect of a given oligonucleotide may be mitigated by replacing any number of phosphorothioate internucleoside linkages with phosphodiester internucleoside linkages and thereby reducing the total number of phosphorothioate internucleoside linkages.

In certain embodiments, it would be desirable to reduce the number of phosphorothioate linkages, if doing so could be done without losing stability and without shifting the distribution from liver to kidney. For example, in certain embodiments, the number of phosphorothioate linkages may be reduced by replacing phosphorothioate linkages with phosphodiester linkages. In such an embodiment, the antisense compound having fewer phosphorothioate linkages and more phosphodiester linkages may induce less proinflammatory reactions or no proinflammatory reaction. Although the antisense compound having fewer phosphorothioate linkages and more phosphodiester linkages may induce fewer proinflammatory reactions, the antisense compound having fewer phosphorothioate linkages and more phosphodiester linkages may not accumulate in the liver and may be less efficacious at the same or similar dose as compared to an antisense compound having more phosphorothioate linkages. In certain embodiments, it is therefore desirable to design an antisense compound that has a plurality of phosphodiester bonds and a plurality of phosphorothioate bonds but which also possesses stability and good distribution to the liver.

In certain embodiments, conjugated antisense compounds accumulate more in the liver and less in the kidney than unconjugated counterparts, even when some of the phosporothioate linkages are replaced with less proinflammatory phosphodiester internucleoside linkages. In certain embodiments, conjugated antisense compounds accumulate more in the liver and are not excreted as much in the urine compared to its unconjugated counterparts, even when some of the phosporothioate linkages are replaced with less proinflammatory phosphodiester internucleoside linkages. In certain embodiments, the use of a conjugate allows one to design more potent and better tolerated antisense drugs. Indeed, in certain embodiments, conjugated antisense compounds have larger therapeutic indexes than unconjugated counterparts. This allows the conjugated antisense compound to be administered at a higher absolute dose, because there is less risk of proinflammatory response and less risk of kidney toxicity. This higher dose, allows one to dose less frequently, since the clearance (metabolism) is expected to be similar. Further, because the compound is more potent, as described above, one can allow the concentration to go lower before the next dose without losing therapeutic activity, allowing for even longer periods between dosing.

In certain embodiments, the inclusion of some phosphorothioate linkages remains desirable. For example, the terminal linkages are vulnerable to exonucleases and so in certain embodiments, those linkages are phosphorothioate or other modified linkage. Internucleoside linkages linking two deoxynucleosides are vulnerable to endonucleases and so in certain embodiments those linkages are phosphorothioate or other modified linkage. Internucleoside linkages between a modified nucleoside and a deoxynucleoside where the deoxynucleoside is on the 5' side of the linkage deoxynucleosides are vulnerable to endonucleases and so in certain embodiments those linkages are phosphorothioate or other modified linkage. Internucleoside linkages between two modified nucleosides of certain types and between a deoxynucleoside and a modified nucleoside of certain type where the modified nucleoside is at the 5' side of the linkage are sufficiently resistant to nuclease digestion, that the linkage can be phosphodiester.

In certain embodiments, the antisense oligonucleotide of a conjugated antisense compound comprises fewer than 16 phosphorthioate linkages. In certain embodiments, the antisense oligonucleotide of a conjugated antisense compound comprises fewer than 15 phosphorthioate linkages. In certain embodiments, the antisense oligonucleotide of a conjugated antisense compound comprises fewer than 14 phosphorthioate linkages. In certain embodiments, the antisense oligonucleotide of a conjugated antisense compound comprises fewer than 13 phosphorthioate linkages. In certain embodiments, the antisense oligonucleotide of a conjugated antisense compound comprises fewer than 12 phosphorthioate linkages. In certain embodiments, the antisense oligonucleotide of a conjugated antisense compound comprises fewer than 11 phosphorthioate linkages. In certain embodiments, the antisense oligonucleotide of a conjugated antisense compound comprises fewer than 10 phosphorthioate linkages. In certain embodiments, the antisense oligonucleotide of a conjugated antisense compound comprises fewer than 9 phosphorthioate linkages. In certain embodiments, the antisense oligonucleotide of a conjugated antisense compound comprises fewer than 8 phosphorthioate linkages.

In certain embodiments, antisense compounds comprising one or more conjugate group described herein has increased activity and/or potency and/or tolerability compared to a parent antisense compound lacking such one or more conjugate group. Accordingly, in certain embodiments, attachment of such conjugate groups to an oligonucleotide is desirable. Such conjugate groups may be attached at the 5'-, and/or 3'-end of an oligonucleotide. In certain instances, attachment at the 5'-end is synthetically desirable. Typically, oligonucleotides are synthesized by attachment of the 3' terminal nucleoside to a solid support and sequential coupling of nucleosides from 3' to 5' using techniques that are well known in the art. Accordingly if a conjugate group is desired at the 3'-terminus, one may (1) attach the conjugate group to the 3'-terminal nucleoside and attach that conjugated nucleoside to the solid support for subsequent preparation of the oligonucleotide or (2) attach the conjugate group to the 3'-terminal nucleoside of a completed oligonucleotide after synthesis. Neither of these approaches is very efficient and thus both are costly. In particular, attachment of the conjugated nucleoside to the solid support, while demonstrated in the Examples herein, is an inefficient process. In certain embodiments, attaching a conjugate group to the 5'-terminal nucleoside is synthetically easier than attachment at the 3'-end. One may attach a non-conjugated 3' terminal nucleoside to the solid support and prepare the oligonucleotide using standard and well characterized reactions. One then needs only to attach a 5'nucleoside having a conjugate group at the final coupling step. In certain embodiments, this is more efficient than attaching a conjugated nucleoside directly to the solid support as is typically done to prepare a 3'-conjugated oligonucleotide. The Examples herein demonstrate attachment at the 5'-end. In addition, certain conjugate groups have synthetic advantages. For Example, certain conjugate groups comprising phosphorus linkage groups are synthetically simpler and more efficiently prepared than other conjugate groups, including conjugate groups reported previously (e.g., WO/2012/037254).

In certain embodiments, conjugated antisense compounds are administered to a subject. In such embodiments, antisense compounds comprising one or more conjugate group described herein has increased activity and/or potency and/or tolerability compared to a parent antisense compound lacking such one or more conjugate group. Without being bound by mechanism, it is believed that the conjugate group helps with distribution, delivery, and/or uptake into a target cell or tissue. In certain embodiments, once inside the target cell or tissue, it is desirable that all or part of the conjugate group to be cleaved to release the active oligonucleotide. In certain embodiments, it is not necessary that the entire conjugate group be cleaved from the oligonucleotide. For example, in Example 20 a conjugated oligonucleotide was administered to mice and a number of different chemical species, each comprising a different portion of the conjugate group remaining on the oligonucleotide, were detected (Table 23a). This conjugated antisense compound demonstrated good potency (Table 23). Thus, in certain embodiments, such metabolite profile of multiple partial cleavage of the conjugate group does not interfere with activity/potency. Nevertheless, in certain embodiments it is desirable that a prodrug (conjugated oligonucleotide) yield a single active compound. In certain instances, if multiple forms of the active compound are found, it may be necessary to determine relative amounts and activities for each one. In certain embodiments where regulatory review is required (e.g., USFDA or counterpart) it is desirable to have a single (or predominantly single) active species. In certain such embodiments, it is desirable that such single active species be the antisense oligonucleotide lacking any portion of the conjugate group. In certain embodiments, conjugate groups at the 5'-end are more likely to result in complete metabolism of the conjugate group. Without being bound by mechanism it may be that endogenous enzymes responsible for metabolism at the 5' end (e.g., 5' nucleases) are more active/efficient than the 3' counterparts. In certain embodiments, the specific conjugate groups are more amenable to metabolism to a single active species. In certain embodiments, certain conjugate groups are more amenable to metabolism to the oligonucleotide.

D. Antisense

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, antisense compounds comprise a portion having a nucleobase sequence at least 70% complementary to the nucleobase sequence of a target nucleic acid. In certain embodiments, antisense compounds comprise a portion having a nucleobase sequence at least 80% complementary to the nucleobase sequence of a target nucleic acid. In certain embodiments, antisense compounds comprise a portion having a nucleobase sequence at least 90% complementary to the nucleobase sequence of a target nucleic acid. In certain embodiments, antisense compounds comprise a portion having a nucleobase sequence at least 95% complementary to the nucleobase sequence of a target nucleic acid. In certain embodiments, antisense compounds comprise a portion having a nucleobase sequence at least 98% complementary to the nucleobase sequence of a target nucleic acid. In certain embodiments, antisense compounds comprise a portion having a nucleobase sequence that is 100% complementary to the nucleobase sequence of a target nucleic acid. In certain embodiments, antisense compounds are at least 70%, 80%, 90%, 95%, 98%, or 100% complementary to the nucleobase sequence of a target nucleic acid over the entire length of the antisense compound.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or polyadenylation of the target nucleic acid or of a nucleic acid with which the target nucleic acid may otherwise interact.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, oligonucleotides comprising conjugates described herein are RNAi compounds. In certain embodiments, oligomeric oligonucleotides comprising conjugates described herein are ssRNA compounds. In certain embodiments, oligonucleotides comprising conjugates described herein are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligonucleotides comprising conjugates described herein is the antisense strand in an siRNA compound. In certain embodiments, the oligonucleotides comprising conjugates described herein is the sense strand in an siRNA compound. In embodiments in which the conjugated oligomeric compound is double-stranded siRnA, the conjugate may be on the sense strand, the antisense strand or both the sense strand and the antisense strand.

D. Ayoligorotein C-III (anoCIII)

In certain embodiments, conjugated antisense compounds target any ApoCIII nucleic acid. In certain embodiments, the target nucleic acid encodes an ApoCIII target protein that is clinically relevant. In such embodiments, modulation of the target nucleic acid results in clinical benefit.

The targeting process usually includes determination of at least one target region, segment, or site within the target nucleic acid for the antisense interaction to occur such that the desired effect will result.

In certain embodiments, a target region is a structurally defined region of the nucleic acid. For example, in certain such embodiments, a target region may encompass a 3' UTR, a 5' UTR, an exon, an intron, a coding region, a translation initiation region, translation termination region, or other defined nucleic acid region or target segment.

In certain embodiments, a target segment is at least about an 8-nucleobase portion of a target region to which a conjugated antisense compound is targeted. Target segments can include DNA or RNA sequences that comprise at least 8 consecutive nucleobases from the 5'-terminus of one of the target segments (the remaining nucleobases being a consecutive stretch of the same DNA or RNA beginning immediately upstream of the 5'-terminus of the target segment and continuing until the DNA or RNA comprises about 8 to about 30 nucleobases). Target segments are also represented by DNA or RNA sequences that comprise at least 8 consecutive nucleobases from the 3'-terminus of one of the target segments (the remaining nucleobases being a consecutive stretch of the same DNA or RNA beginning immediately downstream of the 3'-terminus of the target segment and continuing until the DNA or RNA comprises about 8 to about 30 nucleobases). Target segments can also be represented by DNA or RNA sequences that comprise at least 8 consecutive nucleobases from an internal portion of the sequence of a target segment, and may extend in either or both directions until the conjugated antisense compound comprises about 8 to about 30 nucleobases.

In certain embodiments, antisense compounds targeted to an ApoCIII nucleic acid can be modified as described herein. In certain embodiments, the antisense compounds can have a modified sugar moiety, an unmodified sugar moiety or a mixture of modified and unmodified sugar moieties as described herein. In certain embodiments, the antisense compounds can have a modified internucleoside linkage, an unmodified internucleoside linkage or a mixture of modified and unmodified internucleoside linkages as described herein. In certain embodiments, the antisense compounds can have a modified nucleobase, an unmodified nucleobase or a mixture of modified and unmodified nucleobases as described herein. In certain embodiments, the antisense compounds can have a motif as described herein.

In certain embodiments, antisense compounds targeted to ApoCIII nucleic acids can be conjugated as described herein.

ApoCIII is a constituent of HDL and of triglyceride (TG)-rich lipoproteins. Elevated ApoCIII levels are associated with elevated TG levels and diseases such as cardiovascular disease, metabolic syndrome, obesity and diabetes. Elevated TG levels are associated with pancreatitis. ApoCIII slows clearance of TG-rich lipoproteins by inhibiting lipolysis through inhibition of lipoprotein lipase (LPL) and through interfering with lipoprotein binding to cell-surface glycosaminoglycan matrix. Antisense compounds targeting ApoCIII have been previously disclosed in WO2004/093783 and WO2012/149495, each herein incorporated by reference in its entirety.

Certain Conjugated Antisense Compounds Targeted to an ApoCIII Nucleic Acid

In certain embodiments, conjugated antisense compounds are targeted to an ApoCIII nucleic acid having the sequence of any of GENBANK® Accession No. NM_000040.1 (incorporated herein as SEQ ID NO: 1); GENBANK Accession No. NT_033899.8 truncated from nucleotides 20262640 to 20266603 (incorporated herein as SEQ ID NO: 2); and GenBank Accession No. NT_035088.1 truncated from nucleotides 6238608 to U.S. Pat. No. 6,242,565 (incorporated herein as SEQ ID NO: 3). In certain such embodiments, a conjugated antisense compound is at least 90%, at least 95%, or 100% complementary to any of SEQ ID NOs: 1-3.

In certain embodiments, a conjugated antisense compound targeted to SEQ ID NO: 1 comprises an at least 8 consecutive nucleobase sequence of SEQ ID NO: 87. In certain embodiments, a conjugated antisense compound targeted to SEQ ID NO: 1 comprises a nucleobase sequence of SEQ ID NO: 87.

TABLE A

| Antisense Compounds targeted to ApoCIII SEQ ID NO: 1 | | | | |
|---|---|---|---|---|
| ISIS No | Target Start Site | Sequence (5′-3′) | Motif | SEQ ID NO |
| 304801 | 508 | AGCTTCTTGTCCAGCT TTAT | eeeeeddddddddd deeeee | 87 |
| 647535 | 508 | AGCTTCTTGTCCAGCT TTAT | eeeeeddddddddd deeeeeod | 87 |
| 616468 | 508 | AGCTTCTTGTCCAGCT TTAT | eeeeeddddddddd deeeee | 87 |
| 647536 | 508 | AGCTTCTTGTCCAGCT TTAT | eeoeoeoeoddddd dddddeoeoeeeod | 87 |

ApoCIII Therapeutic Indications

In certain embodiments, the invention provides methods for using a conjugated antisense compound targeted to an ApoCIII nucleic acid for modulating the expression of ApoCIII in a subject. In certain embodiments, the expression of ApoCIII is reduced.

In certain embodiments, the invention provides methods for using a conjugated antisense compound targeted to an ApoCIII nucleic acid in a pharmaceutical composition for treating a subject. In certain embodiments, the subject has a cardiovascular and/or metabolic disease, disorder or condition. In certain embodiments, the subject has hypertriglyceridemia, non-familial hypertriglyceridemia, familial hypertriglyceridemia, heterozygous familial hypertriglyceridemia, homozygous familial hypertriglyceridemia, mixed dyslipidemia, atherosclerosis, a risk of developing atherosclerosis, coronary heart disease, a history of coronary heart disease, early onset coronary heart disease, one or more risk factors for coronary heart disease, type II diabetes, type II diabetes with dyslipidemia, dyslipidemia, hyperlipidemia, hypercholesterolemia, hyper fatty acidemia, hepatic steatosis, non-alcoholic steatohepatitis, pancreatitis and/or non-alcoholic fatty liver disease.

In certain embodiments, the invention provides methods for using a conjugated antisense compound targeted to an ApoCIII nucleic acid in the preparation of a medicament.

E. Certain Nucleic Acid GalNAc Conjugates

In certain embodiments, conjugated antisense compounds comprise antisense compounds having the nucleobase sequence and modifications of the antisense compounds in the Table below attached to a GalNAc conjugate. All internucleoside linkages are phosphorothioate internucleoside linkages unless otherwise indicated. A subscript "1" indicates an LNA bicyclic nucleoside. A subscript "d" indicates a 2'-deoxy nucleoside. A subscript "e" indicates a 2'-MOE modified nucleoside. A "V" indicates a 2-amino-2'-deoxyadenosine.

TABLE B

| Sequence 5′ to 3′ | Motif | Chemistry | Inte mucleo side Linkages | SEQ ID NO. |
|---|---|---|---|---|
| $T_lG_lG_lC_dA_dA_dG_dC_dA_dT_dC_dC_dT_lG_lT_lA_d$ | 3-9-3-1 | LNA/deoxy | phosphorothioate | 222 |
| $C_lT_lC_lA_lA_dT_dC_dC_dA_dT_dG_dG_dC_lA_lG_lC_d$ | 4-8-3-1 | LNA/deoxy | phosphorothioate | 223 |
| $A_lC_lC_lA_dA_dG_dT_dT_dT_dC_dT_dT_dC_dA_lG_lC_l$ | 3-10-3 | LNA/deoxy | phosphorothioate | 224 |
| $G_lC_lA_dT_dT_dG_dG_dT_dA_dT_dT_lC_lA_l$ | 2-8-3 | LNA/deoxy | phosphorothioate | 225 |
| $T_lT_lC_lA_lG_lC_dA_dT_dT_dG_dG_dT_dA_dT_dT_dC_lA_lG_lT_lG_l$ | 5-10-5 | LNA/deoxy | phosphorothioate | 226 |
| $C_lA_lG_lC_dA_dT_dT_dG_dG_dT_dA_dT_dT_lC_lA_lG_d$ | 3-10-3 | LNA/deoxy | phosphorothioate | 227 |
| $C_lA_lG_lC_dA_dT_dT_dG_dG_dT_dA_dT_dT_lC_lA_l$ | 3-9-3 | LNA/deoxy | phosphorothioate | 228 |
| $A_lG_lC_lA_dT_dT_dG_dG_dT_dA_dT_dT_lC_lA_l$ | 3-8-3 | LNA/deoxy | phosphorothioate | 229 |
| $G_lC_lA_dT_dT_dG_dG_dT_dA_dT_dT_lC_l$ | 2-8-2 | LNA/deoxy | phosphorothioate | 230 |
| CGGCATGTCTATTTTGTA | | | phosphorothioate | 231 |
| GGCTAAATCGCTCCACCAAG | | | phosphorothioate | 232 |
| CTCTAGCGTCTTAAAGCCGA | | | phosphorothioate | 233 |
| GCTGCATGATCTCCTTGGCG | | | phosphorothioate | 234 |
| ACGTTGAGGGGCATCGTCGC | | | Morpholino | 235 |
| GGGTCTGCVGCGGGVTGGT | | | phosphorothioate | 236 |
| GTTVCTVCTTCCVCCTGCCTG | | | phosphorothioate | 237 |
| TATCCGGAGGGCTCGCCATGCTGCT | | | phosphorothioate | 238 |
| $T_eC_eC_eC_eG_eC_e$CTGTGACAT$_eG_eC_eA_eT_eT_e$ | 6-8-6 | MOE/deoxy | | 239 |
| $C_eA_eG_eC_e$AGCAGAGTCTTCAT$_eC_eA_eT_e$ | 4-13-4 | MOE/deoxy | | 240 |
| $G_eG_eG_eA_eC_dG_dC_dG_dG_dC_dG_dC_dT_dC_dG_dG_dT_eC_eA_eT_e$ | 4-12-4 | MOE/deoxy | | 241 |

TABLE B-continued

| Sequence 5′ to 3′ | Motif | Chemistry | Inte mucleo side Linkages | SEQ ID NO. |
|---|---|---|---|---|
| $C_eC_eA_eC_eA_eA_dG_dC_dT_dG_dT_dC_dC_dA_dG_dT_eC_eT_eA_eA_e$ | 5-10-5 | MOE/deoxy | | 242 |
| $C_eC_eG_eC_dA_dG_dC_dC_dA_dT_dG_dC_dG_eC_eT_eC_eT_eT_eG_eG_e$ | 3-9-8 | MOE/deoxy | | 243 |

F. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: General Method for the Preparation of Phosphoramidites, Compounds 1, 1a and 2

1

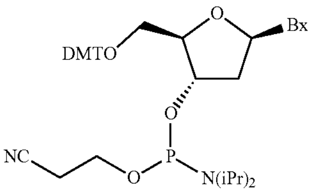

1a

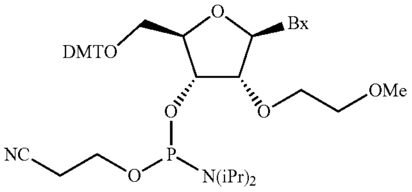

2

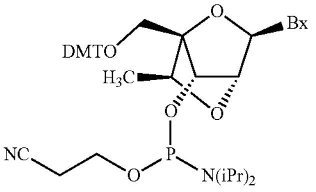

Bx is a heterocyclic base;

Compounds 1, 1a and 2 were prepared as per the procedures well known in the art as described in the specification herein (see Seth et al., Bioorg. Med. Chem., 2011, 21(4), 1122-1125, J. Org. Chem., 2010, 75(5), 1569-1581, Nucleic Acids Symposium Series, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2: Preparation of Compound 7

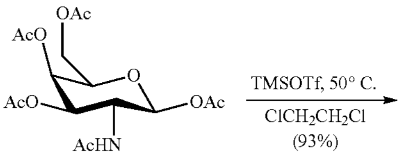

3

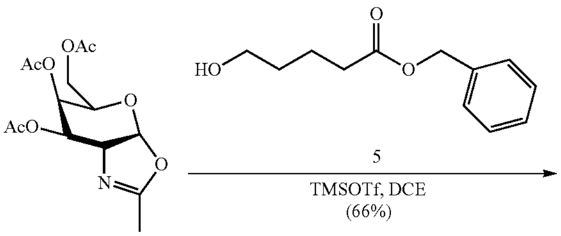

4

-continued

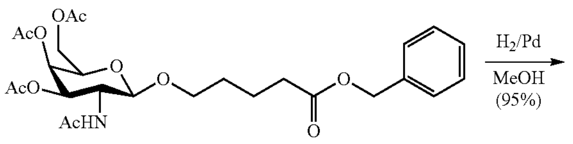

6

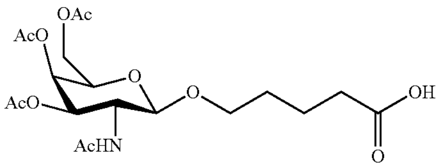

7

Compounds 3 (2-acetamido-1,3,4,6-tetra-O-acetyl-2-deoxy-β-Dgalactopyranose or galactosamine pentaacetate) is commercially available. Compound 5 was prepared according to published procedures (Weber et al., *J. Med. Chem.*, 1991, 34, 2692).

Example 3: Preparation of Compound 11

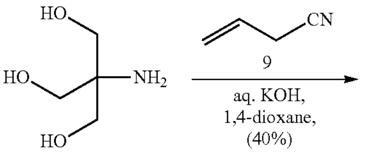

8

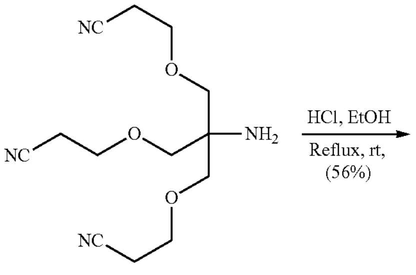

10

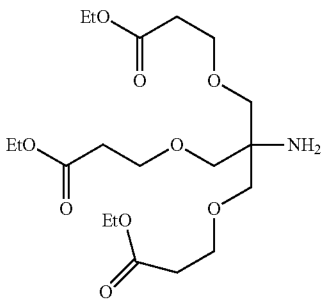

11

Compounds 8 and 9 are commercially available.
Example 4: Preparation of Compound 18
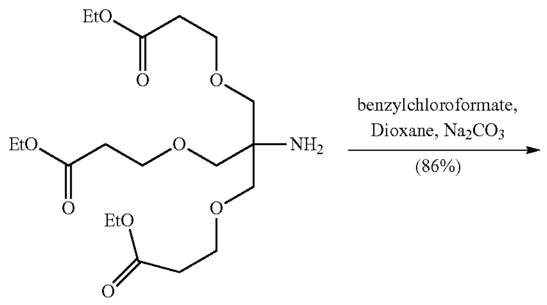
11
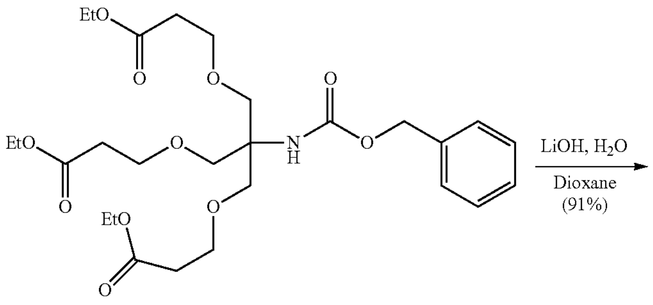
12
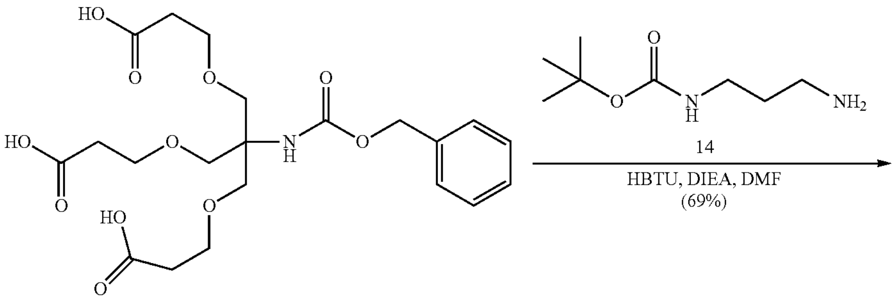
13
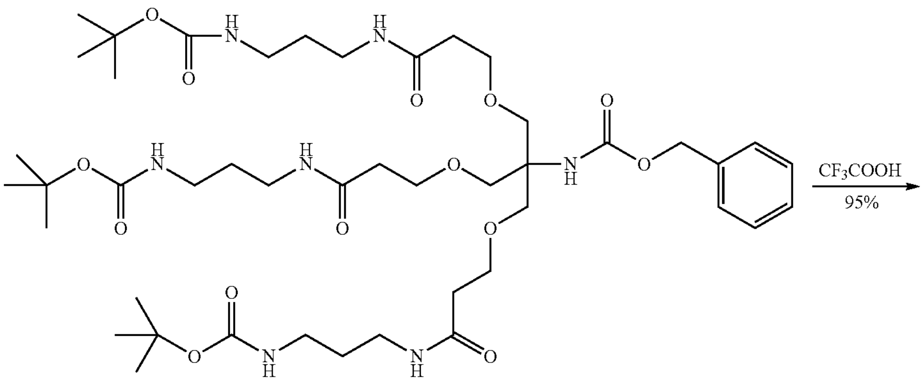
15

-continued
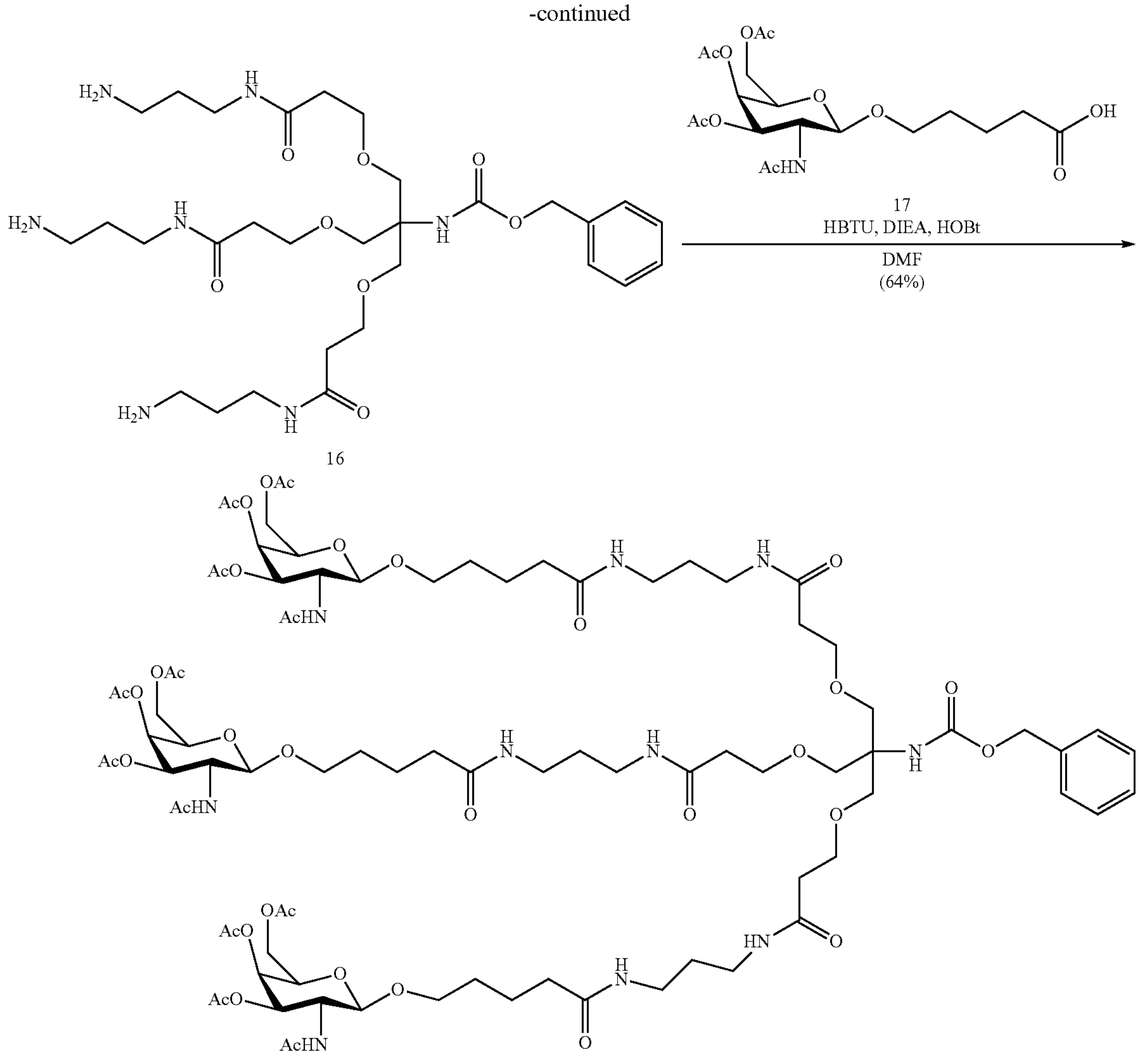
16 17 18
Compound 11 was prepared as per the procedures illustrated in Example 3. Compound 14 is commercially available. Compound 17 was prepared using similar procedures reported by Rensen et al., *J. Med. Chem.*, 2004, 47, 5798-5808.
Example 5: Preparation of Compound 23
-continued
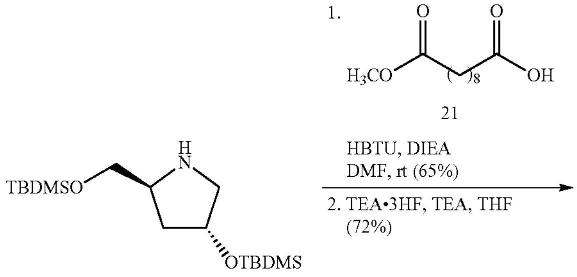
21
20
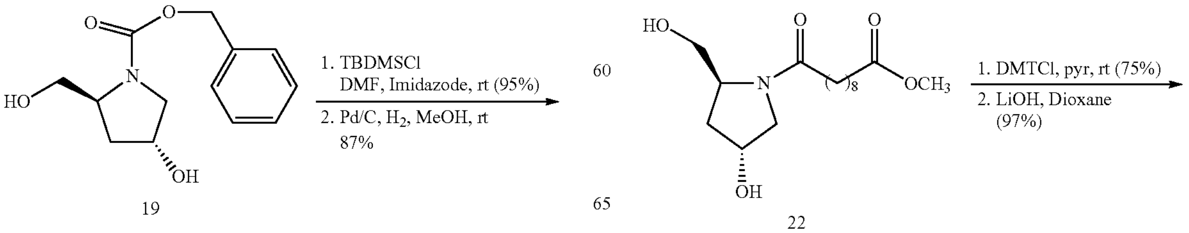
19
22

-continued
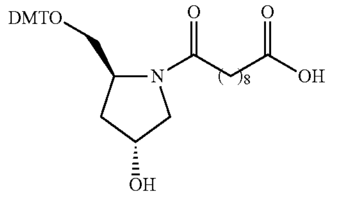
23
Compounds 19 and 21 are commercially available.
Example 6: Preparation of Compound 24
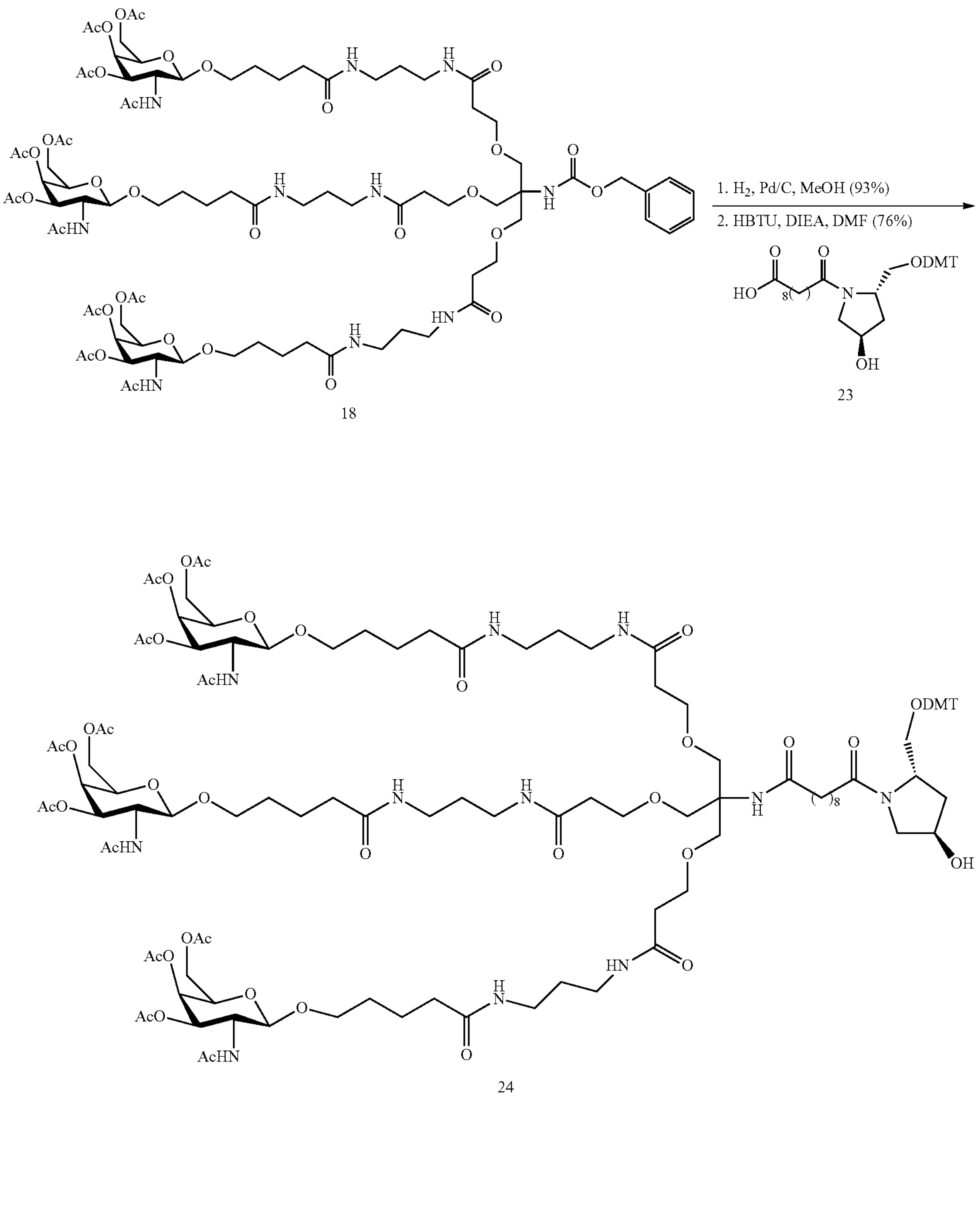
18
23
24

Compounds 18 and 23 were prepared as per the procedures illustrated in Examples 4 and 5.
Example 7: Preparation of Compound 25
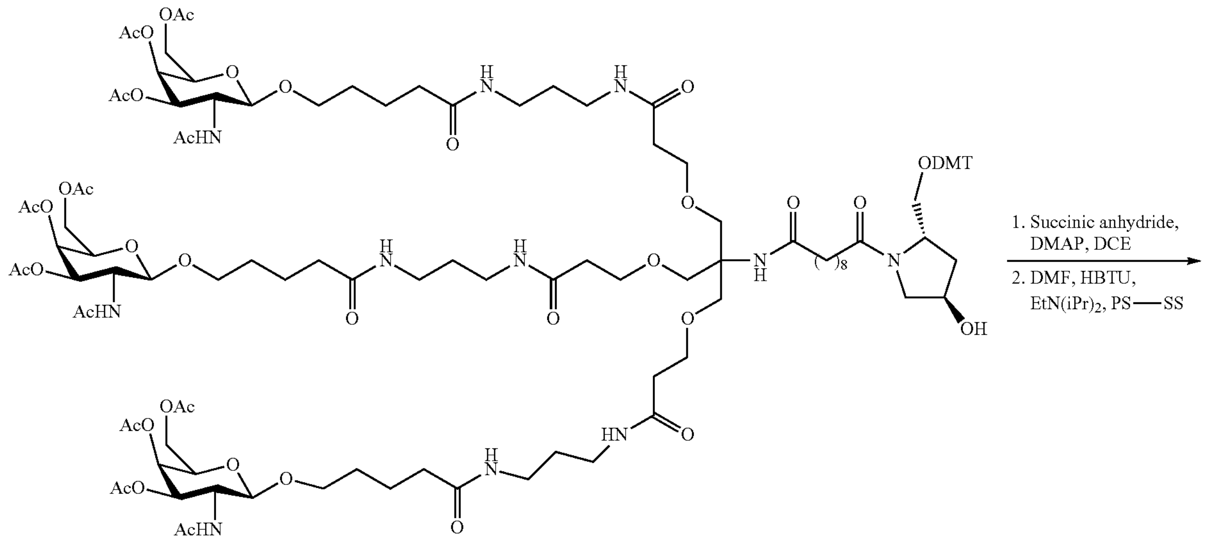
24
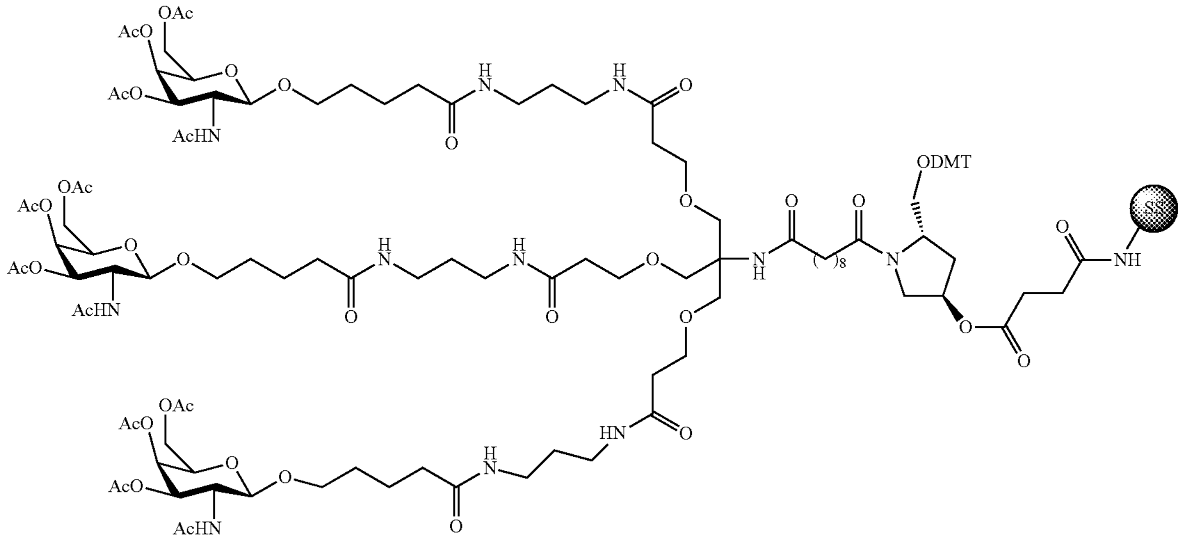
25

Compound 24 was prepared as per the procedures illustrated in Example 6.
Example 8: Preparation of Compound 26
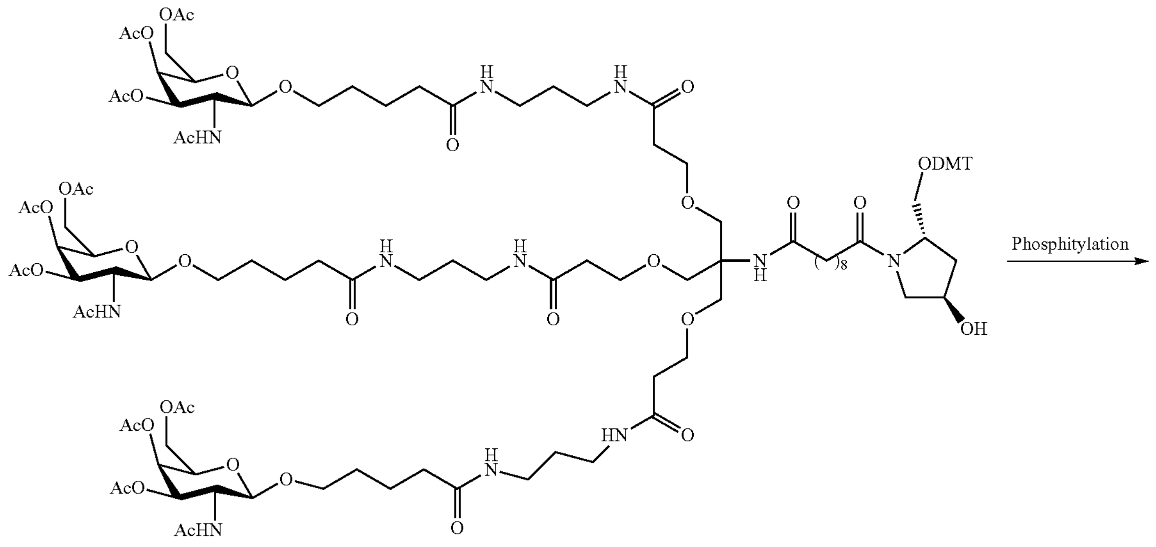
24
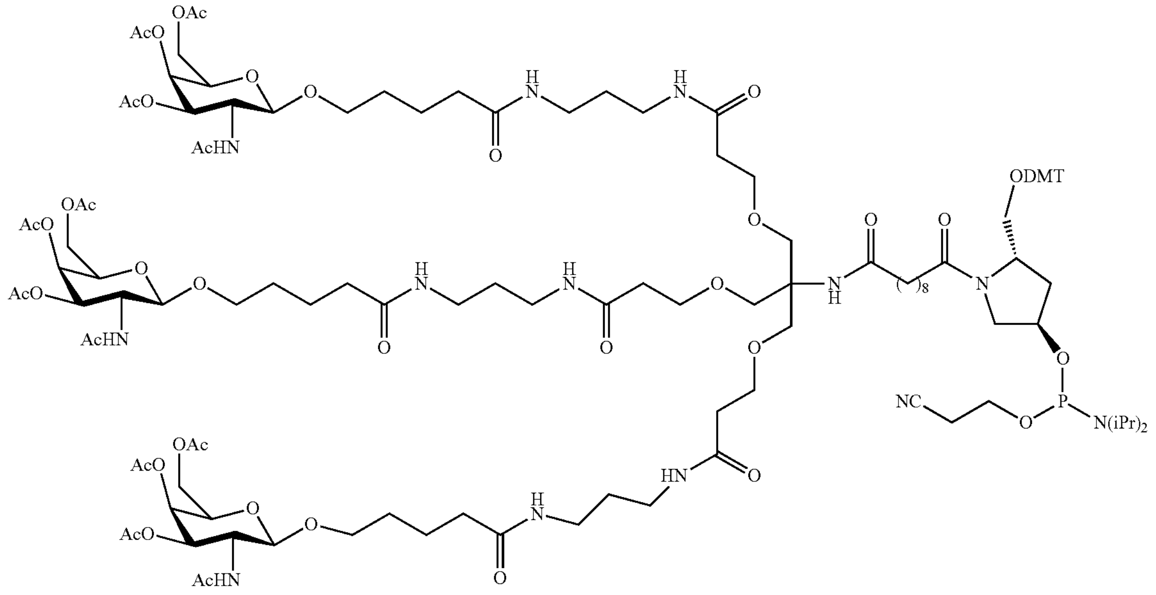
26

Compound 24 is prepared as per the procedures illustrated in Example 6.
Example 9: General Preparation of Conjugated ASOs Comprising GalNAc$_3$-1 at the 3' Terminus, Compound 29
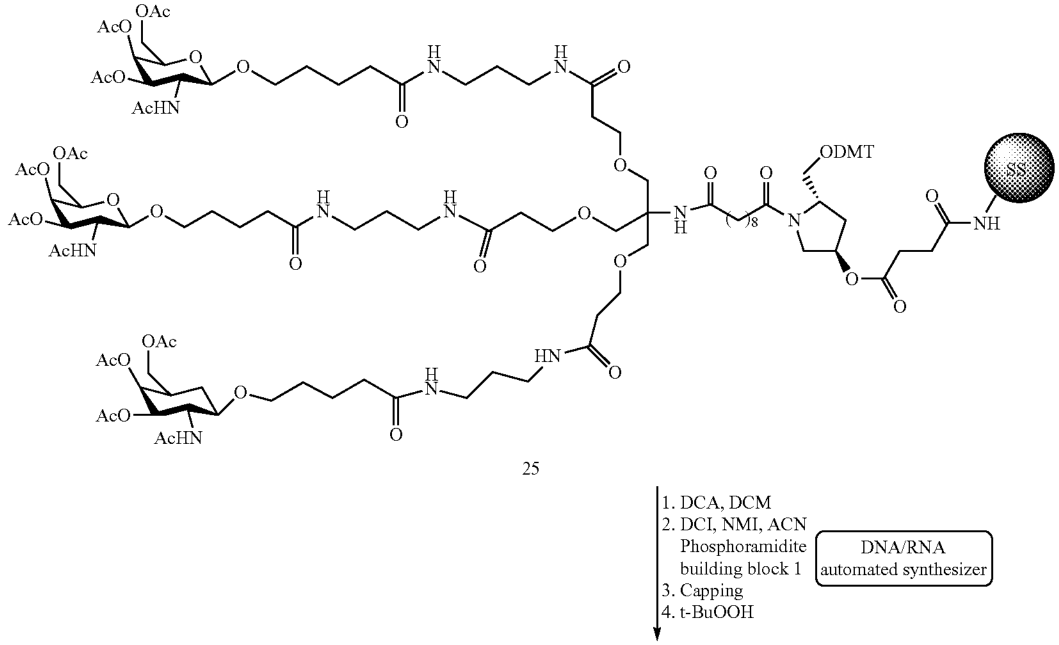
25
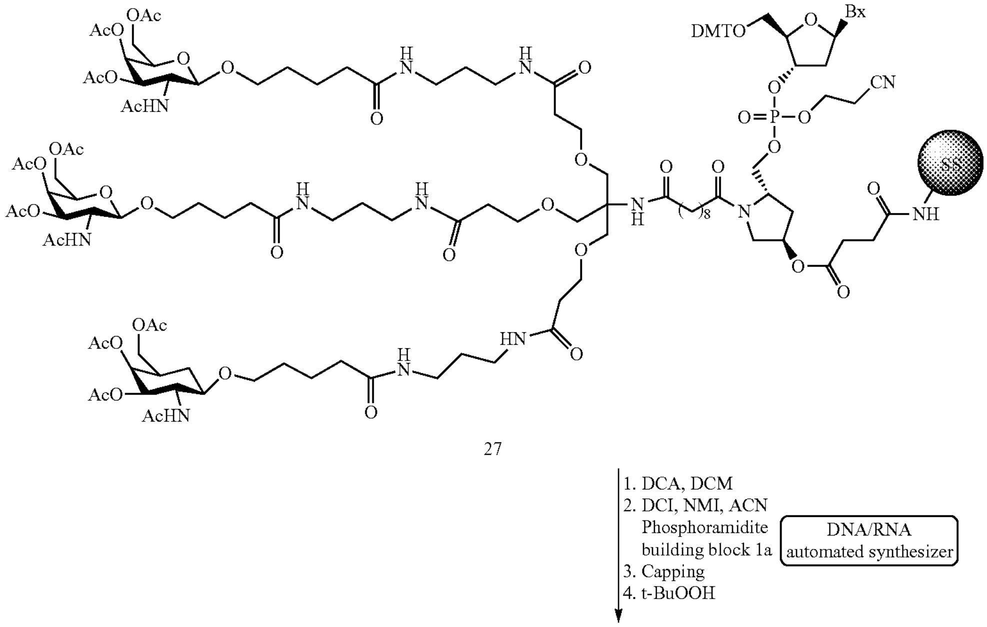
27

-continued
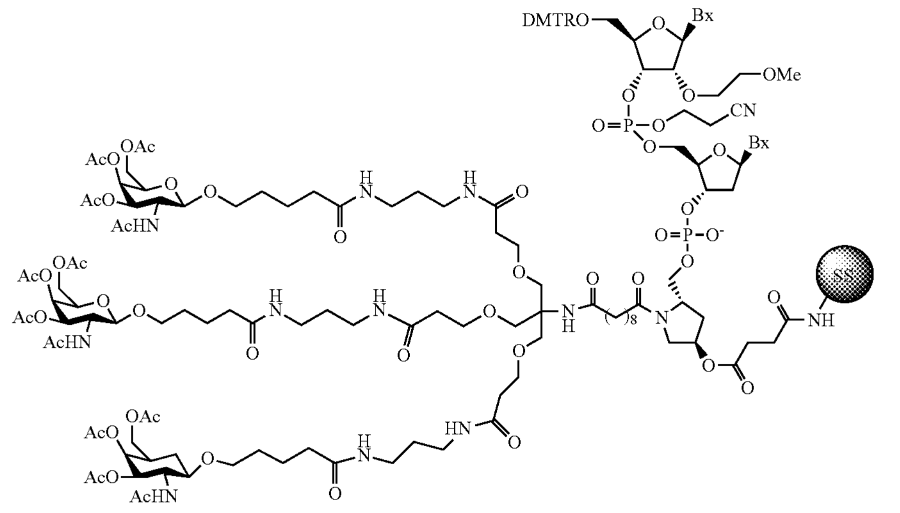
28
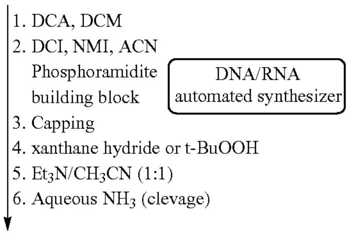
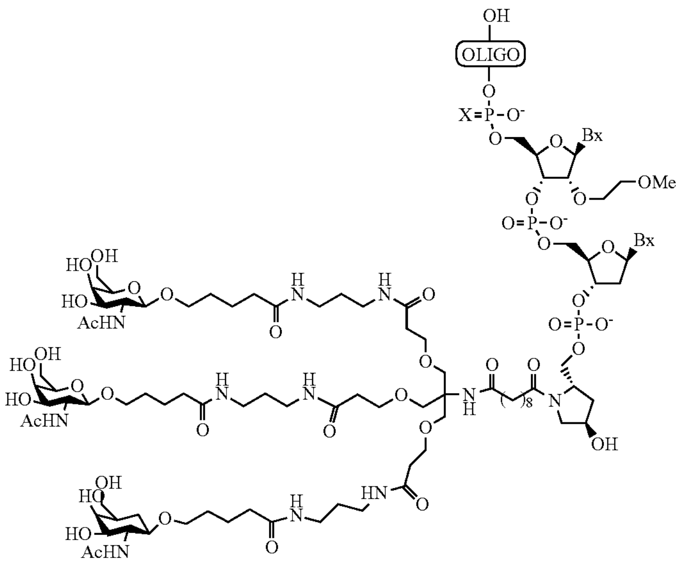
29
Bx = Heterocyclic base
X = O or S Wherein the protected $GalNAc_3$-1 has the structure:

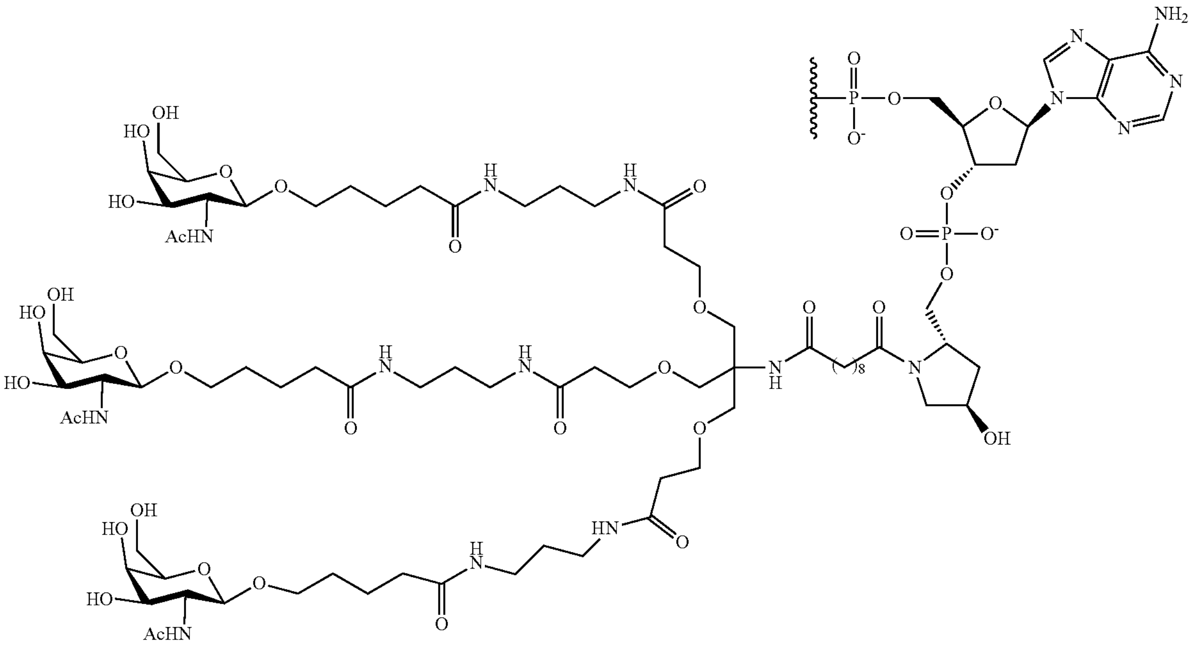

The $GalNAc_3$ cluster portion of the conjugate group $GalNAc_3$-1 ($GalNAc_3$-$1_a$) can be combined with any cleavable moiety to provide a variety of conjugate groups. Wherein $GalNAc_3$-$1_a$ has the formula:

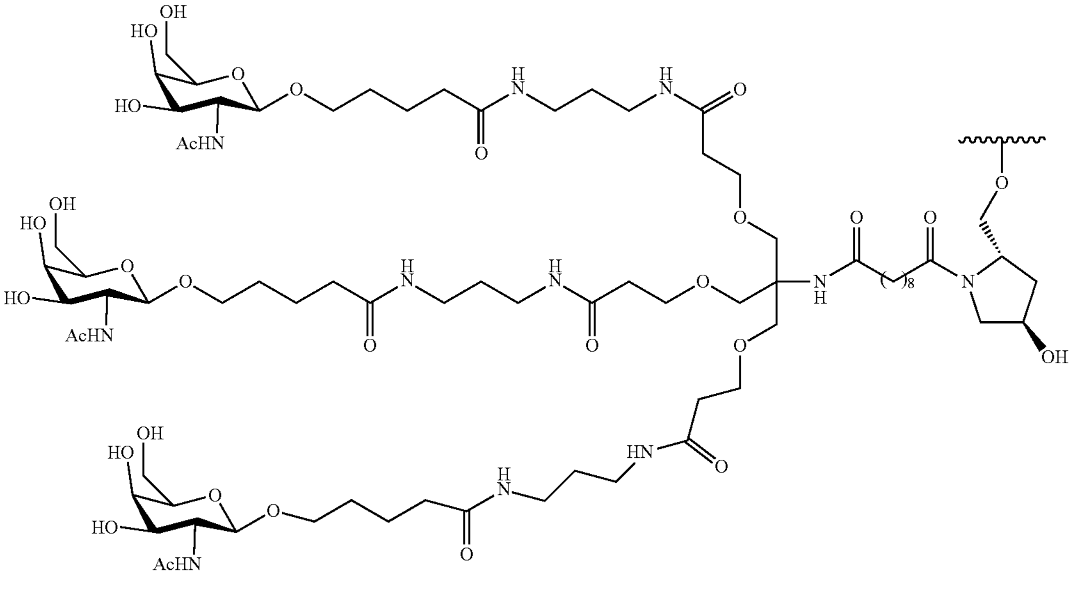

The solid support bound protected $GalNAc_3$-1, Compound 25, was prepared as per the procedures illustrated in Example 7. Oligomeric Compound 29 comprising $GalNAc_3$-1 at the 3' terminus was prepared using standard procedures in automated DNA/RNA synthesis (see Dupouy et al., *Angew. Chem. Int. Ed.,* 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare oligomeric compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10: General Preparation Conjugated ASOs Comprising GalNAc$_3$-1 at the 5' Terminus, Compound 34
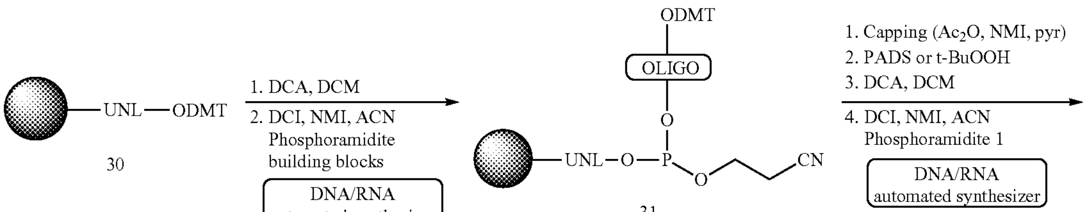
30
31
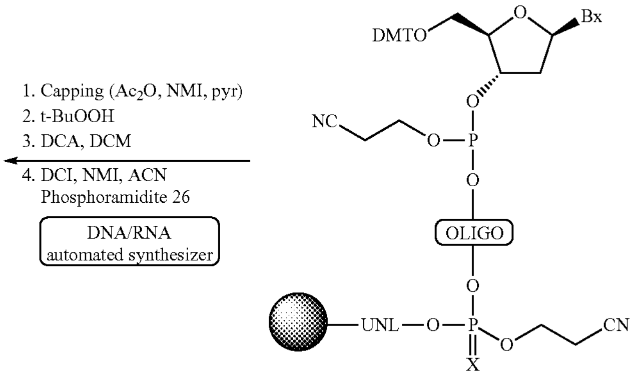
X = O, or S
Bx = Heterocylic base
32
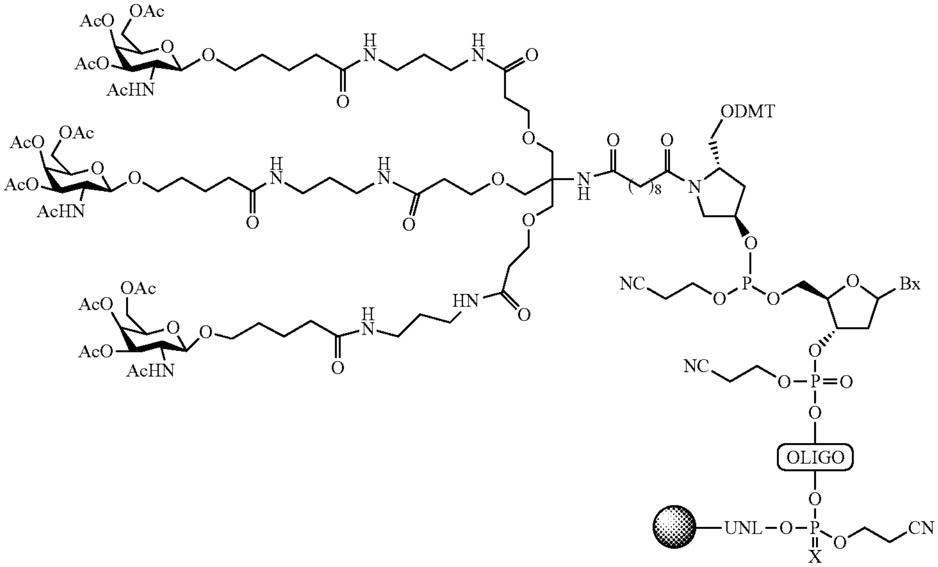
33
1. Capping ($Ac_2O$, NMI, pyr)
2. t-BuOOH
3. $Et_3N$:$CH_3CN$ (1:1 v/v)
4. DCA, DCM
5. $NH_4$, rt (clevage)

-continued

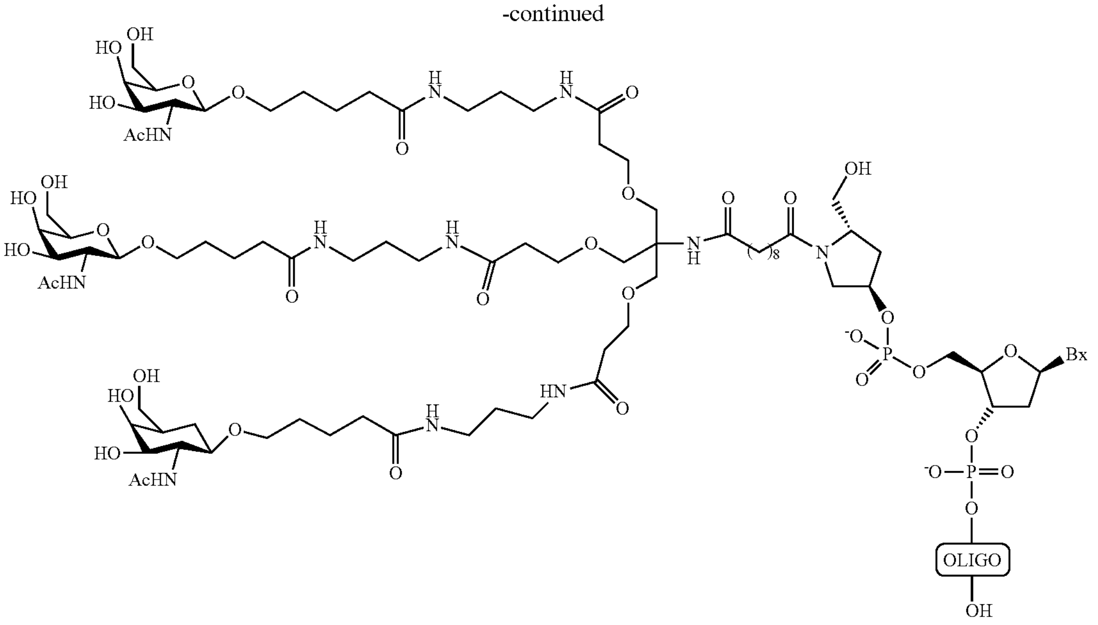

34

The Unylinker™ 30 is commercially available. Oligomeric Compound 34 comprising a $GalNAc_3$-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare an oligomeric compound having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 11: Preparation of Compound 39

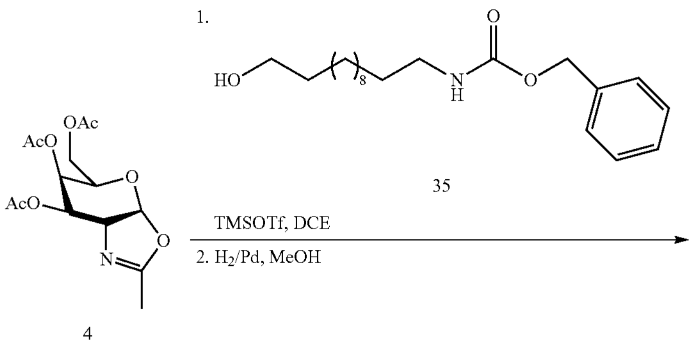

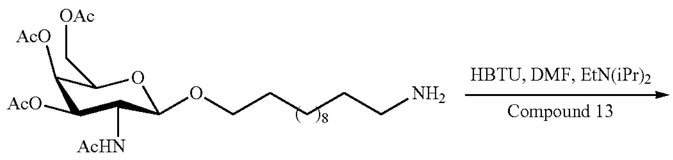

36

-continued
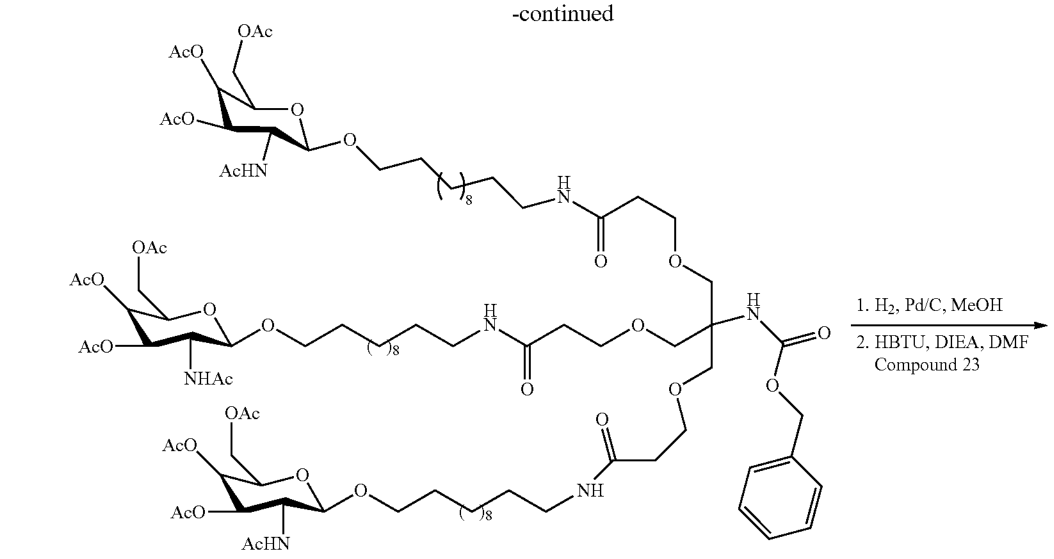
37
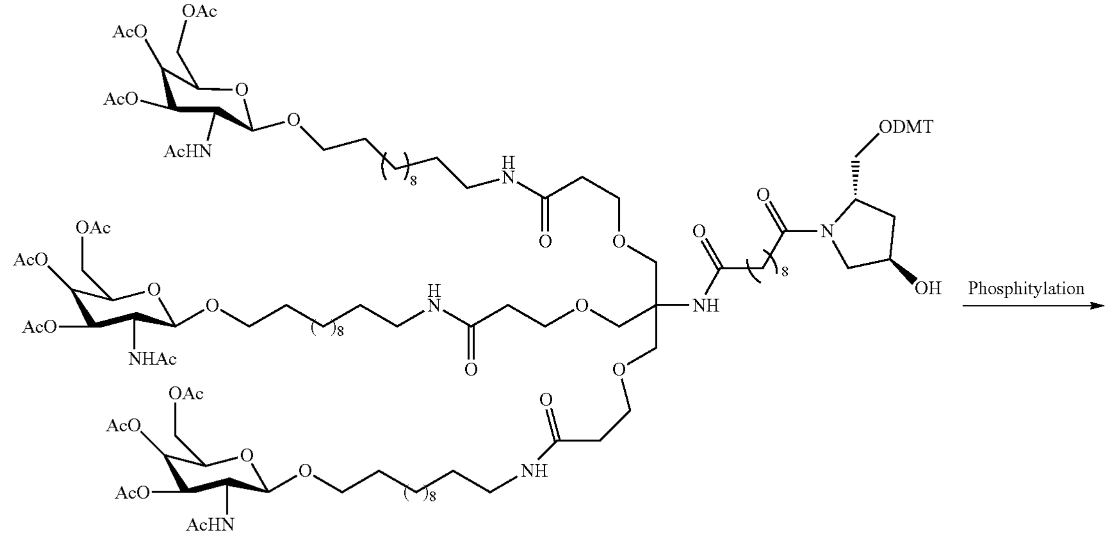
38
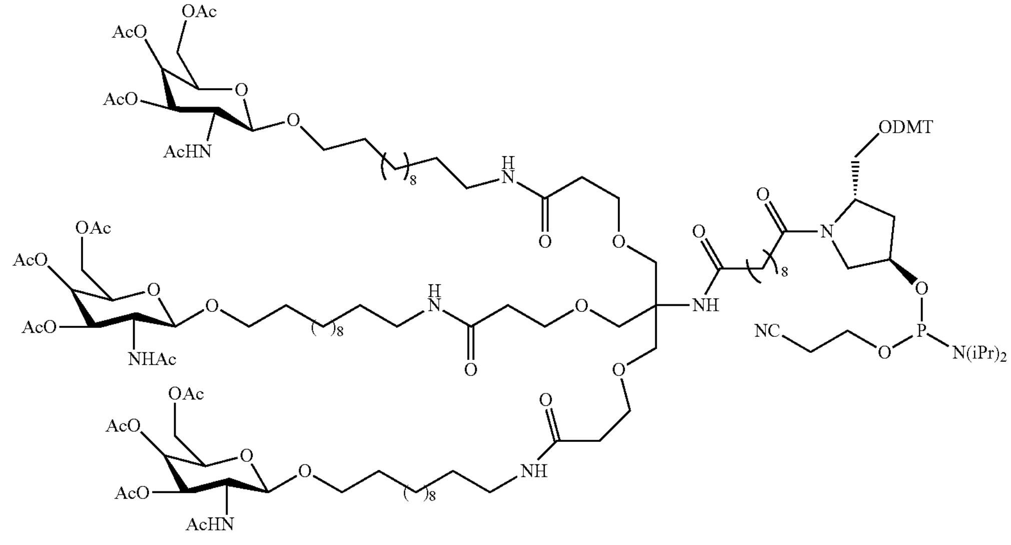
39

Compounds 4, 13 and 23 were prepared as per the procedures illustrated in Examples 2, 4, and 5. Compound 35 is prepared using similar procedures published in Rouchaud et al., *Eur. J. Org. Chem.*, 2011, 12, 2346-2353.
Example 12: Preparation of Compound 40
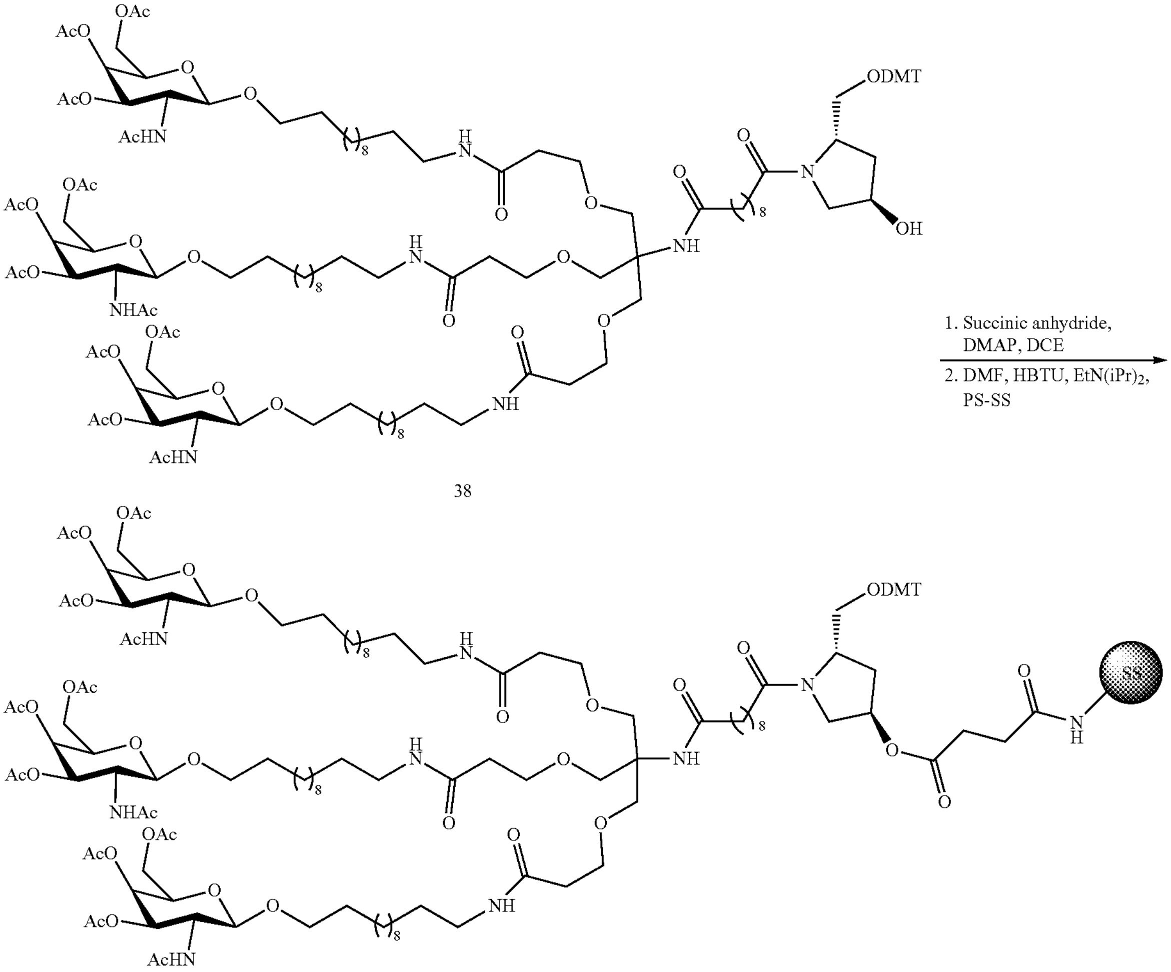
38
40
Compound 38 is prepared as per the procedures illustrated in Example 11.
Example 13: Preparation of Compound 44
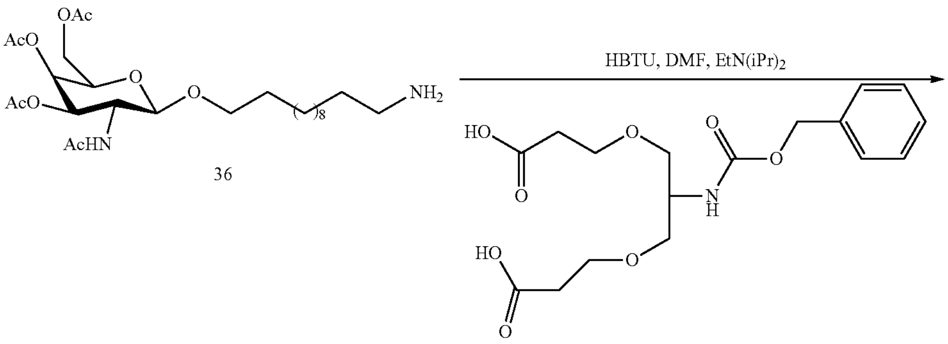
36
41

-continued
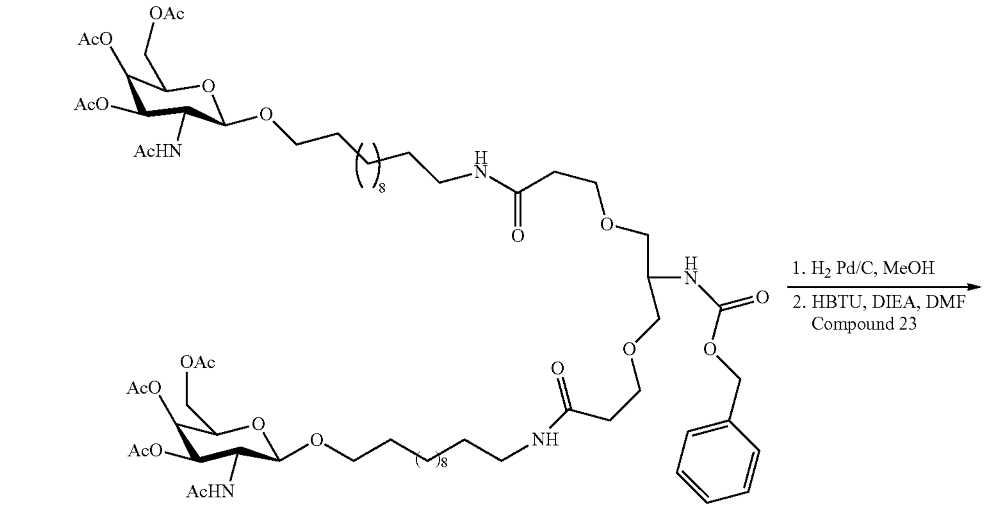
42
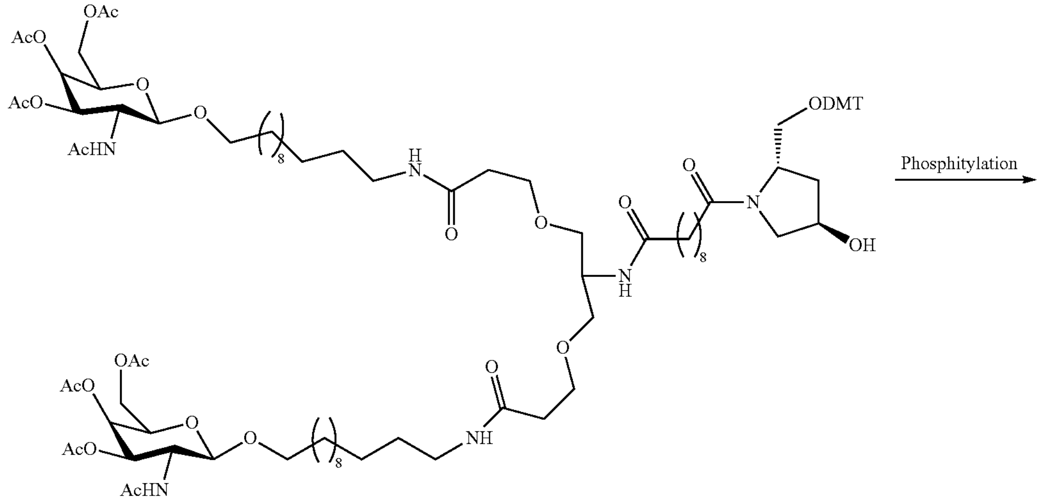
43
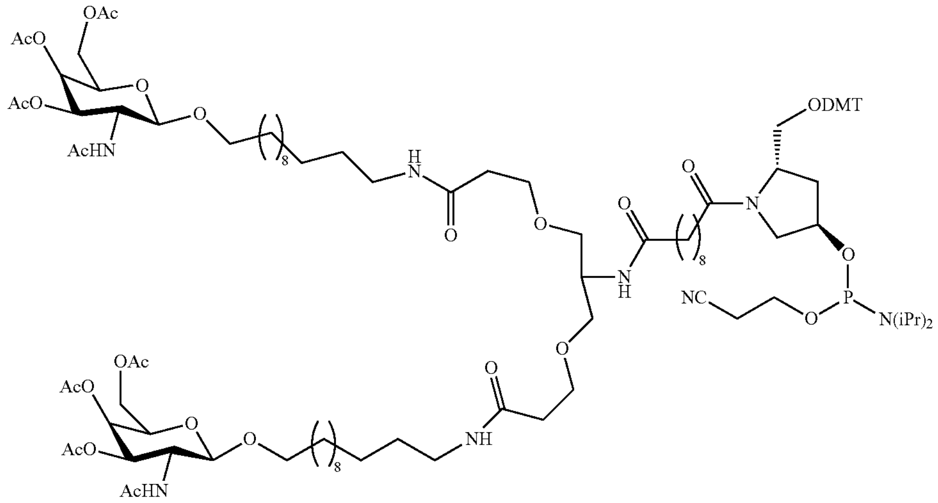
44

Compounds 23 and 36 are prepared as per the procedures illustrated in Examples 5 and 11. Compound 41 is prepared using similar procedures published in WO 2009082607.
Example 14: Preparation of Compound 45
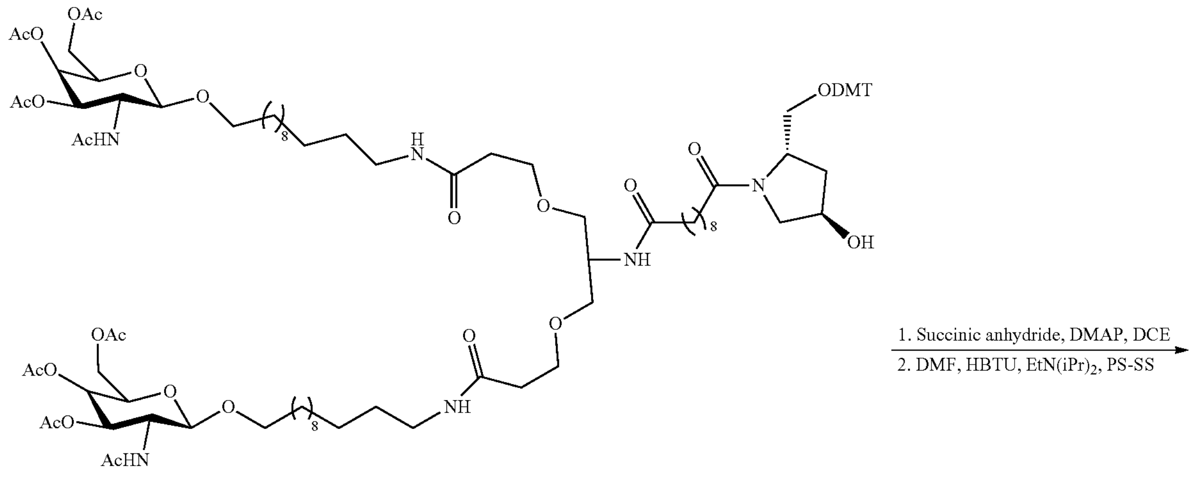
43
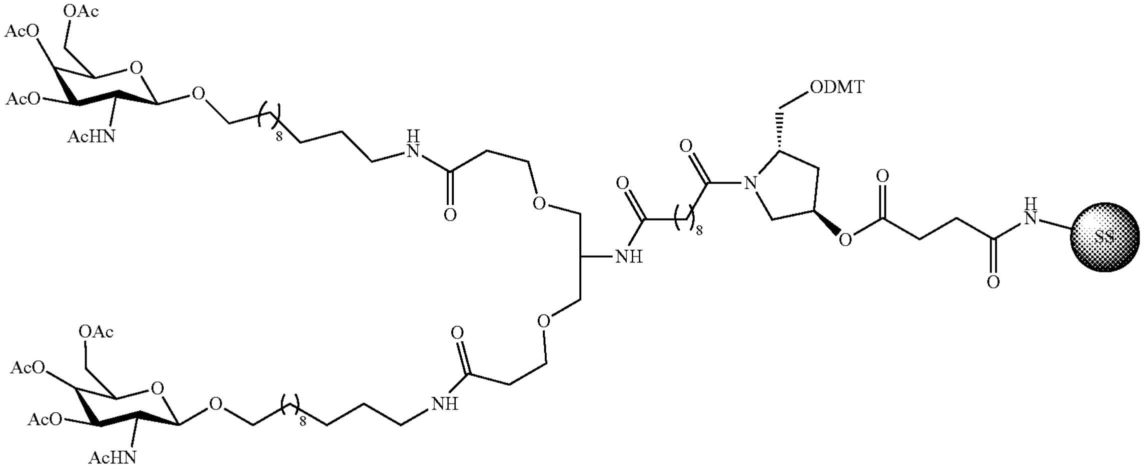
45
Compound 43 is prepared as per the procedures illustrated in Example 13.
Example 15: Preparation of Compound 47
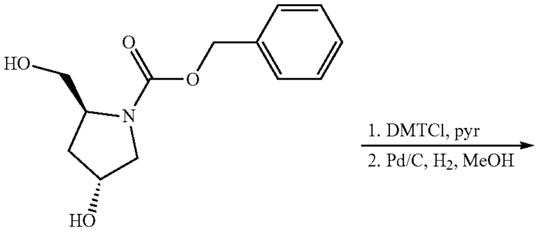
46
-continued
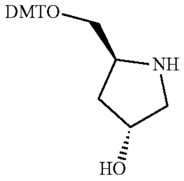
47
Compound 46 is commercially available.

Example 16: Preparation of Compound 53
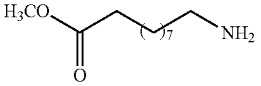
48
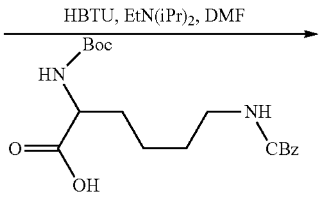
49
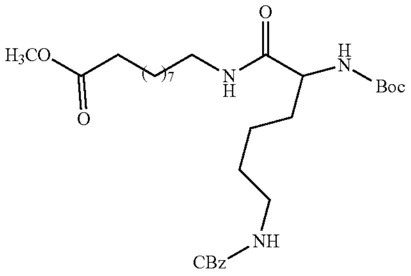
50
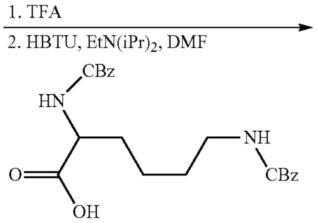
49
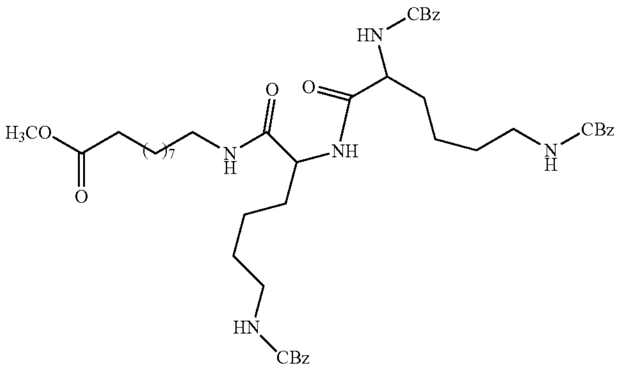
51
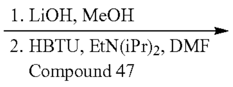
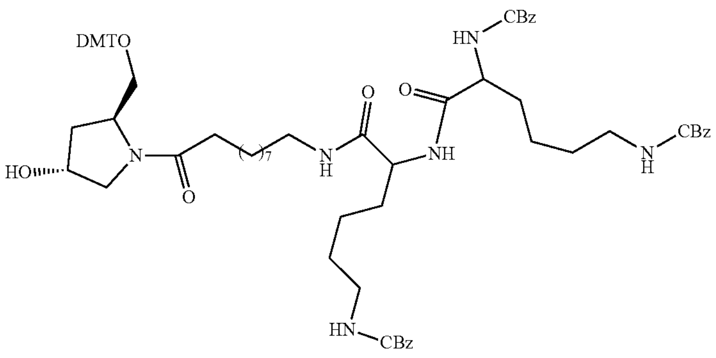
52
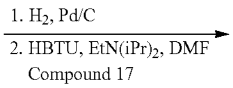

-continued
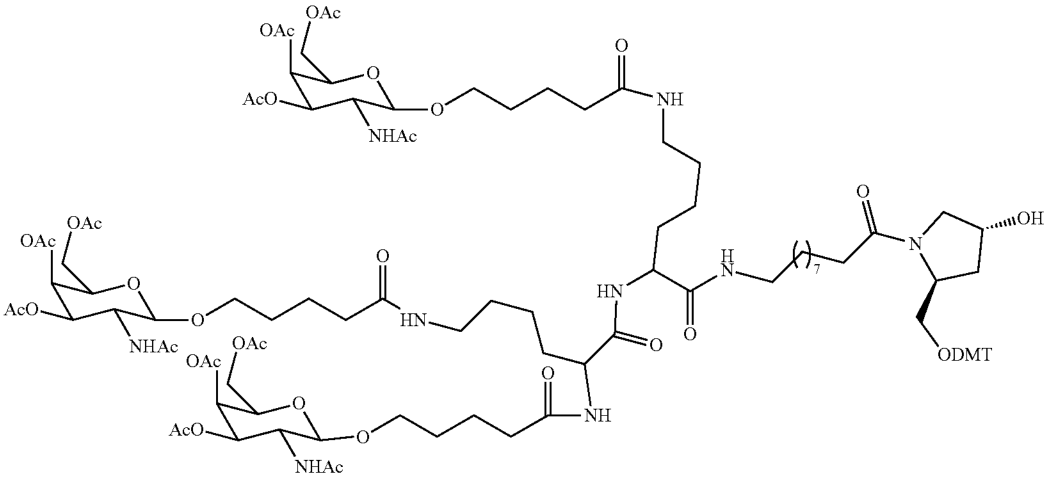
53
Compounds 48 and 49 are commercially available. Compounds 17 and 47 are prepared as per the procedures illustrated in Examples 4 and 15.
Example 17: Preparation of Compound 54
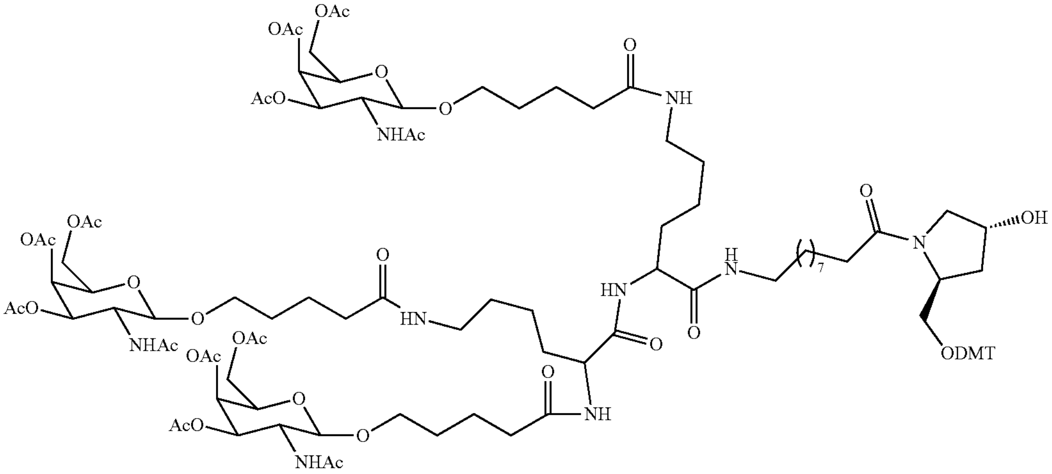
53
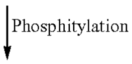

-continued
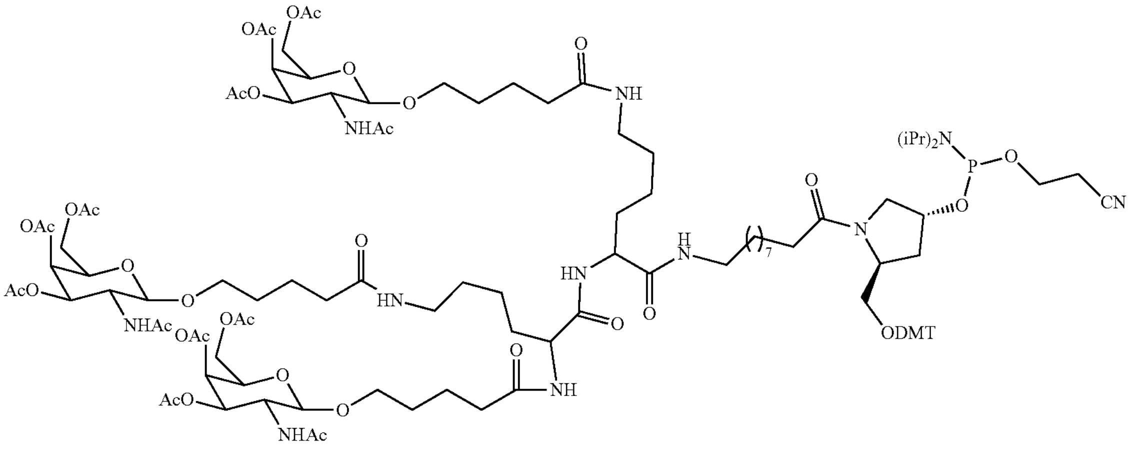
54
Compound 53 is prepared as per the procedures illustrated in Example 16.
Example 18: Preparation of Compound 55
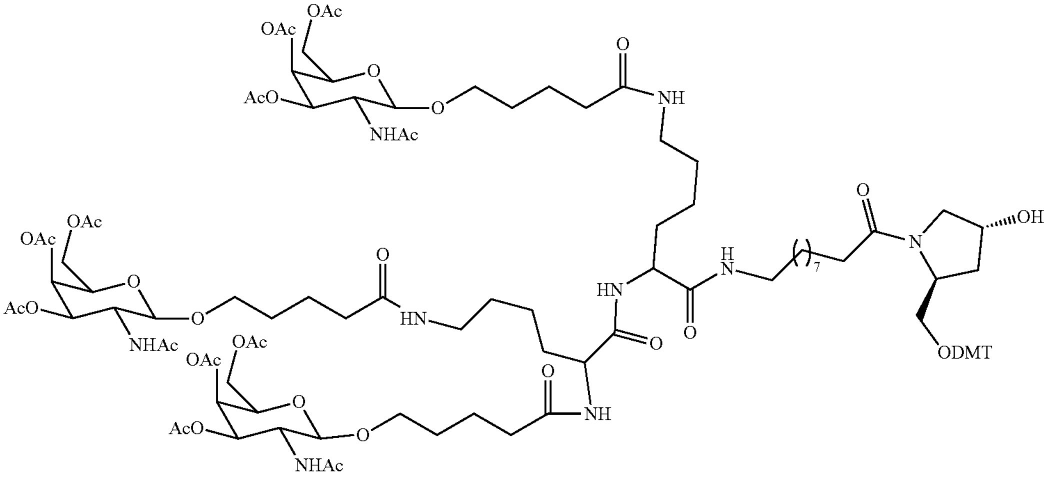
53
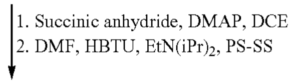

-continued

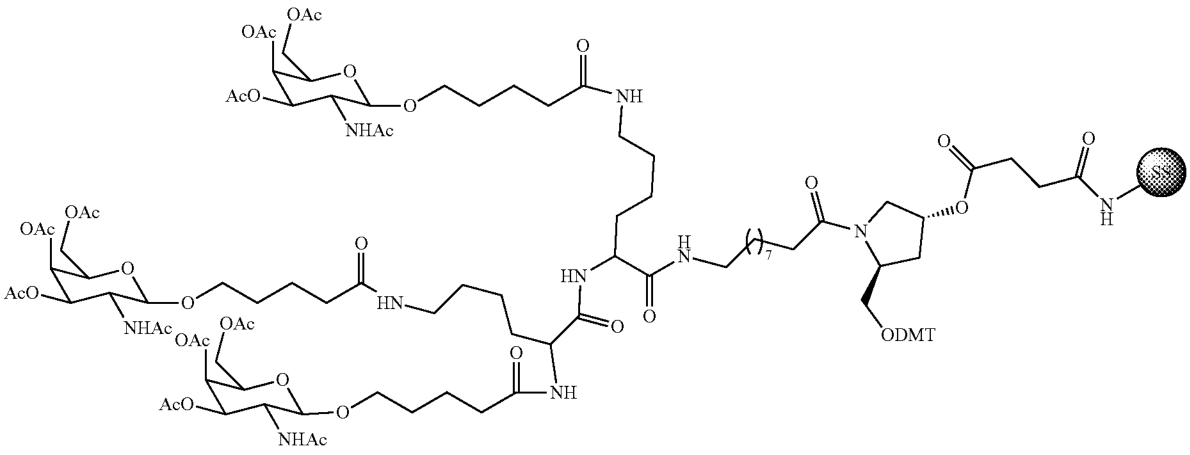

55

Compound 53 is prepared as per the procedures illustrated in Example 16.

Example 19: General Method for the Preparation of Conjugated ASOs Comprising GalNAc$_3$-1 at the 3' Position Via Solid Phase Techniques (Preparation of ISIS 647535, 647536 and 651900)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^{me}$C residues. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on an GalNAc$_3$-1 loaded VIMAD solid support (110 μmol/g, Guzaev et al., 2003) packed in the column. For the coupling step, the phosphoramidites were delivered 4 fold excess over the loading on the solid support and phosphoramidite condensation was carried out for 10 min. All other steps followed standard protocols supplied by the manufacturer. A solution of 6% dichloroacetic acid in toluene was used for removing dimethoxytrityl (DMT) group from 5'-hydroxyl group of the nucleotide. 4,5-Dicyanoimidazole (0.7 M) in anhydrous $CH_3CN$ was used as activator during coupling step. Phosphorothioate linkages were introduced by sulfurization with 0.1 M solution of xanthane hydride in 1:1 pyridine/$CH_3CN$ for a contact time of 3 minutes. A solution of 20% tert-butylhydroperoxide in $CH_3CN$ containing 6% water was used as an oxidizing agent to provide phosphodiester internucleoside linkages with a contact time of 12 minutes.

After the desired sequence was assembled, the cyanoethyl phosphate protecting groups were deprotected using a 1:1 (v/v) mixture of triethylamine and acetonitrile with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min-1, λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

Antisense oligonucleotides not comprising a conjugate were synthesized using standard oligonucleotide synthesis procedures well known in the art.

Using these methods, three separate antisense compounds targeting ApoC III were prepared. As summarized in Table 17, below, each of the three antisense compounds targeting ApoC III had the same nucleobase sequence; ISIS 304801 is a 5-10-5 MOE gapmer having all phosphorothioate linkages; ISIS 647535 is the same as ISIS 304801, except that it had a GalNAc$_3$-1 conjugated at its 3'end; and ISIS 647536 is the same as ISIS 647535 except that certain internucleoside linkages of that compound are phosphodiester linkages. As further summarized in Table 17, two separate antisense compounds targeting SRB-1 were synthesized. ISIS 440762 was a 2-10-2 cEt gapmer with all phosphorothioate internucleoside linkages; ISIS 651900 is the same as ISIS 440762, except that it included a GalNAc$_3$-1 at its 3'-end.

TABLE 17

| Modified ASO targeting ApoC III and SRB-1 | | | | | | |
|---|---|---|---|---|---|---|
| ASO | Sequence (5' to 3') | Target | CalCd Mass | Observed Mass | Unmodified SEQ ID No. | Modified SEQ ID No. |
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | ApoC III | 7165.4 | 7164.4 | 244 | 317 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}$ **$A_{do'}$-GalNAc$_3$-1$_a$** | ApoC III | 9239.5 | 9237.8 | 245 | 367 |
| ISIS 647536 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}$**$A_{do'}$-GalNAc$_3$-1$_a$** | ApoC III | 9142.9 | 9140.8 | 245 | 368 |
| ISIS 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | SRB-1 | 4647.0 | 4646.4 | 246 | 297 |
| ISIS 651900 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ko}$**$A_{do}$'-GalNAc$_3$-1$_a$** | SRB-1 | 6721.1 | 6719.4 | 247 | 303 |

Subscripts:
"e" indicates 2'-MOE modified nucleoside;
"d" indicates β-D-2'-deoxyribonucleoside;
"k" indicates 6'-(S)-$CH_3$ bicyclic nucleoside (e.g. cEt);
"s" indicates phosphorothioate internucleoside linkages (PS);
"o" indicates phosphodiester internucleoside linkages (PO); and
"o'" indicates —O—P(═O)(OH)—.
Superscript "m" indicates 5-methylcytosines.
"GalNAc$_3$-1$_a$." indicates a conjugate group having the structure shown previously in Example 9.
Note
that GalNAc$_3$-1 comprises a cleavable adenosine which links the ASO to remainder of the conjugate, which is designated "GalNAc$_3$-1$_a$." This nomenclature is used in the above table to show the full nucleobase sequence, including the adenosine, which is part of the conjugate. Thus, in the above table, the sequences could also be listed as ending with "GalNAc$_3$-1" with the "$A_{do}$" omitted. This convention of using the subscript "a" to indicate the portion of a conjugate group lacking a cleavable nucleoside or cleavable moiety is used throughout these Examples. This portion of a conjugate group lacking the cleavable moiety is referred to herein as a "cluster" or "conjugate cluster" or "GalNAc$_3$ cluster". In certain instances it is convenient to describe a conjugate group by separately providing its cluster and its cleavable moiety.

Example 20: Dose-Dependent Antisense Inhibition of Human ApoC III in huApoC III Transgenic Mice ISIS 304801 and ISIS 647535, each targeting human ApoC III and described above, were separately tested and evaluated in a dose-dependent study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once a week for two weeks with ISIS 304801 or 647535 at 0.08, 0.25. 0.75, 2.25 or 6.75 μmol/kg or with PBS as a control. Each treatment group consisted of 4 animals. Forty-eight hours after the administration of the last dose, blood was drawn from each mouse and the mice were sacrificed and tissues were collected.

ApoC III mRNA Analysis

ApoC III mRNA levels in the mice's livers were determined using real-time PCR and RIBOGREEN® RNA quantification reagent (Molecular Probes, Inc. Eugene, OR) according to standard protocols. ApoC III mRNA levels were determined relative to total RNA (using Ribogreen), prior to normalization to PBS-treated control. The results below are presented as the average percent of ApoC III mRNA levels for each treatment group, normalized to PBS-treated control and are denoted as "% PBS". The half maximal effective dosage ($ED_{50}$) of each ASO is also presented in Table 18, below.

As illustrated, both antisense compounds reduced ApoC III RNA relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 18

| Effect of ASO treatment on ApoC III mRNA levels in human ApoC III transgenic mice | | | | | | |
|---|---|---|---|---|---|---|
| ASO | Dose (μmol/kg) | % PBS | $ED_{50}$ (μmol/kg) | 3' Conjugate | Internucleoside linkage/Length | SEQ ID No. |
| PBS | 0 | 100 | — | — | — | |
| ISIS | 0.08 | 95 | 0.77 | None | PS/20 | 244 |
| 304801 | 0.75 | 42 | | | | |
| | 2.25 | 32 | | | | |
| | 6.75 | 19 | | | | |
| ISIS | 0.08 | 50 | 0.074 | GalNAc$_3$-1 | PS/20 | 245 |
| 647535 | 0.75 | 15 | | | | |
| | 2.25 | 17 | | | | |
| | 6.75 | 8 | | | | |

ApoC III Protein Analysis (Turbidometric Assay)

Plasma ApoC III protein analysis was determined using procedures reported by Graham et al, Circulation Research, published online before print Mar. 29, 2013.

Approximately 100 μl of plasma isolated from mice was analyzed without dilution using an Olympus Clinical Analyzer and a commercially available turbidometric ApoC III assay (Kamiya, Cat #KAI-006, Kamiya Biomedical, Seattle, WA). The assay protocol was performed as described by the vendor.

As shown in the Table 19 below, both antisense compounds reduced ApoC III protein relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 19

Effect of ASO treatment on ApoC III plasma protein levels in human ApoC III transgenic mice

| ASO | Dose (μmol/kg) | % PBS | $ED_{50}$ (μmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 86 | 0.73 | None | PS/20 | 244 |
| | 0.75 | 51 | | | | |
| | 2.25 | 23 | | | | |
| | 6.75 | 13 | | | | |
| ISIS 647535 | 0.08 | 72 | 0.19 | GalNAc$_3$-1 | PS/20 | 245 |
| | 0.75 | 14 | | | | |
| | 2.25 | 12 | | | | |
| | 6.75 | 11 | | | | |

Plasma triglycerides and cholesterol were extracted by the method of Bligh and Dyer (Bligh, E. G. and Dyer, W. J. Can. J. Biochem. Physiol. 37: 911-917, 1959)(Bligh, E and Dyer, W, *Can J Biochem Physiol,* 37, 911-917, 1959) (Bligh, E and Dyer, W, *Can J Biochem Physiol,* 37, 911-917, 1959) and measured by using a Beckmann Coulter clinical analyzer and commercially available reagents.

The triglyceride levels were measured relative to PBS injected mice and are denoted as "% PBS". Results are presented in Table 20. As illustrated, both antisense compounds lowered triglyceride levels. Further, the antisense compound conjugated to GalNAc$_3$-1 (ISIS 647535) was substantially more potent than the antisense compound lacking the GalNAc$_3$-1 conjugate (ISIS 304801).

TABLE 20

Effect of ASO treatment on triglyceride levels in transgenic mice

| ASO | Dose (μmol/kg) | % PBS | $ED_{50}$ (μmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 87 | 0.63 | None | PS/20 | 244 |
| | 0.75 | 46 | | | | |
| | 2.25 | 21 | | | | |
| | 6.75 | 12 | | | | |
| ISIS 647535 | 0.08 | 65 | 0.13 | GalNAc$_3$-1 | PS/20 | 245 |
| | 0.75 | 9 | | | | |
| | 2.25 | 8 | | | | |
| | 6.75 | 9 | | | | |

Plasma samples were analyzed by HPLC to determine the amount of total cholesterol and of different fractions of cholesterol (HDL and LDL). Results are presented in Tables 21 and 22. As illustrated, both antisense compounds lowered total cholesterol levels; both lowered LDL; and both raised HDL. Further, the antisense compound conjugated to GalNAc$_3$-1 (ISIS 647535) was substantially more potent than the antisense compound lacking the GalNAc$_3$-1 conjugate (ISIS 304801). An increase in HDL and a decrease in LDL levels is a cardiovascular beneficial effect of antisense inhibition of ApoC III.

TABLE 21

Effect of ASO treatment on total cholesterol levels in transgenic mice

| ASO | Dose (μmol/kg) | Total Cholesterol (mg/dL) | 3' Conjugate | Internucleoside Linkage/Length | SEQ ID No. |
|---|---|---|---|---|---|
| PBS | 0 | 257 | — | — | |
| ISIS 304801 | 0.08 | 226 | None | PS/20 | 244 |
| | 0.75 | 164 | | | |
| | 2.25 | 110 | | | |
| | 6.75 | 82 | | | |
| ISIS 647535 | 0.08 | 230 | GalNAc$_3$-1 | PS/20 | 245 |
| | 0.75 | 82 | | | |
| | 2.25 | 86 | | | |
| | 6.75 | 99 | | | |

TABLE 22

Effect of ASO treatment on HDL and LDL cholesterol levels in transgenic mice

| ASO | Dose (μmol/kg) | HDL (mg/dL) | LDL (mg/dL) | 3' Conjugate | Internucleoside Linkage/Length | SEQ ID No. |
|---|---|---|---|---|---|---|
| PBS | 0 | 17 | 28 | — | — | |
| ISIS 304801 | 0.08 | 17 | 23 | None | PS/20 | 244 |
| | 0.75 | 27 | 12 | | | |
| | 2.25 | 50 | 4 | | | |
| | 6.75 | 45 | 2 | | | |
| ISIS 647535 | 0.08 | 21 | 21 | GalNAc$_3$-1 | PS/20 | 245 |
| | 0.75 | 44 | 2 | | | |
| | 2.25 | 50 | 2 | | | |
| | 6.75 | 58 | 2 | | | |

Pharmacokinetics Analysis (PK)

The PK of the ASOs was also evaluated. Liver and kidney samples were minced and extracted using standard protocols. Samples were analyzed on MSD1 utilizing IP-HPLC-MS. The tissue level (μg/g) of full-length ISIS 304801 and 647535 was measured and the results are provided in Table 23. As illustrated, liver concentrations of total full-length antisense compounds were similar for the two antisense compounds. Thus, even though the GalNAc$_3$-1-conjugated antisense compound is more active in the liver (as demonstrated by the RNA and protein data above), it is not present at substantially higher concentration in the liver. Indeed, the calculated $EC_{50}$ (provided in Table 23) confirms that the observed increase in potency of the conjugated compound cannot be entirely attributed to increased accumulation. This result suggests that the conjugate improved potency by a mechanism other than liver accumulation alone, possibly by improving the productive uptake of the antisense compound into cells.

The results also show that the concentration of GalNAc$_3$-1 conjugated antisense compound in the kidney is lower than that of antisense compound lacking the GalNAc conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly, for non-kidney targets, kidney accumulation is undesired. These data suggest that GalNAc$_3$-1 conjugation reduces kidney accumulation.

TABLE 23

| PK analysis of ASO treatment in transgenic mice | | | | | | | |
|---|---|---|---|---|---|---|---|
| ASO | Dose (μmol/kg) | Liver (μg/g) | Kidney (μg/g) | Liver $EC_{50}$ (μg/g) | 3' Conjugate | Internucleoside Linkage/Length | SEQ ID No. |
| ISIS 304801 | 0.1 | 5.2 | 2.1 | 53 | None | PS/20 | 244 |
| | 0.8 | 62.8 | 119.6 | | | | |
| | 2.3 | 142.3 | 191.5 | | | | |
| | 6.8 | 202.3 | 337.7 | | | | |
| ISIS 647535 | 0.1 | 3.8 | 0.7 | 3.8 | $GalNAc_3$-1 | PS/20 | 245 |
| | 0.8 | 72.7 | 34.3 | | | | |
| | 2.3 | 106.8 | 111.4 | | | | |
| | 6.8 | 237.2 | 179.3 | | | | |

Metabolites of ISIS 647535 were also identified and their masses were confirmed by high resolution mass spectrometry analysis. The cleavage sites and structures of the observed metabolites are shown below. The relative % of full length ASO was calculated using standard procedures and the results are presented in Table 23a. The major metabolite of ISIS 647535 was full-length ASO lacking the entire conjugate (i.e. ISIS 304801), which results from cleavage at cleavage site A, shown below. Further, additional metabolites resulting from other cleavage sites were also observed. These results suggest that introducing other cleabable bonds such as esters, peptides, disulfides, phosphoramidates or acyl-hydrazones between the $GalNAc_3$-1 sugar and the ASO, which can be cleaved by enzymes inside the cell, or which may cleave in the reductive environment of the cytosol, or which are labile to the acidic pH inside endosomes and lyzosomes, can also be useful.

TABLE 23a

| Observed full length metabolites of ISIS 647535 | | | |
|---|---|---|---|
| Metabolite | ASO | Cleavage site | Relative % |
| 1 | ISIS 304801 | A | 36.1 |
| 2 | ISIS 304801 + dA | B | 10.5 |
| 3 | ISIS 647535 minus [3 GalNAc] | C | 16.1 |
| 4 | ISIS 647535 minus [3 GalNAc + 1 5-hydroxy-pentanoic acid tether] | D | 17.6 |
| 5 | ISIS 647535 minus [2 GalNAc + 2 5-hydroxy-pentanoic acid tether] | D | 9.9 |
| 6 | ISIS 647535 minus [3 GalNAc + 3 5-hydroxy-pentanoic acid tether] | D | 9.8 |

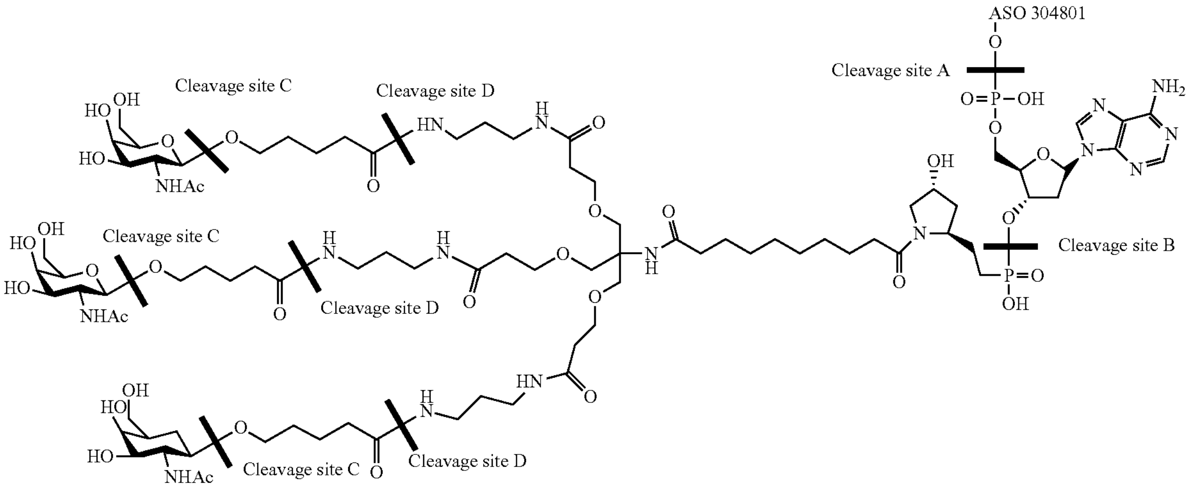

Clevage Sites

Metabolite 1

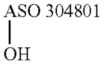

Metabolite 2

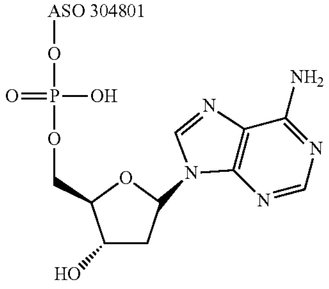

-continued
Metabolite 3
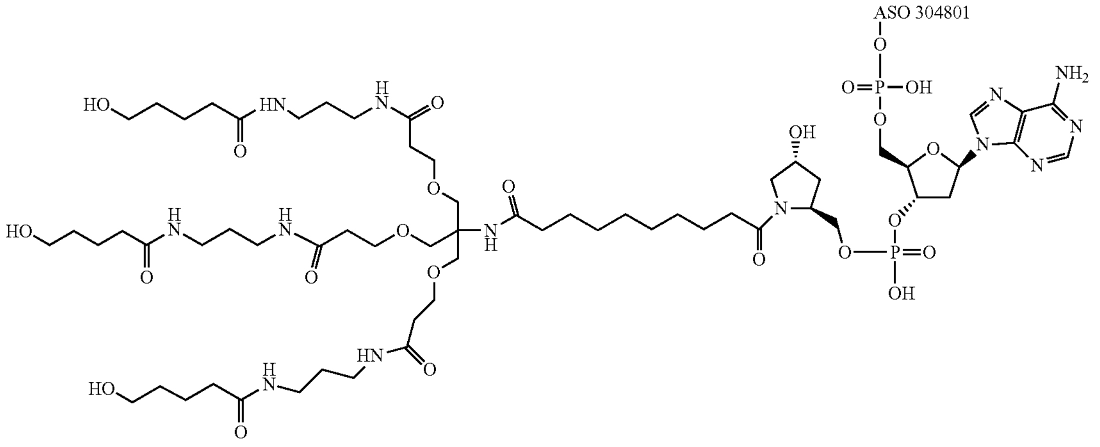
Metabolite 4
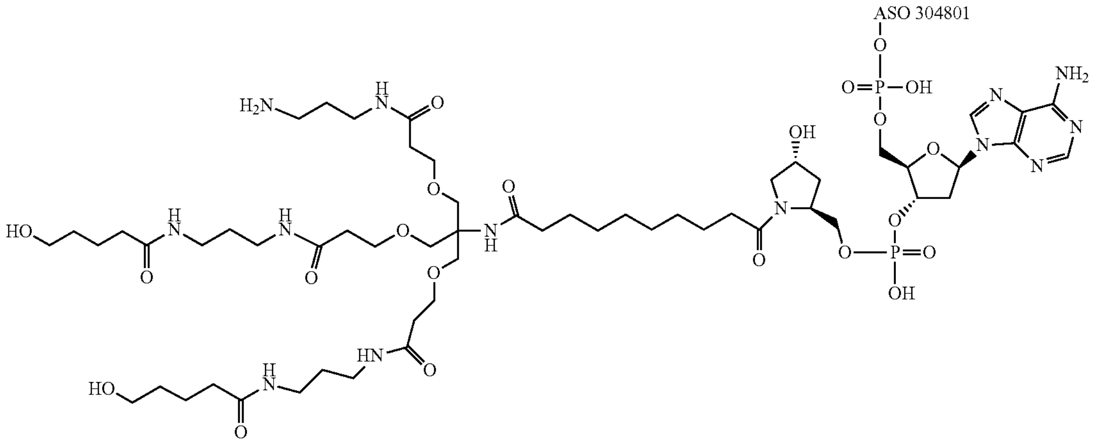
Metabolite 5
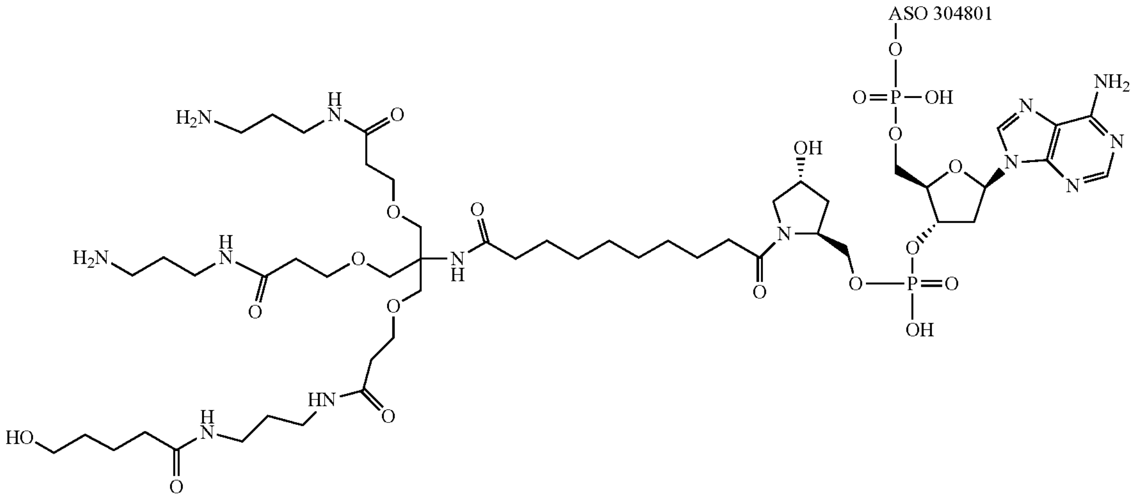

-continued

Metabolite 6

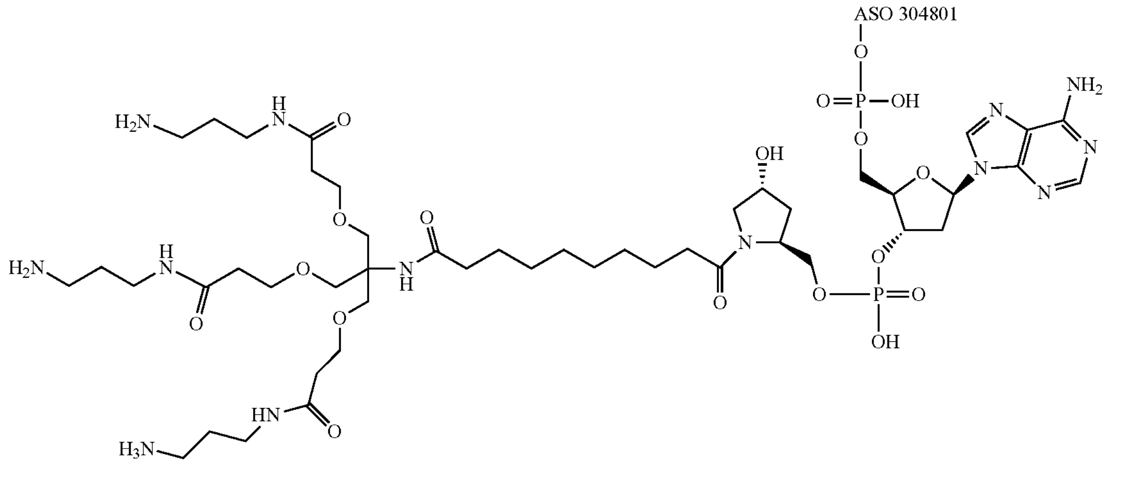

Example 21: Antisense Inhibition of Human ApoC III in Human ApoC III Transgenic Mice in Single Administration Study ISIS 304801, 647535 and 647536 each targeting human ApoC III and described in Table 17, were further evaluated in a single administration study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once at the dosage shown below with ISIS 304801, 647535 or 647536 (described above) or with PBS treated control. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III mRNA and protein levels in the liver; plasma triglycerides; and cholesterol, including HDL and LDL fractions were assessed as described above (Example 20). Data from those analyses are presented in Tables 24-28, below. Liver transaminase levels, alanine aminotransferase (ALT) and aspartate aminotransferase (AST), in serum were measured relative to saline injected mice using standard protocols. The ALT and AST levels showed that the antisense compounds were well tolerated at all administered doses.

These results show improvement in potency for antisense compounds comprising a $GalNAc_3$-1 conjugate at the 3' terminus (ISIS 647535 and 647536) compared to the antisense compound lacking a $GalNAc_3$-1 conjugate (ISIS 304801). Further, ISIS 647536, which comprises a $GalNAc_3$-1 conjugate and some phosphodiester linkages was as potent as ISIS 647535, which comprises the same conjugate and all internucleoside linkages within the ASO are phosphorothioate.

TABLE 24

Effect of ASO treatment on ApoC III mRNA levels in human ApoC III transgenic mice

| ASO | Dose (mg/kg) | % PBS | $ED_{50}$ (mg/kg) | 3' Conjugate | Internucleoside linkage/Length | SEQ ID No. |
|---|---|---|---|---|---|---|
| PBS | 0 | 99 | — | — | — | |
| ISIS 304801 | 1 | 104 | 13.2 | None | PS/20 | 244 |
| | 3 | 92 | | | | |
| | 10 | 71 | | | | |
| | 30 | 40 | | | | |
| ISIS 647535 | 0.3 | 98 | 1.9 | $GalNAc_3$-1 | PS/20 | 245 |
| | 1 | 70 | | | | |
| | 3 | 33 | | | | |
| | 10 | 20 | | | | |
| ISIS 647536 | 0.3 | 103 | 1.7 | $GalNAc_3$-1 | PS/PO/20 | 245 |
| | 1 | 60 | | | | |
| | 3 | 31 | | | | |
| | 10 | 21 | | | | |

TABLE 25

Effect of ASO treatment on ApoC III plasma protein levels in human ApoC III transgenic mice

| ASO | Dose (mg/kg) | % PBS | $ED_{50}$ (mg/kg) | 3' Conjugate | Internucleoside Linkage/Length | SEQ ID No. |
|---|---|---|---|---|---|---|
| PBS | 0 | 99 | — | — | — | |
| ISIS 304801 | 1 | 104 | 23.2 | None | PS/20 | 244 |
| | 3 | 92 | | | | |
| | 10 | 71 | | | | |
| | 30 | 40 | | | | |
| ISIS 647535 | 0.3 | 98 | 2.1 | $GalNAc_3$-1 | PS/20 | 245 |
| | 1 | 70 | | | | |
| | 3 | 33 | | | | |
| | 10 | 20 | | | | |
| ISIS 647536 | 0.3 | 103 | 1.8 | $GalNAc_3$-1 | PS/PO/20 | 245 |
| | 1 | 60 | | | | |
| | 3 | 31 | | | | |
| | 10 | 21 | | | | |

TABLE 26

Effect of ASO treatment on triglyceride levels in transgenic mice

| ASO | Dose (mg/kg) | % PBS | $ED_{50}$ (mg/kg) | 3' Conjugate | Inter-nucleoside Linkage/ Length | SEQ ID No. |
|---|---|---|---|---|---|---|
| PBS | 0 | 98 | — | — | — | |
| ISIS | 1 | 80 | 29.1 | None | PS/20 | 244 |
| 304801 | 3 | 92 | | | | |
| | 10 | 70 | | | | |
| | 30 | 47 | | | | |
| ISIS | 0.3 | 100 | 2.2 | $GalNAc_3$-1 | PS/20 | 245 |
| 647535 | 1 | 70 | | | | |
| | 3 | 34 | | | | |
| | 10 | 23 | | | | |
| ISIS | 0.3 | 95 | 1.9 | $GalNAc_3$-1 | PS/PO/20 | 245 |
| 647536 | 1 | 66 | | | | |
| | 3 | 31 | | | | |
| | 10 | 23 | | | | |

TABLE 27

Effect of ASO treatment on total cholesterol levels in transgenic mice

| ASO | Dose (mg/kg) | % PBS | 3' Conjugate | Internucleoside Linkage/Length | SEQ ID No. |
|---|---|---|---|---|---|
| PBS | 0 | 96 | — | — | |
| ISIS | 1 | 104 | None | PS/20 | 244 |
| 304801 | 3 | 96 | | | |
| | 10 | 86 | | | |
| | 30 | 72 | | | |
| ISIS | 0.3 | 93 | $GalNAc_3$-1 | PS/20 | 245 |
| 647535 | 1 | 85 | | | |
| | 3 | 61 | | | |
| | 10 | 53 | | | |
| ISIS | 0.3 | 115 | $GalNAc_3$-1 | PS/PO/20 | 245 |
| 647536 | 1 | 79 | | | |
| | 3 | 51 | | | |
| | 10 | 54 | | | |

TABLE 28

Effect of ASO treatment on HDL and LDL cholesterol levels in transgenic mice

| ASO | (mg/ kg) | HDL % PBS | LDL % PBS | 3' Conjugate | Inter-nucleoside Linkage/ Length | SEQ ID No. |
|---|---|---|---|---|---|---|
| PBS | 0 | 131 | 90 | — | — | |
| ISIS | 1 | 130 | 72 | None | PS/20 | 244 |
| 304801 | 3 | 186 | 79 | | | |
| | 10 | 226 | 63 | | | |
| | 30 | 240 | 46 | | | |
| ISIS | 0.3 | 98 | 86 | $GalNAc_3$-1 | PS/20 | 245 |
| 647535 | 1 | 214 | 67 | | | |
| | 3 | 212 | 39 | | | |
| | 10 | 218 | 35 | | | |
| ISIS | 0.3 | 143 | 89 | $GalNAc_3$-1 | PS/PO/20 | 245 |
| 647536 | 1 | 187 | 56 | | | |
| | 3 | 213 | 33 | | | |
| | 10 | 221 | 34 | | | |

These results confirm that the $GalNAc_3$-1 conjugate improves potency of an antisense compound. The results also show equal potency of a $GalNAc_3$-1 conjugated antisense compounds where the antisense oligonucleotides have mixed linkages (ISIS 647536 which has six phosphodiester linkages) and a full phosphorothioate version of the same antisense compound (ISIS 647535).

Phosphorothioate linkages provide several properties to antisense compounds. For example, they resist nuclease digestion and they bind proteins resulting in accumulation of compound in the liver, rather than in the kidney/urine. These are desirable properties, particularly when treating an indication in the liver. However, phosphorothioate linkages have also been associated with an inflammatory response. Accordingly, reducing the number of phosphorothioate linkages in a compound is expected to reduce the risk of inflammation, but also lower concentration of the compound in liver, increase concentration in the kidney and urine, decrease stability in the presence of nucleases, and lower overall potency. The present results show that a $GalNAc_3$-1 conjugated antisense compound where certain phosphorothioate linkages have been replaced with phosphodiester linkages is as potent against a target in the liver as a counterpart having full phosphorothioate linkages. Such compounds are expected to be less proinflammatory (See Example 24 describing an experiment showing reduction of PS results in reduced inflammatory effect).

Example 22: Effect of $GalNAc_3$-1 Conjugated Modified ASO Targeting SRB-1 In Vivo ISIS 440762 and 651900, each targeting SRB-1 and described in Table 17, were evaluated in a dose-dependent study for their ability to inhibit SRB-1 in Balb/c mice.

Treatment

Six week old male Balb/c mice (Jackson Laboratory, Bar Harbor, ME) were injected subcutaneously once at the dosage shown below with ISIS 440762, 651900 or with PBS treated control. Each treatment group consisted of 4 animals. The mice were sacrificed 48 hours following the final administration to determine the SRB-1 mRNA levels in liver using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS".

As illustrated in Table 29, both antisense compounds lowered SRB-1 mRNA levels. Further, the antisense compound comprising the $GalNAc_3$-1 conjugate (ISIS 651900) was substantially more potent than the antisense compound lacking the $GalNAc_3$-1 conjugate (ISIS 440762). These results demonstrate that the potency benefit of $GalNAc_3$-1 conjugates are observed using antisense oligonucleotides complementary to a different target and having different chemically modified nucleosides, in this instance modified nucleosides comprise constrained ethyl sugar moieties (a bicyclic sugar moiety).

TABLE 29

Effect of ASO treatment on SRB-1 mRNA levels in Balb/c mice

| ASO | Dose (mg/kg) | Liver % PBS | $ED_{50}$ (mg/kg) | 3' Conjugate | Inter-nucleoside Linkage/ Length | SEQ ID No. |
|---|---|---|---|---|---|---|
| PBS | 0 | 100 | | — | — | |
| ISIS | 0.7 | 85 | 2.2 | None | PS/14 | 246 |
| 440762 | 2 | 55 | | | | |
| | 7 | 12 | | | | |
| | 20 | 3 | | | | |

TABLE 29-continued

Effect of ASO treatment on SRB-1 mRNA levels in Balb/c mice

| ASO | Dose (mg/kg) | Liver % PBS | $ED_{50}$ (mg/kg) | 3' Conjugate | Internucleoside Linkage/ Length | SEQ ID No. |
|---|---|---|---|---|---|---|
| ISIS 651900 | 0.07 | 98 | 0.3 | $GalNAc_3$-1 | PS/14 | 247 |
| | 0.2 | 63 | | | | |
| | 0.7 | 20 | | | | |
| | 2 | 6 | | | | |
| | 7 | 5 | | | | |

Example 23: Human Peripheral Blood Mononuclear Cells (hPBMC) Assay Protocol

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat. #BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS ($Ca^{++}$, $Mg^{++}$ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 µl sample was pipette into a sample vial (Beckman Coulter) with 600 µl VersaLyse reagent (Beckman Coulter Cat #A09777) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to $1\times10^7$ live PBMC/ml in RPMI+10% FBS+pen/strep.

The cells were plated at $5\times10^5$ in 50 µl/well of 96-well tissue culture plate (Falcon Microtest). 50 µl/well of 2× concentration oligos/controls diluted in RPMI+10% FBS+pen/strep. was added according to experiment template (100 µl/well total). Plates were placed on the shaker and allowed to mix for approx. 1 min. After being incubated for 24 hrs at 37° C.; 5% $CO_2$, the plates were centrifuged at 400×g for 10 minutes before removing the supernatant for MSD cytokine assay (i.e. human IL-6, IL-10, IL-8 and MCP-1).

Example 24: Evaluation of Proinflammatory Effects in hPBMC Assay for $GalNAc_3$-1 Conjugated ASOs The antisense oligonucleotides (ASOs) listed in Table 30 were evaluated for proinflammatory effect in hPBMC assay using the protocol described in Example 23. ISIS 353512 is an internal standard known to be a high responder for IL-6 release in the assay. The hPBMCs were isolated from fresh, volunteered donors and were treated with ASOs at 0, 0.0128, 0.064, 0.32, 1.6, 8, 40 and 200 µM concentrations. After a 24 hr treatment, the cytokine levels were measured.

The levels of IL-6 were used as the primary readout. The $EC_{50}$ and $E_{max}$ was calculated using standard procedures. Results are expressed as the average ratio of $E_{max}/EC_{50}$ from two donors and is denoted as "$E_{max}/EC_{50}$." The lower ratio indicates a relative decrease in the proinflammatory response and the higher ratio indicates a relative increase in the proinflammatory response.

With regard to the test compounds, the least proinflammatory compound was the PS/PO linked ASO (ISIS 616468). The $GalNAc_3$-1 conjugated ASO, ISIS 647535 was slightly less proinflammatory than its non-conjugated counterpart ISIS 304801. These results indicate that incorporation of some PO linkages reduces proinflammatory reaction and addition of a $GalNAc_3$-1 conjugate does not make a compound more proinflammatory and may reduce proinflammatory response. Accordingly, one would expect that an antisense compound comprising both mixed PS/PO linkages and a $GalNAc_3$-1 conjugate would produce lower proinflammatory responses relative to full PS linked antisense compound with or without a $GalNAc_3$-1 conjugate. These results show that $GalNAc_3$-1 conjugated antisense compounds, particularly those having reduced PS content are less proinflammatory.

Together, these results suggest that a $GalNAc_3$-1 conjugated compound, particularly one with reduced PS content, can be administered at a higher dose than a counterpart full PS antisense compound lacking a $GalNAc_3$-1 conjugate. Since half-life is not expected to be substantially different for these compounds, such higher administration would result in less frequent dosing. Indeed such administration could be even less frequent, because the $GalNAc_3$-1 conjugated compounds are more potent (See Examples 20-22) and re-dosing is necessary once the concentration of a compound has dropped below a desired level, where such desired level is based on potency.

TABLE 30

Modified ASOs

| ASO | Sequence (5' to 3') | Target | Unmodified SEQ ID No. | Modified SEQ ID No. |
|---|---|---|---|---|
| ISIS 104838 | $G_{es}{}^mC_{es}T_{es}G_{es}A_{es}T_{ds}T_{ds}A_{ds}G_{ds}A_{ds}G_{ds}A_{ds}G_{ds}A_{ds}G_{ds}G_{es}T_{es}{}^mC_{es}{}^mC_{es}{}^mC_e$ | TNFα | 248 | 316 |
| ISIS 353512 | $T_{es}{}^mC_{es}{}^mC_{es}{}^mC_{ds}A_{ds}T_{ds}T_{ds}T_{ds}{}^mC_{ds}A_{ds}G_{ds}G_{ds}A_{ds}G_{ds}A_{ds}{}^mC_{ds}{}^mC_{ds}T_{es}G_{es}G_e$ | CRP | 249 | 319 |
| ISIS 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_e$ | ApoC III | 244 | 317 |
| ISIS 647535 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{eo}$ **$A_{do'}$-GalNAC$_3$-1$_a$** | ApoC III | 245 | 367 |

TABLE 30-continued

| Modified ASOs | | | | |
|---|---|---|---|---|
| ASO | Sequence (5' to 3') | Target | Unmodified SEQ ID No. | Modified SEQ ID No. |
| ISIS 616468 | $A_{es}G_{eo}{}^{m}C_{eo}T_{eo}T_{eo}$ ${}^{m}C_{ds}T_{ds}T_{ds}G_{ds}T_{ds}$ ${}^{m}C_{ds}{}^{m}C_{ds}A_{ds}G_{ds}$ ${}^{m}C_{ds}T_{eo}T_{eo}T_{es}A_{es}T_{e}$ | ApoC III | 244 | 327 |

Subscripts:
"e" indicates 2'-MOE modified nucleoside;
"d" indicates β-D-2'-deoxyribonucleoside;
"k" indicates 6'-(S)-$CH_3$ bicyclic nucleoside (e.g. cEt);
"s" indicates phosphorothioate internucleoside linkages (PS);
"o" indicates phosphodiester internucleoside linkages (PO); and
"o'" indicates —O—P(═O)(OH)—.
Superscript "m" indicates 5-methylcytosines.
"$A_{do'}$-GalNAC$_3$-1$_a$" indicates a conjugate having the structure GalNAC$_3$-1 shown in Example 9 attached to the 3'-end of the antisense oligonucleotide, as indicated.

TABLE 31

| Proinflammatory Effect of ASOs targeting ApoC III in hPBMC assay | | | | | | |
|---|---|---|---|---|---|---|
| ASO | $EC_{50}$ (μM) | $E_{max}$ (μM) | $E_{max}$/ $EC_{50}$ | 3' Conjugate | Internucleoside Linkage/ Length | SEQ ID No. |
| ISIS 353512 (high responder) | 0.01 | 265.9 | 26,590 | None | PS/20 | 249 |
| ISIS 304801 | 0.07 | 106.55 | 1,522 | None | PS/20 | 244 |
| ISIS 647535 | 0.12 | 138 | 1,150 | GalNAc$_3$-1 | PS/20 | 245 |
| ISIS 616468 | 0.32 | 71.52 | 224 | None | PS/PO/20 | 244 |

Example 25: Effect of GalNAc$_3$-1 Conjugated Modified ASO Targeting Human ApoC III In Vitro ISIS 304801 and 647535 described above were tested in vitro. Primary hepatocyte cells from transgenic mice at a density of 25,000 cells per well were treated with 0.03, 0.08, 0.24, 0.74, 2.22, 6.67 and 20 μM concentrations of modified oligonucleotides. After a treatment period of approximately 16 hours, RNA was isolated from the cells and mRNA levels were measured by quantitative real-time PCR and the hApoC III mRNA levels were adjusted according to total RNA content, as measured by RIBOGREEN.

The $IC_{50}$ was calculated using the standard methods and the results are presented in Table 32. As illustrated, comparable potency was observed in cells treated with ISIS 647535 as compared to the control, ISIS 304801.

TABLE 32

| Modified ASO targeting human ApoC III in primary hepatocytes | | | | |
|---|---|---|---|---|
| ASO | $IC_{50}$ (μM) | 3' Conjugate | Internucleoside linkage/Length | SEQ ID No. |
| ISIS 304801 | 0.44 | None | PS/20 | 244 |
| ISIS 647535 | 0.31 | GalNAc$_3$-1 | PS/20 | 245 |

In this experiment, the large potency benefits of GalNAc$_3$-1 conjugation that are observed in vivo were not observed in vitro. Subsequent free uptake experiments in primary hepatocytes in vitro did show increased potency of oligonucleotides comprising various GalNAc conjugates relative to oligonucleotides that lacking the GalNAc conjugate. (see Examples 60, 82, and 92)

Example 26: Effect of PO/PS Linkages on ApoC III ASO Activity

Human ApoC III transgenic mice were injected intraperitoneally once at 25 mg/kg of ISIS 304801, or ISIS 616468 (both described above) or with PBS treated control once per week for two weeks. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III protein levels in the liver as described above (Example 20). Data from those analyses are presented in Table 33, below.

These results show reduction in potency for antisense compounds with PO/PS (ISIS 616468) in the wings relative to full PS (ISIS 304801).

TABLE 33

| Effect of ASO treatment on ApoC III protein levels in human ApoC III transgenic mice | | | | | |
|---|---|---|---|---|---|
| ASO | Dose (mg/kg) | % PBS | 3' Conjugate | Internucleoside linkage/Length | SEQ ID No. |
| PBS | 0 | 99 | — | — | |
| ISIS 304801 | 25 mg/kg/wk for 2 wks | 24 | None | Full PS | 244 |
| ISIS 616468 | 25 mg/kg/wk for 2 wks | 40 | None | 14 PS/6 PO | 244 |

Example 27: Compound 56

56

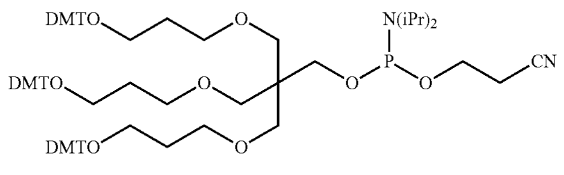

Compound 56 is commercially available from Glen Research or may be prepared according to published procedures reported by Shchepinov et al., *Nucleic Acids Research,* 1997, 25(22), 4447-4454.

Example 28: Preparation of Compound 60

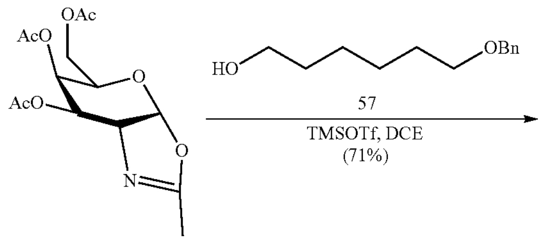

4

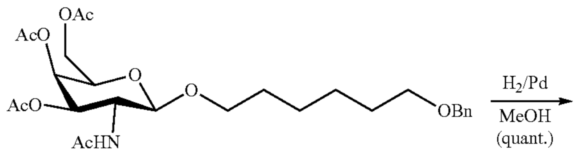

58

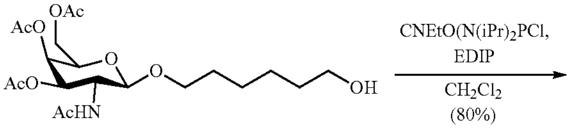

59

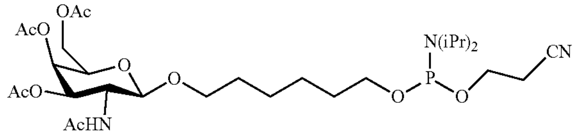

60

Compound 4 was prepared as per the procedures illustrated in Example 2. Compound 57 is commercially available. Compound 60 was confirmed by structural analysis.

Compound 57 is meant to be representative and not intended to be limiting as other monoprotected substituted or unsubstituted alkyl diols including but not limited to those presented in the specification herein can be used to prepare phosphoramidites having a predetermined composition.

Example 29: Preparation of Compound 63

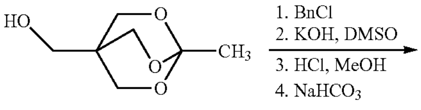

61

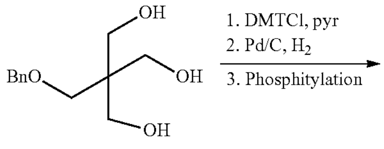

62

-continued

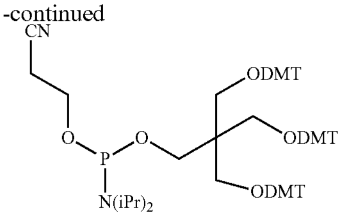

63

Compounds 61 and 62 are prepared using procedures similar to those reported by Tober et al., *Eur. J. Org. Chem.,* 2013, 3, 566-577; and Jiang et al., *Tetrahedron,* 2007, 63(19), 3982-3988.

Alternatively, Compound 63 is prepared using procedures similar to those reported in scientific and patent literature by Kim et al., *Synlett,* 2003, 12, 1838-1840; and Kim et al., published PCT International Application, WO 2004063208.

Example 30: Preparation of Compound 63b

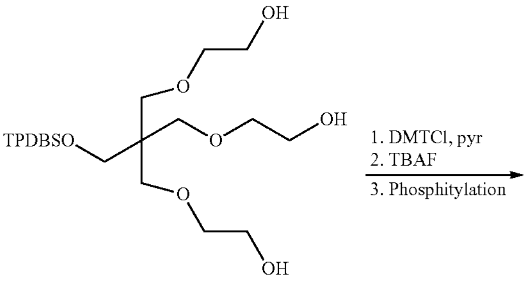

63a

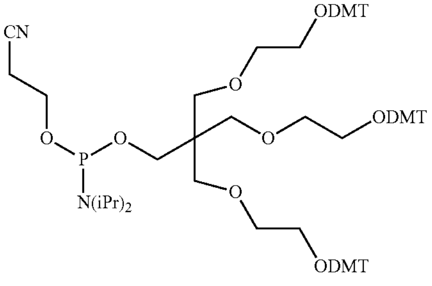

63b

Compound 63a is prepared using procedures similar to those reported by Hanessian et al., *Canadian Journal of Chemistry,* 1996, 74(9), 1731-1737.

Example 31: Preparation of Compound 63d

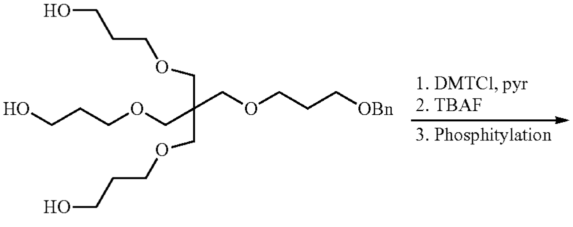

63c

-continued

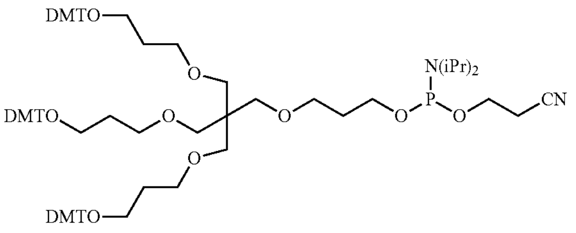

63d

Compound 63c is prepared using procedures similar to those reported by Chen et al., *Chinese Chemical Letters,* 1998, 9(5), 451-453.

Example 32: Preparation of Compound 67

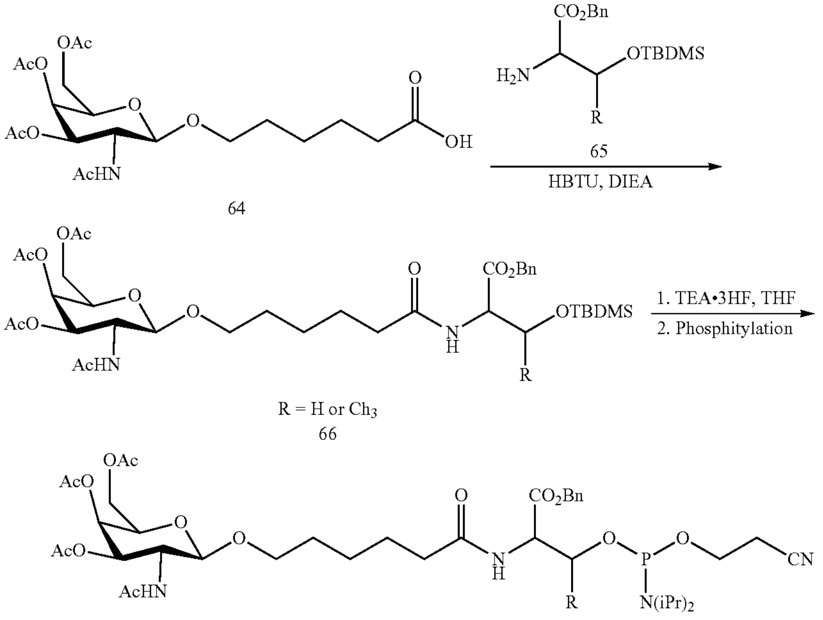

64

65

R = H or Ch3

66

67

Compound 64 was prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 33: Preparation of Compound 70

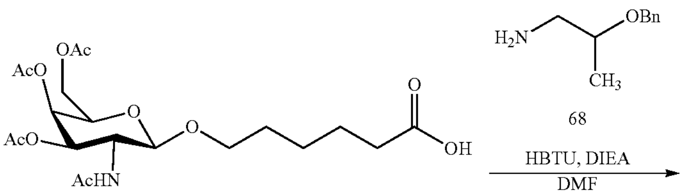

68

64

-continued

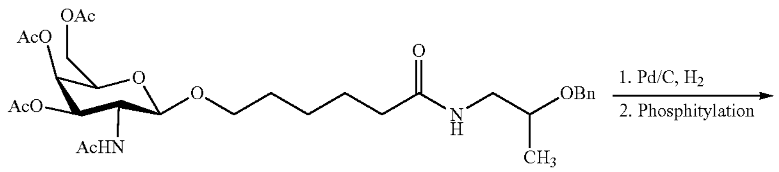

69

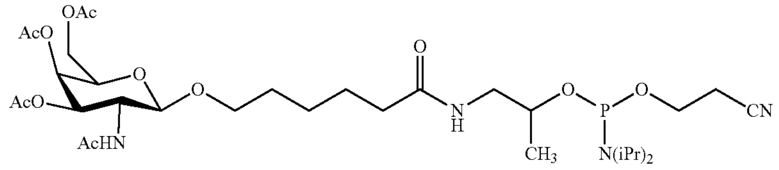

70

Compound 64 was prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 34: Preparation of Compound 75a

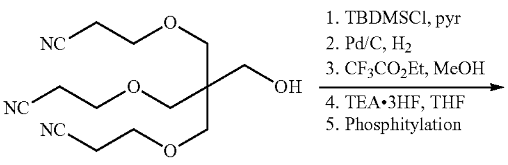

75

-continued

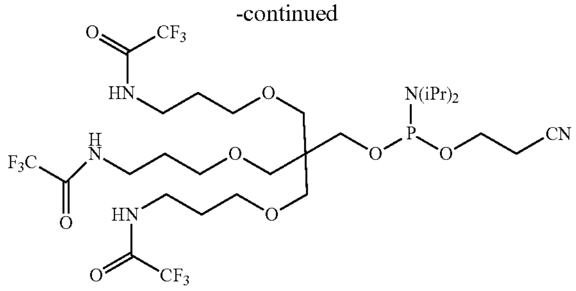

75a

Compound 75 is prepared according to published procedures reported by Shchepinov et al., *Nucleic Acids Research,* 1997, 25(22), 4447-4454.

Example 35: Preparation of Compound 79

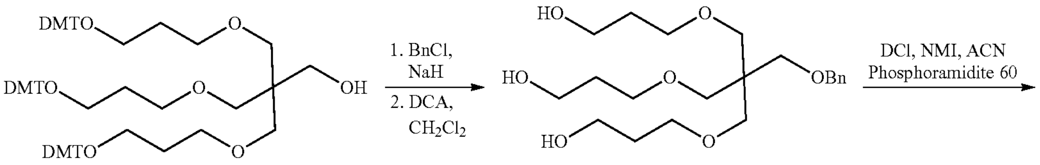

76

77

-continued
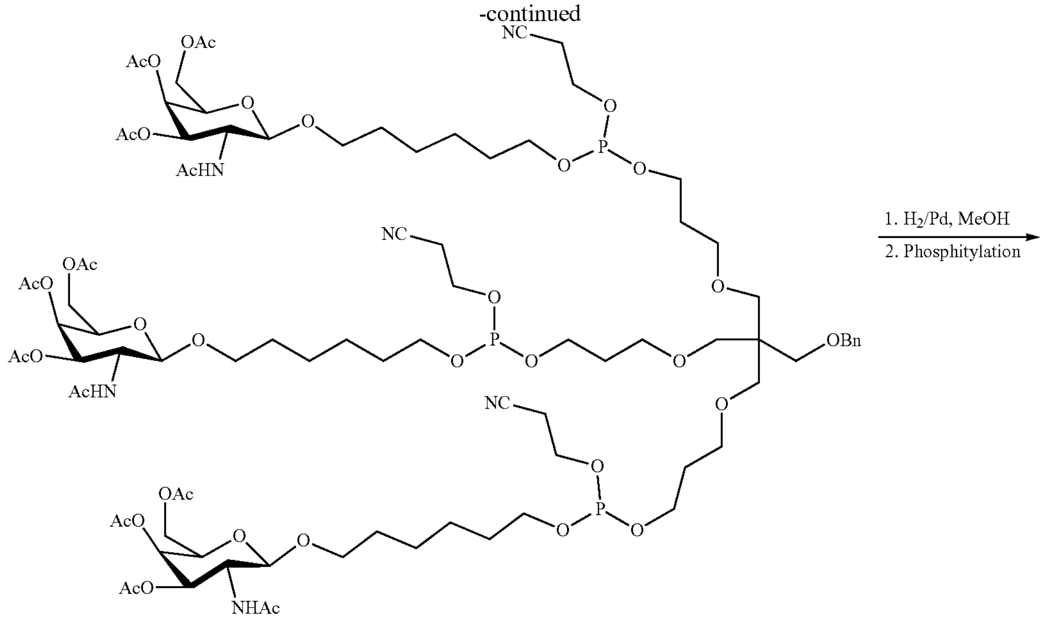
78
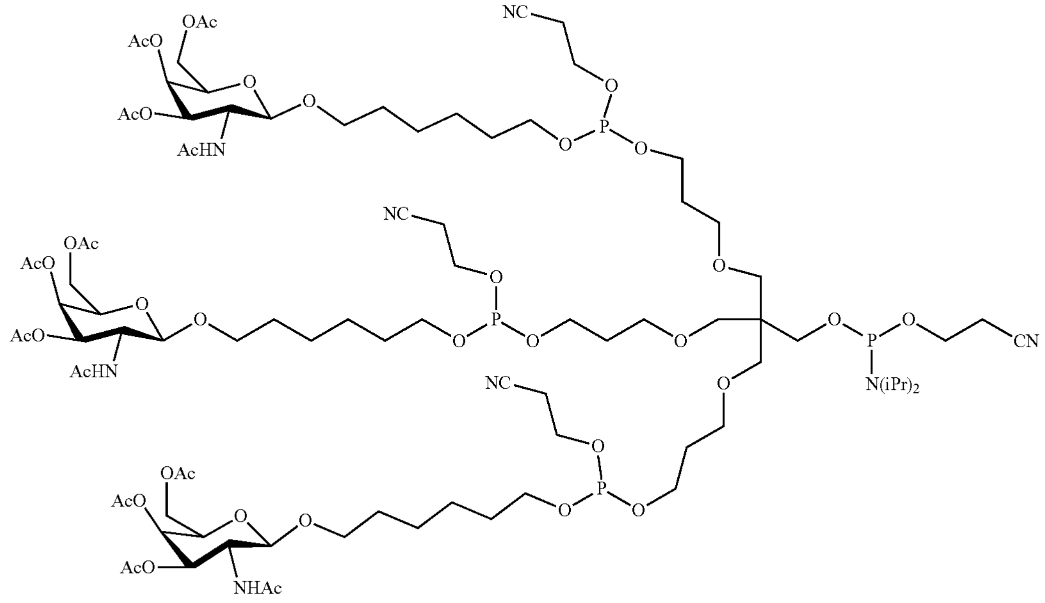
79
Compound 76 was prepared according to published procedures reported by Shchepinov et al., *Nucleic Acids Research,* 1997, 25(22), 4447-4454.
Example 36: Preparation of Compound 79a
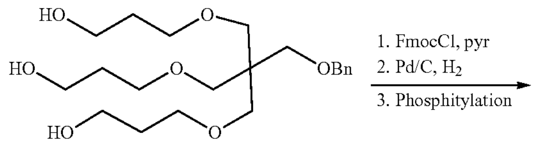
77
-continued
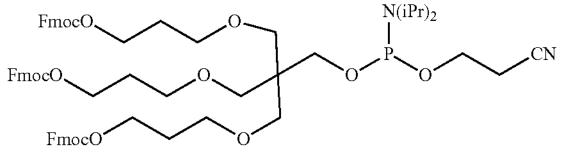
79a
Compound 77 is prepared as per the procedures illustrated in Example 35.

Example 37: General Method for the Preparation of Conjugated Oligomeric Compound 82 Comprising a Phosphodiester Linked GalNAc$_3$-2 Conjugate at 5' Terminus Via Solid Support (Method I)
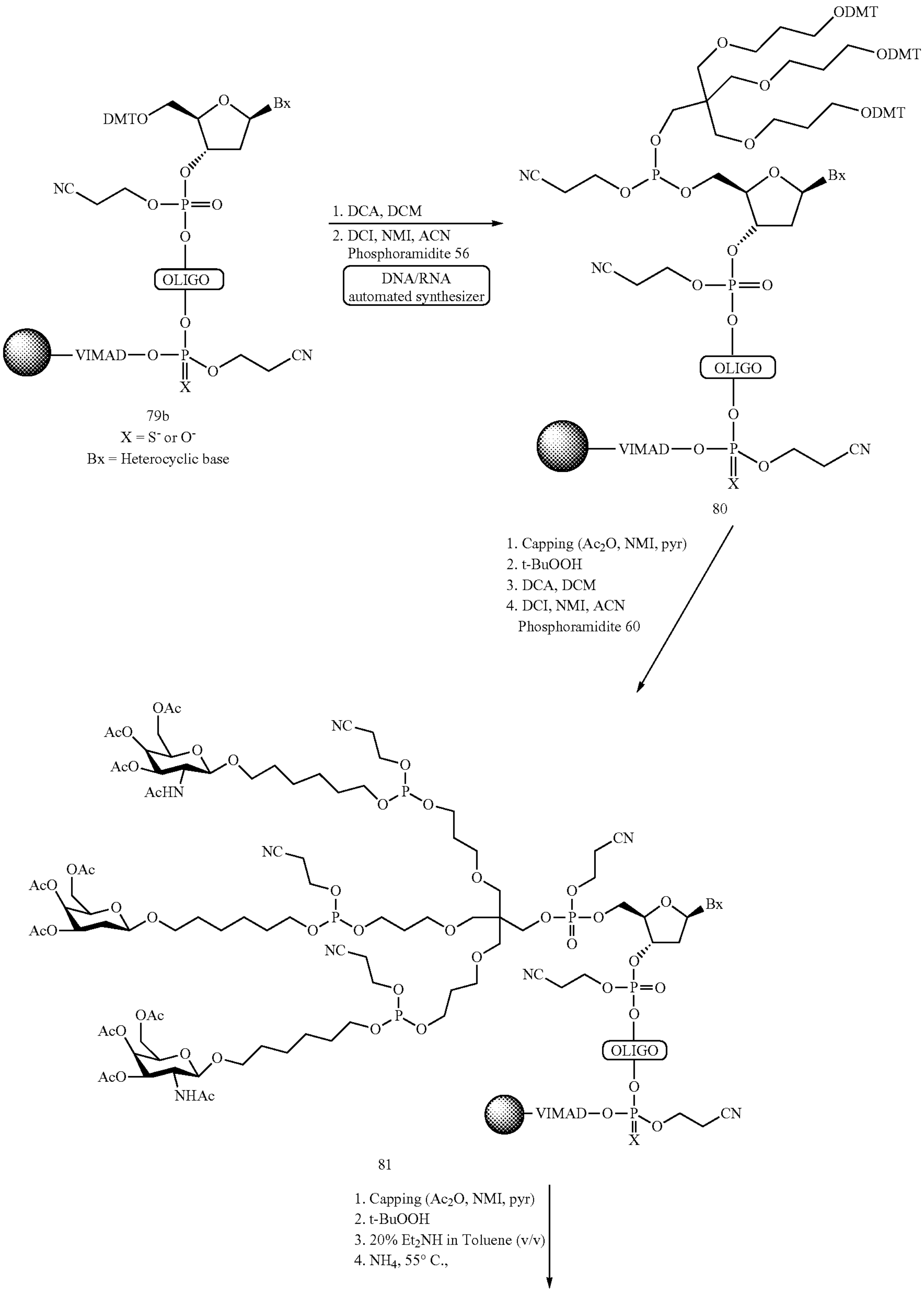
79b
X = $S^-$ or $O^-$
Bx = Heterocyclic base
80
81

-continued
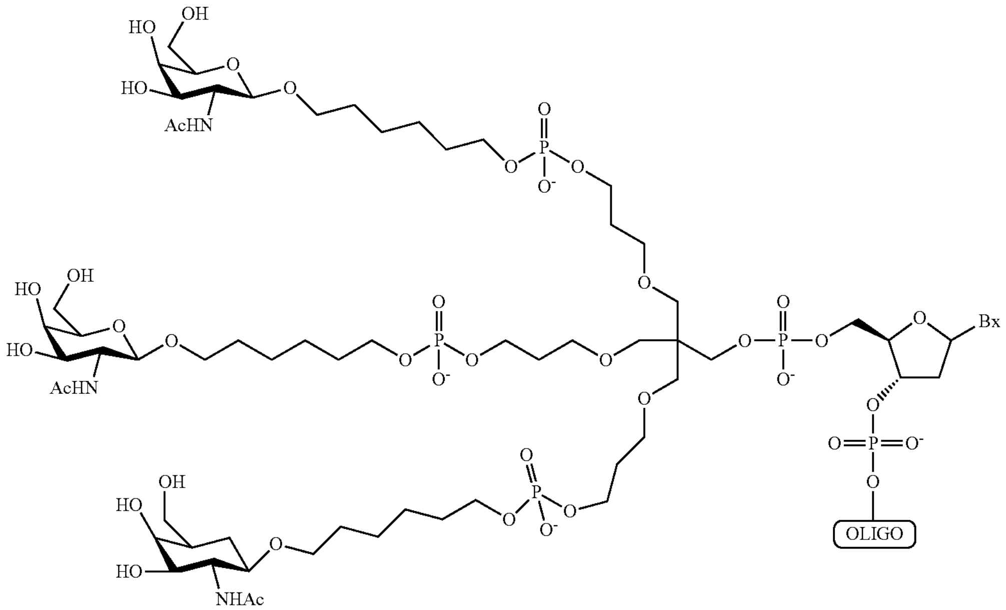
82
wherein $GalNAc_3$-2 has the structure:
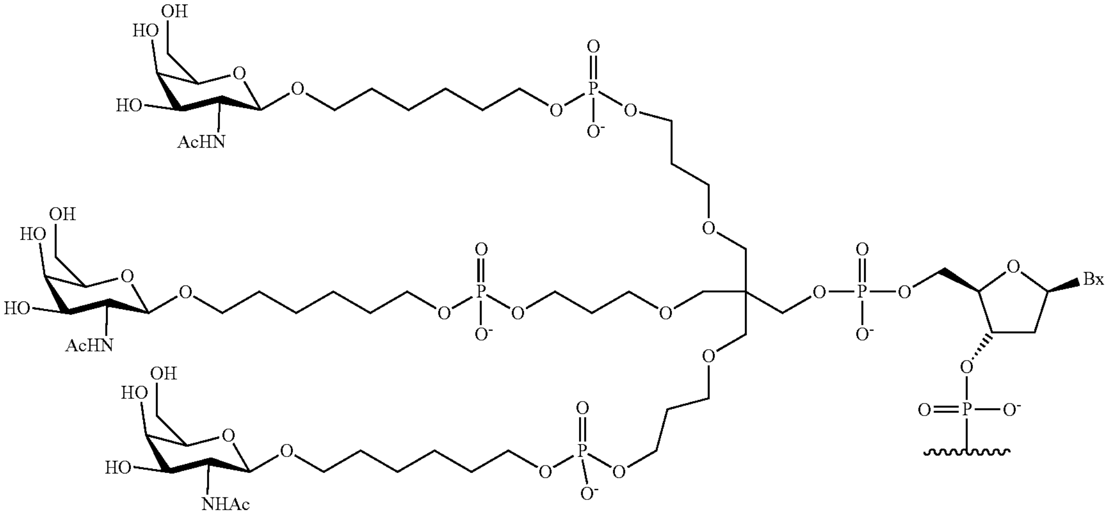

The $GalNAc_3$ cluster portion of the conjugate group $GalNAc_3$-2 ($GalNAc_3$-$2_a$) can be combined with any cleavable moiety to provide a variety of conjugate groups. Wherein $GalNAc_3$-$2_a$ has the formula:

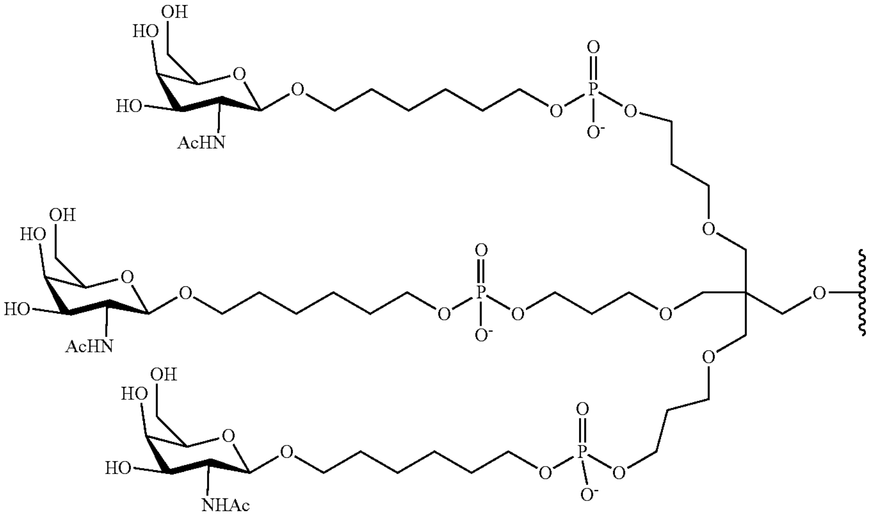

The VIMAD-bound oligomeric compound 79b was prepared using standard procedures for automated DNA/RNA synthesis (see Dupouy et al., *Angew. Chem. Int. Ed.*, 2006, 45, 3623-3627). The phosphoramidite Compounds 56 and 60 were prepared as per the procedures illustrated in Examples 27 and 28, respectively. The phosphoramidites illustrated are meant to be representative and not intended to be limiting as other phosphoramidite building blocks including but not limited those presented in the specification herein can be used to prepare an oligomeric compound having a phosphodiester linked conjugate group at the 5' terminus.

The order and quantity of phosphoramidites added to the solid support can be adjusted to prepare the oligomeric compounds as described herein having any predetermined sequence and composition.

Example 38: Alternative Method for the Preparation of Oligomeric Compound 82 Comprising a Phosphodiester Linked $GalNAc_3$-2 Conjugate at 5' Terminus (Method II)

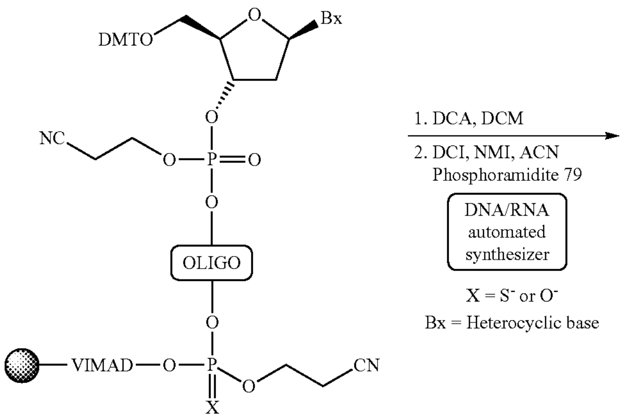

79b

-continued

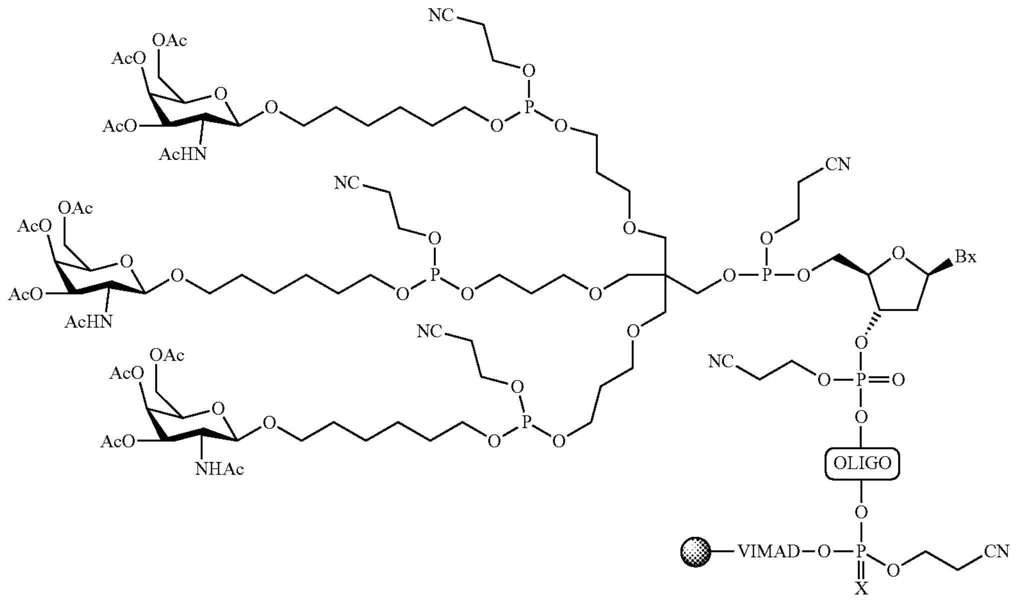

83

1. Capping
2. t-BuOOH
3. $Et_3N$:$CH_3CN$ (1:1 v/v)
4. $NH_4$, 55° C.

Oligomeric Compound 82

The VIMAD-bound oligomeric compound 79b was prepared using standard procedures for automated DNA/RNA synthesis (see Dupouy et al., *Angew. Chem. Int. Ed.*, 2006, 45, 3623-3627). The GalNAc$_3$-2 cluster phosphoramidite, Compound 79 was prepared as per the procedures illustrated in Example 35. This alternative method allows a one-step installation of the phosphodiester linked GalNAc$_3$-2 conjugate to the oligomeric compound at the final step of the synthesis. The phosphoramidites illustrated are meant to be representative and not intended to be limiting, as other phosphoramidite building blocks including but not limited to those presented in the specification herein can be used to prepare oligomeric compounds having a phosphodiester conjugate at the 5' terminus. The order and quantity of phosphoramidites added to the solid support can be adjusted to prepare the oligomeric compounds as described herein having any predetermined sequence and composition.

Example 39: General Method for the Preparation of Oligomeric Compound 83h Comprising a GalNAc$_3$-3 Conjugate at the 5' Terminus (GalNAc$_3$-1 Modified for 5' End Attachment) Via Solid Support
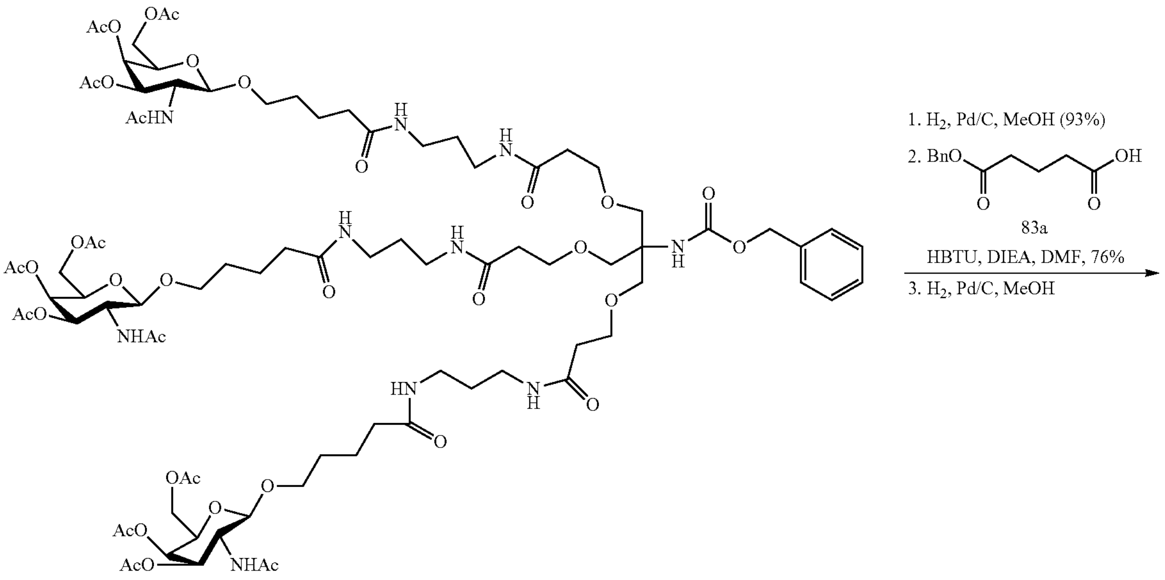
18
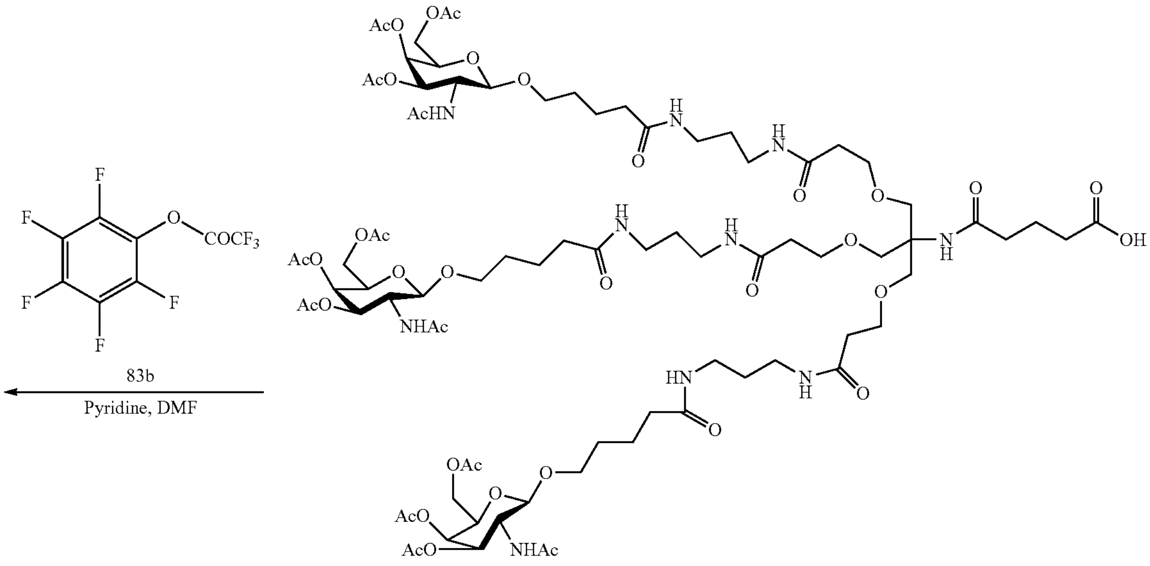
83c -continued
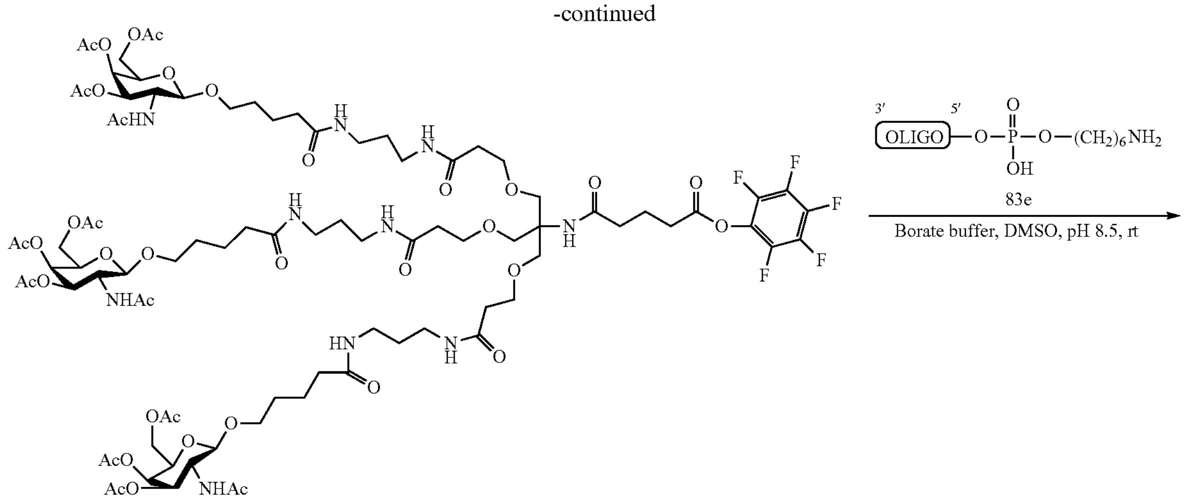
83d
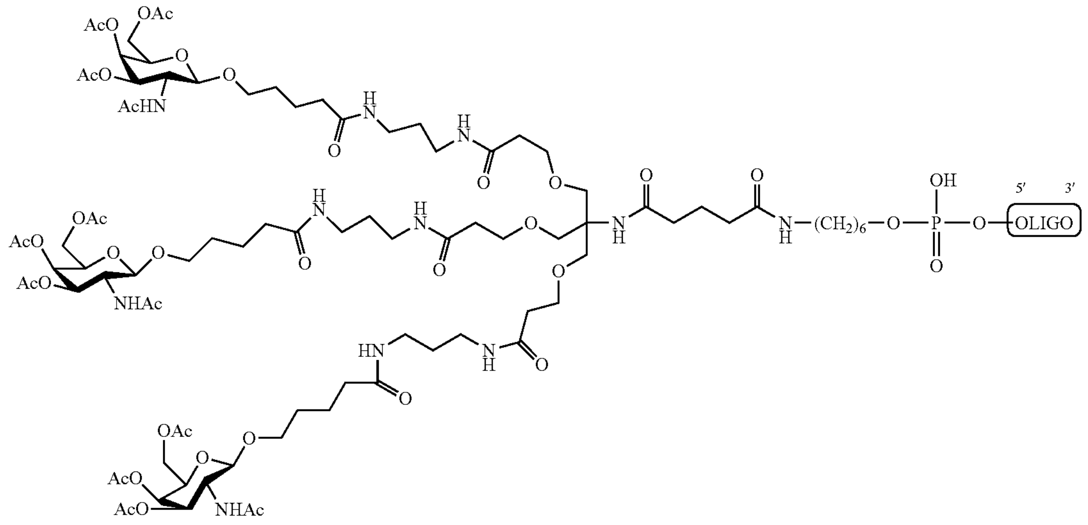
83f
Aqueous ammonia
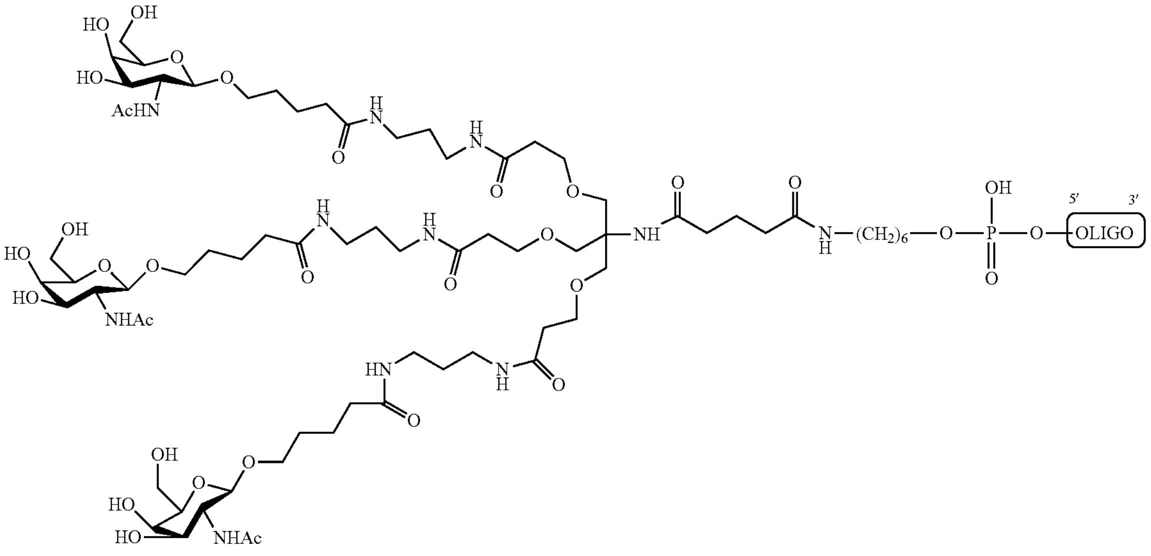
83h Compound 18 was prepared as per the procedures illustrated in Example 4. Compounds 83a and 83b are commercially available. Oligomeric Compound 83e comprising a phosphodiester linked hexylamine was prepared using standard oligonucleotide synthesis procedures. Treatment of the protected oligomeric compound with aqueous ammonia provided the 5'-GalNAc$_3$-3 conjugated oligomeric compound (83h).

Wherein GalNAc$_3$-3 has the structure:

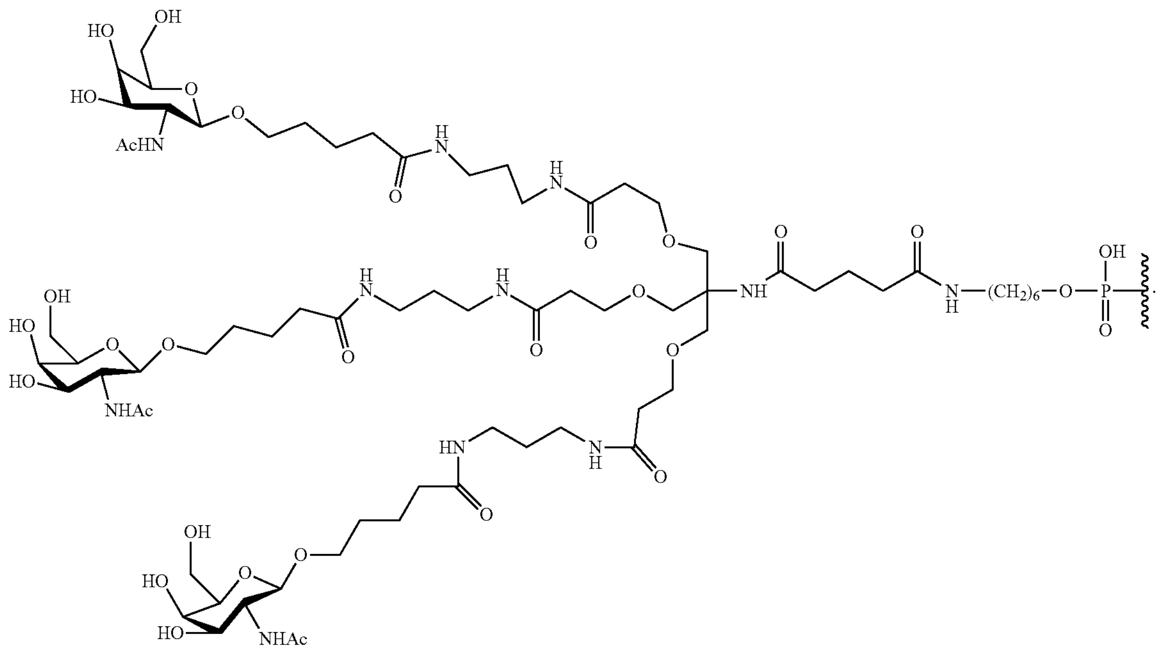

The GalNAc$_3$ cluster portion of the conjugate group GalNAc$_3$-3 (GalNAc$_3$-3$_a$) can be combined with any cleavable moiety to provide a variety of conjugate groups. Wherein GalNAc$_3$-3$_a$ has the formula:

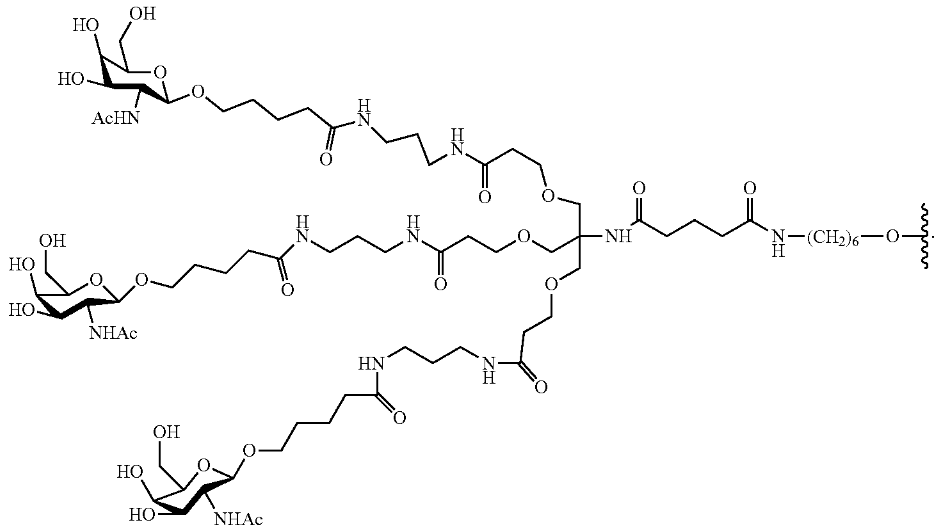

Example 40: General Method for the Preparation of Oligomeric Compound 89 Comprising a Phosphodiester Linked GalNAc$_3$-4 Conjugate at the 3' Terminus Via Solid Support
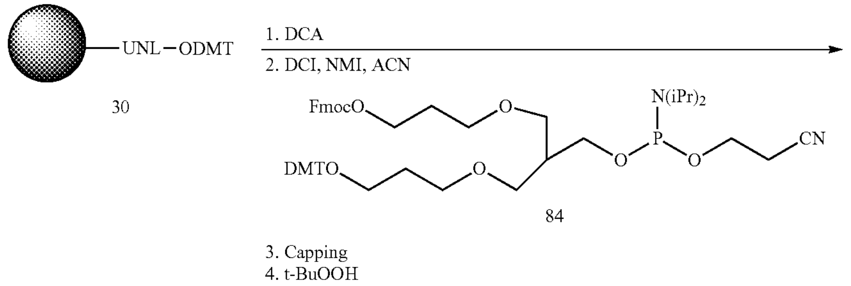
30
84
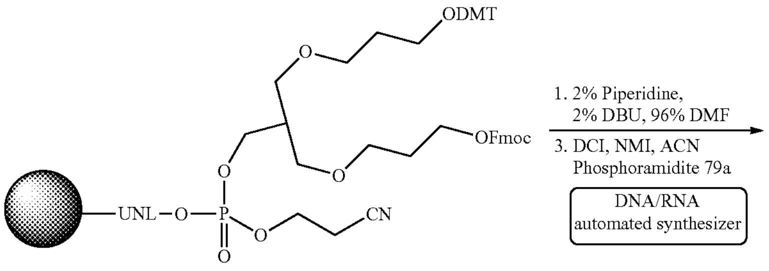
85
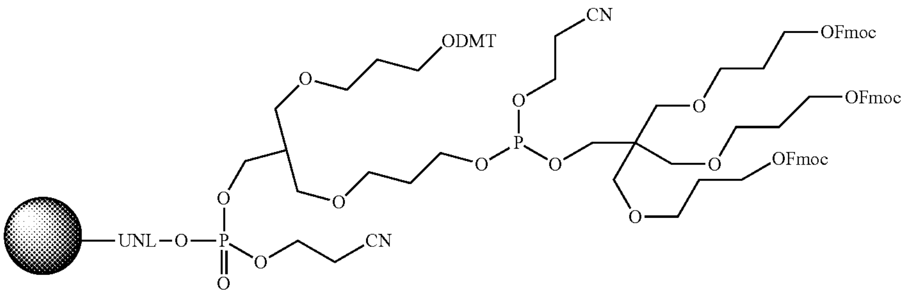
86
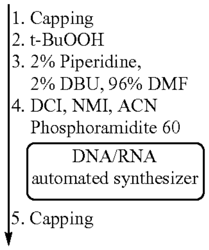

-continued
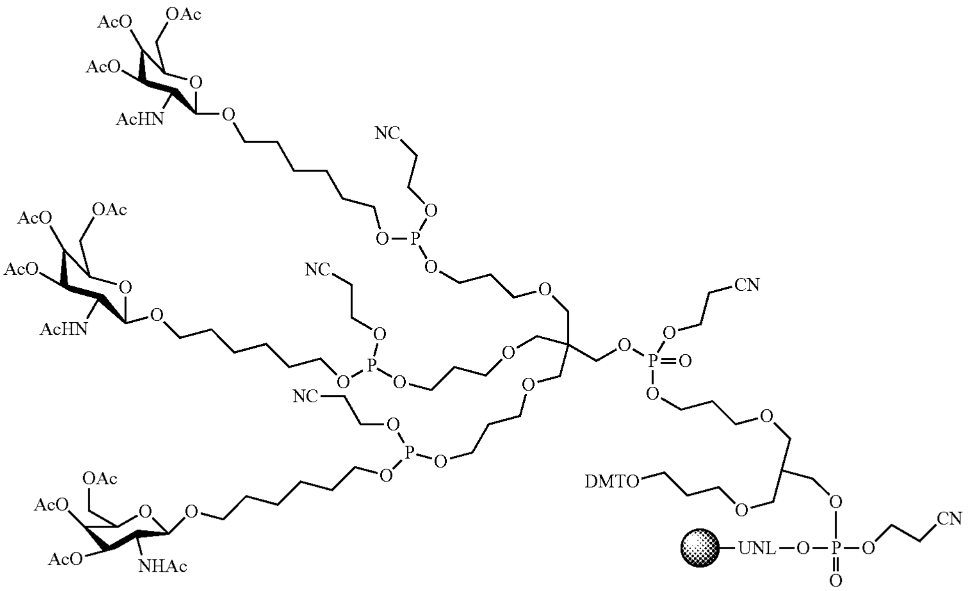
87
1. t-BuOOH
2. DCA
3. Oligo synthesis (DNA/RNA automated synthesizer)
4. Capping
5. Oxidation
6. $Et_3N:CH_3CN$ (1:1, v/v)
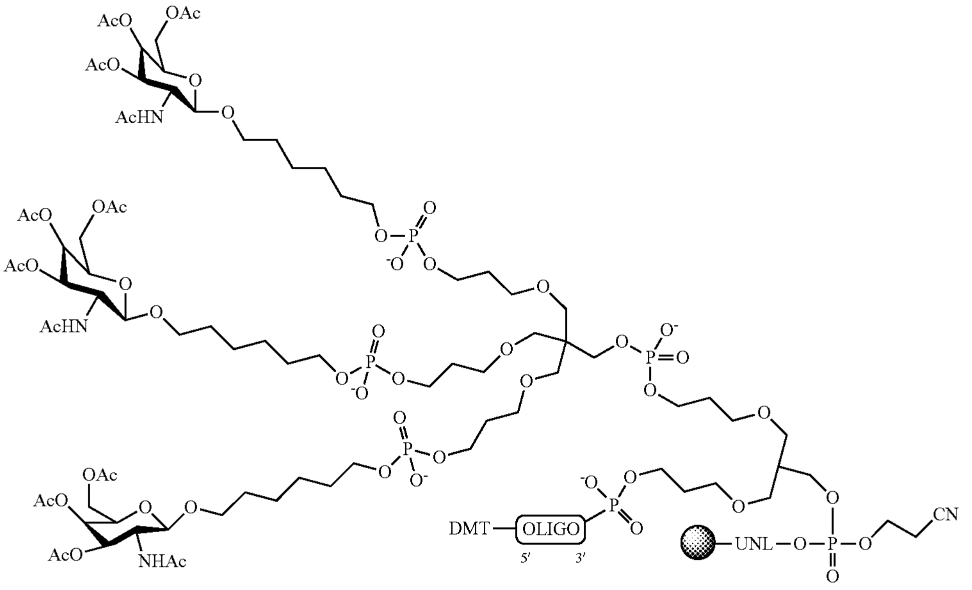
88
$NH_4$, 55° C.

-continued
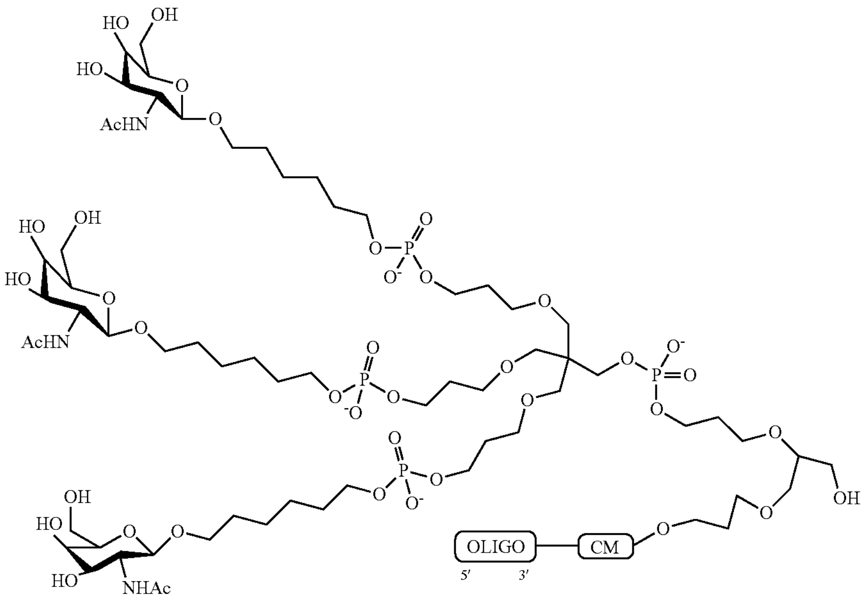
89
Wherein GalNAc$_3$-4 has the structure:
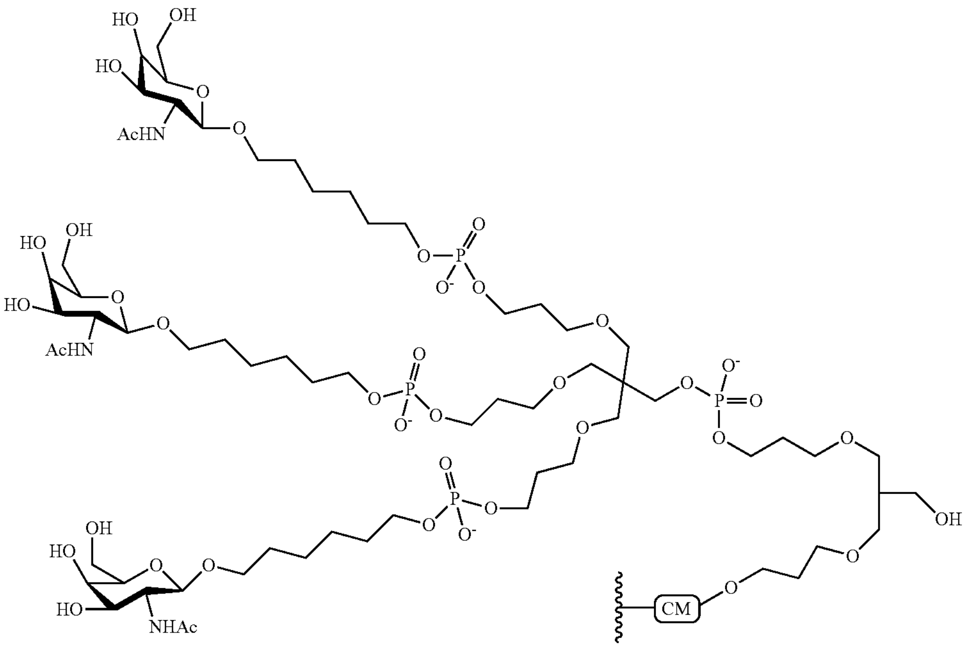

Wherein CM is a cleavable moiety. In certain embodiments, cleavable moiety is:

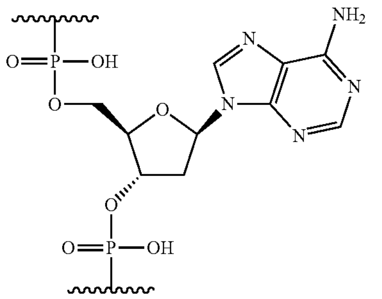 [SMILES: *P(=O)(O)OC[C@H]1O[C@@H](n2cnc3c(N)ncnc32)C[C@@H]1OP(*)(=O)O]

The $GalNAc_3$ cluster portion of the conjugate group $GalNAc_3$-4 ($GalNAc_3$-$4_a$) can be combined with any cleavable moiety to provide a variety of conjugate groups. Wherein $GalNAc_3$-$4_a$ has the formula:

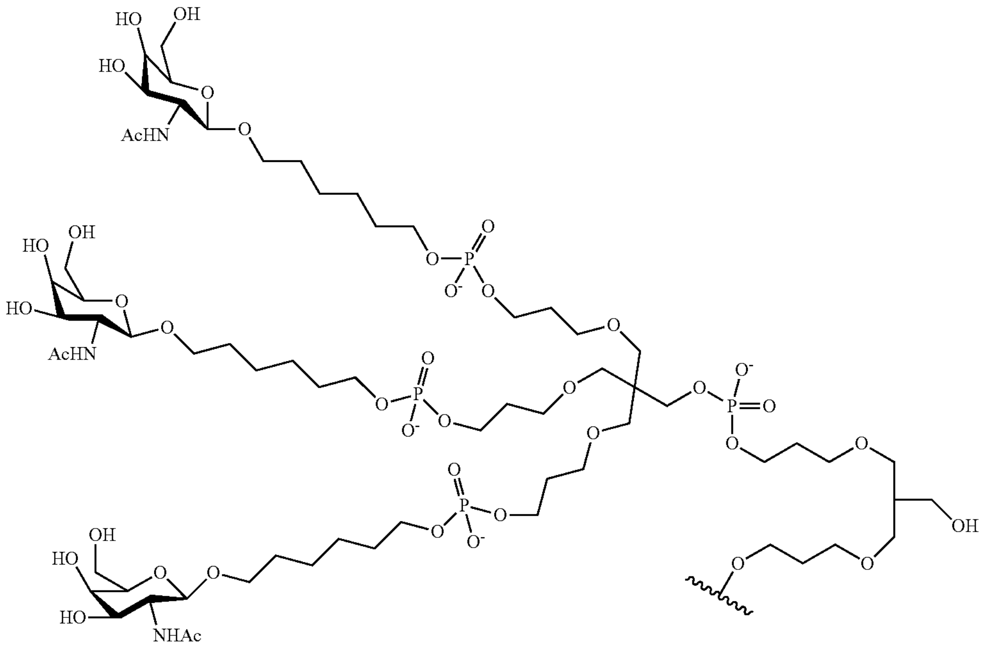

The protected Unylinker functionalized solid support Compound 30 is commercially available. Compound 84 is prepared using procedures similar to those reported in the literature (see Shchepinov et al., *Nucleic Acids Research,* 1997, 25(22), 4447-4454; Shchepinov et al., *Nucleic Acids Research,* 1999, 27, 3035-3041; and Hornet et al., *Nucleic Acids Research,* 1997, 25, 4842-4849).

The phosphoramidite building blocks, Compounds 60 and 79a are prepared as per the procedures illustrated in Examples 28 and 36. The phosphoramidites illustrated are meant to be representative and not intended to be limiting as other phosphoramidite building blocks can be used to prepare an oligomeric compound having a phosphodiester linked conjugate at the 3' terminus with a predetermined sequence and composition. The order and quantity of phosphoramidites added to the solid support can be adjusted to prepare the oligomeric compounds as described herein having any predetermined sequence and composition.

Example 41: General Method for the Preparation of ASOs Comprising a Phosphodiester Linked $GalNAc_3$-2 (See Example 37, Bx is Adenine) Conjugate at the 5' Position Via Solid Phase Techniques (Preparation of ISIS 661134)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^{m}C$ residues. Phosphoramidite compounds 56 and 60 were used to synthesize the phosphodiester linked $GalNAc_3$-2 conjugate at the 5' terminus. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on VIMAD solid support (110 μmol/g, Guzaev et al., 2003) packed in the column. For the coupling step, the phosphoramidites were delivered at a 4 fold excess over the initial loading of the solid support and phosphoramidite coupling was carried out for 10 min. All other steps followed standard protocols supplied by the manufacturer. A solution of 6% dichloroacetic acid in toluene was used for removing the dimethoxytrityl (DMT) groups from 5'-hydroxyl groups of the nucleotide. 4,5-Dicyanoimidazole (0.7 M) in anhydrous $CH_3CN$ was used as activator during the coupling step. Phosphorothioate linkages were introduced by sulfurization with 0.1 M solution of xanthane hydride in 1:1 pyridine/$CH_3CN$ for a contact time of 3 minutes. A solution of 20% tert-butylhydroperoxide in $CH_3CN$ containing 6% water was used as an oxidizing agent to provide phosphodiester internucleoside linkages with a contact time of 12 minutes.

After the desired sequence was assembled, the cyanoethyl phosphate protecting groups were deprotected using a 20% diethylamine in toluene (v/v) with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min-1, λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

TABLE 34

ASO comprising a phosphodiester linked $GalNAc_3$-2 conjugate at the 5' position targeting SRB-1

| ISIS No. | Sequence (5' to 3') | CalCd Mass | Observed Mass | Unmodified SEQ ID No. | Modified SEQ ID No. |
|---|---|---|---|---|---|
| 661134 | **$GalNAc_3$-$2_a$-$_{o'}$**$A_{do}$ $T_{ks}{}^mC_{ks}A_{ds}G_{ds}T_{ds}$ ${}^mC_{ds}A_{ds}T_{ds}G_{ds}A_{ds}$ ${}^mC_{ds}T_{ds}T_{ks}{}^mC_k$ | 6482.2 | 6481.6 | 250 | 305 |

Subscripts:
"e" indicates 2'-MOE modified nucleoside;
"d" indicates β-D-2'-deoxyribonucleoside;
"k" indicates 6'-(S)-$CH_3$ bicyclic nucleoside (e.g. cEt);
"s" indicates phosphorothioate internucleoside linkages (PS);
"o" indicates phosphodiester internucleoside linkages (PO); and
"o'" indicates —O—P(═O)(OH)—.
Superscript "m" indicates 5-methylcytosines.
The structure of $GalNAc_3$-$2_a$ is shown in Example 37.

Example 42: General Method for the Preparation of ASOs Comprising a $GalNAc_3$-3 Conjugate at the 5' Position Via Solid Phase Techniques (Preparation of ISIS 661166)

The synthesis for ISIS 661166 was performed using similar procedures as illustrated in Examples 39 and 41.

ISIS 661166 is a 5-10-5 MOE gapmer, wherein the 5' position comprises a $GalNAc_3$-3 conjugate. The ASO was characterized by ion-pair-HPLC coupled MS analysis with Agilent 1100 MSD system.

TABLE 34a

ASO comprising a $GalNAc_3$-3 conjugate at the 5' position via a hexylamino phosphodiester linkage targeting Malat-1

| ISIS No. | Sequence (5' to 3') | Conjugate | Calcd Mass | Observed Mass | Unmodified SEQ ID No. | Modified SEQ ID No. |
|---|---|---|---|---|---|---|
| 661166 | 5'-**$GalNAc_3$-$3_a$-$_{o'}$**${}^mC_{es}G_{es}$ $G_{es}T_{es}G_{es}{}^mC_{ds}$ $A_{ds}A_{ds}G_{ds}G_{ds}$ | **5'-$GalNAc_3$-3** | 8992.16 | 8990.51 | 251 | 328 |

TABLE 34a-continued

| ASO comprising a $GalNAc_3$-3 conjugate at the 5' position via a hexylamino phosphodiester linkage targeting Malat-1 | | | | | | |
|---|---|---|---|---|---|---|
| ISIS No. | Sequence (5' to 3') | Conjugate | Calcd Mass | Ob-served Mass | Unmodified SEQ ID No. | Modified SEQ ID No. |
| | $^mC_{ds}T_{ds}T_{ds}A_{ds}G_{ds}G_{es}A_{es}A_{es}T_{es}T_e$ | | | | | |

Subscripts:
"e" indicates 2'-MOE modified nucleoside;
"d" indicates β-D-2'-deoxyribonucleoside;
"s" indicates phosphorothioate internucleoside linkages (PS);
"o" indicates phosphodiester internucleoside linkages (PO); and
"o'" indicates —O—P(═O)(OH)—.
Superscript "m" indicates 5-methylcytosines.
The structure of "5'-$GalNAc_3$-3a" is shown in Example 39.

Example 43: Dose-Dependent Study of Phosphodiester Linked $GalNAc_3$-2 (See Examples 37 and 41, Bx is Adenine) at the 5' Terminus Targeting SRB-1 In Vivo ISIS 661134 (see Example 41) comprising a phosphodiester linked $GalNAc_3$-2 conjugate at the 5' terminus was tested in a dose-dependent study for antisense inhibition of SRB-1 in mice. Unconjugated ISIS 440762 and 651900 ($GalNAc_3$-1 conjugate at 3' terminus, see Example 9) were included in the study for comparison and are described previously in Table 17.

Treatment

Six week old male Balb/c mice (Jackson Laboratory, Bar Harbor, ME) were injected subcutaneously once at the dosage shown below with ISIS 440762, 651900, 661134 or with PBS treated control. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The $ED_{50}$s were measured using similar methods as described previously and are presented below.

As illustrated in Table 35, treatment with antisense oligonucleotides lowered SRB-1 mRNA levels in a dose-dependent manner. Indeed, the antisense oligonucleotides comprising the phosphodiester linked $GalNAc_3$-2 conjugate at the 5' terminus (ISIS 661134) or the $GalNAc_3$-1 conjugate linked at the 3' terminus (ISIS 651900) showed substantial improvement in potency compared to the unconjugated antisense oligonucleotide (ISIS 440762). Further, ISIS 661134, which comprises the phosphodiester linked $GalNAc_3$-2 conjugate at the 5' terminus was equipotent compared to ISIS 651900, which comprises the $GalNAc_3$-1 conjugate at the 3' terminus.

TABLE 35

| ASOs containing $GalNAc_3$-1 or $GalNAc_3$-2 targeting SRB-1 | | | | | |
|---|---|---|---|---|---|
| ISIS No. | Dosage (mg/kg) | SRB-1 mRNA levels (% PBS) | $ED_{50}$ (mg/kg) | Conjugate | SEQ ID No. |
| PBS | 0 | 100 | — | — | |
| 440762 | 0.2 | 116 | 2.58 | No conjugate | 250 |
| | 0.7 | 91 | | | |
| | 2 | 69 | | | |
| | 7 | 22 | | | |
| | 20 | 5 | | | |
| 651900 | 0.07 | 95 | 0.26 | 3' $GalNAc_3$-1 | 247 |
| | 0.2 | 77 | | | |
| | 0.7 | 28 | | | |
| | 2 | 11 | | | |
| | 7 | 8 | | | |
| 661134 | 0.07 | 107 | 0.25 | 5' $GalNAc_3$-2 | 250 |
| | 0.2 | 86 | | | |
| | 0.7 | 28 | | | |
| | 2 | 10 | | | |
| | 7 | 6 | | | |

Structures for 3' $GalNAc_3$-1 and 5' $GalNAc_3$-2 were described previously in Examples 9 and 37.

Pharmacokinetics Analysis (PK)

The PK of the ASOs from the high dose group (7 mg/kg) was examined and evaluated in the same manner as illustrated in Example 20. Liver sample was minced and extracted using standard protocols. The full length metabolites of 661134 (5' $GalNAc_3$-2) and ISIS 651900 (3' $GalNAc_3$-1) were identified and their masses were confirmed by high resolution mass spectrometry analysis. The results showed that the major metabolite detected for the ASO comprising a phosphodiester linked $GalNAc_3$-2 conjugate at the 5' terminus (ISIS 661134) was ISIS 440762 (data not shown). No additional metabolites, at a detectable level, were observed. Unlike its counterpart, additional metabolites similar to those reported previously in Table 23a were observed for the ASO having the $GalNAc_3$-1 conjugate at the 3' terminus (ISIS 651900). These results suggest that having the phosphodiester linked $GalNAc_3$-1 or $GalNAc_3$-2 conjugate may improve the PK profile of ASOs without compromising their potency.

Example 44: Effect of PO/PS Linkages on Antisense Inhibition of ASOs Comprising $GalNAc_3$-1 Conjugate (See Example 9) at the 3' Terminus Targeting SRB-1

ISIS 655861 and 655862 comprising a $GalNAc_3$-1 conjugate at the 3' terminus each targeting SRB-1 were tested in a single administration study for their ability to inhibit SRB-1 in mice. The parent unconjugated compound, ISIS 353382 was included in the study for comparison.

The ASOs are 5-10-5 MOE gapmers, wherein the gap region comprises ten 2'-deoxyribonucleosides and each wing region comprises five 2'-MOE modified nucleosides. The ASOs were prepared using similar methods as illustrated previously in Example 19 and are described Table 36, below.

TABLE 36

Modified ASOs comprising $GalNAc_3$-1 conjugate at the 3' terminus targeting SRB-1

| ISIS No. | Sequence (5' to 3') | Chemistry | Unmodified SEQ ID No. | Modified SEQ ID No. |
|---|---|---|---|---|
| 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | Full PS no conjugate | 252 | 318 |
| 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$ **$A_{do'}$-$GalNAc_3$-$1_a$** | Full PS with **$GalNAc_3$-1** conjugate | 253 | 369 |
| 655862 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}$**$A_{do'}$-$GalNAC_3$-$1_a$** | Mixed PS/PO with **$GalNAc_3$-1** conjugate | 253 | 370 |

Subscripts:
"e" indicates 2'-MOE modified nucleoside;
"d" indicates β-D-2'-deoxyribonucleoside;
"s" indicates phosphorothioate internucleoside linkages (PS);
"o" indicates phosphodiester internucleoside linkages (PO); and
"o'" indicates —O—P(═O)(OH)—.
Superscript "m" indicates 5-methylcytosines.
The structure of "$GalNAc_3$-1" is shown in Example 9.

Treatment

Six week old male Balb/c mice (Jackson Laboratory, Bar Harbor, ME) were injected subcutaneously once at the dosage shown below with ISIS 353382, 655861, 655862 or with PBS treated control. Each treatment group consisted of 4 animals. Prior to the treatment as well as after the last dose, blood was drawn from each mouse and plasma samples were analyzed. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The $ED_{50}$s were measured using similar methods as described previously and are reported below.

As illustrated in Table 37, treatment with antisense oligonucleotides lowered SRB-1 mRNA levels in a dose-dependent manner compared to PBS treated control. Indeed, the antisense oligonucleotides comprising the $GalNAc_3$-1 conjugate at the 3' terminus (ISIS 655861 and 655862) showed substantial improvement in potency comparing to the unconjugated antisense oligonucleotide (ISIS 353382). Further, ISIS 655862 with mixed PS/PO linkages showed an improvement in potency relative to full PS (ISIS 655861).

TABLE 37

Effect of PO/PS linkages on antisense inhibition of ASOs comprising $GalNAc_3$-1 conjugate at 3' terminus targeting SRB-1

| ISIS No. | Dosage (mg/kg) | SRB-1 mRNA levels (% PBS) | $ED_{50}$ (mg/kg) | Chemistry | SEQ ID No. |
|---|---|---|---|---|---|
| PBS | 0 | 100 | — | — | |
| 353382 | 3 | 76.65 | 10.4 | Full PS | 252 |
| (parent) | 10 | 52.40 | | without | |
| | 30 | 24.95 | | conjugate | |

TABLE 37-continued

Effect of PO/PS linkages on antisense inhibition of ASOs comprising $GalNAc_3$-1 conjugate at 3' terminus targeting SRB-1

| ISIS No. | Dosage (mg/kg) | SRB-1 mRNA levels (% PBS) | $ED_{50}$ (mg/kg) | Chemistry | SEQ ID No. |
|---|---|---|---|---|---|
| 655861 | 0.5 | 81.22 | 2.2 | Full PS with | 252 |
| | 1.5 | 63.51 | | $GalNAc_3$-1 | |
| | 5 | 24.61 | | conjugate | |
| | 15 | 14.80 | | | |
| 655862 | 0.5 | 69.57 | 1.3 | Mixed | 253 |
| | 1.5 | 45.78 | | PS/PO with | |
| | 5 | 19.70 | | $GalNAc_3$-1 | |
| | 15 | 12.90 | | conjugate | |

Liver transaminase levels, alanine aminotransferase (ALT) and aspartate aminotransferase (AST), in serum were measured relative to saline injected mice using standard protocols. Organ weights were also evaluated. The results demonstrated that no elevation in transaminase levels (Table 38) or organ weights (data not shown) were observed in mice treated with ASOs compared to PBS control. Further, the ASO with mixed PS/PO linkages (ISIS 655862) showed similar transaminase levels compared to full PS (ISIS 655861).

TABLE 38

Effect of PO/PS linkages on transaminase levels of ASOs comprising $GalNAc_3$-1 conjugate at 3' terminus targeting SRB-1

| ISIS No. | Dosage (mg/kg) | ALT (U/L) | AST (U/L) | Chemistry | SEQ ID No. |
|---|---|---|---|---|---|
| PBS | 0 | 28.5 | 65 | — | |
| 353382 | 3 | 50.25 | 89 | Full PS | 252 |
| (parent) | 10 | 27.5 | 79.3 | without | |
| | 30 | 27.3 | 97 | conjugate | |
| 655861 | 0.5 | 28 | 55.7 | Full PS with | 253 |
| | 1.5 | 30 | 78 | $GalNAc_3$-1 | |
| | 5 | 29 | 63.5 | | |
| | 15 | 28.8 | 67.8 | | |
| 655862 | 0.5 | 50 | 75.5 | Mixed | 253 |
| | 1.5 | 21.7 | 58.5 | PS/PO with | |
| | 5 | 29.3 | 69 | $GalNAc_3$-1 | |
| | 15 | 22 | 61 | | |

Example 45: Preparation of PFP Ester, Compound 110a

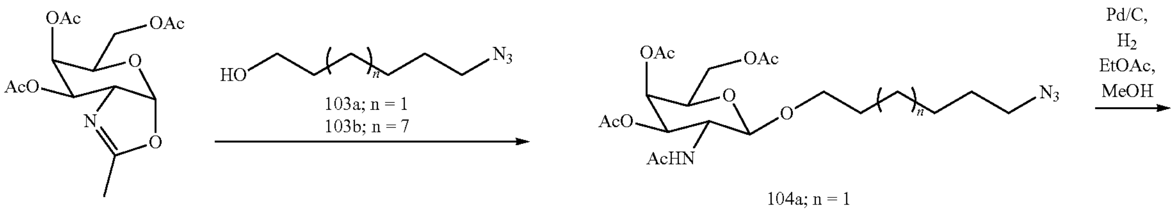

4

104a; n = 1
104b; n = 7

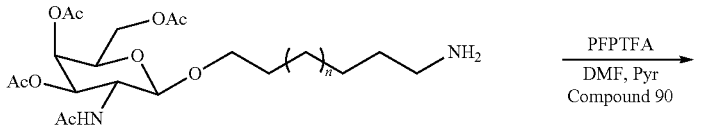

105a; n = 1
105b; n = 7

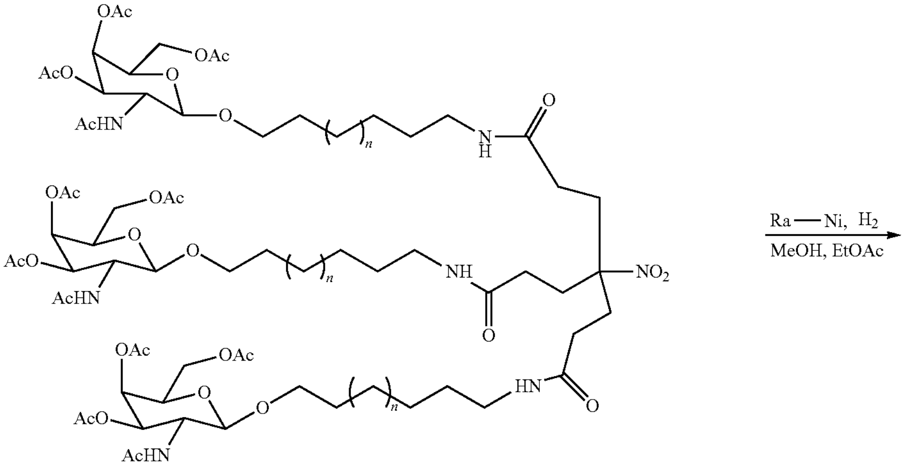

106a; n = 1
106b; n = 7

-continued
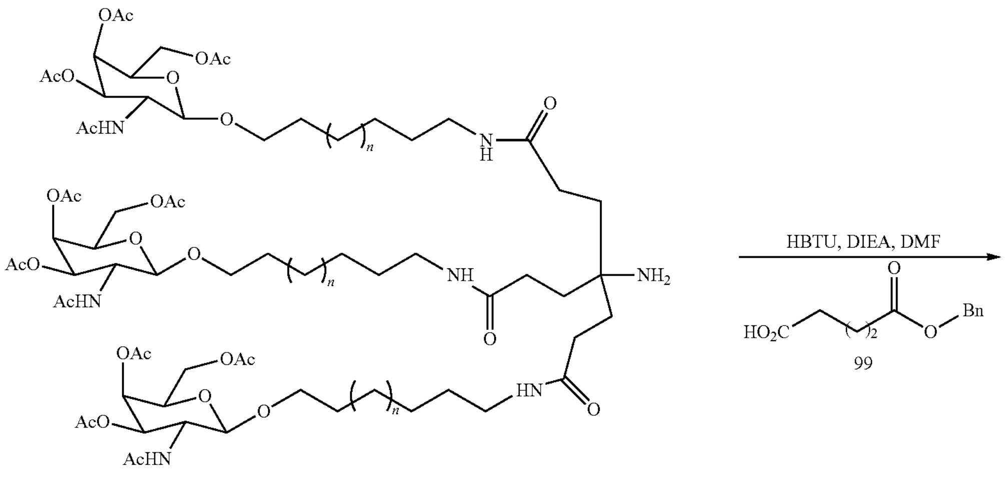
107a; n = 1
107b; n = 7
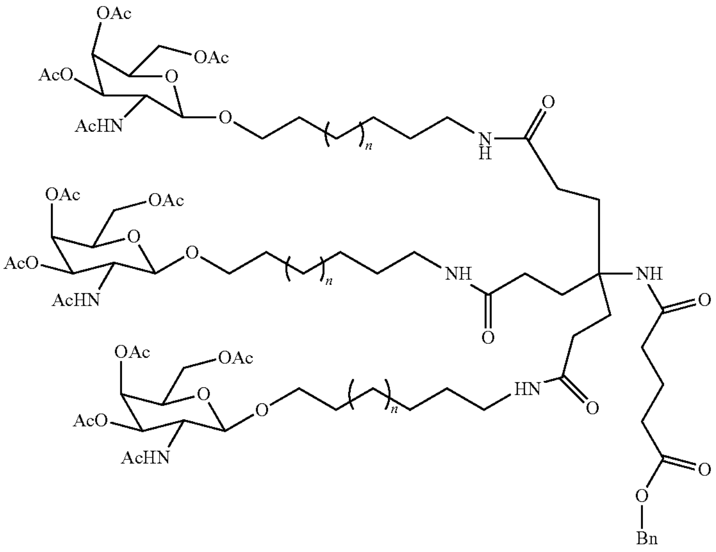
108a; n = 1
108b; n = 7
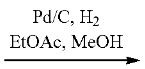
108a; n = 1
108b; n = 7

-continued
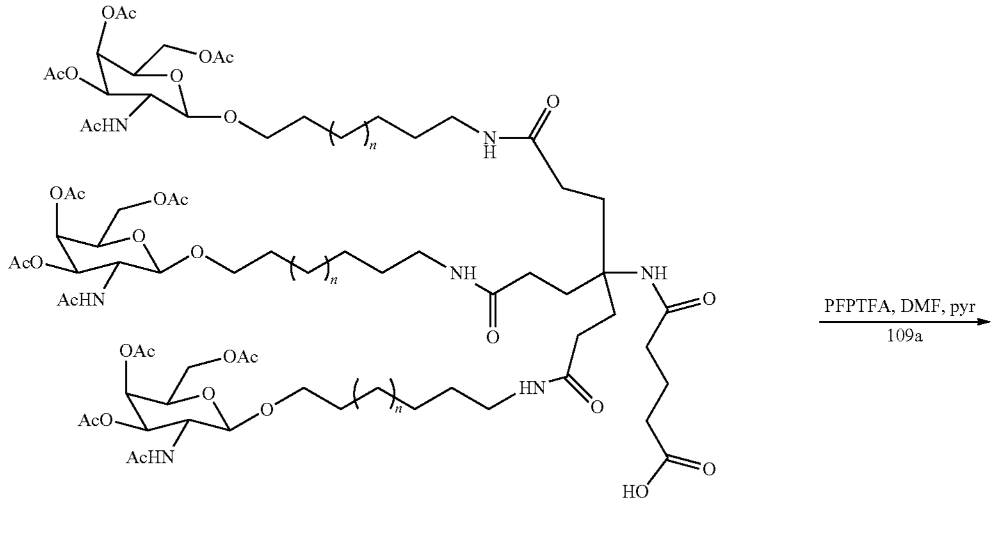
109a; n = 1
109b; n = 7
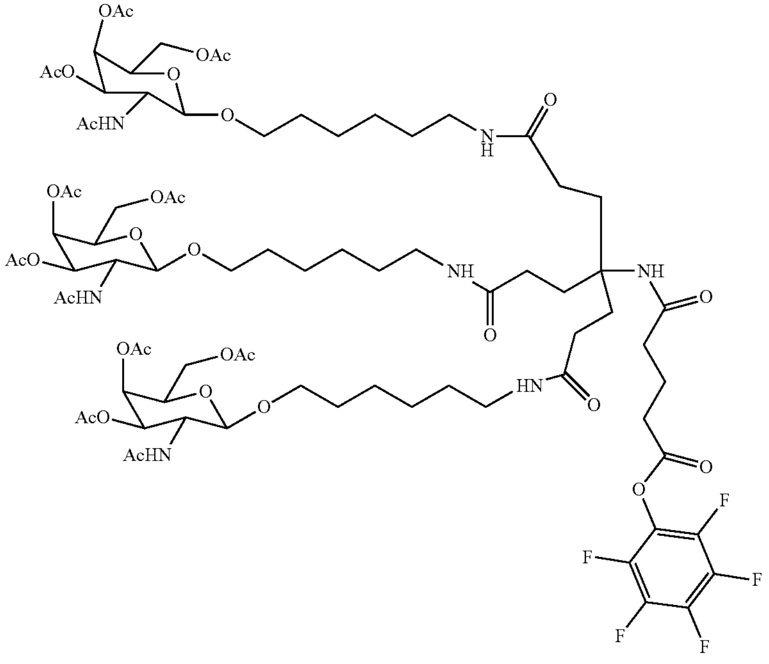
110a

Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%→10% methanol/dichloromethane) to give compounds 104a and 104b in >80% yield. LCMS and proton NMR was consistent with the structure.

Compounds 104a and 104b were treated to the same conditions as for compounds 100a-d (Example 47), to give compounds 105a and 105b in >90% yield. LCMS and proton NMR was consistent with the structure.

Compounds 105a and 105b were treated, individually, with compound 90 under the same conditions as for compounds 901a-d, to give compounds 106a (80%) and 106b (20%). LCMS and proton NMR was consistent with the structure.

Compounds 106a and 106b were treated to the same conditions as for compounds 96a-d (Example 47), to give 107a (60%) and 107b (20%). LCMS and proton NMR was consistent with the structure.

Compounds 107a and 107b were treated to the same conditions as for compounds 97a-d (Example 47), to give compounds 108a and 108b in 40-60% yield. LCMS and proton NMR was consistent with the structure.

Compounds 108a (60%) and 108b (40%) were treated to the same conditions as for compounds 100a-d (Example 47), to give compounds 109a and 109b in >80% yields. LCMS and proton NMR was consistent with the structure.

Compound 109a was treated to the same conditions as for compounds 101a-d (Example 47), to give Compound 110a in 30-60% yield. LCMS and proton NMR was consistent with the structure. Alternatively, Compound 110b can be prepared in a similar manner starting with Compound 109b.

Example 46: General Procedure for Conjugation with PFP Esters (Oligonucleotide 111); Preparation of ISIS 666881 ($GalNAc_3$-10)

A 5'-hexylamino modified oligonucleotide was synthesized and purified using standard solid-phase oligonucleotide procedures. The 5'-hexylamino modified oligonucleotide was dissolved in 0.1 M sodium tetraborate, pH 8.5

(200 μL) and 3 equivalents of a selected PFP esterified $GalNAc_3$ cluster dissolved in DMSO (50 μL) was added. If the PFP ester precipitated upon addition to the ASO solution DMSO was added until all PFP ester was in solution. The reaction was complete after about 16 h of mixing at room temperature. The resulting solution was diluted with water to 12 mL and then spun down at 3000 rpm in a spin filter with a mass cut off of 3000 Da. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligonucleotide was purified and desalted by RP-HPLC and lyophilized to provide the $GalNAc_3$ conjugated oligonucleotide.

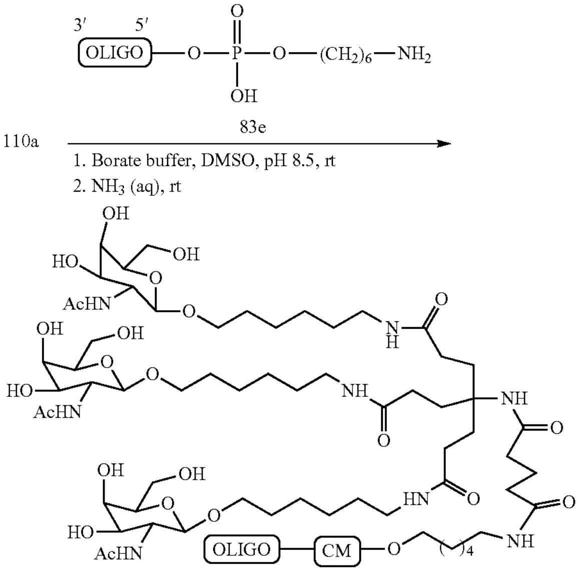

111

Oligonucleotide 111 is conjugated with $GalNAc_3$-10. The $GalNAc_3$ cluster portion of the conjugate group $GalNAc_3$-10 ($GalNAc_3$-$10_a$) can be combined with any cleavable moiety to provide a variety of conjugate groups. In certain embodiments, the cleavable moiety is —P(═O)(OH)-$A_d$-P(═O)(OH)— as shown in the oligonucleotide (ISIS 666881) synthesized with $GalNAc_3$-10 below. The structure of $GalNAc_3$-10 ($GalNAc_3$-$10_a$-CM-) is shown below:

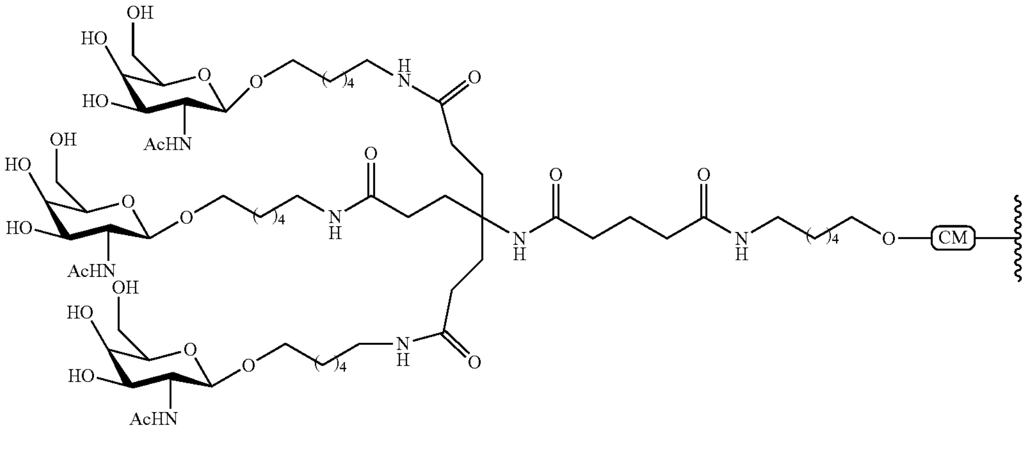

Following this general procedure ISIS 666881 was prepared. 5'-hexylamino modified oligonucleotide, ISIS 660254, was synthesized and purified using standard solid-phase oligonucleotide procedures. ISIS 660254 (40 mg, 5.2 μmol) was dissolved in 0.1 M sodium tetraborate, pH 8.5 (200 μL) and 3 equivalents PFP ester (Compound 110a) dissolved in DMSO (50 μL) was added. The PFP ester precipitated upon addition to the ASO solution requiring additional DMSO (600 μL) to fully dissolve the PFP ester. The reaction was complete after 16 h of mixing at room temperature. The solution was diluted with water to 12 mL total volume and spun down at 3000 rpm in a spin filter with a mass cut off of 3000 Da. This process was repeated twice to remove small molecule impurities. The solution was lyophilized to dryness and redissolved in concentrated aqueous ammonia with mixing at room temperature for 2.5 h followed by concentration in vacuo to remove most of the ammonia. The conjugated oligonucleotide was purified and desalted by RP-HPLC and lyophilized to give ISIS 666881 in 90% yield by weight (42 mg, 4.7 μmol).

GalNAc$_3$-10 conjugated oligonucleotide

| ASO | Sequence (5' to 3') | 5' group | SEQ ID No. | Modified SEQ ID No. |
|---|---|---|---|---|
| ISIS 660254 | $NH_2(CH_2)_6$-${}_oA_{do}$ $G_{es}{}^mC_{es}T_{es}T_{es}$ ${}^mC_{es}A_{ds}G_{ds}T_{ds}$ | Hexylamine | 254 | 374 |

-continued

GalNAc$_3$-10 conjugated oligonucleotide

| ASO | Sequence (5' to 3') | 5' group | SEQ ID No. | Modified SEQ ID No. |
|---|---|---|---|---|
| | ${}^mC_{ds}A_{ds}T_{ds}$ $G_{ds}A_{ds}{}^mC_{ds}$ $T_{ds}T_{es}{}^mC_{es}$ ${}^mC_{es}T_{es}T_e$ | | | |
| ISIS 666881 | **GalNAc$_3$-10$_a$-$_{o'}$** $A_{do}G_{es}{}^mC_{es}T_{es}$ $T_{es}{}^mC_{es}A_{ds}$ $G_{ds}T_{ds}{}^mC_{ds}$ $A_{ds}T_{ds}G_{ds}$ $A_{ds}{}^mC_{ds}T_{ds}$ $T_{es}{}^mC_{es}{}^mC_{es}$ $T_{es}T_e$ | **GalNAc$_3$-10** | 254 | 386 |

Capital letters indicate the nucleobase for each nucleoside and ${}^m$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(═O)(OH)—.
Conjugate groups are in bold.

Example 47: Preparation of Oligonucleotide 102 Comprising GalNAc$_3$-8

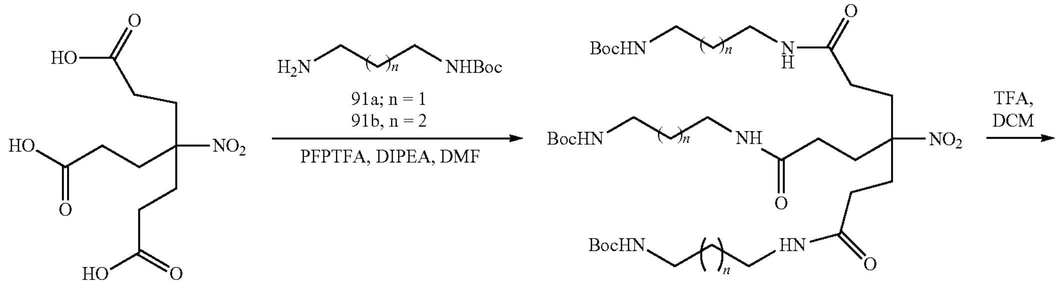

90

92a; n = 1
92b, n = 2

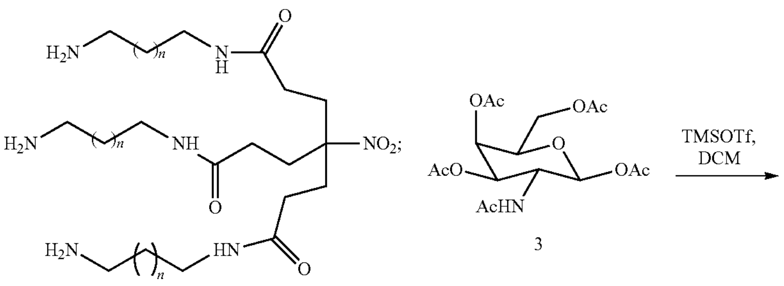

3

93a; n = 1
93b, n = 2

-continued
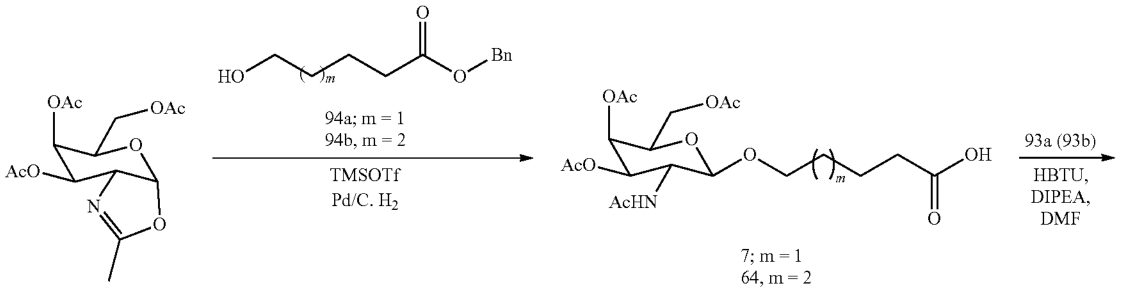
4
7; m = 1
64, m = 2
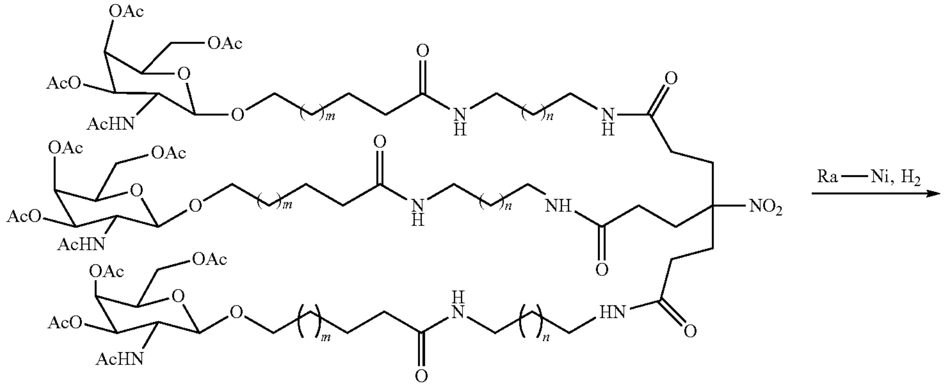
96a; n = 1, m = 1
96b; n = 1, m = 2
96c; n = 2, m = 1
96d; n = 2, m = 2
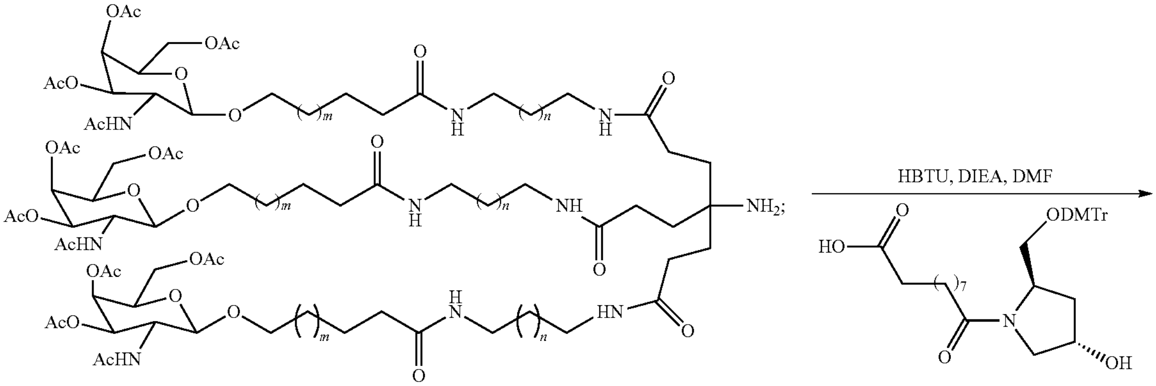
23
97a; n = 1, m = 1
97b; n = 1, m = 2
97c; n = 2, m = 1
97d; n = 2, m = 2

-continued
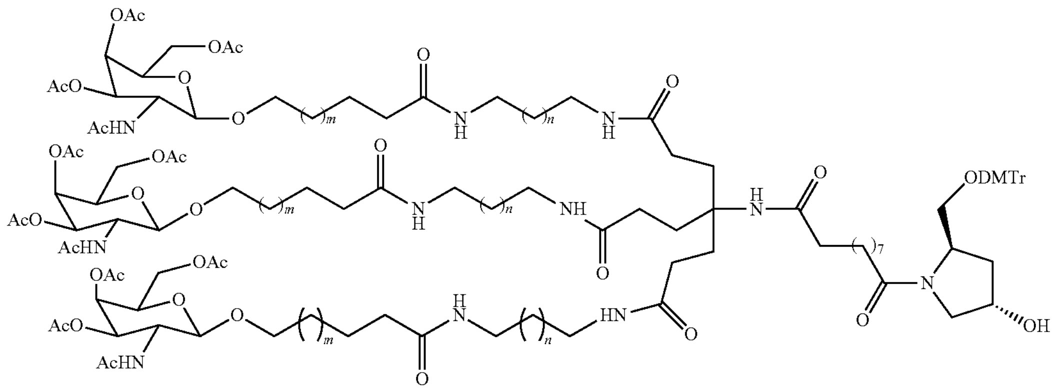
98a; n = 1, m = 1
98b; n = 1, m = 2
98c; n = 2, m = 1
98d; n = 2, m = 2
97a; n = 1, m = 1
97b; n = 1, m = 2
97c; n = 2, m = 1
97d; n = 2, m = 2
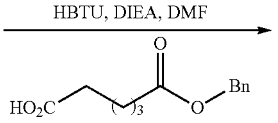
99
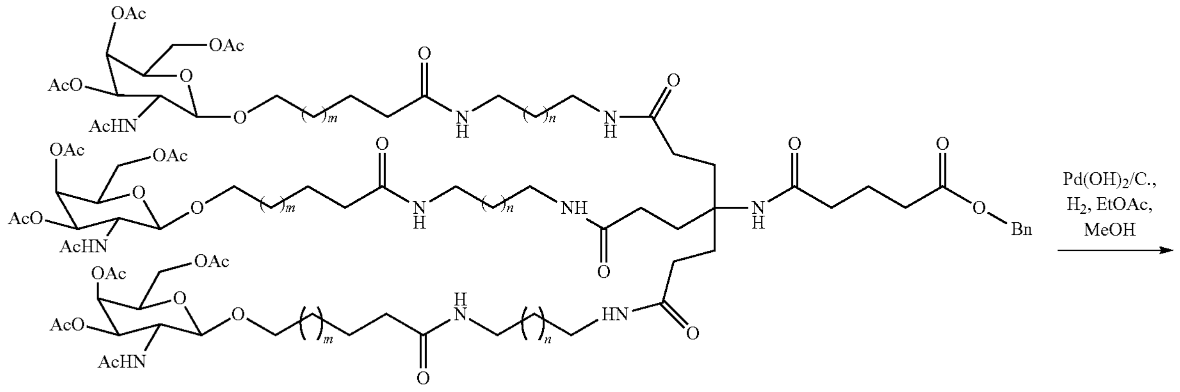
100a; n = 1, m = 1
100b; n = 1, m = 2
100c; n = 2, m = 1
100d; n = 2, m = 2
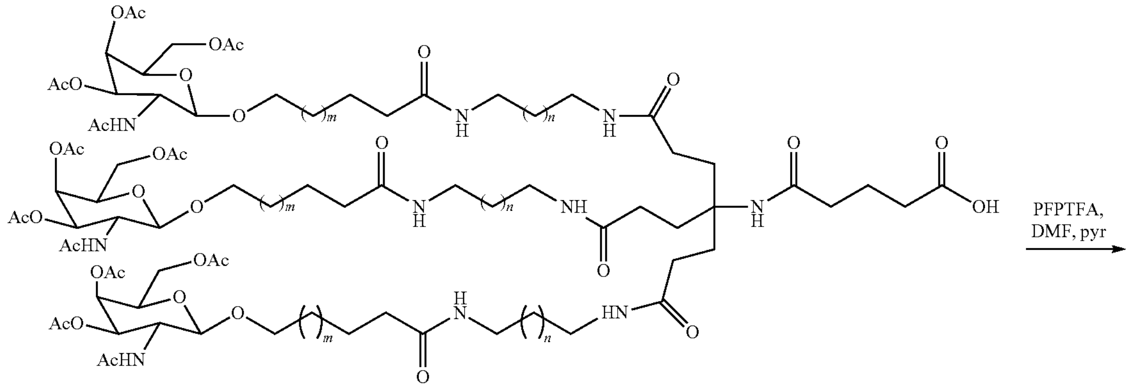
101a; n = 1, m = 1
101b; n = 1, m = 2
101c; n = 2, m = 1
101d; n = 2, m = 2

-continued

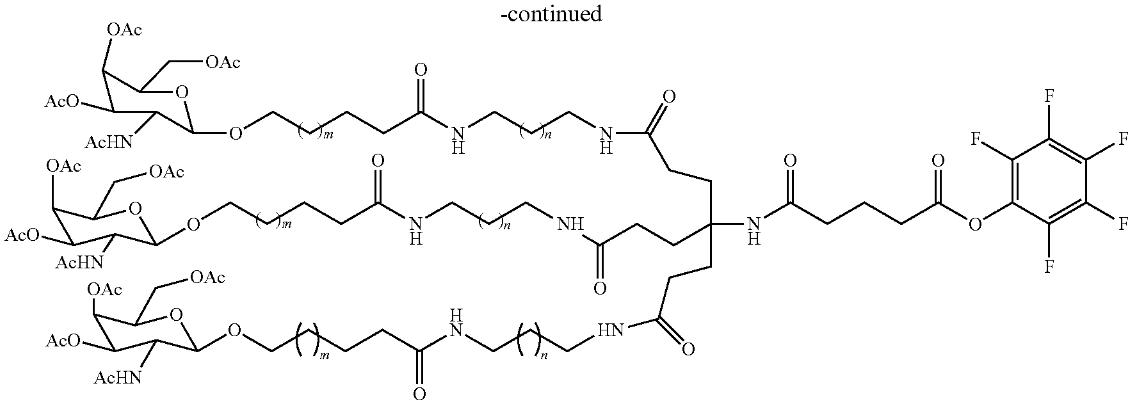

102a; n = 1, m = 1
102b; n = 1, m = 2
102c; n = 2, m = 1
102d; n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→10% methanol/dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 100a-d in 40-60% yield. LCMS and proton NMR was consistent with the structure.

Compounds 100a-d (0.16 mmoles), individually, were hydrogenated over 10% $Pd(OH)_2/C$ for 3 hours in methanol/ethyl acetate (1:1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→5% methanol/dichloromethane) to give compounds 102a-d in an approximate 80% yield. LCMS and proton NMR were consistent with the structure.

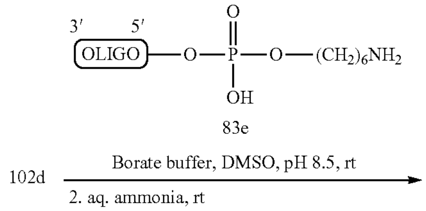

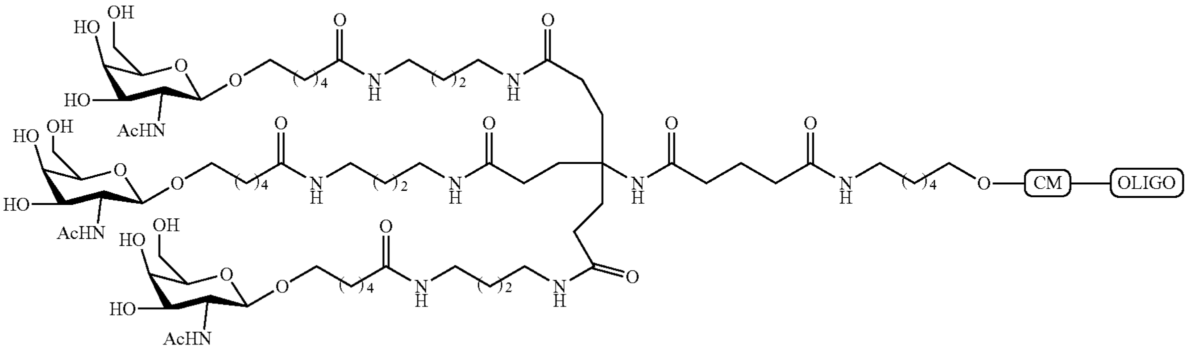

102

Oligomeric Compound 102, comprising a $GalNAc_3$-8 conjugate group, was prepared using the general procedures illustrated in Example 46. The $GalNAc_3$ cluster portion of the conjugate group $GalNAc_3$-8 ($GalNAc_3$-$8_a$) can be combined with any cleavable moiety to provide a variety of conjugate groups. In a preferred embodiment, the cleavable moiety is —P(═O)(OH)-$A_d$-P(═O)(OH)—.

The structure of $GalNAc_3$-8 ($GalNAc_3$-$8_a$-CM-) is shown below:

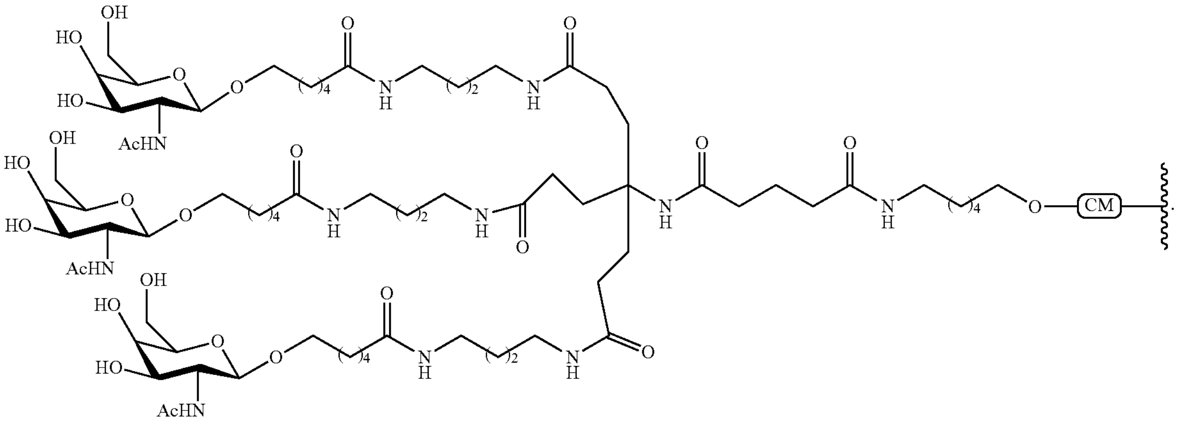

Example 48: Preparation of Oligonucleotide 119 Comprising GalNAc$_3$-7
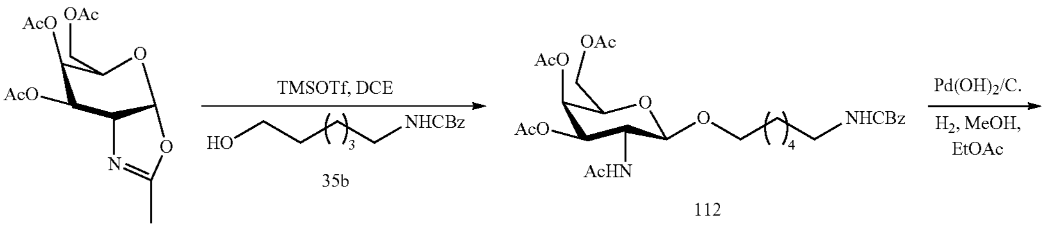
4
35b
112
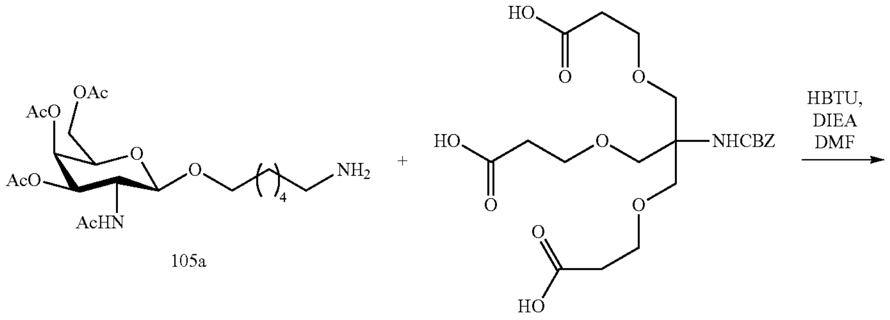
105a
113
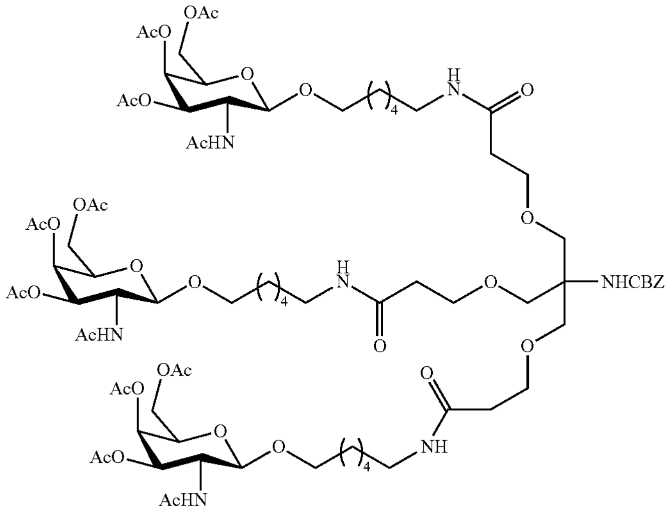
114

-continued

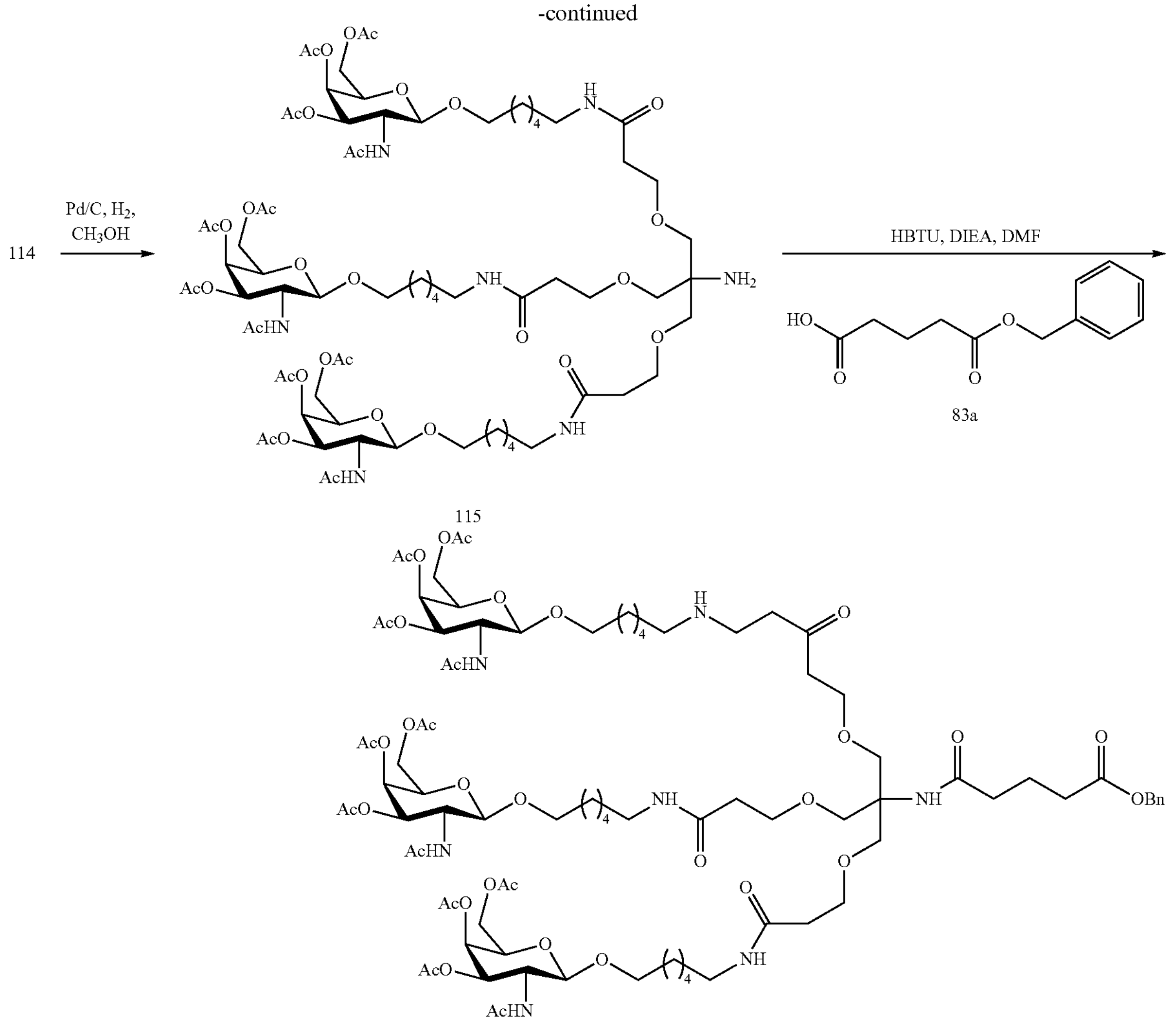

115

83a

116

Compound 112 was synthesized following the procedure described in the literature (*J. Med. Chem.* 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min. To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in $CH_2Cl_2$ (100 mL) and washed with aqueous saturated $NaHCO_3$ solution (100 mL) and brine (100 mL). The organic phase was separated, dried ($Na_2SO_4$), filtered and evaporated. The residue was purified by silica gel column chromatography and eluted with 10 to 20% MeOH in dichloromethane to yield Compound 114 (1.45 g, 30%). The structure was confirmed by LCMS and $^1H$ NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1H$ NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min. To this a solution of Compound 115 (1.22 g, 0.75 mmol) in anhydrous DMF was added and the reaction was stirred at room temperature for 6 h. The solvent was removed under reduced pressure and the residue was dissolved in $CH_2Cl_2$. The organic layer was washed aqueous saturated $NaHCO_3$ solution and brine and dried over anhydrous $Na_2SO_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1$H NMR analysis.

116

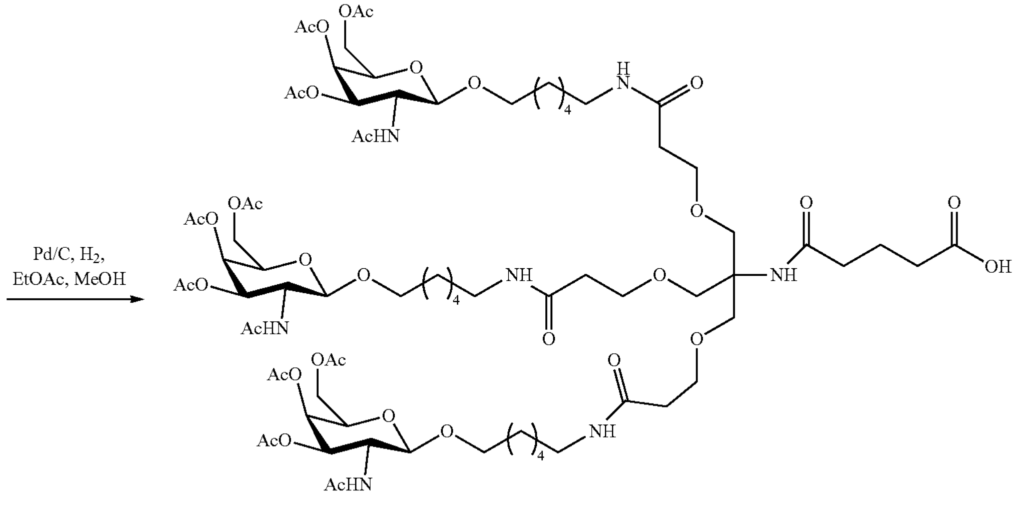

117

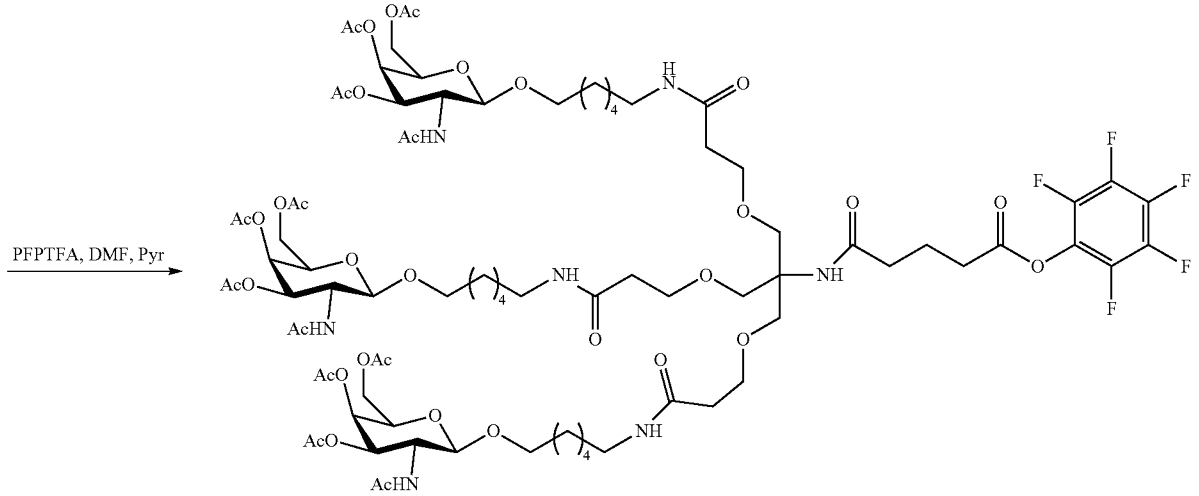

118

Compound 116 (0.74 g, 0.4 mmol) was dissolved in 1:1 methanol/ethyl acetate (5 mL/5 mL). Palladium on carbon (wet, 0.074 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and $^1$H NMR analysis.

Compound 117 (0.63 g, 0.36 mmol) was dissolved in anhydrous DMF (3 mL). To this solution N,N-Diisopropylethylamine (70 μL, 0.4 mmol) and pentafluorophenyl trifluoroacetate (72 μL, 0.42 mmol) were added. The reaction mixture was stirred at room temperature for 12 h and poured into a aqueous saturated $NaHCO_3$ solution. The mixture was extracted with dichloromethane, washed with brine and dried over anhydrous $Na_2SO_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^1$H and $^1$H and $^{19}$F NMR.

118

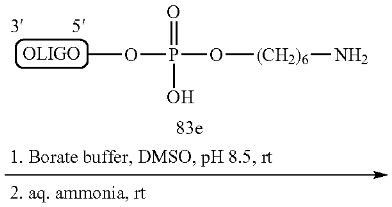

83e

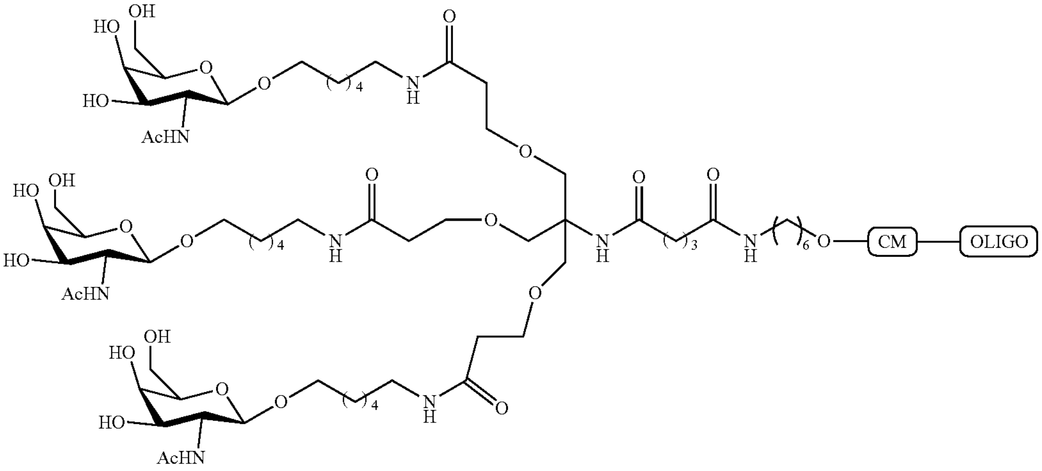

119

Oligomeric Compound 119, comprising a GalNAc$_3$-7 conjugate group, was prepared using the general procedures illustrated in Example 46. The GalNAc$_3$ cluster portion of the conjugate group GalNAc$_3$-7 (GalNAc$_3$-7$_a$) can be combined with any cleavable moiety to provide a variety of conjugate groups. In certain embodiments, the cleavable moiety is —P(═O)(OH)-A$_d$-P(═O)(OH)—.

The structure of GalNAc$_3$-7 (GalNAc$_3$-7$_a$-CM-) is shown below:

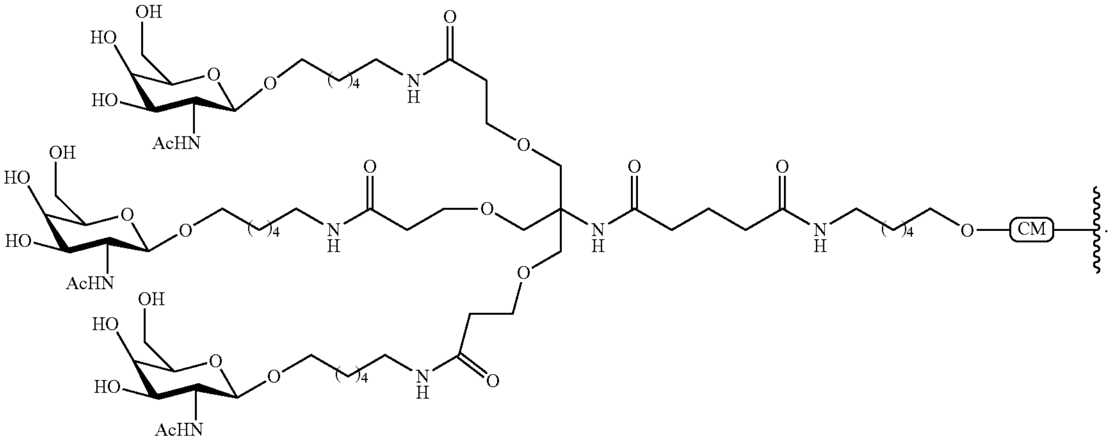

Example 49: Preparation of Oligonucleotide 132 Comprising GalNAc$_3$-5

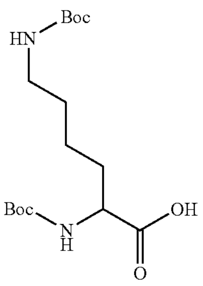

120

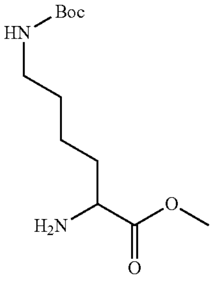

121

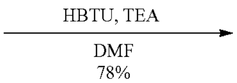

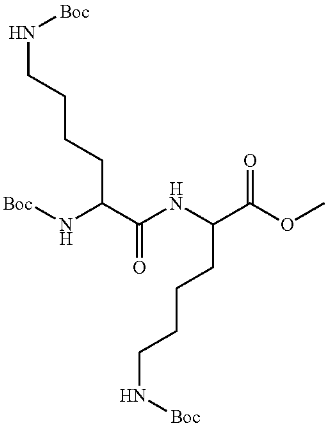

122

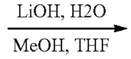

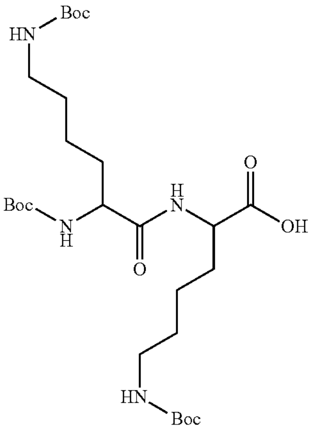

123

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC (ethyl acetate:hexane; 1:1; Rf=0.47). The solvent was removed under reduced pressure. The residue was taken up in EtOAc (300 mL) and washed with 1M $NaHSO_4$ (3×150 mL), aqueous saturated $NaHCO_3$ solution (3×150 mL) and brine (2×100 mL). Organic layer was dried with $Na_2SO_4$. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and $^1H$ NMR analysis. Mass m/z 589.3 $[M+H]^+$.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min. and monitored by TLC (EtOAc:hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried ($Na_2SO_4$), filtered and evaporated to yield Compound 123 (8.42 g). Residual salt is the likely cause of excess mass. LCMS is consistent with structure. Product was used without any further purification. M.W.cal: 574.36; M.W.fd: 575.3 $[M+H]^+$.

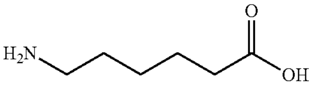

+

124

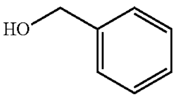

125

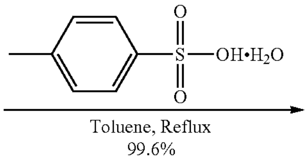

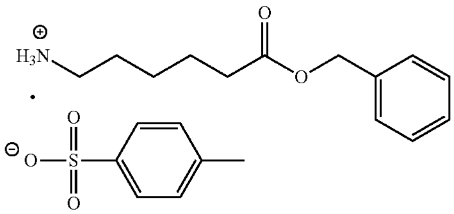

126

Compound 126 was synthesized following the procedure described in the literature (*J. Am. Chem. Soc.* 2011, 133, 958-963).

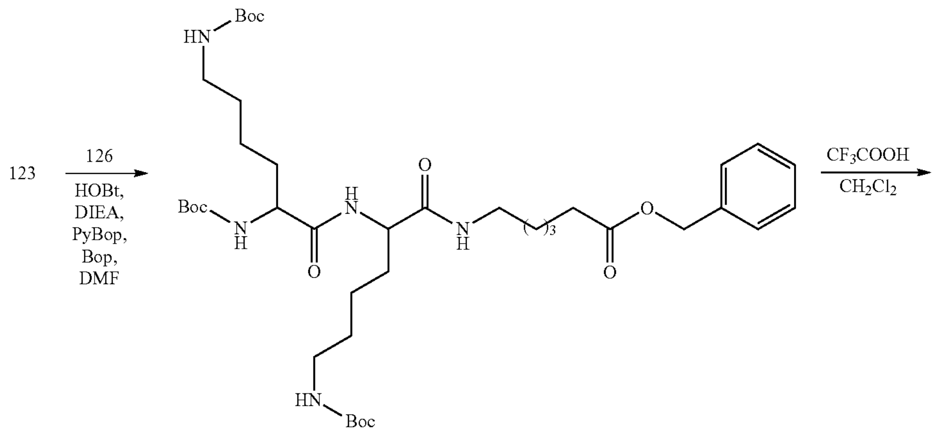
127
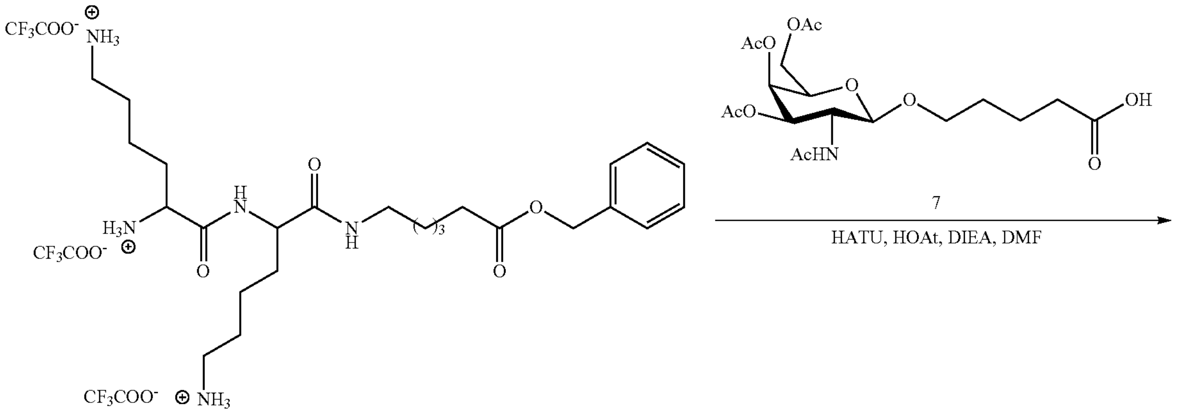
128
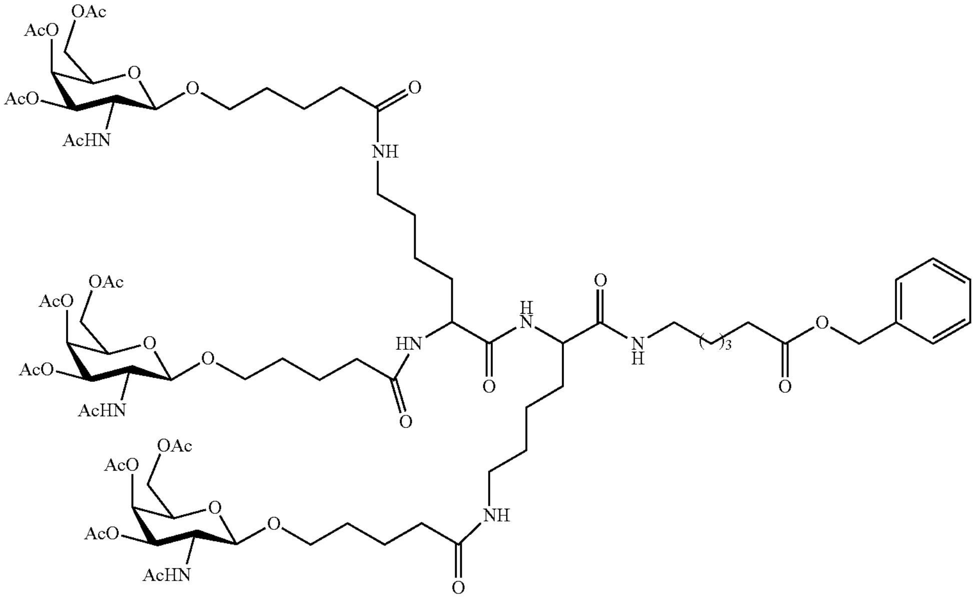
129

-continued

129

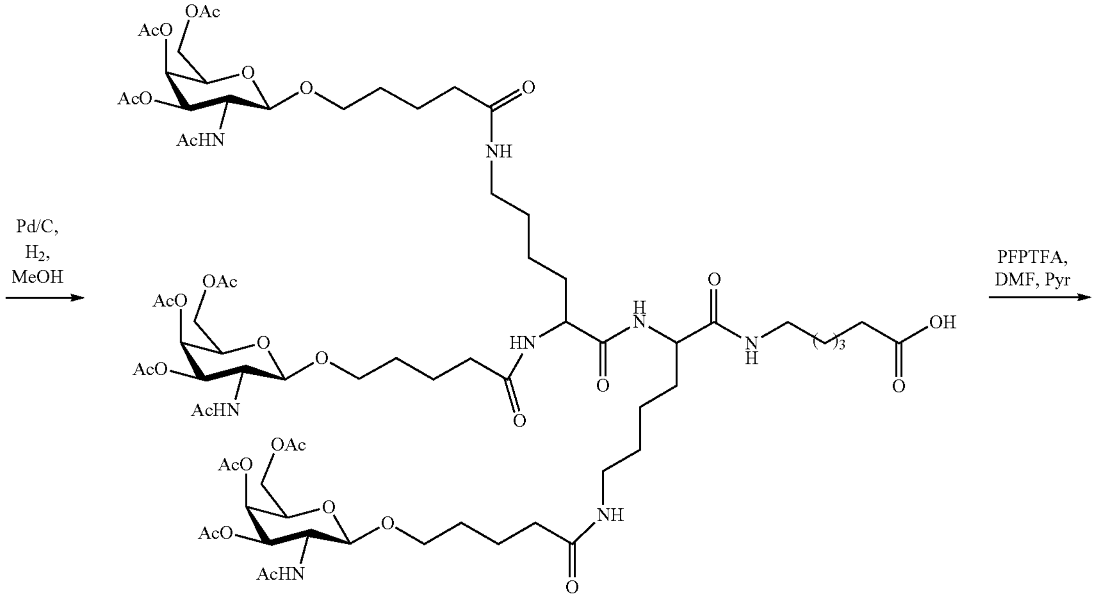

130

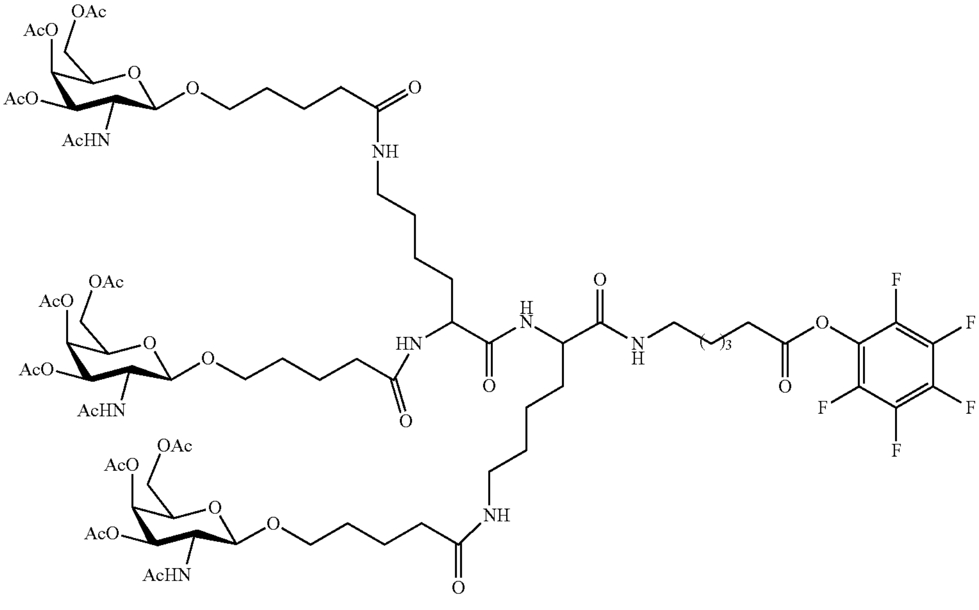

131

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM:MeOH:AA; 89:10:1). The reaction mixture was concentrated under reduced pressure. The residue was dissolved in EtOAc (200 mL) and washed with 1 M $NaHSO_4$ (3×100 mL), aqueous saturated $NaHCO_3$ (3×100 mL) and brine (2×100 mL). The organic phase separated dried ($Na_2SO_4$), filtered and concentrated. The residue was purified by silica gel column chromatography with a gradient of 50% hexanes/EtOAC to 100% EtOAc to yield Compound 127 (9.4 g) as a white foam. LCMS and $^1$H NMR were consistent with structure. Mass m/z 778.4 $[M+H]^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1$H NMR were consistent with structure. Mass m/z 478.2 $[M+H]^+$.

Compound 7 (0.43 g, 0.963 mmol), HATU (0.35 g, 0.91 mmol), and HOAt (0.035 g, 0.26 mmol) were combined together and dried for 4 h over $P_2O_5$ under reduced pressure in a round bottom flask and then dissolved in anhydrous DMF (1 mL) and stirred for 5 min. To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC (7% MeOH/DCM). The reaction mixture was concentrated under reduced pressure. The residue was dissolved in DCM (30 mL) and washed with 1 M $NaHSO_4$ (3x20 mL), aqueous saturated $NaHCO_3$ (3x20 mL) and brine (3x20 mL). The organic phase was separated, dried over $Na_2SO_4$, filtered and concentrated. The residue was purified by silica gel column chromatography using 5-15% MeOH in dichloromethane to yield Compound 129 (96.6 mg). LC MS and $^1H$ NMR are consistent with structure. Mass m/z 883.4 $[M+2H]^+$.

LCMS and $^1H$ NMR were consistent with structure. The product was used without further purification. Mass m/z 838.3 $[M+2H]^+$.

To a 10 mL pointed round bottom flask were added compound 130 (75.8 mg, 0.046 mmol), 0.37 M pyridine/DMF (200 μL) and a stir bar. To this solution was added 0.7 M pentafluorophenyl trifluoroacetate/DMF (100 μL) drop wise with stirring. The reaction was completed after 1 h as determined by LC MS. The solvent was removed under reduced pressure and the residue was dissolved in $CHCl_3$ (~10 mL). The organic layer was partitioned against $NaHSO_4$ (1 M, 10 mL), aqueous saturated $NaHCO_3$ (10 mL) and brine (10 mL) three times each. The organic phase separated and dried over $Na_2SO_4$, filtered and concentrated to yield Compound 131 (77.7 mg). LCMS is consistent with structure. Used without further purification. Mass m/z 921.3 $[M+2H]^+$.

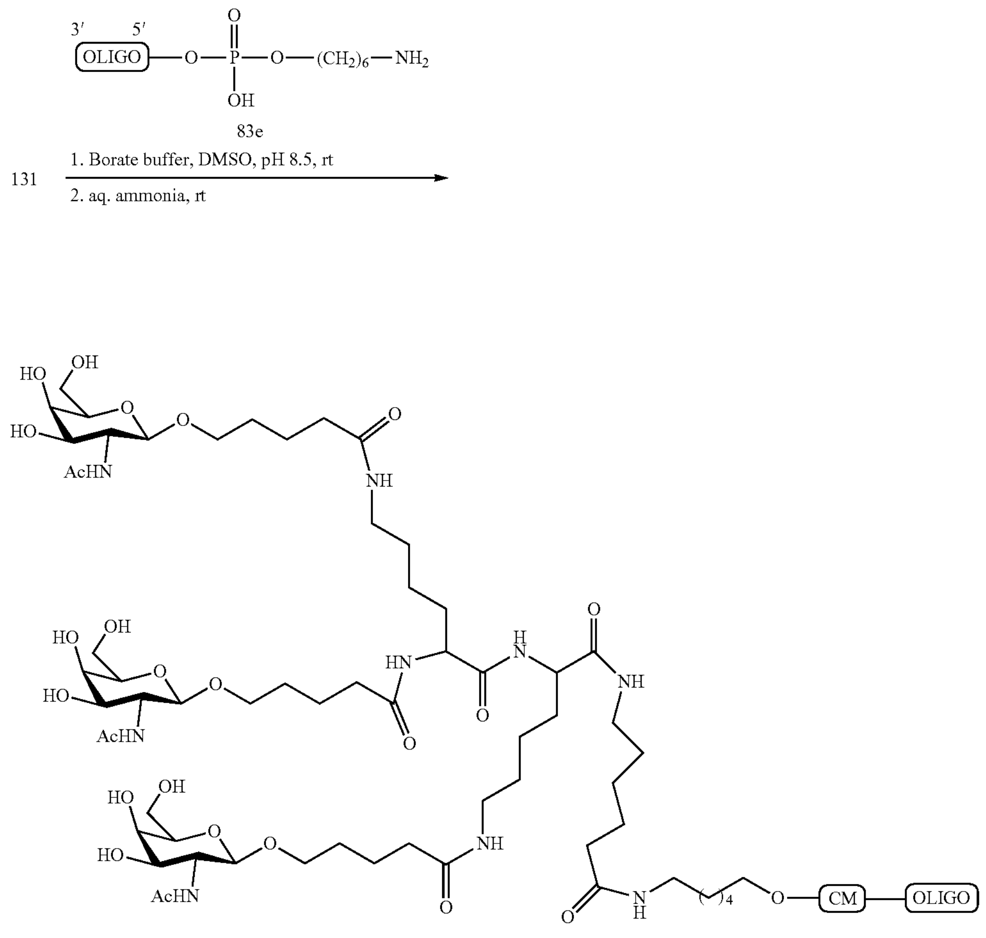

132

Compound 129 (0.09 g, 0.051 mmol) was dissolved in methanol (5 mL) in 20 mL scintillation vial. To this was added a small amount of 10% Pd/C (0.015 mg) and the reaction vessel was flushed with $H_2$ gas. The reaction mixture was stirred at room temperature under $H_2$ atmosphere for 18 h. The reaction mixture was filtered through a pad of Celite and the Celite pad was washed with methanol. The filtrate washings were pooled together and concentrated under reduced pressure to yield Compound 130 (0.08 g).

Oligomeric Compound 132, comprising a $GalNAc_3$-5 conjugate group, was prepared using the general procedures illustrated in Example 46. The $GalNAc_3$ cluster portion of the conjugate group $GalNAc_3$-5 ($GalNAc_3$-$5_a$) can be combined with any cleavable moiety to provide a variety of conjugate groups. In certain embodiments, the cleavable moiety is —P(═O)(OH)-$A_d$-P(═O)(OH)—.

The structure of GalNAc$_3$-5 (GalNAc$_3$-5$_a$-CM-) is shown below:
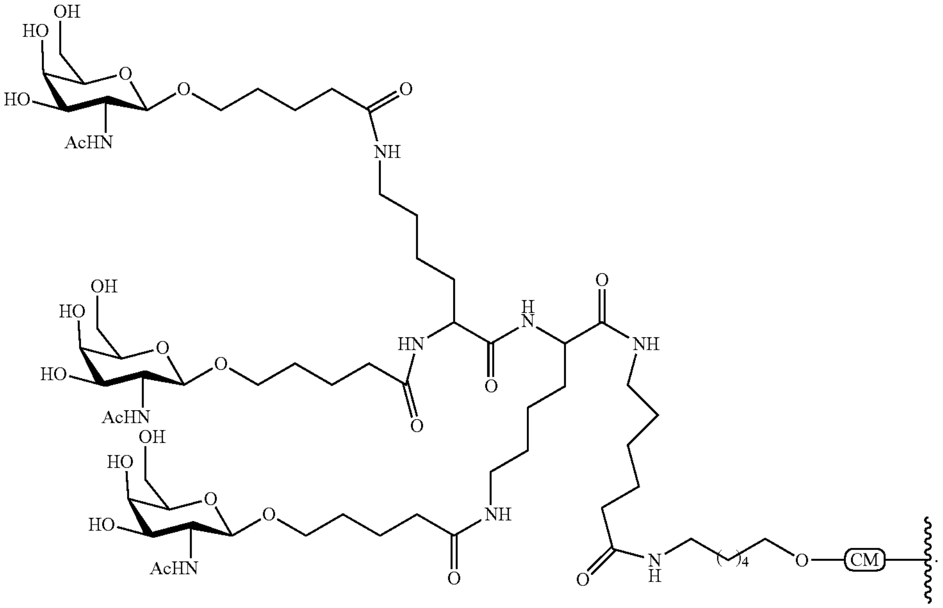
Example 50: Preparation of Oligonucleotide 144 Comprising GalNAc4-11
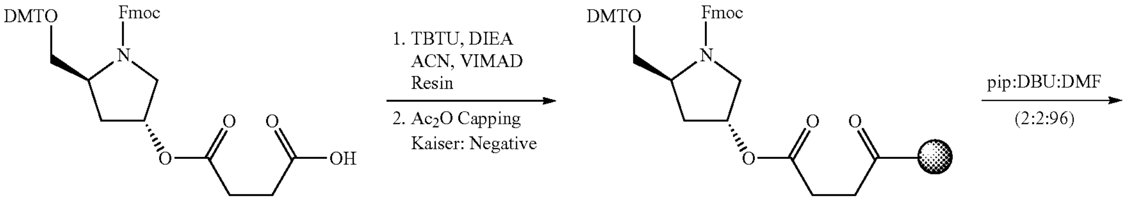
133 134
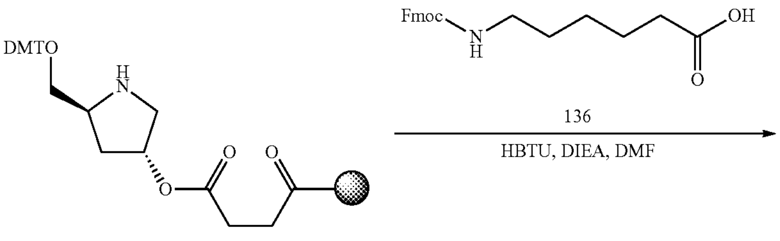
136
135

-continued
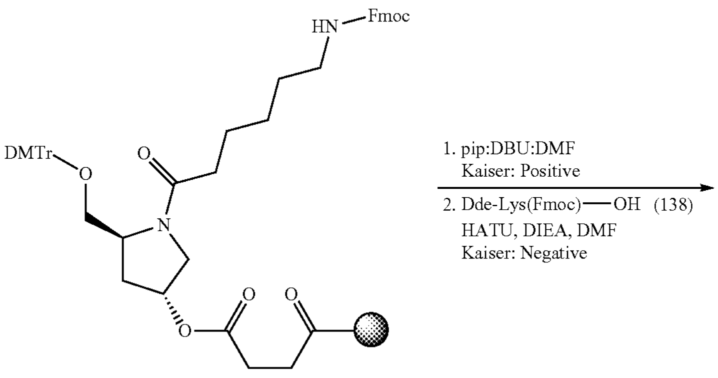
137
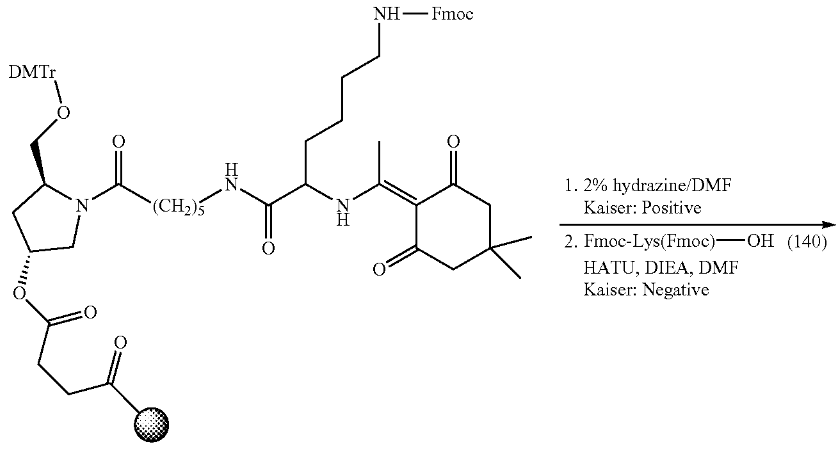
139
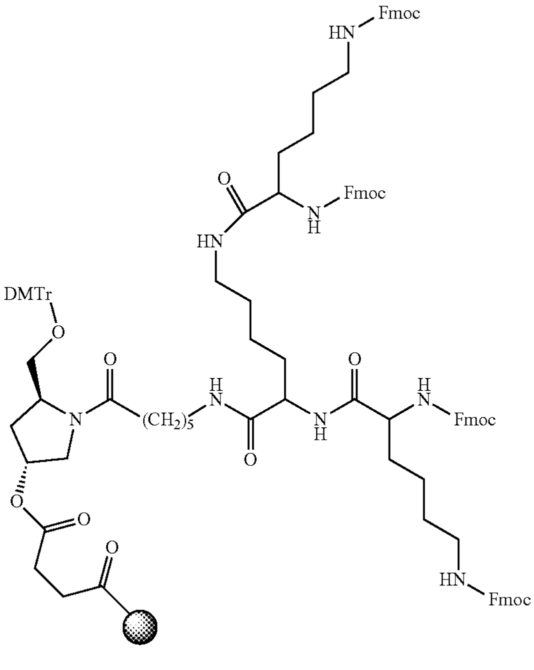
141

-continued

141

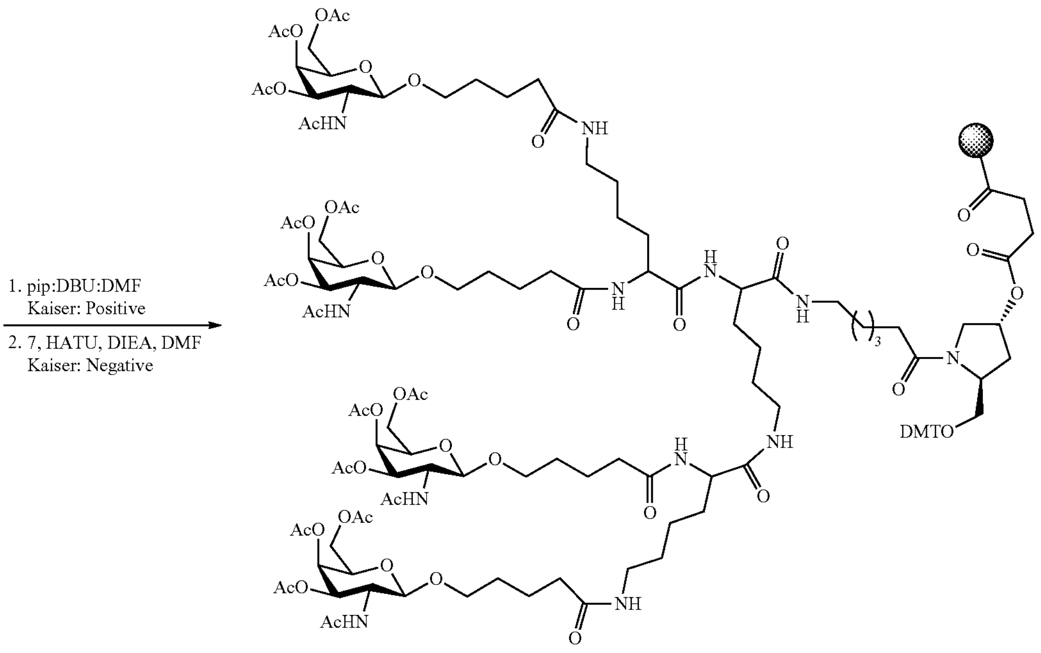

142

Synthesis of Compound 134. To a Merrifield flask was added aminomethyl VIMAD resin (2.5 g, 450 μmol/g) that was washed with acetonitrile, dimethylformamide, dichloromethane and acetonitrile. The resin was swelled in acetonitrile (4 mL). Compound 133 was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 μmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m/z 1063.8 $[M+2H]^+$.

The solid support bound compound 142 was synthesized using solid phase peptide synthesis methods.

142

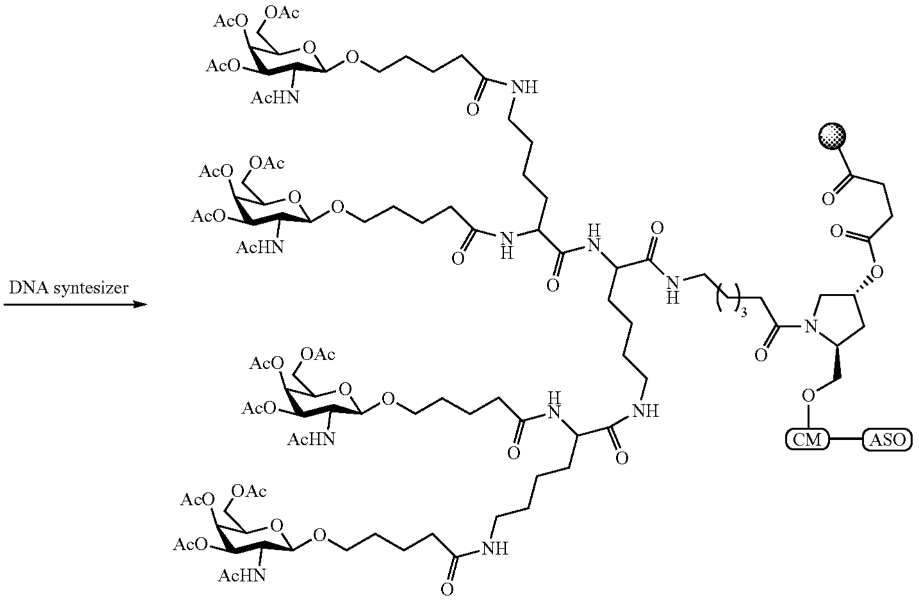

143

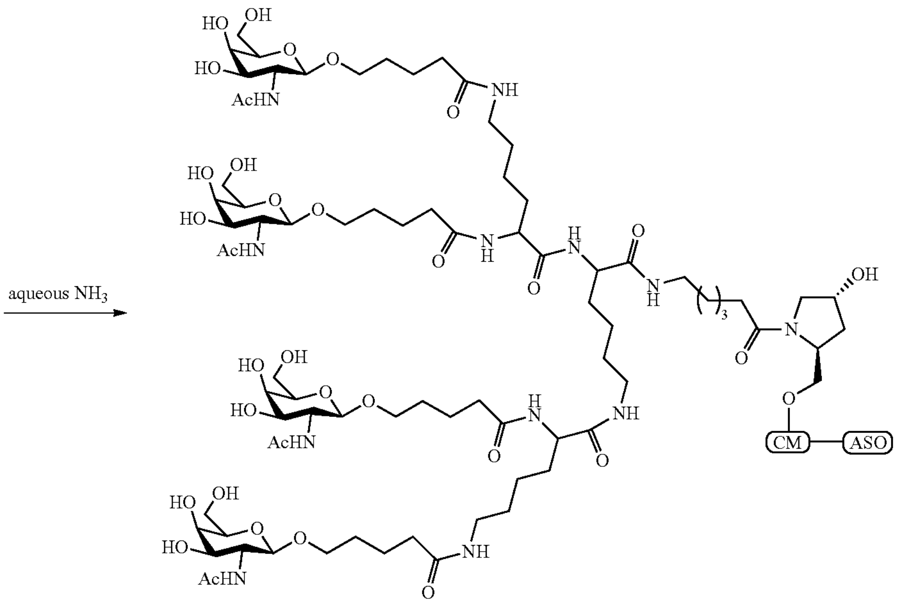

144

The solid support bound compound 143 was synthesized using standard solid phase synthesis on a DNA synthesizer.

The solid support bound compound 143 was suspended in aqueous ammonia (28-30 wt %) and heated at 55° C. for 16 h. The solution was cooled and the solid support was filtered. The filtrate was concentrated and the residue dissolved in water and purified by HPLC on a strong anion exchange column. The fractions containing full length compound 144 were pooled together and desalted. The resulting $GalNAc_4$-11 conjugated oligomeric compound was analyzed by LC-MS and the observed mass was consistent with structure.

The $GalNAc_4$ cluster portion of the conjugate group $GalNAc_4$-11 ($GalNAc_4$-$11_a$) can be combined with any cleavable moiety to provide a variety of conjugate groups. In certain embodiments, the cleavable moiety is —P(═O)(OH)-$A_d$-P(═O)(OH)—.

The structure of GalNAc$_4$-11 (GalNAc$_4$-11$_a$-CM) is shown below:
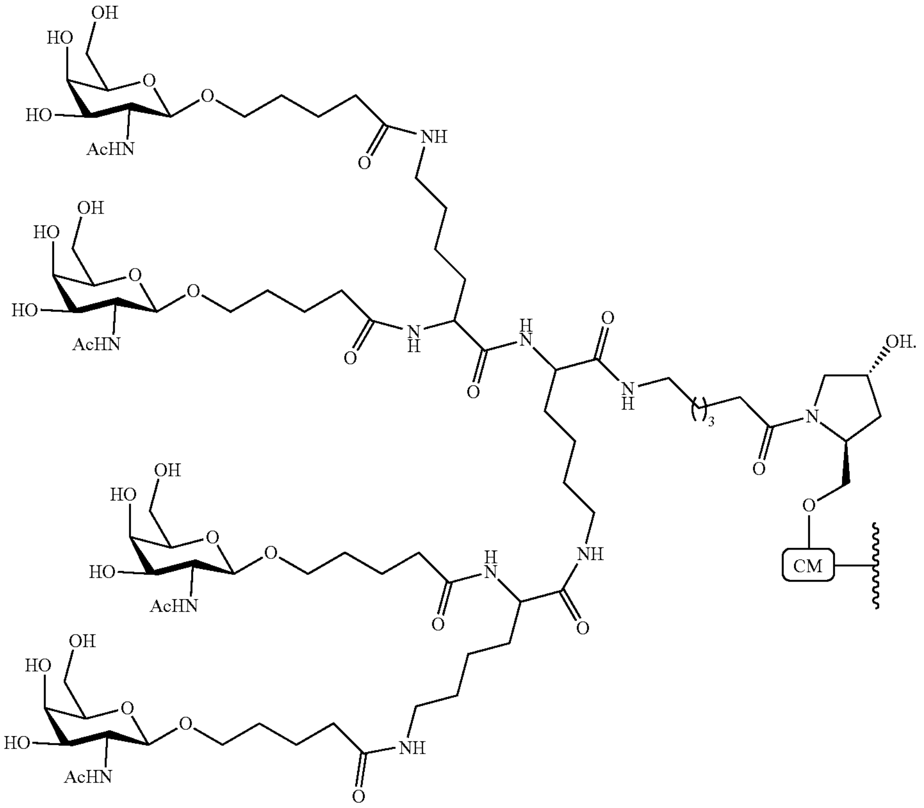
Example 51: Preparation of Oligonucleotide 155 Comprising GalNAc$_3$-6
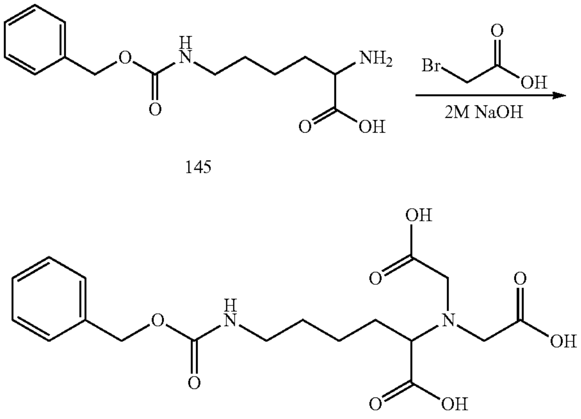
145
146

Compound 146 was synthesized as described in the literature (*Analytical Biochemistry* 1995, 229, 54-60).

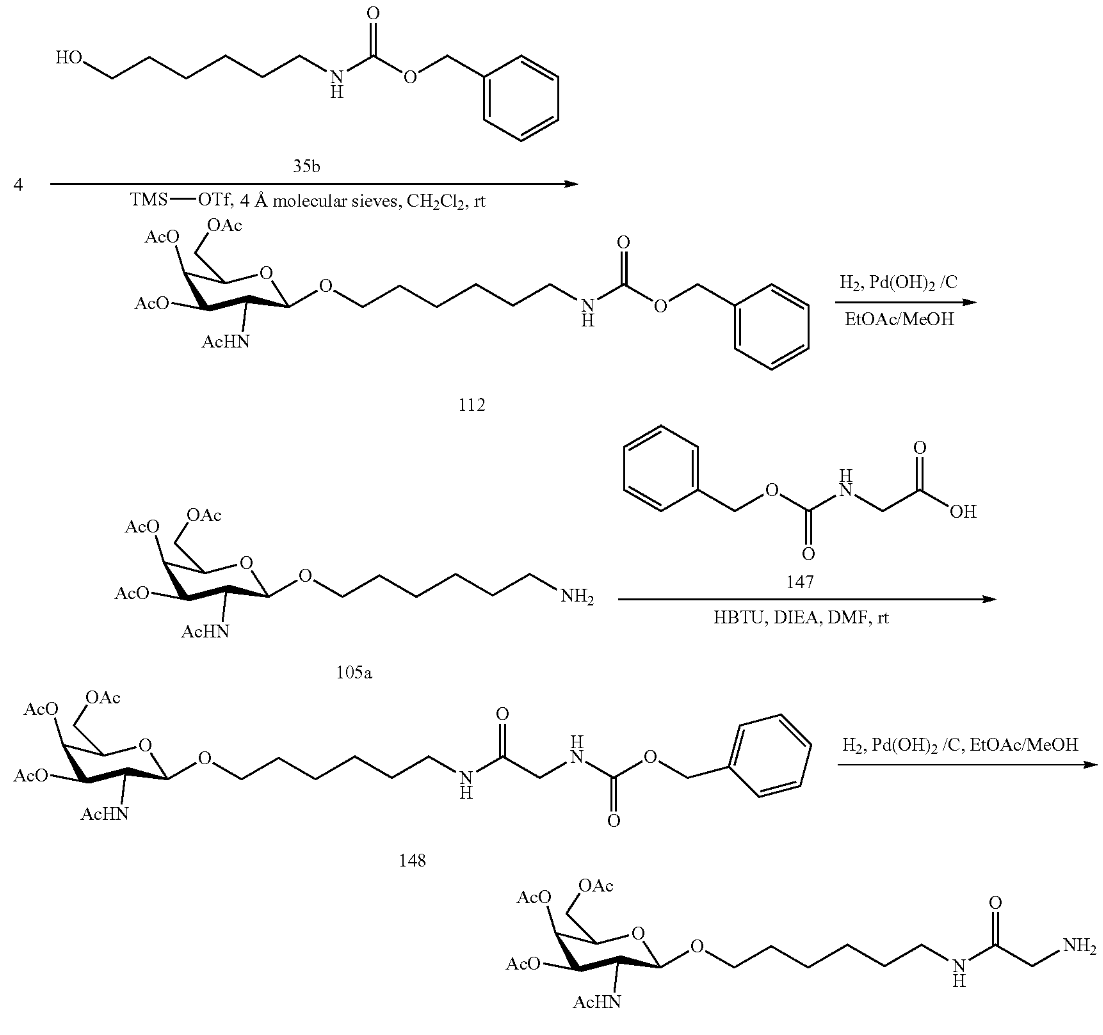

4

35b

112

147

105a

148

149

Compound 4 (15 g, 45.55 mmol) and compound 35b (14.3 grams, 57 mmol) were dissolved in $CH_2Cl_2$ (200 ml). Activated molecular sieves (4 Å. 2 g, powdered) were added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous $NaHCO_3$ (500 ml) and crushed ice (~150 g). The organic layer was separated, washed with brine, dried over $MgSO_4$, filtered, and was concentrated to an orange oil under reduced pressure. The crude material was purified by silica gel column chromatography and eluted with 2-10% MeOH in $CH_2Cl_2$ to yield Compound 112 (16.53 g, 63%). LCMS and $^1H$ NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled through the solution for 30 minutes. Upon completion (TLC 10% MeOH in $CH_2Cl_2$, and LCMS), the catalyst was removed by filtration through a pad of celite. The filtrate was concentrated by rotary evaporation, and was dried briefly under high vacuum to yield Compound 105a (3.28 g). LCMS and 1H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous $NaHCO_3$ and brine. The organics phase was separated, dried ($MgSO_4$), filtered, and concentrated to an orange syrup. The crude material was purified by column chromatography 2-5% MeOH in $CH_2Cl_2$ to yield Compound 148 (3.44 g, 73%). LCMS and $^1H$ NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

organic phase was separated, dried over $MgSO_4$, filtered, and concentrated. The residue was purified by silica gel column chromatography and eluted with 2-10% MeOH in $CH_2Cl_2$ to yield Compound 150 (0.62 g, 20%). LCMS and $^1H$ NMR were consistent with the desired product.

Compound 150 (0.62 g) was dissolved in 1:1 MeOH/EtOAc (5 L). The reaction mixture was purged by bubbling a stream of argon through the solution for 15 minutes.

146

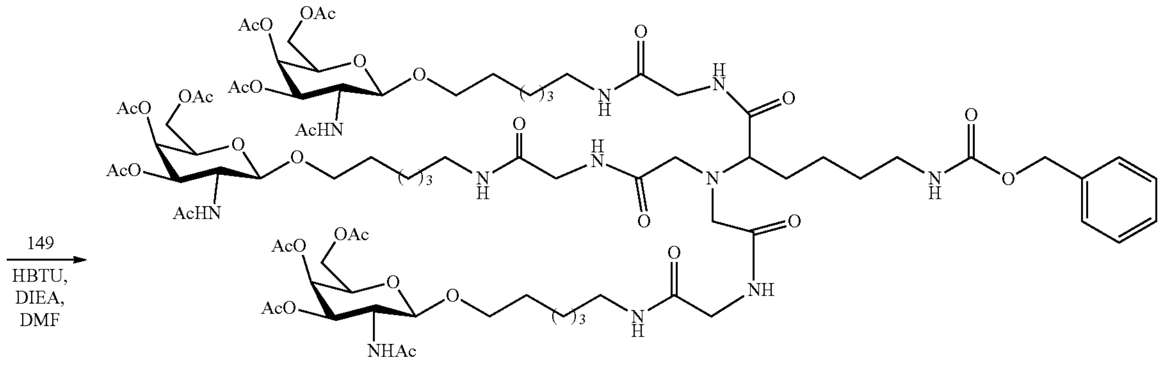

150

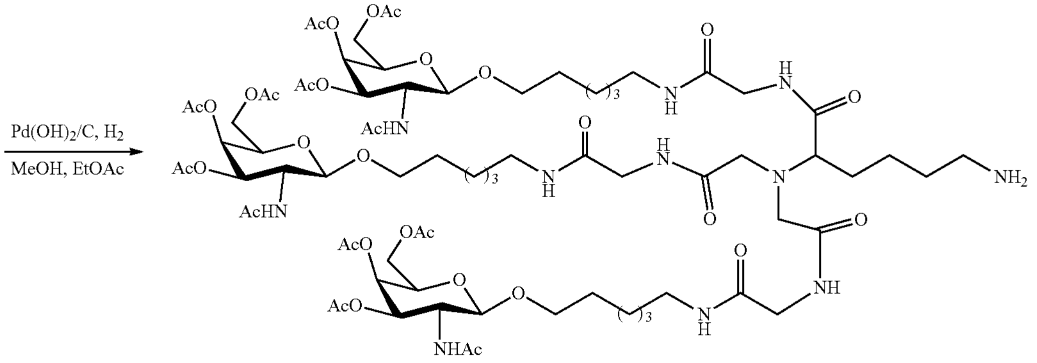

151

Compound 146 (0.68 g, 1.73 mmol) was dissolved in dry DMF (20 ml). To this DIEA (450 μL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous $NaHCO_3$, followed by brine. The Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

151

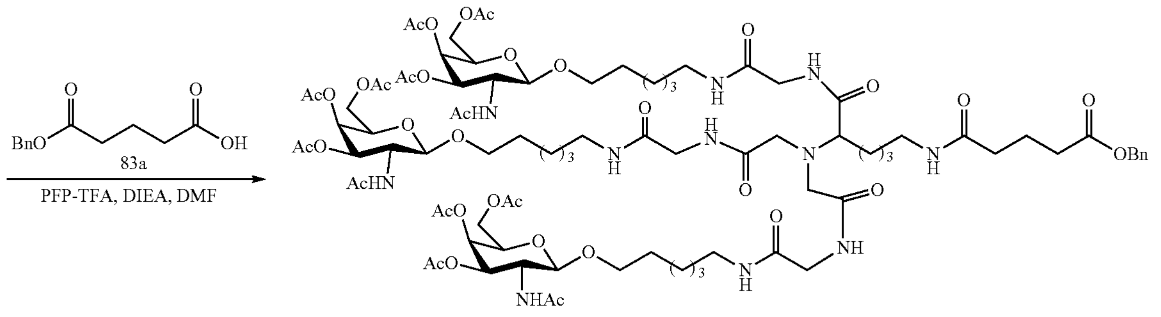

152

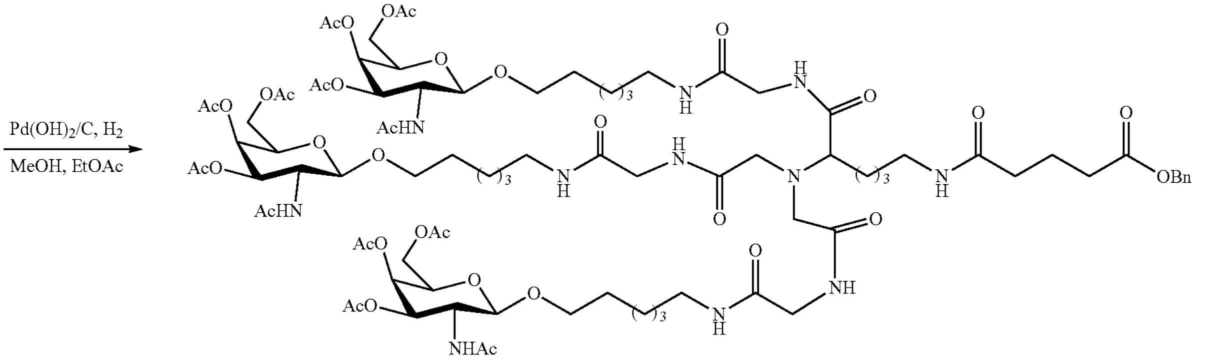

153

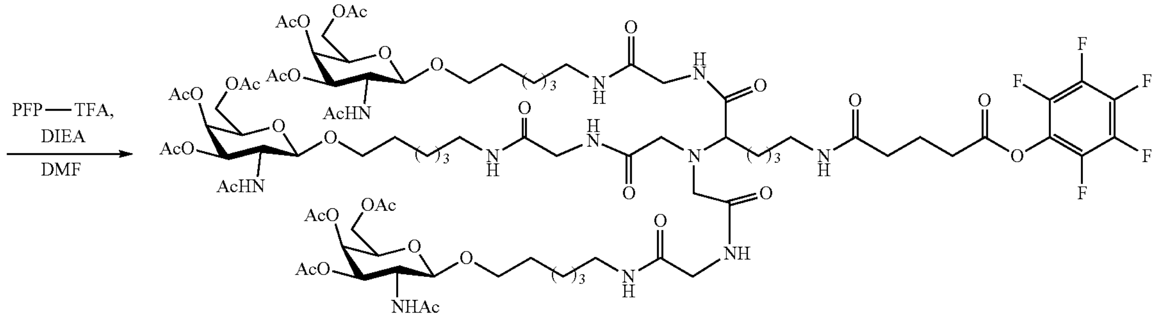

154

Compound 83a (0.11 g, 0.33 mmol) was dissolved in anhydrous DMF (5 mL) and N,N-Diisopropylethylamine (75 μL, 1 mmol) and PFP-TFA (90 μL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~30 min. Upon completion, the majority of the solvent was removed under reduced pressure. The residue was diluted with $CH_2Cl_2$ and washed with aqueous saturated $NaHCO_3$, followed by brine. The organic phase separated, dried over $MgSO_4$, filtered, and concentrated to an orange syrup. The residue was purified by silica gel column chromatography (2-10% MeOH in $CH_2Cl_2$) to yield Compound 152 (0.35 g, 55%). LCMS and $^1$H NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 μL, 0.37 mmol) and PFP-TFA (35 μL, 0.28 mmol) were added. The reaction mixture was stirred under nitrogen for ~30 min. The reaction mixture turned magenta upon contact, and gradually turned orange. The pH of the reaction mixture was maintained at pH=9-10 by adding more N-Diisopropylethylamine. The progress of the reaction was monitored by TLC and LCMS. Upon completion, the majority of the solvent was removed under reduced pressure. The residue was diluted with $CH_2Cl_2$ (50 mL), and washed with saturated aqueous $NaHCO_3$, followed by brine. The organic layer was dried over $MgSO_4$, filtered, and concentrated to an orange syrup. The residue was purified by column chromatography and eluted with 2-10% MeOH in $CH_2Cl_2$ to yield Compound 154 (0.29 g, 79%). LCMS and $^1H$ NMR were consistent with the desired product.

83e

154 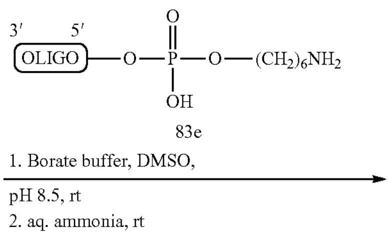

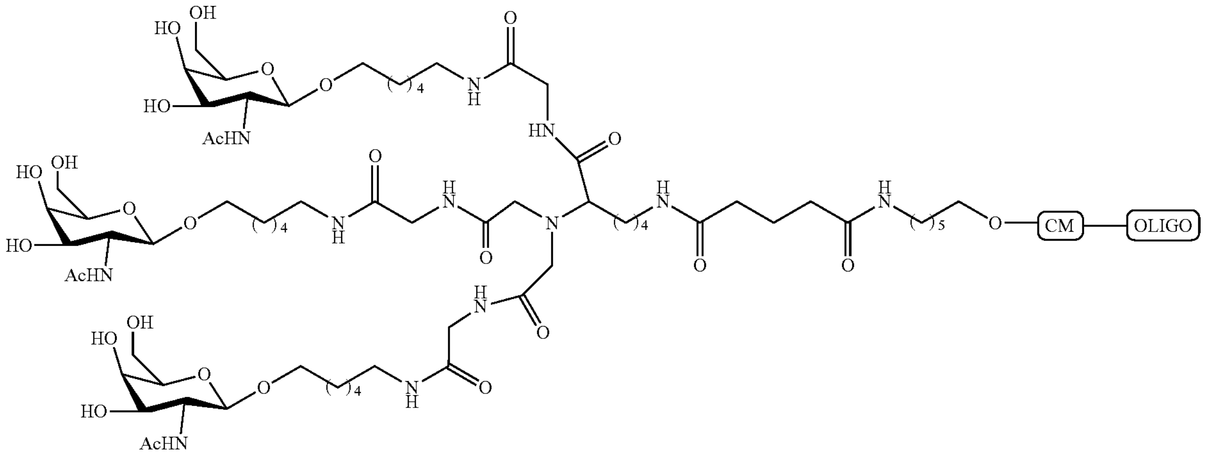

155

Oligomeric Compound 155, comprising a $GalNAc_3$-6 conjugate group, was prepared using the general procedures illustrated in Example 46. The $GalNAc_3$ cluster portion of the conjugate group $GalNAc_3$-6 ($GalNAc_3$-$6_a$) can be combined with any cleavable moiety to provide a variety of conjugate groups. In certain embodiments, the cleavable moiety is —P(═O)(OH)-$A_d$-P(═O)(OH)—.

The structure of $GalNAc_3$-6 ($GalNAc_3$-$6_a$-CM-) is shown below:

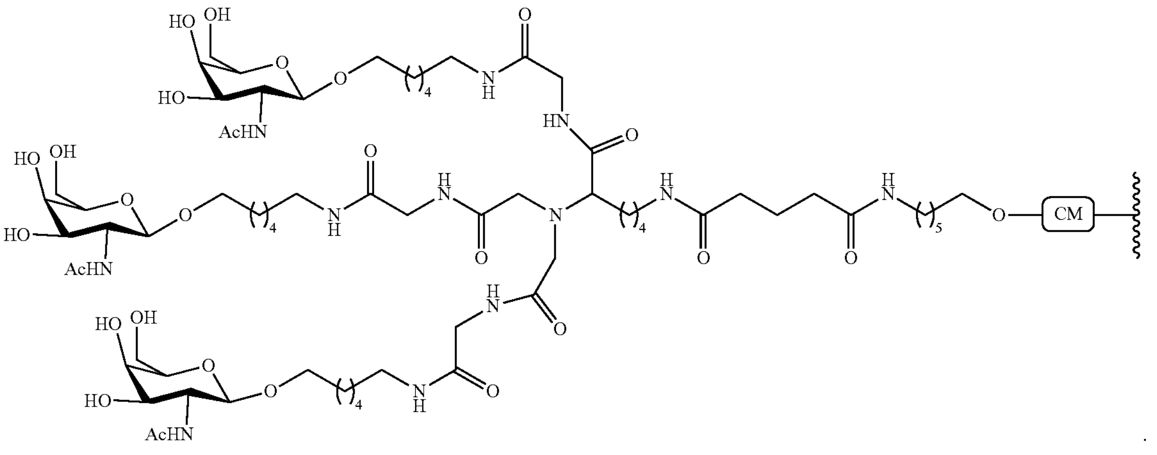

.

Example 52: Preparation of Oligonucleotide 160 Comprising $GalNAc_3$-9

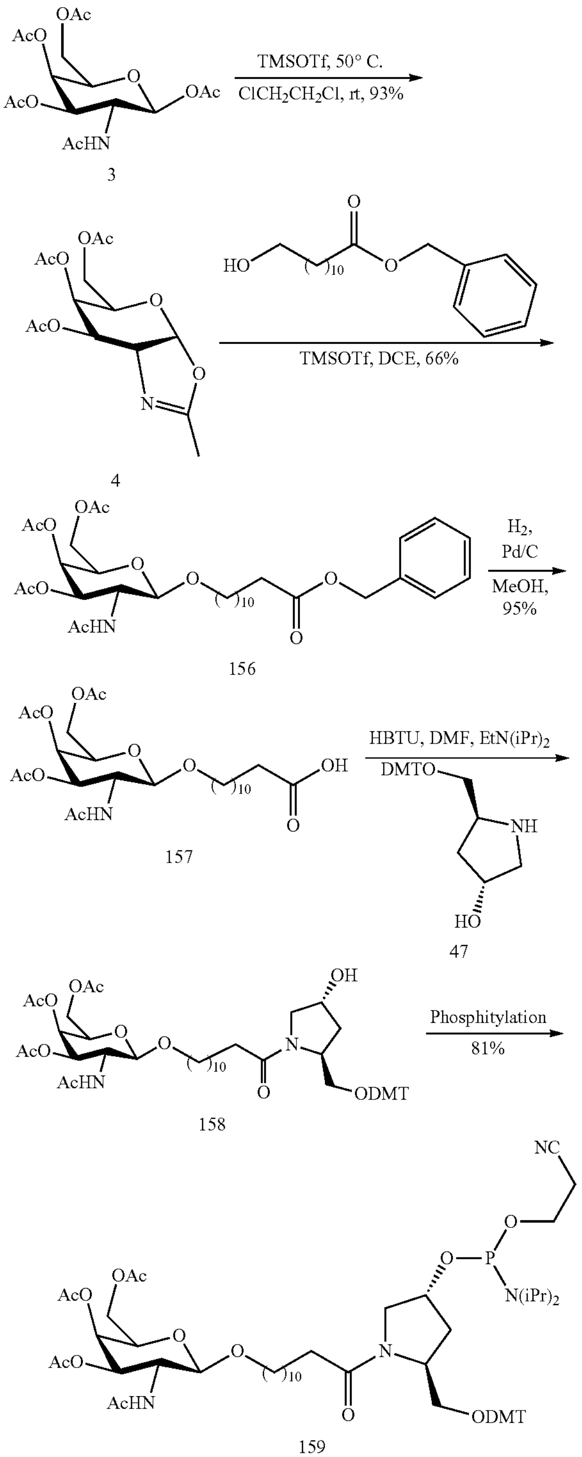

3

4

156

157

47

158

159

Compound 156 was synthesized following the procedure described in the literature (*J. Med. Chem.* 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m/z 544.1 $[M-H]^-$.

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated $NaHCO_3$ aqueous solution. The mixture was extracted with ethyl acetate and the organic layer was washed with brine and dried ($Na_2SO_4$), filtered and evaporated. The residue obtained was purified by silica gel column chromatography and eluted with 50% ethyl acetate in hexane to yield compound 158 (8.25 g, 73.3%). The structure was confirmed by MS and $^1H$ NMR analysis.

Compound 158 (7.2 g, 7.61 mmol) was dried over $P_2O_5$ under reduced pressure. The dried compound was dissolved in anhydrous DMF (50 mL). To this 1H-tetrazole (0.43 g, 6.09 mmol) and N-methylimidazole (0.3 mL, 3.81 mmol) and 2-cyanoethyl-N,N,N',N'-tetraisopropyl phosphorodiamidite (3.65 mL, 11.50 mmol) were added. The reaction mixture was stirred t under an argon atmosphere for 4 h. The reaction mixture was diluted with ethyl acetate (200 mL). The reaction mixture was washed with saturated $NaHCO_3$ and brine. The organic phase was separated, dried ($Na_2SO_4$), filtered and evaporated. The residue was purified by silica gel column chromatography and eluted with 50-90% ethyl acetate in hexane to yield Compound 159 (7.82 g, 80.5%). The structure was confirmed by LCMS and $^{31}P$ NMR analysis.

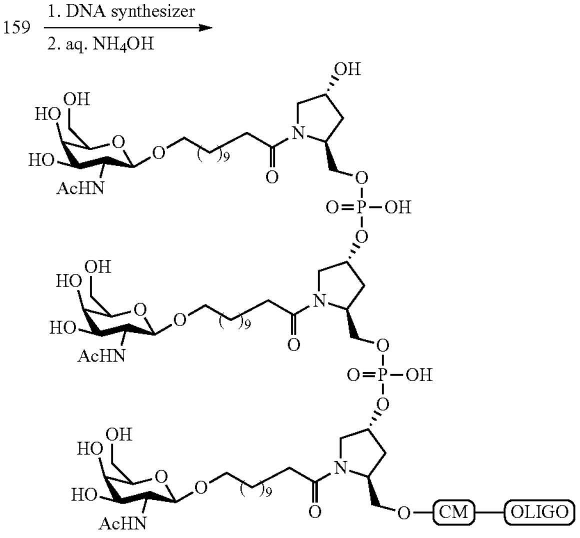

160

Oligomeric Compound 160, comprising a $GalNAc_3$-9 conjugate group, was prepared using standard oligonucleotide synthesis procedures. Three units of compound 159 were coupled to the solid support, followed by nucleotide phosphoramidites. Treatment of the protected oligomeric compound with aqueous ammonia yielded compound 160.

The GalNAc$_3$ cluster portion of the conjugate group GalNAc$_3$-9 (GalNAc$_3$-9$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-9 (GalNAc$_3$-9$_a$-CM) is shown below:

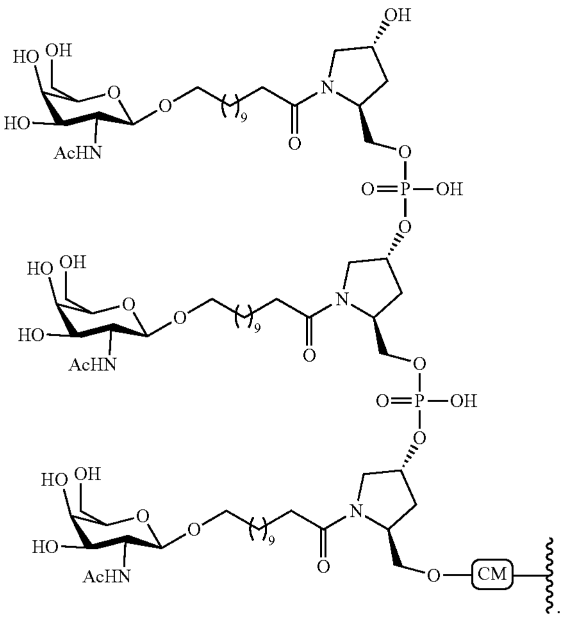

Example 53: Alternate Procedure for Preparation of Compound 18 (GalNAc$_3$-1a and GalNAc$_3$-3a)

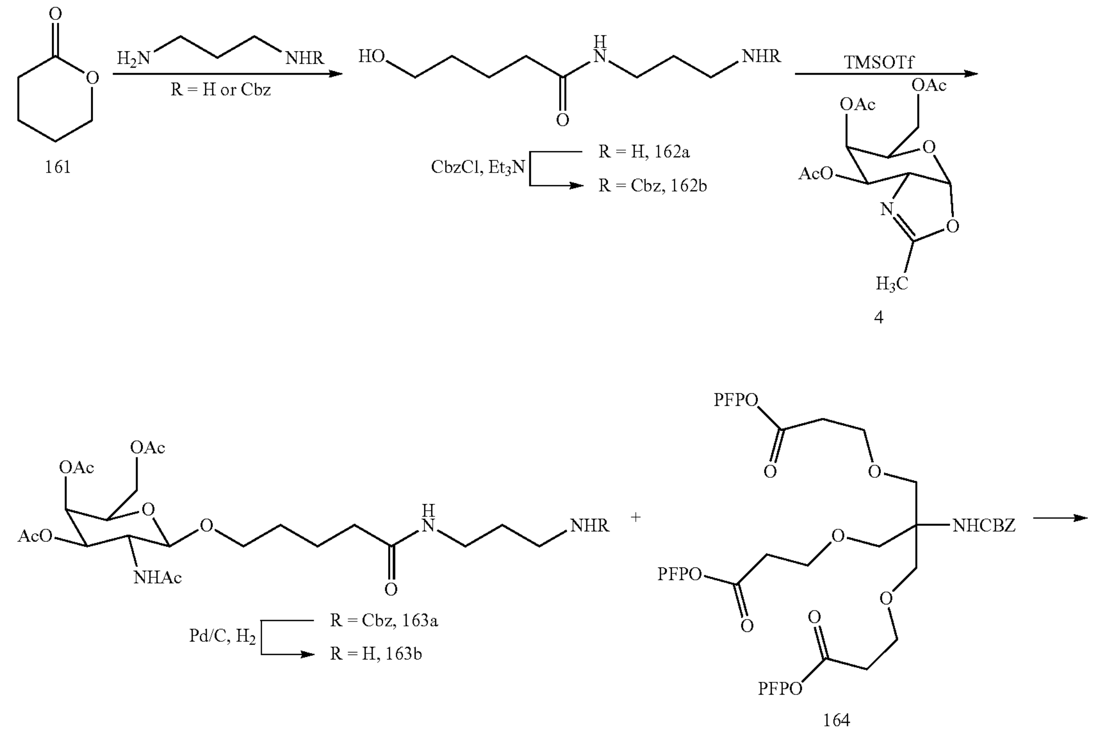

-continued

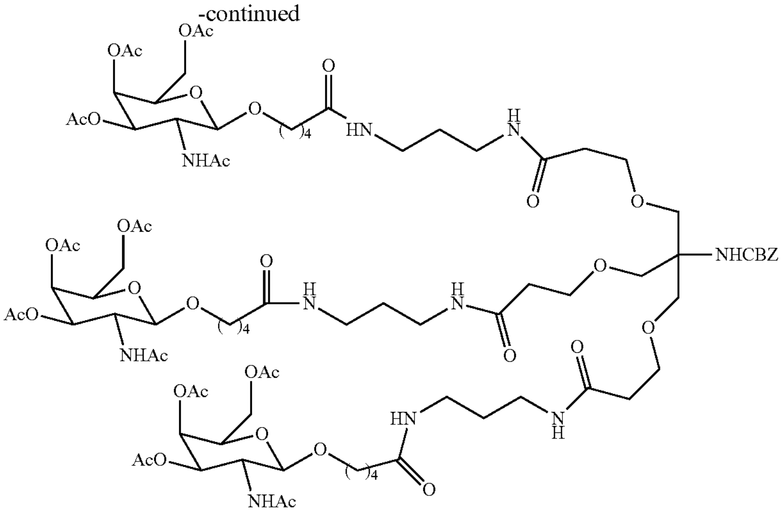

18

Lactone 161 was reacted with diamino propane (3-5 eq) or Mono-Boc protected diamino propane (1 eq) to provide alcohol 162a or 162b. When unprotected propanediamine was used for the above reaction, the excess diamine was removed by evaporation under high vacuum and the free amino group in 162a was protected using CbzCl to provide 162b as a white solid after purification by column chromatography. Alcohol 162b was further reacted with compound 4 in the presence of TMSOTf to provide 163a which was converted to 163b by removal of the Cbz group using catalytic hydrogenation. The pentafluorophenyl (PFP) ester 164 was prepared by reacting triacid 113 (see Example 48) with PFPTFA (3.5 eq) and pyridine (3.5 eq) in DMF (0.1 to 0.5 M). The triester 164 was directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 54: Alternate Procedure for Preparation of Compound 18 (GalNAc$_3$-1a and GalNAc$_3$-3a)

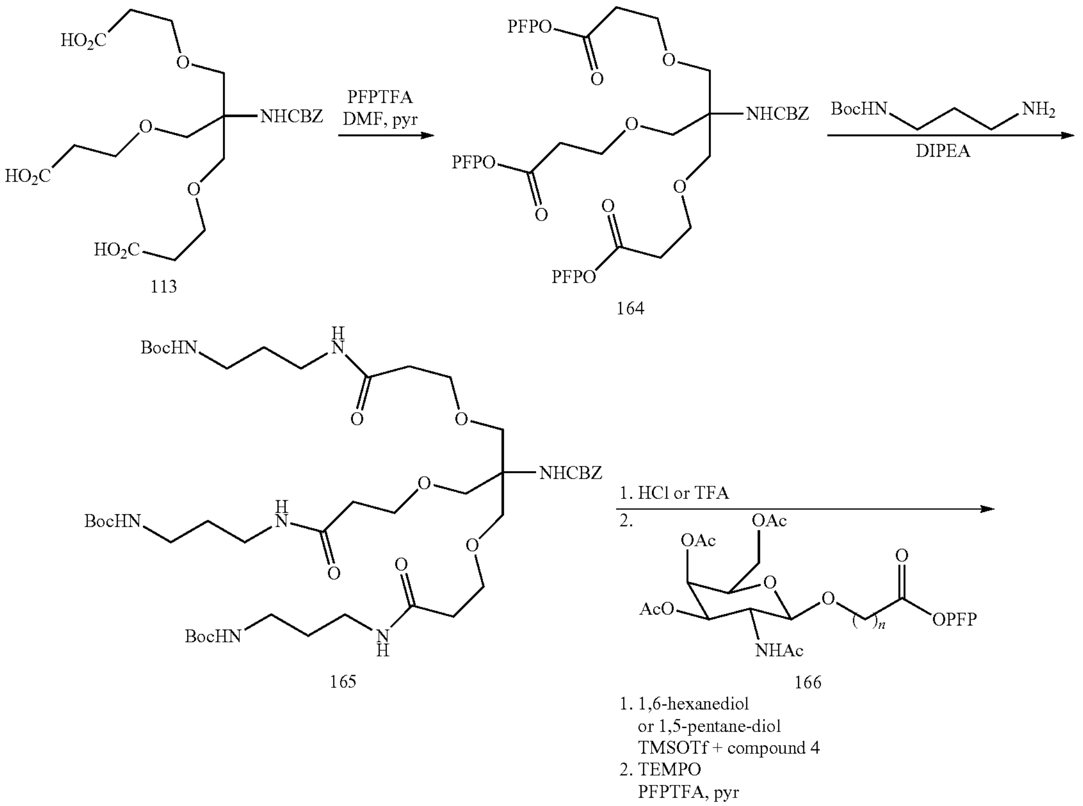

113

164

165

166

-continued

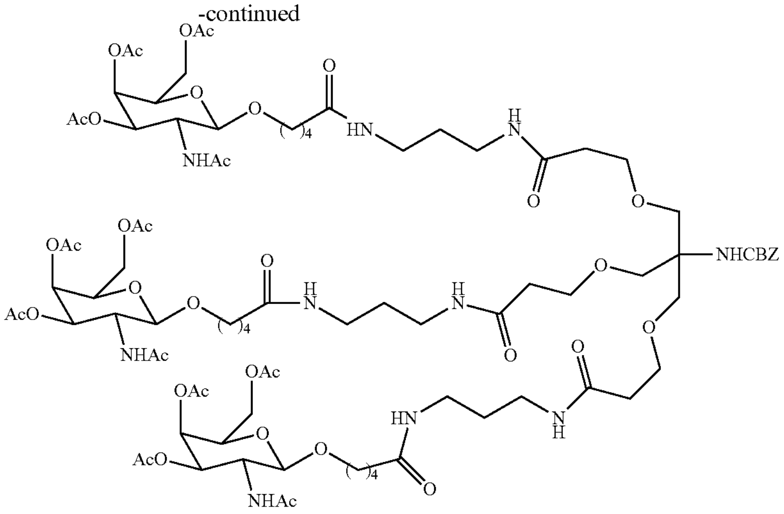

18

The triPFP ester 164 was prepared from acid 113 using the procedure outlined in example 53 above and reacted with mono-Boc protected diamine to provide 165 in essentially quantitative yield. The Boc groups were removed with hydrochloric acid or trifluoroacetic acid to provide the triamine which was reacted with the PFP activated acid 166 in the presence of a suitable base such as DIPEA to provide Compound 18.

The PFP protected Gal-NAc acid 166 was prepared from the corresponding acid by treatment with PFPTFA (1-1.2 eq) and pyridine (1-1.2 eq) in DMF. The precursor acid in turn was prepared from the corresponding alcohol by oxidation using TEMPO (0.2 eq) and BAIB in acetonitrile and water. The precursor alcohol was prepared from sugar intermediate 4 by reaction with 1,6-hexanediol (or 1,5-pentanediol or other diol for other n values) (2-4 eq) and TMSOTf using conditions described previously in example 47.

Example 55: Dose-Dependent Study of Oligonucleotides Comprising Either a 3' or 5'-Conjugate Group (Comparison of GalNAc$_3$-1, 3, 8 and 9) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at either the 3' or 5' terminus of the respective oligonucleotide by a phosphodiester linked 2'-deoxyadenosine nucleoside (cleavable moiety).

TABLE 39

Modified ASO targeting SRB-1

| ASO | Sequence (5' to 3') | Motif | Conjugate | Unmodified SEQ ID No. | Modified SEQ ID No. |
|---|---|---|---|---|---|
| ISIS 353382 (parent) | $G_{es}{}^{m}C_{es}T_{es}T_{es}$<br>${}^{m}C_{es}A_{ds}G_{ds}T_{ds}$<br>${}^{m}C_{ds}A_{ds}T_{ds}G_{ds}$<br>$A_{ds}{}^{m}C_{ds}T_{ds}T_{es}$<br>${}^{m}C_{es}{}^{m}C_{es}T_{es}T_{e}$ | 5/10/5 | none | 252 | 318 |
| ISIS 655861 | $G_{es}{}^{m}C_{es}T_{es}T_{es}$<br>${}^{m}C_{es}A_{ds}G_{ds}T_{ds}$<br>${}^{m}C_{ds}A_{ds}T_{ds}G_{ds}$<br>$A_{ds}{}^{m}C_{ds}T_{ds}T_{es}$<br>${}^{m}C_{es}{}^{m}C_{es}T_{es}T_{eo}$<br>**$A_{do}$'-GalNAc$_3$-1$_a$** | 5/10/5 | **GalNAc$_3$-1** | 253 | 369 |
| ISIS 664078 | $G_{es}{}^{m}C_{es}T_{es}T_{es}$<br>${}^{m}C_{es}A_{ds}G_{ds}T_{ds}$<br>${}^{m}C_{ds}A_{ds}T_{ds}G_{ds}$<br>$A_{ds}{}^{m}C_{ds}T_{ds}T_{es}$<br>${}^{m}C_{es}{}^{m}C_{es}T_{es}T_{eo}$<br>**$A_{do'}$-GalNAc$_3$-9$_a$** | 5/10/5 | **GalNAc$_3$-9** | 253 | 382 |
| ISIS 661161 | **GalNAc$_3$-3$_a$-$_o$'**<br>**$A_{do}$**$G_{es}{}^{m}C_{es}T_{es}T_{es}$<br>${}^{m}C_{es}A_{ds}G_{ds}T_{ds}$<br>${}^{m}C_{ds}A_{ds}T_{ds}G_{ds}$ | 5/10/5 | **GalNAc$_3$-3** | 254 | 376 |

TABLE 39-continued

Modified ASO targeting SRB-1

| ASO | Sequence (5' to 3') | Motif | Conju-gate | Unmodi-fied SEQ ID No. | Modified SEQ ID No. |
|---|---|---|---|---|---|
| | $A_{ds}{}^{m}C_{ds}T_{ds}T_{es}$ ${}^{m}C_{es}{}^{m}C_{es}T_{es}T_{e}$ | | | | |
| ISIS 665001 | **GalNAc$_3$-8$_a$-$_{o'}$** $A_{do}G_{es}{}^{m}C_{es}T_{es}T_{es}$ ${}^{m}C_{es}A_{ds}G_{ds}T_{ds}$ ${}^{m}C_{ds}A_{ds}T_{ds}G_{ds}$ $A_{ds}{}^{m}C_{ds}T_{ds}T_{es}$ ${}^{m}C_{es}{}^{m}C_{es}T_{es}T_{e}$ | 5/10/5 | **GalNAc$_3$-8** | 254 | 384 |

Capital letters indicate the nucleobase for each nucleoside and $^{m}$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(=O)(OH)—.
Conjugate groups are in bold.

The structure of GalNAc$_3$-1$_a$ was shown previously in Example 9. The structure of GalNAc$_3$-9 was shown previously in Example 52. The structure of GalNAc$_3$-3 was shown previously in Example 39. The structure of GalNAc$_3$-8 was shown previously in Example 47.

Treatment

Six week old male Balb/c mice (Jackson Laboratory, Bar Harbor, ME) were injected subcutaneously once at the dosage shown below with ISIS 353382, 655861, 664078, 661161, 665001 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 40, treatment with antisense oligonucleotides lowered SRB-1 mRNA levels in a dose-dependent manner. Indeed, the antisense oligonucleotides comprising the phosphodiester linked GalNAc$_3$-1 and GalNAc$_3$-9 conjugates at the 3' terminus (ISIS 655861 and ISIS 664078) and the GalNAc$_3$-3 and GalNAc$_3$-8 conjugates linked at the 5' terminus (ISIS 661161 and ISIS 665001) showed substantial improvement in potency compared to the unconjugated antisense oligonucleotide (ISIS 353382). Furthermore, ISIS 664078, comprising a GalNAc$_3$-9 conjugate at the 3' terminus was essentially equipotent compared to ISIS 655861, which comprises a GalNAc$_3$-1 conjugate at the 3' terminus. The 5' conjugated antisense oligonucleotides, ISIS 661161 and ISIS 665001, comprising a GalNAc$_3$-3 or GalNAc$_3$-9, respectively, had increased potency compared to the 3' conjugated antisense oligonucleotides (ISIS 655861 and ISIS 664078).

TABLE 40

ASOs containing GalNAc$_3$-1, 3, 8 or 9 targeting SRB-1

| ISIS No. | Dosage (mg/kg) | SRB-1 mRNA (% Saline) | Conjugate |
|---|---|---|---|
| Saline | n/a | 100 | |
| 353382 | 3 | 88 | none |
| | 10 | 68 | |
| | 30 | 36 | |
| 655861 | 0.5 | 98 | GalNac$_3$-1 (3') |
| | 1.5 | 76 | |
| | 5 | 31 | |
| | 15 | 20 | |
| 664078 | 0.5 | 88 | GalNac$_3$-9 (3') |
| | 1.5 | 85 | |
| | 5 | 46 | |
| | 15 | 20 | |
| 661161 | 0.5 | 92 | GalNac$_3$-3 (5') |
| | 1.5 | 59 | |
| | 5 | 19 | |
| | 15 | 11 | |
| 665001 | 0.5 | 100 | GalNac$_3$-8 (5') |
| | 1.5 | 73 | |
| | 5 | 29 | |
| | 15 | 13 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in the table below.

TABLE 41

| ISIS No. | Dosage mg/kg | ALT | AST | Total Bilirubin | BUN | Conjugate |
|---|---|---|---|---|---|---|
| Saline | | 24 | 59 | 0.1 | 37.52 | |
| 353382 | 3 | 21 | 66 | 0.2 | 34.65 | none |
| | 10 | 22 | 54 | 0.2 | 34.2 | |
| | 30 | 22 | 49 | 0.2 | 33.72 | |

TABLE 41-continued

| ISIS No. | Dosage mg/kg | ALT | AST | Total Bilirubin | BUN | Conjugate |
|---|---|---|---|---|---|---|
| 655861 | 0.5 | 25 | 62 | 0.2 | 30.65 | GalNac$_3$-1 (3') |
| | 1.5 | 23 | 48 | 0.2 | 30.97 | |
| | 5 | 28 | 49 | 0.1 | 32.92 | |
| | 15 | 40 | 97 | 0.1 | 31.62 | |
| 664078 | 0.5 | 40 | 74 | 0.1 | 35.3 | GalNac$_3$-9 (3') |
| | 1.5 | 47 | 104 | 0.1 | 32.75 | |
| | 5 | 20 | 43 | 0.1 | 30.62 | |
| | 15 | 38 | 92 | 0.1 | 26.2 | |
| 661161 | 0.5 | 101 | 162 | 0.1 | 34.17 | GalNac$_3$-3 (5') |
| | 1.5 g | 42 | 100 | 0.1 | 33.37 | |
| | 5 g | 23 | 99 | 0.1 | 34.97 | |
| | 15 | 53 | 83 | 0.1 | 34.8 | |

TABLE 41-continued

| ISIS No. | Dosage mg/kg | ALT | AST | Total Bilirubin | BUN | Conjugate |
|---|---|---|---|---|---|---|
| 665001 | 0.5 | 28 | 54 | 0.1 | 31.32 | GalNac$_3$-8 (5') |
| | 1.5 | 42 | 75 | 0.1 | 32.32 | |
| | 5 | 24 | 42 | 0.1 | 31.85 | |
| | 15 | 32 | 67 | 0.1 | 31. | |

Example 56: Dose-Dependent Study of Oligonucleotides Comprising Either a 3' or 5'-Conjugate Group (Comparison of GalNAc$_3$-1, 2, 3, 5, 6, 7 and 10) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at the 5' terminus of the respective oligonucleotide by a phosphodiester linked 2'-deoxyadenosine nucleoside (cleavable moiety) except for ISIS 655861 which had the GalNAc$_3$ conjugate group attached at the 3' terminus.

TABLE 42

Modified ASO targeting SRB-1

| ASO | Sequence (5' to 3') | Motif | Conjugate | Unmodified SEQ ID No. | Modified SEQ ID No. |
|---|---|---|---|---|---|
| ISIS 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | no conjugate | 252 | 318 |
| ISIS 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}T_{es}T_{eo}\mathbf{A}_{do'}$-**GalNAc$_3$-1$_a$** | 5/10/5 | **GalNAc$_3$-1** | 253 | 369 |
| ISIS 664507 | **GalNAc$_3$-2**$_{a-o'}$$\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-2** | 254 | 383 |
| ISIS 661161 | **GalNAc$_3$-3**$_{a-o'}$$\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-3** | 254 | 376 |
| ISIS 666224 | **GalNAc$_3$-5**$_{a-o'}$$\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-5** | 254 | 385 |

TABLE 42-continued

Modified ASO targeting SRB-1

| ASO | Sequence (5' to 3') | Motif | Conjugate | Unmodified SEQ ID No. | Modified SEQ ID No. |
|---|---|---|---|---|---|
| ISIS 666961 | **GalNAc$_3$-6$_{a-o'}$** $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-6** | 254 | 391 |
| ISIS 666981 | **GalNAc$_3$-7$_{a-o'}$** $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-7** | 254 | 392 |
| ISIS 666881 | **GalNAc$_3$-10$_{a-o'}$** $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-10** | 254 | 386 |

Capital letters indicate the nucleobase for each nucleoside and $^{m}$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(═O)(OH)—.
Conjugate groups are in bold.

The structure of GalNAc$_3$-1$_a$ was shown previously in Example 9. The structure of GalNAc$_3$-2$_a$ was shown previously in Example 37. The structure of GalNAc$_3$-3$_a$ was shown previously in Example 39. The structure of GalNAc$_3$-5$_a$ was shown previously in Example 49. The structure of GalNAc$_3$-6$_a$ was shown previously in Example 51. The structure of GalNAc$_3$-7$_a$ was shown previously in Example 48. The structure of GalNAc$_3$-10$_a$ was shown previously in Example 46.

Treatment

Six week old male Balb/c mice (Jackson Laboratory, Bar Harbor, ME) were injected subcutaneously once at the dosage shown below with ISIS 353382, 655861, 664507, 661161, 666224, 666961, 666981, 666881 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 43, treatment with antisense oligonucleotides lowered SRB-1 mRNA levels in a dose-dependent manner. Indeed, the conjugated antisense oligonucleotides showed substantial improvement in potency compared to the unconjugated antisense oligonucleotide (ISIS 353382). The 5' conjugated antisense oligonucleotides showed a slight increase in potency compared to the 3' conjugated antisense oligonucleotide.

TABLE 43

| ISIS No. | Dosage (mg/kg) | SRB-1 mRNA (% Saline) | Conjugate |
|---|---|---|---|
| Saline | n/a | 100.0 | |
| 353382 | 3 | 96.0 | none |
| | 10 | 73.1 | |
| | 30 | 36.1 | |
| 655861 | 0.5 | 99.4 | GalNac$_3$-1 (3') |
| | 1.5 | 81.2 | |
| | 5 | 33.9 | |
| | 15 | 15.2 | |
| 664507 | 0.5 | 102.0 | GalNac$_3$-2 (5') |
| | 1.5 | 73.2 | |
| | 5 | 31.3 | |
| | 15 | 10.8 | |
| 661161 | 0.5 | 90.7 | GalNac$_3$-3 (5') |
| | 1.5 | 67.6 | |
| | 5 | 24.3 | |
| | 15 | 11.5 | |
| 666224 | 0.5 | 96.1 | GalNac$_3$-5 (5') |
| | 1.5 | 61.6 | |
| | 5 | 25.6 | |
| | 15 | 11.7 | |
| 666961 | 0.5 | 85.5 | GalNAc$_3$-6 (5') |
| | 1.5 | 56.3 | |
| | 5 | 34.2 | |
| | 15 | 13.1 | |

TABLE 43-continued

| ISIS No. | Dosage (mg/kg) | SRB-1 mRNA (% Saline) | Conjugate |
|---|---|---|---|
| 666981 | 0.5 | 84.7 | GalNAc$_3$-7 (5') |
| | 1.5 | 59.9 | |
| | 5 | 24.9 | |
| | 15 | 8.5 | |
| 666881 | 0.5 | 100.0 | GalNAc$_3$-10 (5') |
| | 1.5 | 65.8 | |
| | 5 | 26.0 | |
| | 15 | 13.0 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 44 below.

TABLE 44

| ISIS No. | Dosage mg/kg | ALT | AST | Total Bilirubin | BUN | Conjugate |
|---|---|---|---|---|---|---|
| Saline | | 26 | 57 | 0.2 | 27 | |
| 353382 | 3 | 25 | 92 | 0.2 | 27 | none |
| | 10 | 23 | 40 | 0.2 | 25 | |
| | 30 | 29 | 54 | 0.1 | 28 | |
| 655861 | 0.5 | 25 | 71 | 0.2 | 34 | GalNac$_3$-1 (3') |
| | 1.5 | 28 | 60 | 0.2 | 26 | |
| | 5 | 26 | 63 | 0.2 | 28 | |
| | 15 | 25 | 61 | 0.2 | 28 | |
| 664507 | 0.5 | 25 | 62 | 0.2 | 25 | GalNac$_3$-2 (5') |
| | 1.5 | 24 | 49 | 0.2 | 26 | |
| | 5 | 21 | 50 | 0.2 | 26 | |
| | 15 | 59 | 84 | 0.1 | 22 | |
| 661161 | 0.5 | 20 | 42 | 0.2 | 29 | GalNac$_3$-3 (5') |
| | 1.5 g | 37 | 74 | 0.2 | 25 | |
| | 5 g | 28 | 61 | 0.2 | 29 | |
| | 15 | 21 | 41 | 0.2 | 25 | |
| 666224 | 0.5 | 34 | 48 | 0.2 | 21 | GalNac$_3$-5 (5') |
| | 1.5 | 23 | 46 | 0.2 | 26 | |
| | 5 | 24 | 47 | 0.2 | 23 | |
| | 15 | 32 | 49 | 0.1 | 26 | |
| 666961 | 0.5 | 17 | 63 | 0.2 | 26 | GalNAc$_3$-6 (5') |
| | 1.5 | 23 | 68 | 0.2 | 26 | |
| | 5 | 25 | 66 | 0.2 | 26 | |
| | 15 | 29 | 107 | 0.2 | 28 | |
| 666981 | 0.5 | 24 | 48 | 0.2 | 26 | GalNAc$_3$-7 (5') |
| | 1.5 | 30 | 55 | 0.2 | 24 | |
| | 5 | 46 | 74 | 0.1 | 24 | |
| | 15 | 29 | 58 | 0.1 | 26 | |
| 666881 | 0.5 | 20 | 65 | 0.2 | 27 | GalNAc$_3$-10 (5') |
| | 1.5 | 23 | 59 | 0.2 | 24 | |
| | 5 | 45 | 70 | 0.2 | 26 | |
| | 15 | 21 | 57 | 0.2 | 24 | |

Example 57: Duration of Action Study of Oligonucleotides Comprising a 3'-Conjugate Group Targeting ApoC III In Vivo Mice were injected once with the doses indicated below and monitored over the course of 42 days for ApoC-III and plasma triglycerides (Plasma TG) levels. The study was performed using 3 transgenic mice that express human APOC-III in each group.

TABLE 45

Modified ASO targeting ApoC III

| ASO | Sequence (5' to 3') | Linkages | Unmodified SEQ ID No. | Modified SEQ ID No. |
|---|---|---|---|---|
| ISIS 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_e$ | PS | 244 | 317 |
| ISIS 647535 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_{eo}A_{do'}$-**GalNAC$_3$-1$_a$** | PS | 245 | 367 |
| ISIS 647536 | $A_{es}G_{eo}{}^mC_{eo}T_{eo}T_{eo}{}^mC_{ds}T_{ds}T_{ds}G_{ds}T_{ds}{}^mC_{ds}{}^mC_{ds}A_{ds}G_{ds}{}^mC_{ds}T_{eo}T_{eo}T_{es}A_{es}T_{eo}A_{do'}$-**GalNAC$_3$-1$_a$** | PO/PS | 245 | 368 |

Capital letters indicate the nucleobase for each nucleoside and $^m$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(═O)(OH)—.
Conjugate groups are in bold.

The structure of GalNAc$_3$-1$_a$ was shown previously in Example 9.

TABLE 46

ApoC III mRNA (% Saline on Day 1) and Plasma TG Levels (% Saline on Day 1)

| ASO | Dose | Target | Day 3 | Day 7 | Day 14 | Day 35 | Day 42 |
|---|---|---|---|---|---|---|---|
| Saline | 0 mg/kg | ApoC-III | 98 | 100 | 100 | 95 | 116 |
| ISIS 304801 | 30 mg/kg | ApoC-III | 28 | 30 | 41 | 65 | 74 |
| ISIS 647535 | 10 mg/kg | ApoC-III | 16 | 19 | 25 | 74 | 94 |
| ISIS 647536 | 10 mg/kg | ApoC-III | 18 | 16 | 17 | 35 | 51 |
| Saline | 0 mg/kg | Plasma TG | 121 | 130 | 123 | 105 | 109 |

TABLE 46-continued

| ApoC III mRNA (% Saline on Day 1) and Plasma TG Levels (% Saline on Day 1) | | | | | | | |
|---|---|---|---|---|---|---|---|
| ASO | Dose | Target | Day 3 | Day 7 | Day 14 | Day 35 | Day 42 |
| ISIS 304801 | 30 mg/kg | Plasma TG | 34 | 37 | 50 | 69 | 69 |
| ISIS 647535 | 10 mg/kg | Plasma TG | 18 | 14 | 24 | 18 | 71 |
| ISIS 647536 | 10 mg/kg | Plasma TG | 21 | 19 | 15 | 32 | 35 |

As can be seen in the table above the duration of action increased with addition of the 3'-conjugate group compared to the unconjugated oligonucleotide. There was a further increase in the duration of action for the conjugated mixed PO/PS oligonucleotide 647536 as compared to the conjugated full PS oligonucleotide 647535.

Example 58: Dose-Dependent Study of Oligonucleotides Comprising a 3'-Conjugate Group (Comparison of GalNAc$_3$-1 and GalNAc$_4$-11) Targeting SRB-1 In Vivo The oligonucleotides listed below were tested in a dose-dependent study for antisense inhibition of SRB-1 in mice. Unconjugated ISIS 440762 was included as an unconjugated standard. Each of the conjugate groups were attached at the 3' terminus of the respective oligonucleotide by a phosphodiester linked 2'-deoxyadenosine nucleoside cleavable moiety.

The structure of GalNAc$_3$-1$_a$ was shown previously in Example 9. The structure of GalNAc$_3$-11$_a$ was shown previously in Example 50.

Treatment

Six week old male Balb/c mice (Jackson Laboratory, Bar Harbor, ME) were injected subcutaneously once at the dosage shown below with ISIS 440762, 651900, 663748 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 47, treatment with antisense oligonucleotides lowered SRB-1 mRNA levels in a dose-dependent manner. The antisense oligonucleotides comprising the phosphodiester linked GalNAc$_3$-1 and GalNAc$_4$-11 conjugates at the 3' terminus (ISIS 651900 and ISIS 663748) showed substantial improvement in potency compared to the unconjugated antisense oligonucleotide (ISIS 440762). The two conjugated oligonucleotides, GalNAc$_3$-1 and GalNAc$_4$-11, were equipotent.

TABLE 47

| Modified ASO targeting SRB-1 | | | | | |
|---|---|---|---|---|---|
| ASO | Sequence (5' to 3') | Dose mg/kg | % Saline control | Unmodified SEQ ID No. | Modified SEQ ID No. |
| Saline | | | 100 | | |
| ISIS 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | 0.6<br>2<br>6 | 73.45<br>59.66<br>23.50 | 246 | 297 |
| ISIS 651900 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ko}$ **$A_{do}$'-GalNAc$_3$-1$_a$** | 0.2<br>0.6<br>2<br>6 | 62.75<br>29.14<br>8.61<br>5.62 | 247 | 303 |
| ISIS 663748 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ko}$ **$A_{do}$'-GalNAc$_4$-11$_a$** | 0.2<br>0.6<br>2<br>6 | 63.99<br>33.53<br>7.58<br>5.52 | 247 | 306 |

Capital letters indicate the nucleobase for each nucleoside and $^{m}$C indicates a 5-methyl cytosine.
Subscripts:
"e" indicates a 2'-MOE modified nucleoside;
"k" indicates a 6'-(S)-$CH_3$ bicyclic nucleoside;
"d" indicates a β-D-2'-deoxyribonucleoside;
"s" indicates a phosphorothioate internucleoside linkage (PS);
"o" indicates phosphodiester internucleoside linkage (PO); and
"o'" indicates —O—P(═O)(OH)—.
Conjugate groups are in bold.

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 48 below.

TABLE 48

| ISIS No. | Dosage mg/kg | ALT | AST | Total Bilirubin | BUN | Conjugate |
|---|---|---|---|---|---|---|
| Saline | | 30 | 76 | 0.2 | 40 | |
| 440762 | 0.60 | 32 | 70 | 0.1 | 35 | none |
| | 2 | 26 | 57 | 0.1 | 35 | |
| | 6 | 31 | 48 | 0.1 | 39 | |
| 651900 | 0.2 | 32 | 115 | 0.2 | 39 | GalNac$_3$-1 (3') |
| | 0.6 | 33 | 61 | 0.1 | 35 | |
| | 2 | 30 | 50 | 0.1 | 37 | |
| | 6 | 34 | 52 | 0.1 | 36 | |
| 663748 | 0.2 | 28 | 56 | 0.2 | 36 | GalNac$_4$-11 (3') |
| | 0.6 | 34 | 60 | 0.1 | 35 | |
| | 2 | 44 | 62 | 0.1 | 36 | |
| | 6 | 38 | 71 | 0.1 | 33 | |

Example 59: Effects of GalNAc$_3$-1 Conjugated ASOs Targeting FXI In Vivo

The oligonucleotides listed below were tested in a multiple dose study for antisense inhibition of FXI in mice. ISIS 404071 was included as an unconjugated standard. Each of the conjugate groups was attached at the 3' terminus of the respective oligonucleotide by a phosphodiester linked 2'-deoxyadenosine nucleoside cleavable moiety.

TABLE 49

| Modified ASOs targeting FXI | | | | |
|---|---|---|---|---|
| ASO | Sequence (5' to 3') | Linkages | Unmodified SEQ ID No. | Modified SEQ ID No. |
| ISIS 404071 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{e}$ | PS | 255 | 321 |
| ISIS 656172 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{eo}$**$A_{do'}$-GalNAc$_3$-1$_a$** | PS | 256 | 371 |
| ISIS 656173 | $T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{eo}$**$A_{do'}$-GalNAc$_3$-1$_a$** | PO/PS | 256 | 372 |

Capital letters indicate the nucleobase for each nucleoside and $^{m}$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(═O)(OH)—.
Conjugate groups are in bold.

The structure of GalNAc$_3$-1$_a$ was shown previously in Example 9.

Treatment

Six week old male Balb/c mice (Jackson Laboratory, Bar Harbor, ME) were injected subcutaneously twice a week for 3 weeks at the dosage shown below with ISIS 404071, 656172, 656173 or with PBS treated control. Each treatment group consisted of 4 animals. The mice were sacrificed 72 hours following the final administration to determine the liver FXI mRNA levels using real-time PCR and RIBOGREEN® RNA quantification reagent (Molecular Probes, Inc. Eugene, OR) according to standard protocols. Plasma FXI protein levels were also measured using ELISA. FXI mRNA levels were determined relative to total RNA (using RIBOGREEN®), prior to normalization to PBS-treated control. The results below are presented as the average percent of FXI mRNA levels for each treatment group. The data was normalized to PBS-treated control and is denoted as "% PBS". The ED$_{50}$s were measured using similar methods as described previously and are presented below.

TABLE 50

| Factor XI mRNA (% Saline) | | | | |
|---|---|---|---|---|
| ASO | Dose mg/kg | % Control | Conjugate | Linkages |
| Saline | | 100 | none | |
| ISIS | 3 | 92 | none | PS |
| 404071 | 10 | 40 | | |
| | 30 | 15 | | |
| ISIS | 0.7 | 74 | GalNAc$_3$-1 | PS |
| 656172 | 2 | 33 | | |
| | 6 | 9 | | |
| ISIS | 0.7 | 49 | GalNAc$_3$-1 | PO/PS |
| 656173 | 2 | 22 | | |
| | 6 | 1 | | |

As illustrated in Table 50, treatment with antisense oligonucleotides lowered FXI mRNA levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

As illustrated in Table 50a, treatment with antisense oligonucleotides lowered FXI protein levels in a dose-dependent manner. The oligonucleotides comprising a 3'-GalNAc$_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

TABLE 50a

| Factor XI protein (% Saline) | | | | |
|---|---|---|---|---|
| ASO | Dose mg/kg | Protein (% Control) | Conjugate | Linkages |
| Saline | | 100 | none | |
| ISIS 404071 | 3 | 127 | none | PS |
| | 10 | 32 | | |
| | 30 | 3 | | |
| ISIS 656172 | 0.7 | 70 | GalNAc$_3$-1 | PS |
| | 2 | 23 | | |
| | 6 | 1 | | |
| ISIS 656173 | 0.7 | 45 | GalNAc$_3$-1 | PO/PS |
| | 2 | 6 | | |
| | 6 | 0 | | |

Liver transaminase levels, alanine aminotransferase (ALT) and aspartate aminotransferase (AST), in serum were measured relative to saline injected mice using standard protocols. Total bilirubin, total albumin, CRE and BUN were also evaluated. The change in body weights was evaluated with no significant change from the saline group. ALTs, ASTs, total bilirubin and BUN values are shown in the table below.

TABLE 51

| ISIS No. | Dosage mg/kg | ALT | AST | Total Albumin | Total Bilirubin | CRE | BUN | Conjugate |
|---|---|---|---|---|---|---|---|---|
| Saline | | 71.8 | 84.0 | 3.1 | 0.2 | 0.2 | 22.9 | |
| 404071 | 3 | 152.8 | 176.0 | 3.1 | 0.3 | 0.2 | 23.0 | none |
| | 10 | 73.3 | 121.5 | 3.0 | 0.2 | 0.2 | 21.4 | |
| | 30 | 82.5 | 92.3 | 3.0 | 0.2 | 0.2 | 23.0 | |
| 656172 | 0.7 | 62.5 | 111.5 | 3.1 | 0.2 | 0.2 | 23.8 | GalNac$_3$-1 (3') |
| | 2 | 33.0 | 51.8 | 2.9 | 0.2 | 0.2 | 22.0 | |
| | 6 | 65.0 | 71.5 | 3.2 | 0.2 | 0.2 | 23.9 | |
| 656173 | 0.7 | 54.8 | 90.5 | 3.0 | 0.2 | 0.2 | 24.9 | GalNac$_3$-1 (3') |
| | 2 | 85.8 | 71.5 | 3.2 | 0.2 | 0.2 | 21.0 | |
| | 6 | 114.0 | 101.8 | 3.3 | 0.2 | 0.2 | 22.7 | |

Example 60: Effects of Conjugated ASOs Targeting SRB-1 In Vitro

The oligonucleotides listed below were tested in a multiple dose study for antisense inhibition of SRB-1 in primary mouse hepatocytes. ISIS 353382 was included as an unconjugated standard. Each of the conjugate groups were attached at the 3' or 5' terminus of the respective oligonucleotide by a phosphodiester linked 2'-deoxyadenosine nucleoside cleavable moiety.

TABLE 52

| Modified ASO targeting SRB-1 | | | | | |
|---|---|---|---|---|---|
| ASO | Sequence (5' to 3') | Motif | Conjugate | Unmodified SEQ ID No. | Modified SEQ ID No. |
| ISIS 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | none | 252 | 318 |
| ISIS 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A}_{do}$**'-GalNAc$_3$-1$_a$** | 5/10/5 | **GalNAc$_3$-1** | 253 | 369 |
| ISIS 655862 | $G_{eo}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}\mathbf{A}_{do}$**'-GalNAc$_3$-1$_a$** | 5/10/5 | **GalNAc$_3$-1** | 253 | 370 |
| ISIS 661161 | **GalNAc$_3$-3$_a$-$_o$'** $\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-3** | 254 | 376 |

TABLE 52-continued

| Modified ASO targeting SRB-1 | | | | | |
|---|---|---|---|---|---|
| ASO | Sequence (5' to 3') | Motif | Conjugate | Unmodified SEQ ID No. | Modified SEQ ID No. |
| ISIS 665001 | **GalNAc$_3$-8$_a$-$_o$'** $\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}$ | 5/10/5 | **GalNAc$_3$-8** | 254 | 384 |

TABLE 52-continued

| Modified ASO targeting SRB-1 | | | | | |
|---|---|---|---|---|---|
| ASO | Sequence (5' to 3') | Motif | Conjugate | Unmodified SEQ ID No. | Modified SEQ ID No. |
| | $G_{ds}A_{ds}{}^{m}C_{ds}T_{ds}$ $T_{es}{}^{m}C_{es}{}^{m}C_{es}$ $T_{es}T_{e}$ | | | | |
| ISIS 664078 | $G_{es}{}^{m}C_{es}T_{es}T_{es}$ ${}^{m}C_{es}A_{ds}G_{ds}T_{ds}$ ${}^{m}C_{ds}A_{ds}T_{ds}G_{ds}$ $A_{ds}{}^{m}C_{ds}T_{ds}T_{es}$ ${}^{m}C_{es}{}^{m}C_{es}T_{es}$ $T_{eo}$**$A_{do}$'-GalNAc$_3$-9$_a$** | 5/10/5 | **GalNAc$_3$-9** | 253 | 382 |
| ISIS 666961 | **GalNAc$_3$-6$_a$-$_o$'** **$A_{do}$**$G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | 5/10/5 | **GalNAc$_3$-6** | 254 | 391 |
| ISIS 664507 | **GalNAc$_3$-2$_a$-$_o$'** **$A_{do}$**$G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | 5/10/5 | **GalNAc$_3$-2** | 254 | 383 |
| ISIS 666881 | **GalNAc$_3$-10$_a$-$_o$'** **$A_{do}$**$G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | 5/10/5 | **GalNAc$_3$-10** | 254 | 386 |
| ISIS 666224 | **GalNAc$_3$-5$_a$-$_o$'** **$A_{do}$**$G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | 5/10/5 | **GalNAc$_3$-5** | 254 | 385 |
| ISIS 666981 | **GalNAc$_3$-7$_a$-$_o$'** **$A_{do}$**$G_{es}{}^{m}C_{es}T_{es}$ $T_{es}{}^{m}C_{es}A_{ds}G_{ds}$ $T_{ds}{}^{m}C_{ds}A_{ds}T_{ds}$ | 5/10/5 | **GalNAc$_3$-7** | 254 | 392 |

TABLE 52-continued

| Modified ASO targeting SRB-1 | | | | | |
|---|---|---|---|---|---|
| ASO | Sequence (5' to 3') | Motif | Conjugate | Unmodified SEQ ID No. | Modified SEQ ID No. |
| | $G_{ds}A_{ds}{}^{m}C_{ds}T_{ds}$ $T_{es}{}^{m}C_{es}{}^{m}C_{es}$ $T_{es}T_{e}$ | | | | |

Capital letters indicate the nucleobase for each nucleoside and ${}^{m}$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(═O)(OH)—.
Conjugate groups are in bold.

The structure of GalNAc$_3$-1$_a$ was shown previously in Example 9. The structure of GalNAc$_3$-3a was shown previously in Example 39. The structure of GalNAc$_3$-8a was shown previously in Example 47. The structure of GalNAc$_3$-9a was shown previously in Example 52. The structure of GalNAc$_3$-6a was shown previously in Example 51. The structure of GalNAc$_3$-2a was shown previously in Example 37. The structure of GalNAc$_3$-10a was shown previously in Example 46. The structure of GalNAc$_3$-5a was shown previously in Example 49. The structure of GalNAc$_3$-7a was shown previously in Example 48.

Treatment

The oligonucleotides listed above were tested in vitro in primary mouse hepatocyte cells plated at a density of 25,000 cells per well and treated with 0.03, 0.08, 0.24, 0.74, 2.22, 6.67 or 20 nM modified oligonucleotide. After a treatment period of approximately 16 hours, RNA was isolated from the cells and mRNA levels were measured by quantitative real-time PCR and the SRB-1 mRNA levels were adjusted according to total RNA content, as measured by RIBOGREEN®.

The $IC_{50}$ was calculated using standard methods and the results are presented in Table 53. The results show that, under free uptake conditions in which no reagents or electroporation techniques are used to artificially promote entry of the oligonucleotides into cells, the oligonucleotides comprising a GalNAc conjugate were significantly more potent in hepatocytes than the parent oligonucleotide (ISIS 353382) that does not comprise a GalNAc conjugate.

TABLE 53

| ASO | $IC_{50}$ (nM) | Internucleoside linkages | Conjugate | SEQ ID No. |
|---|---|---|---|---|
| ISIS 353382 | 190[a] | PS | none | 829 |
| ISIS 655861 | 11[a] | PS | GalNAc$_3$-1 | 830 |
| ISIS 655862 | 3 | PO/PS | GalNAc$_3$-1 | 830 |
| ISIS 661161 | 15[a] | PS | GalNAc$_3$-3 | 831 |
| ISIS 665001 | 20 | PS | GalNAc$_3$-8 | 831 |
| ISIS 664078 | 55 | PS | GalNAc$_3$-9 | 830 |
| ISIS 666961 | 22[a] | PS | GalNAc$_3$-6 | 831 |
| ISIS 664507 | 30 | PS | GalNAc$_3$-2 | 831 |
| ISIS 666881 | 30 | PS | GalNAc$_3$-10 | 831 |
| ISIS 666224 | 30[a] | PS | GalNAc$_3$-5 | 831 |
| ISIS 666981 | 40 | PS | GalNAc$_3$-7 | 831 |

[a]Average of multiple runs.

Example 61: Preparation of Oligomeric Compound 175 Comprising GalNAc$_3$-12
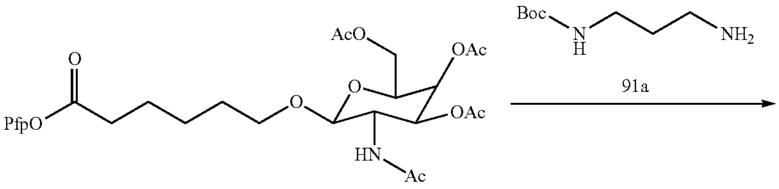
166
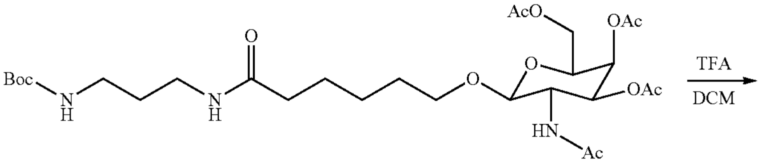
167
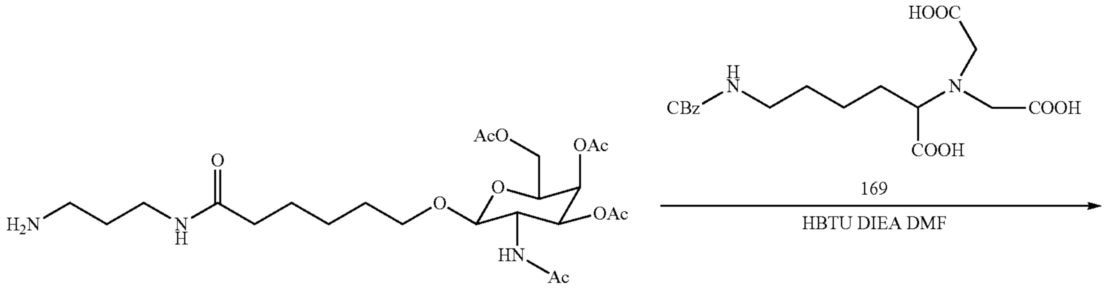
168
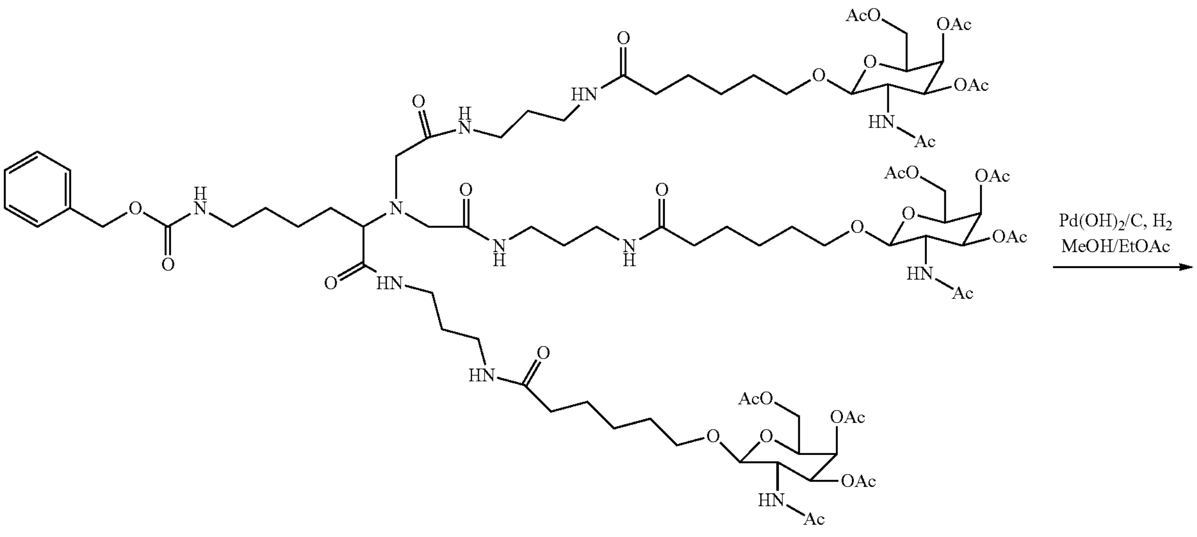
170

-continued
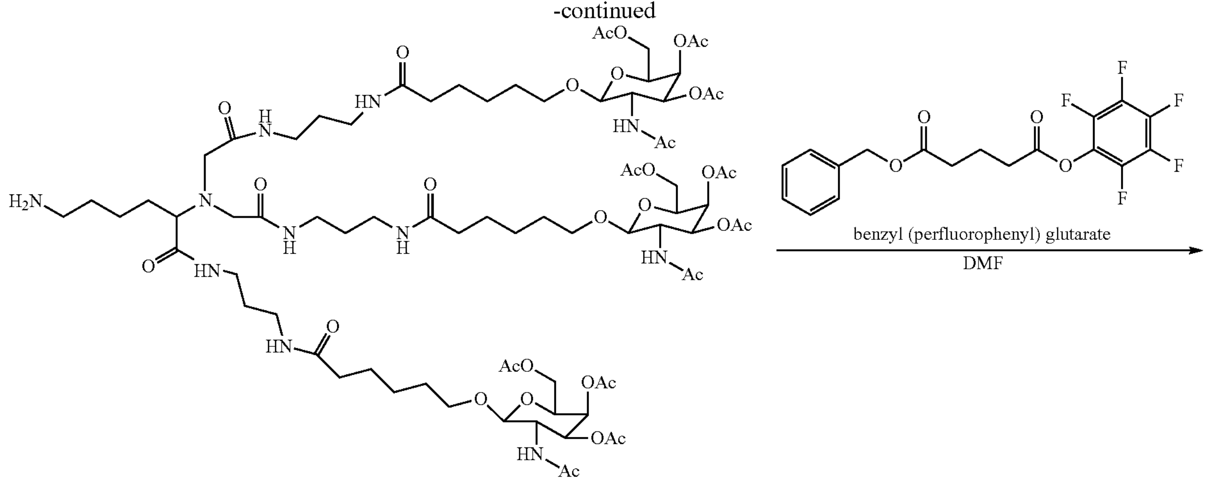
171
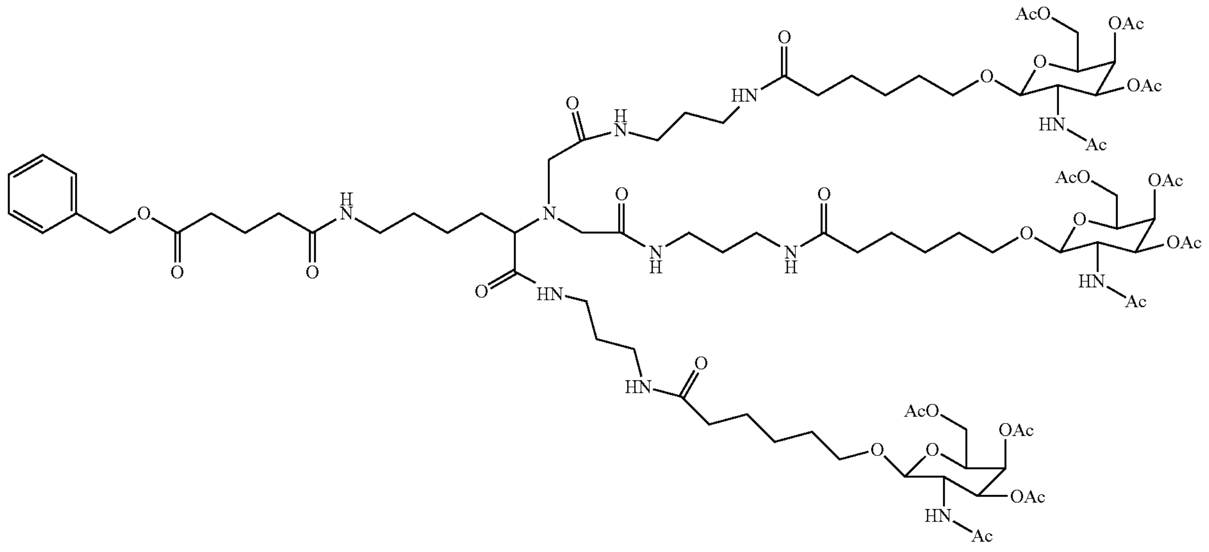
172
172 $\xrightarrow[\text{MeOH/EtOAc}]{Pd(OH)_2/C,\ H_2}$
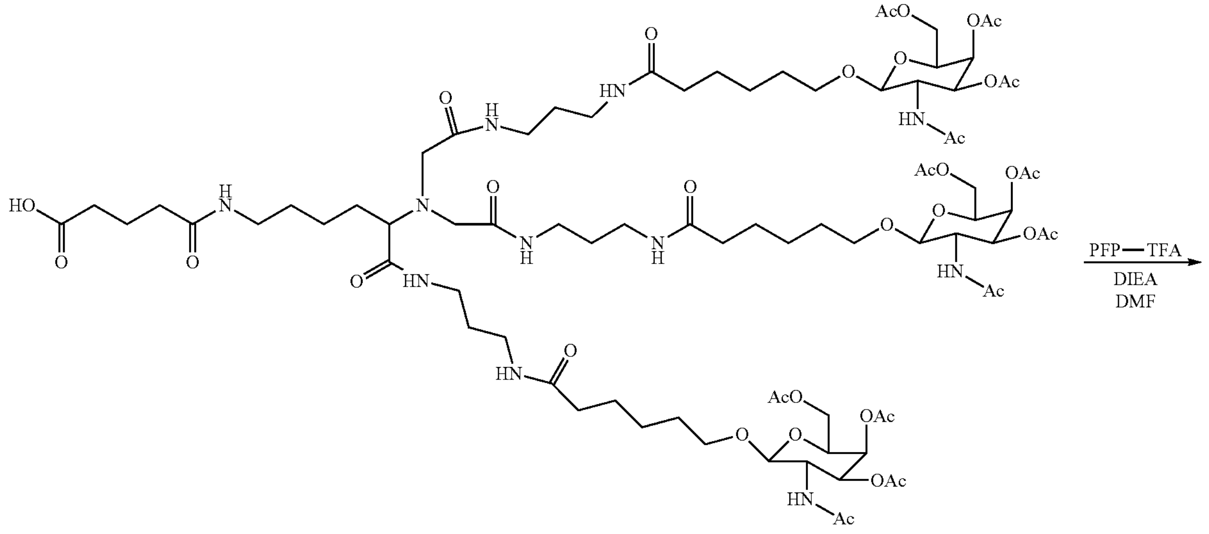
173

-continued

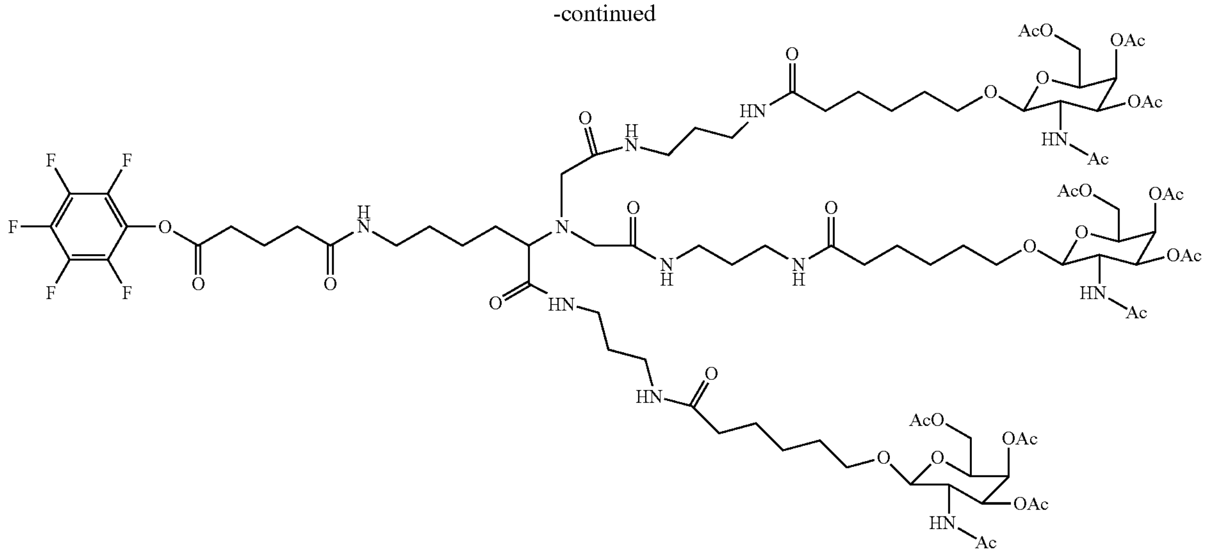

174

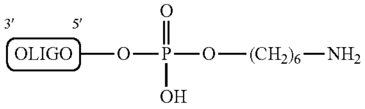

83e

174 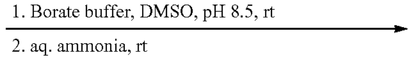

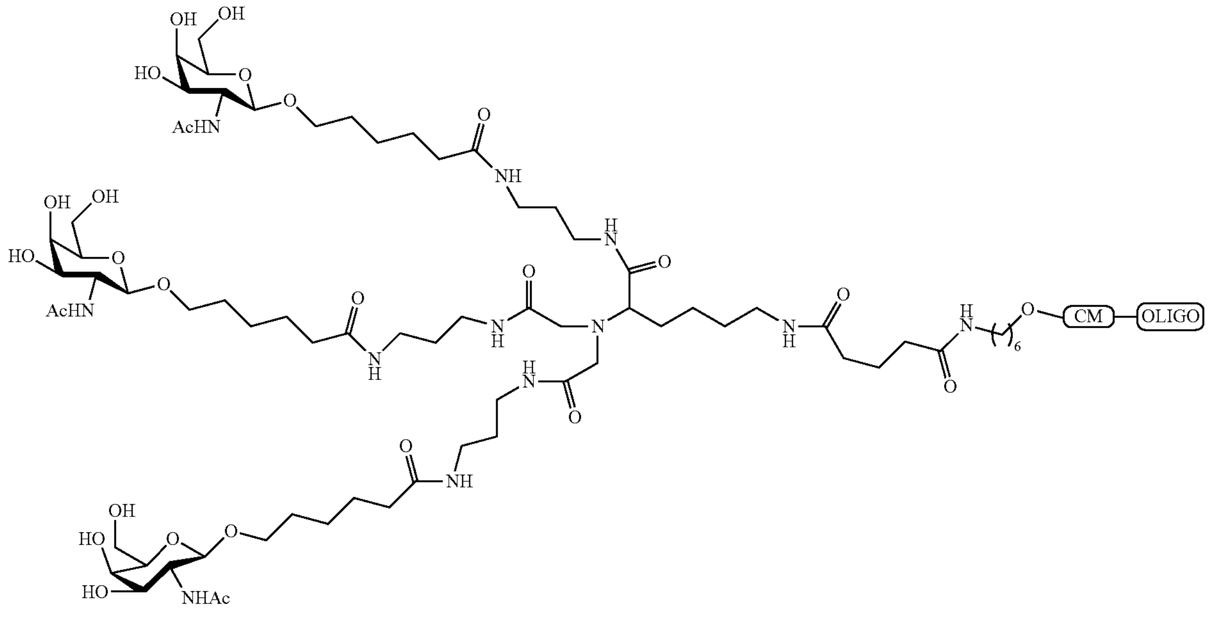

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Oligomeric compound 175, comprising a GalNAc$_3$-12 conjugate group, was prepared from compound 174 using the general procedures illustrated in Example 46. The GalNAc$_3$ cluster portion of the conjugate group GalNAc$_3$-12 (GalNAc$_3$-12$_a$) can be combined with any cleavable moiety to provide a variety of conjugate groups. In a certain embodiments, the cleavable moiety is —P(═O)(OH)-A$_d$-P(═O)(OH)—. The structure of GalNAc$_3$-12 (GalNAc$_3$-12$_a$-CM-) is shown below:

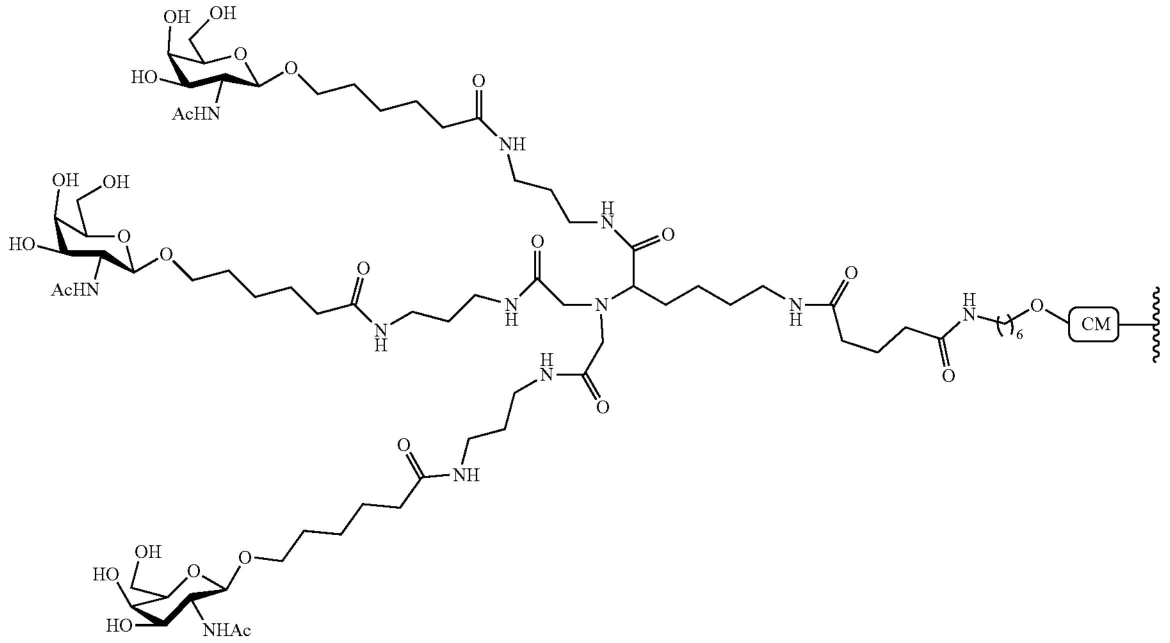
Example 62: Preparation of Oligomeric Compound 180 Comprising $GalNAc_3$-13
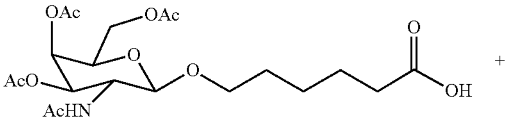
176
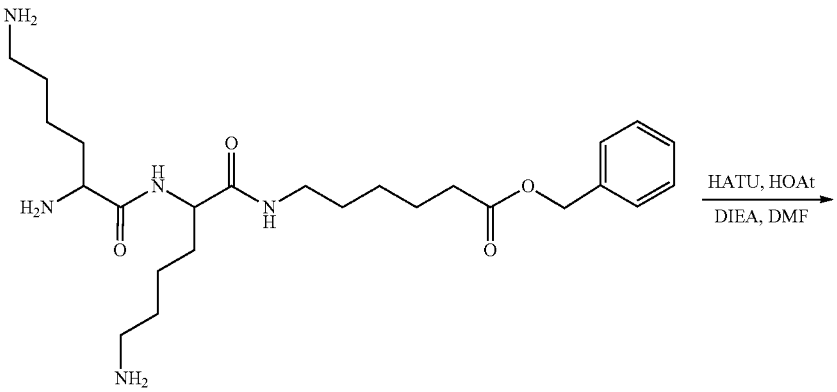
128

-continued
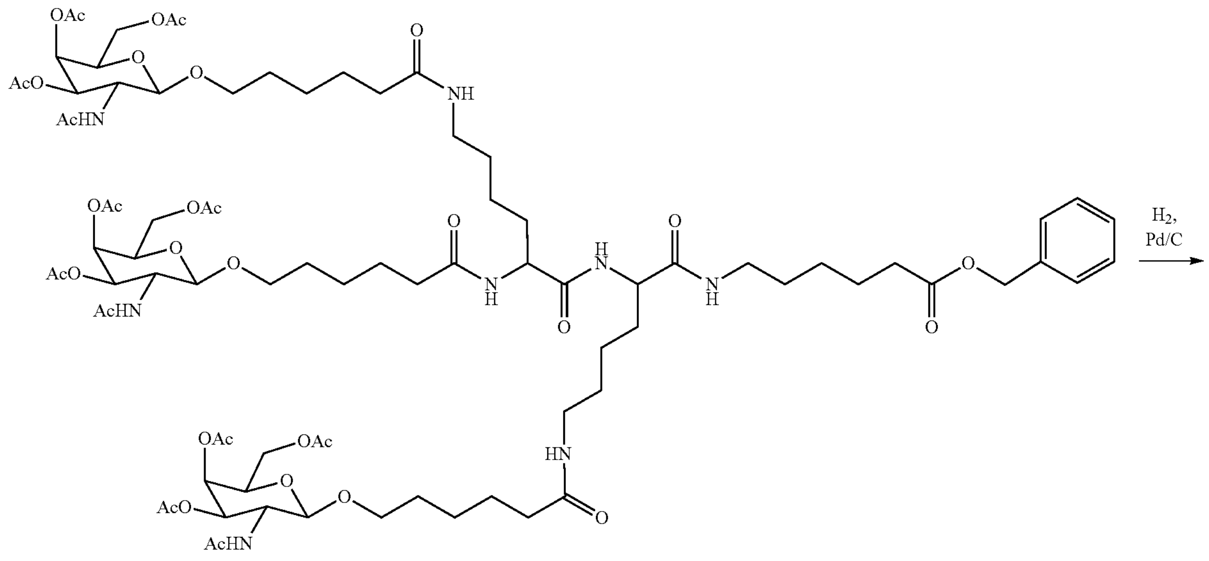
177
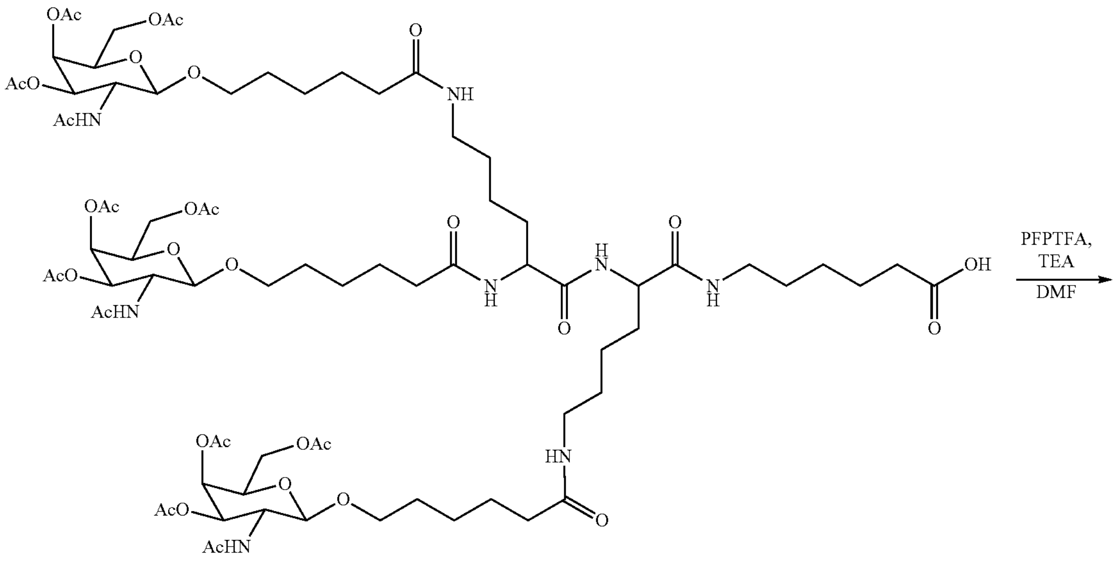
178
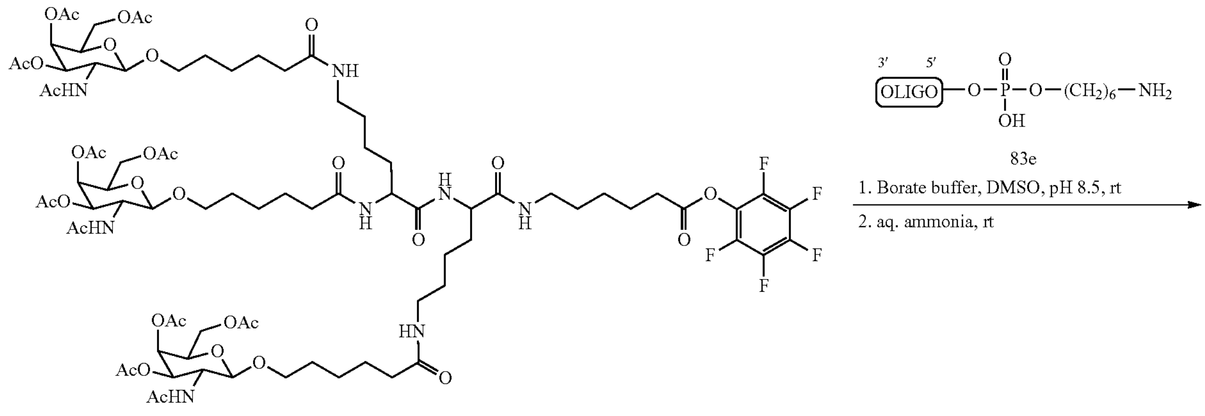
179

-continued

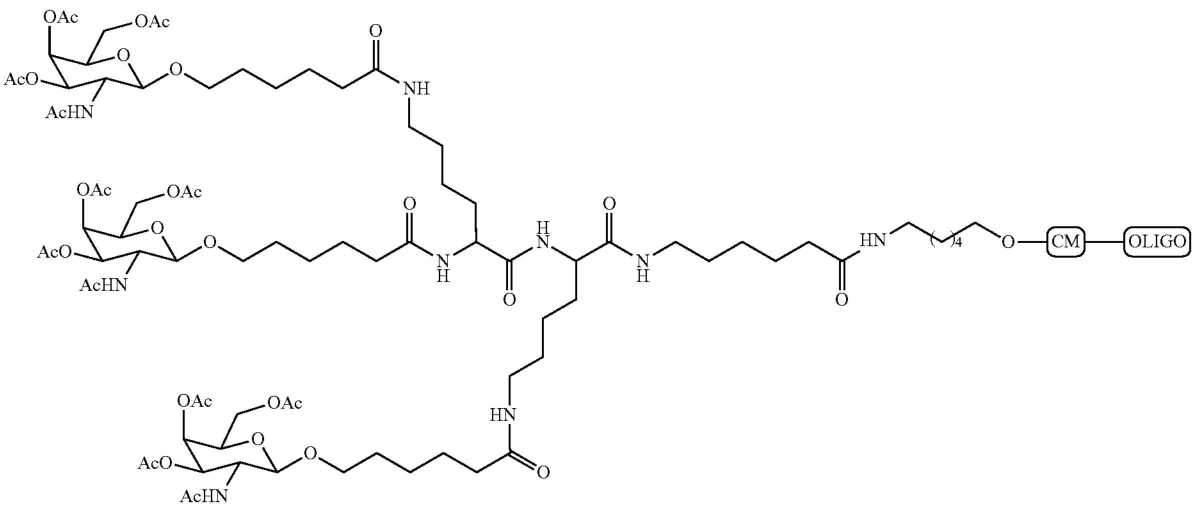

180

Compound 176 was prepared using the general procedure shown in Example 2. Oligomeric compound 180, comprising a GalNAc$_3$-13 conjugate group, was prepared from compound 177 using the general procedures illustrated in Example 49. The GalNAc$_3$ cluster portion of the conjugate group GalNAc$_3$-13 (GalNAc$_3$-13$_a$) can be combined with any cleavable moiety to provide a variety of conjugate groups. In a certain embodiments, the cleavable moiety is —P(=O)(OH)-A$_d$-P(=O)(OH)—. The structure of GalNAc$_3$-13 (GalNAc$_3$-13$_a$-CM-) is shown below:

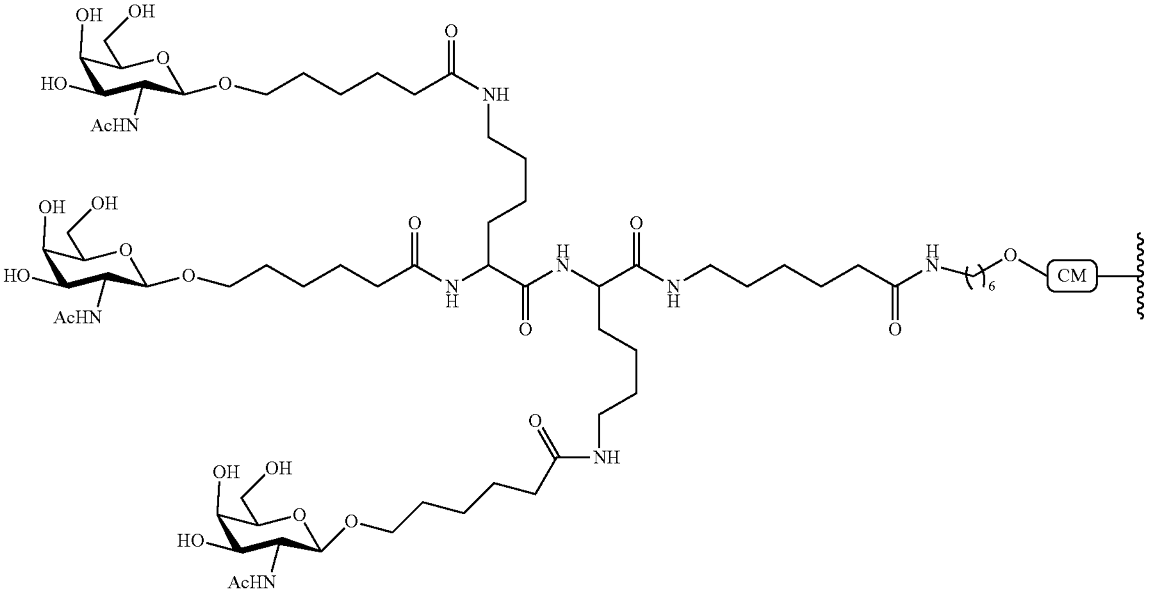

Example 63: Preparation of Oligomeric Compound 188 Comprising GalNAc$_3$-14
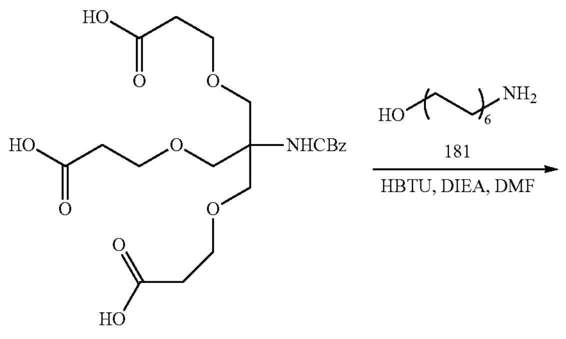
13
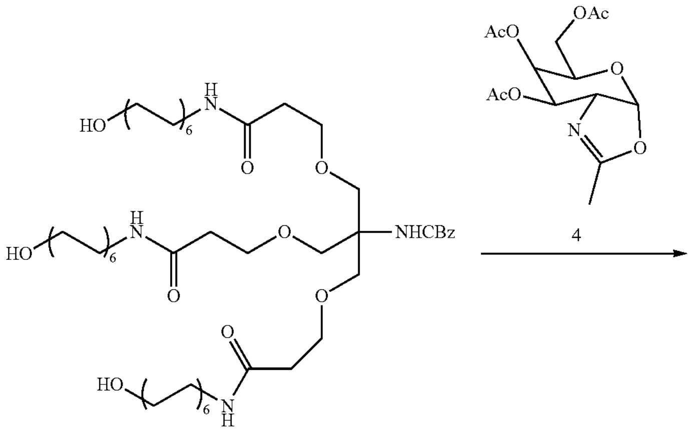
182
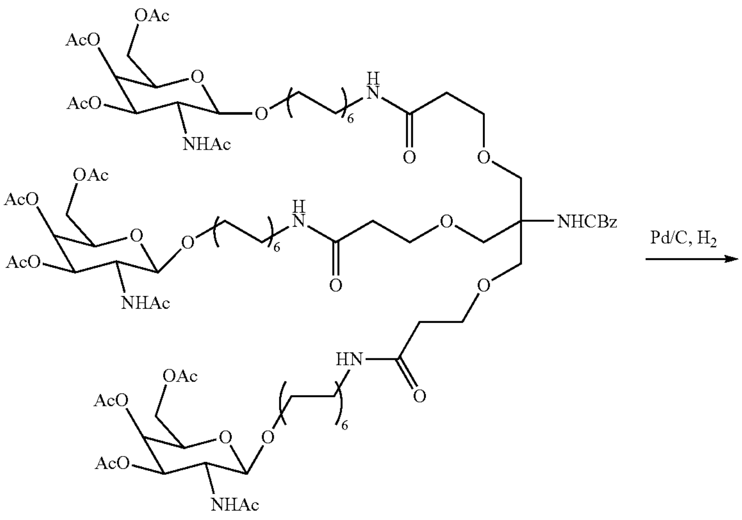
183

-continued
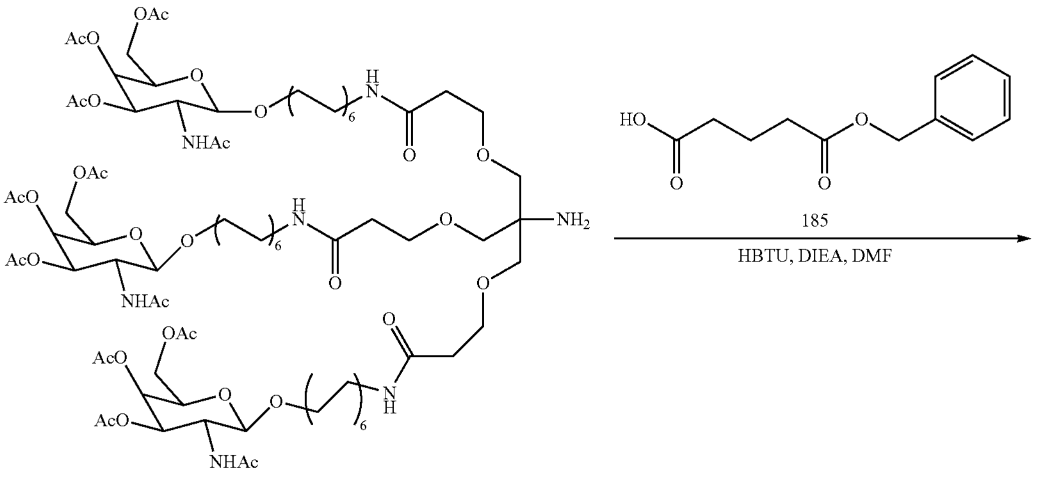
184
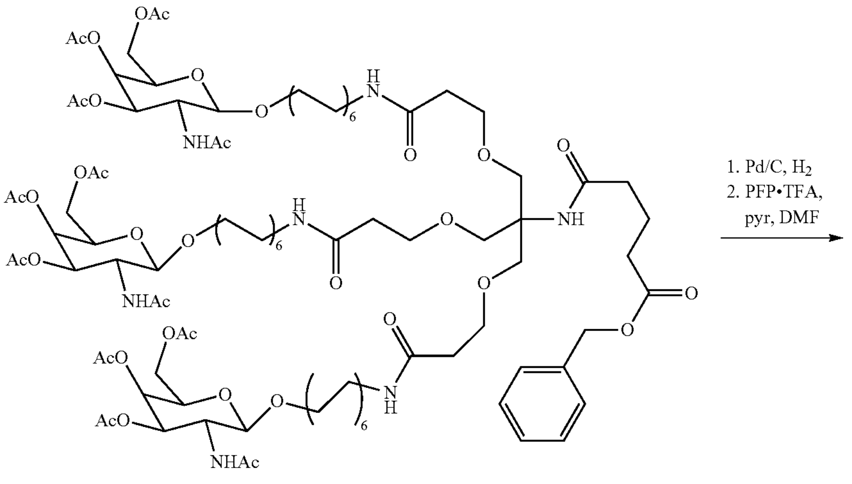
186
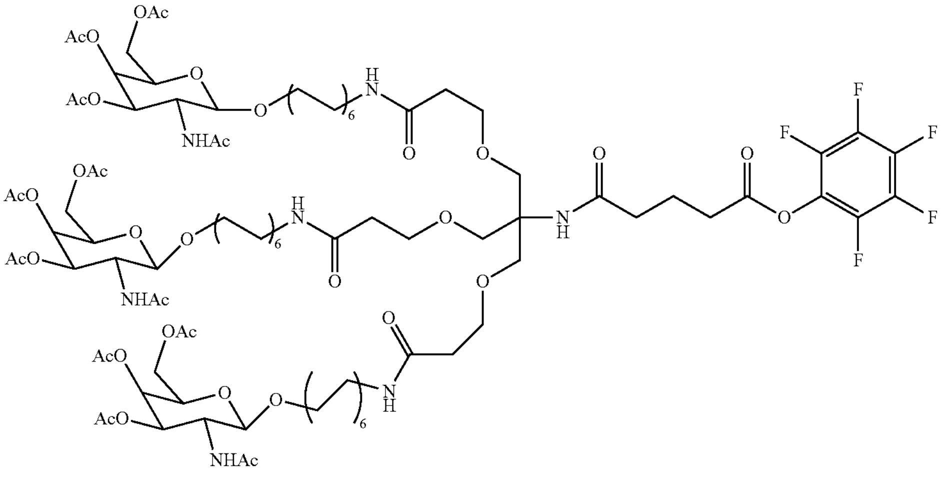
187

-continued

187 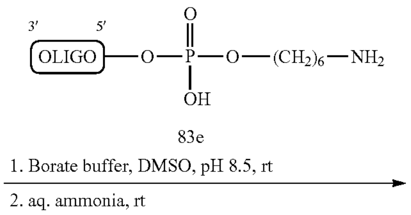

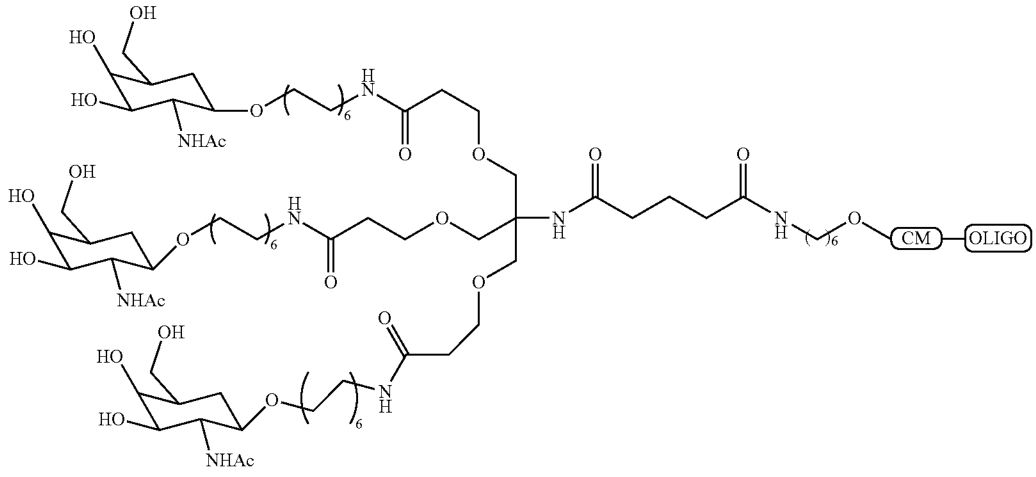

188

Compounds 181 and 185 are commercially available. Oligomeric compound 188, comprising a GalNAc$_3$-14 conjugate group, was prepared from compound 187 using the general procedures illustrated in Example 46. The GalNAc$_3$ cluster portion of the conjugate group GalNAc$_3$-14 (GalNAc$_3$-14$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-14 (GalNAc$_3$-14$_a$-CM-) is shown below:

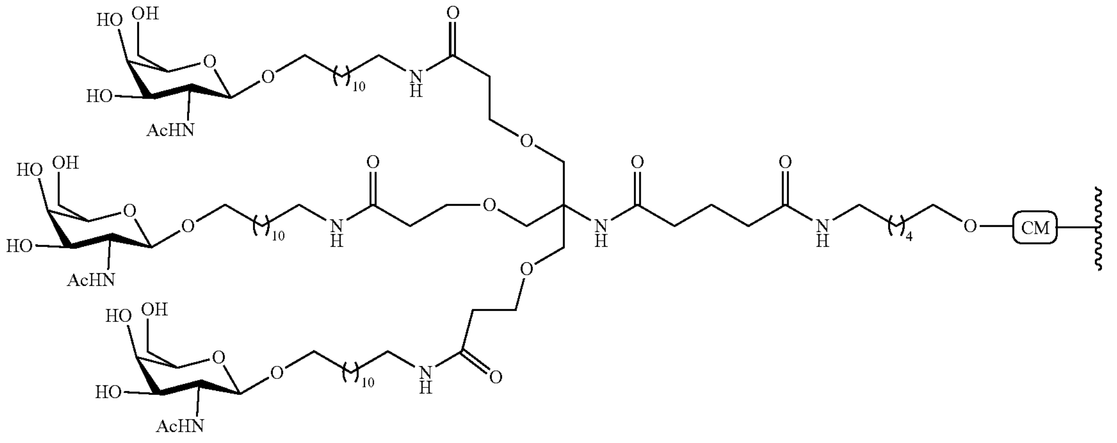

Example 64: Preparation of Oligomeric Compound 197 Comprising GalNAc$_3$-15
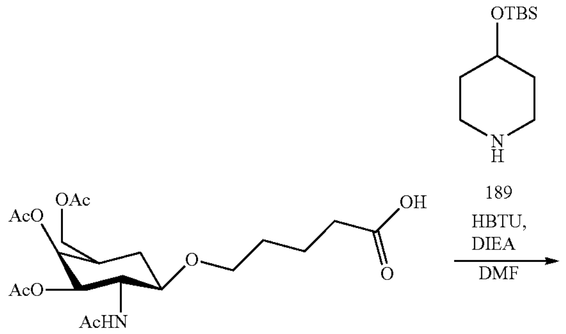
7
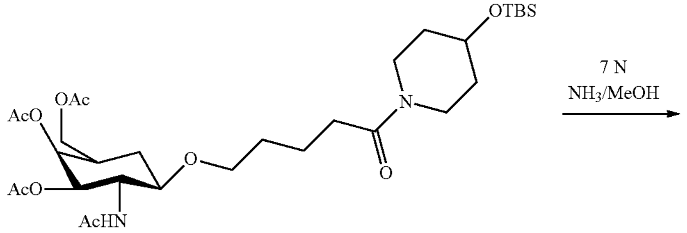
190
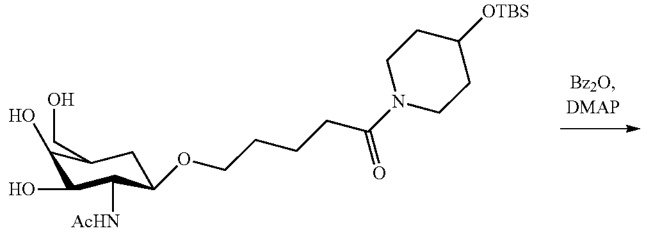
191
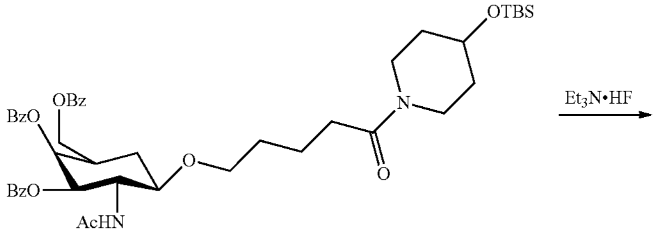
192
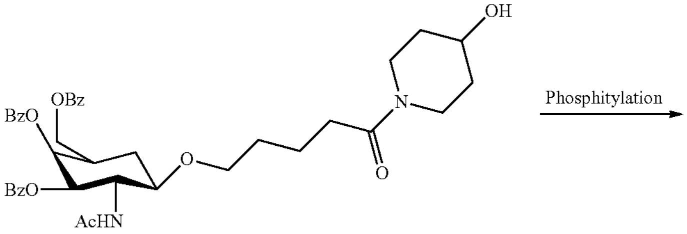
193

-continued

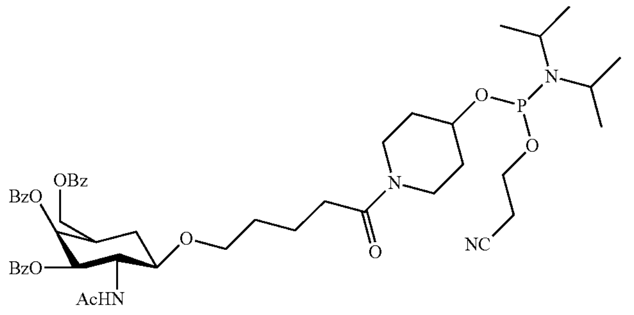

194

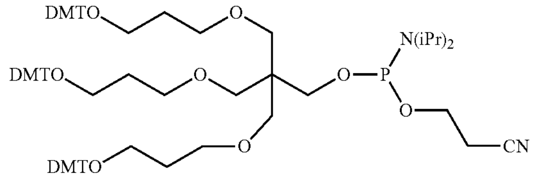

195

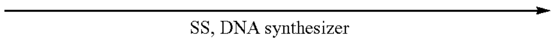

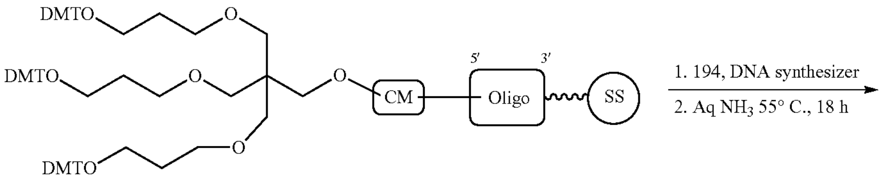

196

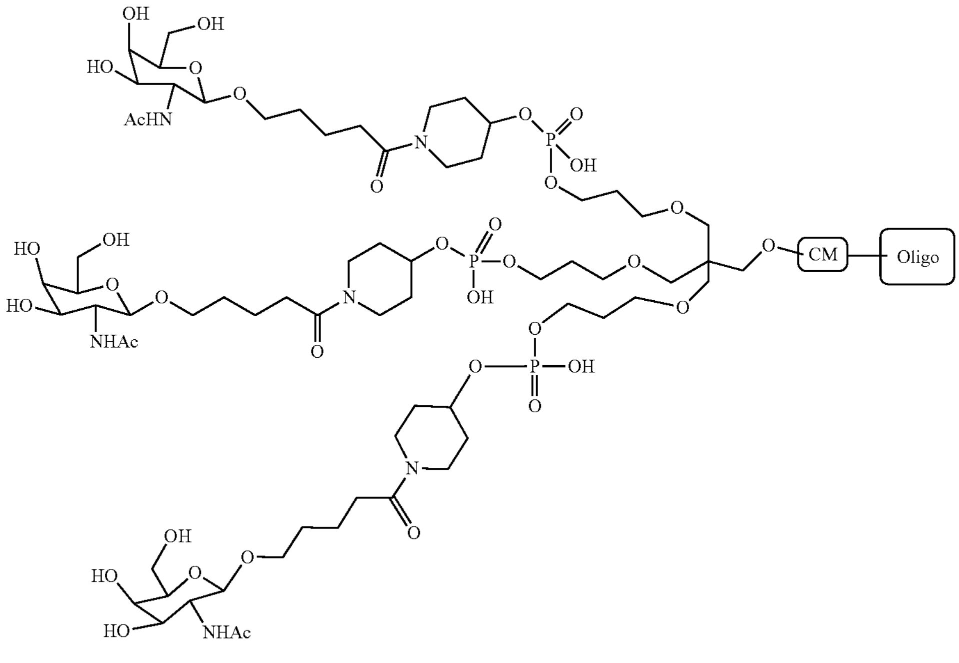

197

Compound 189 is commercially available. Compound 195 was prepared using the general procedure shown in Example 31. Oligomeric compound 197, comprising a GalNAc$_3$-15 conjugate group, was prepared from compounds 194 and 195 using standard oligonucleotide synthesis procedures. The GalNAc$_3$ cluster portion of the conjugate group GalNAc$_3$-15 (GalNAc$_3$-15$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-15 (GalNAc$_3$-15$_a$-CM-) is shown below:

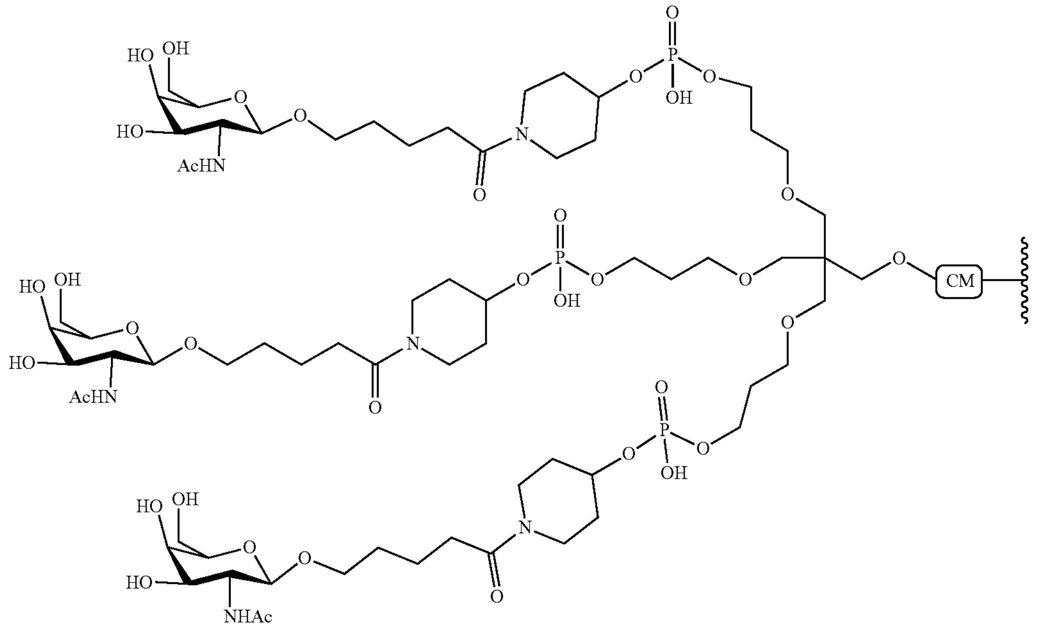

Example 65: Dose-Dependent Study of Oligonucleotides Comprising a 5'-Conjugate Group (Comparison of $GalNAc_3$-3, 12, 13, 14, and 15) Targeting SRB-1 In Vivo The oligonucleotides listed below were tested in a dose-dependent study for antisense inhibition of SRB-1 in mice. Unconjugated ISIS 353382 was included as a standard. Each of the $GalNAc_3$ conjugate groups was attached at the 5' terminus of the respective oligonucleotide by a phosphodiester linked 2'-deoxyadenosine nucleoside (cleavable moiety).

TABLE 54

Modified ASOs targeting SRB-1

| ISIS No. | Sequences (5' to 3') | Conjugate | Unmodified SEQ ID No. | Modified SEQ ID No. |
|---|---|---|---|---|
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | none | 252 | 318 |
| 661161 | **$GalNAc_3$-$3_a$**-$_{o'}$ $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3 | 254 | 376 |
| 671144 | **$GalNAc_3$-$12_a$**-$_{o'}$ $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-12 | 254 | 397 |

TABLE 54-continued

| Modified ASOs targeting SRB-1 | | | | |
|---|---|---|---|---|
| ISIS No. | Sequences (5' to 3') | Conjugate | Unmodified SEQ ID No. | Modified SEQ ID No. |
| 670061 | **$GalNAc_3$-13**$_{a-o'}$ $A_{do}G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | $GalNAc_3$-13 | 254 | 393 |
| 671261 | **$GalNAc_3$-14**$_{a-o'}$ $A_{do}G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | $GalNAc_3$-14 | 254 | 399 |
| 671262 | **$GalNAc_3$-15**$_{a-o'}$ $A_{do}G_{es}{}^{m}C_{es}T_{es}$ $T_{es}{}^{m}C_{es}A_{ds}G_{ds}$ $T_{ds}{}^{m}C_{ds}A_{ds}T_{ds}$ $G_{ds}A_{ds}{}^{m}C_{ds}T_{ds}$ $T_{es}{}^{m}C_{es}{}^{m}C_{es}$ $T_{es}T_{e}$ | $GalNAc_3$-15 | 254 | 400 |

Capital letters indicate the nucleobase for each nucleoside and $^{m}C$ indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(═O)(OH)—.
Conjugate groups are in bold.

The structure of $GalNAc_3$-$3_a$ was shown previously in Example 39. The structure of $GalNAc_3$-12a was shown previously in Example 61. The structure of $GalNAc_3$-13a was shown previously in Example 62. The structure of $GalNAc_3$-14a was shown previously in Example 63. The structure of $GalNAc_3$-15a was shown previously in Example 64.

Treatment

Six to eight week old C57bl6 mice (Jackson Laboratory, Bar Harbor, ME) were injected subcutaneously once or twice at the dosage shown below with ISIS 353382, 661161, 671144, 670061, 671261, 671262, or with saline. Mice that were dosed twice received the second dose three days after the first dose. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 55, treatment with antisense oligonucleotides lowered SRB-1 mRNA levels in a dose-dependent manner. No significant differences in target knockdown were observed between animals that received a single dose and animals that received two doses (see ISIS 353382 dosages 30 and 2×15 mg/kg; and ISIS 661161 dosages 5 and 2×2.5 mg/kg). The antisense oligonucleotides comprising the phosphodiester linked $GalNAc_3$-3, 12, 13, 14, and 15 conjugates showed substantial improvement in potency compared to the unconjugated antisense oligonucleotide (ISIS 335382).

TABLE 55

| SRB-1 mRNA (% Saline) | | | | |
|---|---|---|---|---|
| ISIS No. | Dosage (mg/kg) | SRB-1 mRNA (% Saline) | $ED_{50}$ (mg/kg) | Conjugate |
| Saline | n/a | 100.0 | n/a | n/a |
| 353382 | 3 | 85.0 | 22.4 | none |
| | 10 | 69.2 | | |
| | 30 | 34.2 | | |
| | 2 × 15 | 36.0 | | |
| 661161 | 0.5 | 87.4 | 2.2 | $GalNAc_3$-3 |
| | 1.5 | 59.0 | | |
| | 5 | 25.6 | | |
| | 2 × 2.5 | 27.5 | | |
| | 15 | 17.4 | | |
| 671144 | 0.5 | 101.2 | 3.4 | $GalNAc_3$-12 |
| | 1.5 | 76.1 | | |
| | 5 | 32.0 | | |
| | 15 | 17.6 | | |
| 670061 | 0.5 | 94.8 | 2.1 | $GalNAc_3$-13 |
| | 1.5 | 57.8 | | |
| | 5 | 20.7 | | |
| | 15 | 13.3 | | |
| 671261 | 0.5 | 110.7 | 4.1 | $GalNAc_3$-14 |
| | 1.5 | 81.9 | | |
| | 5 | 39.8 | | |
| | 15 | 14.1 | | |
| 671262 | 0.5 | 109.4 | 9.8 | $GalNAc_3$-15 |
| | 1.5 | 99.5 | | |
| | 5 | 69.2 | | |
| | 15 | 36.1 | | |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 56

| ISIS No. | Dosage (mg/kg) | ALT (U/L) | AST (U/L) | Total Bilirubin (mg/dL) | BUN (mg/dL) | Conjugate |
|---|---|---|---|---|---|---|
| Saline | n/a | 28 | 60 | 0.1 | 39 | n/a |
| 353382 | 3 | 30 | 77 | 0.2 | 36 | none |
| | 10 | 25 | 78 | 0.2 | 36 | |
| | 30 | 28 | 62 | 0.2 | 35 | |
| | 2 × 15 | 22 | 59 | 0.2 | 33 | |
| 661161 | 0.5 | 39 | 72 | 0.2 | 34 | GalNAc$_3$-3 |
| | 1.5 | 26 | 50 | 0.2 | 33 | |
| | 5 | 41 | 80 | 0.2 | 32 | |
| | 2 × 2.5 | 24 | 72 | 0.2 | 28 | |
| | 15 | 32 | 69 | 0.2 | 36 | |
| 671144 | 0.5 | 25 | 39 | 0.2 | 34 | GalNAc$_3$-12 |
| | 1.5 | 26 | 55 | 0.2 | 28 | |
| | 5 | 48 | 82 | 0.2 | 34 | |
| | 15 | 23 | 46 | 0.2 | 32 | |

TABLE 56-continued

| ISIS No. | Dosage (mg/kg) | ALT (U/L) | AST (U/L) | Total Bilirubin (mg/dL) | BUN (mg/dL) | Conjugate |
|---|---|---|---|---|---|---|
| 670061 | 0.5 | 27 | 53 | 0.2 | 33 | GalNAc$_3$-13 |
| | 1.5 | 24 | 45 | 0.2 | 35 | |
| | 5 | 23 | 58 | 0.1 | 34 | |
| | 15 | 24 | 72 | 0.1 | 31 | |
| 671261 | 0.5 | 69 | 99 | 0.1 | 33 | GalNAc$_3$-14 |
| | 1.5 | 34 | 62 | 0.1 | 33 | |
| | 5 | 43 | 73 | 0.1 | 32 | |
| | 15 | 32 | 53 | 0.2 | 30 | |
| 671262 | 0.5 | 24 | 51 | 0.2 | 29 | GalNAc$_3$-15 |
| | 1.5 | 32 | 62 | 0.1 | 31 | |
| | 5 | 30 | 76 | 0.2 | 32 | |
| | 15 | 31 | 64 | 0.1 | 32 | |

Example 66: Effect of Various Cleavable Moieties on Antisense Inhibition In Vivo by Oligonucleotides Targeting SRB-1 Comprising a 5'-GalNAc$_3$ Cluster The oligonucleotides listed below were tested in a dose-dependent study for antisense inhibition of SRB-1 in mice. Each of the GalNAc$_3$ conjugate groups was attached at the 5' terminus of the respective oligonucleotide by a phosphodiester linked nucleoside (cleavable moiety (CM)).

TABLE 57

Modified ASOs targeting SRB-1

| ISIS No. | Sequences (5' to 3') | GalNAc$_3$ Cluster | CM | Unmodified SEQ ID No. | Modified SEQ ID No. |
|---|---|---|---|---|---|
| 661161 | **GalNAc$_3$-3**$_{a}$-$_{o}$' $\mathbf{A}_{do}G_{es}{}^{m}C_{es}T_{es}T_{es}$ $^{m}C_{es}A_{ds}G_{ds}T_{ds}$ $^{m}c_{ds}A_{ds}T_{ds}G_{ds}$ $A_{ds}{}^{m}C_{ds}T_{ds}T_{es}$ $^{m}C_{es}{}^{m}C_{es}T_{es}T_{e}$ | GalNAc$_3$-3a | $A_d$ | 254 | 376 |
| 670699 | **GalNAc$_3$-3**$_{a}$-$_{o}$' $\mathbf{T}_{do}G_{es}{}^{m}C_{eo}T_{eo}T_{eo}$ $^{m}C_{eo}A_{ds}G_{ds}T_{ds}$ $^{m}c_{ds}A_{ds}T_{ds}G_{ds}$ $A_{ds}{}^{m}C_{ds}T_{ds}T_{eo}$ $^{m}C_{eo}{}^{m}C_{es}T_{es}T_{e}$ | GalNAc$_3$-3a | $T_d$ | 257 | 394 |
| 670700 | **GalNAc$_3$-3**$_{a}$-$_{o}$' $\mathbf{A}_{eo}G_{es}{}^{m}C_{eo}T_{eo}T_{eo}$ $^{m}C_{eo}A_{ds}G_{ds}T_{ds}$ $^{m}c_{ds}A_{ds}T_{ds}G_{ds}$ $A_{ds}{}^{m}C_{ds}T_{ds}T_{eo}$ $^{m}C_{eo}{}^{m}C_{es}T_{es}T_{e}$ | GalNAc$_3$-3a | $A_e$ | 254 | 395 |
| 670701 | **GalNAc$_3$-3**$_{a}$-$_{o}$' $\mathbf{T}_{eo}G_{es}{}^{m}C_{eo}T_{eo}T_{eo}$ $^{m}C_{eo}A_{ds}G_{ds}T_{ds}$ $^{m}C_{ds}A_{ds}T_{ds}G_{ds}$ $A_{ds}{}^{m}C_{ds}T_{ds}T_{eo}$ $^{m}C_{eo}{}^{m}C_{es}T_{es}T_{e}$ | GalNAc$_3$-3a | $T_e$ | 257 | 396 |

TABLE 57-continued

Modified ASOs targeting SRB-1

| ISIS No. | Sequences (5' to 3') | GalNAc3 Cluster | CM | Unmodified SEQ ID No. | Modified SEQ ID No. |
|---|---|---|---|---|---|
| 671165 | **GalNAc$_3$-13$_a$-$_{o'}$** $A_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | GalNAc$_3$-13a | $A_d$ | 254 | 398 |

Capital letters indicate the nucleobase for each nucleoside and $^{m}$C indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO); and
"o'" indicates —O—P(=O)(OH)—.
Conjugate groups are in bold.

The structure of GalNAc$_3$-3$_a$ was shown previously in Example 39. The structure of GalNAc$_3$-13a was shown previously in Example 62.

Treatment

Six to eight week old C57bl6 mice (Jackson Laboratory, Bar Harbor, ME) were injected subcutaneously once at the dosage shown below with ISIS 661161, 670699, 670700, 670701, 671165, or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 58, treatment with antisense oligonucleotides lowered SRB-1 mRNA levels in a dose-dependent manner. The antisense oligonucleotides comprising various cleavable moieties all showed similar potencies.

TABLE 58

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 661161 | 0.5 | 87.8 | GalNAc$_3$-3a | $A_d$ |
| | 1.5 | 61.3 | | |
| | 5 | 33.8 | | |
| | 15 | 14.0 | | |
| 670699 | 0.5 | 89.4 | GalNAc$_3$-3a | $T_d$ |
| | 1.5 | 59.4 | | |
| | 5 | 31.3 | | |
| | 15 | 17.1 | | |
| 670700 | 0.5 | 79.0 | GalNAc$_3$-3a | $A_e$ |
| | 1.5 | 63.3 | | |
| | 5 | 32.8 | | |
| | 15 | 17.9 | | |
| 670701 | 0.5 | 79.1 | GalNAc$_3$-3a | $T_e$ |
| | 1.5 | 59.2 | | |
| | 5 | 35.8 | | |
| | 15 | 17.7 | | |

TABLE 58-continued

SRB-1 mRNA (% Saline)

| ISIS No. | Dosage (mg/kg) | SRB-1 mRNA (% Saline) | GalNAc$_3$ Cluster | CM |
|---|---|---|---|---|
| 671165 | 0.5 | 76.4 | GalNAc$_3$-13a | $A_d$ |
| | 1.5 | 43.2 | | |
| | 5 | 22.6 | | |
| | 15 | 10.0 | | |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 56 below.

TABLE 59

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 24 | 64 | 0.2 | 31 | n/a | n/a |
| 661161 | 0.5 | 25 | 64 | 0.2 | 31 | GalNAc$_3$-3a | $A_d$ |
| | 1.5 | 24 | 50 | 0.2 | 32 | | |
| | 5 | 26 | 55 | 0.2 | 28 | | |
| | 15 | 27 | 52 | 0.2 | 31 | | |
| 670699 | 0.5 | 42 | 83 | 0.2 | 31 | GalNAc$_3$-3a | $T_d$ |
| | 1.5 | 33 | 58 | 0.2 | 32 | | |
| | 5 | 26 | 70 | 0.2 | 29 | | |
| | 15 | 25 | 67 | 0.2 | 29 | | |
| 670700 | 0.5 | 40 | 74 | 0.2 | 27 | GalNAc$_3$-3a | $A_e$ |
| | 1.5 | 23 | 62 | 0.2 | 27 | | |
| | 5 | 24 | 49 | 0.2 | 29 | | |
| | 15 | 25 | 87 | 0.1 | 25 | | |
| 670701 | 0.5 | 30 | 77 | 0.2 | 27 | GalNAc$_3$-3a | $T_e$ |
| | 1.5 | 22 | 55 | 0.2 | 30 | | |
| | 5 | 81 | 101 | 0.2 | 25 | | |
| | 15 | 31 | 82 | 0.2 | 24 | | |
| 671165 | 0.5 | 44 | 84 | 0.2 | 26 | GalNAc$_3$-13a | $A_d$ |
| | 1.5 | 47 | 71 | 0.1 | 24 | | |
| | 5 | 33 | 91 | 0.2 | 26 | | |
| | 15 | 33 | 56 | 0.2 | 29 | | |

Example 67: Preparation of Oligomeric Compound 199 Comprising GalNAc$_3$-16
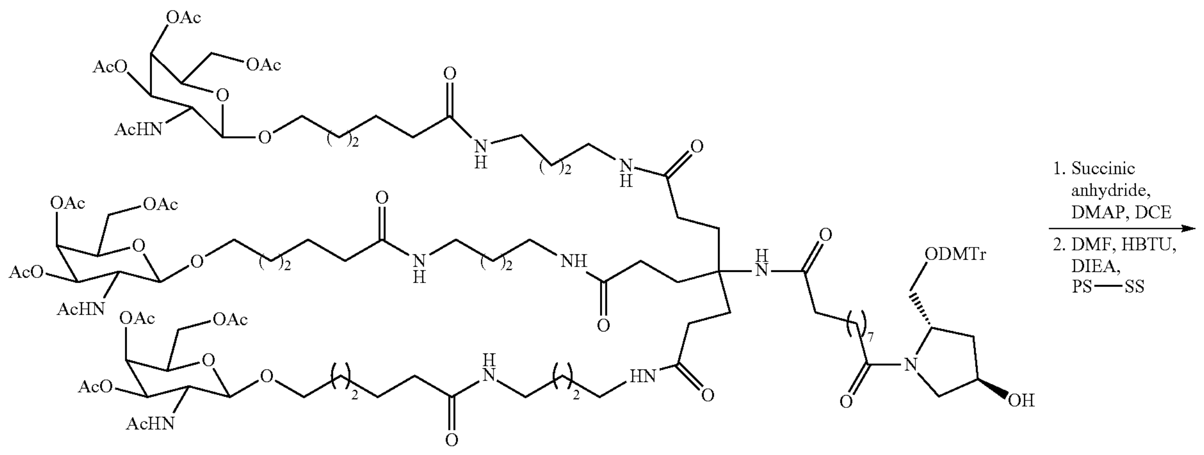
98d
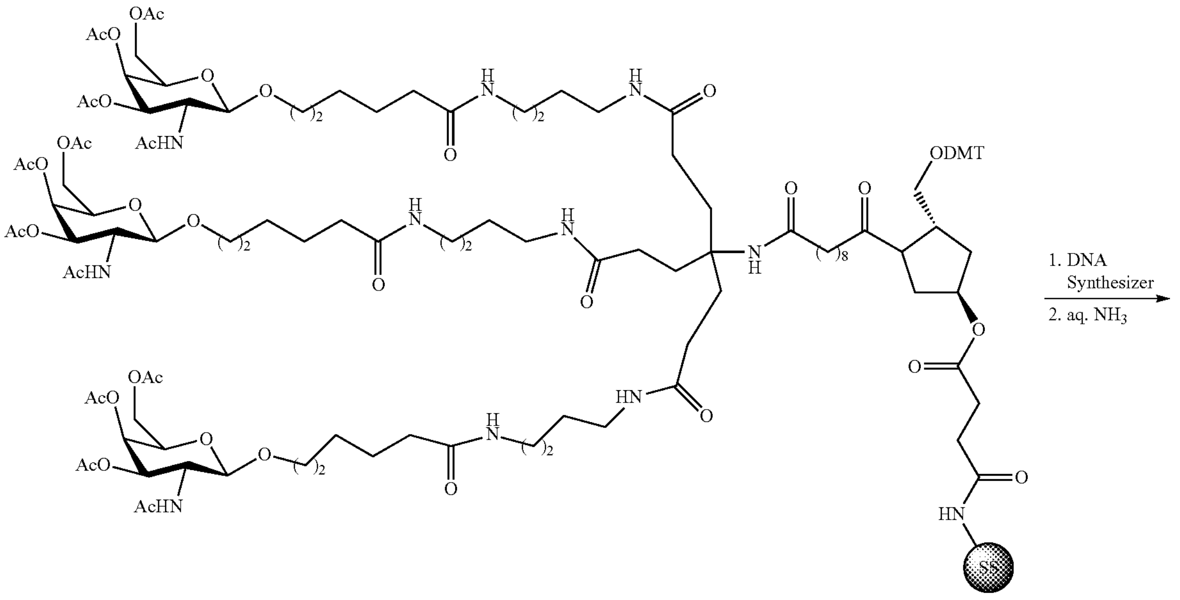
198

-continued

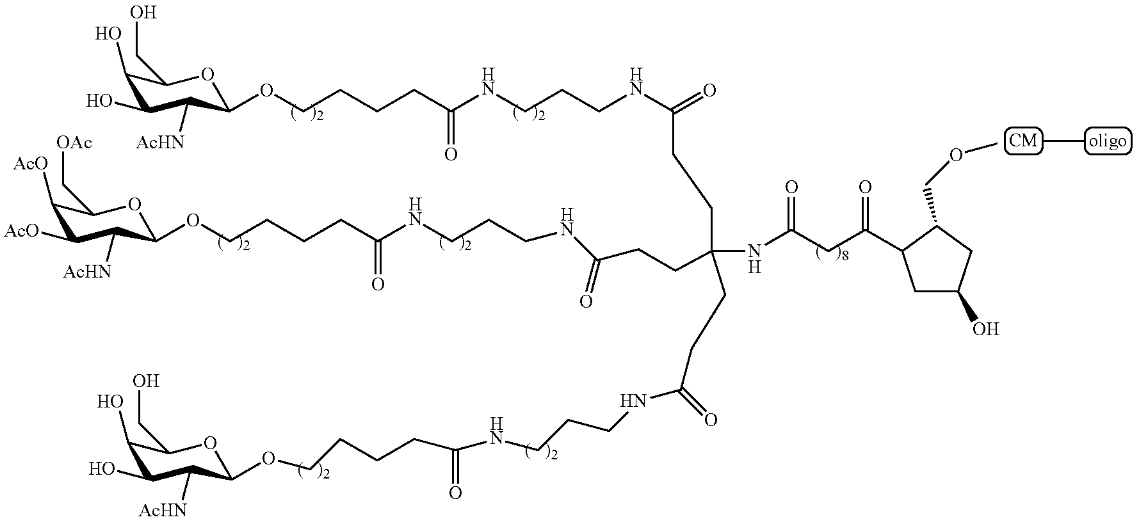

199

Oligomeric compound 199, comprising a GalNAc$_3$-16 conjugate group, is prepared using the general procedures illustrated in Examples 7 and 9. The GalNAc$_3$ cluster portion of the conjugate group GalNAc$_3$-16 (GalNAc$_3$-16$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-16 (GalNAc$_3$-16$_a$-CM-) is shown below:

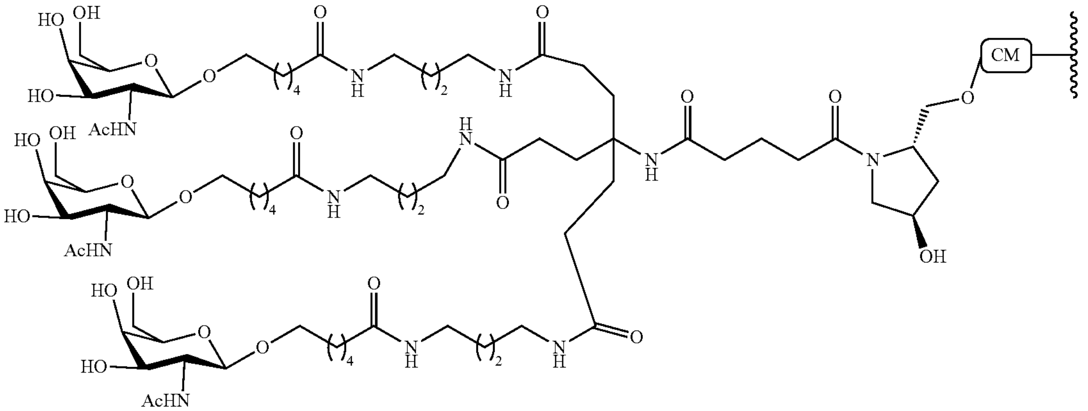

Example 68: Preparation of Oligomeric Compound 200 Comprising $GalNAc_3$-17
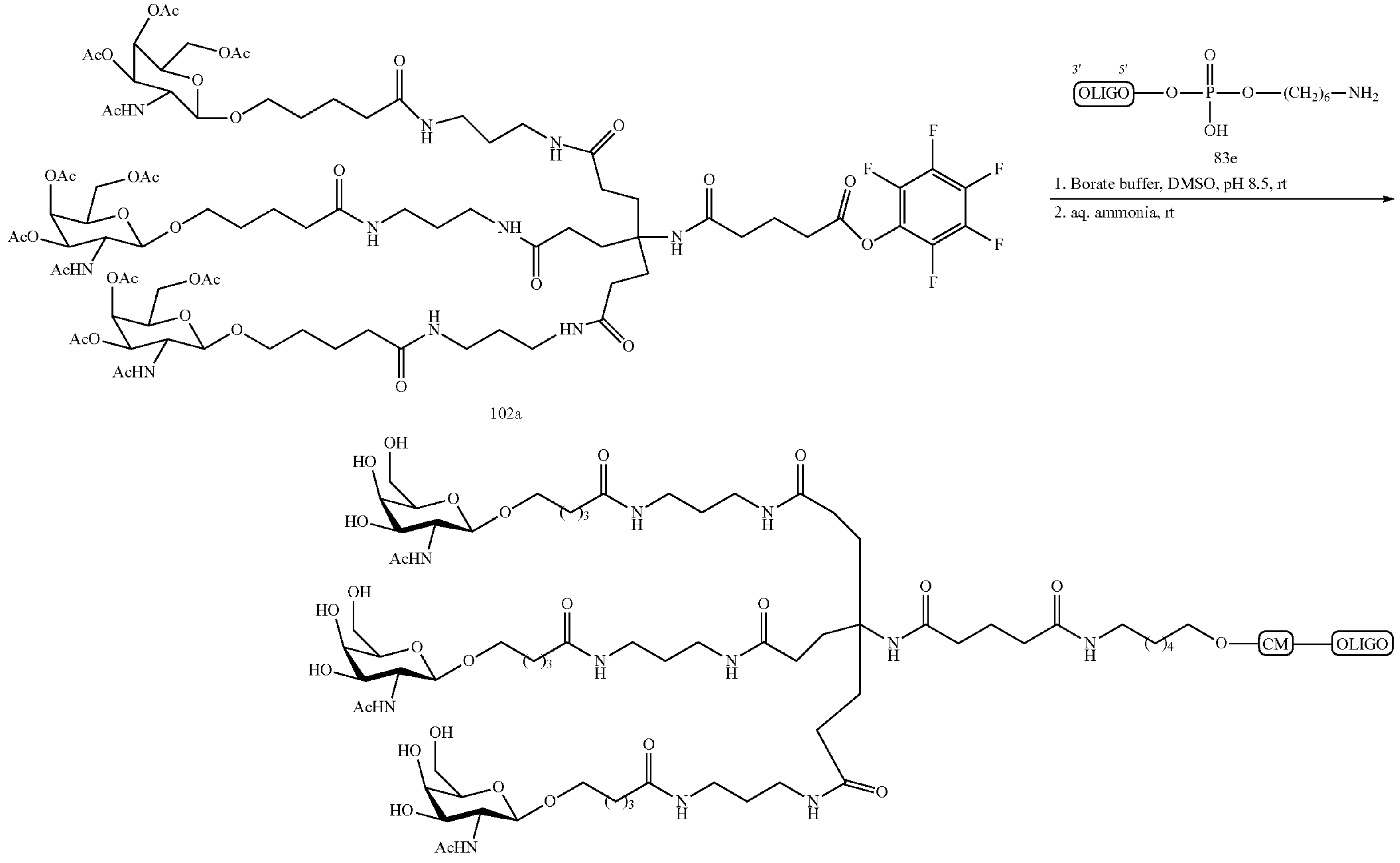
102a
200

Oligomeric compound 200, comprising a GalNAc$_3$-17 conjugate group, was prepared using the general procedures illustrated in Example 46. The GalNAc$_3$ cluster portion of the conjugate group GalNAc$_3$-17 (GalNAc$_3$-17$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-17 (GalNAc$_3$-17$_a$-CM-) is shown below:

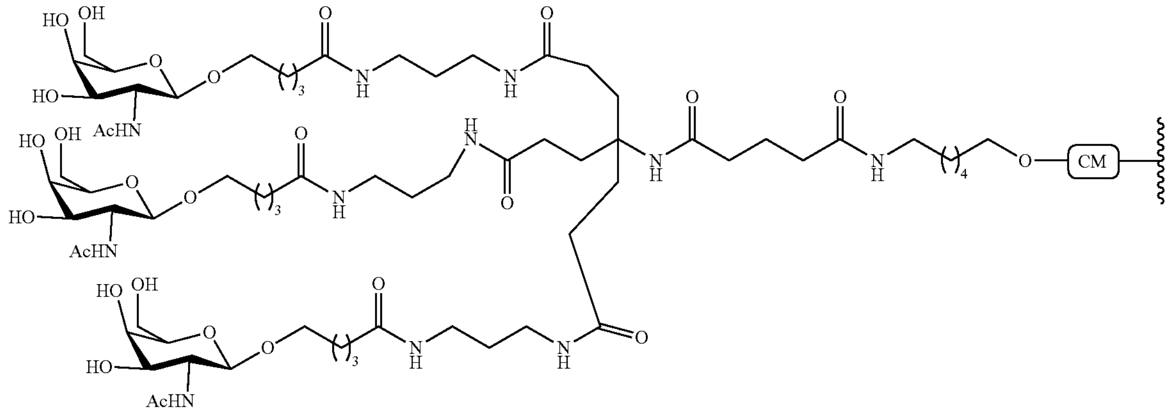

Example 69: Preparation of Oligomeric Compound 201 Comprising $GalNAc_3$-18
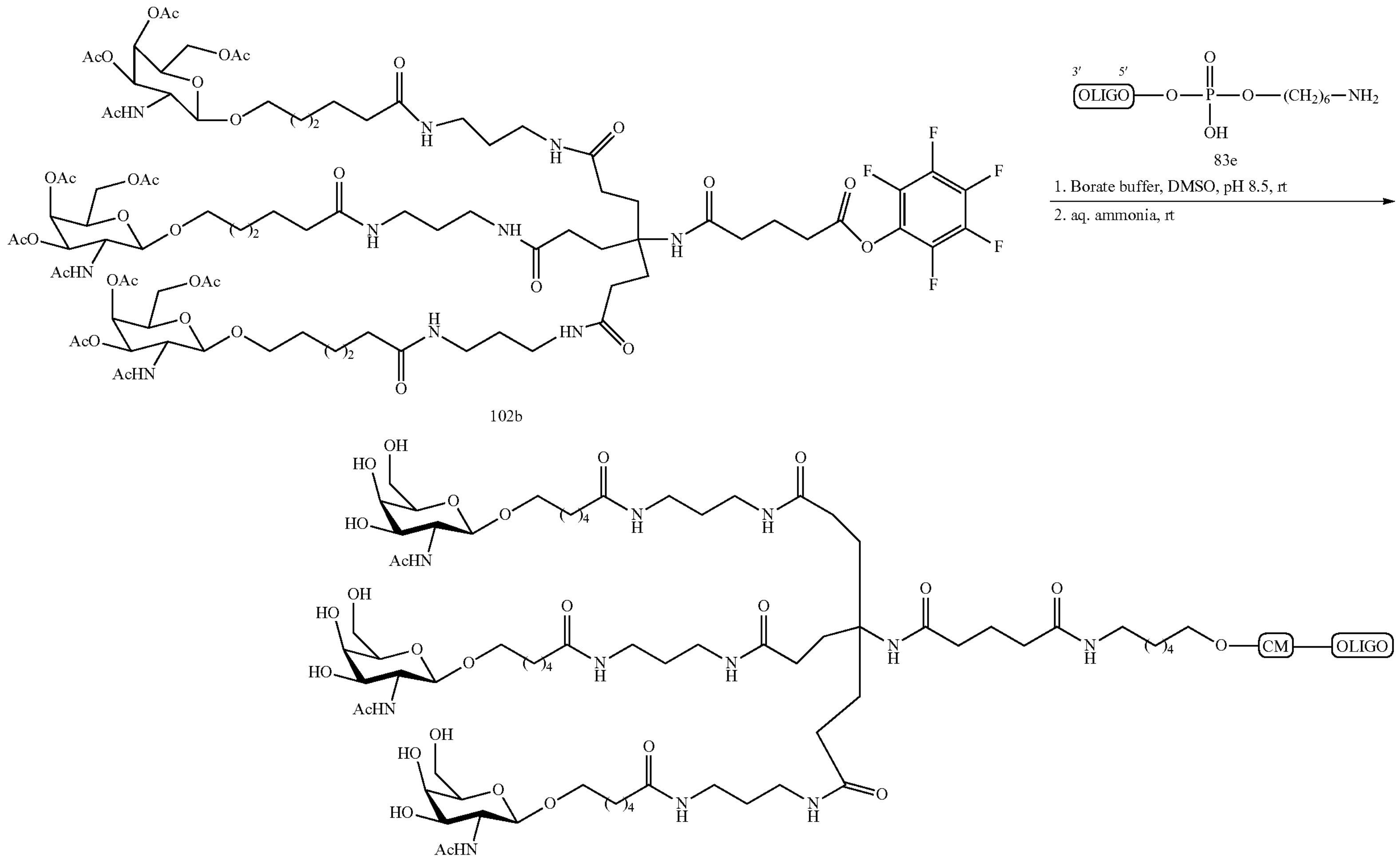
102b
83e
201

Oligomeric compound 201, comprising a $GalNAc_3$-18 conjugate group, was prepared using the general procedures illustrated in Example 46. The $GalNAc_3$ cluster portion of the conjugate group $GalNAc_3$-18 ($GalNAc_3$-$18_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-18 ($GalNAc_3$-$18_a$-CM-) is shown below:

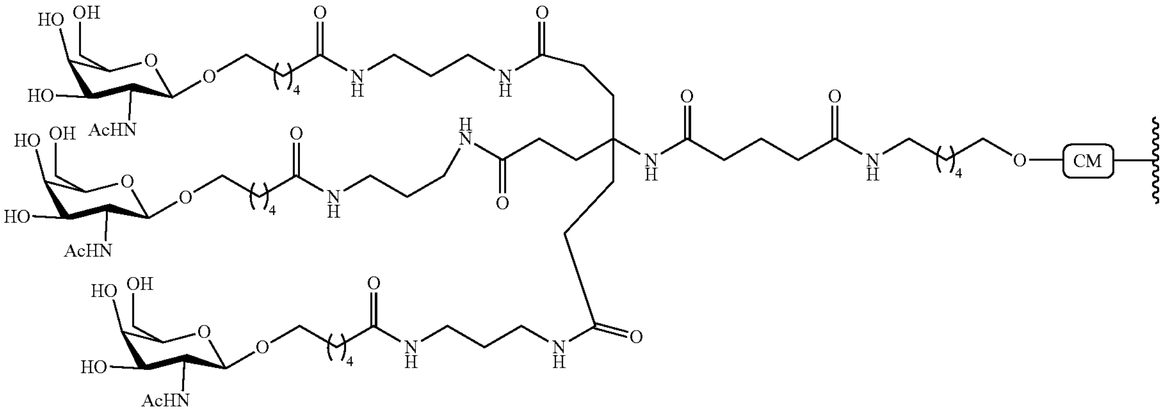

Example 70: Preparation of Oligomeric Compound 204 Comprising $GalNAc_3$-19

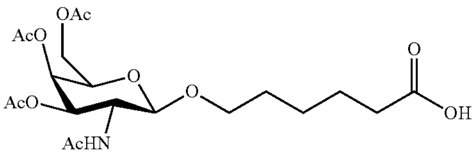

64

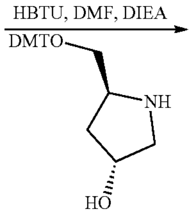

47

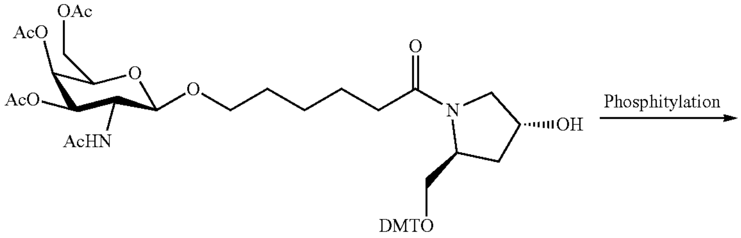

202

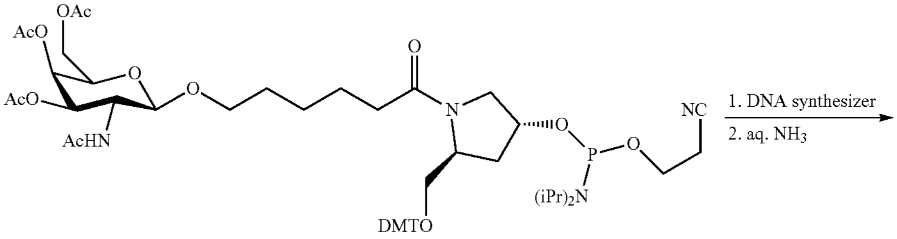

203

-continued

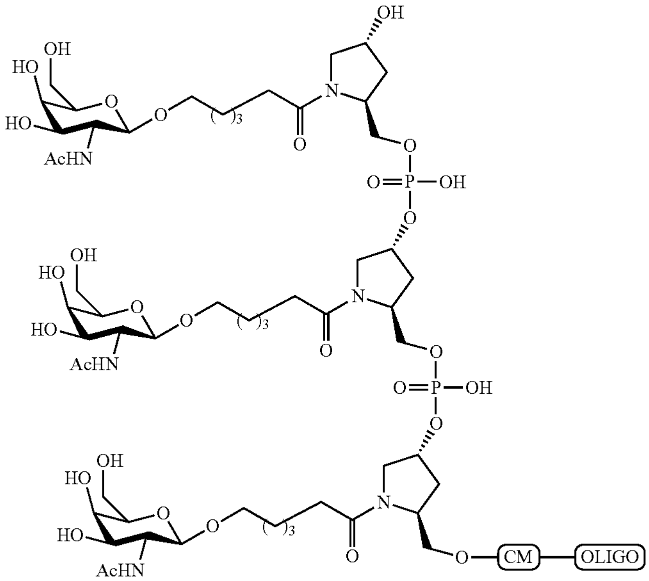

204

Oligomeric compound 204, comprising a $GalNAc_3$-19 conjugate group, was prepared from compound 64 using the general procedures illustrated in Example 52. The $GalNAc_3$ cluster portion of the conjugate group $GalNAc_3$-19 ($GalNAc_3$-$19_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-19 ($GalNAc_3$-$19_a$-CM-) is shown below:

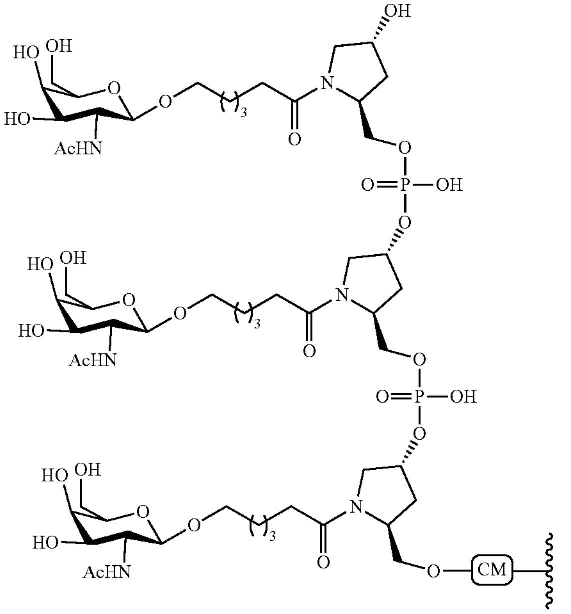

Example 71: Preparation of Oligomeric Compound 210 Comprising $GalNAc_3$-20
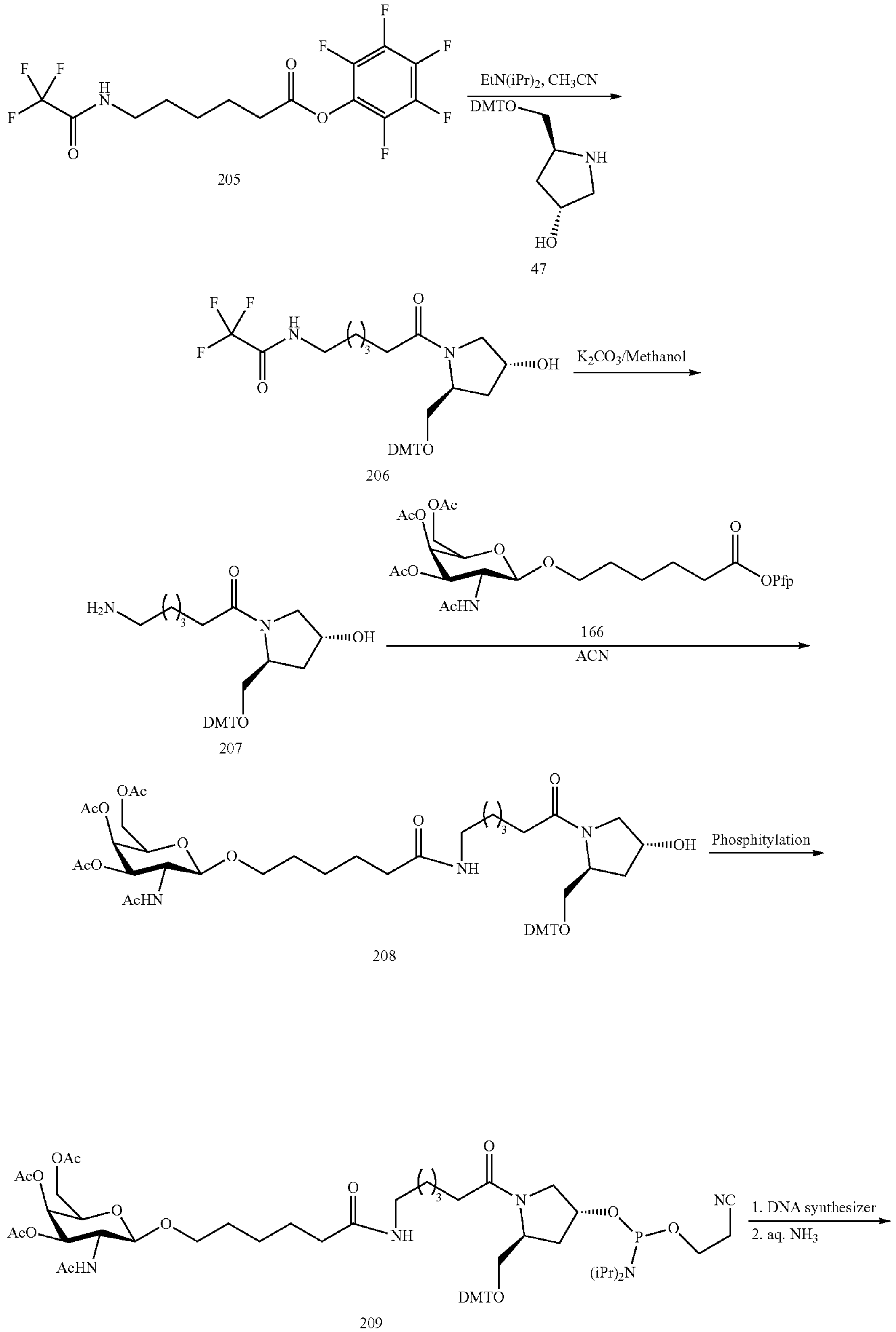
205
47
206
207
208
209

-continued

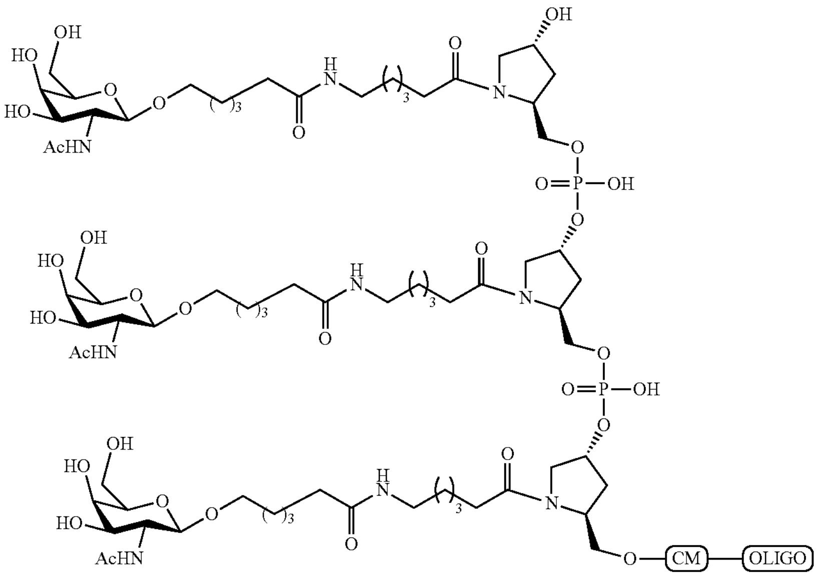

210

Compound 205 was prepared by adding PFP-TFA and DIEA to 6-(2,2,2-trifluoroacetamido)hexanoic acid in acetonitrile, which was prepared by adding triflic anhydride to 6-aminohexanoic acid. The reaction mixture was heated to 80° C., then lowered to rt. Oligomeric compound 210, comprising a $GalNAc_3$-20 conjugate group, was prepared from compound 208 using the general procedures illustrated in Example 52. The $GalNAc_3$ cluster portion of the conjugate group $GalNAc_3$-20 ($GalNAc_3$-$20_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-20 ($GalNAc_3$-$20_a$-CM-) is shown below:

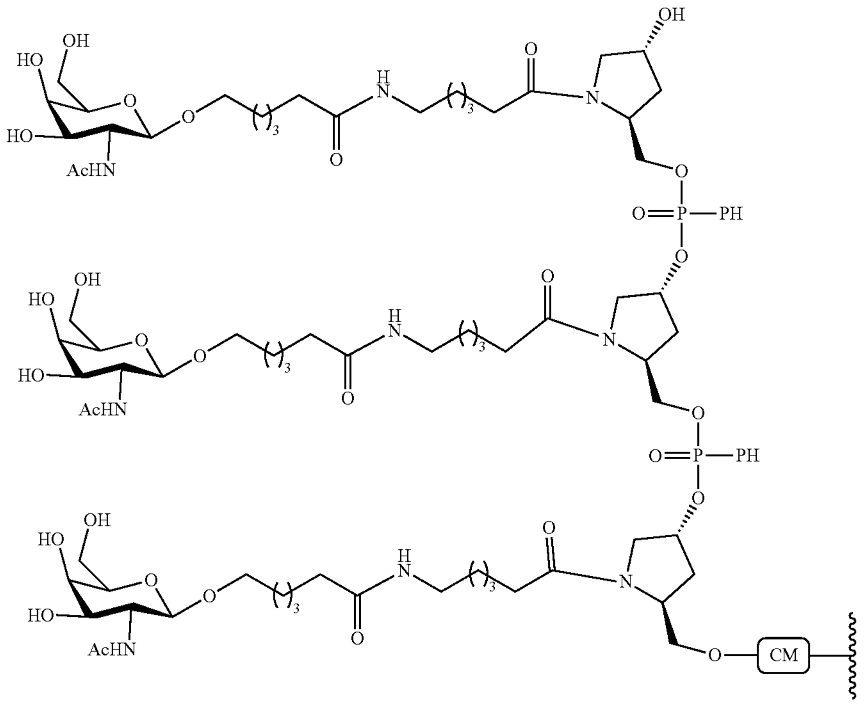

Example 72: Preparation of Oligomeric Compound 215 Comprising GalNAc$_3$-21
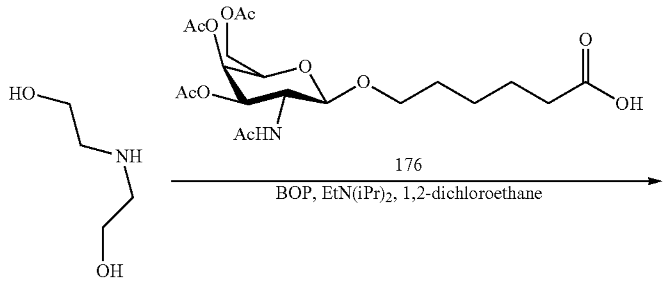
211
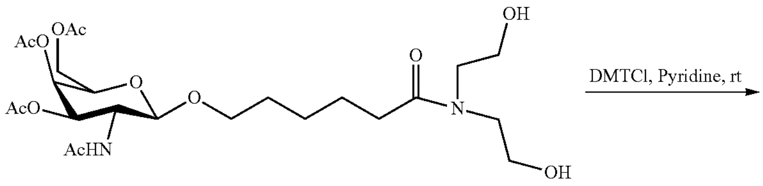
212
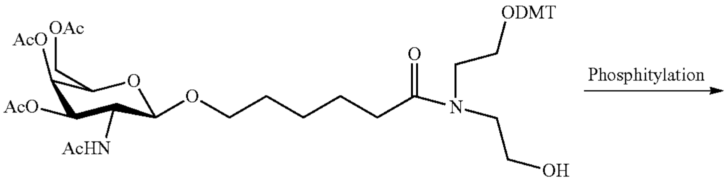
213
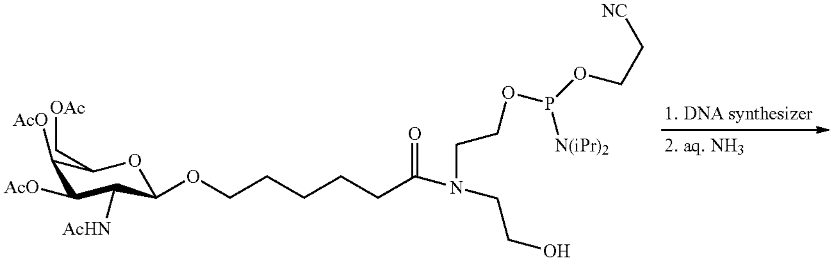
214

-continued

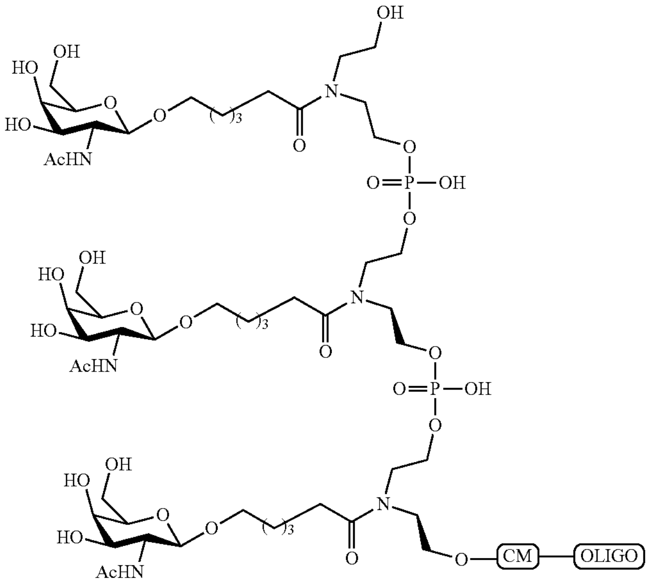

215

Compound 211 is commercially available. Oligomeric compound 215, comprising a $GalNAc_3$-21 conjugate group, was prepared from compound 213 using the general procedures illustrated in Example 52. The $GalNAc_3$ cluster portion of the conjugate group $GalNAc_3$-21 ($GalNAc_3$-$21_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-21 ($GalNAc_3$-$21_a$-CM-) is shown below:

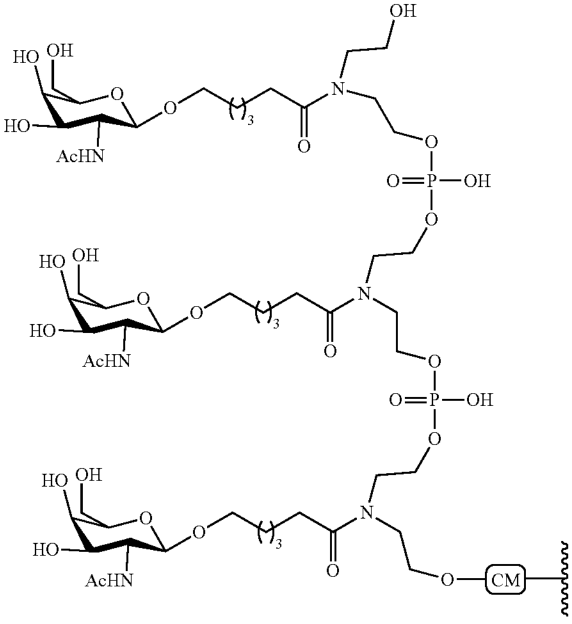

Example 73: Preparation of Oligomeric Compound 221 Comprising GalNAc$_3$-22
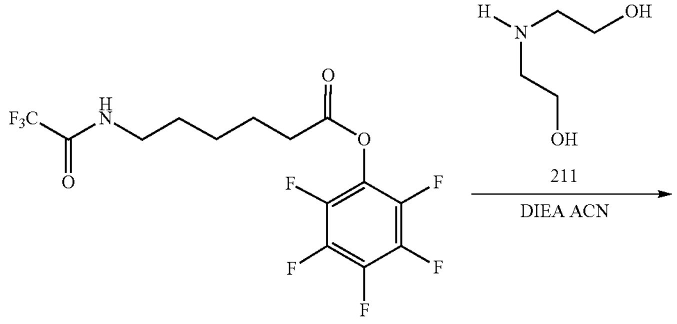
205
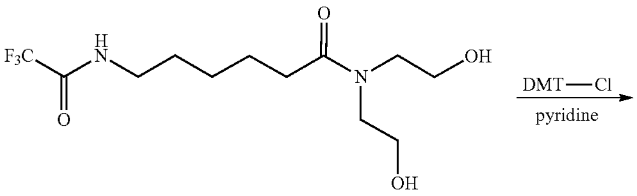
216
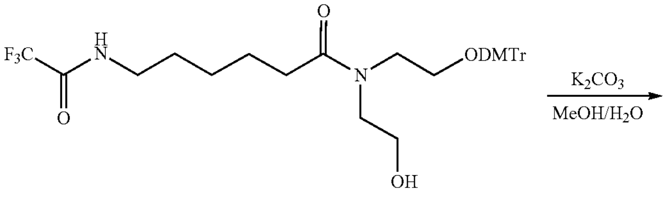
217
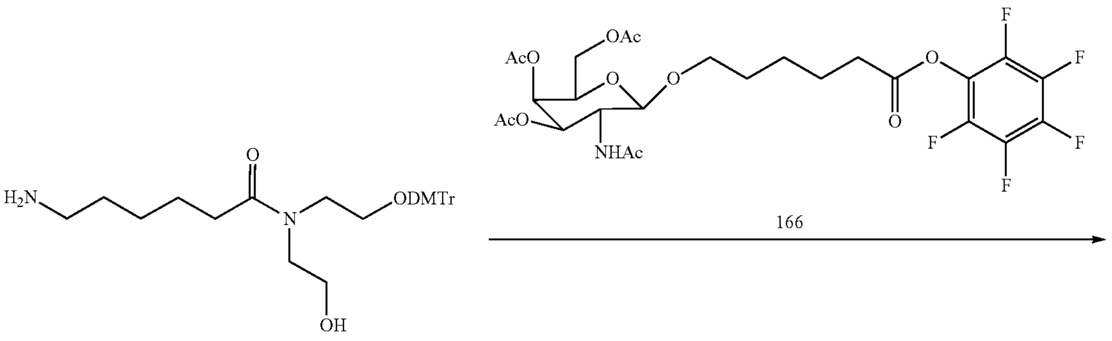
218

-continued

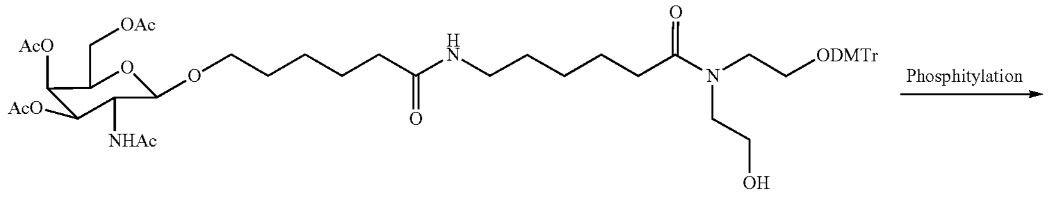

219

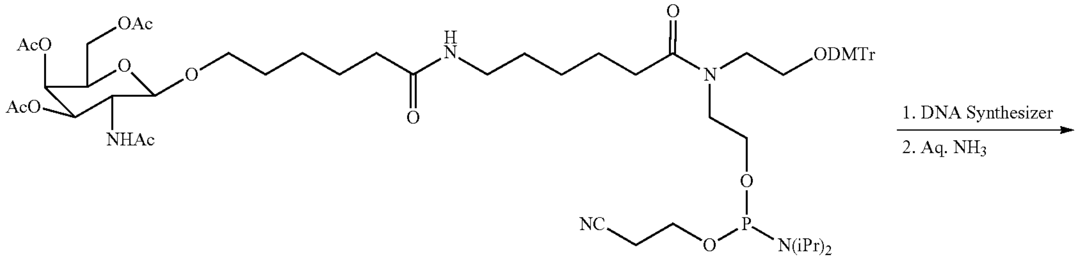

220

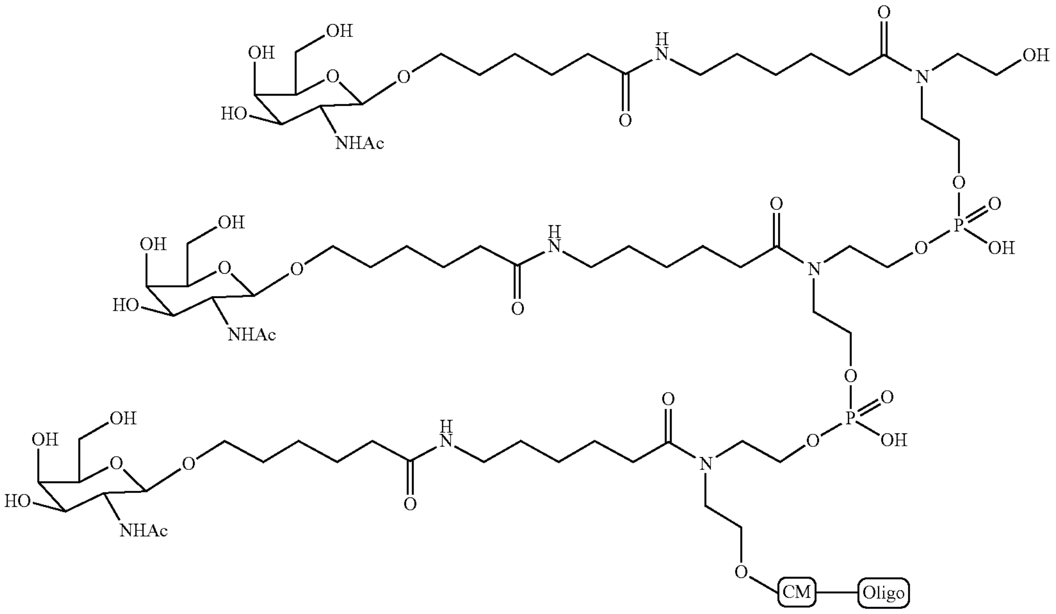

221

Compound 220 was prepared from compound 219 using diisopropylammonium tetrazolide. Oligomeric compound 221, comprising a GalNAc$_3$-21 conjugate group, is prepared from compound 220 using the general procedure illustrated in Example 52. The GalNAc$_3$ cluster portion of the conjugate group GalNAc$_3$-22 (GalNAc$_3$-22$_a$) can be combined with any cleavable moiety to provide a variety of conjugate groups. In certain embodiments, the cleavable moiety is —P(═O)(OH)-A$_d$-P(═O)(OH)—. The structure of GalNAc$_3$-22 (GalNAc$_3$-22$_a$-CM-) is shown below:

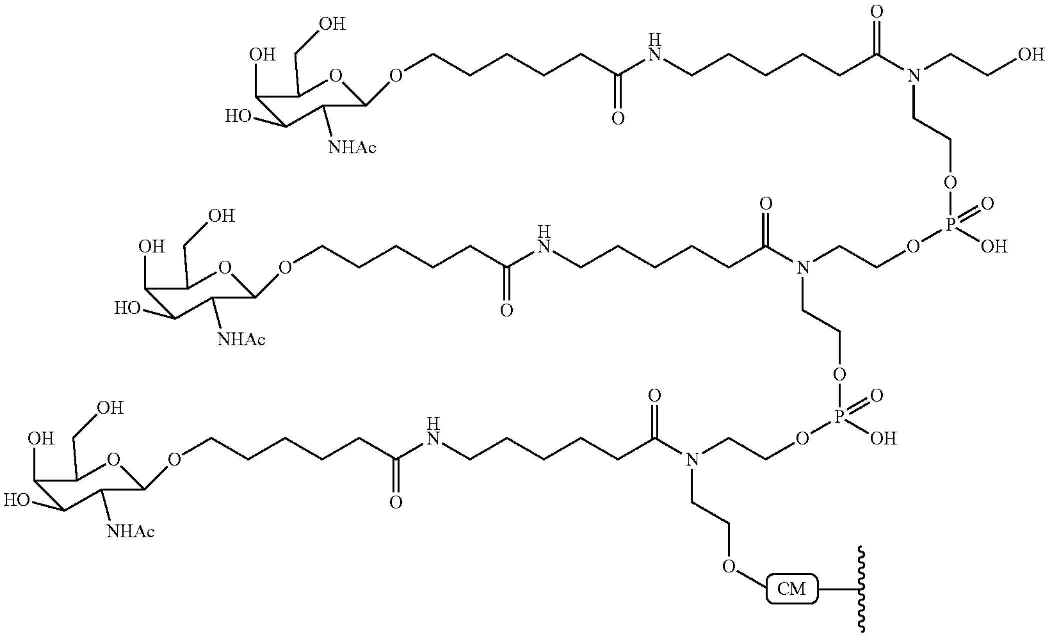

Example 74: Effect of Various Cleavable Moieties on Antisense Inhibition In Vivo by Oligonucleotides Targeting SRB-1 Comprising a 5'-$GalNAc_3$ Conjugate The oligonucleotides listed below were tested in a dose-dependent study for antisense inhibition of SRB-1 in mice. Each of the $GalNAc_3$ conjugate groups was attached at the 5' terminus of the respective oligonucleotide.

TABLE 60

Modified ASOs targeting SRB-1

| ISIS No. | Sequences (5' to 3') | $GalNAc_3$ Cluster | CM | Unmodified SEQ ID No. | Modified SEQ ID No. |
|---|---|---|---|---|---|
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | n/a | n/a | 252 | 318 |
| 661161 | **$GalNAc_3$-3$_a$-$_o$'** $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | $A_d$ | 254 | 376 |
| 666904 | **$GalNAc_3$-3$_a$-$_o$'** $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | PO | 252 | 330 |

TABLE 60-continued

| Modified ASOs targeting SRB-1 | | | | | |
|---|---|---|---|---|---|
| ISIS No. | Sequences (5' to 3') | $GalNAc_3$ Cluster | CM | Unmodified SEQ ID No. | Modified SEQ ID No. |
| 675441 | $\mathbf{GalNAc_3\text{-}17_a\text{-}_{o'}}$ $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-17a | $A_d$ | 254 | 406 |
| 675442 | $\mathbf{GalNAc_3\text{-}18_a\text{-}_{o'}}$ $A_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-18a | $A_d$ | 254 | 407 |

In all tables, capital letters indicate the nucleobase for each nucleoside and ${}^{m}C$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of $GalNAc_3$-$3_a$ was shown previously in Example 39. The structure of $GalNAc_3$-17a was shown previously in Example 68, and the structure of $GalNAc_3$-18a was shown in Example 69.

Treatment

Six to eight week old C57BL/6 mice (Jackson Laboratory, Bar Harbor, ME) were injected subcutaneously once at the dosage shown below with an oligonucleotide listed in Table 60 or with saline. Each treatment group consisted of 4 animals. The mice were sacrificed 72 hours following the final administration to determine the SRB-1 miRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 61, treatment with antisense oligonucleotides lowered SRB-1 mRNA levels in a dose-dependent manner. The antisense oligonucleotides comprising a GalNAc conjugate showed similar potencies and were significantly more potent than the parent oligonucleotide lacking a GalNAc conjugate.

TABLE 61

| SRB-1 mRNA (% Saline) | | | | |
|---|---|---|---|---|
| ISIS No. | Dosage (mg/kg) | SRB-1 mRNA (% Saline) | $GalNAc_3$ Cluster | CM |
| Saline | n/a | 100.0 | n/a | n/a |
| 353382 | 3 | 79.38 | n/a | n/a |
| | 10 | 68.67 | | |
| | 30 | 40.70 | | |
| 661161 | 0.5 | 79.18 | $GalNAc_3$-3a | $A_d$ |
| | 1.5 | 75.96 | | |
| | 5 | 30.53 | | |
| | 15 | 12.52 | | |
| 666904 | 0.5 | 91.30 | $GalNAc_3$-3a | PO |
| | 1.5 | 57.88 | | |
| | 5 | 21.22 | | |
| | 15 | 16.49 | | |
| 675441 | 0.5 | 76.71 | $GalNAc_3$-17a | $A_d$ |
| | 1.5 | 63.63 | | |
| | 5 | 29.57 | | |
| | 15 | 13.49 | | |
| 675442 | 0.5 | 95.03 | $GalNAc_3$-18a | $A_d$ |
| | 1.5 | 60.06 | | |
| | 5 | 31.04 | | |
| | 15 | 19.40 | | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group (data not shown). ALTs, ASTs, total bilirubin and BUN values are shown in Table 62 below.

TABLE 62

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| Saline | n/a | 26 | 59 | 0.16 | 42 | n/a | n/a |
| 353382 | 3 | 23 | 58 | 0.18 | 39 | n/a | n/a |
| | 10 | 28 | 58 | 0.16 | 43 | | |
| | 30 | 20 | 48 | 0.12 | 34 | | |
| 661161 | 0.5 | 30 | 47 | 0.13 | 35 | $GalNAc_3$-3a | $A_d$ |
| | 1.5 | 23 | 53 | 0.14 | 37 | | |
| | 5 | 26 | 48 | 0.15 | 39 | | |
| | 15 | 32 | 57 | 0.15 | 42 | | |
| 666904 | 0.5 | 24 | 73 | 0.13 | 36 | $GalNAc_3$-3a | PO |
| | 1.5 | 21 | 48 | 0.12 | 32 | | |
| | 5 | 19 | 49 | 0.14 | 33 | | |
| | 15 | 20 | 52 | 0.15 | 26 | | |

TABLE 62-continued

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| 675441 | 0.5 | 42 | 148 | 0.21 | 36 | $GalNAc_3$-17a | $A_d$ |
| | 1.5 | 60 | 95 | 0.16 | 34 | | |
| | 5 | 27 | 75 | 0.14 | 37 | | |
| | 15 | 24 | 61 | 0.14 | 36 | | |
| 675442 | 0.5 | 26 | 65 | 0.15 | 37 | $GalNAc_3$-18a | $A_d$ |
| | 1.5 | 25 | 64 | 0.15 | 43 | | |
| | 5 | 27 | 69 | 0.15 | 37 | | |
| | 15 | 30 | 84 | 0.14 | 37 | | |

Example 75: Pharmacokinetic Analysis of Oligonucleotides Comprising a 5'-Conjugate Group The PK of the ASOs in Tables 54, 57 and 60 above was evaluated using liver samples that were obtained following the treatment procedures described in Examples 65, 66, and 74. The liver samples were minced and extracted using standard protocols and analyzed by IP-HPLC-MS alongside an internal standard. The combined tissue level (g/g) of all metabolites was measured by integrating the appropriate UV peaks, and the tissue level of the full-length ASO missing the conjugate ("parent," which is Isis No. 353382 in this case) was measured using the appropriate extracted ion chromatograms (EIC).

TABLE 63

PK Analysis in Liver

| ISIS No. | Dosage (mg/kg) | Total Tissue Level by UV (μg/g) | Parent ASO Tissue Level by EIC (μg/g) | $GalNAc_3$ Cluster | CM |
|---|---|---|---|---|---|
| 353382 | 3 | 8.9 | 8.6 | n/a | n/a |
| | 10 | 22.4 | 21.0 | | |
| | 30 | 54.2 | 44.2 | | |
| 661161 | 5 | 32.4 | 20.7 | $GalNAc_3$-3a | $A_d$ |
| | 15 | 63.2 | 44.1 | | |

TABLE 63-continued

PK Analysis in Liver

| ISIS No. | Dosage (mg/kg) | Total Tissue Level by UV (μg/g) | Parent ASO Tissue Level by EIC (μg/g) | $GalNAc_3$ Cluster | CM |
|---|---|---|---|---|---|
| 671144 | 5 | 20.5 | 19.2 | $GalNAc_3$-12a | $A_d$ |
| | 15 | 48.6 | 41.5 | | |
| 670061 | 5 | 31.6 | 28.0 | $GalNAc_3$-13a | $A_d$ |
| | 15 | 67.6 | 55.5 | | |
| 671261 | 5 | 19.8 | 16.8 | $GalNAc_3$-14a | $A_d$ |
| | 15 | 64.7 | 49.1 | | |
| 671262 | 5 | 18.5 | 7.4 | $GalNAc_3$-15a | $A_d$ |
| | 15 | 52.3 | 24.2 | | |
| 670699 | 5 | 16.4 | 10.4 | $GalNAc_3$-3a | $T_d$ |
| | 15 | 31.5 | 22.5 | | |
| 670700 | 5 | 19.3 | 10.9 | $GalNAc_3$-3a | $A_e$ |
| | 15 | 38.1 | 20.0 | | |
| 670701 | 5 | 21.8 | 8.8 | $GalNAc_3$-3a | $T_e$ |
| | 15 | 35.2 | 16.1 | | |
| 671165 | 5 | 27.1 | 26.5 | $GalNAc_3$-13a | $A_d$ |
| | 15 | 48.3 | 44.3 | | |
| 666904 | 5 | 30.8 | 24.0 | $GalNAc_3$-3a | PO |
| | 15 | 52.6 | 37.6 | | |
| 675441 | 5 | 25.4 | 19.0 | $GalNAc_3$-17a | $A_d$ |
| | 15 | 54.2 | 42.1 | | |
| 675442 | 5 | 22.2 | 20.7 | $GalNAc_3$-18a | $A_d$ |
| | 15 | 39.6 | 29.0 | | |

The results in Table 63 above show that there were greater liver tissue levels of the oligonucleotides comprising a $GalNAc_3$ conjugate group than of the parent oligonucleotide that does not comprise a $GalNAc_3$ conjugate group (ISIS 353382) 72 hours following oligonucleotide administration, particularly when taking into consideration the differences in dosing between the oligonucleotides with and without a $GalNAc_3$ conjugate group. Furthermore, by 72 hours, 40-98% of each oligonucleotide comprising a $GalNAc_3$ conjugate group was metabolized to the parent compound, indicating that the $GalNAc_3$ conjugate groups were cleaved from the oligonucleotides.

Example 76: Preparation of Oligomeric Compound 230 Comprising $GalNAc_3$-23

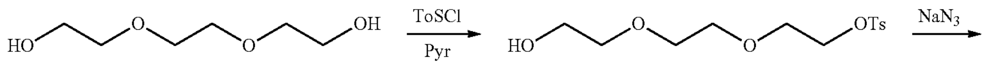

222 223

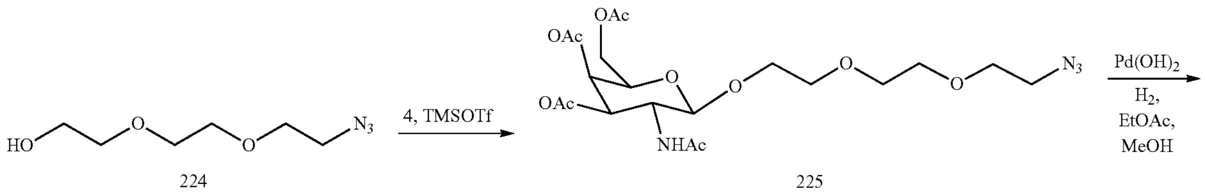

224 225

-continued
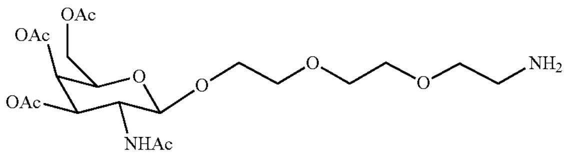
226
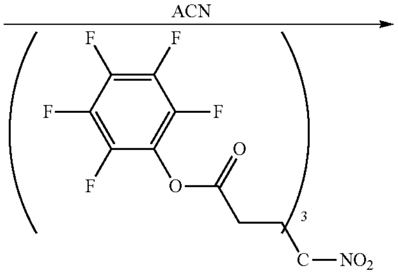
227
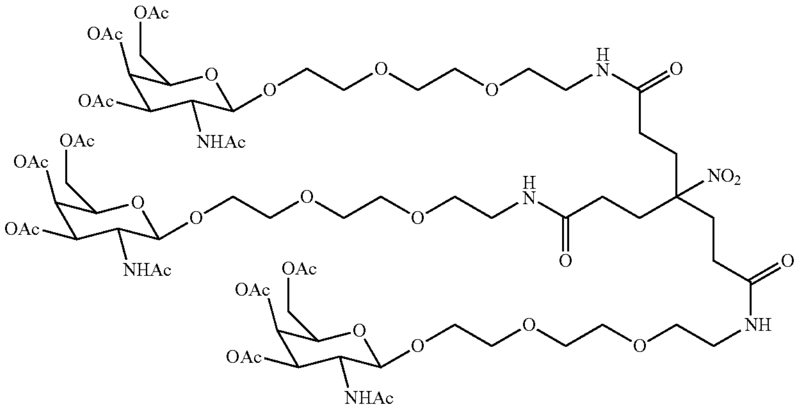
228
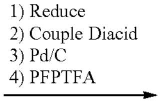
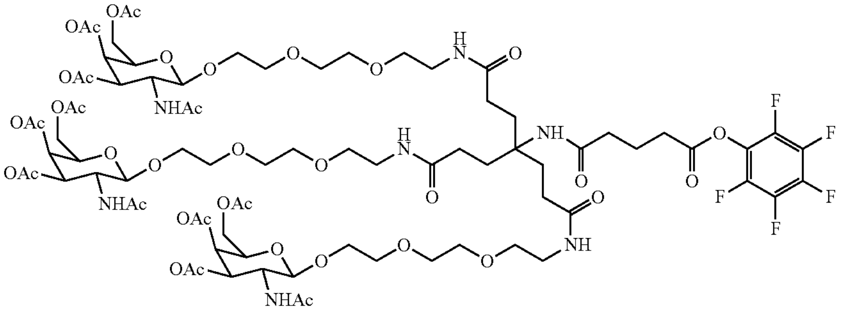
229
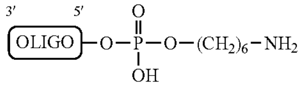
83e
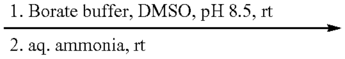
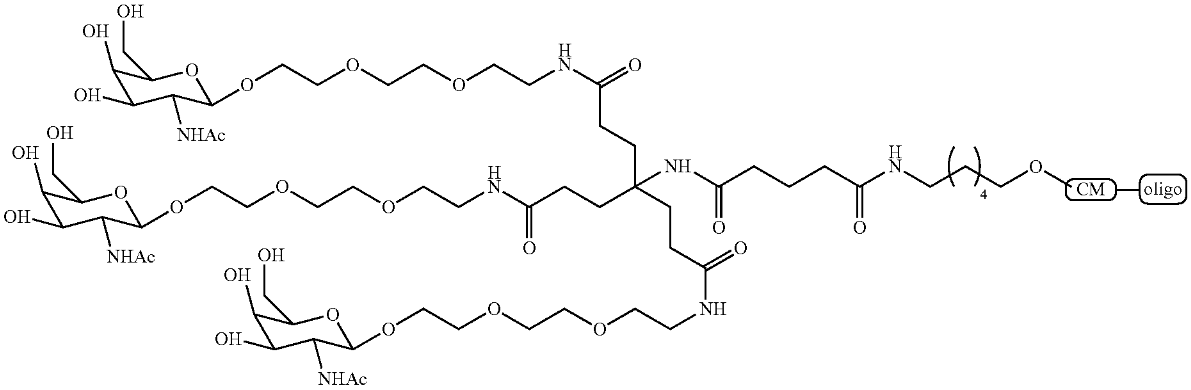
230

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. $NaHCO_3$, brine, and dried over $Na_2SO_4$. The ethyl acetate was concentrated to dryness and purified by column chromatography, eluted with EtOAc/hexanes (1:1) followed by 10% methanol in $CH_2Cl_2$ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO (100 mL) at room temperature for 17 hours. The reaction mixture was then poured onto water, and extracted with EtOAc. The organic layer was washed with water three times and dried over $Na_2SO_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4 A molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. $NaHCO_3$, water, brine, and dried over $Na_2SO_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over $Na_2SO_4$. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 μl, 1.6 mmol) in DMF (5 mL). After 16 hours, the DMF was removed under reduced pressure at 65° C. to an oil, and the oil was dissolved in dichloromethane. The organic layer was washed with sat. $NaHCO_3$, brine, and dried over $Na_2SO_4$. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 μl, 0.66 mmol) was added and the reaction was purged with argon. Pentaflourotriflouro acetate (46.39 μl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with 1N $NaHSO_4$, brine, saturated sodium bicarbonate and brine again. The organics were dried over $Na_2SO_4$, filtered, and were concentrated to dryness to give 225 mg of compound 229 as a brittle yellow foam. LCMS and NMR were consistent with the structure.

Oligomeric compound 230, comprising a GalNAc$_3$-23 conjugate group, was prepared from compound 229 using the general procedure illustrated in Example 46. The GalNAc$_3$ cluster portion of the GalNAc$_3$-23 conjugate group (GalNAc$_3$-23$_a$) can be combined with any cleavable moiety to provide a variety of conjugate groups. The structure of GalNAc$_3$-23 (GalNAc$_3$-23$_a$-CM) is shown below:

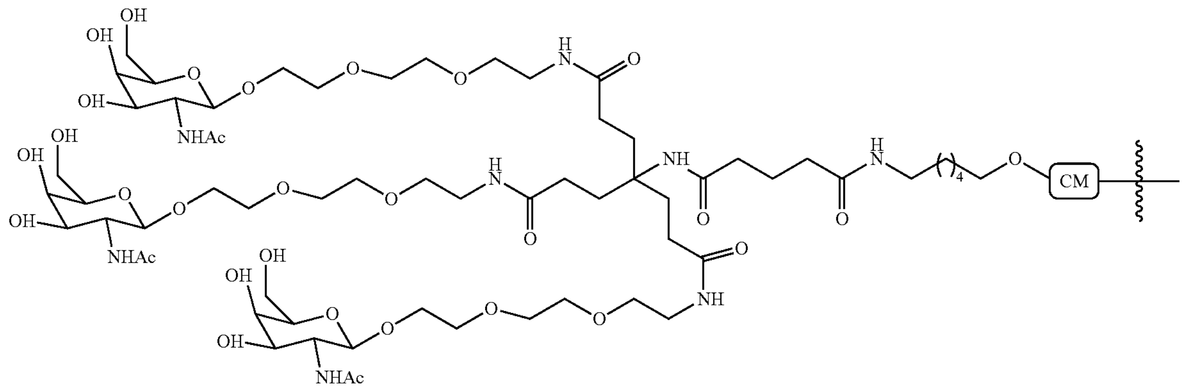

Example 77: Antisense Inhibition In Vivo by Oligonucleotides Targeting SRB-1 Comprising a GalNAc$_3$ Conjugate The oligonucleotides listed below were tested in a dose-dependent study for antisense inhibition of SRB-1 in mice.

TABLE 64

Modified ASOs targeting SRB-1

| ISIS No. | Sequences (5' to 3') | GalNAc$_3$ Cluster | CM | Unmodified SEQ ID No. | Modified SEQ ID No. |
|---|---|---|---|---|---|
| 661161 | **GalNAc$_3$-3$_a$-$_{o'}$A$_{do}$**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | GalNAc$_3$-3a | $A_d$ | 254 | 376 |
| 666904 | **GalNAc$_3$-3$_a$-$_{o'}$**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | GalNAc$_3$-3a | PO | 252 | 330 |
| 673502 | **GalNAc$_3$-10$_a$-$_{o'}$A$_{do}$**$G_{es}{}^mC_{eo}T_{eo}T_{eo}{}^mC_{eo}A_{ds}G_{ds}T_{ds}{}^mC_{ds}A_{ds}T_{ds}G_{ds}A_{ds}{}^mC_{ds}T_{ds}T_{eo}{}^mC_{eo}{}^mC_{es}T_{es}T_e$ | GalNAc$_3$-10a | $A_d$ | 254 | 402 |
| 677844 | **GalNAc$_3$-9$_a$-$_{o'}$A$_{do}$**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | GalNAc$_3$-9a | $A_d$ | 254 | 411 |
| 677843 | **GalNAc$_3$-23$_a$-$_{o'}$A$_{do}$**$G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | GalNAc$_3$-23a | $A_d$ | 254 | 410 |
| 655861 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}$**A$_{do'}$-GalNAc$_3$-1$_a$** | GalNAc$_3$-1a | $A_d$ | 253 | 369 |
| 677841 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}$**A$_{do'}$-GalNAc$_3$-19$_a$** | GalNAc$_3$-19a | $A_d$ | 253 | 408 |
| 677842 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}$**A$_{do'}$-GalNAc$_3$-20$_a$** | GalNAc$_3$-20a | $A_d$ | 253 | 409 |

The structure of GalNAc$_3$-1$_a$ was shown previously in Example 9, GalNAc$_3$-3$_a$ was shown in Example 39, GalNAc$_3$-9a was shown in Example 52, GalNAc$_3$-10a was shown in Example 46, GalNAc$_3$-19$_a$ was shown in Example 70, GalNAc$_3$-20$_a$ was shown in Example 71, and GalNAc$_3$-23$_a$ was shown in Example 76.

Treatment

Six to eight week old C57BL/6 mice (Jackson Laboratory, Bar Harbor, ME) were each injected subcutaneously once at a dosage shown below with an oligonucleotide listed in Table 64 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 65, treatment with antisense oligonucleotides lowered SRB-1 mRNA levels in a dose-dependent manner.

TABLE 65

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 661161 | 0.5 | 89.18 | GalNAc$_3$-3a | $A_d$ |
| | 1.5 | 77.02 | | |
| | 5 | 29.10 | | |
| | 15 | 12.64 | | |
| 666904 | 0.5 | 93.11 | GalNAc$_3$-3a | PO |
| | 1.5 | 55.85 | | |
| | 5 | 21.29 | | |
| | 15 | 13.43 | | |
| 673502 | 0.5 | 77.75 | GalNAc$_3$-10a | $A_d$ |
| | 1.5 | 41.05 | | |
| | 5 | 19.27 | | |
| | 15 | 14.41 | | |
| 677844 | 0.5 | 87.65 | GalNAc$_3$-9a | $A_d$ |
| | 1.5 | 93.04 | | |
| | 5 | 40.77 | | |
| | 15 | 16.95 | | |
| 677843 | 0.5 | 102.28 | GalNAc$_3$-23a | $A_d$ |
| | 1.5 | 70.51 | | |
| | 5 | 30.68 | | |
| | 15 | 13.26 | | |
| 655861 | 0.5 | 79.72 | GalNAc$_3$-1a | $A_d$ |
| | 1.5 | 55.48 | | |
| | 5 | 26.99 | | |
| | 15 | 17.58 | | |
| 677841 | 0.5 | 67.43 | GalNAc$_3$-19a | $A_d$ |
| | 1.5 | 45.13 | | |
| | 5 | 27.02 | | |
| | 15 | 12.41 | | |
| 677842 | 0.5 | 64.13 | GalNAc$_3$-20a | $A_d$ |
| | 1.5 | 53.56 | | |
| | 5 | 20.47 | | |
| | 15 | 10.23 | | |

Liver transaminase levels, alanine aminotransferase (ALT) and aspartate aminotransferase (AST), in serum were also measured using standard protocols. Total bilirubin and BUN were also evaluated. Changes in body weights were evaluated, with no significant change from the saline group (data not shown). ALTs, ASTs, total bilirubin and BUN values are shown in Table 66 below.

TABLE 66

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| Saline | n/a | 21 | 45 | 0.13 | 34 | n/a | n/a |
| 661161 | 0.5 | 28 | 51 | 0.14 | 39 | $GalNAc_3$-3a | $A_d$ |
| | 1.5 | 23 | 42 | 0.13 | 39 | | |
| | 5 | 22 | 59 | 0.13 | 37 | | |
| | 15 | 21 | 56 | 0.15 | 35 | | |
| 666904 | 0.5 | 24 | 56 | 0.14 | 37 | $GalNAc_3$-3a | PO |
| | 1.5 | 26 | 68 | 0.15 | 35 | | |
| | 5 | 23 | 77 | 0.14 | 34 | | |
| | 15 | 24 | 60 | 0.13 | 35 | | |
| 673502 | 0.5 | 24 | 59 | 0.16 | 34 | $GalNAc_3$-10a | $A_d$ |
| | 1.5 | 20 | 46 | 0.17 | 32 | | |
| | 5 | 24 | 45 | 0.12 | 31 | | |
| | 15 | 24 | 47 | 0.13 | 34 | | |
| 677844 | 0.5 | 25 | 61 | 0.14 | 37 | $GalNAc_3$-9a | $A_d$ |
| | 1.5 | 23 | 64 | 0.17 | 33 | | |
| | 5 | 25 | 58 | 0.13 | 35 | | |
| | 15 | 22 | 65 | 0.14 | 34 | | |
| 677843 | 0.5 | 53 | 53 | 0.13 | 35 | $GalNAc_3$-23a | $A_d$ |
| | 1.5 | 25 | 54 | 0.13 | 34 | | |
| | 5 | 21 | 60 | 0.15 | 34 | | |
| | 15 | 22 | 43 | 0.12 | 38 | | |
| 655861 | 0.5 | 21 | 48 | 0.15 | 33 | $GalNAc_3$-1a | $A_d$ |
| | 1.5 | 28 | 54 | 0.12 | 35 | | |
| | 5 | 22 | 60 | 0.13 | 36 | | |
| | 15 | 21 | 55 | 0.17 | 30 | | |
| 677841 | 0.5 | 32 | 54 | 0.13 | 34 | $GalNAc_3$-19a | $A_d$ |
| | 1.5 | 24 | 56 | 0.14 | 34 | | |
| | 5 | 23 | 92 | 0.18 | 31 | | |
| | 15 | 24 | 58 | 0.15 | 31 | | |
| 677842 | 0.5 | 23 | 61 | 0.15 | 35 | $GalNAc_3$-20a | $A_d$ |
| | 1.5 | 24 | 57 | 0.14 | 34 | | |
| | 5 | 41 | 62 | 0.15 | 35 | | |
| | 15 | 24 | 37 | 0.14 | 32 | | |

Example 78: Antisense Inhibition In Vivo by Oligonucleotides Targeting Angiotensinogen Comprising a $GalNAc_3$ Conjugate The oligonucleotides listed below were tested in a dose-dependent study for antisense inhibition of Angiotensinogen (AGT) in normotensive Sprague Dawley rats.

TABLE 67

Modified ASOs targeting AGT

| ISIS No. | Sequences (5' to 3') | $GalNAc_3$ Cluster | CM | Unmodified SEQ ID No. | Modified SEQ ID No. |
|---|---|---|---|---|---|
| 552668 | $^{m}C_{es}A_{es}{}^{m}C_{es}T_{es}G_{es}A_{ds}T_{ds}T_{ds}T_{ds}T_{ds}T_{ds}G_{ds}{}^{m}C_{ds}{}^{m}C_{ds}{}^{m}C_{ds}A_{es}G_{es}G_{es}A_{es}T_{e}$ | n/a | n/a | 258 | 366 |
| 669509 | $^{m}C_{es}A_{es}{}^{m}C_{es}T_{es}G_{es}A_{ds}T_{ds}T_{ds}T_{ds}T_{ds}T_{ds}G_{ds}{}^{m}C_{ds}{}^{m}C_{ds}{}^{m}C_{ds}A_{es}G_{es}G_{es}A_{es}T_{eo}$ **$A_{do'}$-$GalNAc_3$-$1_a$** | $GalNAc_3$-$1_a$ | $A_d$ | 259 | 438 |

The structure of $GalNAc_3$-$1_a$ was shown previously in Example 9.

Treatment

Six week old, male Sprague Dawley rats were each injected subcutaneously once per week at a dosage shown below, for a total of three doses, with an oligonucleotide listed in Table 67 or with PBS. Each treatment group consisted of 4 animals. The rats were sacrificed 72 hours following the final dose. AGT liver mRNA levels were measured using real-time PCR and RIBOGREEN® RNA quantification reagent (Molecular Probes, Inc. Eugene, OR) according to standard protocols. AGT plasma protein levels were measured using the Total Angiotensinogen ELISA (Catalog #JP27412, IBL International, Toronto, ON) with plasma diluted 1:20,000. The results below are presented as the average percent of AGT mRNA levels in liver or AGT protein levels in plasma for each treatment group, normalized to the PBS control.

As illustrated in Table 68, treatment with antisense oligonucleotides lowered AGT liver mRNA and plasma protein levels in a dose-dependent manner, and the oligonucleotide comprising a GalNAc conjugate was significantly more potent than the parent oligonucleotide lacking a GalNAc conjugate.

TABLE 68

AGT liver mRNA and plasma protein levels

| ISIS No. | Dosage (mg/kg) | AGT liver mRNA (% PBS) | AGT plasma protein (% PBS) | $GalNAc_3$ Cluster | CM |
|---|---|---|---|---|---|
| PBS | n/a | 100 | 100 | n/a | n/a |
| 552668 | 3 | 95 | 122 | n/a | n/a |
| | 10 | 85 | 97 | | |
| | 30 | 46 | 79 | | |
| | 90 | 8 | 11 | | |
| 669509 | 0.3 | 95 | 70 | $GalNAc_3$-1a | $A_d$ |
| | 1 | 95 | 129 | | |
| | 3 | 62 | 97 | | |
| | 10 | 9 | 23 | | |

Liver transaminase levels, alanine aminotransferase (ALT) and aspartate aminotransferase (AST), in plasma and body weights were also measured at time of sacrifice using standard protocols. The results are shown in Table 69 below.

TABLE 69

| Liver transaminase levels and rat body weights | | | | | | |
|---|---|---|---|---|---|---|
| ISIS No. | Dosage (mg/kg) | ALT (U/L) | AST (U/L) | Body Weight (% of baseline) | $GalNAc_3$ Cluster | CM |
| PBS | n/a | 51 | 81 | 186 | n/a | n/a |
| 552668 | 3 | 54 | 93 | 183 | n/a | n/a |
| | 10 | 51 | 93 | 194 | | |
| | 30 | 59 | 99 | 182 | | |
| | 90 | 56 | 78 | 170 | | |
| 669509 | 0.3 | 53 | 90 | 190 | $GalNAc_3$-1a | $A_d$ |
| | 1 | 51 | 93 | 192 | | |
| | 3 | 48 | 85 | 189 | | |
| | 10 | 56 | 95 | 189 | | |

Example 79: Duration of Action In Vivo of Oligonucleotides Targeting APOC-III Comprising a $GalNAc_3$ Conjugate The oligonucleotides listed in Table 70 below were tested in a single dose study for duration of action in mice.

TABLE 70

| Modified ASOs targeting APOC-III | | | | | |
|---|---|---|---|---|---|
| ISIS No. | Sequences (5' to 3') | $GalNAc_3$ Cluster | CM | Unmodified SEQ ID No. | Modified SEQ ID No. |
| 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | n/a | n/a | 244 | 317 |
| 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}$ $\mathbf{A_{do'}\text{-}GalNAc_3\text{-}1_a}$ | $GalNAc_3$-1a | $A_d$ | 245 | 367 |
| 663083 | $\mathbf{GalNAc_3\text{-}3_a\text{-}_{o'}A_{do}}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-3a | $A_d$ | 260 | 379 |
| 674449 | $\mathbf{GalNAc_3\text{-}7_a\text{-}_{o'}A_{do}}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-7a | $A_d$ | 260 | 403 |
| 674450 | $\mathbf{GalNAc_3\text{-}10_a\text{-}_{o'}A_{do}}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-10a | $A_d$ | 260 | 404 |
| 674451 | $\mathbf{GalNAc_3\text{-}13_a\text{-}_{o'}A_{do}}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-13a | $A_d$ | 260 | 405 |

The structure of $GalNAc_3$-$1_a$ was shown previously in Example 9, $GalNAc_3$-$3_a$ was shown in Example 39, $GalNAc_3$-$7_a$ was shown in Example 48, $GalNAc_3$-$10_a$ was shown in Example 46, and $GalNAc_3$-$13_a$ was shown in Example 62.

Treatment

Six to eight week old transgenic mice that express human APOC-III were each injected subcutaneously once with an oligonucleotide listed in Table 70 or with PBS. Each treatment group consisted of 3 animals. Blood was drawn before dosing to determine baseline and at 72 hours, 1 week, 2 weeks, 3 weeks, 4 weeks, 5 weeks, and 6 weeks following the dose. Plasma triglyceride and APOC-III protein levels were measured as described in Example 20. The results below are presented as the average percent of plasma triglyceride and APOC-III levels for each treatment group, normalized to baseline levels, showing that the oligonucleotides comprising a GalNAc conjugate group exhibited a longer duration of action than the parent oligonucleotide without a conjugate group (ISIS 304801) even though the dosage of the parent was three times the dosage of the oligonucleotides comprising a GalNAc conjugate group.

TABLE 71

| Plasma triglyceride and APOC-III protein levels in transgenic mice | | | | | | |
|---|---|---|---|---|---|---|
| ISIS No. | Dosage (mg/kg) | Time point (days post-dose) | Triglycerides (% baseline) | APOC-III protein (% baseline) | $GalNAc_3$ Cluster | CM |
| PBS | n/a | 3 | 97 | 102 | n/a | n/a |
| | | 7 | 101 | 98 | | |
| | | 14 | 108 | 98 | | |
| | | 21 | 107 | 107 | | |
| | | 28 | 94 | 91 | | |
| | | 35 | 88 | 90 | | |
| | | 42 | 91 | 105 | | |
| 304801 | 30 | 3 | 40 | 34 | n/a | n/a |
| | | 7 | 41 | 37 | | |
| | | 14 | 50 | 57 | | |
| | | 21 | 50 | 50 | | |
| | | 28 | 57 | 73 | | |
| | | 35 | 68 | 70 | | |
| | | 42 | 75 | 93 | | |
| 647535 | 10 | 3 | 36 | 37 | $GalNAc_3$-1a | $A_d$ |
| | | 7 | 39 | 47 | | |
| | | 14 | 40 | 45 | | |
| | | 21 | 41 | 41 | | |
| | | 28 | 42 | 62 | | |
| | | 35 | 69 | 69 | | |
| | | 42 | 85 | 102 | | |
| 663083 | 10 | 3 | 24 | 18 | $GalNAc_3$-3a | $A_d$ |
| | | 7 | 28 | 23 | | |
| | | 14 | 25 | 27 | | |
| | | 21 | 28 | 28 | | |
| | | 28 | 37 | 44 | | |
| | | 35 | 55 | 57 | | |
| | | 42 | 60 | 78 | | |
| 674449 | 10 | 3 | 29 | 26 | $GalNAc_3$-7a | $A_d$ |
| | | 7 | 32 | 31 | | |
| | | 14 | 38 | 41 | | |
| | | 21 | 44 | 44 | | |
| | | 28 | 53 | 63 | | |
| | | 35 | 69 | 77 | | |
| | | 42 | 78 | 99 | | |
| 674450 | 10 | 3 | 33 | 30 | $GalNAc_3$-10a | $A_d$ |
| | | 7 | 35 | 34 | | |
| | | 14 | 31 | 34 | | |
| | | 21 | 44 | 44 | | |
| | | 28 | 56 | 61 | | |
| | | 35 | 68 | 70 | | |
| | | 42 | 83 | 95 | | |
| 674451 | 10 | 3 | 35 | 33 | $GalNAc_3$-13a | $A_d$ |
| | | 7 | 24 | 32 | | |
| | | 14 | 40 | 34 | | |
| | | 21 | 48 | 48 | | |
| | | 28 | 54 | 67 | | |
| | | 35 | 65 | 75 | | |
| | | 42 | 74 | 97 | | |

Example 80: Antisense Inhibition In Vivo by Oligonucleotides Targeting Alpha-1 Antitrypsin (A1AT) Comprising a $GalNAc_3$ Conjugate The oligonucleotides listed in Table 72 below were tested in a study for dose-dependent inhibition of A1AT in mice.

TABLE 72

| Modified ASOs targeting A1AT | | | | | |
|---|---|---|---|---|---|
| ISIS No. | Sequences (5' to 3') | $GalNAc_3$ Cluster | CM | Unmodified SEQ ID No. | Modified SEQ ID No. |
| 476366 | $A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | n/a | n/a | 261 | 325 |

TABLE 72-continued

| Modified ASOs targeting A1AT | | | | | |
|---|---|---|---|---|---|
| ISIS No. | Sequences (5' to 3') | GalNAc$_3$ Cluster | CM | Unmodified SEQ ID No. | Modified SEQ ID No. |
| 656326 | $A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{eo}$**$A_{do'}$-GalNAc$_3$-1$_a$** | GalNAc$_3$-1a | $A_d$ | 262 | 373 |
| 678381 | **GalNAc$_3$-3$_a$-$_{o'}$$A_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | GalNAc$_3$-3a | $A_d$ | 263 | 415 |
| 678382 | **GalNAc$_3$-7$_a$-$_{o'}$$A_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | GalNAc$_3$-7a | $A_d$ | 263 | 416 |
| 678383 | **GalNAc$_3$-10$_a$-$_{o'}$$A_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | GalNAc$_3$-10a | $A_d$ | 263 | 417 |
| 678384 | **GalNAc$_3$-13$_a$-$_{o'}$$A_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | GalNAc$_3$-13a | $A_d$ | 263 | 418 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six week old, male C57BL/6 mice (Jackson Laboratory, Bar Harbor, ME) were each injected subcutaneously once per week at a dosage shown below, for a total of three doses, with an oligonucleotide listed in Table 72 or with PBS. Each treatment group consisted of 4 animals. The mice were sacrificed 72 hours following the final administration. A1AT liver mRNA levels were determined using real-time PCR and RIBOGREEN® RNA quantification reagent (Molecular Probes, Inc. Eugene, OR) according to standard protocols. A1AT plasma protein levels were determined using the Mouse Alpha 1-Antitrypsin ELISA (catalog #41-A1AMS-E01, Alpco, Salem, NH). The results below are presented as the average percent of A1AT liver mRNA and plasma protein levels for each treatment group, normalized to the PBS control.

As illustrated in Table 73, treatment with antisense oligonucleotides lowered A1AT liver mRNA and A1AT plasma protein levels in a dose-dependent manner. The oligonucleotides comprising a GalNAc conjugate were significantly more potent than the parent (ISIS 476366).

TABLE 73

| A1AT liver mRNA and plasma protein levels | | | | | |
|---|---|---|---|---|---|
| ISIS No. | Dosage (mg/kg) | A1AT liver mRNA (% PBS) | A1AT plasma protein (% PBS) | GalNAc$_3$ Cluster | CM |
| PBS | n/a | 100 | 100 | n/a | n/a |
| 476366 | 5 | 86 | 78 | n/a | n/a |
| | 15 | 73 | 61 | | |
| | 45 | 30 | 38 | | |
| 656326 | 0.6 | 99 | 90 | GalNAc$_3$-1a | $A_d$ |
| | 2 | 61 | 70 | | |
| | 6 | 15 | 30 | | |
| | 18 | 6 | 10 | | |
| 678381 | 0.6 | 105 | 90 | GalNAc$_3$-3a | $A_d$ |
| | 2 | 53 | 60 | | |
| | 6 | 16 | 20 | | |
| | 18 | 7 | 13 | | |
| 678382 | 0.6 | 90 | 79 | GalNAc$_3$-7a | $A_d$ |
| | 2 | 49 | 57 | | |
| | 6 | 21 | 27 | | |
| | 18 | 8 | 11 | | |
| 678383 | 0.6 | 94 | 84 | GalNAc$_3$-10a | $A_d$ |
| | 2 | 44 | 53 | | |
| | 6 | 13 | 24 | | |
| | 18 | 6 | 10 | | |
| 678384 | 0.6 | 106 | 91 | GalNAc$_3$-13a | $A_d$ |
| | 2 | 65 | 59 | | |
| | 6 | 26 | 31 | | |
| | 18 | 11 | 15 | | |

Liver transaminase and BUN levels in plasma were measured at time of sacrifice using standard protocols. Body weights and organ weights were also measured. The results are shown in Table 74 below. Body weight is shown as % relative to baseline. Organ weights are shown as % of body weight relative to the PBS control group.

TABLE 74

| ISIS No. | Dosage (mg/kg) | ALT (U/L) | AST (U/L) | BUN (mg/dL) | Body weight (% baseline) | Liver weight (Rel % BW) | Kidney weight (Rel % BW) | Spleen weight (Rel % BW) |
|---|---|---|---|---|---|---|---|---|
| PBS | n/a | 25 | 51 | 37 | 119 | 100 | 100 | 100 |
| 476366 | 5 | 34 | 68 | 35 | 116 | 91 | 98 | 106 |
| | 15 | 37 | 74 | 30 | 122 | 92 | 101 | 128 |
| | 45 | 30 | 47 | 31 | 118 | 99 | 108 | 123 |
| 656326 | 0.6 | 29 | 57 | 40 | 123 | 100 | 103 | 119 |
| | 2 | 36 | 75 | 39 | 114 | 98 | 111 | 106 |
| | 6 | 32 | 67 | 39 | 125 | 99 | 97 | 122 |
| | 18 | 46 | 77 | 36 | 116 | 102 | 109 | 101 |
| 678381 | 0.6 | 26 | 57 | 32 | 117 | 93 | 109 | 110 |
| | 2 | 26 | 52 | 33 | 121 | 96 | 106 | 125 |
| | 6 | 40 | 78 | 32 | 124 | 92 | 106 | 126 |
| | 18 | 31 | 54 | 28 | 118 | 94 | 103 | 120 |
| 678382 | 0.6 | 26 | 42 | 35 | 114 | 100 | 103 | 103 |
| | 2 | 25 | 50 | 31 | 117 | 91 | 104 | 117 |
| | 6 | 30 | 79 | 29 | 117 | 89 | 102 | 107 |
| | 18 | 65 | 112 | 31 | 120 | 89 | 104 | 113 |
| 678383 | 0.6 | 30 | 67 | 38 | 121 | 91 | 100 | 123 |
| | 2 | 33 | 53 | 33 | 118 | 98 | 102 | 121 |
| | 6 | 32 | 63 | 32 | 117 | 97 | 105 | 105 |
| | 18 | 36 | 68 | 31 | 118 | 99 | 103 | 108 |
| 678384 | 0.6 | 36 | 63 | 31 | 118 | 98 | 103 | 98 |
| | 2 | 32 | 61 | 32 | 119 | 93 | 102 | 114 |
| | 6 | 34 | 69 | 34 | 122 | 100 | 100 | 96 |
| | 18 | 28 | 54 | 30 | 117 | 98 | 101 | 104 |

Example 81: Duration of Action In Vivo of Oligonucleotides Targeting A1AT Comprising a $GalNAc_3$ Cluster The oligonucleotides listed in Table 72 were tested in a single dose study for duration of action in mice.

Treatment

Six week old, male C57BL/6 mice were each injected subcutaneously once with an oligonucleotide listed in Table 72 or with PBS. Each treatment group consisted of 4 animals. Blood was drawn the day before dosing to determine baseline and at 5, 12, 19, and 25 days following the dose. Plasma A1AT protein levels were measured via ELISA (see Example 80). The results below are presented as the average percent of plasma A1AT protein levels for each treatment group, normalized to baseline levels. The results show that the oligonucleotides comprising a GalNAc conjugate were more potent and had longer duration of action than the parent lacking a GalNAc conjugate (ISIS 476366). Furthermore, the oligonucleotides comprising a 5'-GalNAc conjugate (ISIS 678381, 678382, 678383, and 678384) were generally even more potent with even longer duration of action than the oligonucleotide comprising a 3'-GalNAc conjugate (ISIS 656326).

TABLE 75

Plasma A1AT protein levels in mice

| ISIS No. | Dosage (mg/kg) | Time point (days post-dose) | A1AT (% baseline) | $GalNAc_3$ Cluster | CM |
|---|---|---|---|---|---|
| PBS | n/a | 5 | 93 | n/a | n/a |
| | | 12 | 93 | | |
| | | 19 | 90 | | |
| | | 25 | 97 | | |
| 476366 | 100 | 5 | 38 | n/a | n/a |
| | | 12 | 46 | | |
| | | 19 | 62 | | |
| | | 25 | 77 | | |
| 656326 | 18 | 5 | 33 | $GalNAc_3$-1a | $A_d$ |
| | | 12 | 36 | | |
| | | 19 | 51 | | |
| | | 25 | 72 | | |
| 678381 | 18 | 5 | 21 | $GalNAc_3$-3a | $A_d$ |
| | | 12 | 21 | | |
| | | 19 | 35 | | |
| | | 25 | 48 | | |
| 678382 | 18 | 5 | 21 | $GalNAc_3$-7a | $A_d$ |
| | | 12 | 21 | | |
| | | 19 | 39 | | |
| | | 25 | 60 | | |
| 678383 | 18 | 5 | 24 | $GalNAc_3$-10a | $A_d$ |
| | | 12 | 21 | | |
| | | 19 | 45 | | |
| | | 25 | 73 | | |
| 678384 | 18 | 5 | 29 | $GalNAc_3$-13a | $A_d$ |
| | | 12 | 34 | | |
| | | 19 | 57 | | |
| | | 25 | 76 | | |

Example 82: Antisense Inhibition In Vitro by Oligonucleotides Targeting SRB-1 Comprising a $GalNAc_3$ Conjugate Primary mouse liver hepatocytes were seeded in 96 well plates at 15,000 cells/well 2 hours prior to treatment. The oligonucleotides listed in Table 76 were added at 2, 10, 50, or 250 nM in Williams E medium and cells were incubated overnight at 37° C. in 5% $CO_2$. Cells were lysed 16 hours following oligonucleotide addition, and total RNA was purified using RNease 3000 BioRobot (Qiagen). SRB-1 mRNA levels were determined using real-time PCR and RIBOGREEN® RNA quantification reagent (Molecular Probes, Inc. Eugene, OR) according to standard protocols. $IC_{50}$ values were determined using Prism 4 software (Graph- Pad). The results show that oligonucleotides comprising a variety of different GalNAc conjugate groups and a variety of different cleavable moieties are significantly more potent in an in vitro free uptake experiment than the parent oligonucleotides lacking a GalNAc conjugate group (ISIS 353382 and 666841).

TABLE 76

Inhibition of SRB-1 expression in vitro

| ISIS No. | Sequence (5' to 3') | Linkages | GalNAc cluster | CM | $IC_{50}$ (nM) | Unmodified SEQ ID No. | Modified SEQ ID No. |
|---|---|---|---|---|---|---|---|
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$<br>${}^{m}C_{ds}T_{ds}T_{es}{}^{m}C_{es}{}^{m}C_{es}T_{es}T_{e}$ | PS | n/a | n/a | 250 | 252 | 318 |
| 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$<br>${}^{m}C_{ds}T_{ds}T_{es}{}^{m}C_{es}{}^{m}C_{es}T_{es}T_{eo}\mathbf{A}_{do'}\text{-}\mathbf{GalNAc}_3\text{-}\mathbf{1}_a$ | PS | GalNAc$_3$-$1_a$ | $A_d$ | 40 | 253 | 369 |
| 661161 | $\mathbf{GalNAc}_3\text{-}\mathbf{3}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$3_a$ | $A_d$ | 40 | 254 | 376 |
| 661162 | $\mathbf{GalNAc}_3\text{-}\mathbf{3}_a\text{-}_{o'}\mathbf{A}_{do}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | GalNAc$_3$-$3_a$ | $A_d$ | 8 | 254 | 377 |
| 664078 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$<br>${}^{m}C_{ds}T_{ds}T_{es}{}^{m}C_{es}{}^{m}C_{es}T_{es}T_{eo}\mathbf{A}_{do'}\text{-}\mathbf{GalNAc}_3\text{-}\mathbf{9}_a$ | PS | GalNAc$_3$-$9_a$ | $A_d$ | 20 | 253 | 382 |
| 665001 | $\mathbf{GalNAc}_3\text{-}\mathbf{8}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}\text{-}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$8_a$ | $A_d$ | 70 | 254 | 384 |
| 666224 | $\mathbf{GalNAc}_3\text{-}\mathbf{5}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$5_a$ | $A_d$ | 80 | 254 | 385 |
| 666841 | $G_{es}{}^{m}C_{eo}T_{eo}T_{eo}{}^{m}C_{es}A_{ds}G_{ds}T_{ds}{}^{m}C_{ds}A_{ds}T_{ds}G_{ds}A_{ds}$<br>${}^{m}C_{ds}T_{ds}T_{eo}{}^{m}C_{eo}{}^{m}C_{es}T_{es}T_{e}$ | PO/PS | n/a | n/a | >250 | 252 | 329 |
| 666881 | $\mathbf{GalNAc}_3\text{-}\mathbf{10}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$10_a$ | $A_d$ | 30 | 254 | 386 |
| 666904 | $\mathbf{GalNAc}_3\text{-}\mathbf{3}_a\text{-}_{o'}G_{es}{}^{m}C_{es}T_{es}T_{es}{}^{m}C_{es}A_{ds}G_{ds}T_{ds}$<br>${}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$3_a$ | PO | 9 | 252 | 330 |
| 666924 | $\mathbf{GalNAc}_3\text{-}\mathbf{3}_a\text{-}_{o'}\mathbf{T}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$3_a$ | $T_d$ | 15 | 257 | 387 |
| 666961 | $\mathbf{GalNAc}_3\text{-}\mathbf{6}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$6_a$ | $A_d$ | 150 | 254 | 391 |
| 666981 | $\mathbf{GalNAc}_3\text{-}\mathbf{7}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$7_a$ | $A_d$ | 20 | 254 | 392 |
| 670061 | $\mathbf{GalNAc}_3\text{-}\mathbf{13}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$13_a$ | $A_d$ | 30 | 254 | 393 |
| 670699 | $\mathbf{GalNAc}_3\text{-}\mathbf{3}_a\text{-}_{o'}\mathbf{T}_{do}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | GalNAc$_3$-$3_a$ | $T_d$ | 15 | 257 | 394 |
| 670700 | $\mathbf{GalNAc}_3\text{-}\mathbf{3}_a\text{-}_{o'}\mathbf{A}_{eo}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T$ | PO/PS | GalNAc$_3$-$3_a$ | Ae | 30 | 254 | 395 |
| 670701 | $\mathbf{GalNAc}_3\text{-}\mathbf{3}_a\text{-}_{o'}\mathbf{T}_{eo}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | GalNAc$_3$-$3_a$ | Te | 25 | 257 | 396 |
| 671144 | $\mathbf{GalNAc}_3\text{-}\mathbf{12}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$12_a$ | $A_d$ | 40 | 254 | 397 |
| 671165 | $\mathbf{GalNAc}_3\text{-}\mathbf{13}_a\text{-}_{o'}\mathbf{A}_{do}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T$ | PO/PS | GalNAc$_3$-$13_a$ | $A_d$ | 8 | 254 | 398 |
| 671261 | $\mathbf{GalNAc}_3\text{-}\mathbf{14}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$14_a$ | $A_d$ | >250 | 254 | 399 |
| 671262 | $\mathbf{GalNAc}_3\text{-}\mathbf{15}_a\text{-}_{o'}\mathbf{A}_{do}G_{es}{}^{m}C_{es}T_{es}T_{es}{}^{m}C_{es}A_{ds}G_{ds}$<br>$T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-$15_a$ | $A_d$ | >250 | 254 | 400 |
| 673501 | $\mathbf{GalNAc}_3\text{-}\mathbf{7}_a\text{-}_{o'}\mathbf{A}_{do}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | GalNAc$_3$-$7_a$ | $A_d$ | 30 | 254 | 401 |
| 673502 | $\mathbf{GalNAc}_3\text{-}\mathbf{10}_a\text{-}_{o'}\mathbf{A}_{do}G_{es}{}^{m}C_{eo}T_{eo}T_{eo}{}^{m}C_{eo}A_{ds}G_{ds}$<br>$T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | GalNAc$_3$-$10_a$ | $A_d$ | 8 | 254 | 402 |

TABLE 76-continued

Inhibition of SRB-1 expression in vitro

| ISIS No. | Sequence (5' to 3') | Linkages | GalNAc cluster | CM | $IC_{50}$ (nM) | Unmodified SEQ ID No. | Modified SEQ ID No. |
|---|---|---|---|---|---|---|---|
| 675441 | **GalNAc$_3$-17$_a$-$_{o'}$A$_{do}$**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-17$_a$ | $A_d$ | 30 | 254 | 406 |
| 675442 | **GalNAc$_3$-18$_a$-$_{o'}$A$_{do}$**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-18$_a$ | $A_d$ | 20 | 254 | 407 |
| 677841 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**A$_{do'}$-GalNAc$_3$-19$_a$** | PS | GalNAc$_3$-19$_a$ | $A_d$ | 40 | 253 | 408 |
| 677842 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**A$_{do'}$-GalNAc$_3$-20$_a$** | PS | GalNAc$_3$-20$_a$ | $A_d$ | 30 | 253 | 409 |
| 677843 | **GalNAc$_3$-23$_a$-$_{o'}$A$_{do}$**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | GalNAc$_3$-23$_a$ | $A_d$ | 40 | 254 | 410 |

The structure of GalNAc$_3$-1$_a$ was shown previously in Example 9, GalNAc$_3$-3$_a$ was shown in Example 39, GalNAc$_3$-5$_a$ was shown in Example 49, GalNAc$_3$-6$_a$ was shown in Example 51, GalNAc$_3$-7$_a$ was shown in Example 48, GalNAc$_3$-8$_a$ was shown in Example 47, GalNAc$_3$-9$_a$ was shown in Example 52, GalNAc$_3$-10$_a$ was shown in Example 46, GalNAc$_3$-12$_a$ was shown in Example 61, GalNAc$_3$-13$_a$ was shown in Example 62, GalNAc$_3$-14$_a$ was shown in Example 63, GalNAc$_3$-15$_a$ was shown in Example 64, GalNAc$_3$-17$_a$ was shown in Example 68, GalNAc$_3$-18$_a$ was shown in Example 69, GalNAc$_3$-19$_a$ was shown in Example 70, GalNAc$_3$-20$_a$ was shown in Example 71, and GalNAc$_3$-23$_a$ was shown in Example 76.

Example 83: Antisense Inhibition In Vivo by Oligonucleotides Targeting Factor XI Comprising a GalNAc$_3$ Cluster The oligonucleotides listed in Table 77 below were tested in a study for dose-dependent inhibition of Factor XI in mice.

TABLE 77

Modified oligonucleotides targeting Factor XI

| ISIS No. | Sequence (5' to 3') | GalNAc cluster | CM | Unmodified SEQ ID No. | Modified SEQ ID No. |
|---|---|---|---|---|---|
| 404071 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{e}$ | n/a | n/a | 255 | 321 |
| 656173 | $T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{eo}$**A$_{do'}$-GalNAc$_3$-1$_a$** | GalNAc$_3$-1$_a$ | $A_d$ | 256 | 372 |
| 663086 | **GalNAc$_3$-3$_a$-$_{o'}$A$_{do}$**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}$TasTas$^{m}C_{ds}A_{eo}G_{eo}A_{es}G_{es}G_{e}$ | GalNAc$_3$-3$_a$ | $A_d$ | 264 | 381 |
| 678347 | **GalNAc$_3$-7$_a$-$_{o'}$A$_{do}$**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-7$_a$ | $A_d$ | 264 | 412 |
| 678348 | **GalNAc$_3$-10$_a$-$_{o'}$A$_{do}$**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-10$_a$ | $A_d$ | 264 | 413 |
| 678349 | **GalNAc$_3$-13$_a$-$_{o'}$A$_{do}$**$T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{e}$ | GalNAc$_3$-13$_a$ | $A_d$ | 264 | 414 |

The structure of $GalNAc_3$-$1_a$ was shown previously in Example 9, $GalNAc_3$-$3_a$ was shown in Example 39, $GalNAc_3$-$7_a$ was shown in Example 48, $GalNAc_3$-$10_a$ was shown in Example 46, and $GalNAc_3$-$13_a$ was shown in Example 62.

Treatment

Six to eight week old mice were each injected subcutaneously once per week at a dosage shown below, for a total of three doses, with an oligonucleotide listed below or with PBS. Each treatment group consisted of 4 animals. The mice were sacrificed 72 hours following the final dose. Factor XI liver mRNA levels were measured using real-time PCR and normalized to cyclophilin according to standard protocols. Liver transaminases, BUN, and bilirubin were also measured. The results below are presented as the average percent for each treatment group, normalized to the PBS control.

As illustrated in Table 78, treatment with antisense oligonucleotides lowered Factor XI liver mRNA in a dose-dependent manner. The results show that the oligonucleotides comprising a GalNAc conjugate were more potent than the parent lacking a GalNAc conjugate (ISIS 404071). Furthermore, the oligonucleotides comprising a 5'-GalNAc conjugate (ISIS 663086, 678347, 678348, and 678349) were even more potent than the oligonucleotide comprising a 3'-GalNAc conjugate (ISIS 656173).

TABLE 78

Factor XI liver mRNA, liver transaminase, BUN, and bilirubin levels

| ISIS No. | Dosage (mg/kg) | Factor XI mRNA (% PBS) | ALT (U/L) | AST (U/L) | BUN (mg/dL) | Bilirubin (mg/dL) | $GalNAc_3$ Cluster | SEQ ID No. |
|---|---|---|---|---|---|---|---|---|
| PBS | n/a | 100 | 63 | 70 | 21 | 0.18 | n/a | n/a |
| 404071 | 3 | 65 | 41 | 58 | 21 | 0.15 | n/a | 255 |
| | 10 | 33 | 49 | 53 | 23 | 0.15 | | |
| | 30 | 17 | 43 | 57 | 22 | 0.14 | | |
| 656173 | 0.7 | 43 | 90 | 89 | 21 | 0.16 | $GalNAc_3$-1a | 256 |
| | 2 | 9 | 36 | 58 | 26 | 0.17 | | |
| | 6 | 3 | 50 | 63 | 25 | 0.15 | | |
| 663086 | 0.7 | 33 | 91 | 169 | 25 | 0.16 | $GalNAc_3$-3a | 264 |
| | 2 | 7 | 38 | 55 | 21 | 0.16 | | |
| | 6 | 1 | 34 | 40 | 23 | 0.14 | | |
| 678347 | 0.7 | 35 | 28 | 49 | 20 | 0.14 | $GalNAc_3$-7a | 264 |
| | 2 | 10 | 180 | 149 | 21 | 0.18 | | |
| | 6 | 1 | 44 | 76 | 19 | 0.15 | | |
| 678348 | 0.7 | 39 | 43 | 54 | 21 | 0.16 | $GalNAc_3$-10a | 264 |
| | 2 | 5 | 38 | 55 | 22 | 0.17 | | |
| | 6 | 2 | 25 | 38 | 20 | 0.14 | | |
| 678349 | 0.7 | 34 | 39 | 46 | 20 | 0.16 | $GalNAc_3$-13a | 264 |
| | 2 | 8 | 43 | 63 | 21 | 0.14 | | |
| | 6 | 2 | 28 | 41 | 20 | 0.14 | | |

Example 84: Duration of Action In Vivo of Oligonucleotides Targeting Factor XI Comprising a $GalNAc_3$ Conjugate The oligonucleotides listed in Table 77 were tested in a single dose study for duration of action in mice.

Treatment

Six to eight week old mice were each injected subcutaneously once with an oligonucleotide listed in Table 77 or with PBS. Each treatment group consisted of 4 animals. Blood was drawn by tail bleeds the day before dosing to determine baseline and at 3, 10, and 17 days following the dose. Plasma Factor XI protein levels were measured by ELISA using Factor XI capture and biotinylated detection antibodies from R & D Systems, Minneapolis, MN (catalog #AF2460 and #BAF2460, respectively) and the OptEIA Reagent Set B (Catalog #550534, BD Biosciences, San Jose, CA). The results below are presented as the average percent of plasma Factor XI protein levels for each treatment group, normalized to baseline levels. The results show that the oligonucleotides comprising a GalNAc conjugate were more potent with longer duration of action than the parent lacking a GalNAc conjugate (ISIS 404071). Furthermore, the oligonucleotides comprising a 5'-GalNAc conjugate (ISIS 663086, 678347, 678348, and 678349) were even more potent with an even longer duration of action than the oligonucleotide comprising a 3'-GalNAc conjugate (ISIS 656173).

TABLE 79

| Plasma Factor XI protein levels in mice | | | | | | |
|---|---|---|---|---|---|---|
| ISIS No. | Dosage (mg/kg) | Time point (days post-dose) | Factor XI (% baseline) | $GalNAc_3$ Cluster | CM | SEQ ID No. |
| PBS | n/a | 3 | 123 | n/a | n/a | n/a |
| | | 10 | 56 | | | |
| | | 17 | 100 | | | |
| 404071 | 30 | 3 | 11 | n/a | n/a | 255 |
| | | 10 | 47 | | | |
| | | 17 | 52 | | | |
| 656173 | 6 | 3 | 1 | $GalNAc_3$-1a | $A_d$ | 256 |
| | | 10 | 3 | | | |
| | | 17 | 21 | | | |
| 663086 | 6 | 3 | 1 | $GalNAc_3$-3a | $A_d$ | 264 |
| | | 10 | 2 | | | |
| | | 17 | 9 | | | |
| 678347 | 6 | 3 | 1 | $GalNAc_3$-7a | $A_d$ | 264 |
| | | 10 | 1 | | | |
| | | 17 | 8 | | | |
| 678348 | 6 | 3 | 1 | $GalNAc_3$-10a | $A_d$ | 264 |
| | | 10 | 1 | | | |
| | | 17 | 6 | | | |
| 678349 | 6 | 3 | 1 | $GalNAc_3$-13a | $A_d$ | 264 |
| | | 10 | 1 | | | |
| | | 17 | 5 | | | |

Example 85: Antisense Inhibition In Vivo by Oligonucleotides Targeting SRB-1 Comprising a $GalNAc_3$ Conjugate Oligonucleotides listed in Table 76 were tested in a dose-dependent study for antisense inhibition of SRB-1 in mice.

Treatment

Six to eight week old C57BL/6 mice were each injected subcutaneously once per week at a dosage shown below, for a total of three doses, with an oligonucleotide listed in Table 76 or with saline. Each treatment group consisted of 4 animals. The mice were sacrificed 48 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of liver SRB-1 mRNA levels for each treatment group, normalized to the saline control.

As illustrated in Tables 80 and 81, treatment with antisense oligonucleotides lowered SRB-1 mRNA levels in a dose-dependent manner.

TABLE 80

| SRB-1 mRNA in liver | | | | |
|---|---|---|---|---|
| ISIS No. | Dosage (mg/kg) | SRB-1 mRNA (% Saline) | $GalNAc_3$ Cluster | CM |
| Saline | n/a | 100 | n/a | n/a |
| 655861 | 0.1 | 94 | $GalNAc_3$-1a | $A_d$ |
| | 0.3 | 119 | | |
| | 1 | 68 | | |
| | 3 | 32 | | |
| 661161 | 0.1 | 120 | $GalNAc_3$-3a | $A_d$ |
| | 0.3 | 107 | | |
| | 1 | 68 | | |
| | 3 | 26 | | |
| 666881 | 0.1 | 107 | $GalNAc_3$-10a | $A_d$ |
| | 0.3 | 107 | | |
| | 1 | 69 | | |
| | 3 | 27 | | |
| 666981 | 0.1 | 120 | $GalNAc_3$-7a | $A_d$ |
| | 0.3 | 103 | | |

TABLE 80-continued

| SRB-1 mRNA in liver | | | | |
|---|---|---|---|---|
| ISIS No. | Dosage (mg/kg) | SRB-1 mRNA (% Saline) | $GalNAc_3$ Cluster | CM |
| | 1 | 54 | | |
| | 3 | 21 | | |
| 670061 | 0.1 | 118 | $GalNAc_3$-13a | $A_d$ |
| | 0.3 | 89 | | |
| | 1 | 52 | | |
| | 3 | 18 | | |
| 677842 | 0.1 | 119 | $GalNAc_3$-20a | $A_d$ |
| | 0.3 | 96 | | |
| | 1 | 65 | | |
| | 3 | 23 | | |

TABLE 81

| SRB-1 mRNA in liver | | | | |
|---|---|---|---|---|
| ISIS No. | Dosage (mg/kg) | SRB-1 mRNA (% Saline) | $GalNAc_3$ Cluster | CM |
| 661161 | 0.1 | 107 | $GalNAc_3$-3a | $A_d$ |
| | 0.3 | 95 | | |
| | 1 | 53 | | |
| | 3 | 18 | | |
| 677841 | 0.1 | 110 | $GalNAc_3$-19a | $A_d$ |
| | 0.3 | 88 | | |
| | 1 | 52 | | |
| | 3 | 25 | | |

Liver transaminase levels, total bilirubin, BUN, and body weights were also measured using standard protocols. Average values for each treatment group are shown in Table 82 below.

TABLE 82

| ISIS No. | Dosage (mg/kg) | ALT (U/L) | AST (U/L) | Bilirubin (mg/dL) | BUN (mg/dL) | Body Weight (% baseline) | $GalNAc_3$ Cluster | CM |
|---|---|---|---|---|---|---|---|---|
| Saline | n/a | 19 | 39 | 0.17 | 26 | 118 | n/a | n/a |
| 655861 | 0.1 | 25 | 47 | 0.17 | 27 | 114 | $GalNAc_3$-1a | $A_d$ |
| | 0.3 | 29 | 56 | 0.15 | 27 | 118 | | |
| | 1 | 20 | 32 | 0.14 | 24 | 112 | | |
| | 3 | 27 | 54 | 0.14 | 24 | 115 | | |
| 661161 | 0.1 | 35 | 83 | 0.13 | 24 | 113 | $GalNAc_3$-3a | $A_d$ |
| | 0.3 | 42 | 61 | 0.15 | 23 | 117 | | |
| | 1 | 34 | 60 | 0.18 | 22 | 116 | | |
| | 3 | 29 | 52 | 0.13 | 25 | 117 | | |
| 666881 | 0.1 | 30 | 51 | 0.15 | 23 | 118 | $GalNAc_3$-10a | $A_d$ |
| | 0.3 | 49 | 82 | 0.16 | 25 | 119 | | |
| | 1 | 23 | 45 | 0.14 | 24 | 117 | | |
| | 3 | 20 | 38 | 0.15 | 21 | 112 | | |
| 666981 | 0.1 | 21 | 41 | 0.14 | 22 | 113 | $GalNAc_3$-7a | $A_d$ |
| | 0.3 | 29 | 49 | 0.16 | 24 | 112 | | |
| | 1 | 19 | 34 | 0.15 | 22 | 111 | | |
| | 3 | 77 | 78 | 0.18 | 25 | 115 | | |
| 670061 | 0.1 | 20 | 63 | 0.18 | 24 | 111 | $GalNAc_3$-13a | $A_d$ |
| | 0.3 | 20 | 57 | 0.15 | 21 | 115 | | |
| | 1 | 20 | 35 | 0.14 | 20 | 115 | | |
| | 3 | 27 | 42 | 0.12 | 20 | 116 | | |
| 677842 | 0.1 | 20 | 38 | 0.17 | 24 | 114 | $GalNAc_3$-20a | $A_d$ |
| | 0.3 | 31 | 46 | 0.17 | 21 | 117 | | |
| | 1 | 22 | 34 | 0.15 | 21 | 119 | | |
| | 3 | 41 | 57 | 0.14 | 23 | 118 | | |

Example 86: Antisense Inhibition In Vivo by Oligonucleotides Targeting TTR Comprising a $GalNAc_3$ Cluster Oligonucleotides listed in Table 83 below were tested in a dose-dependent study for antisense inhibition of human transthyretin (TTR) in transgenic mice that express the human TTR gene.

Treatment

Eight week old TTR transgenic mice were each injected subcutaneously once per week for three weeks, for a total of three doses, with an oligonucleotide and dosage listed in the tables below or with PBS. Each treatment group consisted of 4 animals. The mice were sacrificed 72 hours following the final administration. Tail bleeds were performed at various time points throughout the experiment, and plasma TTR protein, ALT, and AST levels were measured and reported in Tables 85-87. After the animals were sacrificed, plasma ALT, AST, and human TTR levels were measured, as were body weights, organ weights, and liver human TTR mRNA levels. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Tables 84-87 are the average values for each treatment group. The mRNA levels are the average values relative to the average for the PBS group. Plasma protein levels are the average values relative to the average value for the PBS group at baseline. Body weights are the average percent weight change from baseline until sacrifice for each individual treatment group. Organ weights shown are normalized to the animal's body weight, and the average normalized organ weight for each treatment group is then presented relative to the average normalized organ weight for the PBS group.

In Tables 84-87, "BL" indicates baseline, measurements that were taken just prior to the first dose. As illustrated in Tables 84 and 85, treatment with antisense oligonucleotides lowered TTR expression levels in a dose-dependent manner. The oligonucleotides comprising a GalNAc conjugate were more potent than the parent lacking a GalNAc conjugate (ISIS 420915). Furthermore, the oligonucleotides comprising a GalNAc conjugate and mixed PS/PO internucleoside linkages were even more potent than the oligonucleotide comprising a GalNAc conjugate and full PS linkages.

TABLE 83

Oligonucleotides targeting human TTR

| Isis No. | Sequence 5' to 3' | Linkages | GalNAc cluster | CM | Unmodified SEQ ID No. | Modified SEQ ID No. |
|---|---|---|---|---|---|---|
| 420915 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | Ps | n/a | n/a | 265 | 323 |
| 660261 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}$ **$A_{do'}$-GalNAc$_3$-1$_a$** | PS | $GalNAc_3$-1a | $A_d$ | 266 | 375 |

TABLE 83-continued

| Oligonucleotides targeting human TTR | | | | | | |
|---|---|---|---|---|---|---|
| Isis No. | Sequence 5' to 3' | Linkages | GalNAc cluster | CM | Unmodified SEQ ID No. | Modified SEQ ID No. |
| 682883 | **$GalNAc_3$-$3_a$**-$_{o'}T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-3a | PO | 265 | 345 |
| 682884 | **$GalNAc_3$-$7_a$**-$_{o'}T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-7a | PO | 265 | 346 |
| 682885 | **$GalNAc_3$-$10_a$**-$_{o'}T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-10a | PO | 265 | 347 |
| 682886 | **$GalNAc_3$-$13_a$**-$_{o'}T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-13a | PO | 265 | 348 |
| 684057 | $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{eo}$**$A_{do'}$-$GalNAc_3$-$19_a$** | PS/PO | $GalNAc_3$-19a | $A_d$ | 266 | 430 |

The legend for Table 85 can be found in Example 74. The structure of $GalNAc_3$-1 was shown in Example 9. The structure of $GalNAc_3$-$3_a$ was shown in Example 39. The structure of $GalNAc_3$-$7_a$ was shown in Example 48. The structure of $GalNAc_3$-$10_a$ was shown in Example 46. The structure of $GalNAc_3$-$13_a$ was shown in Example 62. The structure of $GalNAc_3$-$19_a$ was shown in Example 70.

TABLE 84

| Antisense inhibition of human TTR in vivo | | | | | | |
|---|---|---|---|---|---|---|
| Isis No. | Dosage (mg/kg) | TTR mRNA (% PBS) | Plasma TTR protein (% PBS) | GalNAc cluster | CM | SEQ ID No. |
| PBS | n/a | 100 | 100 | n/a | n/a | |
| 420915 | 6 | 99 | 95 | n/a | n/a | 265 |
| | 20 | 48 | 65 | | | |
| | 60 | 18 | 28 | | | |
| 660261 | 0.6 | 113 | 87 | $GalNAc_3$-1a | $A_d$ | 266 |
| | 2 | 40 | 56 | | | |
| | 6 | 20 | 27 | | | |
| | 20 | 9 | 11 | | | |

TABLE 85

| Antisense inhibition of human TTR in vivo | | | | | | | | | |
|---|---|---|---|---|---|---|---|---|---|
| | | TTR | Plasma TTR protein (% PBS at BL) | | | | | | |
| Isis No. | Dosage (mg/kg) | mRNA (% PBS) | BL | Day 3 | Day 10 | Day 17 (After sac) | GalNAc cluster | CM | SEQ ID No. |
| PBS | n/a | 100 | 100 | 96 | 90 | 114 | n/a | n/a | |
| 420915 | 6 | 74 | 106 | 86 | 76 | 83 | n/a | n/a | 265 |
| | 20 | 43 | 102 | 66 | 61 | 58 | | | |
| | 60 | 24 | 92 | 43 | 29 | 32 | | | |
| 682883 | 0.6 | 60 | 88 | 73 | 63 | 68 | $GalNAc_3$-3a | PO | 265 |
| | 2 | 18 | 75 | 38 | 23 | 23 | | | |
| | 6 | 10 | 80 | 35 | 11 | 9 | | | |
| 682884 | 0.6 | 56 | 88 | 78 | 63 | 67 | $GalNAc_3$-7a | PO | 265 |
| | 2 | 19 | 76 | 44 | 25 | 23 | | | |
| | 6 | 15 | 82 | 35 | 21 | 24 | | | |

TABLE 85-continued

Antisense inhibition of human TTR in vivo

| Isis No. | Dosage (mg/kg) | TTR mRNA (% PBS) | Plasma TTR protein (% PBS at BL) BL | Day 3 | Day 10 | Day 17 (After sac) | GalNAc cluster | CM | SEQ ID No. |
|---|---|---|---|---|---|---|---|---|---|
| 682885 | 0.6 | 60 | 92 | 77 | 68 | 76 | GalNAc$_3$-10a | PO | 265 |
| | 2 | 22 | 93 | 58 | 32 | 32 | | | |
| | 6 | 17 | 85 | 37 | 25 | 20 | | | |
| 682886 | 0.6 | 57 | 91 | 70 | 64 | 69 | GalNAc$_3$-13a | PO | 265 |
| | 2 | 21 | 89 | 50 | 31 | 30 | | | |
| | 6 | 18 | 102 | 41 | 24 | 27 | | | |
| 684057 | 0.6 | 53 | 80 | 69 | 56 | 62 | GalNAc$_3$-19a | $A_d$ | 266 |
| | 2 | 21 | 92 | 55 | 34 | 30 | | | |
| | 6 | 11 | 82 | 50 | 18 | 13 | | | |

TABLE 86

Transaminase levels, body weight changes, and relative organ weights

| Isis No. | Dosage (mg/kg) | ALT (U/L) BL | Day 3 | Day 10 | Day 17 | AST (U/L) BL | Day 3 | Day 10 | Day 17 | Body (% BL) | Liver (% PBS) | Spleen (% PBS) | Kidney (% PBS) | SEQ ID No. |
|---|---|---|---|---|---|---|---|---|---|---|---|---|---|---|
| PBS | n/a | 33 | 34 | 33 | 24 | 58 | 62 | 67 | 52 | 105 | 100 | 100 | 100 | n/a |
| 420915 | 6 | 34 | 33 | 27 | 21 | 64 | 59 | 73 | 47 | 115 | 99 | 89 | 91 | 265 |
| | 20 | 34 | 30 | 28 | 19 | 64 | 54 | 56 | 42 | 111 | 97 | 83 | 89 | |
| | 60 | 34 | 35 | 31 | 24 | 61 | 58 | 71 | 58 | 113 | 102 | 98 | 95 | |
| 660261 | 0.6 | 33 | 38 | 28 | 26 | 70 | 71 | 63 | 59 | 111 | 96 | 99 | 92 | 266 |
| | 2 | 29 | 32 | 31 | 34 | 61 | 60 | 68 | 61 | 118 | 100 | 92 | 90 | |
| | 6 | 29 | 29 | 28 | 34 | 58 | 59 | 70 | 90 | 114 | 99 | 97 | 95 | |
| | 20 | 33 | 32 | 28 | 33 | 64 | 54 | 68 | 95 | 114 | 101 | 106 | 92 | |

TABLE 87

Transaminase levels, body weight changes, and relative organ weights

| Isis No. | Dosage (mg/kg) | ALT (U/L) BL | Day 3 | Day 10 | Day 17 | AST (U/L) BL | Day 3 | Day 10 | Day 17 | Body (% BL) | Liver (% PBS) | Spleen (% PBS) | Kidney (% PBS) | SEQ ID No. |
|---|---|---|---|---|---|---|---|---|---|---|---|---|---|---|
| PBS | n/a | 32 | 34 | 37 | 41 | 62 | 78 | 76 | 77 | 104 | 100 | 100 | 100 | n/a |
| 420915 | 6 | 32 | 30 | 34 | 34 | 61 | 71 | 72 | 66 | 102 | 103 | 102 | 105 | 265 |
| | 20 | 41 | 34 | 37 | 33 | 80 | 76 | 63 | 54 | 106 | 107 | 135 | 101 | |
| | 60 | 36 | 30 | 32 | 34 | 58 | 81 | 57 | 60 | 106 | 105 | 104 | 99 | |
| 682883 | 0.6 | 32 | 35 | 38 | 40 | 53 | 81 | 74 | 76 | 104 | 101 | 112 | 95 | 265 |
| | 2 | 38 | 39 | 42 | 43 | 71 | 84 | 70 | 77 | 107 | 98 | 116 | 99 | |
| | 6 | 35 | 35 | 41 | 38 | 62 | 79 | 103 | 65 | 105 | 103 | 143 | 97 | |
| 682884 | 0.6 | 33 | 32 | 35 | 34 | 70 | 74 | 75 | 67 | 101 | 100 | 130 | 99 | 265 |
| | 2 | 31 | 32 | 38 | 38 | 63 | 77 | 66 | 55 | 104 | 103 | 122 | 100 | |
| | 6 | 38 | 32 | 36 | 34 | 65 | 85 | 80 | 62 | 99 | 105 | 129 | 95 | |
| 682885 | 0.6 | 39 | 26 | 37 | 35 | 63 | 63 | 77 | 59 | 100 | 109 | 109 | 112 | 265 |
| | 2 | 30 | 26 | 38 | 40 | 54 | 56 | 71 | 72 | 102 | 98 | 111 | 102 | |
| | 6 | 27 | 27 | 34 | 35 | 46 | 52 | 56 | 64 | 102 | 98 | 113 | 96 | |
| 682886 | 0.6 | 30 | 40 | 34 | 36 | 58 | 87 | 54 | 61 | 104 | 99 | 120 | 101 | 265 |
| | 2 | 27 | 26 | 34 | 36 | 51 | 55 | 55 | 69 | 103 | 91 | 105 | 92 | |
| | 6 | 40 | 28 | 34 | 37 | 107 | 54 | 61 | 69 | 109 | 100 | 102 | 99 | |
| 684057 | 0.6 | 35 | 26 | 33 | 39 | 56 | 51 | 51 | 69 | 104 | 99 | 110 | 102 | 266 |
| | 2 | 33 | 32 | 31 | 40 | 54 | 57 | 56 | 87 | 103 | 100 | 112 | 97 | |
| | 6 | 39 | 33 | 35 | 40 | 67 | 52 | 55 | 92 | 98 | 104 | 121 | 108 | |

Example 87: Duration of Action In Vivo by Single Doses of Oligonucleotides Targeting TTR Comprising a GalNAc$_3$ Cluster ISIS numbers 420915 and 660261 (see Table 83) were tested in a single dose study for duration of action in mice. ISIS numbers 420915, 682883, and 682885 (see Table 83) were also tested in a single dose study for duration of action in mice.

Treatment

Eight week old, male transgenic mice that express human TTR were each injected subcutaneously once with 100 mg/kg ISIS No. 420915 or 13.5 mg/kg ISIS No. 660261. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 88

Plasma TTR protein levels

| ISIS No. | Dosage (mg/kg) | Time point (days post-dose) | TTR (% base-line) | $GalNAc_3$ Cluster | CM | SEQ ID No. |
|---|---|---|---|---|---|---|
| 420915 | 100 | 3 | 30 | n/a | n/a | 265 |
| | | 7 | 23 | | | |
| | | 10 | 35 | | | |
| | | 17 | 53 | | | |
| | | 24 | 75 | | | |
| | | 39 | 100 | | | |
| 660261 | 13.5 | 3 | 27 | $GalNAc_3$-1a | $A_d$ | 266 |
| | | 7 | 21 | | | |
| | | 10 | 22 | | | |
| | | 17 | 36 | | | |
| | | 24 | 48 | | | |
| | | 39 | 69 | | | |

Treatment

Female transgenic mice that express human TTR were each injected subcutaneously once with 100 mg/kg ISIS No. 420915, 10.0 mg/kg ISIS No. 682883, or 10.0 mg/kg 682885. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 89

Plasma TTR protein levels

| ISIS No. | Dosage (mg/kg) | Time point (days post-dose) | TTR (% base-line) | $GalNAc_3$ Cluster | CM | SEQ ID No. |
|---|---|---|---|---|---|---|
| 420915 | 100 | 3 | 48 | n/a | n/a | 265 |
| | | 7 | 48 | | | |
| | | 10 | 48 | | | |
| | | 17 | 66 | | | |
| | | 31 | 80 | | | |
| 682883 | 10.0 | 3 | 45 | $GalNAc_3$-3a | PO | 265 |
| | | 7 | 37 | | | |
| | | 10 | 38 | | | |
| | | 17 | 42 | | | |
| | | 31 | 65 | | | |

TABLE 89-continued

Plasma TTR protein levels

| ISIS No. | Dosage (mg/kg) | Time point (days post-dose) | TTR (% base-line) | $GalNAc_3$ Cluster | CM | SEQ ID No. |
|---|---|---|---|---|---|---|
| 682885 | 10.0 | 3 | 40 | $GalNAc_3$-10a | PO | 265 |
| | | 7 | 33 | | | |
| | | 10 | 34 | | | |
| | | 17 | 40 | | | |
| | | 31 | 64 | | | |

The results in Tables 88 and 89 show that the oligonucleotides comprising a GalNAc conjugate are more potent with a longer duration of action than the parent oligonucleotide lacking a conjugate (ISIS 420915).

Example 88: Splicing Modulation In Vivo by Oligonucleotides Targeting SMN Comprising a $GalNAc_3$ Conjugate The oligonucleotides listed in Table 90 were tested for splicing modulation of human survival of motor neuron (SMN) in mice.

TABLE 90

Modified ASOs targeting SMN

| ISIS No. | Sequences (5' to 3') | $GalNAc_3$ Cluster | CM | Unmodified SEQ ID No. | Modified SEQ ID No. |
|---|---|---|---|---|---|
| 387954 | $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_e$ | n/a | n/a | 267 | 320 |
| 699819 | **$GalNAc_3$-7**$_a$-$_{o'}$$A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{e}T_{es}G_{es}G_e$ | $GalNAc_3$-7a | PO | 267 | 352 |
| 699821 | **$GalNAc_3$-7**$_a$-$_{o'}$$A_{es}T_{eo}T_{eo}{}^{m}C_{eo}A_{eo}{}^{m}C_{eo}T_{eo}T_{eo}T_{eo}{}^{m}C_{eo}A_{eo}T_{eo}A_{eo}A_{eo}T_{eo}G_{eo}{}^{m}C_{eo}T_{es}G_{es}G_e$ | $GalNAc_3$-7a | PO | 267 | 353 |
| 700000 | $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_{eo}$**A**$_{do'}$-**$GalNAc_3$-1**$_a$ | $GalNAc_3$-1a | $A_d$ | 268 | 431 |
| 703421 | X-ATT$^m$CA$^m$CTTT$^m$CATAATG$^m$CTGG | n/a | n/a | 267 | N/A |
| 703422 | **$GalNAc_3$-7**$_b$-X-ATT$^m$CA$^m$CTTT$^m$CATAATG$^m$CTGG | $GalNAc_3$-7b | n/a | 267 | N/A |

The structure of $GalNAc_3$-$7_a$ was shown previously in Example 48. "X" indicates a 5' primary amine generated by Gene Tools (Philomath, OR), and $GalNAc_3$-$7_b$ indicates the structure of $GalNAc_3$-$7_a$ lacking the —NH—$C_6$—O portion of the linker as shown below:

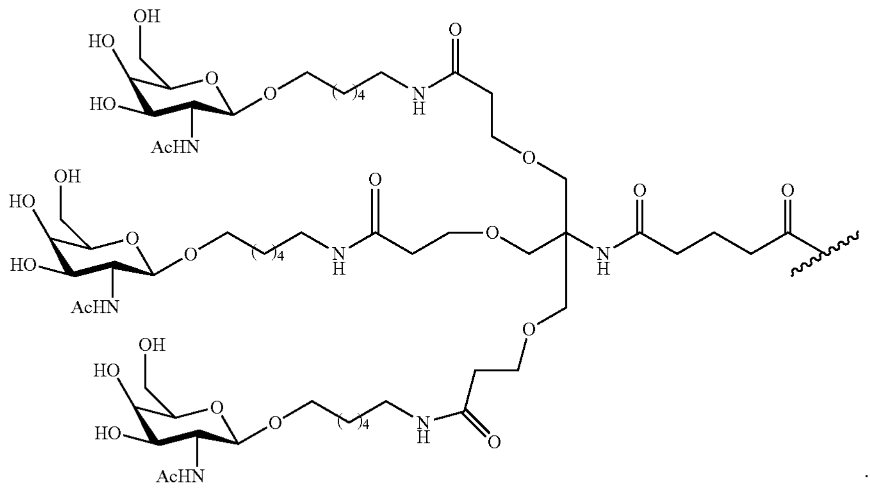

ISIS numbers 703421 and 703422 are morpholino oligonucleotides, wherein each nucleotide of the two oligonucleotides is a morpholino nucleotide.

Treatment

Six week old transgenic mice that express human SMN were injected subcutaneously once with an oligonucleotide listed in Table 91 or with saline. Each treatment group consisted of 2 males and 2 females. The mice were sacrificed 3 days following the dose to determine the liver human SMN mRNA levels both with and without exon 7 using real-time PCR according to standard protocols. Total RNA was measured using Ribogreen reagent. The SMN mRNA levels were normalized to total mRNA, and further normalized to the averages for the saline treatment group. The resulting average ratios of SMN mRNA including exon 7 to SMN mRNA missing exon 7 are shown in Table 91. The results show that fully modified oligonucleotides that modulate splicing and comprise a GalNAc conjugate are significantly more potent in altering splicing in the liver than the parent oligonucleotides lacking a GlaNAc conjugate. Furthermore, this trend is maintained for multiple modification chemistries, including 2'-MOE and morpholino modified oligonucleotides.

TABLE 91

Effect of oligonucleotides targeting human SMN in vivo

| ISIS No. | Dose (mg/kg) | +Exon 7/ −Exon 7 | $GalNAc_3$ Cluster | CM | SEQ ID No. |
|---|---|---|---|---|---|
| Saline | n/a | 1.00 | n/a | n/a | n/a |
| 387954 | 32 | 1.65 | n/a | n/a | 267 |
| 387954 | 288 | 5.00 | n/a | n/a | 267 |
| 699819 | 32 | 7.84 | $GalNAc_3$-7a | PO | 267 |
| 699821 | 32 | 7.22 | $GalNAc_3$-7a | PO | 267 |
| 700000 | 32 | 6.91 | $GalNAc_3$-1a | $A_d$ | 268 |
| 703421 | 32 | 1.27 | n/a | n/a | 267 |
| 703422 | 32 | 4.12 | $GalNAc_3$-7b | n/a | 267 |

Example 89: Antisense Inhibition In Vivo by Oligonucleotides Targeting Apolipoprotein A (Apo(a)) Comprising a $GalNAc_3$ Conjugate The oligonucleotides listed in Table 92 below were tested in a study for dose-dependent inhibition of Apo(a) in transgenic mice.

TABLE 92

Modified ASOs targeting Apo(a)

| ISIS No. | Sequences (5' to 3') | $GalNAc_3$ Cluster | CM | Unmodified SEQ ID No. | Modified SEQ ID No. |
|---|---|---|---|---|---|
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 277 | 326 |
| 681257 | **$GalNAc_3$-$7_a$-$_{o'}$**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-7a | PO | 277 | 338 |

The structure of $GalNAc_3$-$7_a$ was shown in Example 48.

Treatment

Eight week old, female C57BL/6 mice (Jackson Laboratory, Bar Harbor, ME) were each injected subcutaneously once per week at a dosage shown below, for a total of six doses, with an oligonucleotide listed in Table 92 or with PBS. Each treatment group consisted of 3-4 animals. Tail bleeds were performed the day before the first dose and weekly following each dose to determine plasma Apo(a) protein levels. The mice were sacrificed two days following the final administration. Apo(a) liver mRNA levels were determined using real-time PCR and RIBOGREEN® RNA quantification reagent (Molecular Probes, Inc. Eugene, OR) according to standard protocols. Apo(a) plasma protein levels were determined using ELISA, and liver transaminase levels were determined. The mRNA and plasma protein results in Table 93 are presented as the treatment group average percent relative to the PBS treated group. Plasma protein levels were further normalized to the baseline (BL) value for the PBS group. Average absolute transaminase levels and body weights (% relative to baseline averages) are reported in Table 94.

As illustrated in Table 93, treatment with the oligonucleotides lowered Apo(a) liver mRNA and plasma protein levels in a dose-dependent manner. Furthermore, the oligonucleotide comprising the GalNAc conjugate was significantly more potent with a longer duration of action than the parent oligonucleotide lacking a GalNAc conjugate. As illustrated in Table 94, transaminase levels and body weights were unaffected by the oligonucleotides, indicating that the oligonucleotides were well tolerated.

TABLE 93

| Apo(a) liver mRNA and plasma protein levels | | | | | | | | | |
|---|---|---|---|---|---|---|---|---|---|
| ISIS No. | Dosage (mg/kg) | Apo(a) mRNA (% PBS) | Apo(a) plasma protein (% PBS) | | | | | | |
| | | | BL | Week 1 | Week 2 | Week 3 | Week 4 | Week 5 | Week 6 |
| PBS | n/a | 100 | 100 | 120 | 119 | 113 | 88 | 121 | 97 |
| 494372 | 3 | 80 | 84 | 89 | 91 | 98 | 87 | 87 | 79 |
| | 10 | 30 | 87 | 72 | 76 | 71 | 57 | 59 | 46 |
| | 30 | 5 | 92 | 54 | 28 | 10 | 7 | 9 | 7 |
| 681257 | 0.3 | 75 | 79 | 76 | 89 | 98 | 71 | 94 | 78 |
| | 1 | 19 | 79 | 88 | 66 | 60 | 54 | 32 | 24 |
| | 3 | 2 | 82 | 52 | 17 | 7 | 4 | 6 | 5 |
| | 10 | 2 | 79 | 17 | 6 | 3 | 2 | 4 | 5 |

TABLE 94

| ISIS No. | Dosage (mg/kg) | ALT (U/L) | AST (U/L) | Body weight (% baseline) |
|---|---|---|---|---|
| PBS | n/a | 37 | 54 | 103 |
| 494372 | 3 | 28 | 68 | 106 |
| | 10 | 22 | 55 | 102 |
| | 30 | 19 | 48 | 103 |
| 681257 | 0.3 | 30 | 80 | 104 |
| | 1 | 26 | 47 | 105 |
| | 3 | 29 | 62 | 102 |
| | 10 | 21 | 52 | 107 |

Example 90: Antisense Inhibition In Vivo by Oligonucleotides Targeting TTR Comprising a $GalNAc_3$ Cluster Oligonucleotides listed in Table 95 below were tested in a dose-dependent study for antisense inhibition of human transthyretin (TTR) in transgenic mice that express the human TTR gene.

Treatment

TTR transgenic mice were each injected subcutaneously once per week for three weeks, for a total of three doses, with an oligonucleotide and dosage listed in Table 96 or with PBS. Each treatment group consisted of 4 animals. Prior to the first dose, a tail bleed was performed to determine plasma TTR protein levels at baseline (BL). The mice were sacrificed 72 hours following the final administration. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Table 96 are the average values for each treatment group. The mRNA levels are the average values relative to the average for the PBS group. Plasma protein levels are the average values relative to the average value for the PBS group at baseline. "BL" indicates baseline, measurements that were taken just prior to the first dose. As illustrated in Table 96, treatment with antisense oligonucleotides lowered TTR expression levels in a dose-dependent manner. The oligonucleotides comprising a GalNAc conjugate were more potent than the parent lacking a GalNAc conjugate (ISIS 420915), and oligonucleotides comprising a phosphodiester or deoxyadenosine cleavable moiety showed significant improvements in potency compared to the parent lacking a conjugate (see ISIS numbers 682883 and 666943 vs 420915 and see Examples 86 and 87).

TABLE 95

| Oligonucleotides targeting human TTR | | | | | | |
|---|---|---|---|---|---|---|
| Isis No. | Sequence 5' to 3' | Linkages | GalNAc cluster | CM | Unmodified SEQ ID No. | Modified SEQ ID No. |
| 420915 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | PS | n/a | n/a | 265 | 323 |
| 682883 | **GalNAc$_3$-3**$_{a\text{-}o'}$$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAc$_3$-3a | PO | 265 | 345 |
| 666943 | **GalNAc$_3$-3**$_{a\text{-}o'}$**A**$_{do}$$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAc$_3$-3a | $A_d$ | 269 | 390 |
| 682887 | **GalNAc$_3$-7**$_{a\text{-}o'}$**A**$_{do}$$T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAc$_3$-7a | $A_d$ | 269 | 425 |

TABLE 95-continued

| Oligonucleotides targeting human TTR | | | | | | |
|---|---|---|---|---|---|---|
| Isis No. | Sequence 5' to 3' | Linkages | GalNAc cluster | CM | Unmodified SEQ ID No. | Modified SEQ ID No. |
| 682888 | **GalNAc$_3$-10$_{a}$-$_{o'}$A$_{do}$**T$_{es}$$^{m}$C$_{eo}$T$_{eo}$ T$_{eo}$G$_{eo}$G$_{ds}$T$_{ds}$T$_{ds}$A$_{ds}$$^{m}$C$_{ds}$A$_{ds}$T$_{ds}$ G$_{ds}$A$_{ds}$A$_{ds}$A$_{eo}$T$_{eo}$$^{m}$C$_{es}$$^{m}$C$_{es}$$^{m}$C$_{e}$ | PS/PO | GalNAc$_3$-10a | A$_d$ | 269 | 426 |
| 682889 | **GalNAc$_3$-13$_{a}$-$_{o'}$A$_{do}$**T$_{es}$$^{m}$C$_{eo}$T$_{eo}$ T$_{eo}$G$_{eo}$G$_{ds}$T$_{ds}$T$_{ds}$A$_{ds}$$^{m}$C$_{ds}$A$_{ds}$T$_{ds}$ G$_{ds}$A$_{ds}$A$_{ds}$A$_{eo}$T$_{eo}$$^{m}$C$_{es}$$^{m}$C$_{es}$$^{m}$C$_{e}$ | PS/PO | GalNAc$_3$-13a | A$_d$ | 269 | 427 |

The legend for Table 95 can be found in Example 74. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62.

TABLE 96

| Antisense inhibition of human TTR in vivo | | | | | |
|---|---|---|---|---|---|
| Isis No. | Dosage (mg/kg) | TTR mRNA (% PBS) | TTR protein (% BL) | GalNAc cluster | CM |
| PBS | n/a | 100 | 124 | n/a | n/a |
| 420915 | 6 | 69 | 114 | n/a | n/a |
| | 20 | 71 | 86 | | |
| | 60 | 21 | 36 | | |
| 682883 | 0.6 | 61 | 73 | GalNAc$_3$-3a | PO |
| | 2 | 23 | 36 | | |
| | 6 | 18 | 23 | | |
| 666943 | 0.6 | 74 | 93 | GalNAc$_3$-3a | A$_d$ |
| | 2 | 33 | 57 | | |
| | 6 | 17 | 22 | | |
| 682887 | 0.6 | 60 | 97 | GalNAc$_3$-7a | A$_d$ |
| | 2 | 36 | 49 | | |
| | 6 | 12 | 19 | | |
| 682888 | 0.6 | 65 | 92 | GalNAc$_3$-10a | A$_d$ |
| | 2 | 32 | 46 | | |
| | 6 | 17 | 22 | | |
| 682889 | 0.6 | 72 | 74 | GalNAc$_3$-13a | A$_d$ |
| | 2 | 38 | 45 | | |
| | 6 | 16 | 18 | | |

Example 91: Antisense Inhibition In Vivo by Oligonucleotides Targeting Factor VII Comprising a GalNAc$_3$ Conjugate in Non-Human Primates Oligonucleotides listed in Table 97 below were tested in a non-terminal, dose escalation study for antisense inhibition of Factor VII in monkeys.

Treatment

Non-naïve monkeys were each injected subcutaneously on days 0, 15, and 29 with escalating doses of an oligonucleotide listed in Table 97 or with PBS. Each treatment group consisted of 4 males and 1 female. Prior to the first dose and at various time points thereafter, blood draws were performed to determine plasma Factor VII protein levels. Factor VII protein levels were measured by ELISA. The results presented in Table 98 are the average values for each treatment group relative to the average value for the PBS group at baseline (BL), the measurements taken just prior to the first dose. As illustrated in Table 98, treatment with antisense oligonucleotides lowered Factor VII expression levels in a dose-dependent manner, and the oligonucleotide comprising the GalNAc conjugate was significantly more potent in monkeys compared to the oligonucleotide lacking a GalNAc conjugate.

TABLE 97

| Oligonucleotides targeting Factor VII | | | | | | |
|---|---|---|---|---|---|---|
| Isis No. | Sequence 5' to 3' | Linkages | GalNAc cluster | CM | Unmodified SEQ ID No. | Modified SEQ ID No. |
| 407935 | A$_{es}$T$_{es}$G$_{es}$$^{m}$C$_{es}$A$_{es}$T$_{ds}$G$_{ds}$G$_{ds}$T$_{ds}$G$_{ds}$ A$_{ds}$T$_{ds}$G$_{ds}$$^{m}$C$_{ds}$T$_{ds}$T$_{es}$$^{m}$C$_{es}$T$_{es}$G$_{es}$A$_{e}$ | PS | n/a | n/a | 270 | 322 |
| 686892 | **GalNAc$_3$-10$_{a}$-$_{o'}$**A$_{es}$T$_{es}$G$_{es}$$^{m}$C$_{es}$A$_{es}$ T$_{ds}$G$_{ds}$G$_{ds}$T$_{ds}$G$_{ds}$A$_{ds}$T$_{ds}$G$_{ds}$$^{m}$C$_{ds}$T$_{ds}$ T$_{es}$$^{m}$C$_{es}$T$_{es}$G$_{es}$A$_{e}$ | PS | GalNAc$_3$-10a | PO | 270 | 349 |

The legend for Table 97 can be found in Example 74. The structure of GalNAc$_3$-10$_a$ was shown in Example 46.

TABLE 98

| Factor VII plasma protein levels | | | |
|---|---|---|---|
| ISIS No. | Day | Dose (mg/kg) | Factor VII (% BL) |
| 407935 | 0 | n/a | 100 |
| | 15 | 10 | 87 |
| | 22 | n/a | 92 |
| | 29 | 30 | 77 |
| | 36 | n/a | 46 |
| | 43 | n/a | 43 |
| 686892 | 0 | 3 | 100 |
| | 15 | 10 | 56 |
| | 22 | n/a | 29 |
| | 29 | 30 | 19 |
| | 36 | n/a | 15 |
| | 43 | n/a | 11 |

Example 92: Antisense Inhibition in Primary Hepatocytes by Antisense Oligonucleotides Targeting Apo-CIII Comprising a GalNAc$_3$ Conjugate Primary mouse hepatocytes were seeded in 96-well plates at 15,000 cells per well, and the oligonucleotides listed in Table 99, targeting mouse ApoC-III, were added at 0.46, 1.37, 4.12, or 12.35, 37.04, 111.11, or 333.33 nM or 1.00 μM. After incubation with the oligonucleotides for 24 hours, the cells were lysed and total RNA was purified using RNeasy (Qiagen). ApoC-III mRNA levels were determined using real-time PCR and RIBOGREEN® RNA quantification reagent (Molecular Probes, Inc.) according to standard protocols. IC$_{50}$ values were determined using Prism 4 software (GraphPad). The results show that regardless of whether the cleavable moiety was a phosphodiester or a phosphodiester-linked deoxyadenosine, the oligonucleotides comprising a GalNAc conjugate were significantly more potent than the parent oligonucleotide lacking a conjugate.

TABLE 99

| Inhibition of mouse APOC-III expression in mouse primary hepatocytes | | | | | |
|---|---|---|---|---|---|
| ISIS No. | Sequence (5' to 3') | CM | IC$_{50}$ (nM) | Unmodified SEQ ID No. | Modified SEQ ID No. |
| 440670 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a | 13.20 | 271 | 324 |
| 661180 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{eo}$**A**$_{do'}$-**GalNAc$_3$-1$_a$** | A$_d$ | 1.40 | 272 | 378 |
| 680771 | **GalNAc$_3$-3$_a$**-$_{o'}$${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | PO | 0.70 | 271 | 331 |
| 680772 | **GalNAc$_3$-7$_a$**-$_{o'}$${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | PO | 1.70 | 271 | 332 |
| 680773 | **GalNAc$_3$-10$_a$**-$_{o'}$${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | PO | 2.00 | 271 | 333 |
| 680774 | **GalNAc$_3$-13$_a$**-$_{o'}$${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | PO | 1.50 | 271 | 334 |
| 681272 | **GalNAc$_3$-3$_a$**-$_{o'}$${}^{m}C_{es}A_{eo}G_{eo}{}^{m}C_{eo}T_{eo}T_{ds}T_{ds}A_{ds}T_{ds}T_{ds}A_{ds}G_{ds}G_{ds}G_{ds}A_{ds}{}^{m}C_{eo}A_{eo}G_{es}{}^{m}C_{es}A_{e}$ | PO | <0.46 | 271 | 340 |
| 681273 | **GalNAc$_3$-3$_a$**-$_{o'}$**A**$_{do}$${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | A$_d$ | 1.10 | 273 | 421 |
| 683733 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{eo}$**A**$_{do'}$-**GalNAc$_3$-19$_a$** | A$_d$ | 2.50 | 272 | 428 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, GalNAc$_3$-13$_a$ was shown in Example 62, and GalNAc$_3$-19$_a$ was shown in Example 70.

Example 93: Antisense Inhibition In Vivo by Oligonucleotides Targeting SRB-1 Comprising Mixed Wings and a 5'-GalNAc$_3$ Conjugate The oligonucleotides listed in Table 100 were tested in a dose-dependent study for antisense inhibition of SRB-1 in mice.

TABLE 100

| Modified ASOs targeting SRB-1 | | | | | |
|---|---|---|---|---|---|
| ISIS No. | Sequences (5' to 3') | GalNAc$_3$ Cluster | CM | Unmodified SEQ ID No. | Modified SEQ ID No. |
| 449093 | $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | n/a | n/a | 274 | 309 |
| 699806 | **GalNAc$_3$-3$_a$**-$_{o'}$$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | GalNAc$_3$-3a | PO | 274 | 310 |
| 699807 | **GalNAc$_3$-7$_a$**-$_{o'}$$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | GalNAc$_3$-7a | PO | 274 | 311 |
| 699809 | **GalNAc$_3$-7$_a$**-$_{o'}$$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{e}$ | GalNAc$_3$-7a | PO | 274 | 312 |

TABLE 100-continued

| Modified ASOs targeting SRB-1 | | | | | |
|---|---|---|---|---|---|
| ISIS No. | Sequences (5' to 3') | GalNAc$_3$ Cluster | CM | Unmodified SEQ ID No. | Modified SEQ ID No. |
| 699811 | **GalNAc$_3$-7$_a$-$_{o'}$**$T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | GalNAc$_3$-7a | PO | 274 | 313 |
| 699813 | **GalNAc$_3$-7$_a$-$_{o'}$**$T_{ks}T_{ds}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ds}{}^{m}C_{k}$ | GalNAc$_3$-7a | PO | 274 | 314 |
| 699815 | **GalNAc$_3$-7$_a$-$_{o'}$**$T_{es}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{e}$ | GalNAc$_3$-7a | PO | 274 | 315 |

The structure of GalNAc$_3$-3$_a$ was shown previously in Example 39, and the structure of GalNAc$_3$-7a was shown previously in Example 48. Subscripts: "e" indicates 2'-MOE modified nucleoside; "d" indicates β-D-2'-deoxyribonucleoside; "k" indicates 6'-(S)—$CH_3$ bicyclic nucleoside (cEt); "s" indicates phosphorothioate internucleoside linkages (PS); "o" indicates phosphodiester internucleoside linkages (P0). Superscript "in" indicates 5-methylcytosines.

Treatment

Six to eight week old C57BL/6 mice (Jackson Laboratory, Bar Harbor, ME) were injected subcutaneously once at the dosage shown below with an oligonucleotide listed in Table 100 or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The results are presented as the average percent of SRB-1 mRNA levels for each treatment group relative to the saline control group. As illustrated in Table 101, treatment with antisense oligonucleotides lowered SRB-1 mRNA levels in a dose-dependent manner, and the gapmer oligonucleotides comprising a GalNAc conjugate and having wings that were either full cEt or mixed sugar modifications were significantly more potent than the parent oligonucleotide lacking a conjugate and comprising full cEt modified wings.

Body weights, liver transaminases, total bilirubin, and BUN were also measured, and the average values for each treatment group are shown in Table 101. Body weight is shown as the average percent body weight relative to the baseline body weight (% BL) measured just prior to the oligonucleotide dose.

TABLE 101

SRB-1 mRNA, ALT, AST, BUN, and total bilirubin levels and body weights

| ISIS No. | Dosage (mg/kg) | SRB-1 mRNA (% PBS) | ALT (U/L) | AST (U/L) | Bil | BUN | Body weight (% BL) |
|---|---|---|---|---|---|---|---|
| PBS | n/a | 100 | 31 | 84 | 0.15 | 28 | 102 |
| 449093 | 1 | 111 | 18 | 48 | 0.17 | 31 | 104 |
| | 3 | 94 | 20 | 43 | 0.15 | 26 | 103 |
| | 10 | 36 | 19 | 50 | 0.12 | 29 | 104 |
| 699806 | 0.1 | 114 | 23 | 58 | 0.13 | 26 | 107 |
| | 0.3 | 59 | 21 | 45 | 0.12 | 27 | 108 |
| | 1 | 25 | 30 | 61 | 0.12 | 30 | 104 |
| 699807 | 0.1 | 121 | 19 | 41 | 0.14 | 25 | 100 |
| | 0.3 | 73 | 23 | 56 | 0.13 | 26 | 105 |
| | 1 | 24 | 22 | 69 | 0.14 | 25 | 102 |
| 699809 | 0.1 | 125 | 23 | 57 | 0.14 | 26 | 104 |
| | 0.3 | 70 | 20 | 49 | 0.10 | 25 | 105 |
| | 1 | 33 | 34 | 62 | 0.17 | 25 | 107 |
| 699811 | 0.1 | 123 | 48 | 77 | 0.14 | 24 | 106 |
| | 0.3 | 94 | 20 | 45 | 0.13 | 25 | 101 |
| | 1 | 66 | 57 | 104 | 0.14 | 24 | 107 |
| 699813 | 0.1 | 95 | 20 | 58 | 0.13 | 28 | 104 |
| | 0.3 | 98 | 22 | 61 | 0.17 | 28 | 105 |
| | 1 | 49 | 19 | 47 | 0.11 | 27 | 106 |
| 699815 | 0.1 | 93 | 30 | 79 | 0.17 | 25 | 105 |
| | 0.3 | 64 | 30 | 61 | 0.12 | 26 | 105 |
| | 1 | 24 | 18 | 41 | 0.14 | 25 | 106 |

Example 94: Antisense Inhibition In Vivo by Oligonucleotides Targeting SRB-1 Comprising 2'-Sugar Modifications and a 5'-GalNAc$_3$ Conjugate The oligonucleotides listed in Table 102 were tested in a dose-dependent study for antisense inhibition of SRB-1 in mice.

TABLE 102

| Modified ASOs targeting SRB-1 | | | | | |
|---|---|---|---|---|---|
| ISIS No. | Sequences (5' to 3') | GalNAc$_3$ Cluster | CM | Unmodified SEQ ID No. | Modified SEQ ID No. |
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | n/a | n/a | 252 | 318 |
| 700989 | $G_{ms}C_{ms}U_{ms}U_{ms}C_{ms}A_{ds}G_{ds}T_{ds}{}^{m}C_{ds}A_{ds}T_{ds}G_{ds}A_{ds}{}^{m}C_{ds}T_{ds}U_{ms}C_{ms}C_{ms}U_{ms}U_{m}$ | n/a | n/a | 275 | 354 |
| 666904 | **GalNAc$_3$-3$_a$-$_{o'}$**$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-3a | PO | 252 | 330 |

TABLE 102-continued

| Modified ASOs targeting SRB-1 | | | | | |
|---|---|---|---|---|---|
| ISIS No. | Sequences (5' to 3') | $GalNAc_3$ Cluster | CM | Unmodified SEQ ID No. | Modified SEQ ID No. |
| 700991 | $\mathbf{GalNAc_3\text{-}7}_{a}\text{-}_{o'}G_{ms}C_{ms}U_{ms}U_{ms}C_{ms}A_{ds}G_{ds}T_{ds}{}^{m}C_{ds}A_{ds}T_{ds}G_{ds}A_{ds}{}^{m}C_{ds}T_{ds}U_{ms}C_{ms}C_{ms}U_{ms}U_{m}$ | $GalNAc_3$-7a | PO | 275 | 355 |

Subscript "m" indicates a 2'-O—methyl modified nucleoside. See Example 74 for complete table legend. The structure of $GalNAc_3$-$3_a$ was shown previously in Example 39, and the structure of $GalNAc_3$-7a was shown previously in Example 48.

Treatment

The study was completed using the protocol described in Example 93. Results are shown in Table 103 below and show that both the 2'-MOE and 2'-OMe modified oligonucleotides comprising a GalNAc conjugate were significantly more potent than the respective parent oligonucleotides lacking a conjugate. The results of the body weights, liver transaminases, total bilirubin, and BUN measurements indicated that the compounds were all well tolerated.

TABLE 103

| SRB-1 mRNA | | |
|---|---|---|
| ISIS No. | Dosage (mg/kg) | SRB-1 mRNA (% PBS) |
| PBS | n/a | 100 |
| 353382 | 5 | 116 |
| | 15 | 58 |
| | 45 | 27 |

TABLE 103-continued

| SRB-1 mRNA | | |
|---|---|---|
| ISIS No. | Dosage (mg/kg) | SRB-1 mRNA (% PBS) |
| 700989 | 5 | 120 |
| | 15 | 92 |
| | 45 | 46 |
| 666904 | 1 | 98 |
| | 3 | 45 |
| | 10 | 17 |
| 700991 | 1 | 118 |
| | 3 | 63 |
| | 10 | 14 |

Example 95: Antisense Inhibition In Vivo by Oligonucleotides Targeting SRB-1 Comprising Bicyclic Nucleosides and a 5'-$GalNAc_3$ Conjugate The oligonucleotides listed in Table 104 were tested in a dose-dependent study for antisense inhibition of SRB-1 in mice.

TABLE 104

| Modified ASOs targeting SRB-1 | | | | | |
|---|---|---|---|---|---|
| ISIS No. | Sequences (5' to 3') | $GalNAc_3$ Cluster | CM | Unmodified SEQ ID No. | Modified SEQ ID No. |
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | n/a | 246 | 297 |
| 666905 | $\mathbf{GalNAc_3\text{-}3}_{a}\text{-}_{o'}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$3_a$ | PO | 246 | 298 |
| 699782 | $\mathbf{GalNAc_3\text{-}7}_{a}\text{-}_{o'}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$7_a$ | PO | 246 | 299 |
| 699783 | $\mathbf{GalNAc_3\text{-}3}_{a}\text{-}_{o'}T_{ls}{}^{m}C_{ls}A_{ds}G_{ds}T_{ds}{}^{m}C_{ds}A_{ds}T_{ds}G_{ds}A_{ds}{}^{m}C_{ds}T_{ds}T_{ls}{}^{m}C_{l}$ | $GalNAc_3$-$3_a$ | PO | 246 | 300 |
| 653621 | $T_{ls}{}^{m}C_{ls}A_{ds}G_{ds}T_{ds}{}^{m}C_{ds}A_{ds}T_{ds}G_{ds}A_{ds}{}^{m}C_{ds}T_{ds}T_{ls}{}^{m}C_{lo}A_{do'}\text{-}\mathbf{GalNAc_3\text{-}1}_{a}$ | $GalNAc_3$-$1_a$ | $A_d$ | 247 | 304 |
| 439879 | $T_{gs}{}^{m}C_{gs}A_{ds}G_{ds}T_{ds}{}^{m}C_{ds}A_{ds}T_{d}G_{ds}A_{ds}{}^{m}C_{ds}T_{ds}T_{gs}{}^{m}C_{g}$ | n/a | n/a | 246 | 296 |
| 699789 | $\mathbf{GalNAc_3\text{-}3}_{a}\text{-}_{o'}T_{gs}{}^{m}C_{gs}A_{ds}G_{ds}T_{ds}{}^{m}C_{ds}A_{ds}T_{d}G_{ds}A_{ds}{}^{m}C_{ds}T_{ds}T_{gs}{}^{m}C_{g}$ | $GalNAc_3$-$3_a$ | PO | 246 | 301 |

Subscript "g" indicates a fluoro-HNA nucleoside, subscript "l" indicates a locked nucleoside comprising a 2'-O—CH2—4' bridge. See the Example 74 table legend for other abbreviations. The structure of $GalNAc_3$-$1_a$ was shown previously in Example 9, the structure of $GalNAc_3$-$3_a$, was shown previously in Example 39, and the structure of $GalNAc_3$-7a was shown previously in Example 48.

Treatment

The study was completed using the protocol described in Example 93. Results are shown in Table 105 below and show that oligonucleotides comprising a GalNAc conjugate and various bicyclic nucleoside modifications were significantly more potent than the parent oligonucleotide lacking a conjugate and comprising bicyclic nucleoside modifications. Furthermore, the oligonucleotide comprising a GalNAc conjugate and fluoro-HNA modifications was significantly more potent than the parent lacking a conjugate and comprising fluoro-HNA modifications. The results of the body weights, liver transaminases, total bilirubin, and BUN measurements indicated that the compounds were all well tolerated.

TABLE 105

SRB-1 mRNA, ALT, AST, BUN, and total bilirubin levels and body weights

| ISIS No. | Dosage (mg/kg) | SRB-1 mRNA (% PBS) |
|---|---|---|
| PBS | n/a | 100 |
| 440762 | 1 | 104 |
| | 3 | 65 |
| | 10 | 35 |
| 666905 | 0.1 | 105 |
| | 0.3 | 56 |
| | 1 | 18 |
| 699782 | 0.1 | 93 |
| | 0.3 | 63 |
| | 1 | 15 |
| 699783 | 0.1 | 105 |
| | 0.3 | 53 |
| | 1 | 12 |
| 653621 | 0.1 | 109 |
| | 0.3 | 82 |
| | 1 | 27 |
| 439879 | 1 | 96 |
| | 3 | 77 |
| | 10 | 37 |
| 699789 | 0.1 | 82 |
| | 0.3 | 69 |
| | 1 | 26 |

Example 96: Plasma Protein Binding of Antisense Oligonucleotides Comprising a $GalNAc_3$ Conjugate Group Oligonucleotides listed in Table 70 targeting ApoC-III and oligonucleotides in Table 106 targeting Apo(a) were tested in an ultra-filtration assay in order to assess plasma protein binding.

TABLE 106

Modified oligonucleotides targeting Apo(a)

| ISIS No. | Sequences (5' to 3') | $GalNAc_3$ Cluster | CM | Unmodified SEQ ID No | Modified SEQ ID No |
|---|---|---|---|---|---|
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 277 | 326 |
| 693401 | $T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | n/a | n/a | 277 | 350 |
| 681251 | **$GalNAc_3$-7**$_{a}$-$_{o'}$$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | $GalNAc_3$-$7_a$ | PO | 277 | 335 |
| 681257 | **$GalNAc_3$**-7$_{a}$-$_{o'}$$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-$7_a$ | PO | 277 | 338 |

See the Example 74 for table legend. The structure of $GalNAc_3$-7a was shown previously in Example 48.

Ultrafree-MC ultrafiltration units (30,000 NMWL, low-binding regenerated cellulose membrane, Millipore, Bedford, MA) were pre-conditioned with 300 μL of 0.5% Tween 80 and centrifuged at 2000 g for 10 minutes, then with 300 μL of a 300 μg/mL solution of a control oligonucleotide in $H_2O$ and centrifuged at 2000 g for 16 minutes. In order to assess non-specific binding to the filters of each test oligonucleotide from Tables 70 and 106 to be used in the studies, 300 μL of a 250 ng/mL solution of oligonucleotide in $H_2O$ at pH 7.4 was placed in the pre-conditioned filters and centrifuged at 2000 g for 16 minutes. The unfiltered and filtered samples were analyzed by an ELISA assay to determine the oligonucleotide concentrations. Three replicates were used to obtain an average concentration for each sample. The average concentration of the filtered sample relative to the unfiltered sample is used to determine the percent of oligonucleotide that is recovered through the filter in the absence of plasma (% recovery).

Frozen whole plasma samples collected in K3-EDTA from normal, drug-free human volunteers, cynomolgus monkeys, and CD-1 mice, were purchased from Bioreclamation LLC (Westbury, NY). The test oligonucleotides were added to 1.2 mL aliquots of plasma at two concentrations (5 and 150 μg/mL). An aliquot (300 μL) of each spiked plasma sample was placed in a pre-conditioned filter unit and incubated at 37° C. for 30 minutes, immediately followed by centrifugation at 2000 g for 16 minutes. Aliquots of filtered and unfiltered spiked plasma samples were analyzed by an ELISA to determine the oligonucleotide concentration in each sample. Three replicates per concentration were used to determine the average percentage of bound and unbound oligonucleotide in each sample. The average concentration of the filtered sample relative to the concentration of the unfiltered sample is used to determine the percent of oligonucleotide in the plasma that is not bound to plasma proteins (% unbound). The final unbound oligonucleotide values are corrected for non-specific binding by dividing the % unbound by the % recovery for each oligonucleotide. The final % bound oligonucleotide values are determined by subtracting the final % unbound values from 100. The results are shown in Table 107 for the two concentrations of oligonucleotide tested (5 and 150 μg/mL) in each species of plasma. The results show that GalNAc conjugate groups do not have a significant impact on plasma protein binding. Furthermore, oligonucleotides with full PS internucleoside linkages and mixed PO/PS linkages both bind plasma proteins, and those with full PS linkages bind plasma proteins to a somewhat greater extent than those with mixed PO/PS linkages.

TABLE 107

Percent of modified oligonucleotide bound to plasma proteins

| ISIS No. | Human plasma 5 µg/mL | Human plasma 150 µg/mL | Monkey plasma 5 µg/mL | Monkey plasma 150 µg/mL | Mouse plasma 5 µg/mL | Mouse plasma 150 µg/mL |
|---|---|---|---|---|---|---|
| 304801 | 99.2 | 98.0 | 99.8 | 99.5 | 98.1 | 97.2 |
| 663083 | 97.8 | 90.9 | 99.3 | 99.3 | 96.5 | 93.0 |
| 674450 | 96.2 | 97.0 | 98.6 | 94.4 | 94.6 | 89.3 |
| 494372 | 94.1 | 89.3 | 98.9 | 97.5 | 97.2 | 93.6 |
| 693401 | 93.6 | 89.9 | 96.7 | 92.0 | 94.6 | 90.2 |
| 681251 | 95.4 | 93.9 | 99.1 | 98.2 | 97.8 | 96.1 |
| 681257 | 93.4 | 90.5 | 97.6 | 93.7 | 95.6 | 92.7 |

Example 97: Modified Oligonucleotides Targeting TTR Comprising a GalNAc$_3$ Conjugate Group The oligonucleotides shown in Table 108 comprising a GalNAc conjugate were designed to target TTR.

TABLE 108

Modified oligonucleotides targeting TTR

| ISIS No. | Sequences (5' to 3') | GalNAc$_3$ Cluster | CM | Unmodified SEQ ID No | Modified SEQ ID No |
|---|---|---|---|---|---|
| 666941 | **GalNAC$_3$-3$_a$-$_{o'}$A$_{do}$** T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-3 | A$_d$ | 269 | 388 |
| 666942 | T$_{es}$ $^m$C$_{eo}$ T$_{eo}$ T$_{eo}$ G$_{eo}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{eo}$ T$_{eo}$ $^m$C$_{es}$ $^m$C$_{es}$ $^m$C$_{eo}$ **A$_{do'}$-GalNAc$_3$-3$_a$** | GalNAc$_3$-1 | A$_d$ | 266 | 389 |
| 682876 | **GalNAc$_3$-3$_a$-$_{o'}$**T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-3 | PO | 265 | 341 |
| 682877 | **GalNAc$_3$-7$_a$-$_{o'}$**T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-7 | PO | 265 | 342 |
| 682878 | **GalNAc$_3$-10$_a$-$_{o'}$**T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ mC$_{es}$ $^m$C$_e$ | GalNAc$_3$-10 | PO | 265 | 343 |
| 682879 | **GalNAc$_3$-13$_a$-$_{o'}$**T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-13 | PO | 265 | 344 |
| 682880 | **GalNAc3-7$_a$-$_{o'}$A$_{do}$** T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-7 | A$_d$ | 269 | 422 |
| 682881 | **GalNAc$_3$-10$_a$-$_{o'}$A$_{do}$** T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-10 | A$_d$ | 269 | 423 |
| 682882 | **GalNAc$_3$-13$_a$-$_{o'}$A$_{do}$** T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_e$ | GalNAc$_3$-13 | A$_d$ | 269 | 424 |
| 684056 | T$_{es}$ $^m$C$_{es}$ T$_{es}$ T$_{es}$ G$_{es}$ G$_{ds}$ T$_{ds}$ T$_{ds}$ A$_{ds}$ $^m$C$_{ds}$ A$_{ds}$ T$_{ds}$ G$_{ds}$ A$_{ds}$ A$_{ds}$ A$_{es}$ T$_{es}$ $^m$C$_{es}$ $^m$C$_{es}$ $^m$C$_{eo}$ **A$_{do'}$-GalNAc$_3$-19$_a$** | GalNAc$_3$-19 | A$_d$ | 266 | 429 |

The legend for Table 108 can be found in Example 74. The structure of GalNAc$_3$-1 was shown in Example 9. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62. The structure of GalNAc$_3$-19$_a$ was shown in Example 70.

Example 98: Evaluation of Pro-Inflammatory Effects of Oligonucleotides Comprising a GalNAc Conjugate in hPMBC Assay The oligonucleotides listed in Table 109 and were tested for pro-inflammatory effects in an hPMBC assay as described in Examples 23 and 24. (See Tables 30, 83, 95, and 108 for descriptions of the oligonucleotides.) ISIS 353512 is a high responder used as a positive control, and the other oligonucleotides are described in Tables 83, 95, and 108. The results shown in Table 109 were obtained using blood from one volunteer donor. The results show that the oligonucleotides comprising mixed PO/PS internucleoside linkages produced significantly lower pro-inflammatory responses compared to the same oligonucleotides having full PS linkages. Furthermore, the GalNAc conjugate group did not have a significant effect in this assay.

TABLE 109

| ISIS No. | $E_{max}/EC_{50}$ | GalNAc$_3$ cluster | Linkages | CM |
|---|---|---|---|---|
| 353512 | 3630 | n/a | PS | n/a |
| 420915 | 802 | n/a | PS | n/a |
| 682881 | 1311 | GalNAc$_3$-10 | PS | A$_d$ |
| 682888 | 0.26 | GalNAc$_3$-10 | PO/PS | A$_d$ |
| 684057 | 1.03 | GalNAc$_3$-19 | PO/PS | A$_d$ |

Example 99: Binding Affinities of Oligonucleotides Comprising a GalNAc Conjugate for the Asialoglycoprotein Receptor The binding affinities of the oligonucleotides listed in Table 110 (see Table 76 for descriptions of the oligonucleotides) for the asialoglycoprotein receptor were tested in a competitive receptor binding assay. The competitor ligand, α1-acid glycoprotein (AGP), was incubated in 50 mM sodium acetate buffer (pH 5) with 1 U neuraminidase-agarose for 16 hours at 37° C., and >90% desialylation was confirmed by either sialic acid assay or size exclusion chromatography (SEC). Iodine monochloride was used to iodinate the AGP according to the procedure by Atsma et al. (see J Lipid Res. 1991 January; 32(1):173-81.) In this method, desialylated al-acid glycoprotein (de-AGP) was added to 10 mM iodine chloride, $Na^{125}I$, and 1 M glycine in 0.25 M NaOH. After incubation for 10 minutes at room temperature, $^{125}I$-labeled de-AGP was separated from free $^{125}I$ by concentrating the mixture twice utilizing a 3 KDMWCO spin column. The protein was tested for labeling efficiency and purity on a HPLC system equipped with an Agilent SEC-3 column (7.8×300 mm) and a ß-RAM counter. Competition experiments utilizing $^{125}I$-labeled de-AGP and various GalNAc-cluster containing ASOs were performed as follows. Human HepG2 cells ($10^6$ cells/ml) were plated on 6-well plates in 2 ml of appropriate growth media. MEM media supplemented with 10% fetal bovine serum (FBS), 2 mM L-Glutamine and 10 mM HEPES was used. Cells were incubated 16-20 hours @ 37° C. with 5% and 10% $CO_2$ respectively. Cells were washed with media without FBS prior to the experiment. Cells were incubated for 30 min @37° C. with 1 ml competition mix containing appropriate growth media with 2% FBS, $10^{-8}$M $^{125}I$-labeled de-AGP and GalNAc-cluster containing ASOs at concentrations ranging from $10^{-11}$ to $10^{-5}$ M. Non-specific binding was determined in the presence of $10^{-2}$ M GalNAc sugar. Cells were washed twice with media without FBS to remove unbound $^{125}I$-labeled de-AGP and competitor GalNAc ASO. Cells were lysed using Qiagen's RLT buffer containing 1% ß-mercaptoethanol. Lysates were transferred to round bottom assay tubes after a brief 10 min freeze/thaw cycle and assayed on a γ-counter. Non-specific binding was subtracted before dividing $^{125}I$ protein counts by the value of the lowest GalNAc-ASO concentration counts. The inhibition curves were fitted according to a single site competition binding equation using a nonlinear regression algorithm to calculate the binding affinities ($K_D$'s).

The results in Table 110 were obtained from experiments performed on five different days. Results for oligonucleotides marked with superscript "a" are the average of experiments run on two different days. The results show that the oligonucleotides comprising a GalNAc conjugate group on the 5'-end bound the asialoglycoprotein receptor on human HepG2 cells with 1.5 to 16-fold greater affinity than the oligonucleotides comprising a GalNAc conjugate group on the 3'-end.

TABLE 110

Asialoglycoprotein receptor binding assay results

| ISIS No. | GalNAc conjugate | Oligonucleotide end to which GalNAc conjugate is attached | $K_D$ (nM) |
|---|---|---|---|
| 661161[a] | $GalNAc_3$-3 | 5' | 3.7 |
| 666881[a] | $GalNAc_3$-10 | 5' | 7.6 |
| 666981 | $GalNAc_3$-7 | 5' | 6.0 |
| 670061 | $GalNAc_3$-13 | 5' | 7.4 |
| 655861[a] | $GalNAc_3$-1 | 3' | 11.6 |
| 677841[a] | $GalNAc_3$-19 | 3' | 60.8 |

Example 100: Antisense Inhibition In Vivo by Oligonucleotides Comprising a GalNAc Conjugate Group Targeting Apo(a) In Vivo The oligonucleotides listed in Table 111a below were tested in a single dose study for duration of action in mice.

TABLE 111a

Modified ASOs targeting APO(a)

| ISIS No. | Sequences (5' to 3') | $GalNAc_3$ Cluster | CM | Unmodified SEQ ID No | Modified SEQ ID No |
|---|---|---|---|---|---|
| 681251 | **$GalNAc_3$-$7_a$**-$_{o'}$$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | $GalNAc_3$-7a | PO | 277 | 335 |
| 681257 | **$GalNAC_3$-$7_a$**-$_{o'}$$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-7a | PO | 277 | 338 |

The structure of $GalNAc_3$-$7_a$ was shown in Example 48.

Treatment

Female transgenic mice that express human Apo(a) were each injected subcutaneously once per week, for a total of 6 doses, with an oligonucleotide and dosage listed in Table 111b or with PBS. Each treatment group consisted of 3 animals. Blood was drawn the day before dosing to determine baseline levels of Apo(a) protein in plasma and at 72 hours, 1 week, and 2 weeks following the first dose. Additional blood draws will occur at 3 weeks, 4 weeks, 5 weeks, and 6 weeks following the first dose. Plasma Apo(a) protein levels were measured using an ELISA. The results in Table 111b are presented as the average percent of plasma Apo(a) protein levels for each treatment group, normalized to baseline levels (% BL), The results show that the oligonucleotides comprising a GalNAc conjugate group exhibited potent reduction in Apo(a) expression. This potent effect was observed for the oligonucleotide that comprises full PS internucleoside linkages and the oligonucleotide that comprises mixed PO and PS linkages.

TABLE 111b

Apo(a) plasma protein levels

| ISIS No. | Dosage (mg/kg) | Apo(a) at 72 hours (% BL) | Apo(a) at 1 week (% BL) | Apo(a) at 3 weeks (% BL) |
|---|---|---|---|---|
| PBS | n/a | 116 | 104 | 107 |
| 681251 | 0.3 | 97 | 108 | 93 |
| | 1.0 | 85 | 77 | 57 |
| | 3.0 | 54 | 49 | 11 |
| | 10.0 | 23 | 15 | 4 |

TABLE 111b-continued

| Apo(a) plasma protein levels | | | | |
|---|---|---|---|---|
| ISIS No. | Dosage (mg/kg) | Apo(a) at 72 hours (% BL) | Apo(a) at 1 week (% BL) | Apo(a) at 3 weeks (% BL) |
| 681257 | 0.3 | 114 | 138 | 104 |
| | 1.0 | 91 | 98 | 54 |
| | 3.0 | 69 | 40 | 6 |
| | 10.0 | 30 | 21 | 4 |

Example 101: Antisense Inhibition by Oligonucleotides Comprising a GalNAc Cluster Linked Via a Stable Moiety The oligonucleotides listed in Table 112 were tested for inhibition of mouse APOC-III expression in vivo. C57Bl/6 mice were each injected subcutaneously once with an oligonucleotide listed in Table 112 or with PBS. Each treatment group consisted of 4 animals. Each mouse treated with ISIS 440670 received a dose of 2, 6, 20, or 60 mg/kg. Each mouse treated with ISIS 680772 or 696847 received 0.6, 2, 6, or 20 mg/kg. The GalNAc conjugate group of ISIS 696847 is linked via a stable moiety, a phosphorothioate linkage instead of a readily cleavable phosphodiester containing linkage. The animals were sacrificed 72 hours after the dose. Liver APOC-II mRNA levels were measured using real-time PCR. APOC-III mRNA levels were normalized to cyclophilin mRNA levels according to standard protocols. The results are presented in Table 112 as the average percent of APOC-III mRNA levels for each treatment group relative to the saline control group. The results show that the oligonucleotides comprising a GalNAc conjugate group were significantly more potent than the oligonucleotide lacking a conjugate group. Furthermore, the oligonucleotide comprising a GalNAc conjugate group linked to the oligonucleotide via a cleavable moiety (ISIS 680772) was even more potent than the oligonucleotide comprising a GalNAc conjugate group linked to the oligonucleotide via a stable moiety (ISIS 696847).

The structure of $GalNAc_3$-$7_a$ was shown in Example 48.

Example 102: Distribution in Liver of Antisense Oligonucleotides Comprising a GalNAc Conjugate The liver distribution of ISIS 353382 (see Table 36) that does not comprise a GalNAc conjugate and ISIS 655861 (see Table 36) that does comprise a GalNAc conjugate was evaluated. Male balb/c mice were subcutaneously injected once with ISIS 353382 or 655861 at a dosage listed in Table 113. Each treatment group consisted of 3 animals except for the 18 mg/kg group for ISIS 655861, which consisted of 2 animals. The animals were sacrificed 48 hours following the dose to determine the liver distribution of the oligonucleotides. In order to measure the number of antisense oligonucleotide molecules per cell, a Ruthenium (II) tris-bipyridine tag (MSD TAG, Meso Scale Discovery) was conjugated to an oligonucleotide probe used to detect the antisense oligonucleotides. The results presented in Table 113 are the average concentrations of oligonucleotide for each treatment group in units of millions of oligonucleotide molecules per cell. The results show that at equivalent doses, the oligonucleotide comprising a GalNAc conjugate was present at higher concentrations in the total liver and in hepatocytes than the oligonucleotide that does not comprise a GalNAc conjugate. Furthermore, the oligonucleotide comprising a GalNAc conjugate was present at lower concentrations in non-parenchymal liver cells than the oligonucleotide that does not comprise a GalNAc conjugate. And while the concentrations of ISIS 655861 in hepatocytes and non-parenchymal liver cells were similar per cell, the liver is approximately 80% hepatocytes by volume. Thus, the majority of the ISIS 655861 oligonucleotide that was present in the liver was found in hepatocytes, whereas the majority of the ISIS 353382 oligonucleotide that was present in the liver was found in non-parenchymal liver cells.

TABLE 112

| Modified oligonucleotides targeting mouse APOC-III | | | | | | |
|---|---|---|---|---|---|---|
| ISIS No. | Sequences (5' to 3') | CM | Dosage (mg/kg) | APOC-III mRNA (% PBS) | Unmodified SEQ ID No | Modified SEQ ID No |
| 440670 | $^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a | 2 | 92 | 271 | 324 |
| | | | 6 | 86 | | |
| | | | 20 | 59 | | |
| | | | 60 | 37 | | |
| 680772 | **GalNAc**$_3$**-7**$_{a}$-$_{o'}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | PO | 0.6 | 79 | 271 | 332 |
| | | | 2 | 58 | | |
| | | | 6 | 31 | | |
| | | | 20 | 13 | | |
| 696847 | **GalNAc**$_3$**-7**$_{a}$-$_{s'}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a (PS) | 0.6 | 83 | 271 | 351 |
| | | | 2 | 73 | | |
| | | | 6 | 40 | | |
| | | | 20 | 28 | | |

TABLE 113

| ISIS No. | Dosage (mg/kg) | Concentration in whole liver (molecules*10^6 per cell) | Concentration in hepatocytes (molecules*10^6 per cell) | Concentration in non-parenchymal liver cells (molecules*10^6 per cell) |
|---|---|---|---|---|
| 353382 | 3 | 9.7 | 1.2 | 37.2 |
| | 10 | 17.3 | 4.5 | 34.0 |
| | 20 | 23.6 | 6.6 | 65.6 |
| | 30 | 29.1 | 11.7 | 80.0 |
| | 60 | 73.4 | 14.8 | 98.0 |
| | 90 | 89.6 | 18.5 | 119.9 |
| 655861 | 0.5 | 2.6 | 2.9 | 3.2 |
| | 1 | 6.2 | 7.0 | 8.8 |
| | 3 | 19.1 | 25.1 | 28.5 |
| | 6 | 44.1 | 48.7 | 55.0 |
| | 18 | 76.6 | 82.3 | 77.1 |

Example 103: Duration of Action In Vivo of Oligonucleotides Targeting APOC-III Comprising a $GalNAc_3$ Conjugate The oligonucleotides listed in Table 114 below were tested in a single dose study for duration of action in mice.

TABLE 114

Modified ASOs targeting APOC-III

| ISIS No. | Sequences (5' to 3') | $GalNAc_3$ Cluster | CM | Unmodified SEQ ID No | Modified SEQ ID No |
|---|---|---|---|---|---|
| 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | n/a | n/a | 244 | 317 |
| 663084 | $\mathbf{GalNAc_3\text{-}3_a\text{-}_{o'}A_{do}}A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{e}$ | $GalNAc_3$-3a | $A_d$ | 260 | 380 |
| 679241 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}\mathbf{A_{do'}\text{-}GalNAc_3\text{-}19_a}$ | $GalNAc_3$-19a | $A_d$ | 245 | 419 |

The structure of $GalNAc_3$-$3_a$ was shown in Example 39, and $GalNAc_3$-$19_a$ was shown in Example 70.

Treatment

Female transgenic mice that express human APOC-III were each injected subcutaneously once with an oligonucleotide listed in Table 114 or with PBS. Each treatment group consisted of 3 animals. Blood was drawn before dosing to determine baseline and at 3, 7, 14, 21, 28, 35, and 42 days following the dose. Plasma triglyceride and APOC-III protein levels were measured as described in Example 20. The results in Table 115 are presented as the average percent of plasma triglyceride and APOC-III levels for each treatment group, normalized to baseline levels. A comparison of the results in Table 71 of example 79 with the results in Table 115 below show that oligonucleotides comprising a mixture of phosphodiester and phosphorothioate internucleoside linkages exhibited increased duration of action than equivalent oligonucleotides comprising only phosphorothioate internucleoside linkages.

TABLE 115

Plasma triglyceride and APOC-III protein levels in transgenic mice

| ISIS No. | Dosage (mg/kg) | Time point (days post-dose) | Triglycerides (% baseline) | APOC-III protein (% baseline) | $GalNAc_3$ Cluster | CM |
|---|---|---|---|---|---|---|
| PBS | n/a | 3 | 96 | 101 | n/a | n/a |
| | | 7 | 88 | 98 | | |
| | | 14 | 91 | 103 | | |
| | | 21 | 69 | 92 | | |
| | | 28 | 83 | 81 | | |
| | | 35 | 65 | 86 | | |
| | | 42 | 72 | 88 | | |
| 304801 | 30 | 3 | 42 | 46 | n/a | n/a |
| | | 7 | 42 | 51 | | |
| | | 14 | 59 | 69 | | |
| | | 21 | 67 | 81 | | |
| | | 28 | 79 | 76 | | |
| | | 35 | 72 | 95 | | |
| | | 42 | 82 | 92 | | |
| 663084 | 10 | 3 | 35 | 28 | $GalNAc_3$-3a | $A_d$ |
| | | 7 | 23 | 24 | | |
| | | 14 | 23 | 26 | | |
| | | 21 | 23 | 29 | | |
| | | 28 | 30 | 22 | | |
| | | 35 | 32 | 36 | | |

TABLE 115-continued

Plasma triglyceride and APOC-III protein levels in transgenic mice

| ISIS No. | Dosage (mg/kg) | Time point (days post-dose) | Triglycerides (% baseline) | APOC-III protein (% baseline) | $GalNAc_3$ Cluster | CM |
|---|---|---|---|---|---|---|
| | | 42 | 37 | 47 | | |
| 679241 | 10 | 3 | 38 | 30 | $GalNAc_3$-19a | $A_d$ |
| | | 7 | 31 | 28 | | |
| | | 14 | 30 | 22 | | |
| | | 21 | 36 | 34 | | |
| | | 28 | 48 | 34 | | |
| | | 35 | 50 | 45 | | |
| | | 42 | 72 | 64 | | |

Example 104: Synthesis of Oligonucleotides Comprising a 5'-GalNAc$_2$ Conjugate
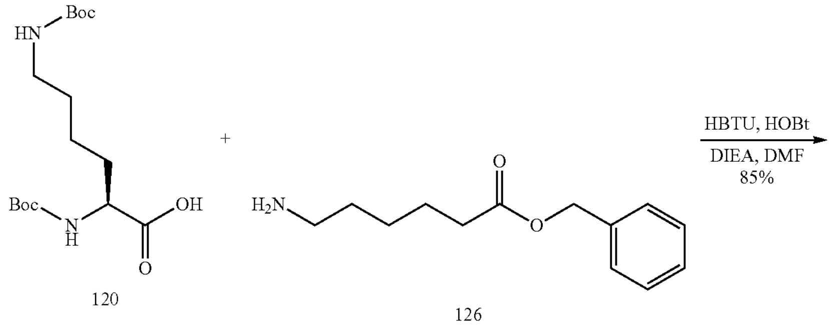
120
126
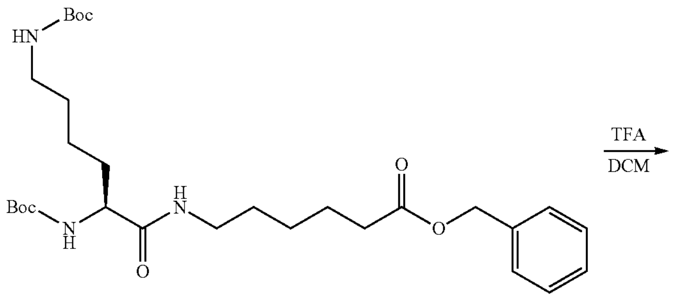
231
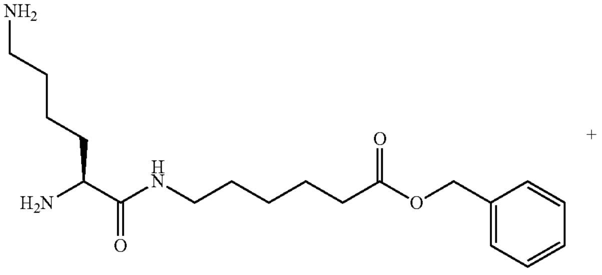
232
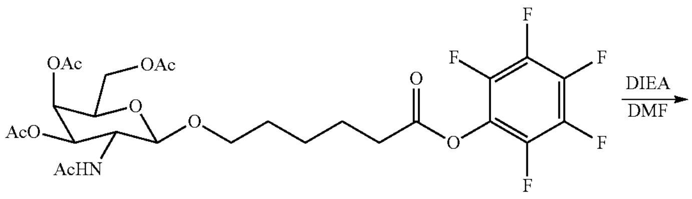
166
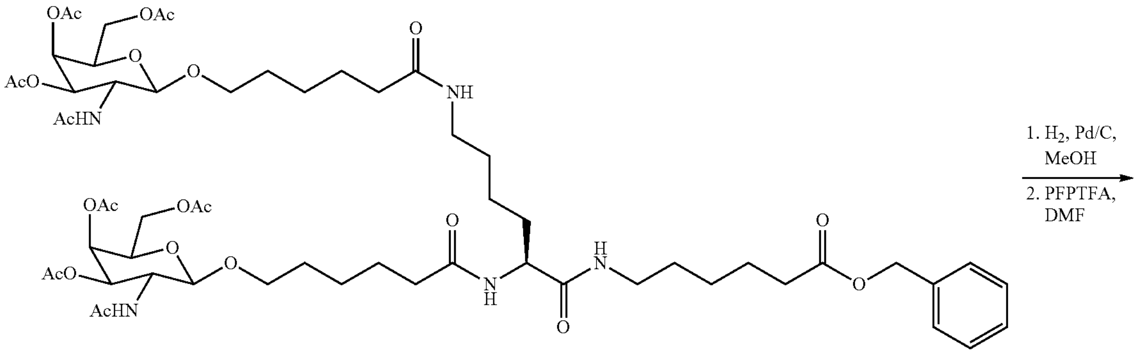
233

-continued

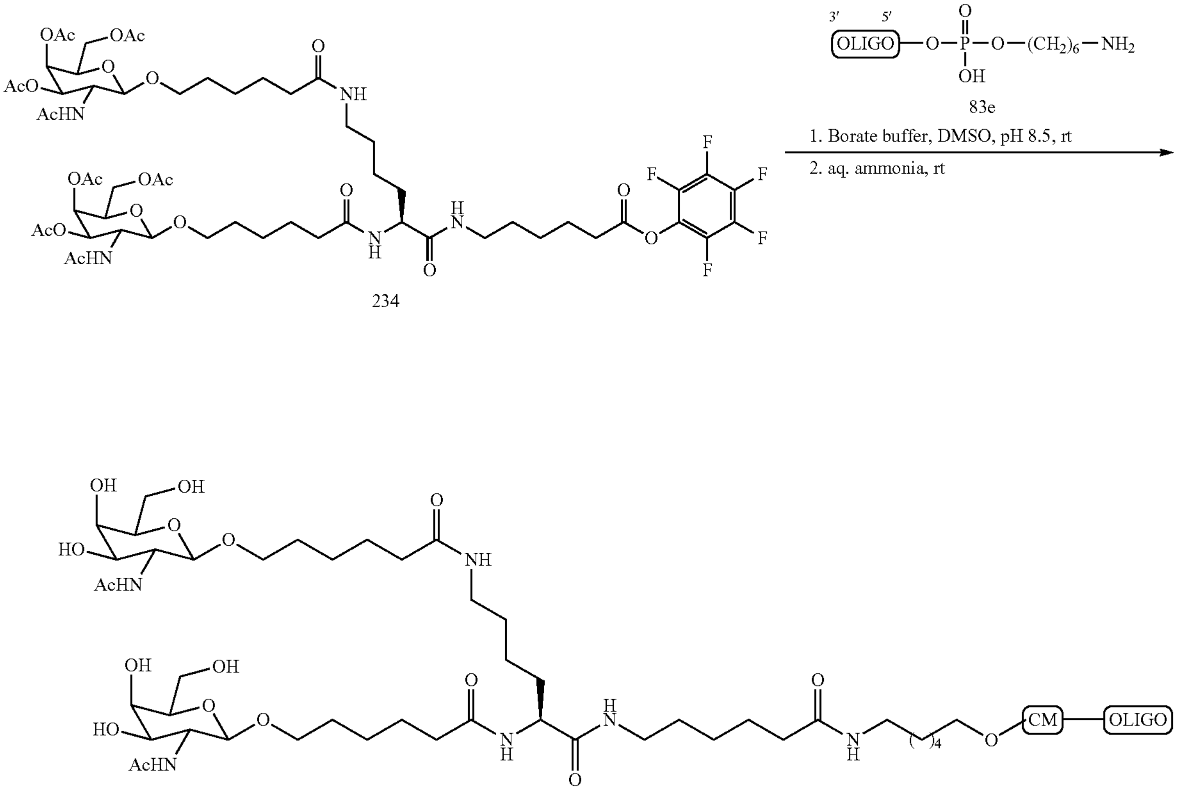

234

235

Compound 120 is commercially available, and the synthesis of compound 126 is described in Example 49. Compound 120 (1 g, 2.89 mmol), HBTU (0.39 g, 2.89 mmol), and HOBt (1.64 g, 4.33 mmol) were dissolved in DMF (10 mL. and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M NaHSO4 and extracted with 2×50 mL ethyl acetate. Organic layers were combined and washed with 3×40 mL sat $NaHCO_3$ and 2×brine, dried with $Na_2SO_4$, filtered and concentrated. The product was purified by silica gel column chromatography (DCM:EA:Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifluoracetate salt. The synthesis of compound 166 is described in Example 54. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×100 mL). The organic phase was separated and washed with sat. aqueous $NaHCO_3$ (3×80 mL), 1 M $NaHSO_4$ (3×80 mL) and brine (2×80 mL), then dried ($Na_2SO_4$), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylehtylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Oligonucleotide 235 was prepared using the general procedure described in Example 46. The $GalNAc_2$ cluster portion ($GalNAc_2$-$24_a$) of the conjugate group $GalNAc_2$-24 can be combined with any cleavable moiety present on the oligonucleotide to provide a variety of conjugate groups. The structure of $GalNAc_2$-24 ($GalNAc_2$-$24_a$-CM) is shown below:

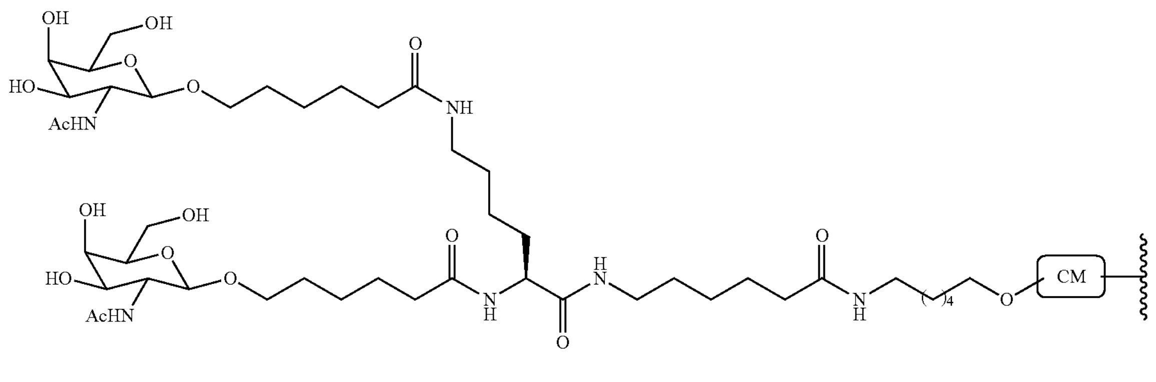

Example 105: Synthesis of Oligonucleotides Comprising a $GalNAc_1$-25 Conjugate

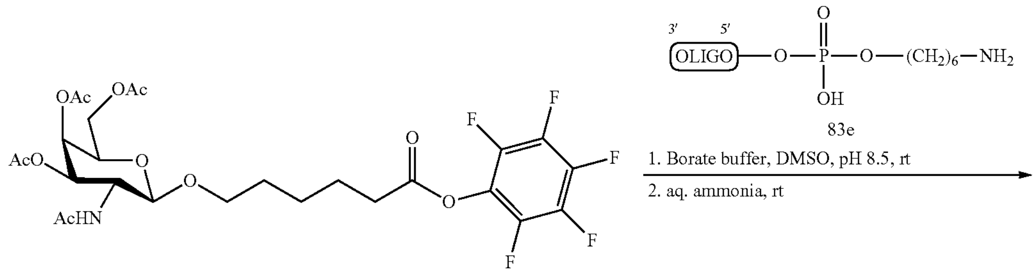

166

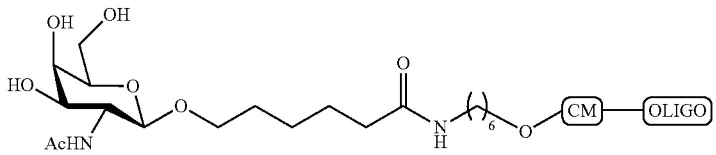

236

The synthesis of compound 166 is described in Example 54. Oligonucleotide 236 was prepared using the general procedure described in Example 46.

Alternatively, oligonucleotide 236 was synthesized using the scheme shown below, and compound 238 was used to form the oligonucleotide 236 using procedures described in Example 10.

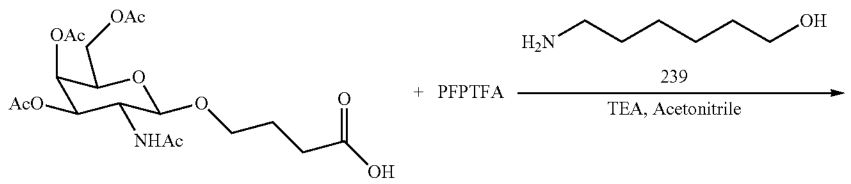

64

-continued

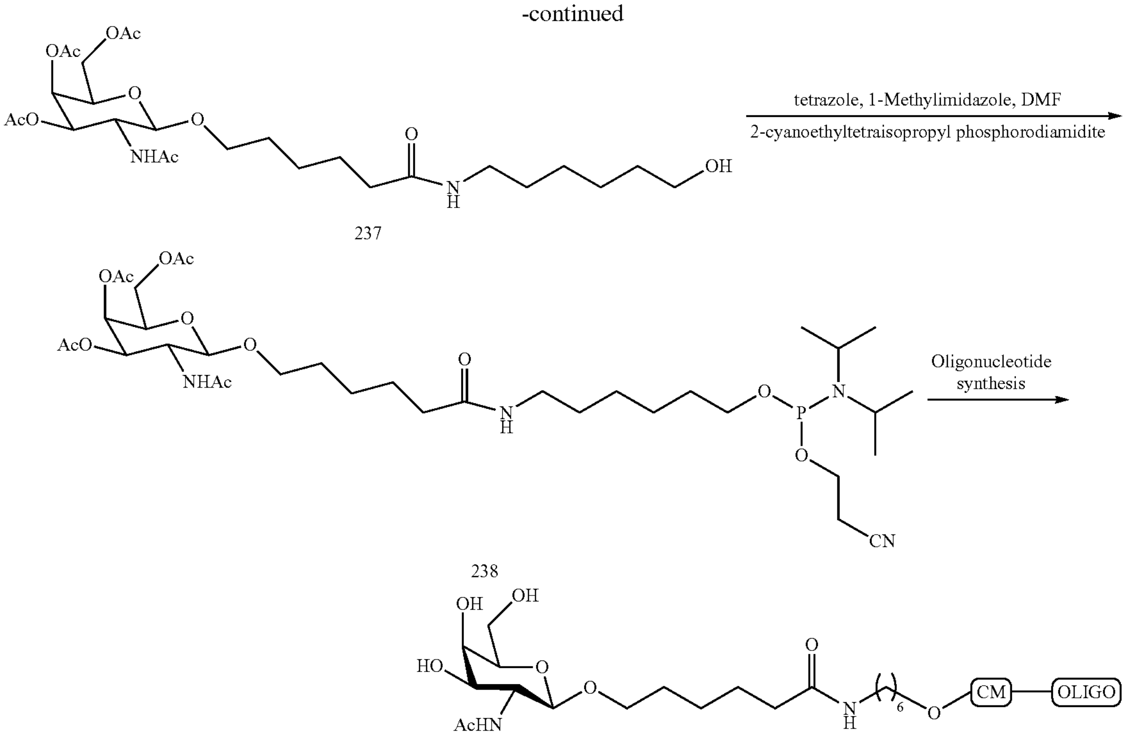

237

238

236

The $GalNAc_1$ cluster portion ($GalNAc_1$-$25_a$) of the conjugate group $GalNAc_1$-25 can be combined with any cleavable moiety present on the oligonucleotide to provide a variety of conjugate groups. The structure of $GalNAc_1$-25 ($GalNAc_1$-$25_a$-CM) is shown below:

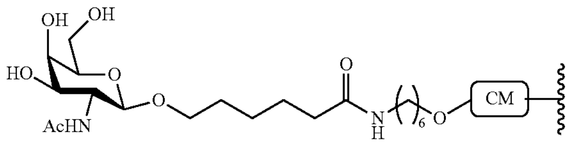

Example 106: Antisense Inhibition In Vivo by Oligonucleotides Targeting SRB-1 Comprising a 5'-$GalNAc_2$ or a 5'-$GalNAc_3$ Conjugate Oligonucleotides listed in Tables 116 and 117 were tested in dose-dependent studies for antisense inhibition of SRB-1 in mice.

Treatment

Six to week old, male C57BL/6 mice (Jackson Laboratory, Bar Harbor, ME) were injected subcutaneously once with 2, 7, or 20 mg/kg of ISIS No. 440762; or with 0.2, 0.6, 2, 6, or 20 mg/kg of ISIS No. 686221, 686222, or 708561; or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The antisense oligonucleotides lowered SRB-1 mRNA levels in a dose-dependent manner, and the $ED_{50}$ results are presented in Tables 116 and 117. Although previous studies showed that trivalent GalNAc-conjugated oligonucleotides were significantly more potent than divalent GalNAc-conjugated oligonucleotides, which were in turn significantly more potent than monovalent GalNAc conjugated oligonucleotides (see, e.g., Khorev et al., *Bioorg. & Med. Chem.*, Vol. 16, 5216-5231 (2008)), treatment with antisense oligonucleotides comprising monovalent, divalent, and trivalent GalNAc clusters lowered SRB-1 mRNA levels with similar potencies as shown in Tables 116 and 117.

TABLE 116

Modified oligonucleotides targeting SRB-1

| ISIS No. | Sequences (5' to 3') | GalNAc Cluster | $ED_{50}$ (mg/kg) | Unmodified SEQ ID No | Modified SEQ ID No |
|---|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | 4.7 | 246 | 297 |
| 686221 | **$GalNAc_2$-$24_a$-$_o$'$A_{do}$**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}c_{k}$ | $GalNAc_2$-$24_a$ | 0.39 | 250 | 307 |
| 686222 | **$GalNAc_3$-$13_a$-$_o$'$A_{do}$**$T_{ks}{}^{m}C_{ks}A_{ds}G_{ds}T_{ds}{}^{m}C_{ds}A_{ds}T_{ds}G_{ds}A_{ds}C_{ds}T_{ds}T_{ks}{}^{m}C_{k}$ | $GalNAc_3$-$13_a$ | 0.41 | 250 | 308 |

See Example 93 for table legend. The structure of GalNAc$_3$-13a was shown in Example 62, and the structure of GalNAc$_2$-24a was shown in Example 104.

TABLE 117

Modified oligonucleotides targeting SRB-1

| ISIS No. | Sequences (5' to 3') | GalNAc Cluster | $ED_{50}$ (mg/kg) | Unmodified SEQ ID No | Modified SEQ ID No |
|---|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | 5 | 246 | 297 |
| 708561 | **GalNAc$_1$-25$_a$-$_{o'}$**$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | GalNAc$_1$-25$_a$ | 0.4 | 246 | 302 |

See Example 93 for table legend. The structure of GalNAc$_1$-25a was shown in Example 105.

The concentrations of the oligonucleotides in Tables 116 and 117 in liver were also assessed, using procedures described in Example 75. The results shown in Tables 117a and 117b below are the average total antisense oligonucleotide tissues levels for each treatment group, as measured by UV in units of g oligonucleotide per gram of liver tissue. The results show that the oligonucleotides comprising a GalNAc conjugate group accumulated in the liver at significantly higher levels than the same dose of the oligonucleotide lacking a GalNAc conjugate group. Furthermore, the antisense oligonucleotides comprising one, two, or three GalNAc ligands in their respective conjugate groups all accumulated in the liver at similar levels. This result is surprising in view of the Khorev et al. literature reference cited above and is consistent with the activity data shown in Tables 116 and 117 above.

TABLE 117a

Liver concentrations of oligonucleotides comprising a GalNAc$_2$ or GalNAc$_3$ conjugate group

| ISIS No. | Dosage (mg/kg) | [Antisense oligonucleotide] (µg/g) | GalNAc cluster | CM |
|---|---|---|---|---|
| 440762 | 2 | 2.1 | n/a | n/a |
| | 7 | 13.1 | | |
| | 20 | 31.1 | | |
| 686221 | 0.2 | 0.9 | GalNAc$_2$-24$_a$ | $A_d$ |
| | 0.6 | 2.7 | | |
| | 2 | 12.0 | | |
| | 6 | 26.5 | | |
| 686222 | 0.2 | 0.5 | GalNAc$_3$-13$_a$ | $A_d$ |
| | 0.6 | 1.6 | | |
| | 2 | 11.6 | | |
| | 6 | 19.8 | | |

TABLE 117b

Liver concentrations of oligonucleotides comprising a GalNAc$_1$ conjugate group

| ISIS No. | Dosage (mg/kg) | [Antisense oligonucleotide] (µg/g) | GalNAc cluster | CM |
|---|---|---|---|---|
| 440762 | 2 | 2.3 | n/a | n/a |
| | 7 | 8.9 | | |
| | 20 | 23.7 | | |

TABLE 117b-continued

Liver concentrations of oligonucleotides comprising a GalNAc$_1$ conjugate group

| ISIS No. | Dosage (mg/kg) | [Antisense oligonucleotide] (µg/g) | GalNAc cluster | CM |
|---|---|---|---|---|
| 708561 | 0.2 | 0.4 | GalNAc$_1$-25$_a$ | PO |
| | 0.6 | 1.1 | | |
| | 2 | 5.9 | | |
| | 6 | 23.7 | | |
| | 20 | 53.9 | | |

Example 107: Synthesis of Oligonucleotides Comprising a GalNAc$_1$-26 or GalNAc$_1$-27 Conjugate

239

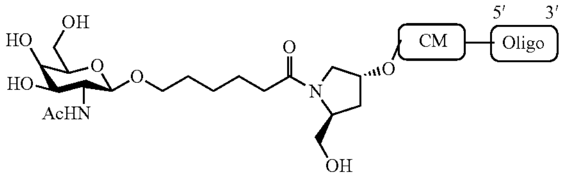

Oligonucleotide 239 is synthesized via coupling of compound 47 (see Example 15) to acid 64 (see Example 32) using HBTU and DIEA in DMF. The resulting amide containing compound is phosphitylated, then added to the 5'-end of an oligonucleotide using procedures described in Example 10. The GalNAc$_1$ cluster portion (GalNAc$_1$-26$_a$) of the conjugate group GalNAc$_1$-26 can be combined with any cleavable moiety present on the oligonucleotide to provide a variety of conjugate groups. The structure of GalNAc$_1$-26 (GalNAc$_1$-26$_a$-CM) is shown below:

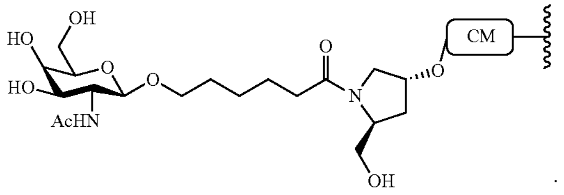

.

In order to add the GalNAc$_1$ conjugate group to the 3'-end of an oligonucleotide, the amide formed from the reaction of compounds 47 and 64 is added to a solid support using procedures described in Example 7. The oligonucleotide synthesis is then completed using procedures described in Example 9 in order to form oligonucleotide 240.

240

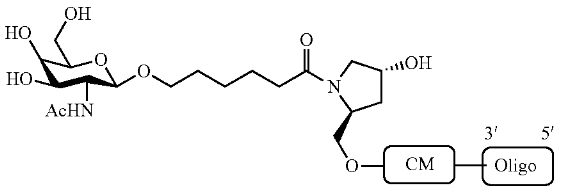

The GalNAc$_1$ cluster portion (GalNAc$_1$-27$_a$) of the conjugate group GalNAc$_1$-27 can be combined with any cleavable moiety present on the oligonucleotide to provide a variety of conjugate groups. The structure of GalNAc$_1$-27 (GalNAc$_1$-27$_a$-CM) is shown below:

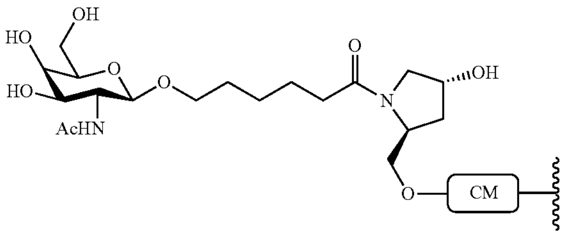

Example 108: Antisense Inhibition In Vivo by Oligonucleotides Comprising a GalNAc Conjugate Group Targeting Apo(a) In Vivo The oligonucleotides listed in Table 118 below were tested in a single dose study in mice.

TABLE 118

Modified ASOs targeting APO(a)

| ISIS No. | Sequences (5' to 3') | GalNAc$_3$ Cluster | CM | Unmodified SEQ ID No | Modified SEQ ID No |
|---|---|---|---|---|---|
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 277 | 326 |
| 681251 | **GalNAc$_3$-7$_a$-$_{o'}$**$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | GalNAc$_3$-7a | PO | 277 | 335 |
| 681255 | **GalNAC$_3$-3$_a$-$_{o'}$**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | GalNAc$_3$-3a | PO | 277 | 336 |
| 681256 | **GalNAc$_3$-10$_a$-$_{o'}$**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | GalNAc$_3$-10a | PO | 277 | 337 |
| 681257 | **GalNAc$_3$-7$_a$-$_{o'}$**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | GalNAc$_3$-7a | PO | 277 | 338 |
| 681258 | **GalNAc$_3$-13$_a$-$_{o'}$**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | GalNAc$_3$-13a | PO | 277 | 339 |
| 681260 | $T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{eo}$**A**$_{do'}$**-GalNAc$_3$-19** | GalNAc$_3$-19a | $A_d$ | 276 | 420 |

The structure of GalNAc$_3$-7$_a$ was shown in Example 48.

Treatment

Male transgenic mice that express human Apo(a) were each injected subcutaneously once with an oligonucleotide and dosage listed in Table 119 or with PBS. Each treatment group consisted of 4 animals. Blood was drawn the day before dosing to determine baseline levels of Apo(a) protein in plasma and at 1 week following the first dose. Additional blood draws will occur weekly for approximately 8 weeks. Plasma Apo(a) protein levels were measured using an ELISA. The results in Table 119 are presented as the average percent of plasma Apo(a) protein levels for each treatment group, normalized to baseline levels (% BL), The results show that the antisense oligonucleotides reduced Apo(a) protein expression. Furthermore, the oligonucleotides comprising a GalNAc conjugate group exhibited even more potent reduction in Apo(a) expression than the oligonucleotide that does not comprise a conjugate group.

TABLE 119

Apo(a) plasma protein levels

| ISIS No. | Dosage (mg/kg) | Apo(a) at 1 week (% BL) |
|---|---|---|
| PBS | n/a | 143 |
| 494372 | 50 | 58 |
| 681251 | 10 | 15 |
| 681255 | 10 | 14 |
| 681256 | 10 | 17 |
| 681257 | 10 | 24 |
| 681258 | 10 | 22 |
| 681260 | 10 | 26 |

Example 109: Synthesis of Oligonucleotides Comprising a $GalNAc_1$-28 or $GalNAc_1$-29 Conjugate

241

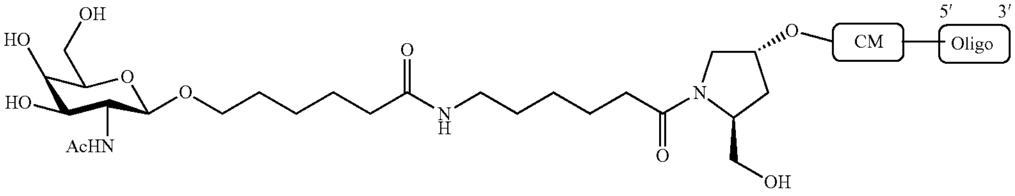

Oligonucleotide 241 is synthesized using procedures similar to those described in Example 71 to form the phosphoramidite intermediate, followed by procedures described in Example 10 to synthesize the oligonucleotide. The $GalNAc_1$ cluster portion ($GalNAc_1$-$28_a$) of the conjugate group $GalNAc_1$-28 can be

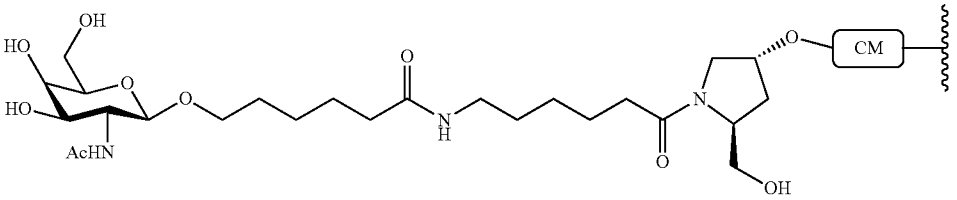

combined with any cleavable moiety present on the oligonucleotide to provide a variety of conjugate groups. The structure of $GalNAc_1$-28 ($GalNAc_1$-$28_a$-CM) is shown below:

In order to add the $GalNAc_1$ conjugate group to the 3'-end of an oligonucleotide, procedures similar to those described in Example 71 are used to form the hydroxyl intermediate, which is then added to the solid support using procedures described in Example 7. The oligonucleotide synthesis is then completed using procedures described in Example 9 in order to form oligonucleotide 242.

242

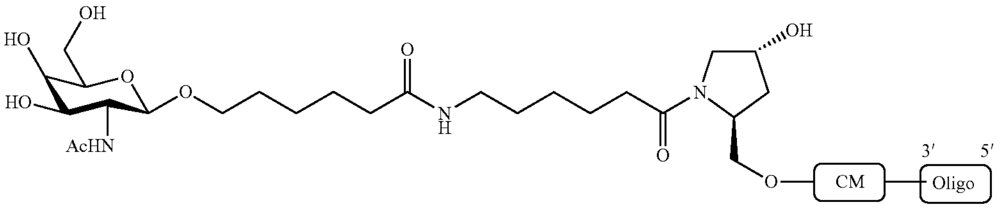

The $GalNAc_1$ cluster portion ($GalNAc_1$-$29_a$) of the conjugate group $GalNAc_1$-29 can be combined with any cleavable moiety present on the oligonucleotide to provide a variety of conjugate groups. The structure of $GalNAc_1$-29 ($GalNAc_1$-$29_a$-CM) is shown below:

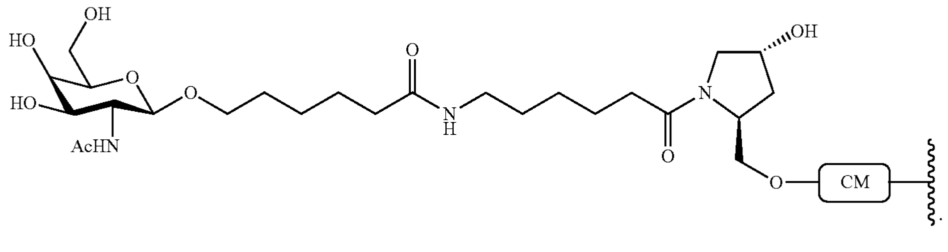

Example 110: Synthesis of Oligonucleotides Comprising a $GalNAc_1$-30 Conjugate

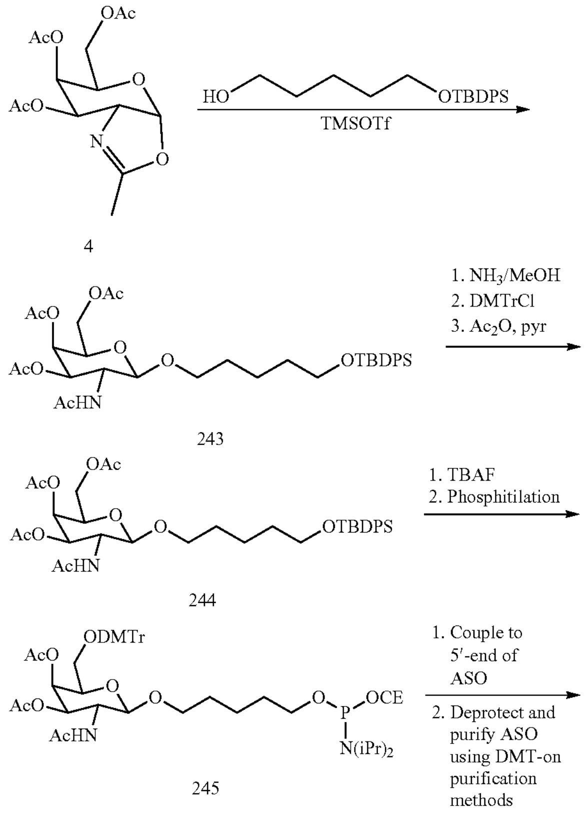

4

243

244

245

-continued

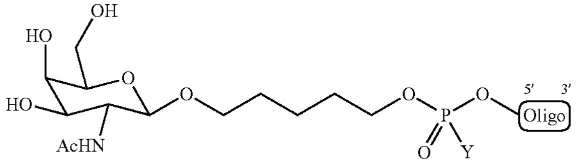

246

Oligonucleotide 246 comprising a $GalNAc_1$-30 conjugate group, wherein Y is selected from O, S, a substituted or unsubstituted $C_1$-$C_{10}$ alkyl, amino, substituted amino, azido, alkenyl or alkynyl, is synthesized as shown above. The $GalNAc_1$ cluster portion ($GalNAc_1$-$30_a$) of the conjugate group $GalNAc_1$-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of $GalNAc_1$-$30_a$ is shown below:

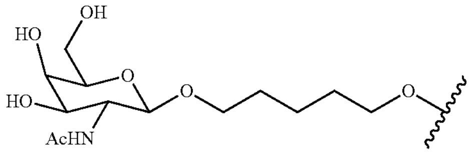 [SMILES: *OCCCCCOC1OC(CO)C(O)C(O)C1NC(C)=O]

Example 111: Synthesis of Oligonucleotides Comprising a $GalNAc_2$-31 or $GalNAc_2$-32 Conjugate

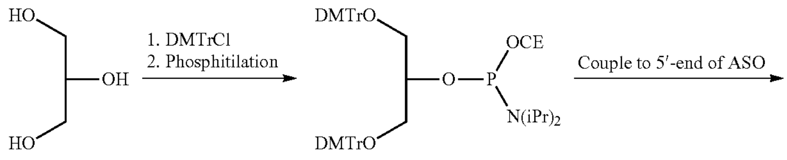

247

248

-continued

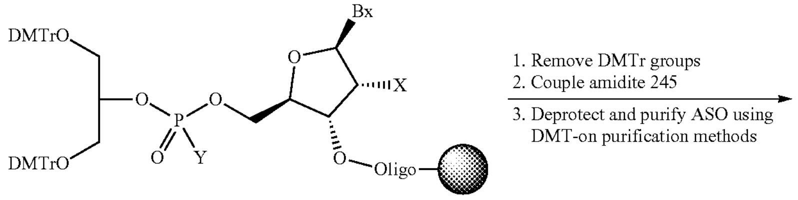

249

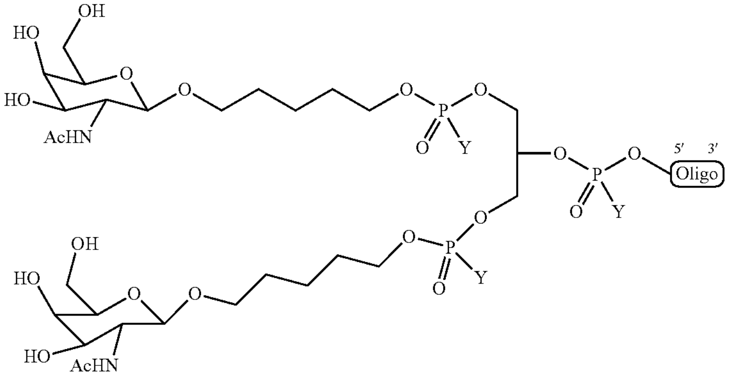

250

Oligonucleotide 250 comprising a GalNAc$_2$-31 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc$_2$ cluster portion (GalNAc$_2$-31$_a$) of the conjugate group GalNAc$_2$-31 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc$_2$-31$_a$ is shown below:

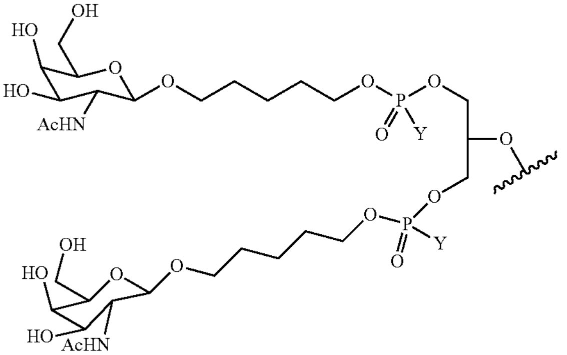

The synthesis of an oligonucleotide comprising a GalNAc$_2$-32 conjugate is shown below.

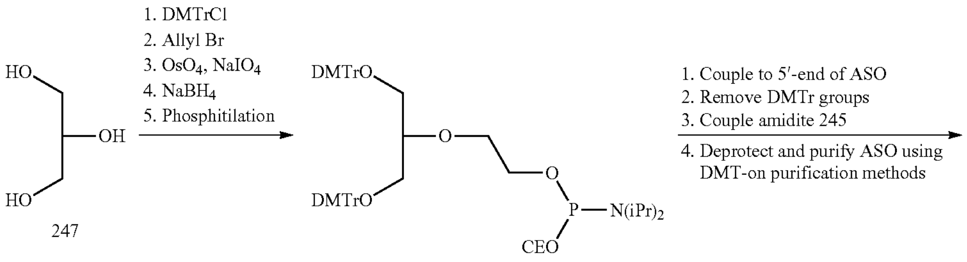

247

251

-continued

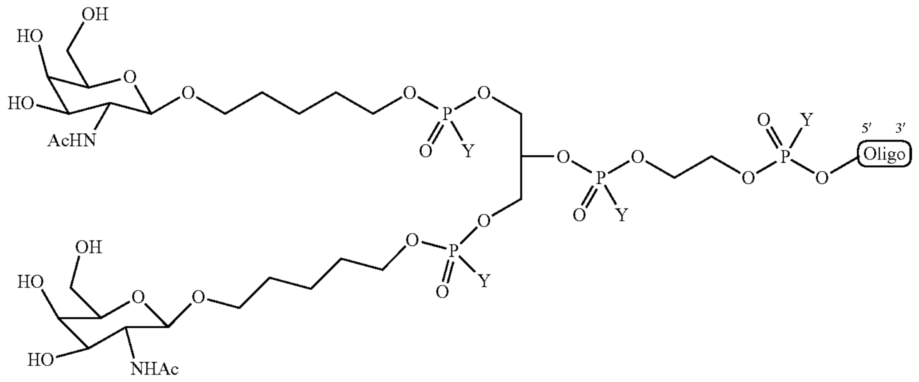

252

Oligonucleotide 252 comprising a $GalNAc_2$-32 conjugate group, wherein Y is selected from O, S, a substituted or unsubstituted $C_1$-$C_{10}$ alkyl, amino, substituted amino, azido, alkenyl or alkynyl, is synthesized as shown above. The $GalNAc_2$ cluster portion ($GalNAc_2$-$32_a$) of the conjugate group $GalNAc_2$-32 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of $GalNAc_2$-$32_a$ is shown below:

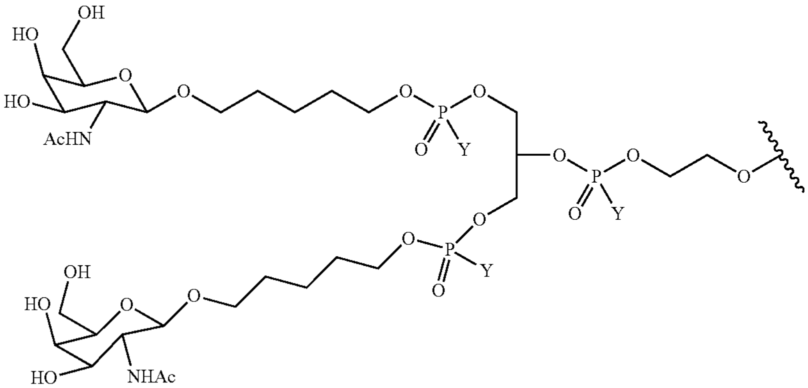

Example 112: Modified Oligonucleotides Comprising a $GalNAc_1$ Conjugate

The oligonucleotides in Table 120 targeting SRB-1 were synthesized with a $GalNAc_1$ conjugate group in order to further test the potency of oligonucleotides comprising conjugate groups that contain one GalNAc ligand.

TABLE 120

| ISIS No. | Sequence (5' to 3') | GalNAc cluster | CM | Unmodified SEQ ID No | Modified SEQ ID No |
|---|---|---|---|---|---|
| 711461 | **GalNAc**$_1$**-25**$_{a-o'}$$A_{do}$ $G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{e}$ | GalNAc$_1$-25$_a$ | $A_d$ | 254 | 432 |
| 711462 | **GalNAc**$_1$**-25**$_{a-o'}$$G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{e}$ | GalNAc$_1$-25$_a$ | PO | 252 | 356 |
| 711463 | **GalNAc**$_1$**-25**$_{a-o}$'$G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{e}$ | GalNAc$_1$-25$_a$ | PO | 252 | 357 |
| 711465 | **GalNAc**$_1$**-26**$_{a-o'}$**A**$_{do}$ $G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{e}$ | GalNAc$_1$-26$_a$ | $A_d$ | 254 | 433 |
| 711466 | **GalNAc**$_1$**-26**$_{a-o'}$$G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{e}$ | GalNAc$_1$-26$_a$ | PO | 252 | 358 |
| 711467 | **GalNAc**$_1$**-26**$_{a-o'}$$G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{e}$ | GalNAc$_1$-26$_a$ | PO | 252 | 359 |
| 711468 | **GalNAc**$_1$**-28**$_{a-o'}$**A**$_{do}$ $G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{e}$ | GalNAc$_1$-28$_a$ | $A_d$ | 254 | 434 |
| 711469 | **GalNAc**$_1$**-28**$_{a-o'}$$G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{e}$ | GalNAc$_1$-28$_a$ | PO | 252 | 360 |
| 711470 | **GalNAc**$_1$**-28**$_{a-o'}$$G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{e}$ | GalNAc$_1$-28$_a$ | PO | 252 | 361 |
| 713844 | $G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{eo'}$**-GalNAc**$_1$**-27**$_a$ | GalNAc$_1$-27$_a$ | PO | 252 | 362 |
| 713845 | $G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{eo'}$**-GalNAc**$_1$**-27**$_a$ | GalNAc$_1$-27$_a$ | PO | 252 | 363 |
| 713846 | $G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{eo}$ **A**$_{do'}$**-GalNAc**$_1$**-27**$_a$ | GalNAc$_1$-27$_a$ | $A_d$ | 253 | 435 |
| 713847 | $G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{eo'}$**-GalNAc**$_1$**-29**$_a$ | GalNAc$_1$-29$_a$ | PO | 252 | 364 |
| 713848 | $G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{eo'}$**-GalNAc**$_1$**-29**$_a$ | GalNAc$_1$-29$_a$ | PO | 252 | 365 |
| 713849 | $G_{es}$ $^{m}C_{es}$ $T_{es}$ $T_{es}$ $^{m}C_{es}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{es}$ $^{m}C_{es}$ $^{m}C_{es}$ $T_{es}$ $T_{eo}$ **A**$_{do'}$**-GalNAc**$_1$**-29**$_a$ | GalNAc$_1$-29$_a$ | $A_d$ | 253 | 436 |
| 713850 | $G_{es}$ $^{m}C_{eo}$ $T_{eo}$ $T_{eo}$ $^{m}C_{eo}$ $A_{ds}$ $G_{ds}$ $T_{ds}$ $^{m}C_{ds}$ $A_{ds}$ $T_{ds}$ $G_{ds}$ $A_{ds}$ $^{m}C_{ds}$ $T_{ds}$ $T_{eo}$ $^{m}C_{eo}$ $^{m}C_{es}$ $T_{es}$ $T_{eo}$ **A**$_{do'}$**-GalNAc**$_1$**-29**$_a$ | GalNAc$_1$-29$_a$ | $A_d$ | 253 | 437 |

Example 113: Design and Screening of Duplexed Antisense Compounds Targeting Apolipoprotein C-III In accordance with the present invention, a series of nucleic acid duplexes comprising the antisense compounds of the present invention and their complements are designed to target apolipoprotein C-Ill. The nucleobase sequence of the antisense strand of the duplex comprises at least a portion of an oligonucleotide in Table 121. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 12) and having a two-nucleobase overhang of deoxythymidine(dT) would have the following structure (Antisense SEQ ID NO: 13, Complement SEQ ID NO: 14):

```
  cgagaggcggacgggaccgTT    Antisense Strand (SEQ ID NO: 13)
  |||||||||||||||||||
TTgctctccgcctgccctggc      Complement (SEQ ID NO: 14)
```

In another embodiment, a duplex comprising an antisense strand having the same sequence CGAGAGGCGGACGGGACCG (SEQ ID NO: 12) may be prepared with blunt ends (no single stranded overhang) as shown (Antisense SEQ ID NO: 15, Complement SEQ ID NO: 16):

```
 cgagaggcggacgggaccg       Antisense Strand (SEQ ID NO: 15)
 |||||||||||||||||||
gctctccgcctgccctggc        Complement (SEQ ID NO: 16)
```

RNA strands of the duplex can be synthesized by methods disclosed herein or purchased from Dharmacon Research Inc., (Lafayette, CO). Once synthesized, the complementary strands are annealed. The single strands are aliquoted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate apolipoprotein C-III expression.

When cells reached 80% confluency, they are treated with duplexed antisense compounds of the invention. For cells grown in 96-well plates, wells are washed once with 200 μL OPTI-MEM-1™ reduced-serum medium (Gibco BRL) and then treated with 130 μL of OPTI-MEM-1™ medium containing 12 μg/mL LIPOFECTIN™ reagent (Gibco BRL) and the desired duplex antisense compound at a final concentration of 200 nM. After 5 hours of treatment, the medium is replaced with fesh medium. Cells are harvested 16 hours after treatment, at which time RNA is isolated and target reduction measured by RT-PCR.

Example 114: Antisense Inhibition of Human Apolipoprotein C-III Expression by Chimeric Phosphorothioate Oligonucleotides Having 2'-MOE Wings and a Deoxy Gap In accordance with the present invention, a series of antisense compounds was designed to target different regions of the human apolipoprotein C-III RNA, using published sequences (nucleotides 6238608 to 6242565 of GenBank accession number NT_035088.1, representing a genomic sequence, incorporated herein as SEQ ID NO: 3, and GenBank accession number NM_000040.1, incorporated herein as SEQ ID NO: 1). The compounds are shown in Table 121. "Target site" indicates the first (5'-most) nucleotide number on the particular target sequence to which the compound binds. All compounds in Table 121 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl) nucleotides, also known as (2'-MOE)nucleotides. The internucleoside (backbone) linkages are phosphorothioate (P=S) throughout the oligonucleotide. All cytidine residues are 5-methylcytidines. The compounds were analyzed for their effect on human apolipoprotein C-III mRNA levels by quantitative real-time PCR as described in other examples herein. Data are averages from three experiments in which HepG2 cells were treated with the antisense oligonucleotides of the present invention. The positive control for each datapoint is identified in the table by sequence ID number. If present, "N.D." indicates "no data".

TABLE 121

Inhibition of human apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 167824 | 5'UTR | 3 | 414 | ctggagcagctgcctctagg | 79 | 19 | 1 |
| 167835 | Coding | 3 | 1292 | ccctgcatgaagctgagaag | 60 | 20 | 1 |
| 167837 | Coding | 1 | 141 | gtgcttcatgtaaccctgca | 88 | 21 | 1 |
| 167846 | Coding | 3 | 1369 | tggcctgctgggccacctgg | 66 | 22 | 1 |
| 167848 | Coding | 3 | 3278 | tgctccagtagtctttcagg | 81 | 23 | 1 |
| 167851 | Coding | 3 | 3326 | tgacctcagggtccaaatcc | 41 | 24 | 1 |
| 304739 | 5'UTR | 3 | 401 | ctctagggatgaactgagca | 62 | 25 | 1 |
| 304740 | 5'UTR | 3 | 408 | cagctgcctctagggatgaa | 44 | 26 | 1 |
| 304741 | 5'UTR | 1 | 17 | ttcctggagcagctgcctct | 57 | 27 | 1 |
| 304742 | 5'UTR | 1 | 24 | acctctgttcctggagcagc | 78 | 28 | 1 |
| 304743 | Start Codon | 1 | 29 | atggcacctctgttcctgga | 78 | 29 | 1 |

TABLE 121-continued

Inhibition of human apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 304744 | Start Codon | 3 | 1065 | gggctgcatggcacctctgt | 73 | 30 | 1 |
| 304745 | Coding | 3 | 1086 | ggcaacaacaaggagtaccc | 90 | 31 | 1 |
| 304746 | Coding | 3 | 1090 | ggagggcaacaacaaggagt | 80 | 32 | 1 |
| 304747 | Coding | 1 | 87 | agctcgggcagaggccagga | 49 | 33 | 1 |
| 304748 | Coding | 1 | 92 | tctgaagctcgggcagaggc | 72 | 34 | 1 |
| 304749 | Coding | 1 | 97 | cggcctctgaagctcgggca | 11 | 35 | 1 |
| 304750 | Coding | 3 | 1267 | catcctcggcctctgaagct | 49 | 36 | 1 |
| 304751 | Coding | 3 | 1273 | gggaggcatcctcggcctct | 65 | 37 | 1 |
| 304752 | Coding | 3 | 1278 | gagaagggaggcatcctcgg | 82 | 38 | 1 |
| 304753 | Coding | 3 | 1281 | gctgagaagggaggcatcct | 75 | 39 | 1 |
| 304754 | Coding | 3 | 1289 | tgcatgaagctgagaaggga | 74 | 40 | 1 |
| 304755 | Coding | 1 | 143 | gcgtgcttcatgtaaccctg | 95 | 41 | 1 |
| 304756 | Coding | 3 | 1313 | ttggtggcgtgcttcatgta | 92 | 42 | 1 |
| 304757 | Coding | 3 | 1328 | gcatccttggcggtcttggt | 98 | 43 | 1 |
| 304758 | Coding | 3 | 1334 | ctcagtgcatccttggcggt | 97 | 44 | 1 |
| 304759 | Coding | 3 | 1336 | tgctcagtgcatccttggcg | 93 | 45 | 1 |
| 304760 | Coding | 3 | 1347 | ctcctgcacgctgctcagtg | 65 | 46 | 1 |
| 304761 | Coding | 3 | 1349 | gactcctgcacgctgctcag | 77 | 47 | 1 |
| 304762 | Coding | 3 | 1358 | gccacctgggactcctgcac | 89 | 48 | 1 |
| 304763 | Coding | 1 | 210 | gcccctggcctgctgggcca | 71 | 49 | 1 |
| 304764 | Coding | 1 | 211 | agcccctggcctgctgggcc | 62 | 50 | 1 |
| 304765 | Coding | 3 | 3253 | gaagccatcggtcacccagc | 71 | 51 | 1 |
| 304766 | Coding | 3 | 3255 | ctgaagccatcggtcaccca | 85 | 52 | 1 |
| 304767 | Coding | 3 | 3265 | tttcagggaactgaagccat | 73 | 53 | 1 |
| 304768 | Coding | 3 | 3273 | cagtagtctttcagggaact | 40 | 54 | 1 |
| 304769 | Coding | 3 | 3283 | aacggtgctccagtagtctt | 66 | 55 | 1 |
| 304770 | Coding | 3 | 3287 | ccttaacggtgctccagtag | 88 | 56 | 1 |
| 304771 | Coding | 3 | 3295 | gaacttgtccttaacggtgc | 59 | 57 | 1 |
| 304772 | Coding | 3 | 3301 | ctcagagaacttgtccttaa | 88 | 58 | 1 |
| 304773 | Coding | 3 | 3305 | agaactcagagaacttgtcc | 75 | 59 | 1 |
| 304774 | Coding | 3 | 3310 | atcccagaactcagagaact | 0 | 60 | 1 |
| 304775 | Coding | 3 | 3320 | cagggtccaaatcccagaac | 70 | 61 | 1 |
| 304776 | Coding | 3 | 3332 | ttggtctgacctcagggtcc | 90 | 62 | 1 |
| 304777 | Coding | 3 | 3333 | gttggtctgacctcagggtc | 84 | 63 | 1 |
| 304778 | Coding | 3 | 3339 | gctgaagttggtctgacctc | 81 | 64 | 1 |
| 304779 | Coding | 3 | 3347 | cagccacggctgaagttggt | 75 | 65 | 1 |
| 304780 | Stop Codon | 3 | 3351 | caggcagccacggctgaagt | 83 | 66 | 1 |

TABLE 121-continued

Inhibition of human apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 304781 | Stop Codon | 3 | 3361 | attgaggtctcaggcagcca | 79 | 67 | 1 |
| 304782 | 3'UTR | 3 | 3385 | tggataggcaggtggacttg | 64 | 68 | 1 |
| 304783 | 3'UTR | 1 | 369 | ctcgcaggatggataggcag | 76 | 69 | 1 |
| 304784 | 3'UTR | 1 | 374 | aggagctcgcaggatggata | 58 | 70 | 1 |
| 304785 | 3'UTR | 1 | 380 | gacccaaggagctcgcagga | 73 | 71 | 1 |
| 304786 | 3'UTR | 1 | 385 | tgcaggacccaaggagctcg | 92 | 72 | 1 |
| 304787 | 3'UTR | 3 | 3417 | tggagattgcaggacccaag | 88 | 73 | 1 |
| 304788 | 3'UTR | 3 | 3422 | agccctggagattgcaggac | 69 | 74 | 1 |
| 304789 | 3'UTR | 3 | 3425 | ggcagccctggagattgcag | 76 | 75 | 1 |
| 304790 | 3'UTR | 3 | 3445 | ccttttaagcaacctacagg | 65 | 76 | 1 |
| 304791 | 3'UTR | 3 | 3450 | ctgtcccttttaagcaacct | 53 | 77 | 1 |
| 304792 | 3'UTR | 3 | 3456 | agaatactgtcccttttaag | 72 | 78 | 1 |
| 304793 | 3'UTR | 3 | 3461 | cactgagaatactgtccctt | 67 | 79 | 1 |
| 304794 | 3'UTR | 3 | 3469 | taggagagcactgagaatac | 59 | 80 | 1 |
| 304795 | 3'UTR | 3 | 3472 | gggtaggagagcactgagaa | 74 | 81 | 1 |
| 304796 | 3'UTR | 3 | 3509 | aggccagcatgcctggaggg | 63 | 82 | 1 |
| 304797 | 3'UTR | 3 | 3514 | ttgggaggccagcatgcctg | 55 | 83 | 1 |
| 304798 | 3'UTR | 3 | 3521 | agctnattgggaggccagc | 90 | 84 | 1 |
| 304799 | 3'UTR | 3 | 3526 | tgtccagctnattgggagg | 85 | 85 | 1 |
| 304800 | 3'UTR | 3 | 3528 | cttgtccagctttattggga | 94 | 86 | 1 |
| 304801 | 3'UTR | 3 | 3533 | agcttcttgtccagctttat | 74 | 87 | 1 |
| 304802 | 3'UTR | 3 | 3539 | catagcagcttcttgtccag | 73 | 88 | 1 |
| 304803 | exon:intron junction | 3 | 416 | acctggagcagctgcctcta | 87 | 89 | 1 |
| 304804 | exon:intron junction | 3 | 424 | agggcattacctggagcagc | 68 | 90 | 1 |
| 304805 | intron:exon junction | 3 | 1053 | acctctgttcctgcaaggaa | 74 | 91 | 1 |
| 304806 | exon:intron junction | 3 | 1121 | aagtgcttacgggcagaggc | 78 | 92 | 1 |
| 304807 | exon:intron junction | 3 | 1380 | gcgggtgtacctggcctgct | 52 | 93 | 1 |
| 304808 | intron | 3 | 2337 | aaccctgttgtgaactgcac | 59 | 94 | 1 |
| 304809 | intron | 3 | 2405 | agtgagcaataccgcctgag | 80 | 95 | 1 |
| 304810 | intron | 3 | 2542 | cgggcttgaattaggtcagg | 56 | 96 | 1 |

As shown in the table above, SEQ ID NOs 19, 20, 21, 22, 23, 25, 27, 28, 29, 30, 31, 32, 33, 34, 36, 37, 38, 39, 40, 41, 42, 43, 44, 45, 46, 47, 48, 49, 50, 51, 52, 53, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 and 96 demonstrated at least 45% inhibition of human apolipoprotein C-III expression in this assay and are therefore preferred. More preferred are SEQ ID NOs 75, 86 and 85. The target regions to which these preferred sequences are complementary are herein referred to as "preferred target segments" and are therefore preferred for targeting by compounds of the present invention. These preferred target segments are shown in a Table 123 below. The sequences represent the reverse complement of the preferred antisense compounds shown in the table above. "Target site" indicates the first (5-most) nucleotide number on the particular target nucleic acid to which the oligonucleotide binds. Also shown in Table 123 is the species in which each of the preferred target segments was found.

Example 115: Antisense Inhibition of Mouse Apolipoprotein C-III Expression by Chimeric Phosphorothioate Oligonucleotides Having 2'-MOE Wings and a Deoxy Gap In accordance with the present invention, a second series of antisense compounds was designed to target different regions of the mouse apolipoprotein C-III RNA, using published sequences (GenBank accession number L04150.1, incorporated herein as SEQ ID NO: 11). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl)nucleotides, also known as (2'-MOE)nucleotides. The internucleoside (backbone) linkages are phosphorothioate (P=S) throughout the oligonucleotide. All cytidine residues are 5-methylcytidines. The compounds were analyzed for their effect on mouse apolipoprotein C-III mRNA levels by quantitative real-time PCR as described in other examples herein. Data are averages from three experiments in which mouse primary hepatocyte cells were treated with the antisense oligonucleotides of the present invention. If present, "N.D." indicates "no data".

TABLE 122

Inhibition of mouse apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 167858 | 5'UTR | 11 | 1 | tagggataaaactgagcagg | 47 | 97 |
| 167859 | 5'UTR | 11 | 21 | ctggagtagctagctgcttc | 30 | 98 |
| 167860 | start codon | 11 | 41 | gctgcatggcacctacgtac | 80 | 99 |
| 167861 | coding | 11 | 62 | ccacagtgaggagcgtccgg | 86 | 100 |
| 167862 | coding | 11 | 88 | ggcagatgccaggagagcca | 55 | 101 |
| 167863 | coding | 11 | 104 | ctacctcttcagctcgggca | 56 | 102 |
| 167864 | coding | 11 | 121 | cagcagcaaggatccctcta | 83 | 103 |
| 167865 | coding | 11 | 131 | gcacagagcccagcagcaag | 49 | 104 |
| 167867 | coding | 11 | 215 | ccctggccaccgcagctata | 67 | 105 |
| 167868 | coding | 11 | 239 | atctgaagtgattgtccatc | 11 | 106 |
| 167869 | coding | 11 | 254 | agtagcctttcaggaatctg | 57 | 107 |
| 167870 | coding | 11 | 274 | cttgtcagtaaacttgctcc | 89 | 108 |
| 167871 | coding | 11 | 286 | gaagccggtgaacttgtcag | 55 | 109 |
| 167872 | coding | 11 | 294 | gaatcccagaagccggtgaa | 29 | 110 |
| 167873 | coding | 11 | 299 | ggttagaatcccagaagccg | 55 | 111 |
| 167874 | coding | 11 | 319 | tggagttggttggtcctcag | 79 | 112 |
| 167875 | stop codon | 11 | 334 | tcacgactcaatagctggag | 77 | 113 |
| 167877 | 3'UTR | 11 | 421 | cccttaaagcaaccttcagg | 71 | 114 |
| 167878 | 3'UTR | 11 | 441 | agacatgagaacatactttc | 81 | 115 |
| 167879 | 3'UTR | 11 | 471 | catgtttaggtgagatctag | 87 | 116 |
| 167880 | 3'UTR | 11 | 496 | tcttatccagctttattagg | 98 | 117 |

As shown in the tale above, SEQ ID NOs 97, 99, 100, 101, 102, 103, 104, 105, 107, 108, 109, 111, 112, 113, 114, 115, 116 and 117 demonstrated at least 45% inhibition of mouse apolipoprotein C-III expression in this experiment and are therefore preferred. More preferred are SEQ ID NOs 117, 116, and 100. The target regions to which these preferred sequences are complementary are herein referred to as "preferred target segments" and are therefore preferred for targeting by compounds of the present invention. These preferred target segments are shown in the table below. The sequences represent the reverse complement of the preferred antisense compounds shown in the table above. These sequences are shown to contain thymine (T) but one of skill in the art will appreciate that thymine (T) is generally replaced by uracil (U) in RNA sequences. "Target site" indicates the first (5'-most) nucleotide number on the particular target nucleic acid to which the oligonucleotide binds. Also shown in Table 3 is the species in which each of the preferred target segments was found.

TABLE 123

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---|---|---|---|---|---|---|
| 82975 | 3 | 414 | cctagaggcagctgctccag | 19 | *H. sapiens* | 118 |
| 82980 | 3 | 1292 | cttctcagcttcatgcaggg | 20 | *H. sapiens* | 119 |
| 82981 | 1 | 141 | tgcagggttacatgaagcac | 21 | *H. sapiens* | 120 |
| 82985 | 3 | 1369 | ccaggtggcccagcaggcca | 22 | *H. sapiens* | 121 |
| 82987 | 3 | 3278 | cctgaaagactactggagca | 23 | *H. sapiens* | 122 |
| 220510 | 3 | 401 | tgctcagttcatccctagag | 25 | *H. sapiens* | 123 |
| 220512 | 1 | 17 | agaggcagctgctccaggaa | 27 | *H. sapiens* | 124 |
| 220513 | 1 | 24 | gctgctccaggaacagaggt | 28 | *H. sapiens* | 125 |
| 220514 | 1 | 29 | tccaggaacagaggtgccat | 29 | *H. sapiens* | 126 |
| 220515 | 3 | 1065 | acagaggtgccatgcagccc | 30 | *H. sapiens* | 127 |
| 220516 | 3 | 1086 | gggtactccttgttgttgcc | 31 | *H. sapiens* | 128 |
| 220517 | 3 | 1090 | actccttgttgttgccctcc | 32 | *H. sapiens* | 129 |
| 220518 | 1 | 87 | tcctggcctctgcccgagct | 33 | *H. sapiens* | 130 |
| 220519 | 1 | 92 | gcctctgcccgagcttcaga | 34 | *H. sapiens* | 131 |
| 220521 | 3 | 1267 | agcttcagaggccgaggatg | 36 | *H. sapiens* | 132 |
| 220522 | 3 | 1273 | agaggccgaggatgcctccc | 37 | *H. sapiens* | 133 |
| 220523 | 3 | 1278 | ccgaggatgcctcccttctc | 38 | *H. sapiens* | 134 |
| 220524 | 3 | 1281 | aggatgcctcccttctcagc | 39 | *H. sapiens* | 135 |
| 220525 | 3 | 1289 | tcccttctcagcttcatgca | 40 | *H. sapiens* | 136 |
| 220526 | 1 | 143 | cagggttacatgaagcacgc | 41 | *H. sapiens* | 137 |
| 220527 | 3 | 1313 | tacatgaagcacgccaccaa | 42 | *H. sapiens* | 138 |
| 220528 | 3 | 1328 | accaagaccgccaaggatgc | 43 | *H. sapiens* | 139 |
| 220529 | 3 | 1334 | accgccaaggatgcactgag | 44 | *H. sapiens* | 140 |
| 220530 | 3 | 1336 | cgccaaggatgcactgagca | 45 | *H. sapiens* | 141 |
| 220531 | 3 | 1347 | cactgagcagcgtgcaggag | 46 | *H. sapiens* | 142 |
| 220532 | 3 | 1349 | ctgagcagcgtgcaggagtc | 47 | *H. sapiens* | 143 |
| 220533 | 3 | 1358 | gtgcaggagtcccaggtggc | 48 | *H. sapiens* | 144 |
| 220534 | 1 | 210 | tggcccagcaggccaggggc | 49 | *H. sapiens* | 145 |
| 220535 | 1 | 211 | ggcccagcaggccaggggct | 50 | *H. sapiens* | 146 |
| 220536 | 3 | 3253 | gctgggtgaccgatggcttc | 51 | *H. sapiens* | 147 |

TABLE 123-continued

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---|---|---|---|---|---|---|
| 220537 | 3 | 3255 | tgggtgaccgatggcttcag | 52 | *H. sapiens* | 148 |
| 220538 | 3 | 3265 | atggcttcagttccctgaaa | 53 | *H. sapiens* | 149 |
| 220540 | 3 | 3283 | aagactactggagcaccgtt | 55 | *H. sapiens* | 150 |
| 220541 | 3 | 3287 | ctactggagcaccgttaagg | 56 | *H. sapiens* | 151 |
| 220542 | 3 | 3295 | gcaccgttaaggacaagttc | 57 | *H. sapiens* | 152 |
| 220543 | 3 | 3301 | ttaaggacaagttctctgag | 58 | *H. sapiens* | 153 |
| 220544 | 3 | 3305 | ggacaagttctctgagttct | 59 | *H. sapiens* | 154 |
| 220546 | 3 | 3320 | gttctgggatttggaccctg | 61 | *H. sapiens* | 155 |
| 220547 | 3 | 3332 | ggaccctgaggtcagaccaa | 62 | *H. sapiens* | 156 |
| 220548 | 3 | 3333 | gaccctgaggtcagaccaac | 63 | *H. sapiens* | 157 |
| 220549 | 3 | 3339 | gaggtcagaccaacttcagc | 64 | *H. sapiens* | 158 |
| 220550 | 3 | 3347 | accaacttcagccgtggctg | 65 | *H. sapiens* | 159 |
| 220551 | 3 | 3351 | acttcagccgtggctgcctg | 66 | *H. sapiens* | 160 |
| 220552 | 3 | 3361 | tggctgcctgagacctcaat | 67 | *H. sapiens* | 161 |
| 220553 | 3 | 3385 | caagtccacctgcctatcca | 68 | *H. sapiens* | 162 |
| 220554 | 1 | 369 | ctgcctatccatcctgcgag | 69 | *H. sapiens* | 163 |
| 220555 | 1 | 374 | tatccatcctgcgagctcct | 70 | *H. sapiens* | 164 |
| 220556 | 1 | 380 | tcctgcgagctccttgggtc | 71 | *H. sapiens* | 165 |
| 220557 | 1 | 385 | cgagctccttgggtcctgca | 72 | *H. sapiens* | 166 |
| 220558 | 3 | 3417 | cttgggtcctgcaatctcca | 73 | *H. sapiens* | 167 |
| 220559 | 3 | 3422 | gtcctgcaatctccagggct | 74 | *H. sapiens* | 168 |
| 220560 | 3 | 3425 | ctgcaatctccagggctgcc | 75 | *H. sapiens* | 169 |
| 220561 | 3 | 3445 | cctgtaggttgcttaaaagg | 76 | *H. sapiens* | 170 |
| 220562 | 3 | 3450 | aggttgcttaaaagggacag | 77 | *H. sapiens* | 171 |
| 220563 | 3 | 3456 | cttaaaagggacagtattct | 78 | *H. sapiens* | 172 |
| 220564 | 3 | 3461 | aagggacagtattctcagtg | 79 | *H. sapiens* | 173 |
| 220565 | 3 | 3469 | gtattctcagtgctctccta | 80 | *H. sapiens* | 174 |
| 220566 | 3 | 3472 | ttctcagtgctctcctaccc | 81 | *H. sapiens* | 175 |
| 220567 | 3 | 3509 | ccctccaggcatgctggcct | 82 | *H. sapiens* | 176 |
| 220568 | 3 | 3514 | caggcatgctggcctcccaa | 83 | *H. sapiens* | 177 |
| 220569 | 3 | 3521 | gctggcctcccaataaagct | 84 | *H. sapiens* | 178 |
| 220570 | 3 | 3526 | cctcccaataaagctggaca | 85 | *H. sapiens* | 179 |
| 220571 | 3 | 3528 | tcccaataaagctggacaag | 86 | *H. sapiens* | 180 |
| 220572 | 3 | 3533 | ataaagctggacaagaagct | 87 | *H. sapiens* | 181 |
| 220573 | 3 | 3539 | ctggacaagaagctgctatg | 88 | *H. sapiens* | 182 |
| 220574 | 3 | 416 | tagaggcagctgctccaggt | 89 | *H. sapiens* | 183 |
| 220575 | 3 | 424 | gctgctccaggtaatgccct | 90 | *H. sapiens* | 184 |

TABLE 123-continued

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---|---|---|---|---|---|---|
| 220576 | 3 | 1053 | ttccttgcaggaacagaggt | 91 | *H. sapiens* | 185 |
| 220577 | 3 | 1121 | gcctctgcccgtaagcactt | 92 | *H. sapiens* | 186 |
| 220578 | 3 | 1380 | agcaggccaggtacacccgc | 93 | *H. sapiens* | 187 |
| 220579 | 3 | 2337 | gtgcagttcacaacagggtt | 94 | *H. sapiens* | 188 |
| 220580 | 3 | 2405 | ctcaggcggtattgctcact | 95 | *H. sapiens* | 189 |
| 220581 | 3 | 2542 | cctgacctaattcaagcccg | 96 | *H. sapiens* | 190 |
| 82997 | 11 | 1 | cctgctcagttttatcccta | 97 | *M. musculus* | 191 |
| 82999 | 11 | 41 | gtacgtaggtgccatgcagc | 99 | *M. musculus* | 192 |
| 83000 | 11 | 62 | ccggacgctcctcactgtgg | 100 | *M. musculus* | 193 |
| 83001 | 11 | 88 | tggctctcctggcatctgcc | 101 | *M. musculus* | 194 |
| 83002 | 11 | 104 | tgcccgagctgaagaggtag | 102 | *M. musculus* | 195 |
| 83003 | 11 | 121 | tagagggatccttgctgctg | 103 | *M. musculus* | 196 |
| 83004 | 11 | 131 | cttgctgctgggctctgtgc | 104 | *M. musculus* | 197 |
| 83006 | 11 | 215 | tatagctgcggtggccaggg | 105 | *M. musculus* | 198 |
| 83008 | 11 | 254 | cagattcctgaaaggctact | 107 | *M. musculus* | 199 |
| 83009 | 11 | 274 | ggagcaagtttactgacaag | 108 | *M. musculus* | 200 |
| 83010 | 11 | 286 | ctgacaagttcaccggcttc | 109 | *M. musculus* | 201 |
| 83012 | 11 | 299 | cggcttctgggattctaacc | 111 | *M. musculus* | 202 |
| 83013 | 11 | 319 | ctgaggaccaaccaactcca | 112 | *M. musculus* | 203 |
| 83014 | 11 | 334 | ctccagctattgagtcgtga | 113 | *M. musculus* | 204 |
| 83016 | 11 | 421 | cctgaaggttgctttaaggg | 114 | *M. musculus* | 205 |
| 83017 | 11 | 441 | gaaagtatgttctcatgtct | 115 | *M. musculus* | 206 |
| 83018 | 11 | 471 | ctagatctcacctaaacatg | 116 | *M. musculus* | 207 |
| 83019 | 11 | 496 | cctaataaagctggataaga | 117 | *M. musculus* | 208 |

As these “preferred target segments” have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of apolipoprotein C-III.

According to the present invention, antisense compounds include antisense oligomeric compounds, antisense oligonucleotides, ribozymes, external guide sequence (EGS) oligonucleotides, alternate splicers, primers, probes, and other short oligomeric compounds that hybridize to at least a portion of the target nucleic acid.

Example 116: Antisense Inhibition of Human Apolipoprotein C-III Expression by Chimeric Phosphorothioate Oligonucleotides Having 2'-MOE Wings and a Deoxy Gap—Additional Antisense Compounds In accordance with the present invention, an additional series of antisense compounds was designed to target different regions of the human apolipoprotein C-III RNA, using published sequences (nucleotides 6238608 to 6242565 of the sequence with GenBank accession number NT_035088.1, representing a genomic sequence, incorporated herein as SEQ ID NO: 3, and GenBank accession number NM_000040.1, incorporated herein as SEQ ID NO: 1). The compounds are shown in Table 124. “Target site” indicates the first (5'-most) nucleotide number on the particular target sequence to which the compound binds. All compounds in Table 124 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl) nucleotides, also known as (2'-MOE) nucleotides. The internucleoside (backbone) linkages are phosphorothioate (P=S) throughout the oligonucleotide. All cytidine residues are 5-methylcytidines. The compounds were analyzed for their effect on human apolipoprotein C-III mRNA levels by quantitative real-time PCR as described in other examples herein. Data are averages from three experiments in which HepG2 cells were treated with the antisense oligonucleotides of the present invention. If present, "N.D." indicates "no data".

TABLE 124

Inhibition of human apolipoprotein C-III mRNA levels by chimeric phosphorothioate oligonucleotides having 2'-MOE wings and a deoxy gap

| ISIS # | TARGET SEQ ID NO | TARGET SITE | SEQUENCE | % INHIB | SEQ ID NO |
|---|---|---|---|---|---|
| 167826 | 3 | 1063 | gctgcatggcacctctgttc | 0 | 209 |
| 167828 | 3 | 1110 | ggcagaggccaggagcgcca | 0 | 210 |
| 167830 | 1 | 91 | ctgaagctcgggcagaggcc | 9 | 211 |
| 167832 | 1 | 101 | tcctcggcctctgaagctcg | 0 | 212 |
| 167840 | 3 | 1315 | tcttggtggcgtgcttcatg | 0 | 213 |
| 167842 | 3 | 1335 | gctcagtgcatccttggcgg | 38 | 214 |
| 167844 | 3 | 1345 | cctgcacgctgctcagtgca | 28 | 215 |
| 167847 | 3 | 3256 | actgaagccatcggtcaccc | 0 | 216 |
| 167850 | 3 | 3306 | cagaactcagagaacttgtc | 0 | 217 |
| 167852 | 3 | 3336 | gaagttggtctgacctcagg | 0 | 218 |
| 167853 | 3 | 3420 | ccctggagattgcaggaccc | 0 | 219 |
| 167854 | 3 | 3426 | gggcagccctggagattgca | 22 | 220 |
| 167855 | 3 | 3446 | cccttttaagcaacctacag | 27 | 221 |

Example 117: Antisense Inhibition of Human Apolipoprotein C-III Expression by Chimeric Phosphorothioate Oligonucleotides Having 2'-MOE Wings and a Deoxy Gap: Dose-Response Study in HepG2 Cells In accordance with the present invention, a subset of the antisense oligonucleotides from Examples 15 and 17 was further investigated in a dose-response study. Treatment doses of ISIS 167842 (SEQ ID NO: 214), ISIS 167844 (SEQ ID NO: 215), ISIS 167846 (SEQ ID NO: 22), ISIS 167837 (SEQ ID NO: 21), ISIS 304789 (SEQ ID NO: 75), ISIS 304799 (SEQ ID NO: 85), and ISIS 304800 (SEQ ID: 86) were 50, 150 and 300 nM. The compounds were analyzed for their effect on human apolipoprotein C-III mRNA levels in HepG2 cells by quantitative real-time PCR as described in other examples herein. Data are averages from two experiments and are shown in the table below.

TABLE 125

Inhibition of human apolipoprotein C-III mRNA levels by chimeric phosphorothioate oligonucleotides having 2'-MOE wings and a deoxy gap

| | | Dose of oligonucleotide | | |
|---|---|---|---|---|
| ISIS # | SEQ ID NO | 50 nM | 150 nM | 300 nM |
| | | Percent Inhibition | | |
| 167842 | 214 | 88 | 77 | 92 |
| 167844 | 215 | 86 | 86 | 84 |
| 167846 | 22 | 79 | 80 | 79 |
| 167837 | 21 | 83 | 86 | 84 |
| 304789 | 75 | 81 | 91 | 92 |
| 304799 | 85 | 82 | 93 | 88 |
| 304800 | 86 | 80 | 86 | 91 |

These data demonstrate that the expression of apolipoprotein C-III is inhibited in a dose-dependent manner upon treatment of cells with antisense compounds targeting apolipoprotein C-III. These compounds were further analyzed in Hep3B cells for their ability to reduce mRNA levels in Hep3B cells and it was determined that ISIS 167842 and 167837 inhibited apolipoprotein C-III expression in a dose dependent manner in this cell line as well.

Example 118: Antisense Inhibition of Apolipoprotein C-III in Cynomolgus Monkey Primary Hepatocytes In a further embodiment, antisense compounds targeted to human apolipoprotein C-III were tested for their effects on apolipoprotein C-III expression in primary Cynomolgus monkey hepatocytes. Pre-plated primary Cynomolgus monkey hepatocytes were purchased from InVitro Technologies (Baltimore, MD). Cells were cultured in high-glucose DMEM (Invitrogen Life Technologies, Carlsbad, CA) supplemented with 10% fetal bovine serum (Invitrogen Life Technologies, Carlsbad, CA), 100 units/mL and 100 μg/mL streptomycin (Invitrogen Life Technologies, Carlsbad, CA).

Cells at a density of 80,000 cells per well in a 24-well plate were treated with 10, 50, 150 and 300 nM of ISIS 304789 (SEQ ID NO: 75), ISIS 304799 (SEQ ID NO: 85) or ISIS 304800 (SEQ ID NO: 86). ISIS 113529 (CTCTTACTGTGCTGTGGACA, SEQ ID NO: 17) served as a control oligonucleotide. ISIS 113529 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl)nucleotides, also known as (2'-MOE) nucleotides. The internucleoside (backbone) linkages are phosphorothioate (P=S) throughout the oligonucleotide. All cytidine residues are 5-methylcytidines.

Following 24 hours of treatment with antisense oligonucleotides, apolipoprotein C-III mRNA was measured by real-time PCR as described by other examples herein, using the primers and probe designed to the human apolipoprotein C-III sequence (forward primer: TCAGCTTCATGCAGGGTTACAT (SEQ ID NO: 5) reverse primer: ACGCTGCTCAGTGCATCCT (SEQ ID NO: 6) and the PCR probe was: FAM-AAGCACGCCACCAAGACCGCC-TAMRA (SEQ ID NO: 7)) to measure Cynomolgous monkey apolipoprotein C-III mRNA. Primers and probe designed to human GAPDH (forward primer: GAAGGTGAAGGTCGGAGTC (SEQ ID NO: 8) reverse primer: GAAGATGGTGATGGGATTTC (SEQ ID NO: 9) and the PCR probe was: 5' JOE-CAAGCTTCCCGTTCTCAGCC-TAMRA 3' (SEQ ID NO: 10)) were used to measure Cynomolgous monkey GAPDH mRNA expression, for the purpose of normalizing gene target quantities obtained by real-time PCR. Untreated cells served as the control to which data were normalized. Data are the average of three experiments and are presented in the table below.

TABLE 126

Antisense inhibition of apolipoprotein C-III in Cynomolgus monkey primary hepatocytes

| ISIS # | SEQ ID NO | Dose of Oligonucleotide 10 nM | 50 nM | 150 nM | 300 nM |
|---|---|---|---|---|---|
| | | % Inhibition | | | |
| 304789 | 75 | 0 | 7 | 1 | 55 |
| 304799 | 85 | 34 | 60 | 66 | 48 |
| 304800 | 86 | 9 | 53 | 59 | 57 |
| 113529 | 222 | N.D. | N.D. | 0 | 0 |

Example 119: Cynomolgus Monkey Apolipoprotein C-III Sequence

In a further embodiment, a portion of the Cynomolgus monkey apolipoprotein C-III gene was sequenced. Positions 8 to 476 of the human apolipoprotein C-III mRNA sequence (incorporated in its entirety herein as SEQ ID NO: 1) contain the target segment to which ISIS 304789 hybridizes. The corresponding region of Cynomolgus monkey apolipoprotein C-III mRNA was sequenced. RNA was isolated and purified from primary Cynomolgus monkey hepatocytes (InVitro Technologies, Gaithersburg, MD) and was subjected to a reverse transcriptase reaction (kit from Invitrogen Life Technologies, Carlsbad, CA). The resultant cDNA was the substrate for 40 rounds of PCR amplification, using 5' and 3' primers designed to positions 8 and 476, respectively, of the human apolipoprotein C-III mRNA (Amplitaq PCR kit, Invitrogen Life Technologies, Carlsbad, CA). Following gel purification of the resultant 468 bp fragment, the forward and reverse sequencing reactions of each product were performed by Retrogen (San Diego, CA). This Cynomolgus monkey sequence is incorporated herein as SEQ ID NO: 223 and is 92% identical to positions 8 to 476 of the human apolipoprotein C-III mRNA.

Example 120: Chimeric Phosphorothioate Oligonucleotide Having 2'-MOE Wings and a Deoxy Gap, Targeted to Cynomolgus Monkey Apolipoprotein C-III In a further embodiment, the sequence of Cynomolgus monkey apolipoprotein C-III incorporated herein as SEQ ID NO: 223 was used to design an antisense oligonucleotide having 100% complementarity to Cynomolgus apolipoprotein C-III mRNA. ISIS 340340 (GGCAGCCCTGGAGGCTGCAG; incorporated herein as SEQ ID NO: 18) targets nucleotide 397 of SEQ ID NO: 223, within a region corresponding to the 3' UTR of the human apolipoprotein C-III to which ISIS 304789 hybridizes. ISIS 340340 is a chimeric oligonucleotide ("gapmer") 20 nucleotide in length composed of a central "gap" region consisting of 2'deoxynucleotides, which is flanked on both sides (5' and 3' directions) by 5 nucleotide "wings". The wings are composed of 2'methoxyethyl (2'-MOE) nucleotides. Internucleoside (backbone) linkages are phosphorothioate (P=S) throughout the nucleotide. All cytidine residues are 5-methyl cytidines.

The invention claimed is:

1. A method of reducing expression of apolipoprotein C3 in a subject comprising administering a compound comprising a modified oligonucleotide and a conjugate group, or a pharmaceutically acceptable salt thereof, to a subject having familial chylomicronemia syndrome (FCS), wherein the modified oligonucleotide consists of 12 to 30 linked nucleosides, comprises a nucleobase sequence comprising a portion of at least 20 contiguous nucleobases complementary to an equal length portion of nucleobases 3533 to 3552 of SEQ ID NO: 3, wherein the nucleobase sequence of the modified oligonucleotide is at least 80% complementary to SEQ ID NO: 3, and wherein the modified oligonucleotide comprises:

a gap segment consisting of ten linked deoxynucleosides;

a 5' wing segment consisting of five linked nucleosides;

a 3' wing segment consisting of five linked nucleosides; wherein the gap segment is positioned between the 5' wing segment and the 3' wing segment, wherein each nucleoside of each wing segment comprises a 2'-O-methoxyethyl sugar, and wherein each cytosine residue is a 5-methylcytosine; and wherein the conjugate group comprises:

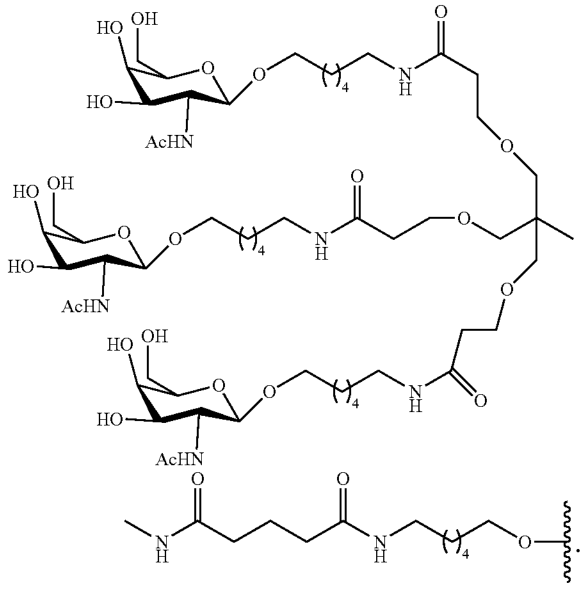

2. The method of claim 1, wherein the conjugate group is linked to the modified oligonucleotide at the 5' end of the modified oligonucleotide.

3. The method of claim 1, wherein the conjugate group is linked to the modified oligonucleotide at the 3' end of the modified oligonucleotide.

4. The method of claim 1, wherein each internucleoside linkage of the modified oligonucleotide is selected from a phosphodiester internucleoside linkage and a phosphorothioate internucleoside linkage.

5. The method of claim 4, wherein the modified oligonucleotide comprises at least 5 phosphodiester internucleoside linkages.

6. The method of claim 4, wherein each internucleoside linkage in the gap segment of the modified oligonucleotide is a phosphorothioate linkage.

7. The method of claim 6, wherein the modified oligonucleotide further comprises at least one phosphorothioate internucleoside linkage in each wing segment.

8. The method of claim 1, wherein the modified oligonucleotide comprises the nucleoside sequence of SEQ ID NO: 244, and wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar, wherein each internucleoside linkage in the gap segment is a phosphorothioate linkage and in each wing segment at least one internucleoside linkage is a phosphorothioate internucleoside linkage; and wherein each cytosine residue is a 5-methylcytosine.

9. The method of claim 1, wherein the compound has the formula:

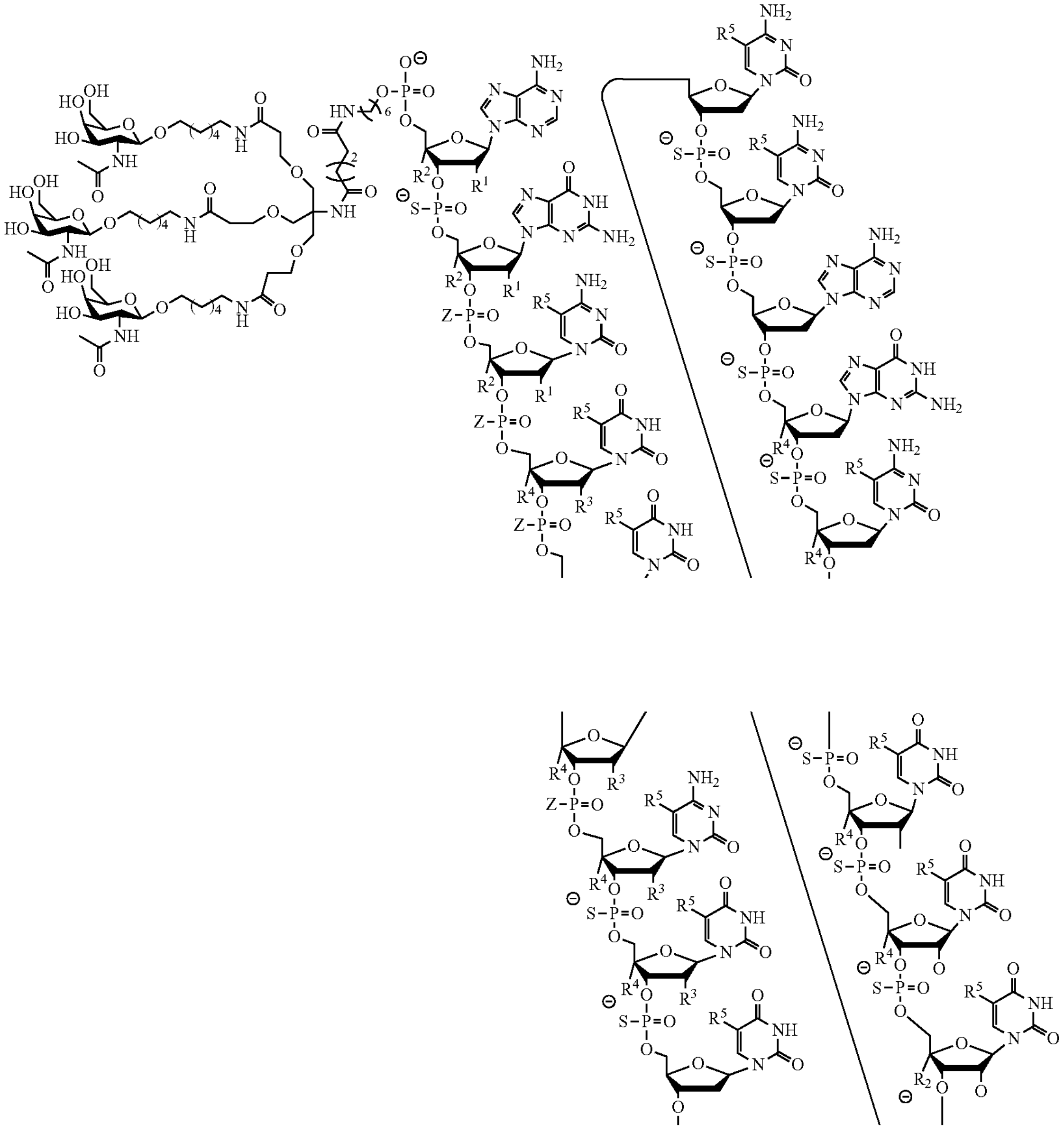

-continued

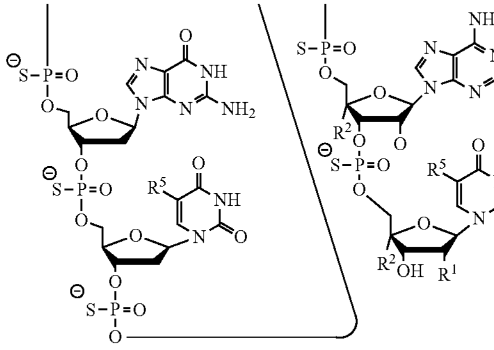

or a pharmaceutically acceptable salt thereof;

wherein either $R^1$ is $—OCH_2CH_2OCH_3$ and $R^2$ is H;

and for each pair of $R^3$ and $R^4$ on the same ring, independently for each ring: either $R^3$ is selected from H and $—OCH_2CH_2OCH_3$ and $R^4$ is H; or $R^3$ and $R^4$ together form a bridge, wherein $R^3$ is —O—, and $R^4$ is $—CH_2$, $—CH(CH_3)—$, or $—CH_2CH_2—$ and $R^3$ and $R^4$ are directly connected such that the resulting bridge is selected from $—O—CH_2$, $—O—CH(CH_3)—$, and $—O—CH_2CH_2$;

$R^5$ is selected from H and $—CH_3$;

and Z is selected from $S^-$ and $O^-$.

10. The method of claim 9, wherein each internucleoside linkage of the modified oligonucleotide is a phosphorothioate linkage.

11. The method of claim 1, wherein the compound has the formula:

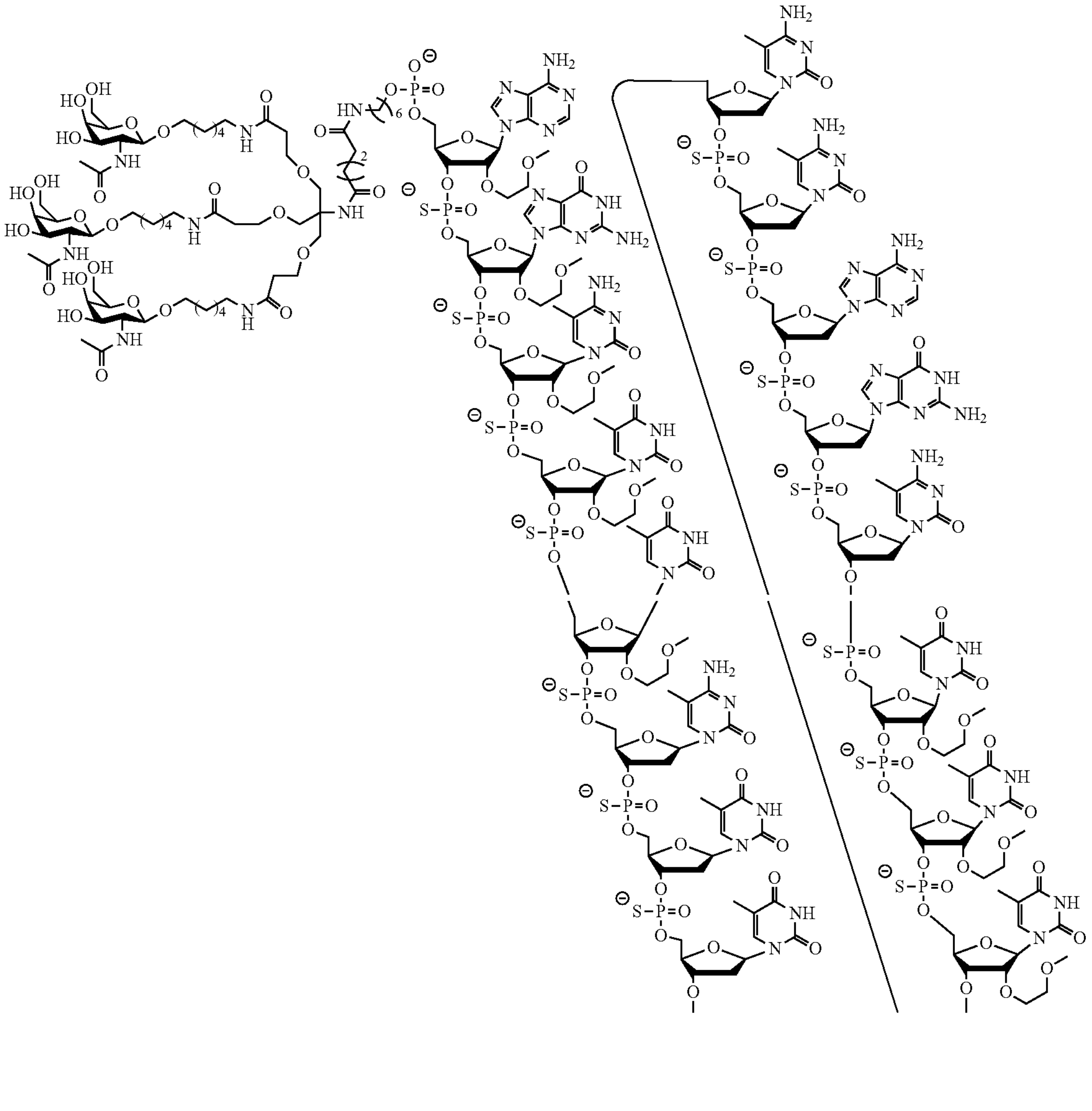

-continued

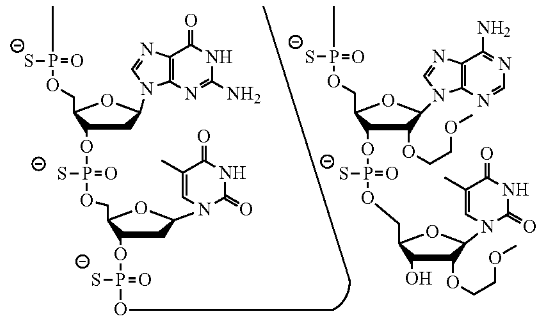

or a pharmaceutically acceptable salt thereof.

12. The method of claim 1, wherein said pharmaceutically acceptable salt is a sodium salt or a potassium salt.

13. The method of claim 1, comprising administering to the subject a composition comprising the pharmaceutically acceptable salt of the compound, wherein the composition further comprises a pharmaceutically acceptable diluent or carrier.

14. The method of claim 1, wherein the compound or the pharmaceutically acceptable salt thereof is administered by parenteral administration.

15. The method of claim 1, wherein the compound or the pharmaceutically acceptable salt thereof is administered by subcutaneous administration.

16. The method of claim 1, wherein the administration reduces triglyceride levels in the subject.

17. The method of claim 1, wherein the administration increases HDL levels in the subject.

18. The method of claim 1, wherein the administration increases chylomicron clearance in the subject, whereby the increase in chylomicron clearance treats, prevents, delays or ameliorates pancreatitis in the subject.

19. A method of treating hypertriglyceridemia in a subject comprising administering to the subject having hypertriglyceridemia a compound comprising a modified oligonucleotide and a conjugate group, or a pharmaceutically acceptable salt thereof, wherein the modified oligonucleotide consists of 12 to 30 linked nucleosides, comprises a nucleobase sequence comprising a portion of at least 20 contiguous nucleobases complementary to an equal length portion of nucleobases 3533 to 3552 of SEQ ID NO: 3, wherein the nucleobase sequence of the modified oligonucleotide is at least 80% complementary to SEQ ID NO: 3, and wherein the modified oligonucleotide comprises:

a gap segment consisting of ten linked deoxynucleosides;

a 5' wing segment consisting of five linked nucleosides;

a 3' wing segment consisting of five linked nucleosides; wherein the gap segment is positioned between the 5' wing segment and the 3' wing segment, wherein each nucleoside of each wing segment comprises a 2'-O-methoxyethyl sugar, and wherein each cytosine residue is a 5-methylcytosine; and wherein the conjugate group comprises:

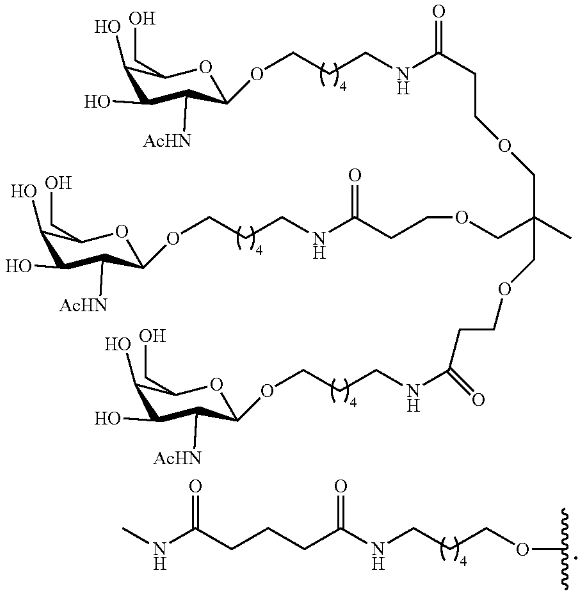

20. A method of treating familial chylomicronemia syndrome (FCS) in a subject comprising administering to the subject having FCS a compound comprising a modified oligonucleotide and a conjugate group, or a pharmaceutically acceptable salt thereof, wherein the modified oligonucleotide consists of 12 to 30 linked nucleosides, comprises a nucleobase sequence comprising a portion of at least 20 contiguous nucleobases complementary to an equal length portion of nucleobases 3533 to 3552 of SEQ ID NO: 3, wherein the nucleobase sequence of the modified oligonucleotide is at least 80% complementary to SEQ ID NO: 3, and wherein the modified oligonucleotide comprises:

a gap segment consisting of ten linked deoxynucleosides;

a 5' wing segment consisting of five linked nucleosides;

a 3' wing segment consisting of five linked nucleosides; wherein the gap segment is positioned between the 5' wing segment and the 3' wing segment, wherein each nucleoside of each wing segment comprises a 2'-O-methoxyethyl sugar, and wherein each cytosine residue is a 5-methylcytosine; and wherein the conjugate group comprises:

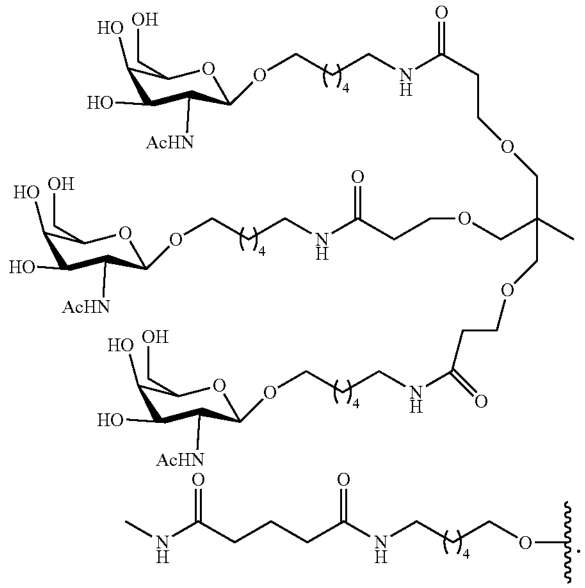
* * * * *